United States Patent
Ji et al.

(10) Patent No.: US 11,910,712 B2
(45) Date of Patent: Feb. 20, 2024

(54) COMPOUND, ORGANIC OPTOELECTRONIC DIODE, AND DISPLAY DEVICE

(71) Applicant: LT MATERIALS CO., LTD., Yongin-Si (KR)

(72) Inventors: Hye-Su Ji, Hwaseong-si (KR); Seong-Jong Park, Hwaseong-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 424 days.

(21) Appl. No.: 17/423,332

(22) PCT Filed: Jan. 22, 2020

(86) PCT No.: PCT/KR2020/001071
§ 371 (c)(1),
(2) Date: Jul. 15, 2021

(87) PCT Pub. No.: WO2020/153740
PCT Pub. Date: Jul. 30, 2020

(65) Prior Publication Data
US 2022/0173329 A1 Jun. 2, 2022

(30) Foreign Application Priority Data
Jan. 25, 2019 (KR) .......................... 10-2019-0009759

(51) Int. Cl.
*H10K 85/60* (2023.01)
*C07D 215/06* (2006.01)
*C07D 401/14* (2006.01)
(Continued)

(52) U.S. Cl.
CPC ....... *H10K 85/6572* (2023.02); *C07D 215/06* (2013.01); *C07D 401/14* (2013.01);
(Continued)

(58) Field of Classification Search
CPC ............. H10K 85/6572; H10K 85/615; H10K 85/622; H10K 85/626; H10K 85/654;
(Continued)

(56) References Cited

U.S. PATENT DOCUMENTS

2013/0123501 A1  5/2013 Castelhano et al.
2018/0366652 A1  12/2018 Mo et al.
(Continued)

FOREIGN PATENT DOCUMENTS

CN    108947898 A    12/2018
KR    10-2017-0064379 A    6/2017
(Continued)

OTHER PUBLICATIONS

International Search Report (PCT/ISA/210) issued in PCT/KR2020/001071 dated May 1, 2020.
(Continued)

*Primary Examiner* — Douglas W Owens
(74) *Attorney, Agent, or Firm* — Birch, Stewart, Kolasch & Birch, LLP

(57) ABSTRACT

The present application relates to a compound represented by Chemical Formula 1, an organic optoelectronic diode and a display device.

20 Claims, 2 Drawing Sheets

(51) Int. Cl.
*C07D 471/04* (2006.01)
*C09K 11/06* (2006.01)
*H10K 50/00* (2023.01)
*H10K 50/18* (2023.01)
*H10K 50/13* (2023.01)

(52) U.S. Cl.
CPC ............ *C07D 471/04* (2013.01); *C09K 11/06* (2013.01); *H10K 85/615* (2023.02); *H10K 85/622* (2023.02); *H10K 85/626* (2023.02); *H10K 85/654* (2023.02); *C09K 2211/1018* (2013.01); *H10K 50/00* (2023.02); *H10K 50/131* (2023.02); *H10K 50/18* (2023.02)

(58) Field of Classification Search
CPC ...... H10K 50/00; H10K 50/131; H10K 50/18; H10K 50/166; C07D 215/06; C07D 401/14; C07D 471/04; C09K 11/06; C09K 2211/1018
See application file for complete search history.

(56) References Cited

U.S. PATENT DOCUMENTS

2019/0263834 A1 8/2019 Jeong et al.
2019/0312211 A1 10/2019 Lee et al.
2021/0091314 A1* 3/2021 Shin .................... C07D 405/04

FOREIGN PATENT DOCUMENTS

WO  WO 2018/012845 A1  1/2018
WO  WO 2018/097648 A1  5/2018

OTHER PUBLICATIONS

Xin et al., "Color-Stable White Organic Light-Emitting Diodes Utilizing a Blue-Emitting Electron-Transport Layer," American Chemical Society Omega, 2018, vol. 3, pp. 12549-12553.

* cited by examiner

【FIG. 1】
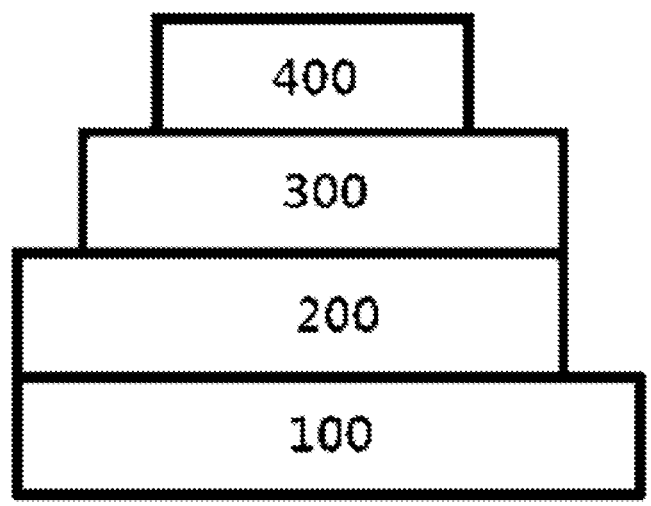
【FIG. 2】
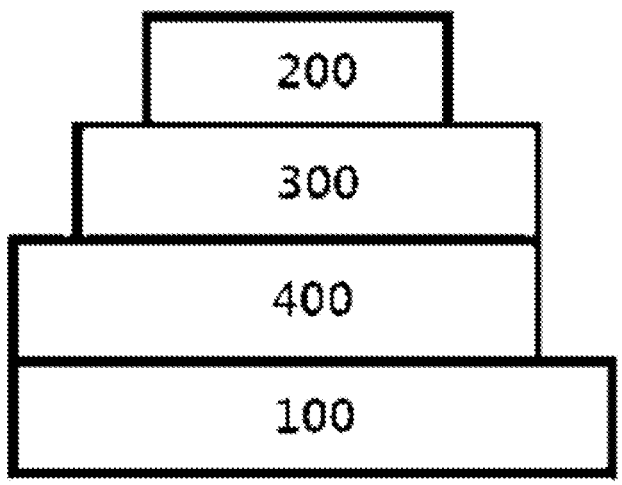

[FIG. 3]
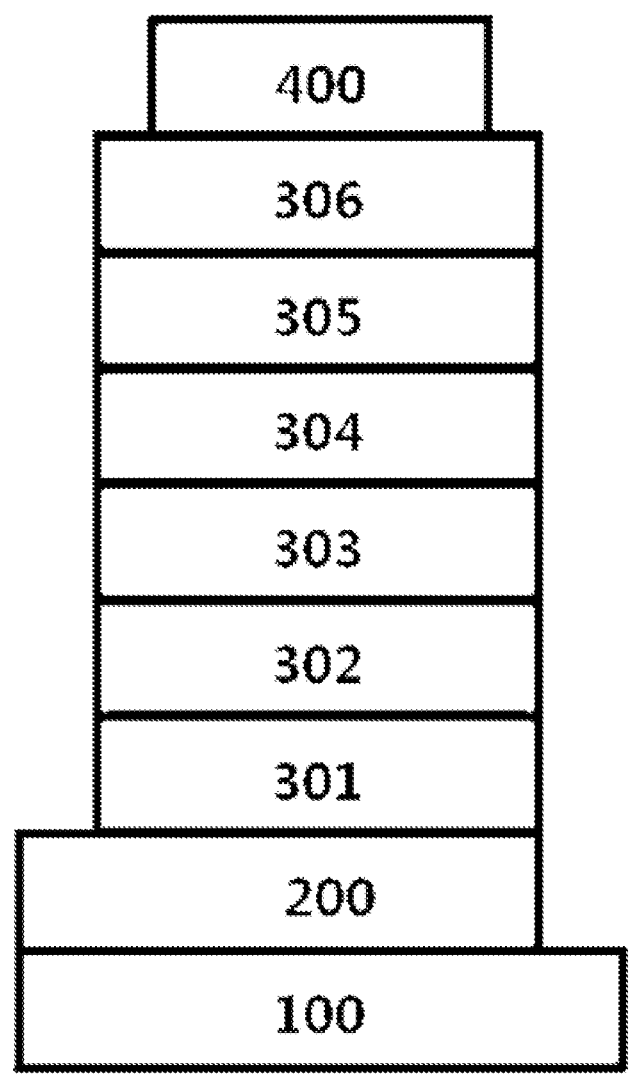

COMPOUND, ORGANIC OPTOELECTRONIC DIODE, AND DISPLAY DEVICE

TECHNICAL FIELD

This application claims priority to and the benefits of Korean Patent Application No. 10-2019-0009759, filed with the Korean Intellectual Property Office on Jan. 25, 2019, the entire contents of which are incorporated herein by reference.

The present application relates to a compound, an organic optoelectronic diode and a display device.

BACKGROUND ART

An organic optoelectronic diode is a device capable of interconverting electrical energy and light energy.

An organic optoelectronic diode may be divided into two types depending on the operating principle. One is an optoelectronic diode in which excitons formed by light energy are separated into electrons and holes and electrical energy is generated while the electrons and the holes are each transferred to different electrodes, and the other one is a light emitting diode generating light energy from electrical energy by supplying a voltage or a current to electrodes.

Examples of the organic optoelectronic diode may include an organic photoelectric diode, an organic light emitting diode, an organic solar cell, an organic photo conductor drum and the like.

Among these, an organic light emitting diode (OLED) has received much attention recently as demands for flat panel display devices have increased. An organic light emitting diode is a device converting electrical energy to light, and performance of an organic light emitting diode is greatly affected by organic materials disposed between electrodes.

An organic light emitting diode has a structure disposing an organic thin film between two electrodes. When a voltage is applied to an organic light emitting diode having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used.

In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting diode.

DISCLOSURE

Technical Problem

One embodiment of the present specification is directed to providing a compound capable of obtaining an organic optoelectronic diode with high efficiency and long lifetime.

Another embodiment of the present specification is directed to providing an organic optoelectronic diode including the compound.

Still another embodiment of the present specification is directed to providing a display device including the organic optoelectronic diode.

Technical Solution

One embodiment of the present specification provides a compound represented by the following Chemical Formula 1.

[Chemical Formula 1]

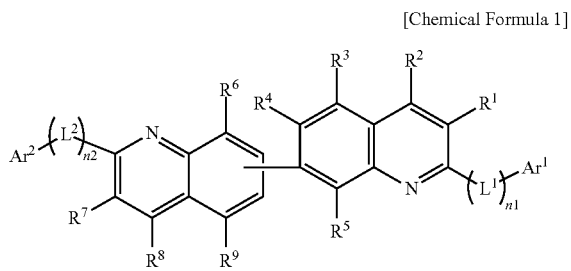

In Chemical Formula 1,
$Ar^1$ and $Ar^2$ are each independently a substituted or unsubstituted C6 to C60 aryl group or a substituted or unsubstituted C2 to C60 heteroaryl group, at least one of $Ar^1$ and $Ar^2$ is a substituted or unsubstituted C2 to C60 heteroaryl group, $L^1$ and $L^2$ are each independently a single bond, a substituted or unsubstituted C6 to C60 arylene group or a substituted or unsubstituted C2 to C60 heteroarylene group, n1 and n2 are each independently one of integers of 0 to 2, and $R^1$ to $R^9$ are each independently hydrogen, deuterium, a cyano group, a substituted or unsubstituted C1 to C60 alkyl group or a substituted or unsubstituted C6 to C60 aryl group.

More specifically, the compound may be represented by any one of the following Chemical Formulae 2 and 3.

[Chemical Formula 2]

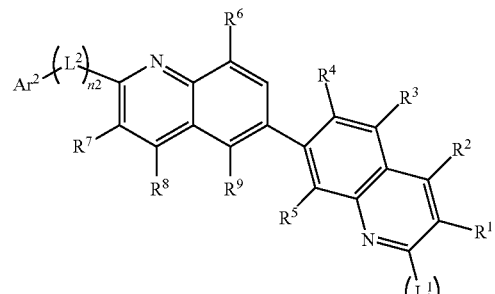

[Chemical Formula 3]

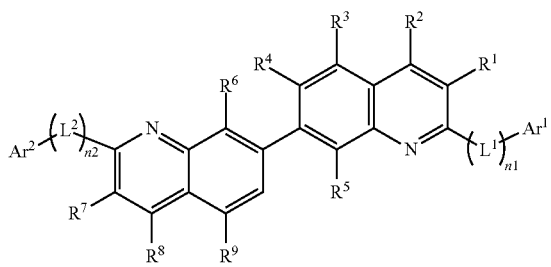

Another embodiment of the present specification provides an organic optoelectronic diode including an anode and a cathode facing each other, and at least one organic layer disposed between the anode and the cathode, wherein the organic layer includes the compound.

Still another embodiment of the present specification provides a display device including the organic optoelectronic diode.

Advantageous Effects

An organic optoelectronic diode with high efficiency and long lifetime can be obtained.

DESCRIPTION OF DRAWINGS

FIG. 1 to FIG. 3 are sectional diagrams each illustrating an organic light emitting diode according to one embodiment of the present specification.
- 100: Substrate
- 200: Anode
- 300: Organic Material Layer
- 301: Hole Injection Layer
- 302: Hole Transfer Layer
- 303: Light Emitting Layer
- 304: Hole Blocking Layer
- 305: Electron Transfer Layer
- 306: Electron Injection Layer
- 400: Cathode

Mode for Disclosure

Hereinafter, embodiments of the present disclosure will be described in detail. However, these are for illustrative purposes only, and the present disclosure is not limited thereto, and is only defined by the category of claims to describe later.

In the present specification, "substituted or unsubstituted" means being substituted with one or more substituents selected from the group consisting of deuterium; a halogen group; —CN; a C1 to C60 linear alkyl group; a C3 to C60 branched alkyl group; a C2 to C60 linear alkenyl group; a C3 to C60 branched alkenyl group; a C2 to C60 linear alkynyl group; a C4 to C60 branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; —SiRR'R"; —P(=O)RR'; a C1 to C20 alkylamine group; a C6 to C60 monocyclic or polycyclic arylamine group; a C2 to C60 monocyclic or polycyclic heteroarylamine group, a substituted or unsubstituted alkoxy group, a substituted or unsubstituted aryloxy group, a substituted or unsubstituted heteroaryloxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted boron group, a substituted or unsubstituted silyl group, a substituted or unsubstituted arylphosphine group, a substituted or unsubstituted phosphine oxide group, a substituted or unsubstituted fluorenyl group and a substituted or unsubstituted aromatic or aliphatic heterocyclic group including one or more of N, O and S atoms, or being unsubstituted, or being substituted with a substituent bonding two or more of the substituents, or being unsubstituted, or being substituted with a substituent linking two or more substituents selected from among the above-mentioned substituents, or being unsubstituted. In addition, these may further form a ring with adjacent substituents.

For example, the "substituent linking two or more substituents" may include a biphenyl group. In other words, a biphenyl group may be an aryl group, or interpreted as a substituent linking two phenyl groups. The additional substituents may be further substituted. R, R' and R" are the same as or different from each other, and each independently hydrogen; deuterium; —CN; a substituted or unsubstituted C1 to C60 linear alkyl group; a substituted or unsubstituted C3 to C60 branched alkyl group; a substituted or unsubstituted C3 to C60 monocyclic or polycyclic cycloalkyl group; a substituted or unsubstituted C6 to C60 monocyclic or polycyclic aryl group; or a substituted or unsubstituted C2 to C60 monocyclic or polycyclic heteroaryl group.

According to one embodiment of the present application, the "substituted or unsubstituted" means being substituted with one or more substituents selected from the group consisting of deuterium, a halogen group, —CN, —SiRR'R", —P(=O)RR', a C1 to C20 linear alkyl group, a C3 to C20 branched alkyl group, a C6 to C60 monocyclic or polycyclic aryl group and a C2 to C60 monocyclic or polycyclic heteroaryl group, or being unsubstituted, and R, R' and R" are the same as or different from each other and each independently hydrogen; deuterium; —CN; a C1 to C60 alkyl group unsubstituted or substituted with deuterium, a halogen group, —CN, a C1 to C20 alkyl group, a C6 to C60 aryl group and a C2 to C60 heteroaryl group; a C3 to C60 cycloalkyl group unsubstituted or substituted with deuterium, halogen, —CN, a C1 to C20 alkyl group, a C6 to C60 aryl group and a C2 to C60 heteroaryl group; a C6 to C60 aryl group unsubstituted or substituted with deuterium, halogen, —CN, a C1 to C20 alkyl group, a C6 to C60 aryl group and a C2 to C60 heteroaryl group; or a C2 to C60 heteroaryl group unsubstituted or substituted with deuterium, halogen, —CN, a C1 to C20 alkyl group, a C6 to C60 aryl group and a C2 to C60 heteroaryl group.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may include fluorine, chlorine, bromine or iodine.

In the present specification, the alkyl group includes a C1 to C60 linear or branched, and may be further substituted with other substituents. The number of carbon atoms of the alkyl group may be from 1 to 60, specifically from 1 to 40, more specifically from 1 to 20 and more specifically from 1 to 10, and when the alkyl group is branched, the number of carbon atoms is 3 or greater. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes a C2 to C60 linear or branched, and may be further substituted with other substituents. The number of carbon atoms of the alkenyl group may be from 2 to 60, specifically from 2 to 40 and more specifically from 2 to 20, and when the alkenyl group is branched, the number of carbon atoms is 3 or greater. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes a C2 to C60 linear or branched, and may be further substituted with other substituents. The number of carbon atoms of the alkynyl group may be from 2 to 60, specifically from 2 to 40 and more specifically from 2 to 20, and when the alkynyl group is branched, the number of carbon atoms is 4 or greater.

In the present specification, the cycloalkyl group includes a C3 to C60 monocyclic or polycyclic, and may be further substituted with other substituents. Herein, the polycyclic means a group in which the cycloalkyl group is directly linked to or fused with another cyclic group. Herein, the another cyclic group may be a cycloalkyl group, but may also include other types of cyclic groups such as a heterocycloalkyl group, an aryl group and a heteroaryl group. The number of carbon atoms of the cycloalkyl group may be from 3 to 60, specifically from 3 to 40 and more specifically from 5 to 20, and when the cycloalkyl group is polycyclic, the number of carbon atoms is 4 or greater. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may include a C1 to C10 alkoxy group, and more specifically, a methoxy group, an ethoxy group, a propoxy group, a butoxy group, a pentoxy group and the like.

In the present specification, the silyl group may be represented by —SiRR'R", and R, R' and R" have the same definitions as above. More specifically, a dimethylsilyl group, a diethylsilyl group, a methylethylsilyl group and the like may be included.

In the present specification, the phosphine oxide group may be represented by —P(=O)RR', and R and R' have the same definitions as above. More specifically, a dimethylphosphine group, a diethylphosphine group, a methylethylphosphine group and the like may be included.

In the present specification, the fluorenyl group means a substituent including various substituents at the number 9 position. Specifically, a concept including a fluorenyl group in which the number 9 position is substituted with two hydrogens, two alkyl groups, two aryl groups or two heteroaryl groups may be used. More specifically, a 9-di-H-fluorenyl group, a 9-di-methyl-fluorenyl group, a 9-di-phenyl-fluorenyl group or the like may be used.

In the present specification, the heterocycloalkyl group includes O, S, Se, N or Si as a heteroatom, includes a C2 to C60 monocyclic or polycyclic, and may be further substituted with other substituents. Herein, the polycyclic means a group in which the heterocycloalkyl group is directly linked to or fused with another cyclic group. Herein, the another cyclic group may be a heterocycloalkyl group, but may also include other types of cyclic groups such as a cycloalkyl group, an aryl group and a heteroaryl group. The number of carbon atoms of the heterocycloalkyl group may be from 2 to 60, specifically from 2 to 40, and more specifically from 3 to 20.

In the present specification, the aryl group includes a C6 to C60 monocyclic or polycyclic, and may be further substituted with other substituents. Herein, the polycyclic means a group in which the aryl group is directly linked to or fused with another cyclic group. Herein, the another cyclic group may be an aryl group, but may also include other types of cyclic groups such as a cycloalkyl group, a heterocycloalkyl group and a heteroaryl group. The aryl group includes a spiro group. The number of carbon atoms of the aryl group may be from 6 to 60, specifically from 6 to 40, specifically from 6 to and more specifically from 6 to 25, and when the aryl group is polycyclic, the number of carbon atoms is 7 or greater. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof and the like, but are not limited thereto.

In the present specification, the spiro group is a group including a spiro structure, and may be from C15 to C60. For example, the spiro group may include a structure in which a 2,3-dihydro-1H-indene group or a cyclohexane group spiro-bonds to a fluorenyl group. Specifically, the spiro group may include any one of the groups of the following structural formulae.

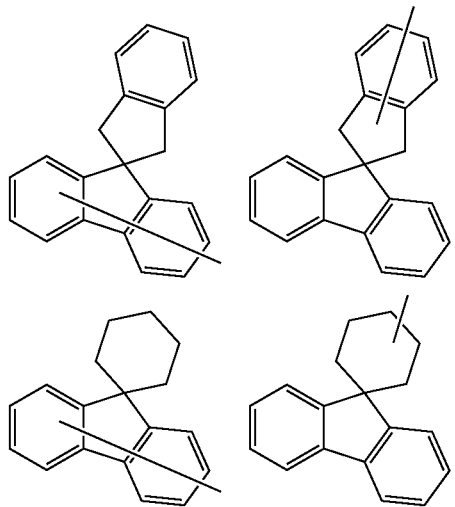

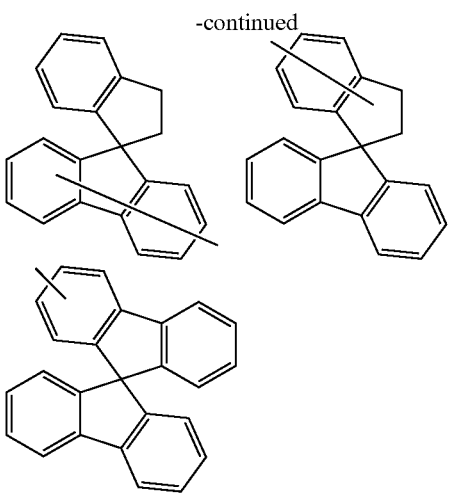

In the present specification, the heteroaryl group includes S, O, Se, N or Si as a heteroatom, includes a C2 to C60 monocyclic or polycyclic, and may be further substituted with other substituents. Herein, the polycyclic means a group in which the heteroaryl group is directly linked to or fused with another cyclic group. Herein, the another cyclic group may be a heteroaryl group, but may also include other types of cyclic groups such as a cycloalkyl group, a heterocycloalkyl group and an aryl group. The number of carbon atoms of the heteroaryl group may be from 2 to 60, specifically from 2 to 40, specifically from 2 to 30 and more specifically from 3 to 25, and when the heteroaryl group is polycyclic, the number of carbon atoms is 3 or greater. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolinyl group, a naphthyridyl group, an acridinyl group, a phenanthridinyl group, an imidazopyridinyl group, diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, 9,10-dihydroacridinyl group, a phenanthrazinyl group, a phenothiathiazinyl group, a phthalazinyl group, a naphthyridinyl group, a phenanthrolinyl group, a benzo[c][1,2,5]thiadiazolyl group, 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means an aryl group having two bonding sites, that is, a divalent group. Descriptions on the aryl group provided above may be applied thereto except for each being a divalent group. In addition, the heteroarylene group means a heteroaryl group having two bonding sites, that is, a divalent group. Descriptions on the heteroaryl group provided above may be applied thereto except for each being a divalent group.

In the present specification, hole properties refer to properties capable of forming holes by donating electrons when applying an electric field, and means properties of, by having conducting properties along the HOMO level, facilitating injection of holes forming in an anode to a light emitting layer, migration of holes formed in a light emitting layer to an anode and migration in the light emitting layer.

Substituents having hole properties include a substituted or unsubstituted C6 to C60 aryl group having hole properties, a substituted or unsubstituted C2 to C60 heteroaryl group having hole properties, a substituted or unsubstituted arylamine group, a substituted or unsubstituted heteroarylamine group, or the like.

More specifically, the substituted or unsubstituted C6 to C60 aryl group having hole properties may be a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluorenyl group, a substituted or unsubstituted terphenyl group, a substituted or unsubstituted pyrenyl group, a substituted or unsubstituted perylenyl group, or a combination thereof.

More specifically, the substituted or unsubstituted C2 to C60 heteroaryl group having hole properties is a substituted or unsubstituted carbazolyl group, a substituted or unsubstituted dibenzofuranyl group, a substituted or unsubstituted dibenzothiophenyl group, a substituted or unsubstituted indolecarbazolyl group, or the like.

The aryl group or the heteroaryl group, a substituent bonding to the nitrogen of the substituted or unsubstituted arylamine group and the substituted or unsubstituted heteroarylamine group may be, more specifically, a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

In addition, electron properties refer to properties capable of receiving electrons when applying an electric field, and means properties of, by having conducting properties along the LUMO level, facilitating injection of electrons forming in a cathode to a light emitting layer, migration of electrons formed in a light emitting layer to a cathode and migration in the light emitting layer.

The substituted or unsubstituted C2 to C60 heteroaryl group having electron properties may be a substituted or unsubstituted imidazolyl group, a substituted or unsubstituted tetrazolyl group, a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazoline group, a substituted or unsubstituted benzoxadiazoline group, a substituted or unsubstituted oxatriazolyl group, a substituted or unsubstituted thiophenyl group, a substituted or unsubstituted benzothiophenyl group, a substituted or unsubstituted isothiazoline group, a substituted or unsubstituted benzoisothiazoline group, a substituted or unsubstituted thiazoline group, a substituted or unsubstituted benzothiazoline group, a substituted or unsubstituted pyridazinyl group, a substituted or unsubstituted benzopyridazinyl group, a substituted or unsubstituted pyrazinyl group, a substituted or unsubstituted benzopyrazinyl group, a substituted or unsubstituted phthalazinyl group, a substituted or unsubstituted benzoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

More specifically, the substituted or unsubstituted C2 to C60 heteroaryl group having electron properties may be any one of the following Chemical Formulae X-1 to X-5.

[Chemical Formula X-1]

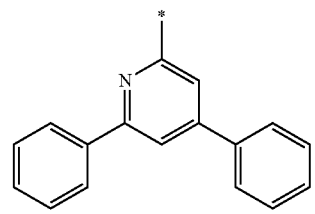

[Chemical Formula X-2]

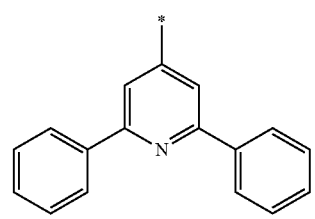

[Chemical Formula X-3]

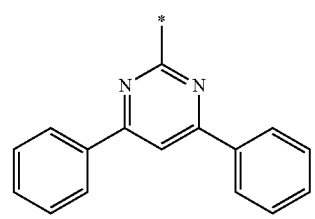

[Chemical Formula X-4)

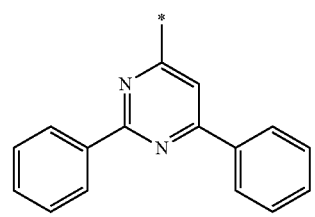

[Chemical Formula X-5]

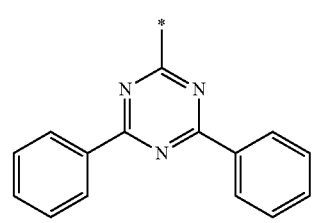

In one embodiment of the present application, L″ may be a direct bond (or a single bond); a substituted or unsubstituted arylene group; or a substituted or unsubstituted heteroarylene group.

In another embodiment, L″ may be a direct bond; a substituted or unsubstituted C6 to C60 arylene group; or a substituted or unsubstituted C2 to C60 heteroarylene group.

In another embodiment, L″ may be a direct bond; a substituted or unsubstituted C6 to C40 arylene group; or a substituted or unsubstituted C2 to C40 heteroarylene group.

In L″, n means a number for distinguishing substituents.

In one embodiment of the present application, $L^1$ and $L^2$ may be each independently a direct bond (or single bond); a substituted or unsubstituted arylene group; or a substituted or unsubstituted heteroarylene group.

In one embodiment of the present application, $L^1$ and $L^2$ may be each independently a direct bond; a substituted or unsubstituted C6 to C60 arylene group; or a substituted or unsubstituted C2 to C60 heteroarylene group.

In one embodiment of the present application, $L^1$ and $L^2$ may be each independently a direct bond; a substituted or unsubstituted C6 to C40 arylene group; or a substituted or unsubstituted C2 to C40 heteroarylene group.

Hereinafter, a compound according to one embodiment will be described.

The compound according to one embodiment is represented by the following Chemical Formula 1.

[Chemical Formula 1]

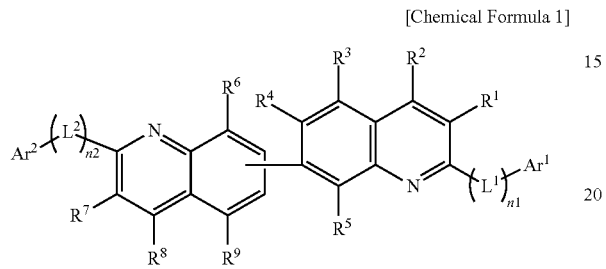

In Chemical Formula 1, $Ar^1$ and $Ar^2$ are each independently a substituted or unsubstituted C6 to C60 aryl group or a substituted or unsubstituted C2 to C60 heteroaryl group, at least one of $Ar^1$ and $Ar^2$ is a substituted or unsubstituted C2 to C60 heteroaryl group, $L^1$ and $L^2$ are each independently a single bond, a substituted or unsubstituted C6 to C60 arylene group or a substituted or unsubstituted C2 to C60 heteroarylene group, n1 and n2 are each independently one of integers of 0 to 2, and $R^1$ to $R^9$ are each independently hydrogen, deuterium, a cyano group, a substituted or unsubstituted C1 to C60 alkyl group or a substituted or unsubstituted C6 to C60 aryl group.

The compound represented by Chemical Formula 1 is a biquinoline type, and may specifically be substituted or unsubstituted 6,7-biquinoline or substituted or unsubstituted 7,7-biquinoline. When comparing 6,7-biquinoline and 7,7-biquinoline with compounds including other types of biquinoline, advantages of lowering a device driving voltage, enhancing light efficiency, and enhancing device lifetime properties by thermal stability of the compound are obtained.

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting diode to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and thereby has excellent thermal stability. Such an increase in the thermal stability becomes an important factor in providing driving stability to a device.

As one example, the compound may be represented by the following Chemical Formula 2.

[Chemical Formula 2]

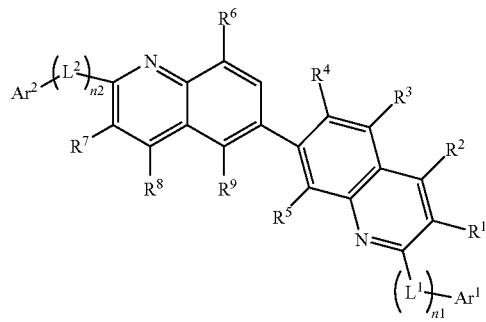

In Chemical Formula 2, $Ar^1$ and $Ar^2$ are each independently a substituted or unsubstituted C6 to C60 aryl group or a substituted or unsubstituted C2 to C60 heteroaryl group, at least one of $Ar^1$ and $Ar^2$ is a substituted or unsubstituted C2 to C60 heteroaryl group, $L^1$ and $L^2$ are each independently a single bond, a substituted or unsubstituted C6 to C60 arylene group or a substituted or unsubstituted C2 to C60 heteroarylene group, n1 and n2 are each independently one of integers of 0 to 2, and $R^1$ to $R^9$ are each independently hydrogen, deuterium, a cyano group, a substituted or unsubstituted C1 to C60 alkyl group or a substituted or unsubstituted C6 to C60 aryl group.

As another example, the compound may be represented by the following Chemical Formula 3.

[Chemical Formula 3]

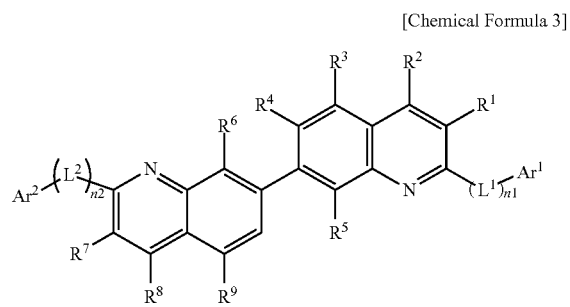

In Chemical Formula 3, $Ar^1$ and $Ar^2$ are each independently a substituted or unsubstituted C6 to C60 aryl group or a substituted or unsubstituted C2 to C60 heteroaryl group, at least one of $Ar^1$ and $Ar^2$ is a substituted or unsubstituted C2 to C60 heteroaryl group, $L^1$ and $L^2$ are each independently a single bond, a substituted or unsubstituted C6 to C60 arylene group or a substituted or unsubstituted C2 to C60 heteroarylene group, n1 and n2 are each independently one of integers of 0 to 2, and $R^1$ to $R^9$ are each independently hydrogen, deuterium, a cyano group, a substituted or unsubstituted C1 to C60 alkyl group or a substituted or unsubstituted C6 to C60 aryl group.

$Ar^1$ may be any one of the following Chemical Formula 4-1 to Chemical Formula 4-5.

[Chemical Formula 4-1]

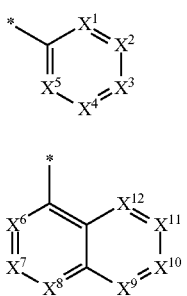

[Chemical Formula 4-2]

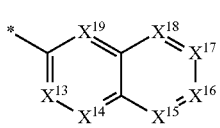

[Chemical Formula 4-3]

[Chemical Formula 4-4]

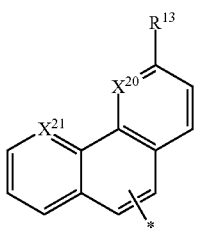

[Chemical Formula 4-5]

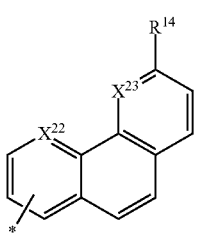

[Chemical Formula 5]

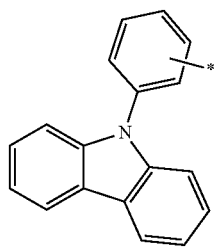

In Chemical Formula 4-1 to Chemical Formula 4-5, at least one of $X^1$ to $X^5$ is —N— and the rest are —CH—, —CR— or —CR$^{10}$—, at least one of $X^6$ to $X^{12}$ is —N— and the rest are —CH—, —CR— or —CR$^{11}$—, at least one of $X^{13}$ to $X^{19}$ is —N— and the rest are —CH—, —CR— or —CR$^{12}$—, $X^{20}$ and $X^{21}$ are each independently —N—, —CH— or —CR— and at least one of $X^{20}$ and $X^{21}$ is —N—, $X^{22}$ and $X^{23}$ are each independently —N—, —CH— or —CR— and at least one of $X^{22}$ and $X^{23}$ is —N—, Rs are each independently deuterium, a cyano group, a substituted or unsubstituted C1 to C60 alkyl group or a substituted or unsubstituted C6 to C60 aryl group, $R^{10}$ to $R^{12}$ are each independently any one of a phenyl group, a pyridinyl group and a substituent of the following Chemical Formula 5, and $R^{13}$ and $R_{14}$ are each independently any one of hydrogen, deuterium, a phenyl group, a pyridinyl group and a substituent of the following Chemical Formula 5, herein, in Chemical Formula 4-1 to Chemical Formula 4-5 and Chemical Formula 5,

* means a bonding position.

In Chemical Formula 4-1 to Chemical Formula 4-5, at least one of $X^1$ to $X^5$ is —N— and the rest are —CH—, —CR— or —CR$^{10}$—, at least one of $X^6$ to $X^{12}$ is —N— and the rest are —CH—, —CR— or —CR$^{11}$—, at least one of $X^{13}$ to $X^{19}$ is —N— and the rest are —CH—, —CR— or —CR$^{12}$—, $X^{20}$ and $X^{21}$ are each independently —N—, —CH— or —CR— and at least one of $X^{20}$ and $X^{21}$ is —N—, $X^{22}$ and $X^{23}$ are each independently —N—, —CH— or —CR— and at least one of $X^{22}$ and $X^{23}$ is —N—, Rs are each independently deuterium, a cyano group, a substituted or unsubstituted C1 to C60 alkyl group or a substituted or unsubstituted C8 to C60 aryl group, $R^{10}$ to $R^{12}$ are each independently any one of a phenyl group, a pyridinyl group and the substituent of Chemical Formula 5, and $R^{13}$ and $R^{14}$ are each independently any one of hydrogen, deuterium, a phenyl group, a pyridinyl group and the substituent of Chemical Formula 5.

Specifically, $Ar^1$ may be represented by chemical formulae as follows. When represented by chemical formulae as follows, light emission efficiency of a manufactured organic light emitting diode may be more superior compared to compounds represented by other chemical formulae.

The chemical formulae as follows are as follows.

$Ar^1$ is represented by Chemical Formula 4-1, and Chemical Formula 4-1 may be a compound in which, $X^1$ is —N—, and the rest are —CH—, $X^2$ is —N—, and the rest are —CH—, $X^3$ is —N—, and the rest are —CH—, $X^1$ and $X^5$ are —N—, $X^3$ is —CH—, the rest are one of —CH— and —CR$^{10}$—, and $R^{10}$ is a phenyl group, $X^1$ and $X^5$ are —N—, $X^3$ is —CH—, the rest are one of —CH— and —CR$^{10}$—, and $R^{10}$ is a pyridinyl group, $X^1$ and $X^3$ are —N—, $X^5$ is —CH—, the rest are one of —CH— and —CR$^{10}$—, and $R^{10}$ is a phenyl group, $X^1$ and $X^4$ are —N—, and the rest are —CH—, $X^1$, $X^3$ and $X^5$ are —N—, the rest are —CR$^{10}$—, and $R^{10}$ is a phenyl group, or $X^1$, $X^3$ and $X^5$ are —N—, and the rest are —CH—.

Herein, the organic electroluminescent diode manufactured using the compound of the present specification may have effects of low driving voltage and high light emission efficiency.

In addition, $Ar^1$ is represented by Chemical Formula 4-2, and Chemical Formula 4-2 may be a compound in which, $X^7$ is —N—, and the rest are —CH—, $X^8$ is —N—, and the rest are —CH—, $X^9$ is —N—, and the rest are —CH—, $X^{10}$ is —N—, and the rest are —CH—, $X^{11}$ is —N—, and the rest are —CH—, or $X^{12}$ is —N—, and the rest are —CH—.

Herein, the organic electroluminescent diode manufactured using the compound of the present specification may have effects of low driving voltage and high light emission efficiency.

In addition, $Ar^1$ is represented by Chemical Formula 4-3, and Chemical Formula 4-3 may be a compound in which, $X^{13}$ is —N—, and the rest are —CH—,
$X^{14}$ is —N—, and the rest are —CH—,
$X^{15}$ is —N—, and the rest are —CH—,
$X^{17}$ is —N—, and the rest are —CH—,
$X^{18}$ is —N—, and the rest are —CH—,
$X^{19}$ is —N—, and the rest are —CH—, or
$X^{13}$ and $X^{19}$ are —N—, and the rest are —CH—.

Herein, the organic electroluminescent diode manufactured using the compound of the present specification may have effects of low driving voltage and high light emission efficiency.

In addition, $Ar^1$ is represented by Chemical Formula 4-4, and Chemical Formula 4-4 may be a compound in which, $X^{20}$ is —N—, $X^{21}$ is —CH—, and $R^{13}$ is hydrogen, or
$X^{20}$ and $X^{21}$ are —N—, and $R^{13}$ is hydrogen or deuterium.

Herein, the organic electroluminescent diode manufactured using the compound of the present specification may have effects of low driving voltage and high light emission efficiency.

In addition, $Ar^1$ is represented by Chemical Formula 4-5, and Chemical Formula 4-5 may be a compound in which, $X^{22}$ is —N—, $X^{23}$ is —CH—, and $R^{14}$ is hydrogen, or
$X^{22}$ and $X^{23}$ are —N—, and $R^{14}$ is one of hydrogen, deuterium and a phenyl group.

Herein, the organic electroluminescent diode manufactured using the compound of the present specification may have effects of low driving voltage and high light emission efficiency.

$Ar^1$ may be a substituted or unsubstituted pyridine group; a substituted or unsubstituted pyrimidine group; a substituted or unsubstituted triazine group; a substituted or unsubstituted quinoline group; a substituted or unsubstituted isoquinoline group; a substituted or unsubstituted quinazoline group; a substituted or unsubstituted quinoxaline group; a substituted or unsubstituted benzoquinoline group; or a substituted or unsubstituted phenanthroline group.

In addition, $Ar^2$ may be any one of the following Chemical Formula 6-1 to Chemical Formula 6-8.

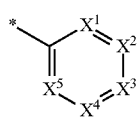

[Chemical Formula 6-1]

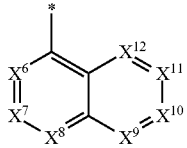

[Chemical Formula 6-2]

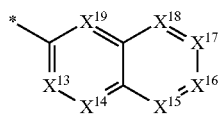

[Chemical Formula 6-3]

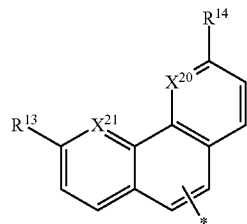

[Chemical Formula 6-4]

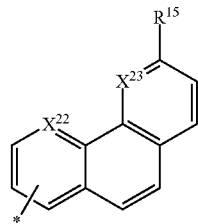

[Chemical Formula 6-5]

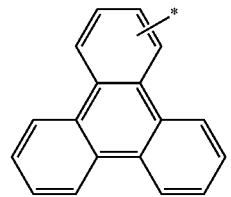

[Chemical Formula 6-6]

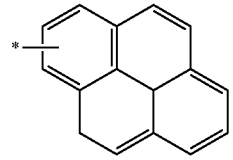

[Chemical Formula 6-7]

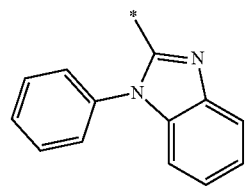

[Chemical Formula 6-8]

In Chemical Formula 6-1 to Chemical Formula 6-8, $X^1$ to $X^5$ are each independently —N—, —CH—, —CR— or —CR$^{10}$—, $X^6$ to $X^{12}$ are each independently —N—, —CH—, —CR— or —CR$^{11}$—, $X^{13}$ to $X^{19}$ are each independently —N—, —CH—, —CR— or —CR$^{12}$—, $X^{20}$ and $X^{21}$ are each independently —N—, —CH— or —CR—, $X^{22}$ and $X^{23}$ are each independently —N—, —CH— or —CR—, Rs are each independently deuterium, a cyano group, a substituted or unsubstituted C1 to C60 alkyl group or a substituted or unsubstituted C6 to C60 aryl group, $R^{10}$ to $R^{12}$ are each independently any one of a phenyl group, a pyridinyl group and a substituent of the following Chemical Formula 5, and $R^{13}$ to $R^{15}$ are each independently any one of hydrogen, deuterium, a phenyl group, a pyridinyl group or a substituent of the following Chemical Formula 5,

[Chemical Formula 5]

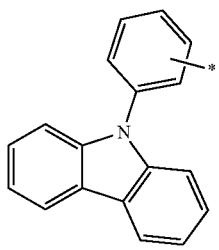

in Chemical Formula 6-1 to Chemical Formula 6-8 and Chemical Formula 5,
means a bonding position.

In Chemical Formula 6-1 to Chemical Formula 6-8, $X^1$ to $X^5$ are each independently —N—, —CH—, —CR— or —CR$^{10}$—, $X^6$ to $X^{12}$ are each independently —N—, —CH—, —CR— or —CR$^{11}$—, $X^{13}$ to $X^{19}$ are each independently —N—, —CH—, —CR— or —CR$^{12}$—, $X^{20}$ and $X^{21}$ are each independently —N—, —CH— or —CR—, $X^{22}$ and $X^{23}$ are each independently —N—, —CH— or —CR—, Rs are each independently deuterium, a cyano group, a substituted or unsubstituted C1 to C60 alkyl group or a substituted or unsubstituted C8 to C60 aryl group, $R^{10}$ to $R^{12}$ are each independently any one of a phenyl group, a pyridinyl group and the substituent of Chemical Formula 5, and $R^{13}$ to $R^{15}$ are each independently any one of hydrogen, deuterium, a phenyl group, a pyridinyl group and the substituent of Chemical Formula 5.

Specifically, $Ar^2$ may be represented by chemical formulae as follows. When represented by chemical formulae as follows, light emission efficiency of a manufactured organic light emitting diode may be more superior compared to compounds represented by other chemical formulae.

The chemical formulae as follows are as follows.

$Ar^2$ is represented by Chemical Formula 6-1, and Chemical Formula 6-1 may be a compound in which,
$X^1$ to $X^5$ are —CH—,
$X^1$, $X^3$ and $X^5$ are —CH—, the rest are —CR$^{10}$—, and $R^{10}$ is a phenyl group or a pyridinyl group,
$X^1$ is —N—, and the rest are —CH—,
$X^2$ is —N—, and the rest are —CH—,
$X^1$ and $X^5$ are —N—, $X^3$ is —CH—, the rest are one of —CH— and —CR$^{10}$—, and $R^{10}$ is a phenyl group or the substituent of Chemical Formula 5,
$X^1$ and $X^3$ are —N—, $X^5$ is —CH—, the rest are one of —CH— and —CR$^{10}$—, and $R^{10}$ is a phenyl group or the substituent of Chemical Formula 5,
$X^1$, $X^3$ and $X^5$ are —N—, the rest are one of —CH— and —CR$^{10}$—, and $R^{10}$ is the substituent of Chemical Formula 5, or
$X^1$, $X^3$ and $X^5$ are —N—, the rest are one of —CH— and —CR$^{10}$—, and $R^{10}$ is a phenyl group.

Herein, the organic electroluminescent diode manufactured using the compound of the present specification may have effects of low driving voltage and high light emission efficiency.

In addition, $Ar^2$ is represented by Chemical Formula 6-2, and Chemical Formula 6-2 may be a compound in which,
$X^6$ to $X^{12}$ are —CH—,
$X^9$ is —N—, and the rest are —CH—,
$X^{11}$ is —N—, and the rest are —CH—, or
$X^{12}$ is —N—, and the rest are —CH—.

Herein, the organic electroluminescent diode manufactured using the compound of the present specification may have effects of low driving voltage and high light emission efficiency.

In addition, $Ar^2$ is represented by Chemical Formula 6-3, and Chemical Formula 6-3 may be a compound in which,
$X^{13}$ to $X^{19}$ are —CH—,
$X^{15}$ is —N—, and the rest are —CH—,
$X^{17}$ is —N—, and the rest are —CH—, or
$X^{18}$ is —N—, and the rest are —CH—.

Herein, the organic electroluminescent diode manufactured using the compound of the present specification may have effects of low driving voltage and high light emission efficiency.

In addition, $Ar^2$ is represented by Chemical Formula 6-4, and Chemical Formula 6-4 may be a compound in which,
$X^{20}$ and $X^{21}$ are —CH—, and $R^{13}$ and $R^{14}$ are each independently hydrogen or deuterium,
$X^{20}$ and $X^{21}$ are —N—, and $R^{13}$ and $R^{14}$ are each independently hydrogen or deuterium,
$X^{20}$ and $X^{21}$ are —N—, and $R^{13}$ and $R^{14}$ are a phenyl group, or
$X^{20}$ and $X^{21}$ are —N—, any one of $R^{13}$ and $R^{14}$ is a phenyl group, and the rest is hydrogen or deuterium.

Herein, the organic electroluminescent diode manufactured using the compound of the present specification may have effects of low driving voltage and high light emission efficiency.

In addition, $Ar^2$ is represented by Chemical Formula 6-5, and Chemical Formula 6-5 may be a compound in which,
$X^{22}$ and $X^{23}$ are —N—, and $R^{15}$ is hydrogen or deuterium, or
$X^{22}$ and $X^{23}$ are —N—, and $R^{15}$ is a phenyl group.

Herein, the organic electroluminescent diode manufactured using the compound of the present specification may have effects of low driving voltage and high light emission efficiency.

$Ar^2$ may be represented by Chemical Formula 6-6.
$Ar^2$ may be represented by Chemical Formula 6-7.
$Ar^2$ may be represented by Chemical Formula 6-8.
$Ar^2$ may be a phenanthrenyl group; or a phenyl group substituted with a quinoline group or a phenanthroline group.

$Ar^2$ may be a substituted or unsubstituted phenyl group; a substituted or unsubstituted naphthyl group; a substituted or unsubstituted phenanthrenyl group; a substituted or unsubstituted triphenylene group; a substituted or unsubstituted pyrene group; a substituted or unsubstituted pyridine group; a substituted or unsubstituted pyrimidine group; a substituted or unsubstituted triazine group; a substituted or unsubstituted quinoline group; a substituted or unsubstituted isoquinoline group; a substituted or unsubstituted quinazoline group; a substituted or unsubstituted quinoxaline group; a substituted or unsubstituted benzoquinoline group; a substituted or unsubstituted benzimidazole group; or a substituted or unsubstituted phenanthroline group.

$L^1$ and $L^2$ may be each independently a single bond, a phenylene group, a naphthylene group or an anthracenylene group.

$L^1$ and $L^2$ may be each independently a single bond or any one of substituents of the following Group I.

[Group I]

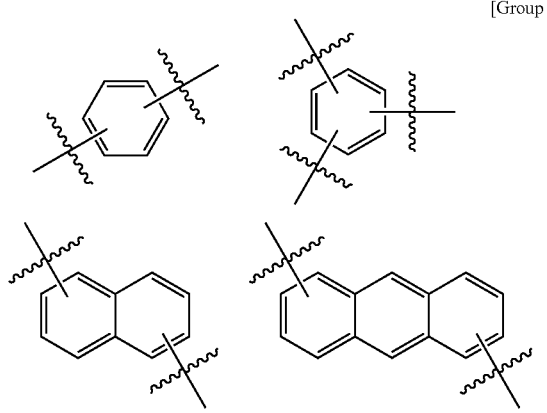

In Group I, ⌇ means a bonding position.

When the substituents of $L^1$ and $L^2$ are one of the substituents of Group I, hole mobility may be improved, and properties of low driving voltage value may be obtained even when used in a hole transfer layer.

The compound of the one example described above may be represented by any one of compounds of the following Group II.

[Group II]

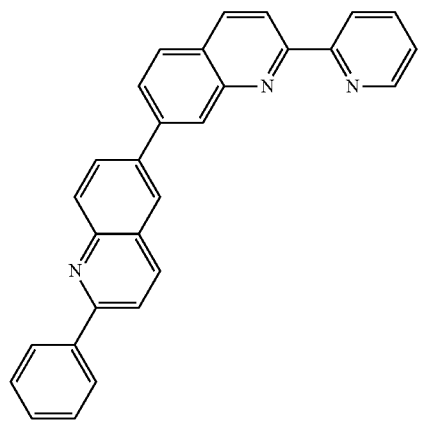

1

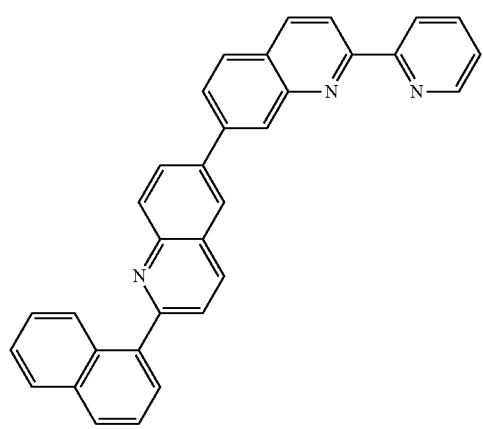

2

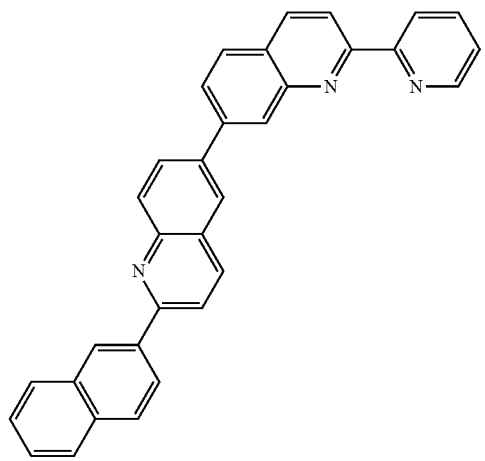

3

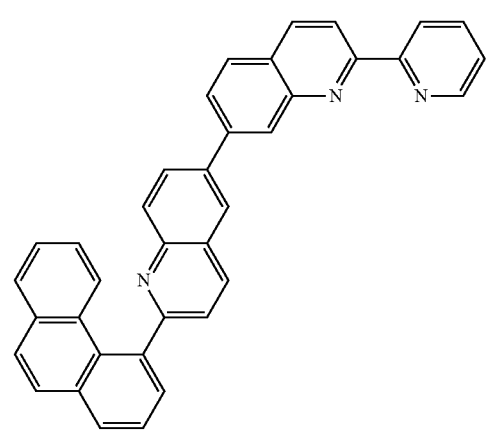

4

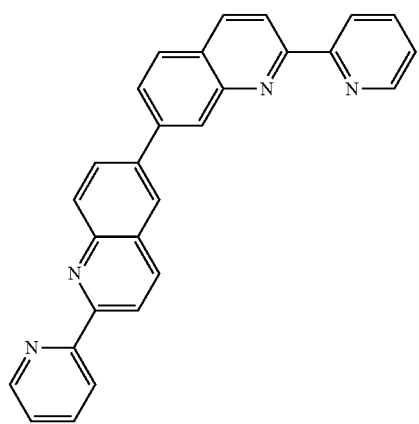

5

6
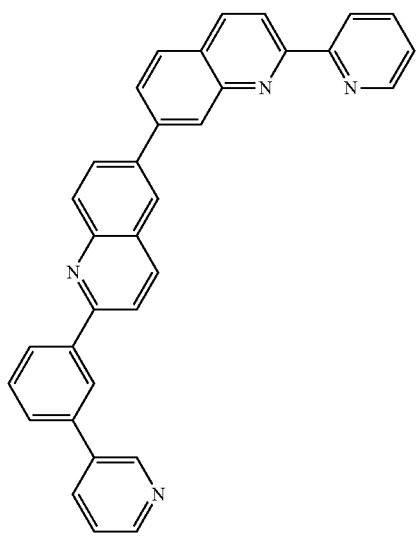
7
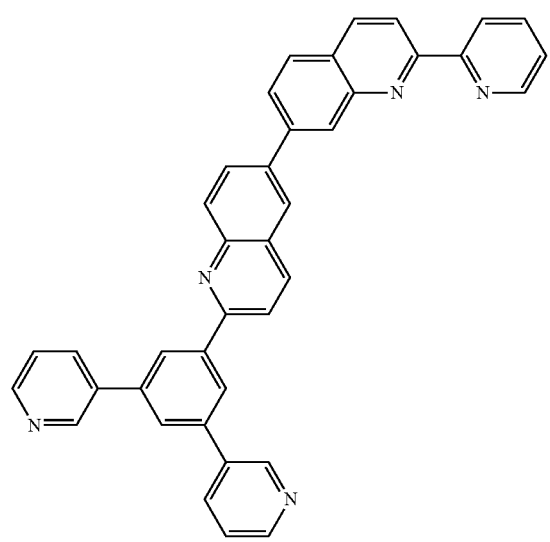
8
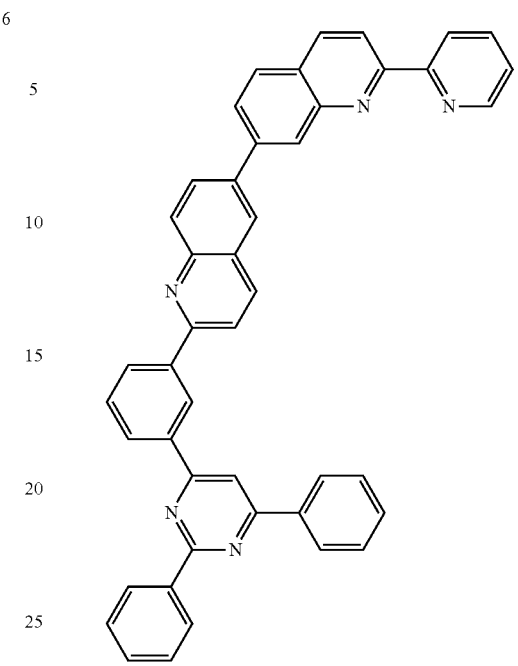
9
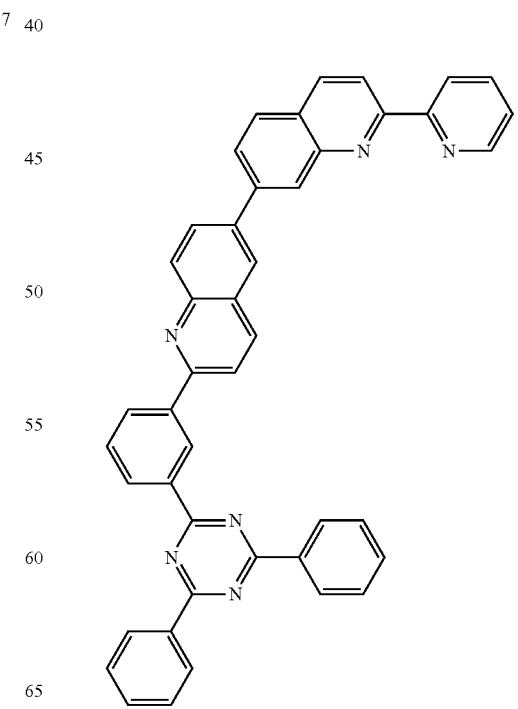

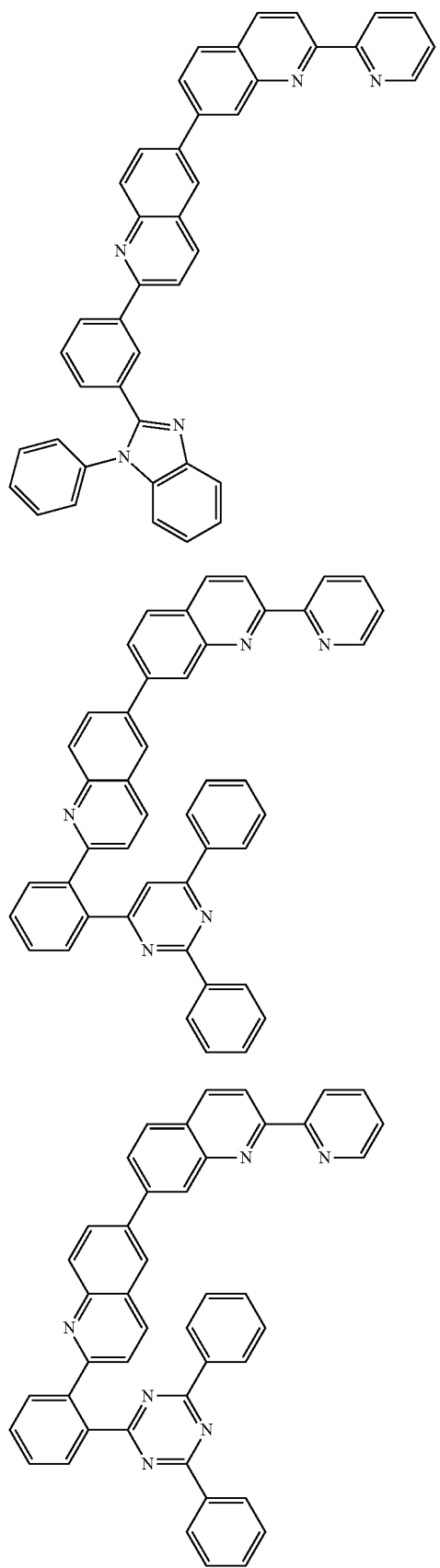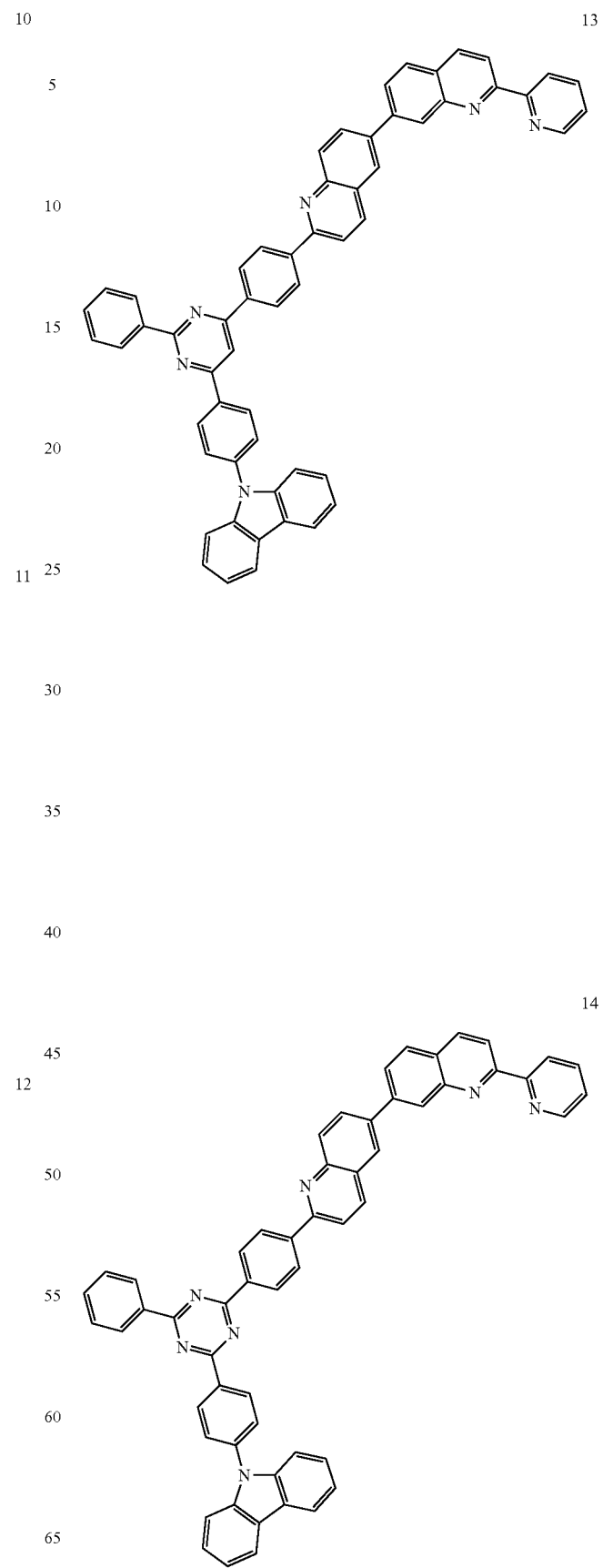

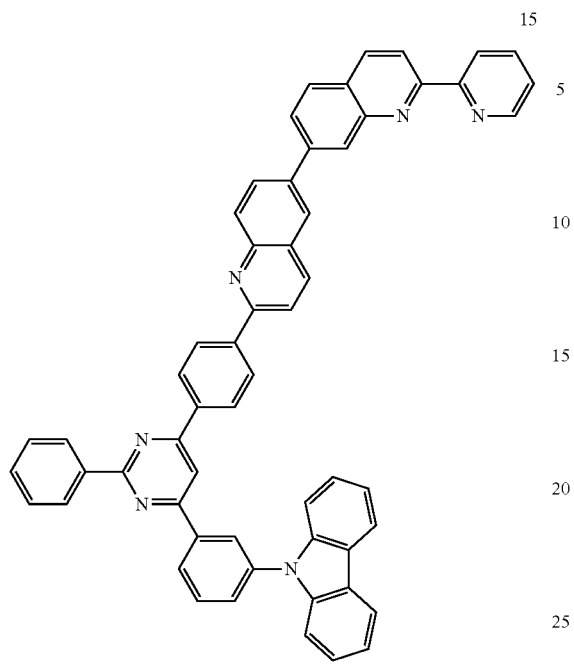
15
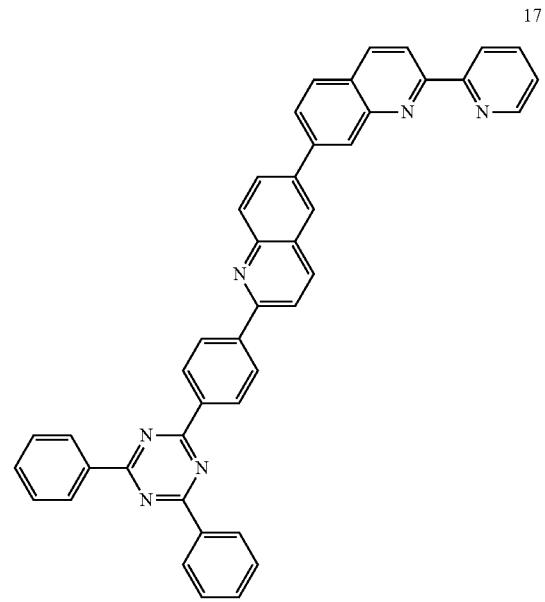
17
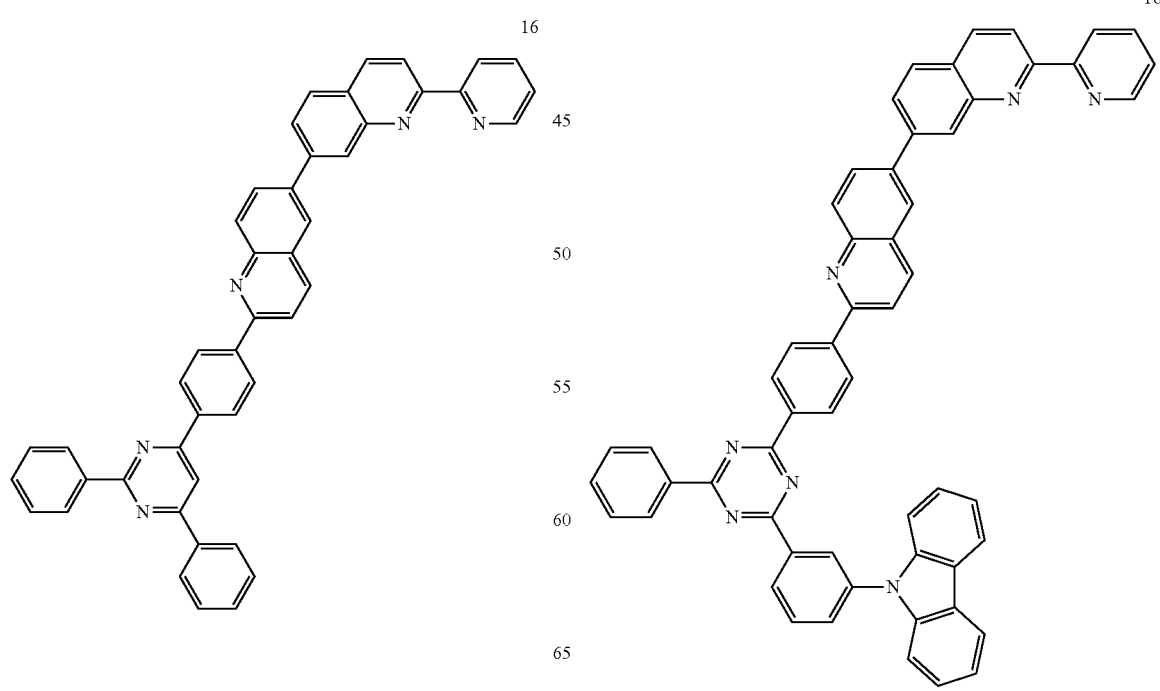

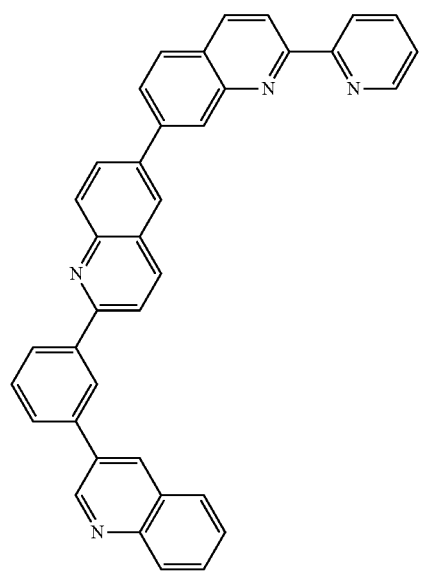
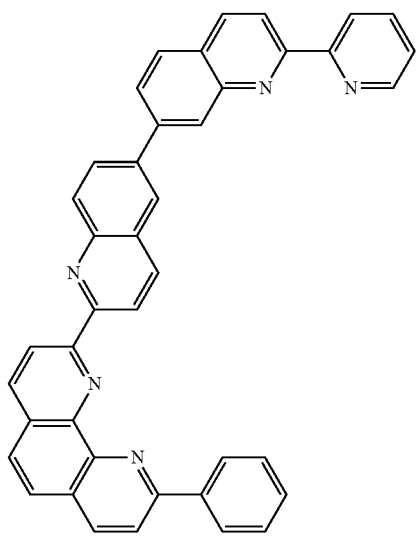
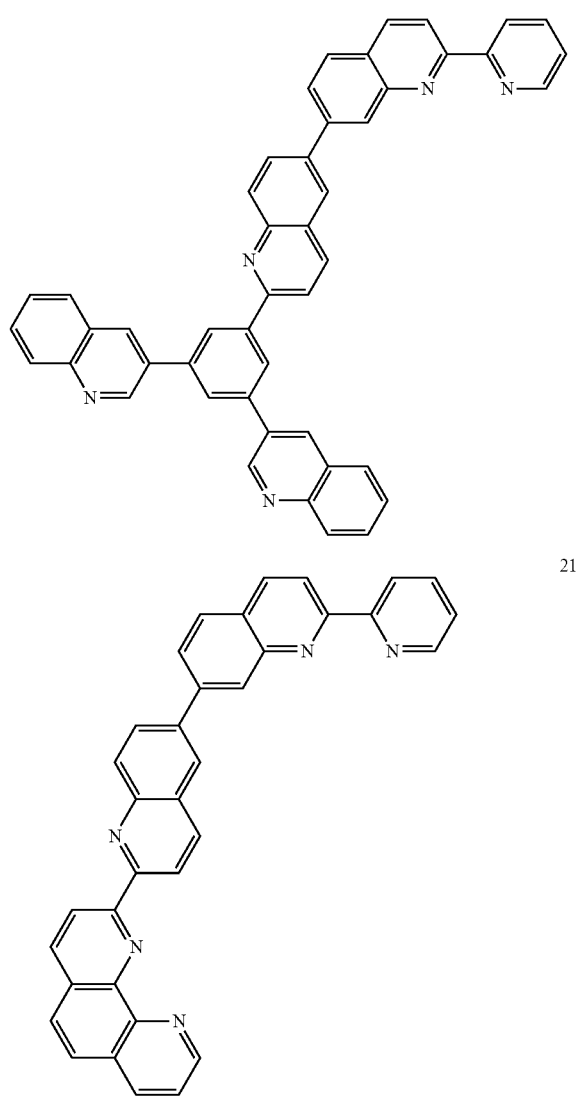
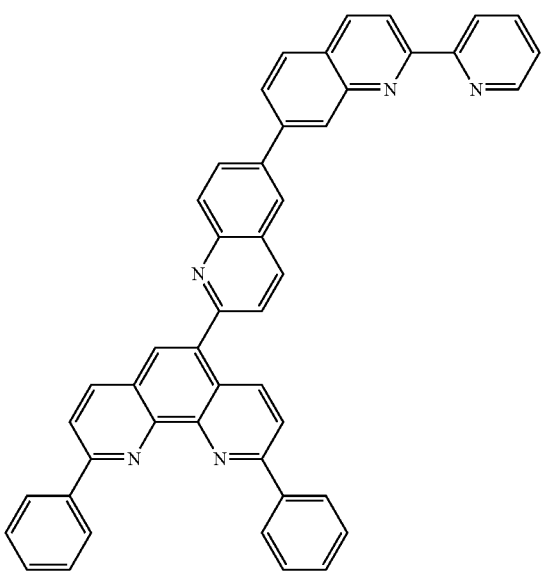

-continued
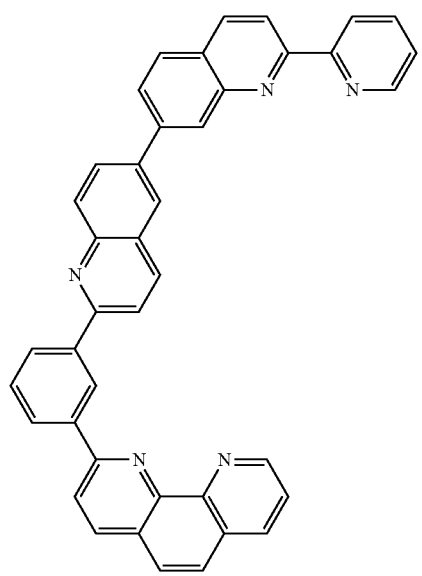
24
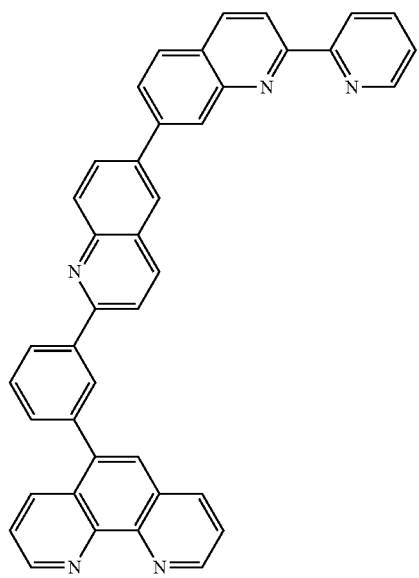
26
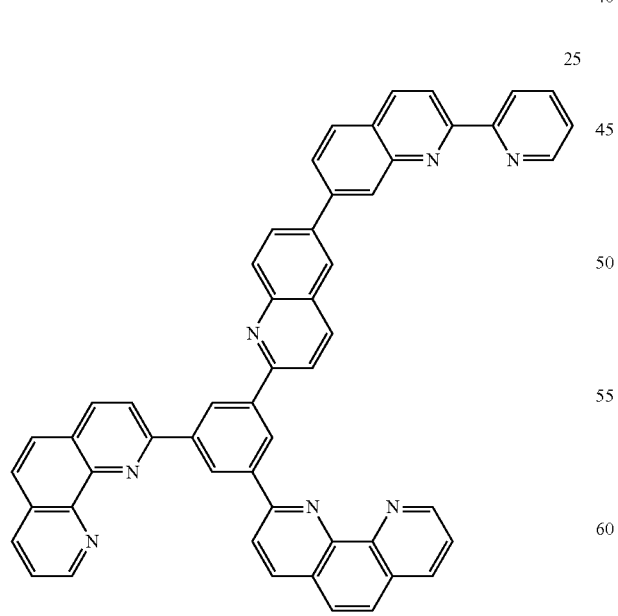
25
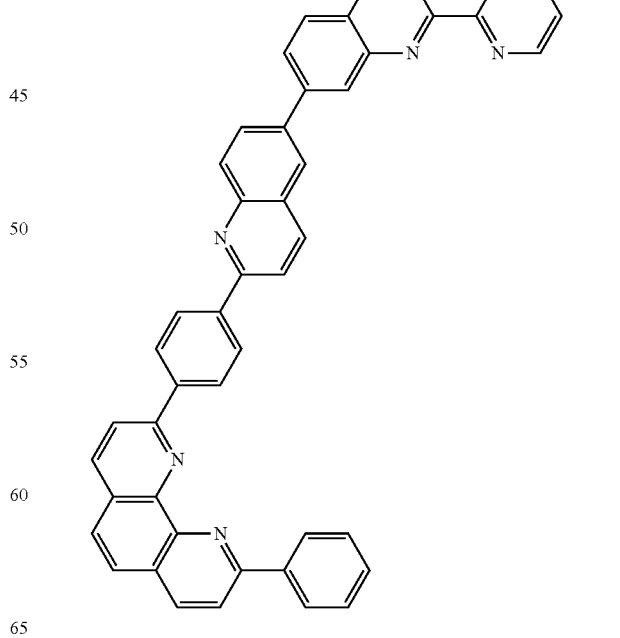
27

28
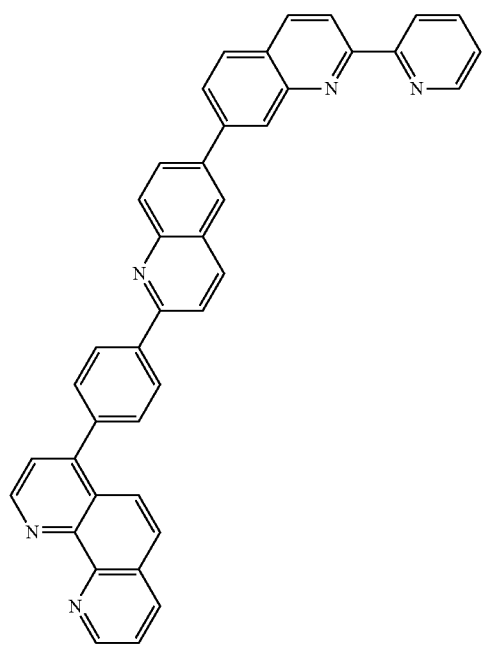
30
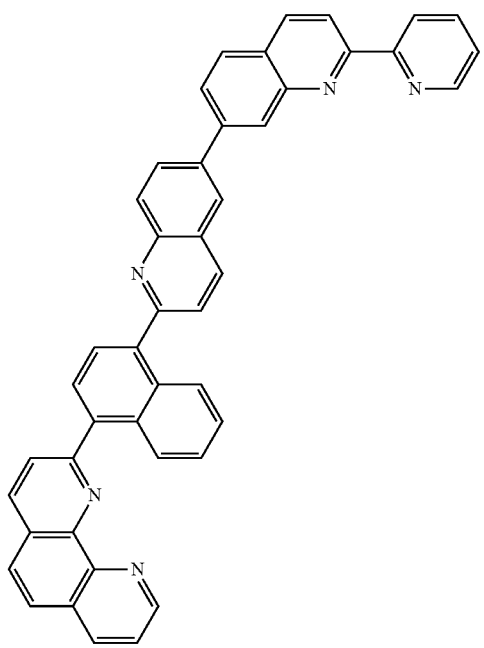
29
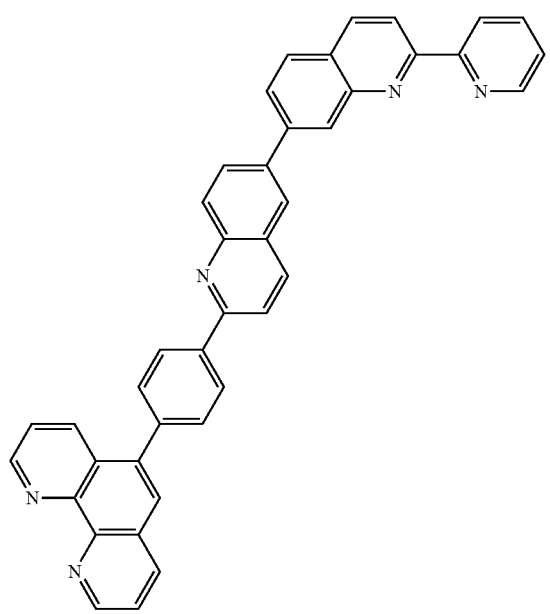
31
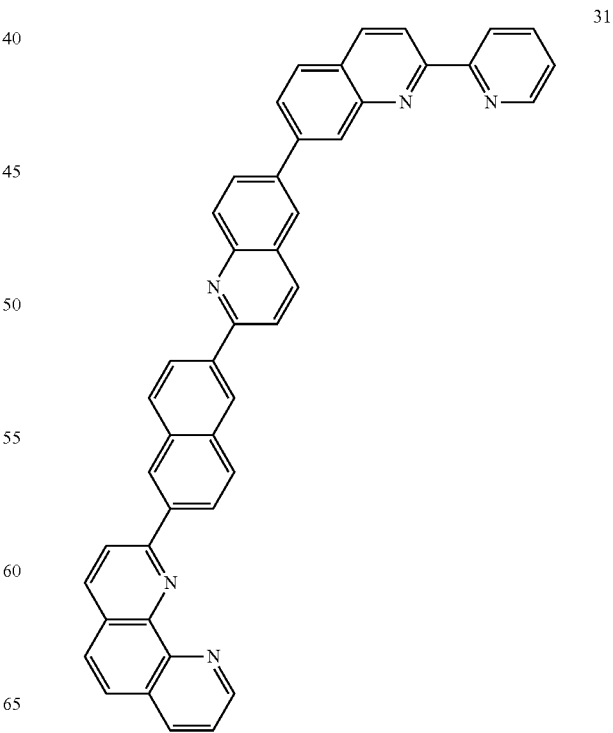

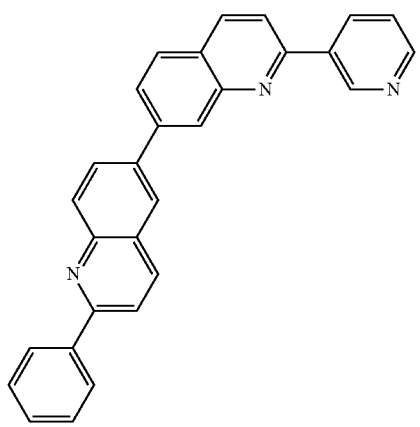
32
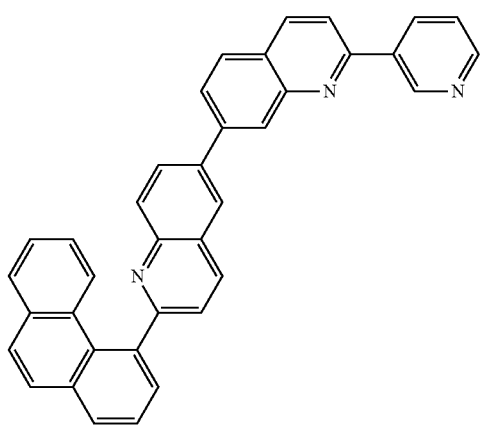
35
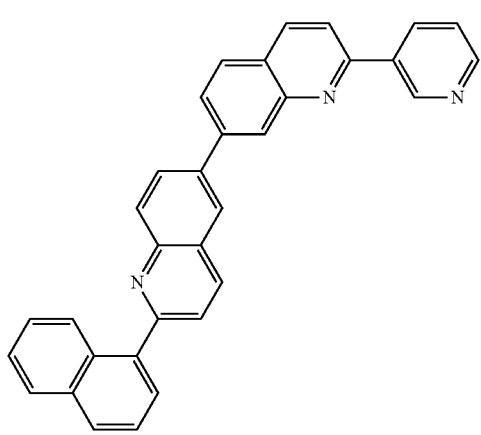
33
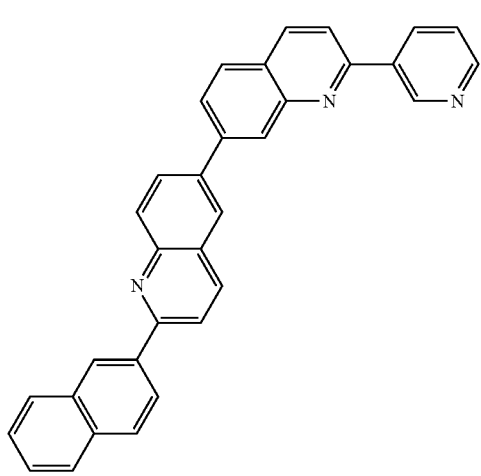
34

37
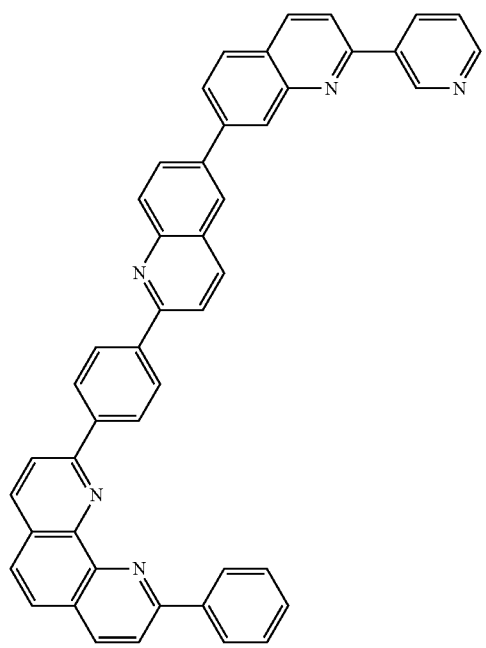
38
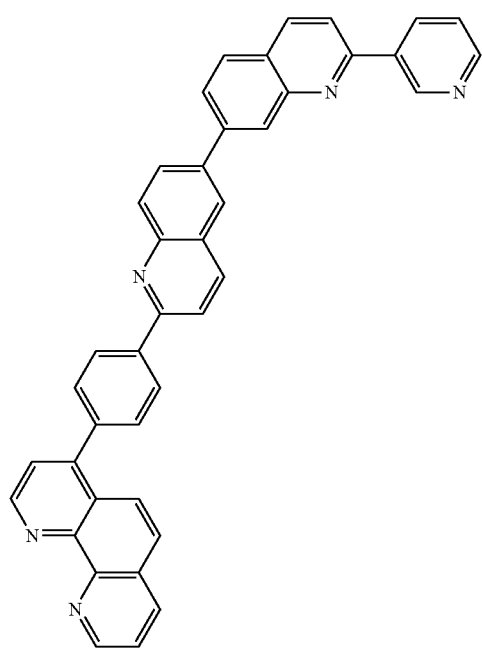
39
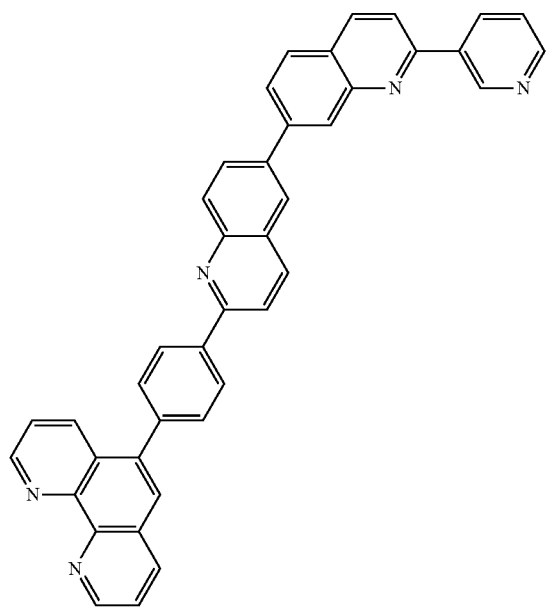
40
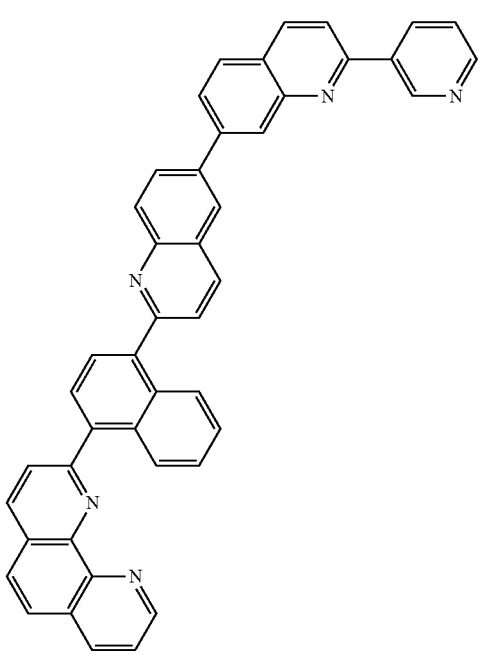

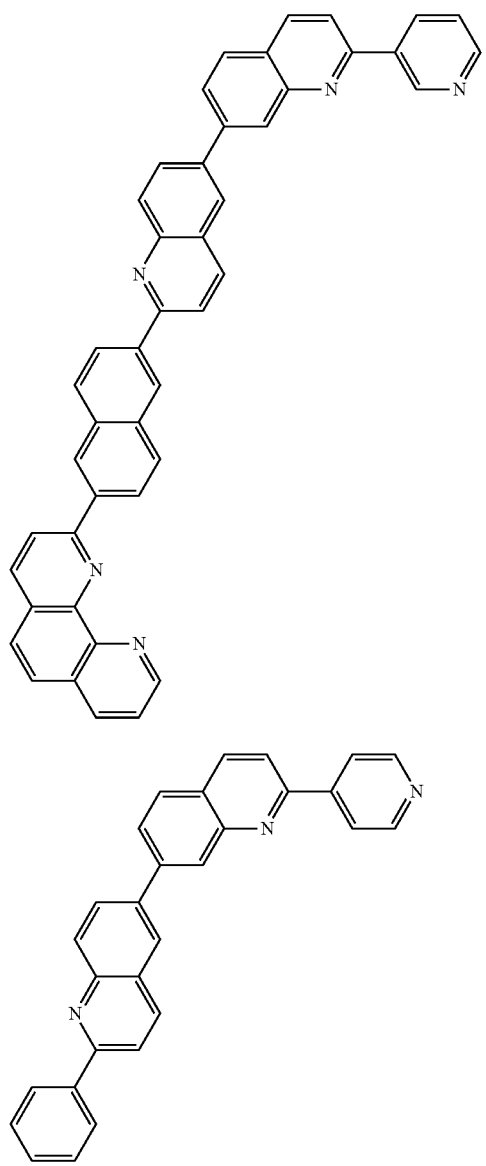
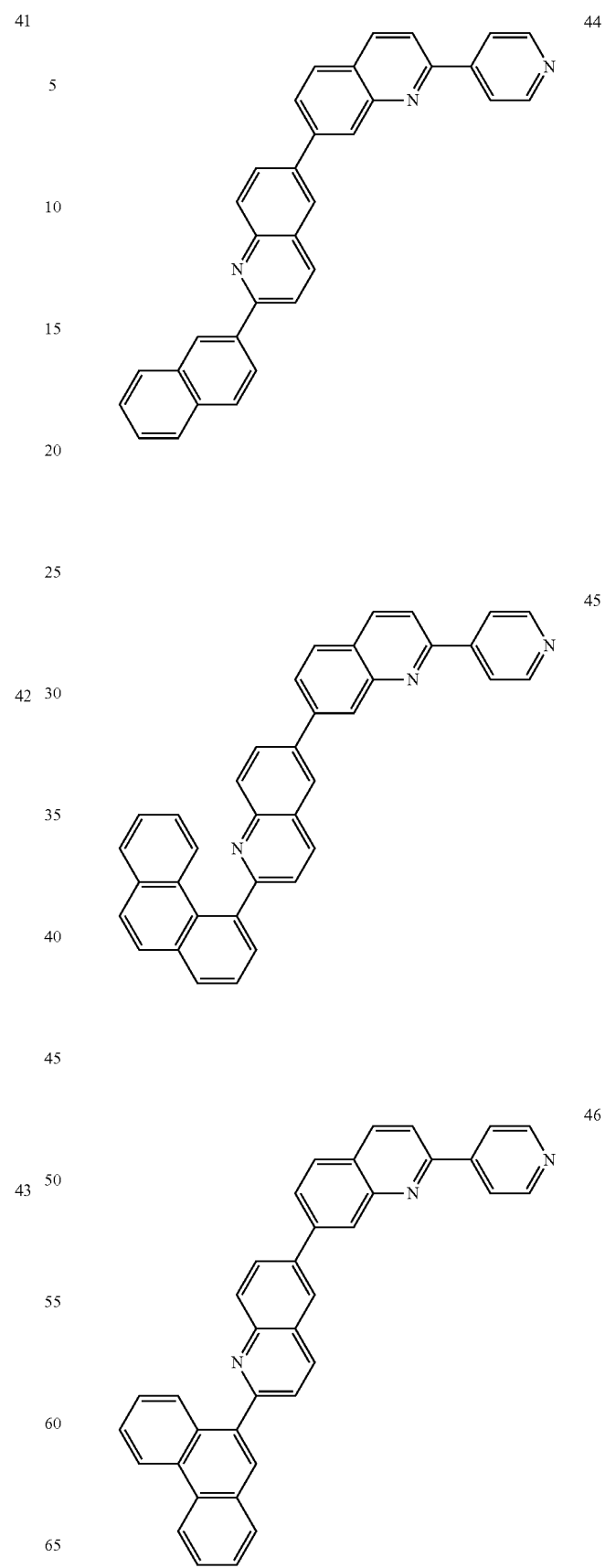

47
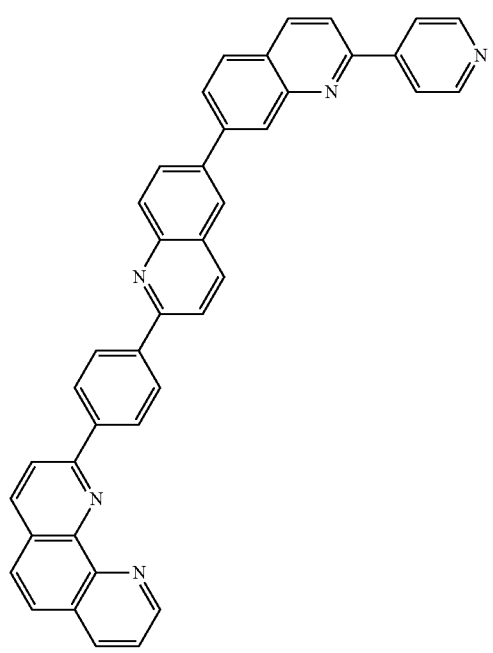
48
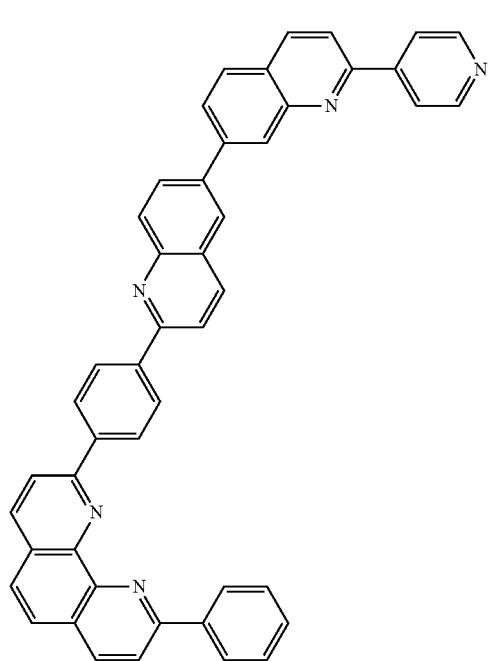
49
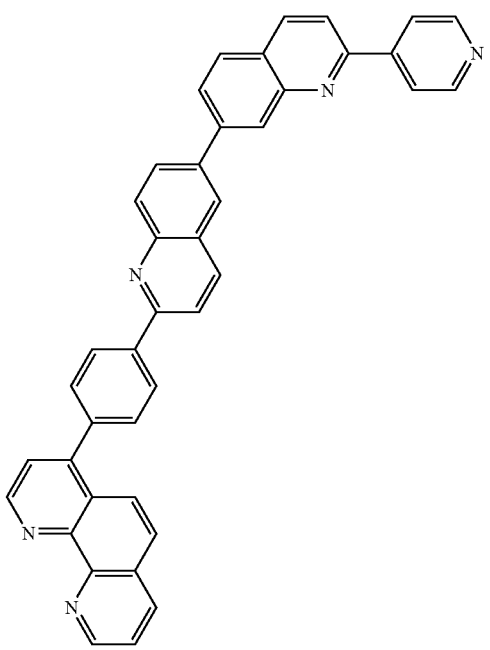
50
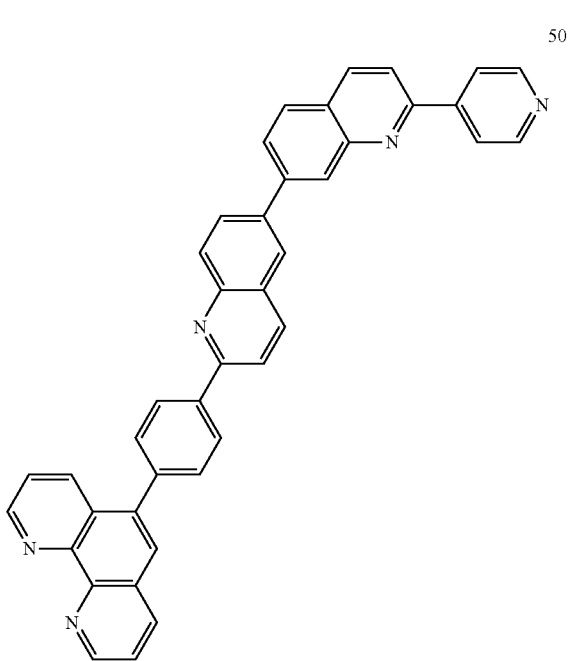

41
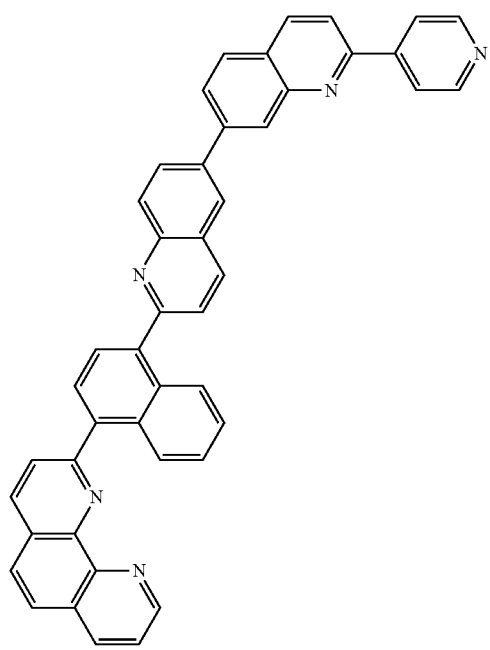
51
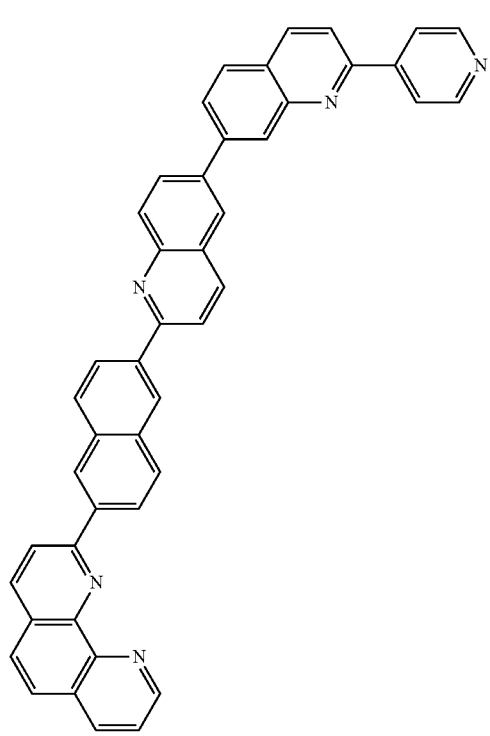
52
42
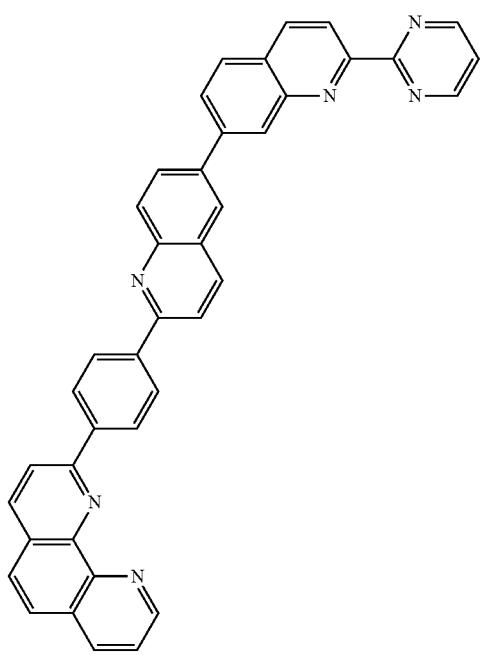
53
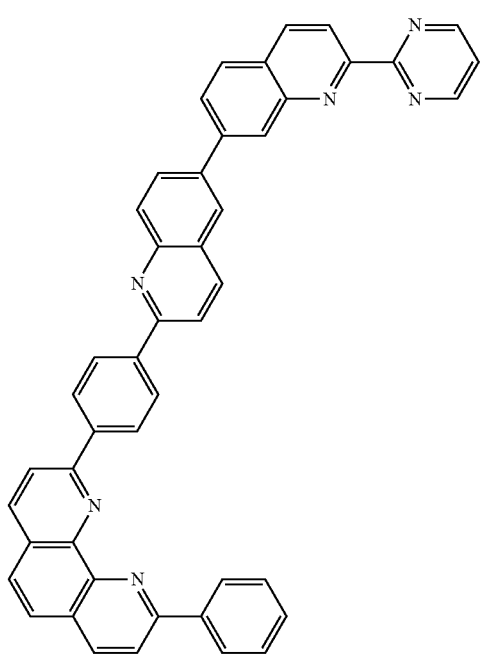
54

55
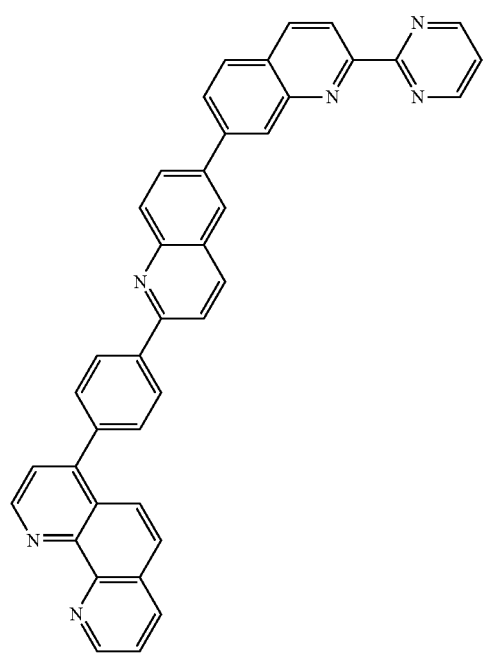
56
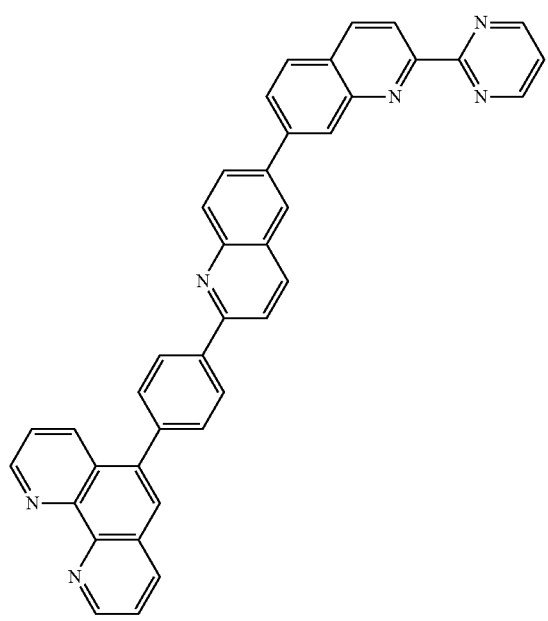
57
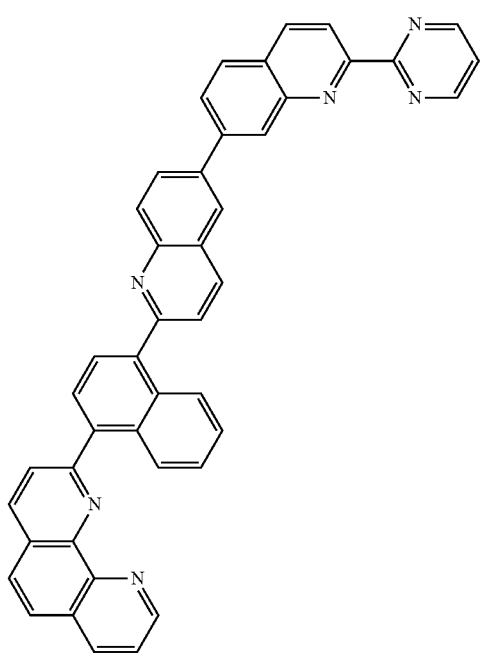
58
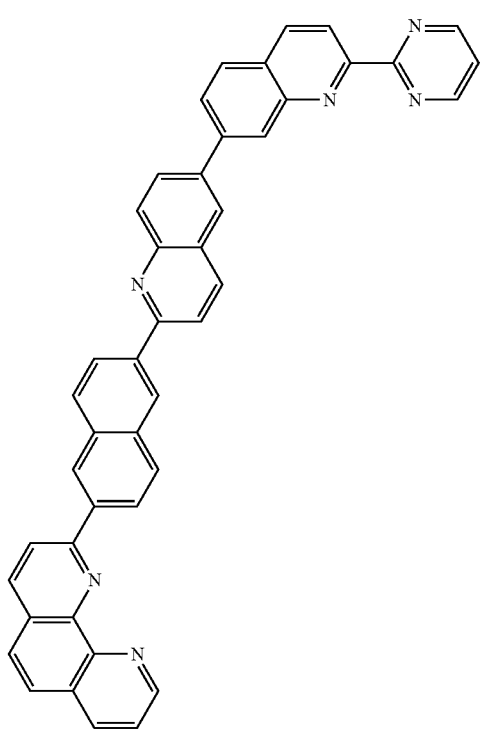

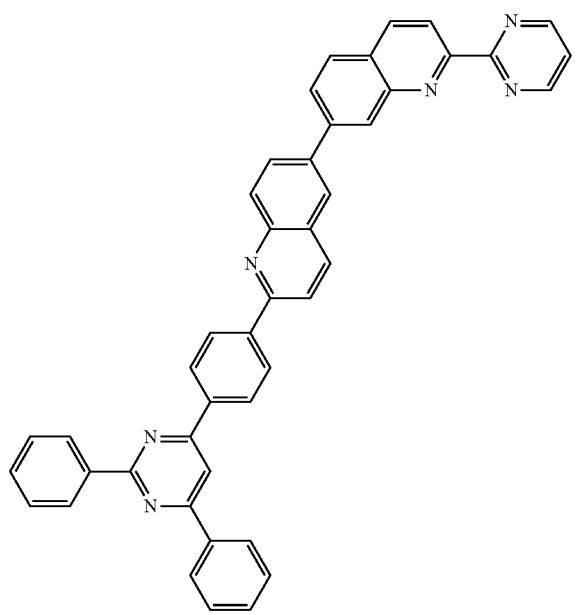
59
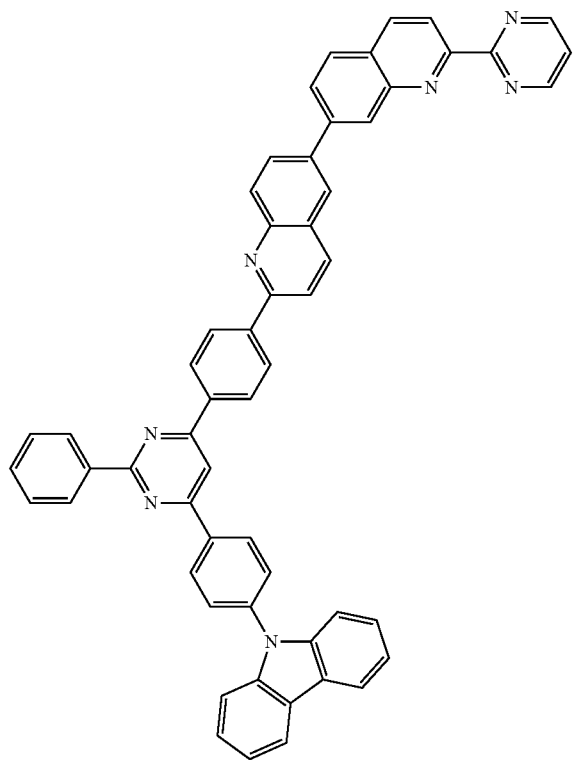
61
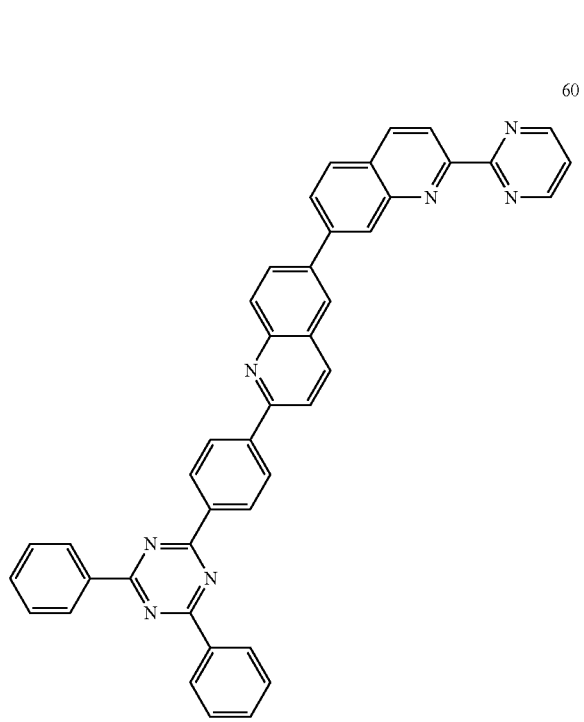
60
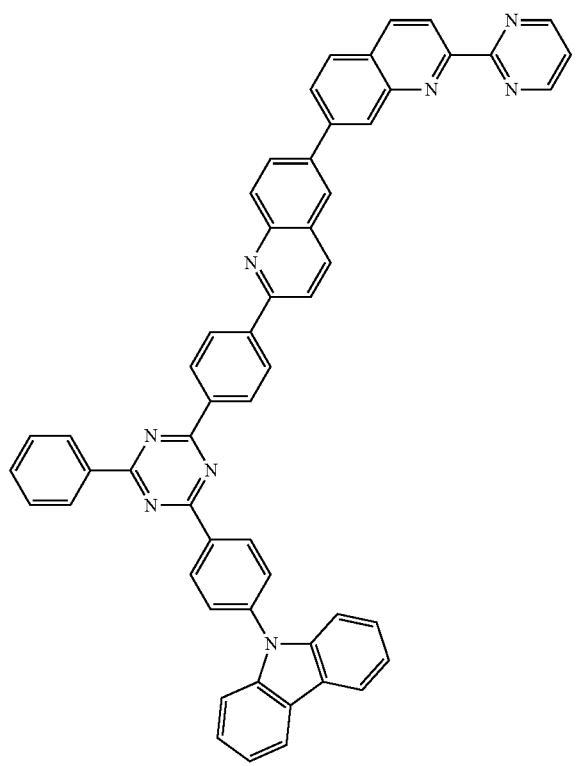
62

63
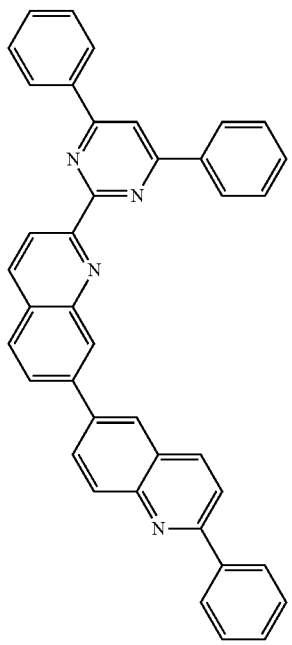
64
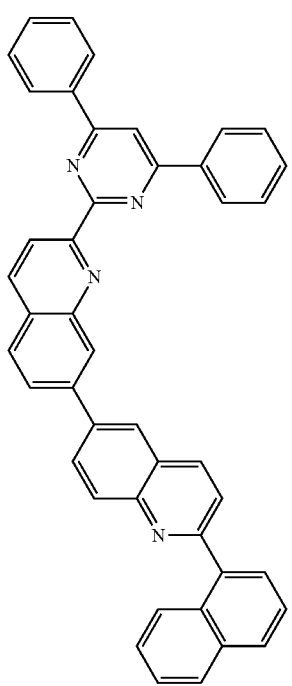
65
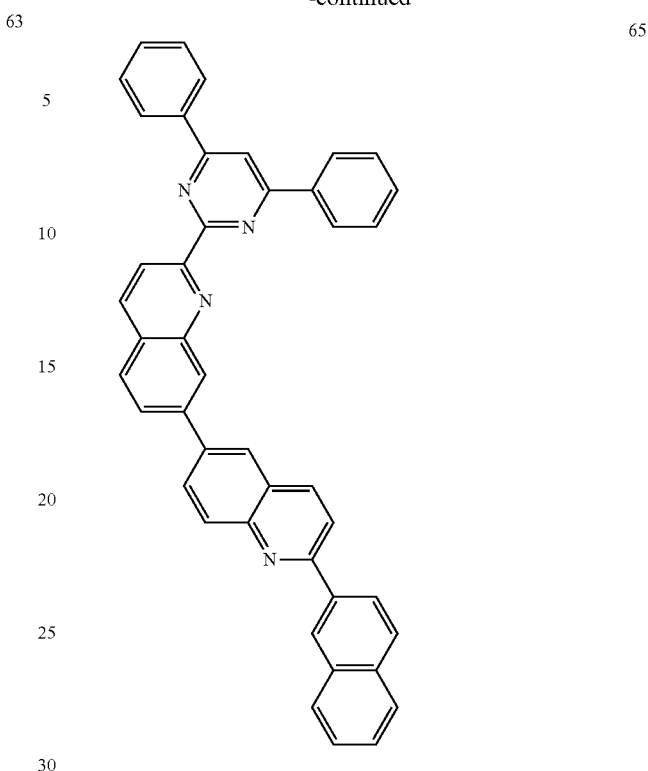
66
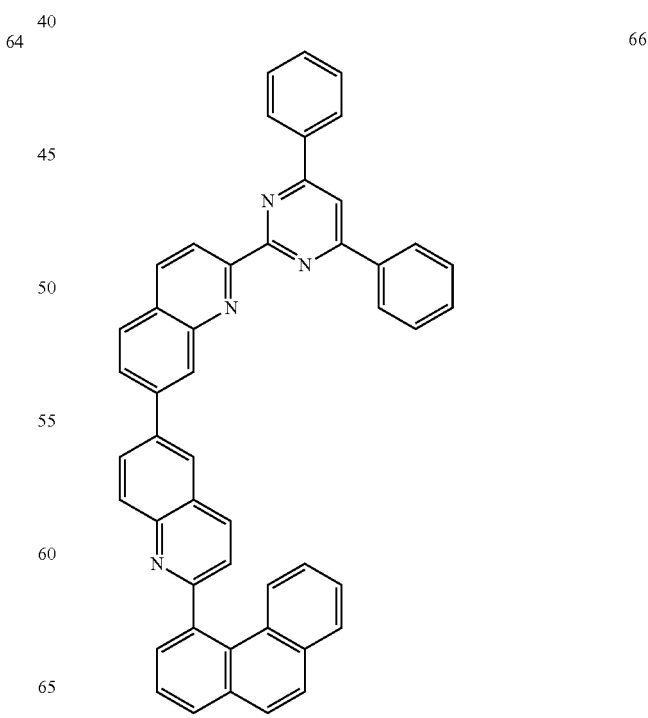

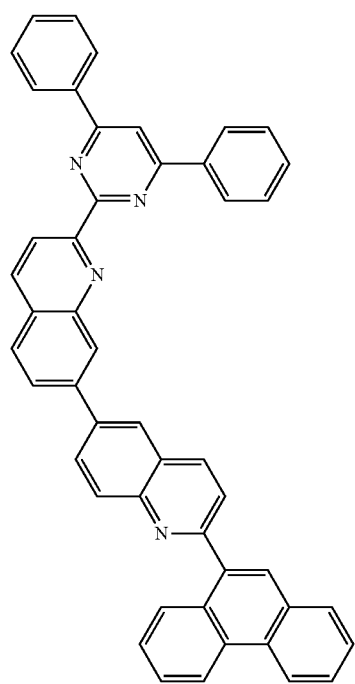
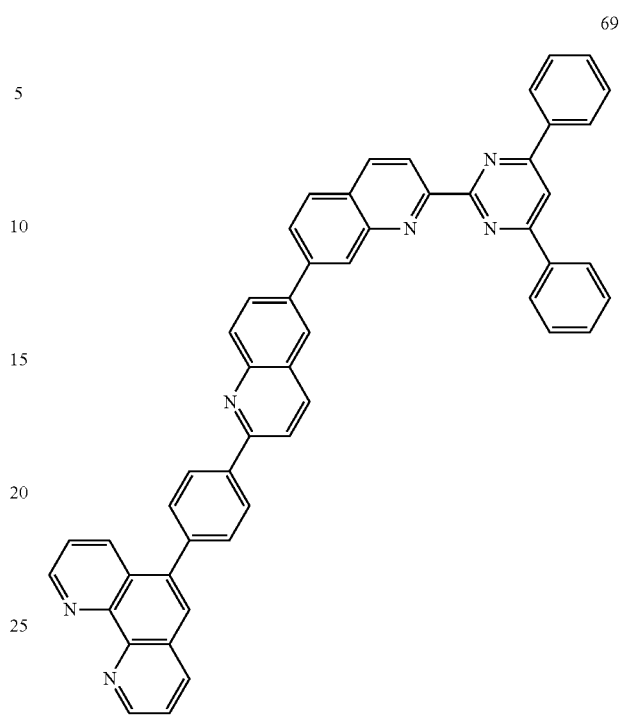
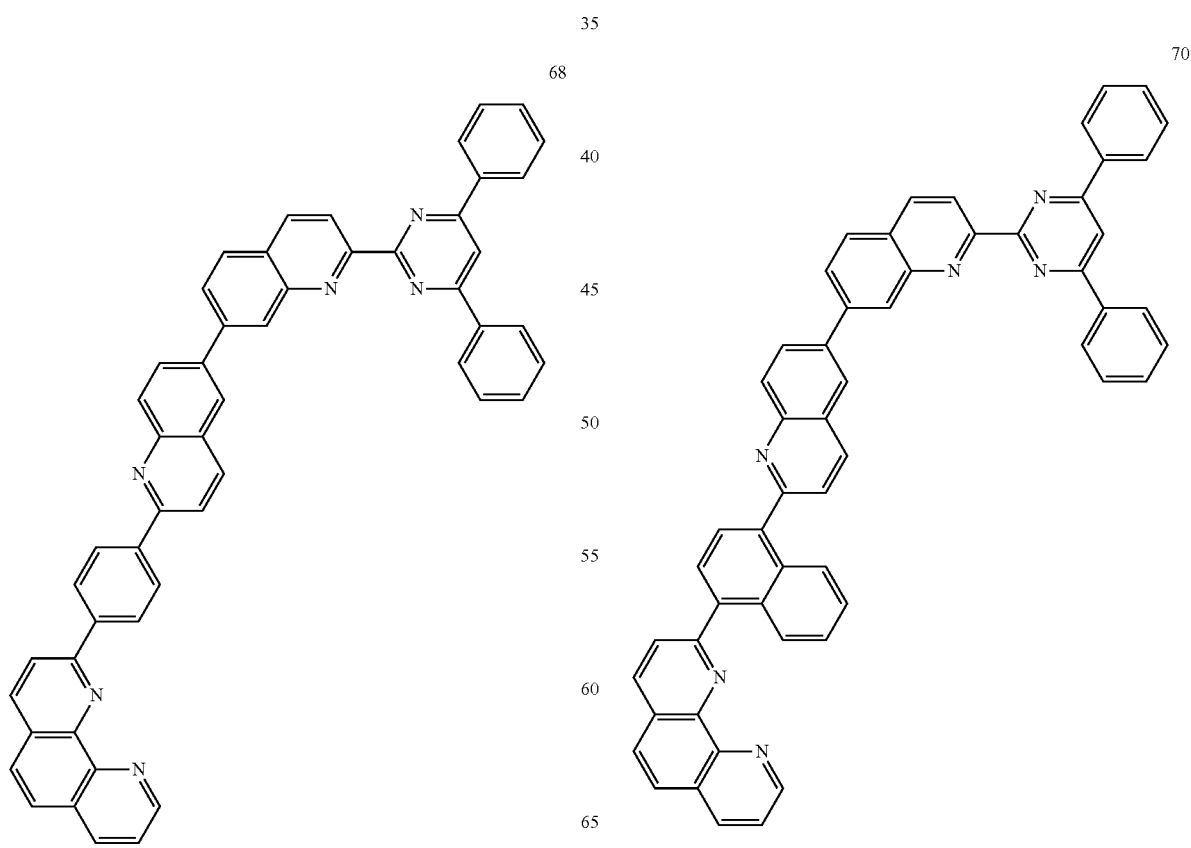

71
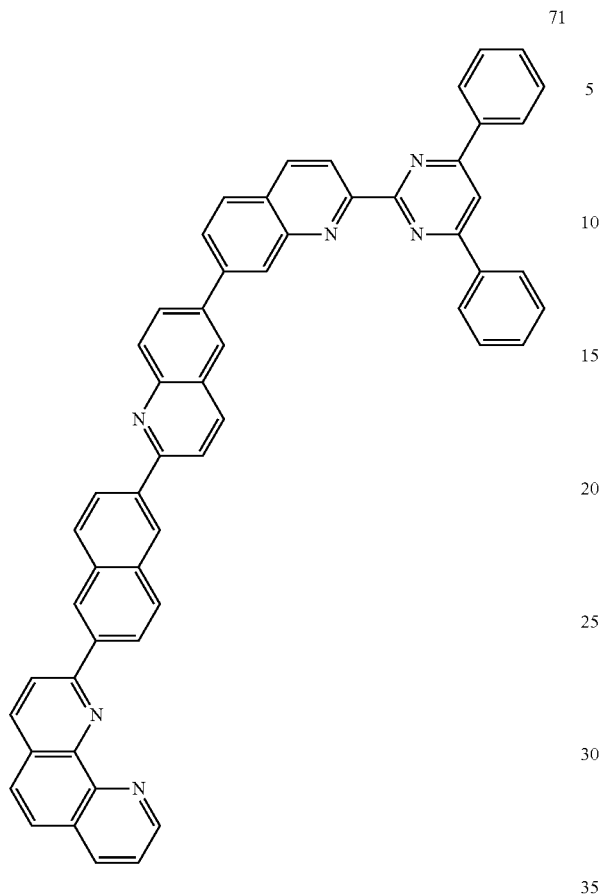
72
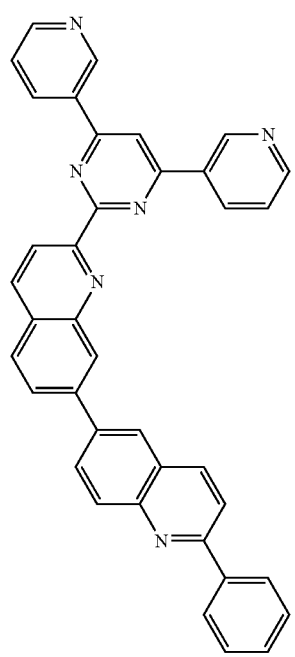
73
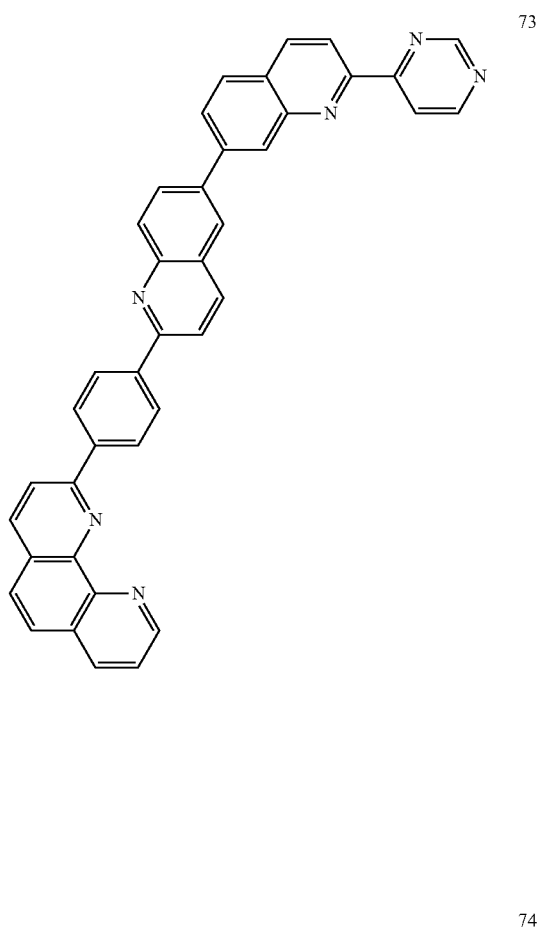
74

53
-continued
75
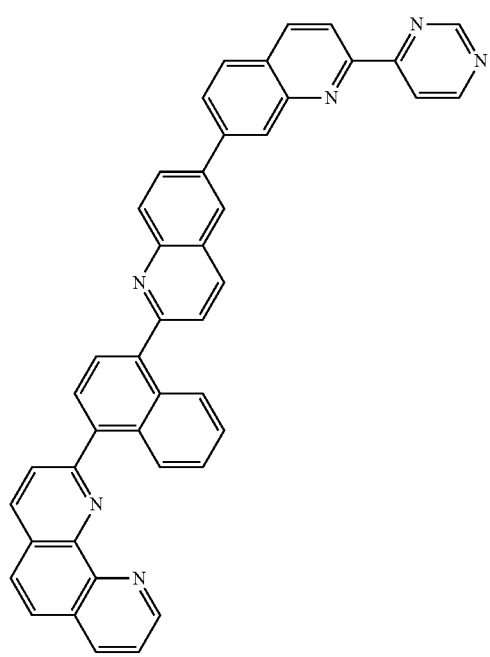
76
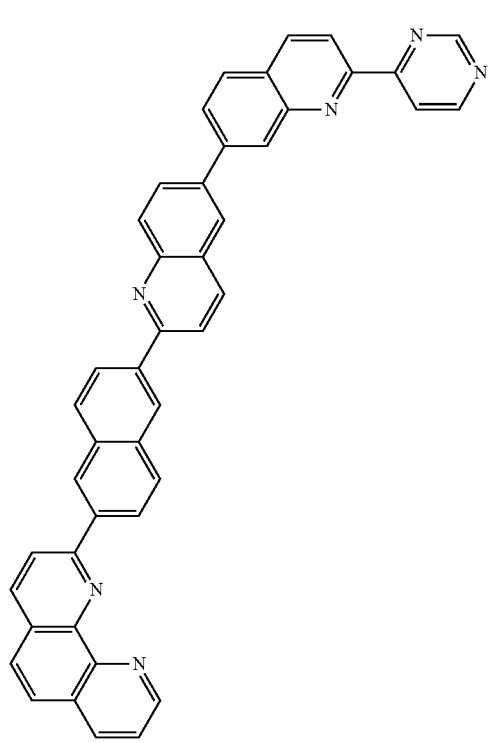
54
-continued
77
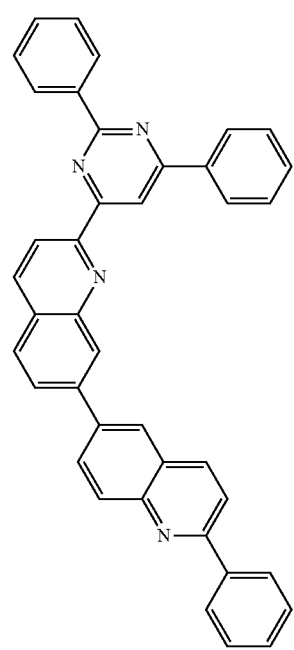
78

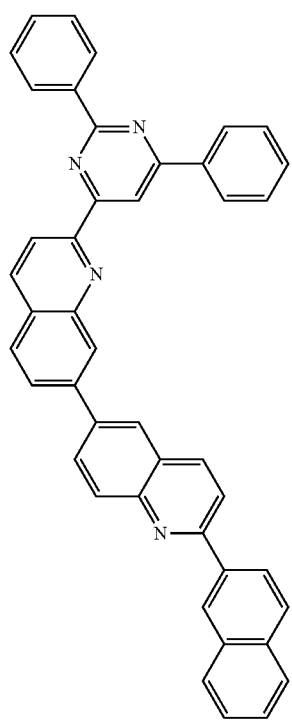
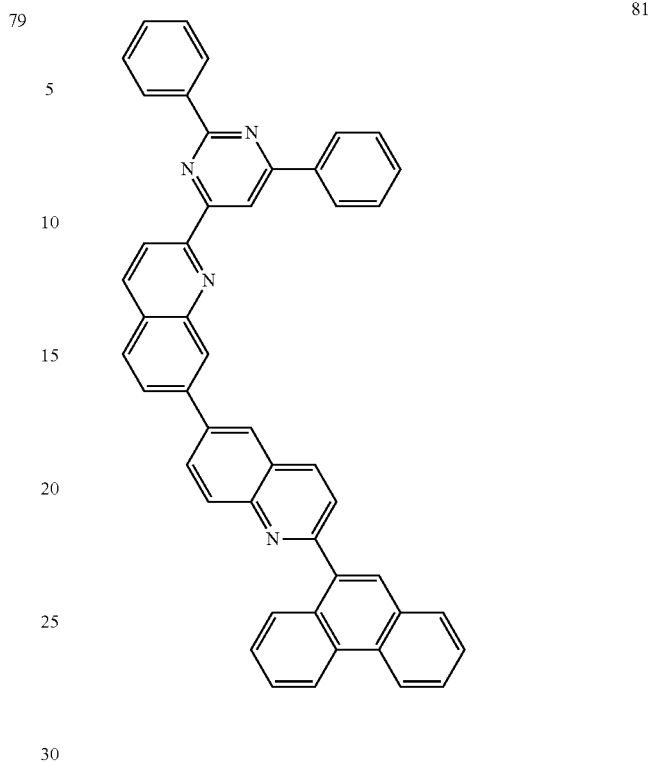
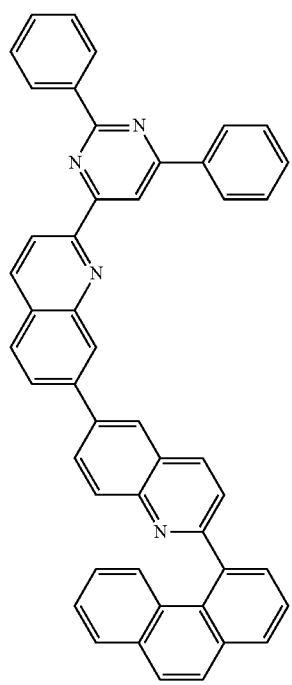
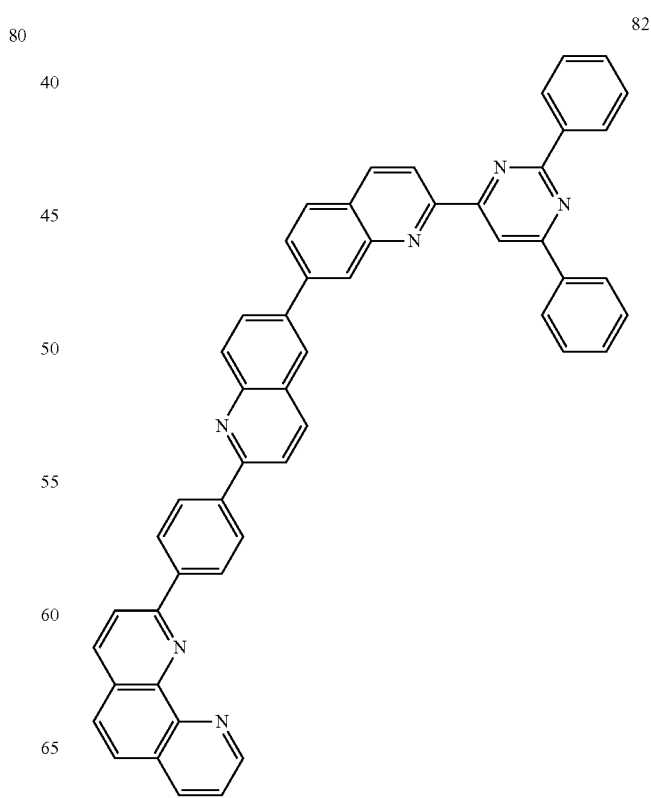

83
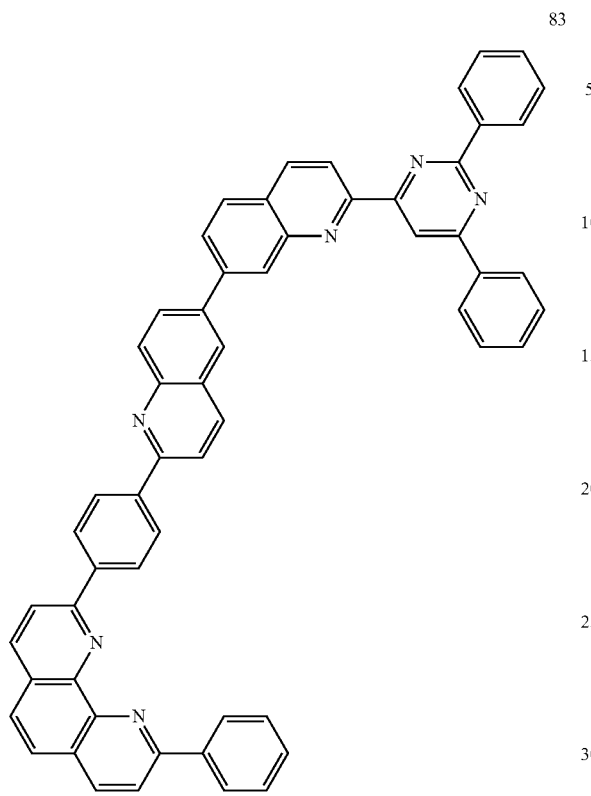
84
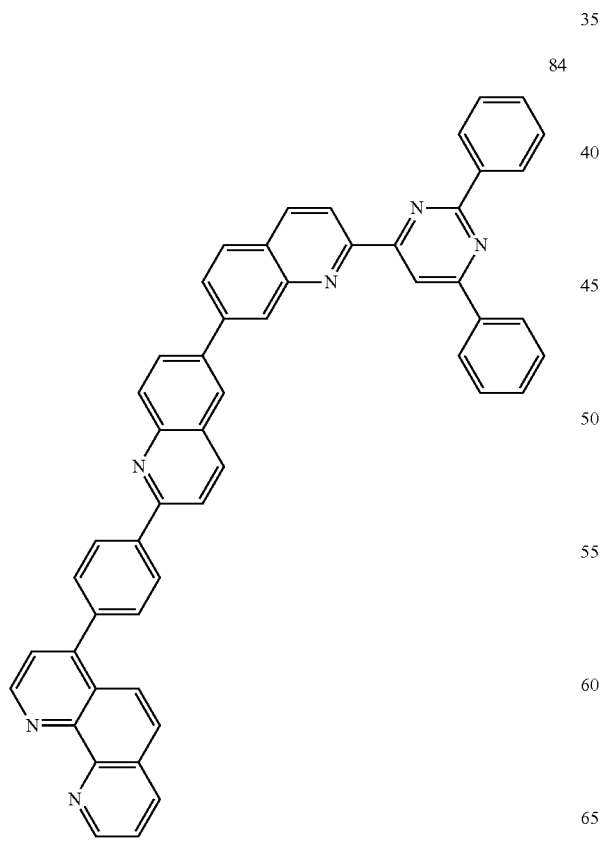
85
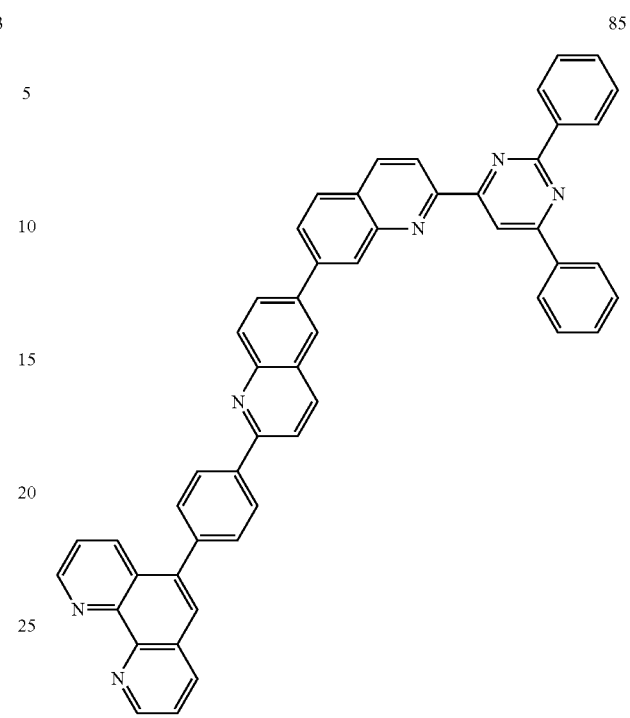
86
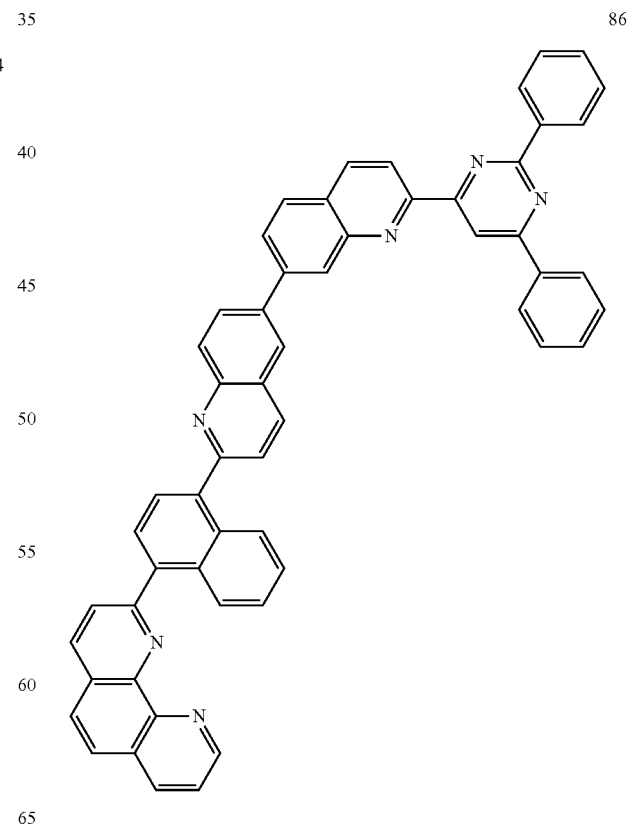

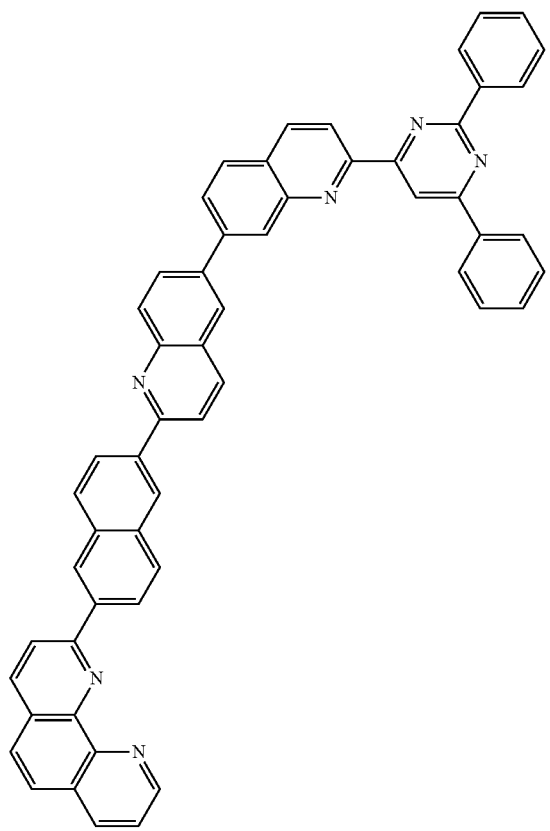
87
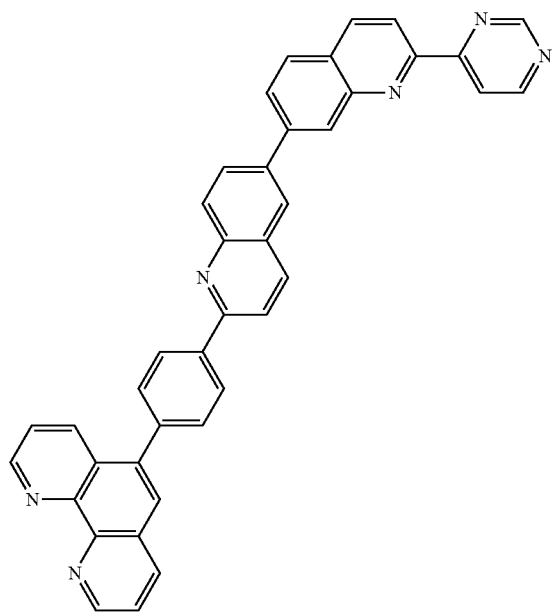
89
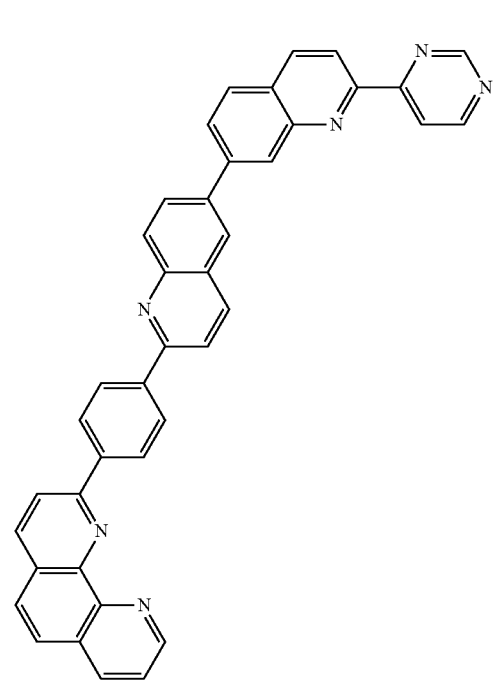
88
90

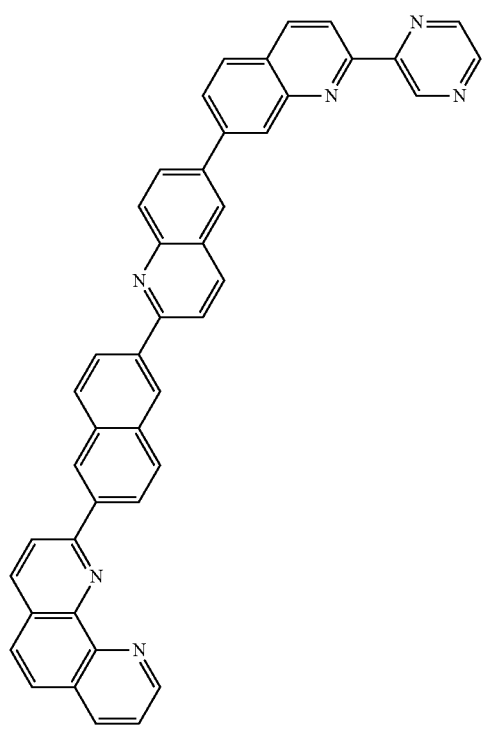
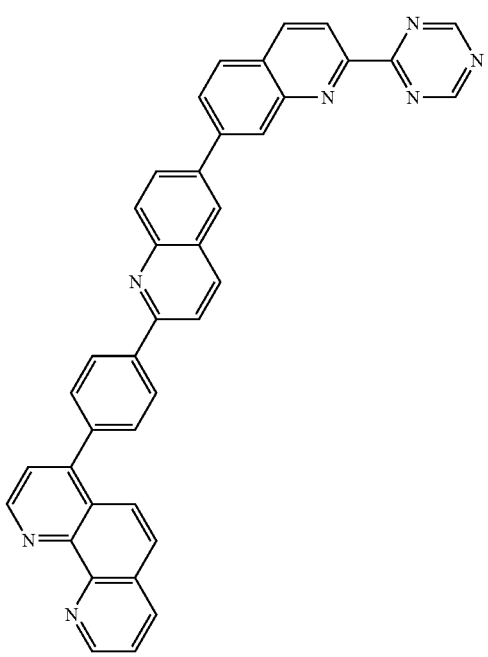
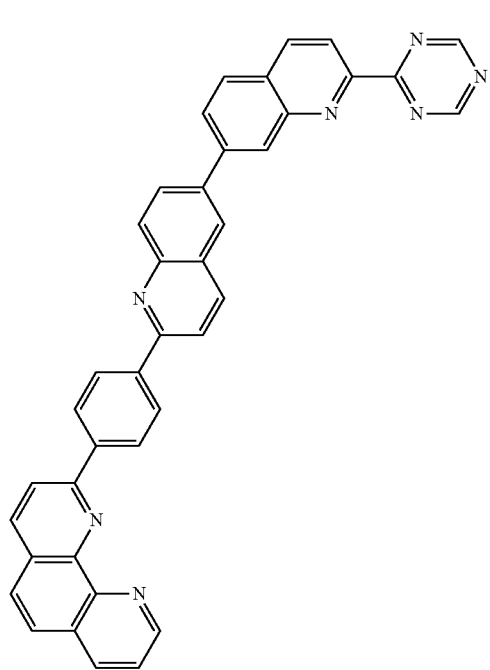

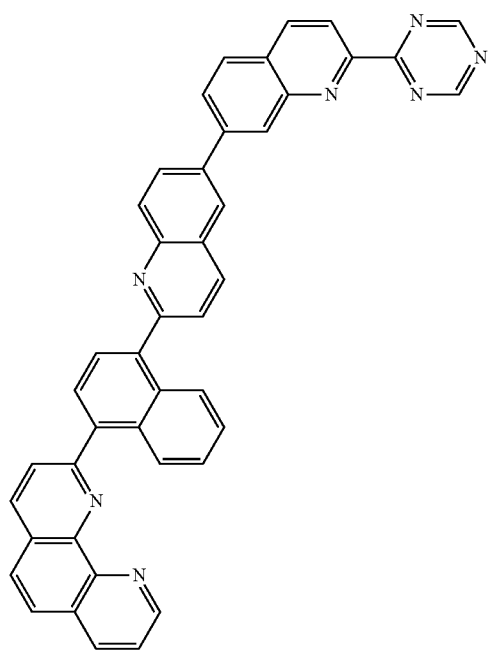
95
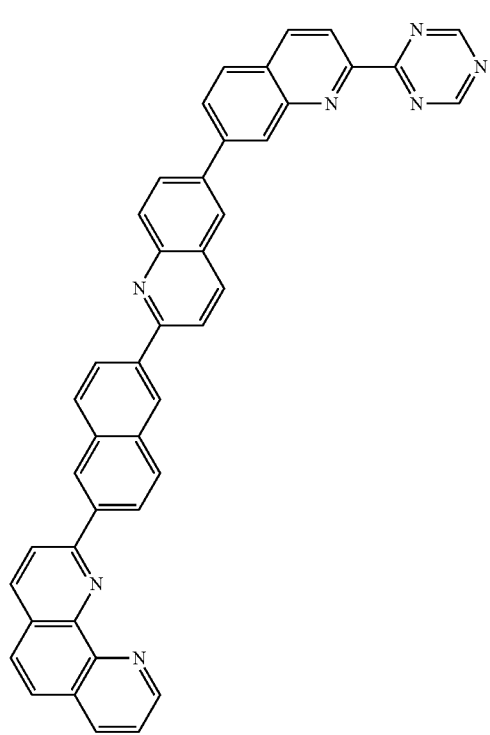
96
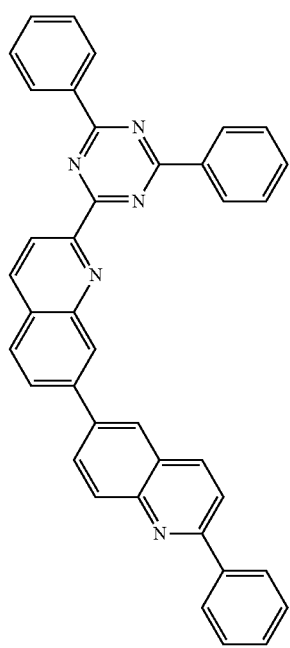
97
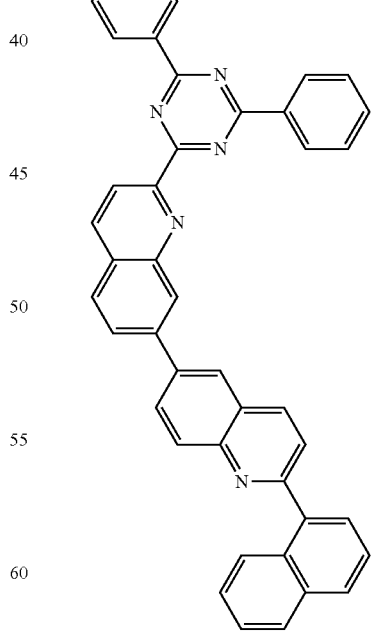
98

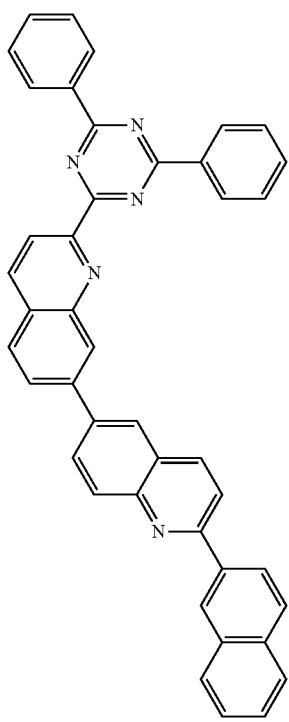
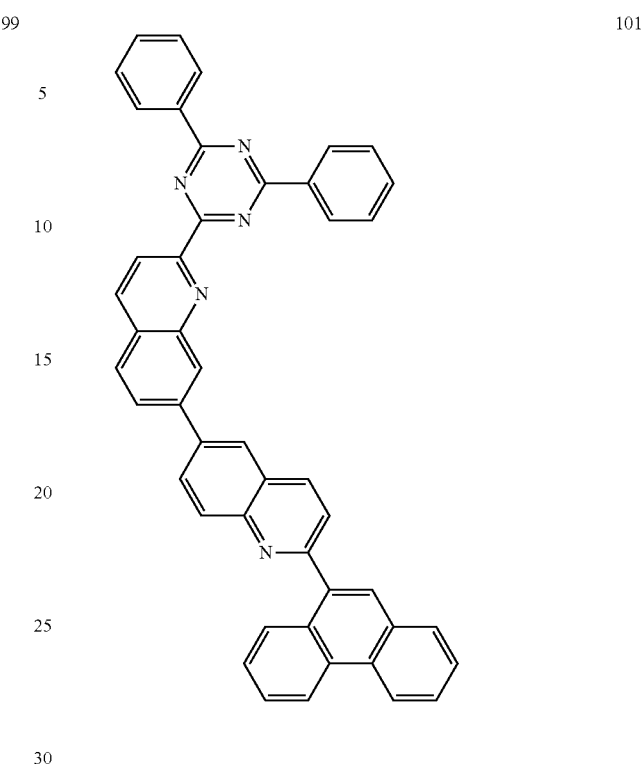
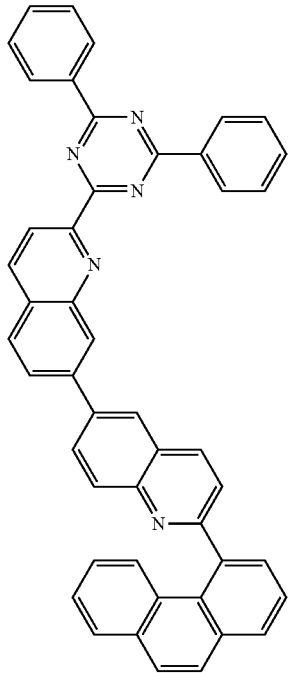
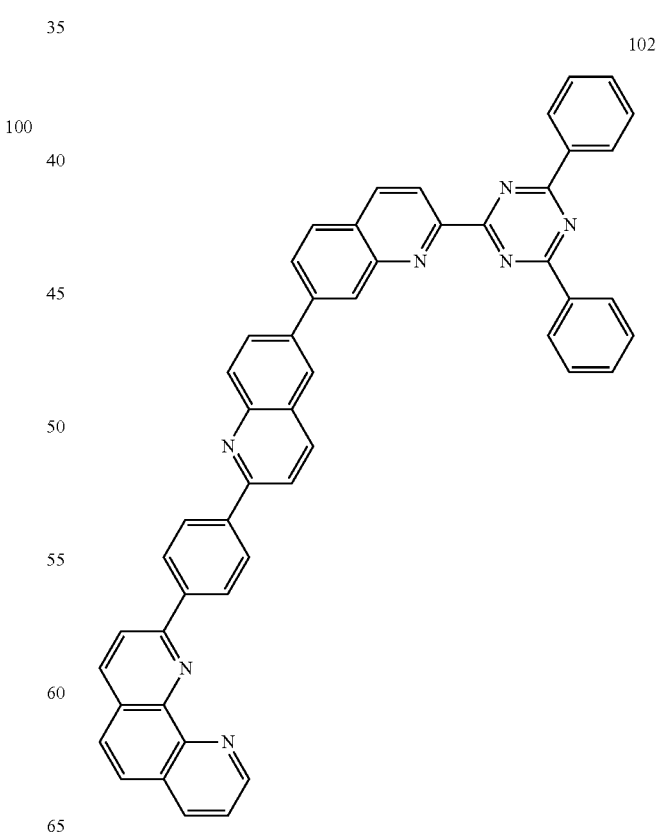

-continued
103
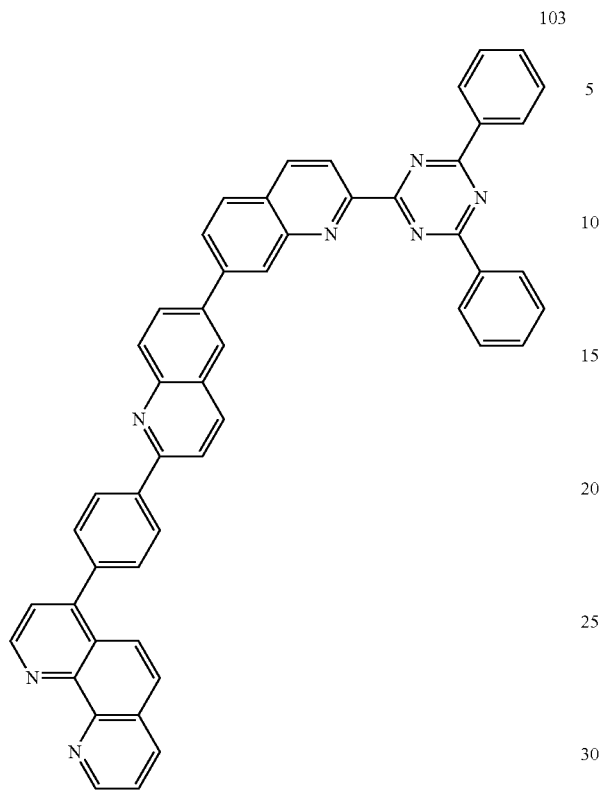
105
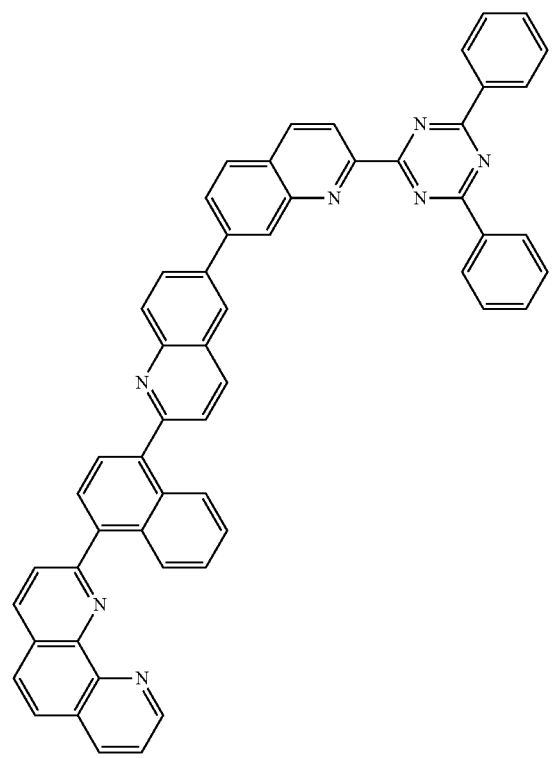
104
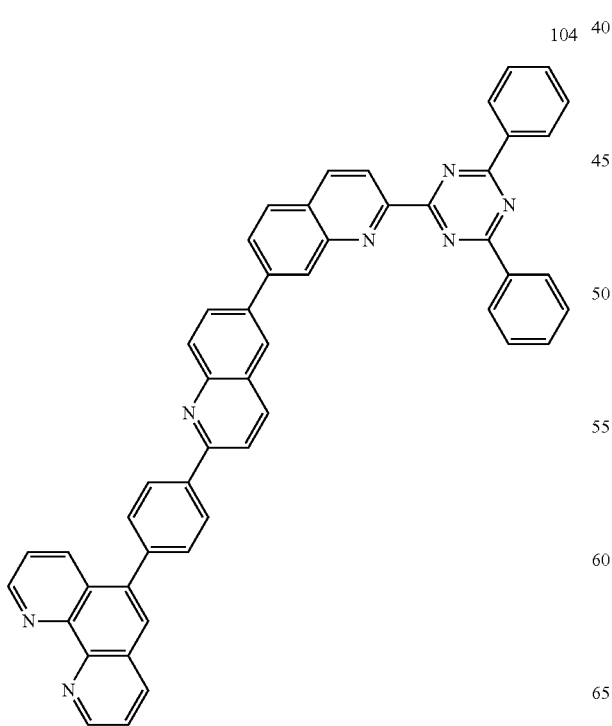
106
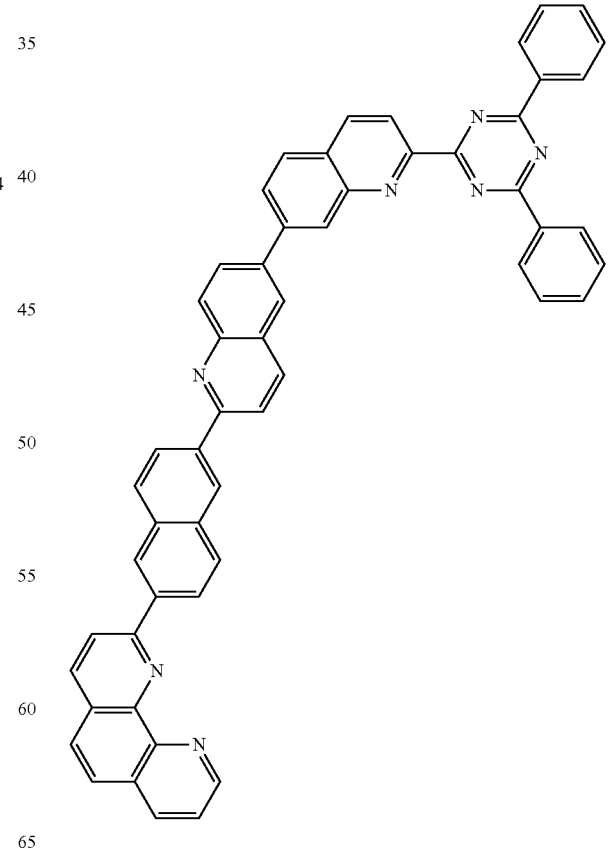

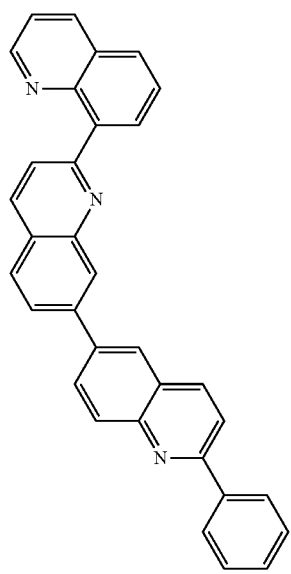
107
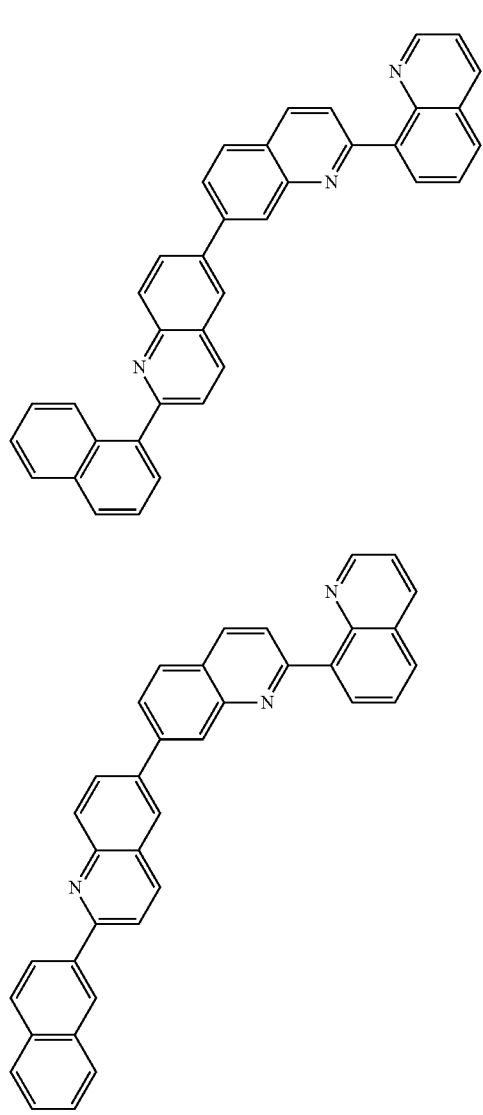
108
109
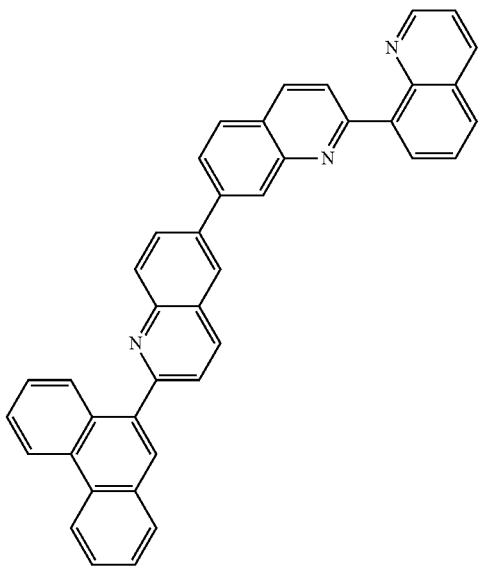
110
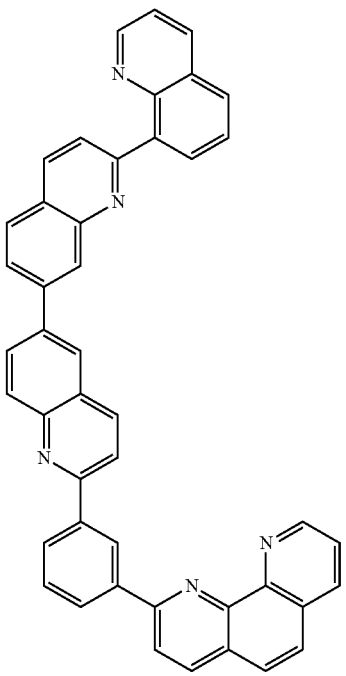
111

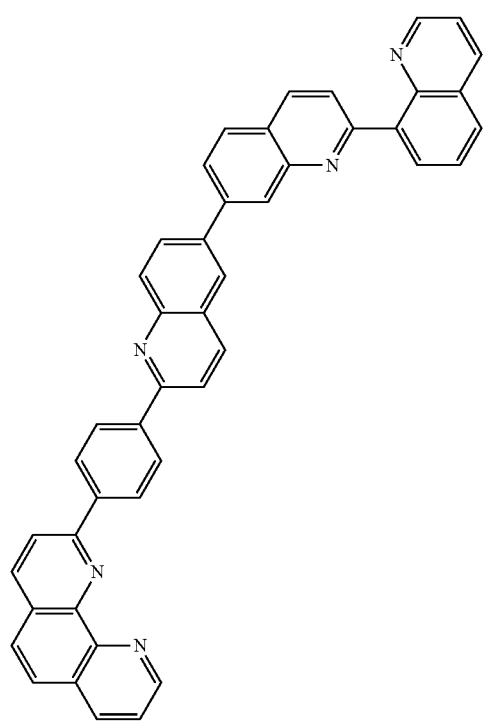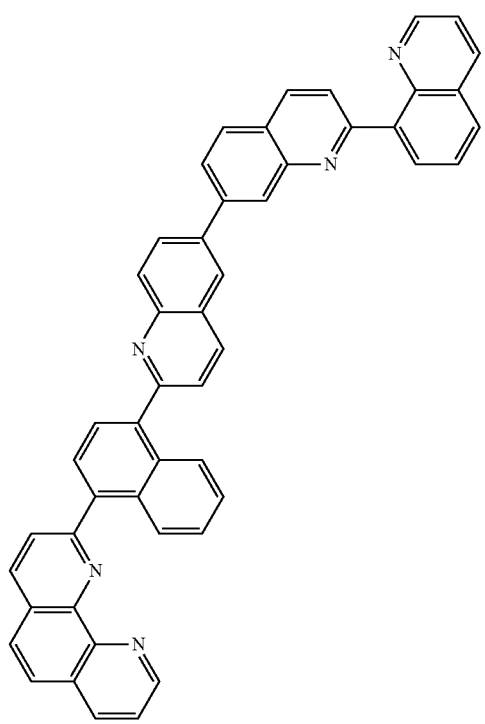

116 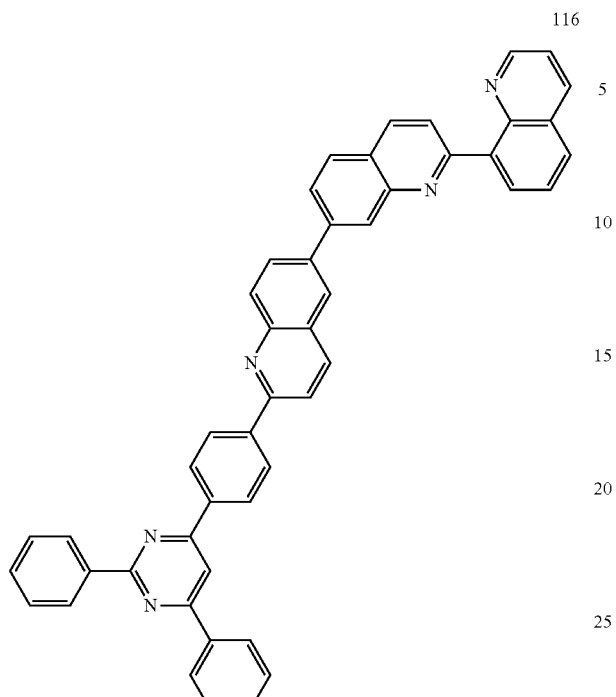
118 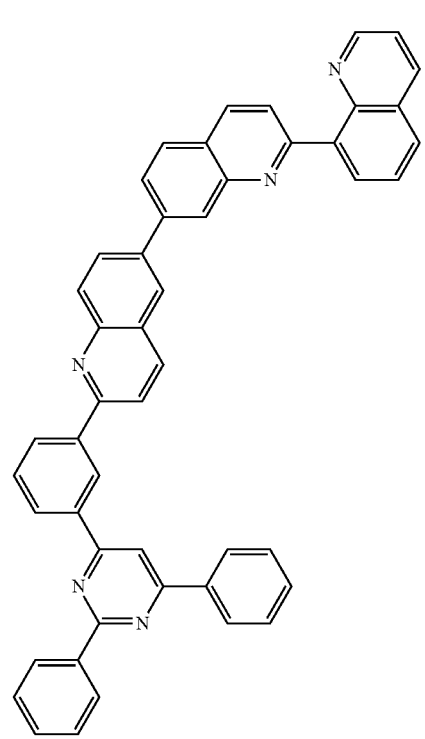
117 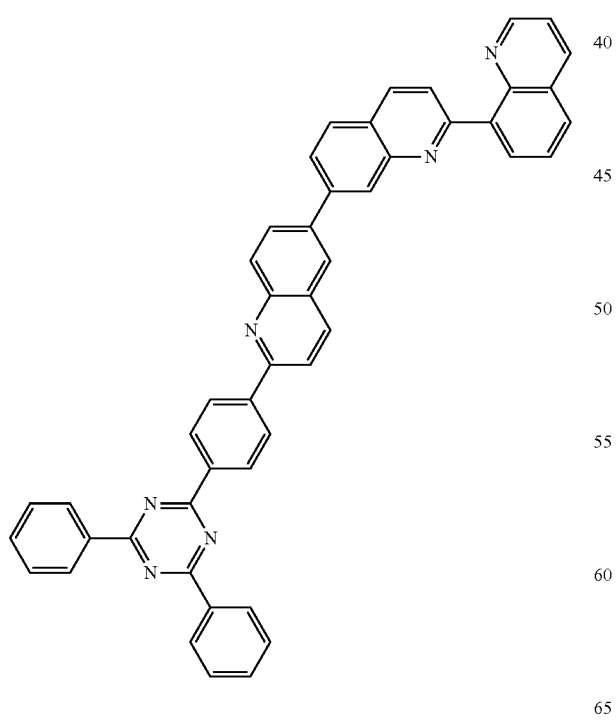
119 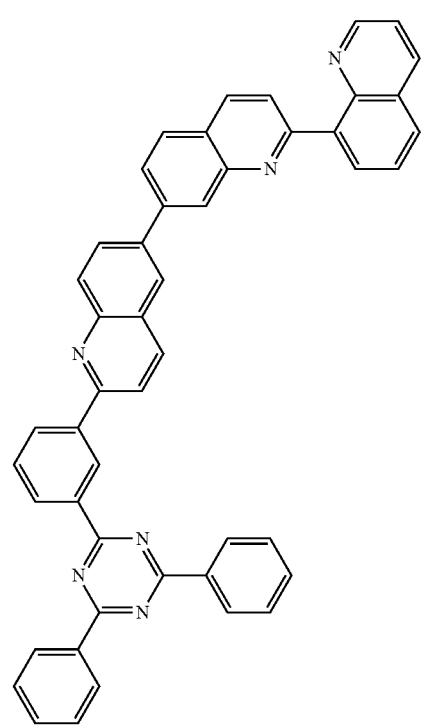

75
-continued
120
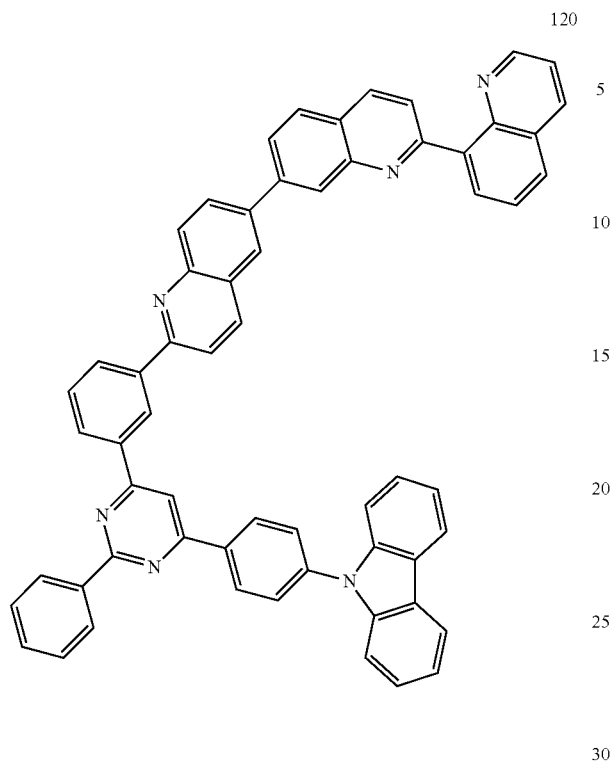
121
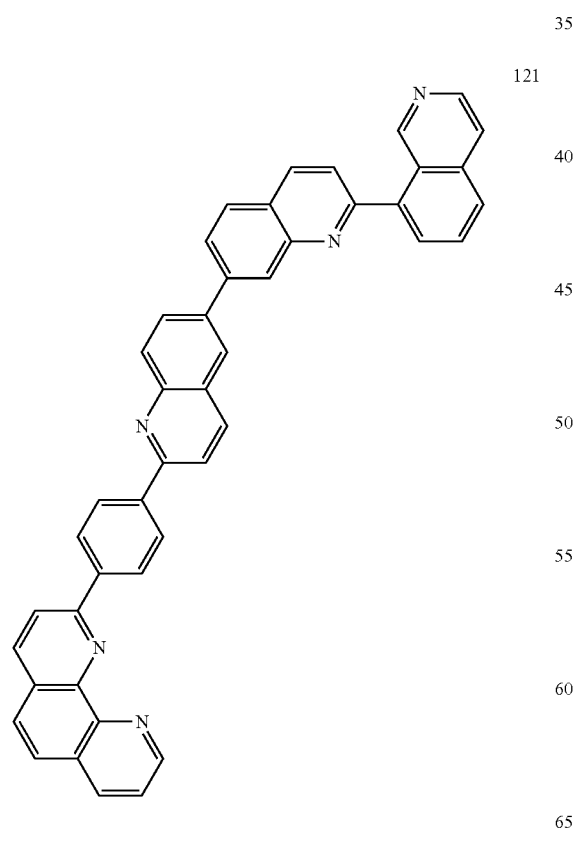
76
-continued
122
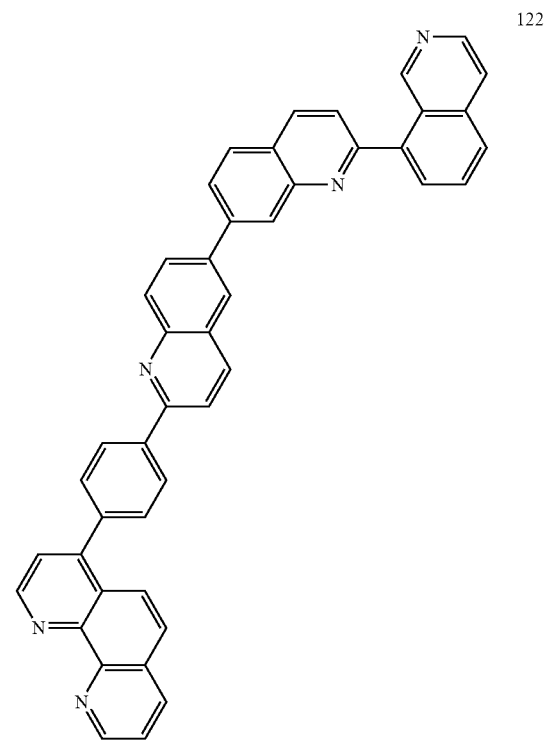 [SMILES: c1cnc2c(c1)ccc1c(-c3ccc(-c4ccc5cc(-c6ccc7ccc(-c8ccnc9ccccc89)nc7c6)ccc5n4)cc3)ccnc12]
123

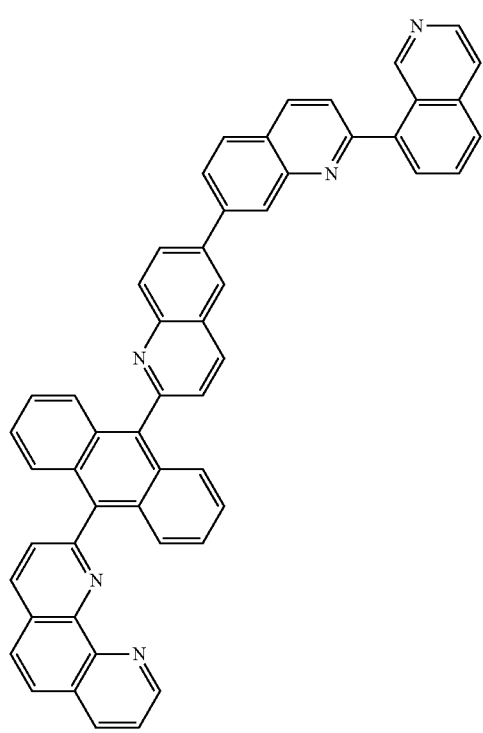
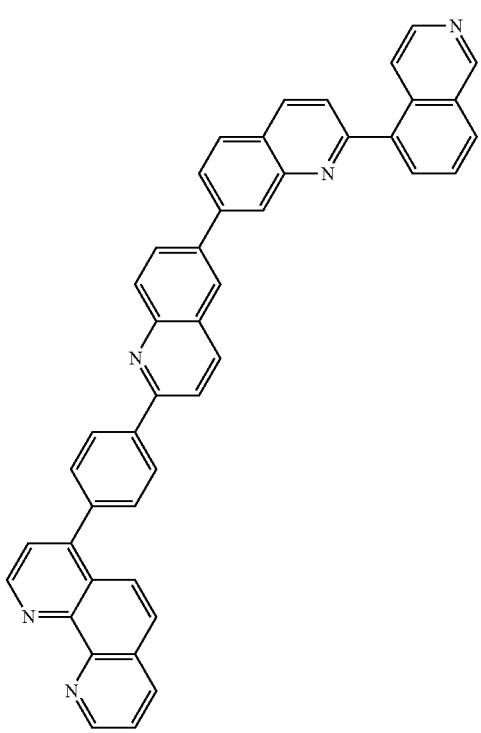

-continued
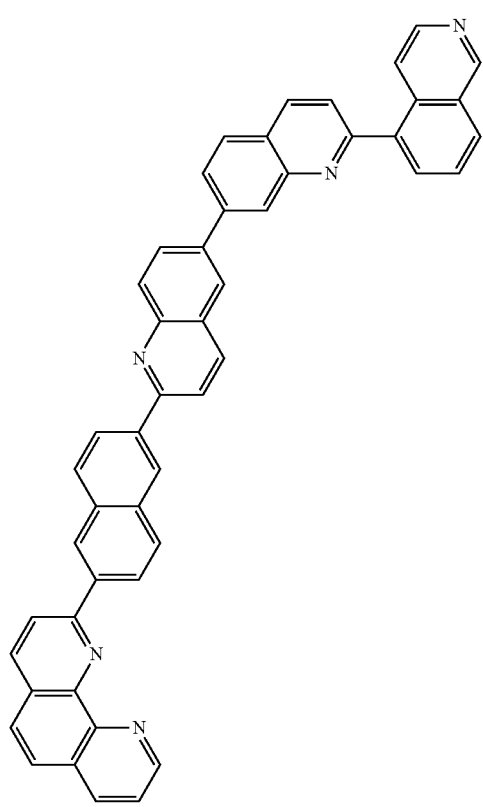
128

129
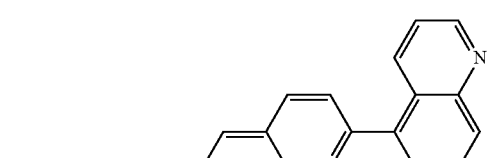
130
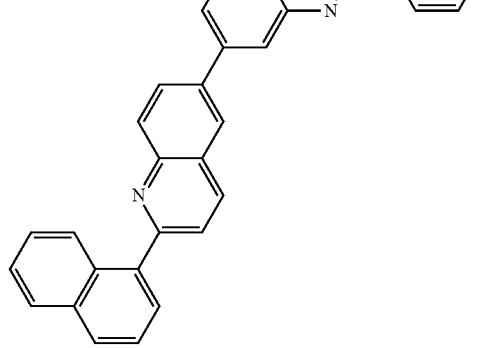
131
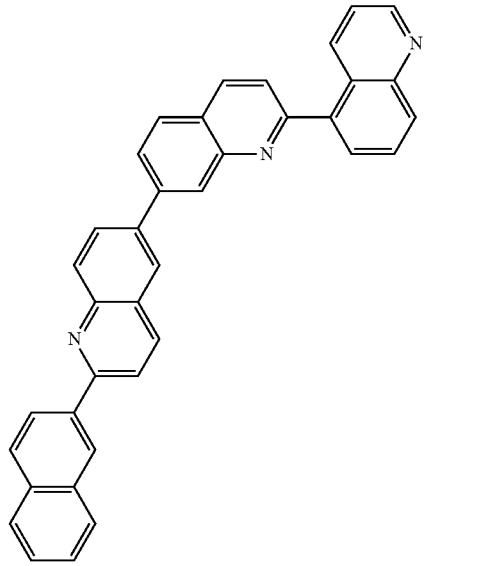
132
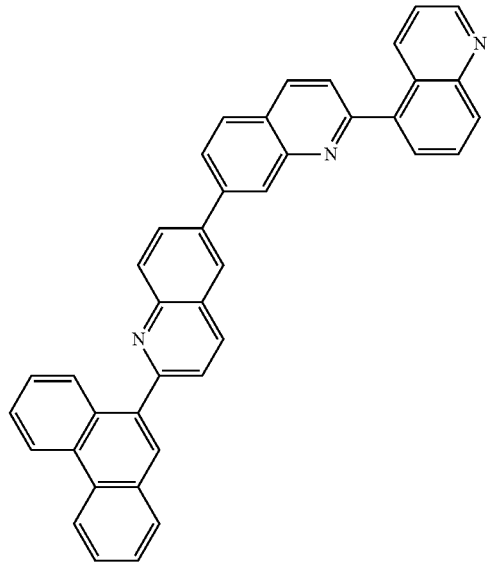

-continued
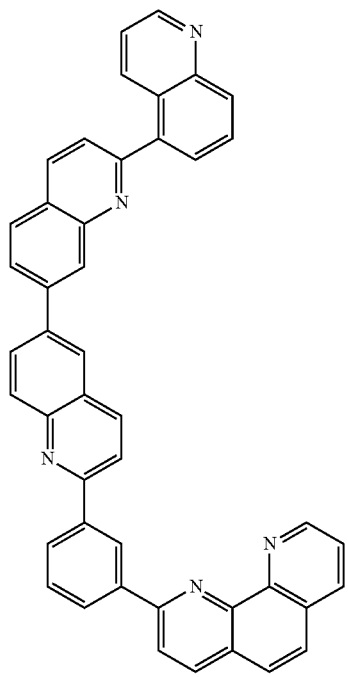
133
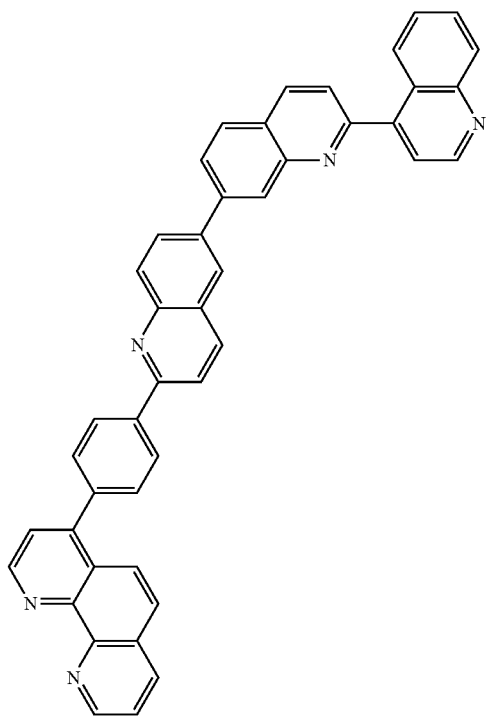
135
134
136

137
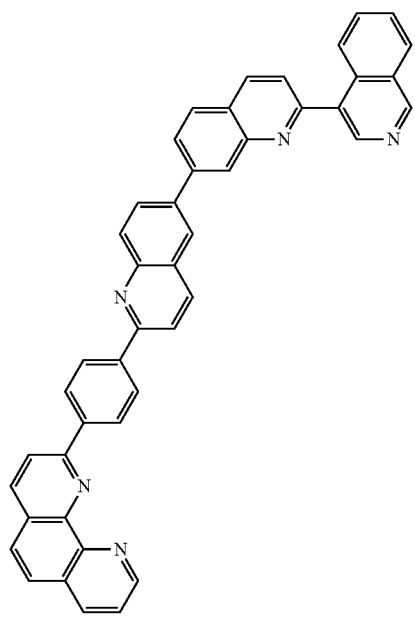
138
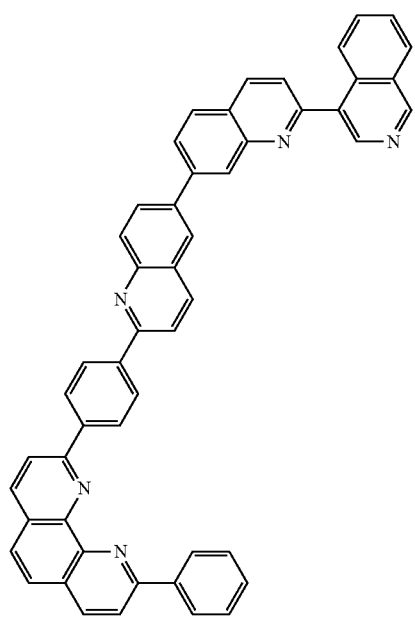
139
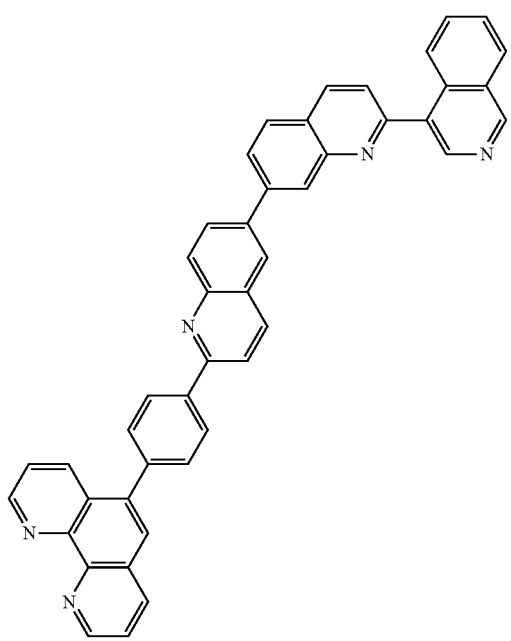
140
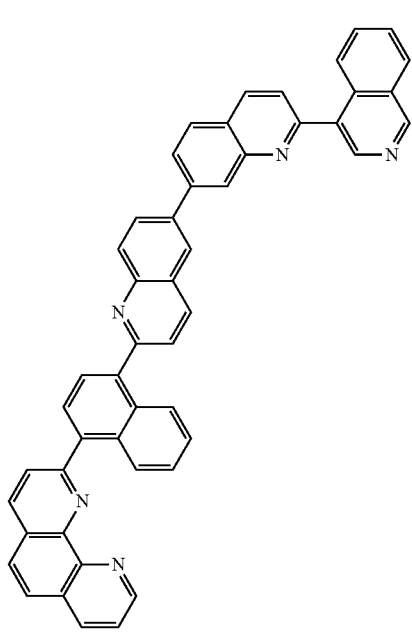

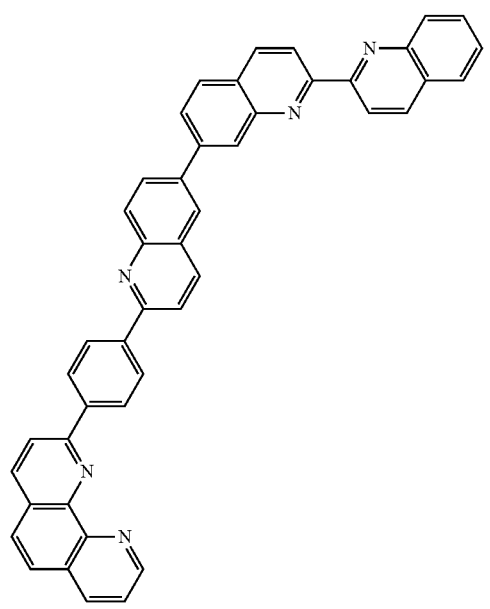
141
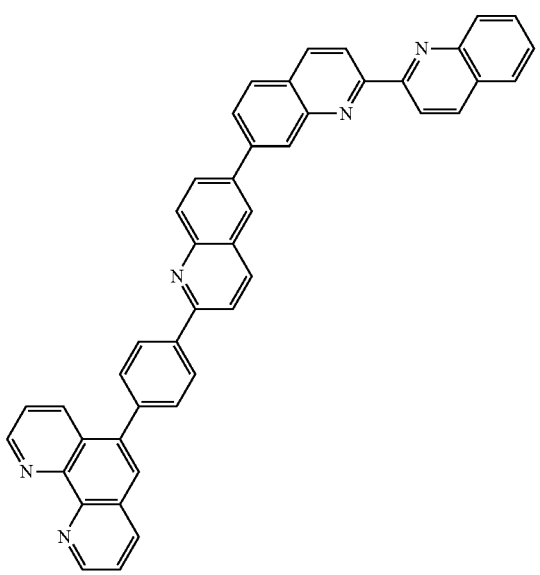
143
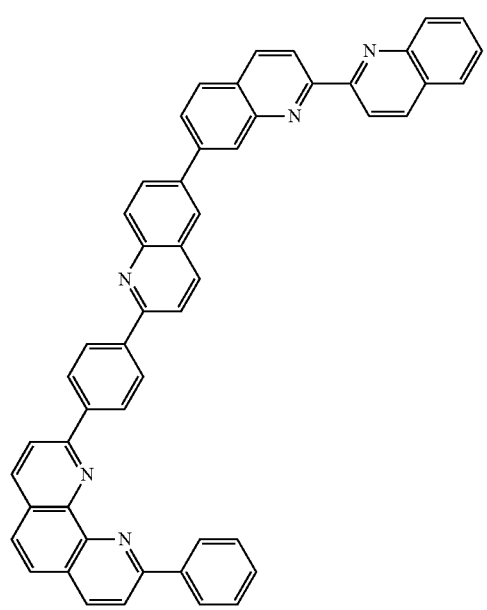
142
144

87
-continued
145
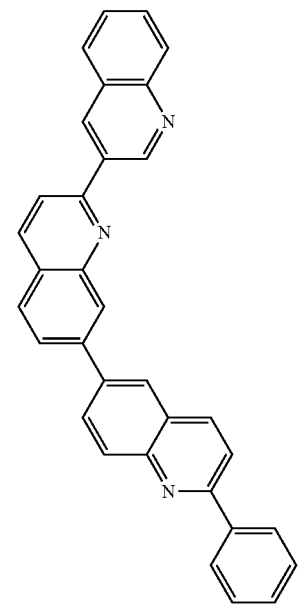
146
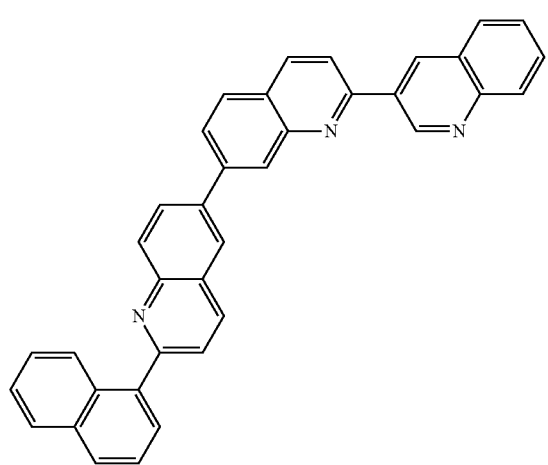
147
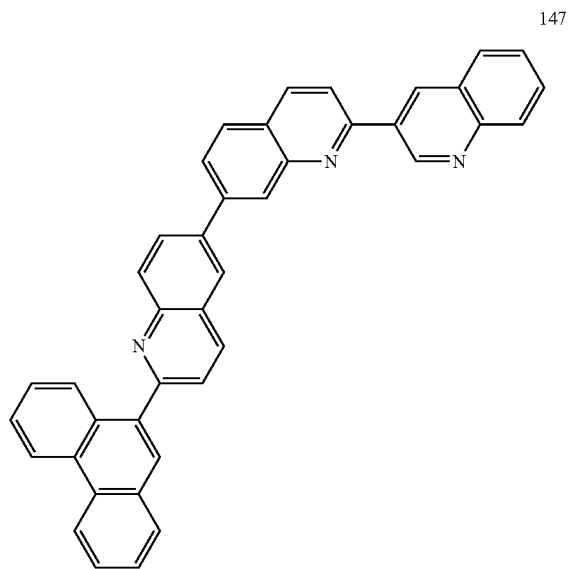
88
-continued
148
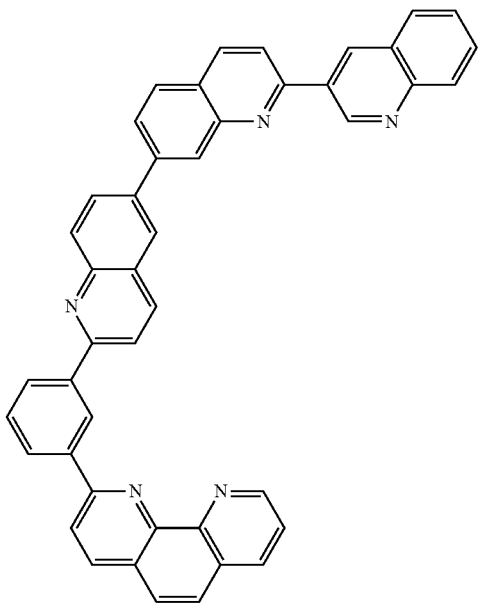
149
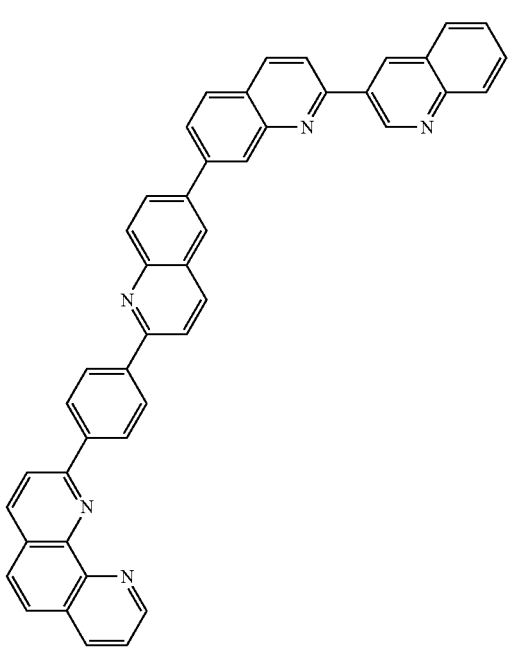

150
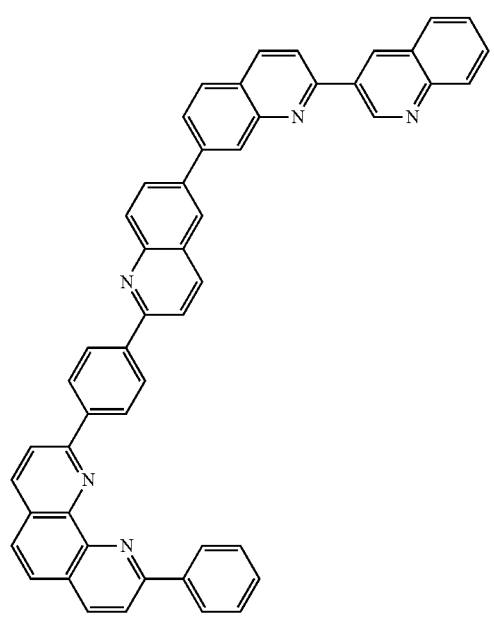
151
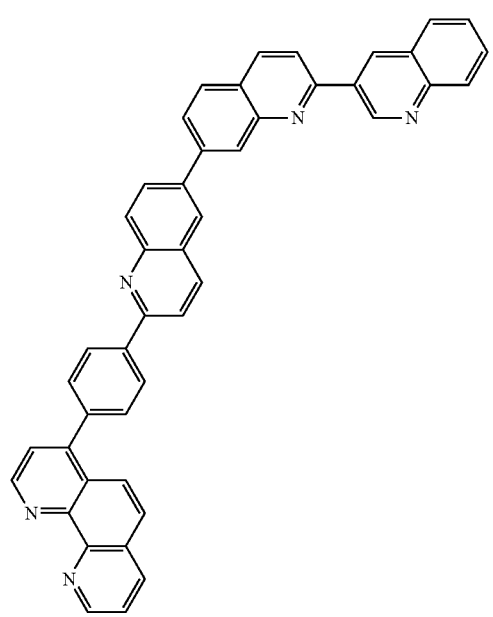
152
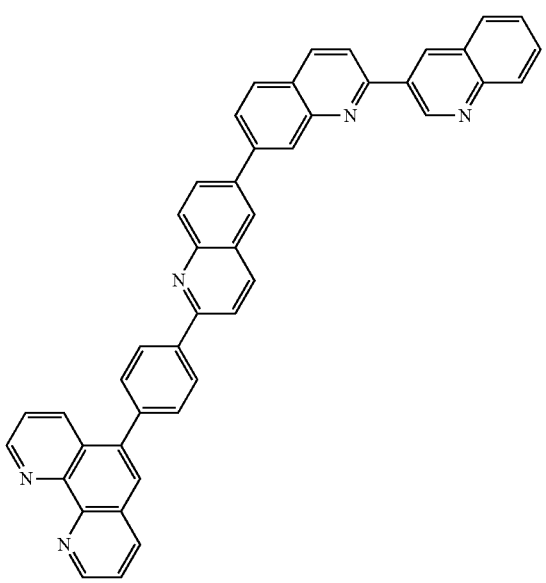
153
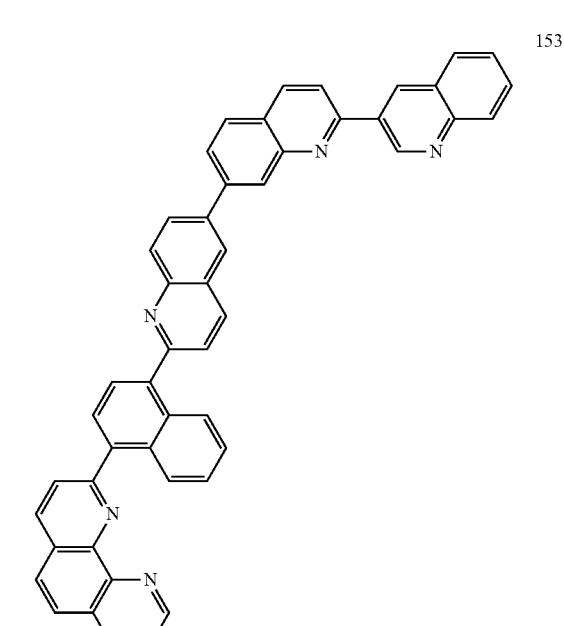

154
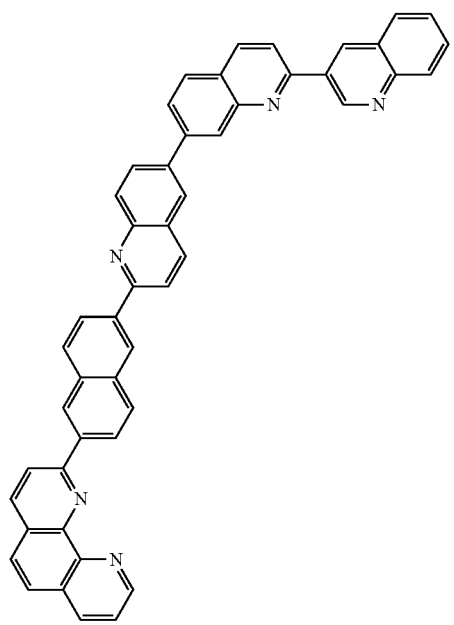
155
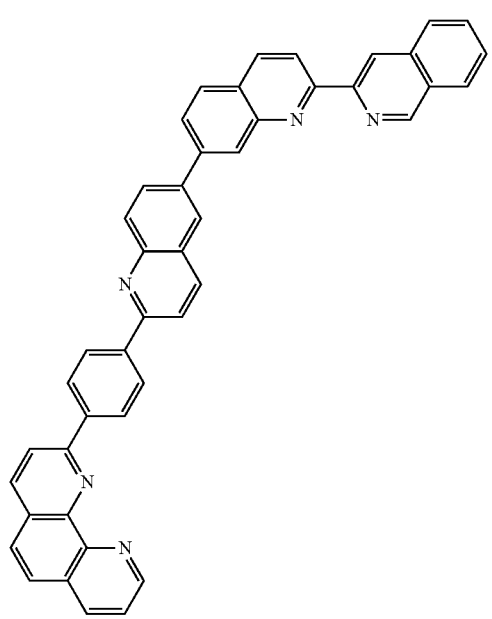
156
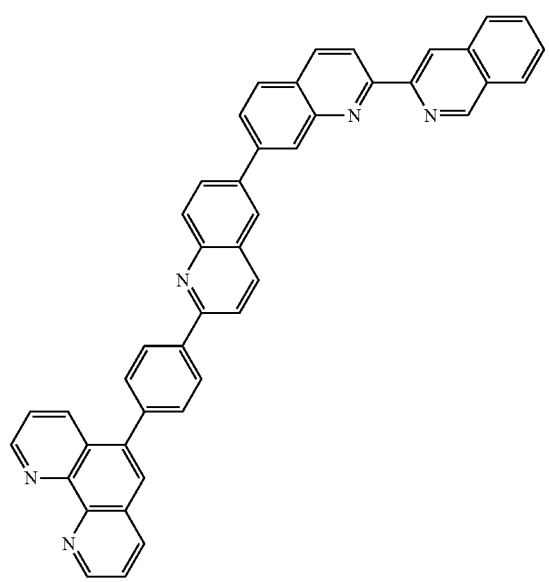
157
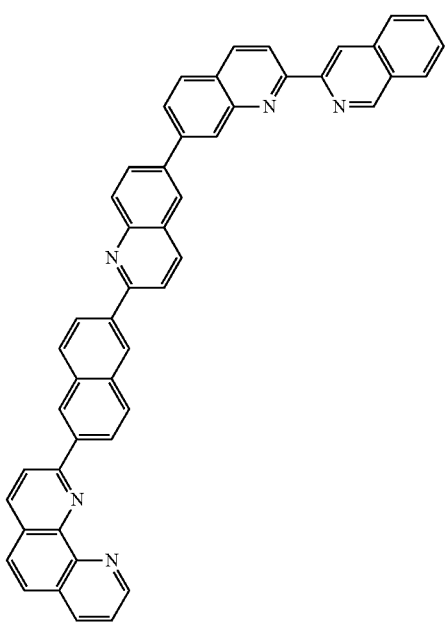

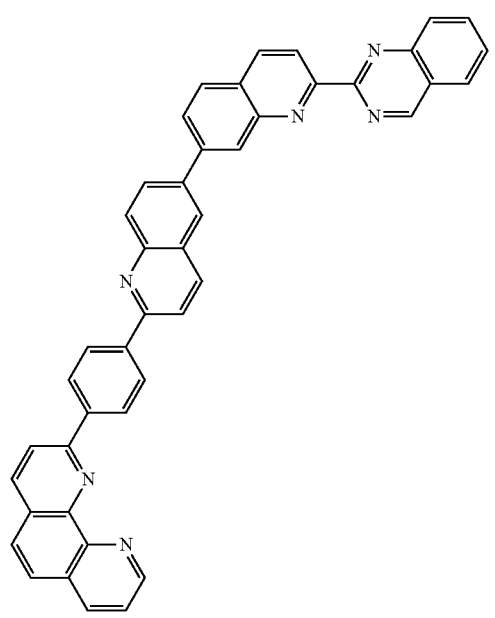
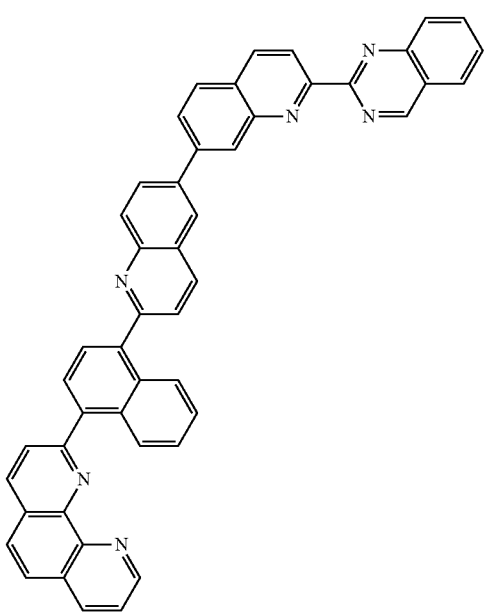

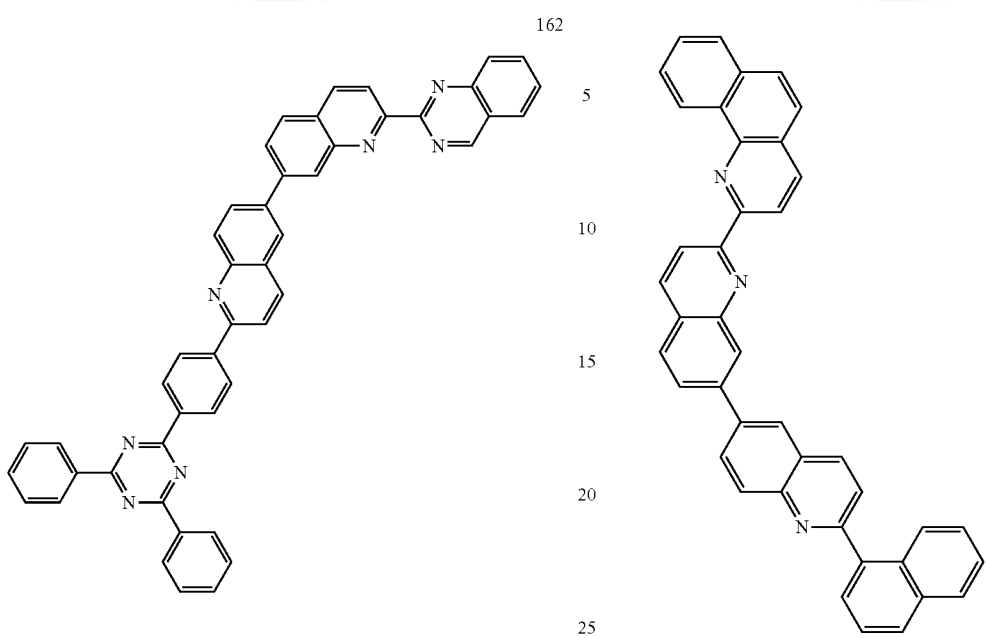
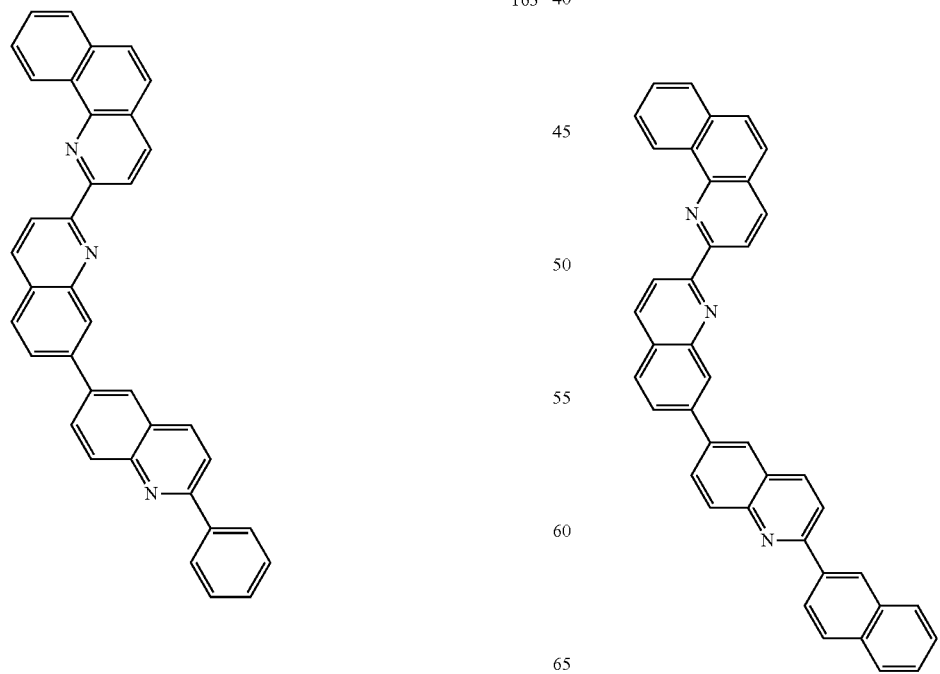

166
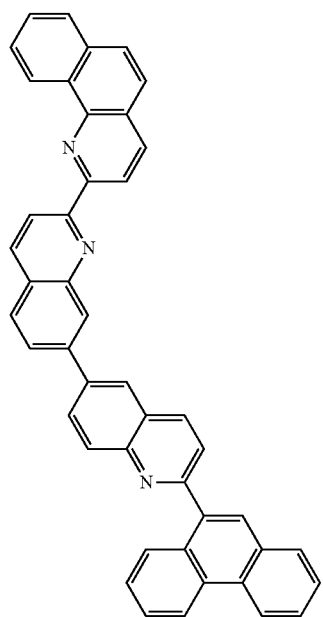
167
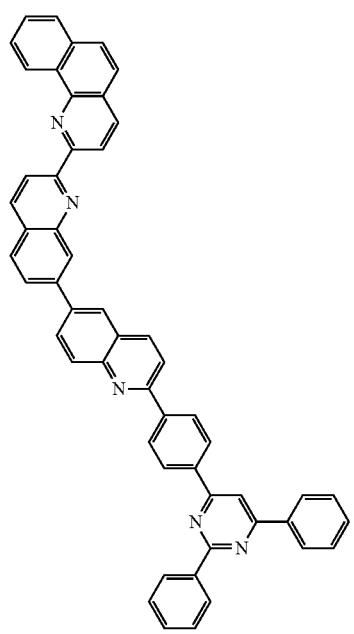
168
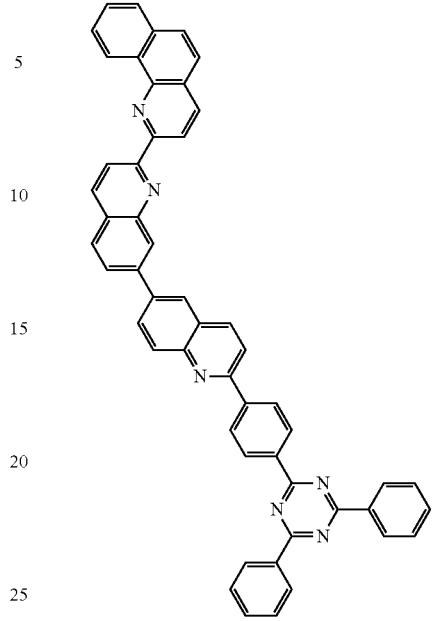
169

170
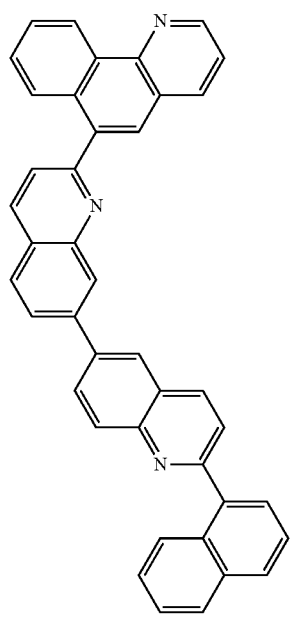
172
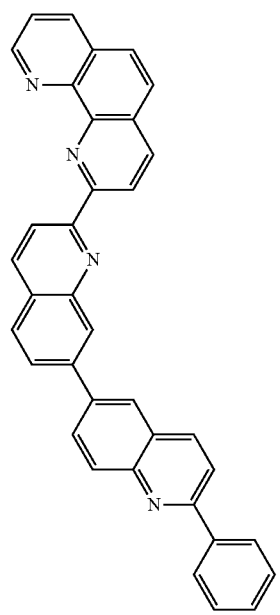
171
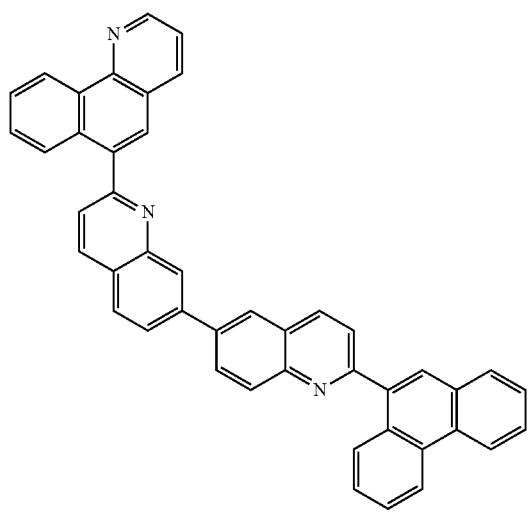
173
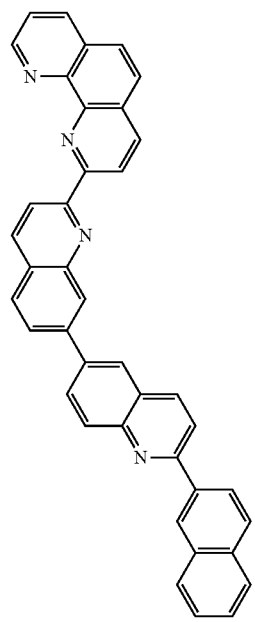

174
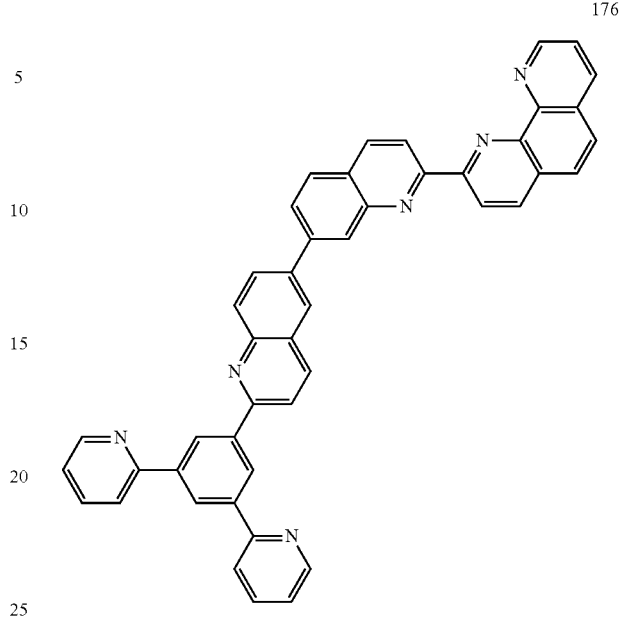
176
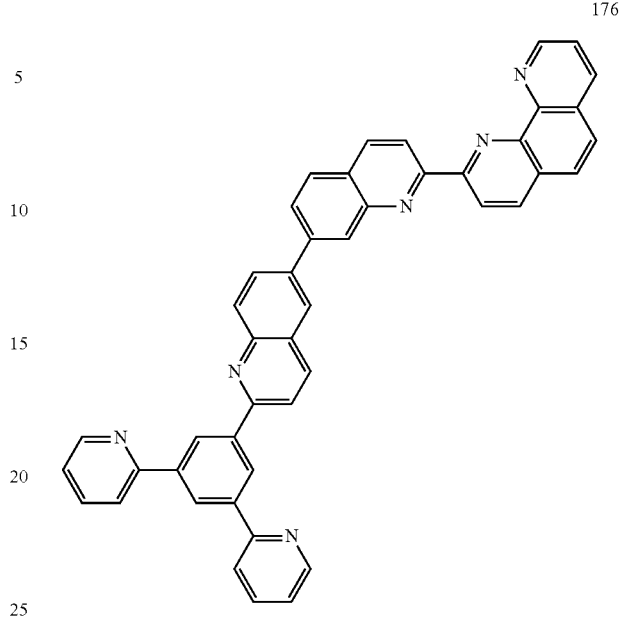
175
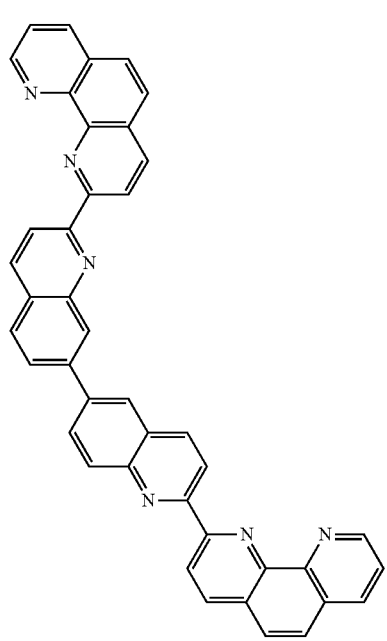
177
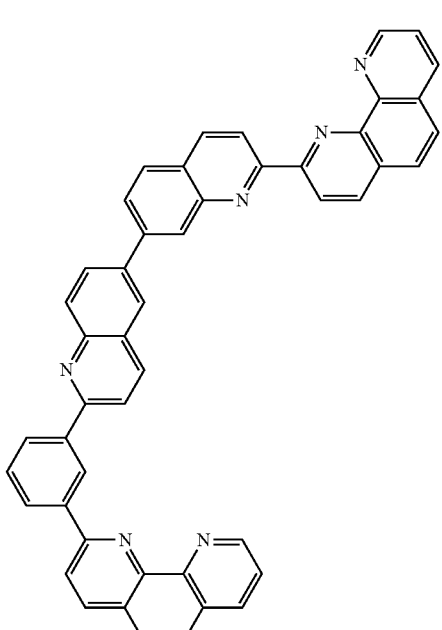

178
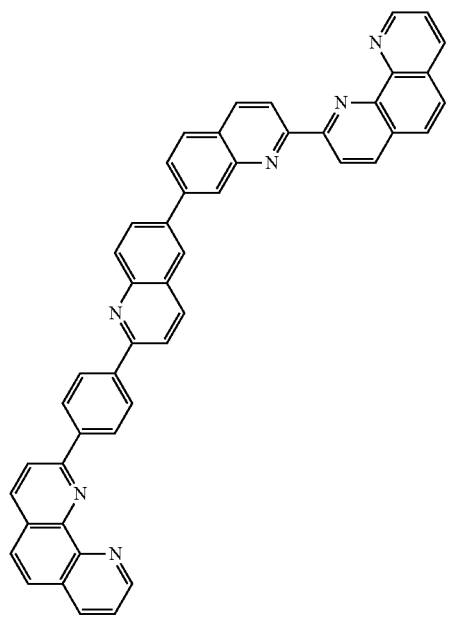
180
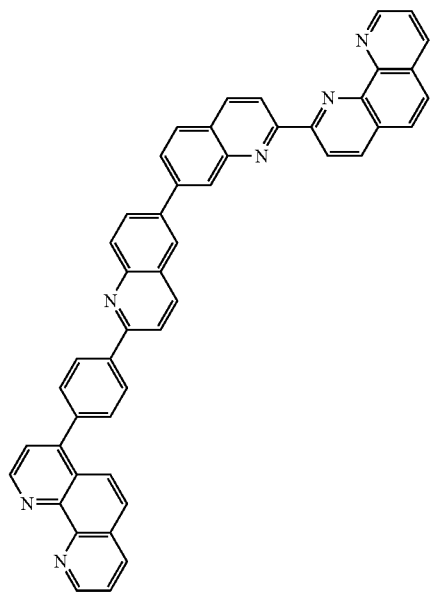
179
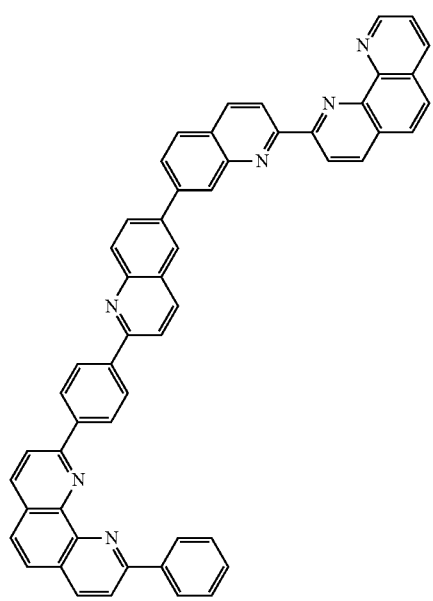
181
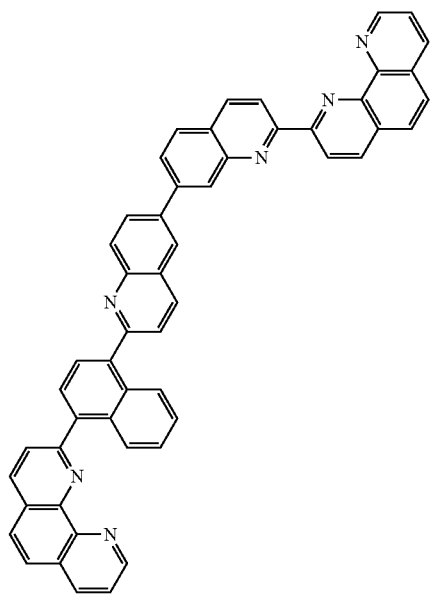

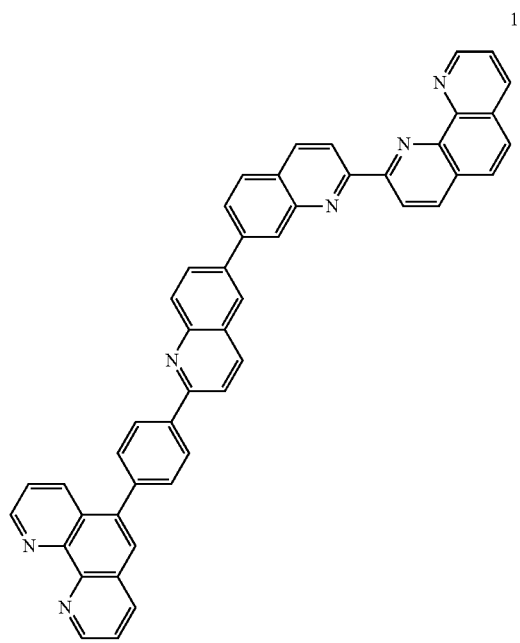
182
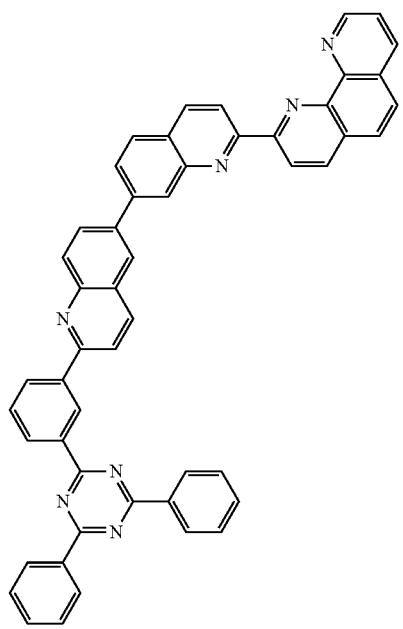
184
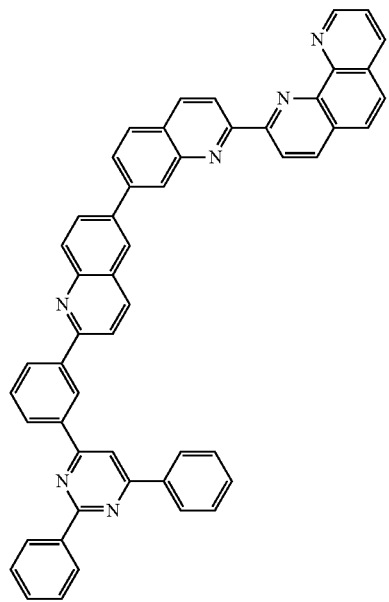
183
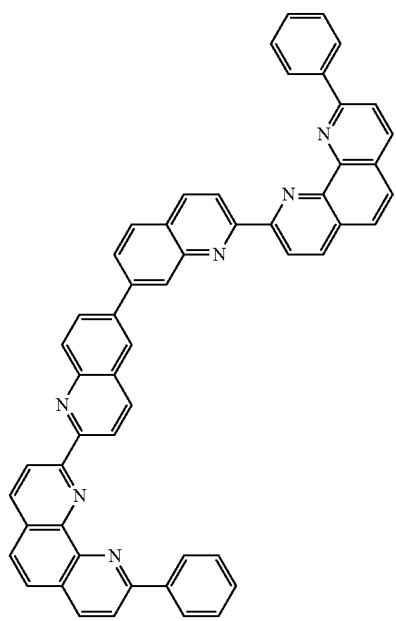
185

186
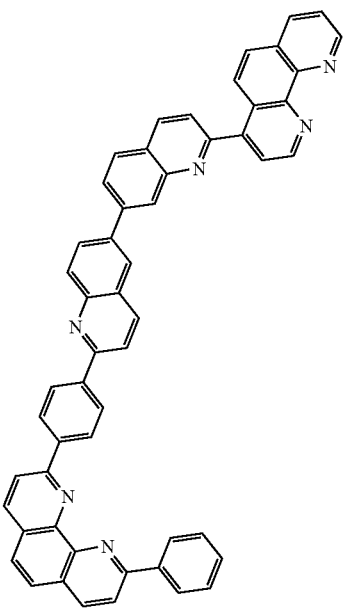
187
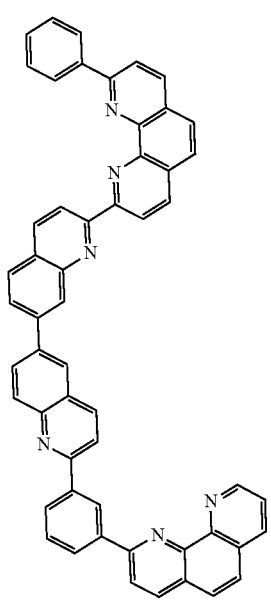
188
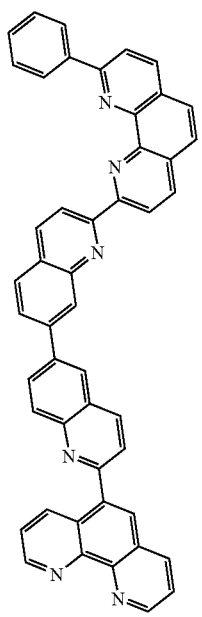
189
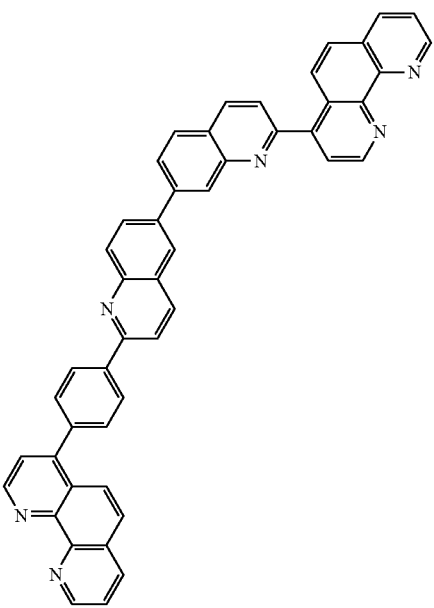

109
-continued
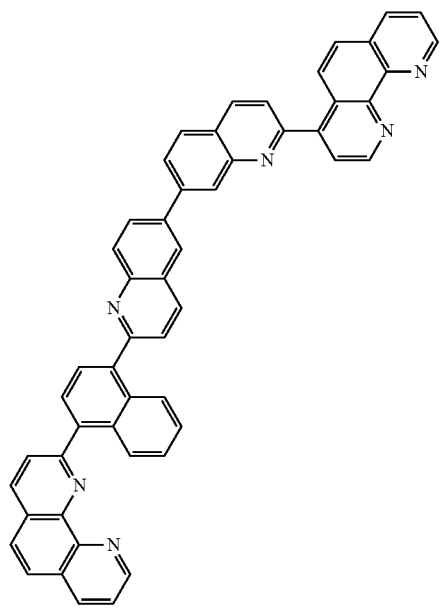
190
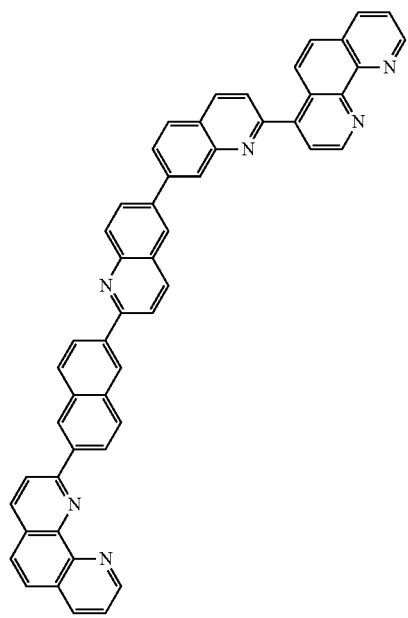
191
110
-continued
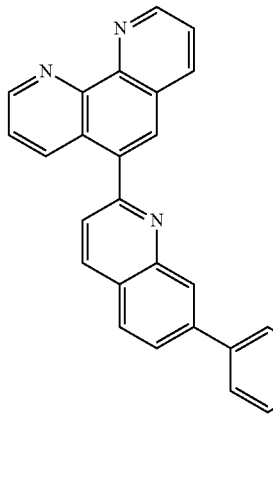
192
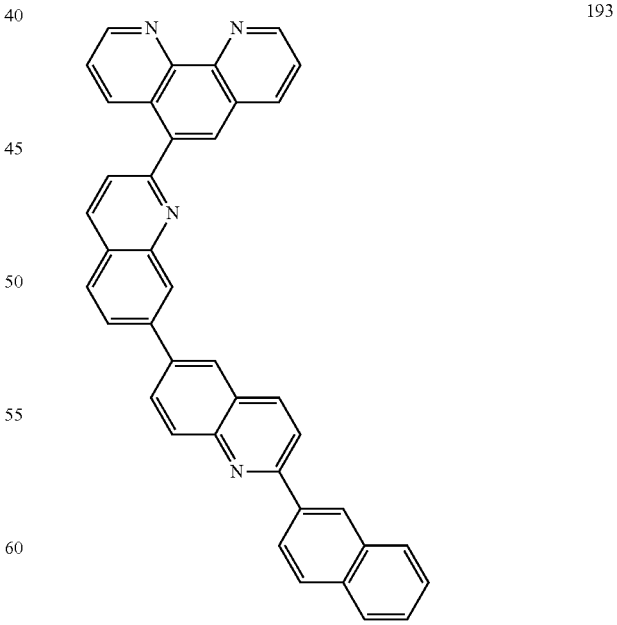
193

111
-continued
194
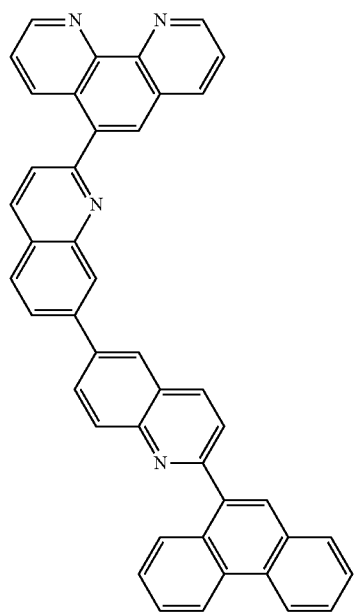
195
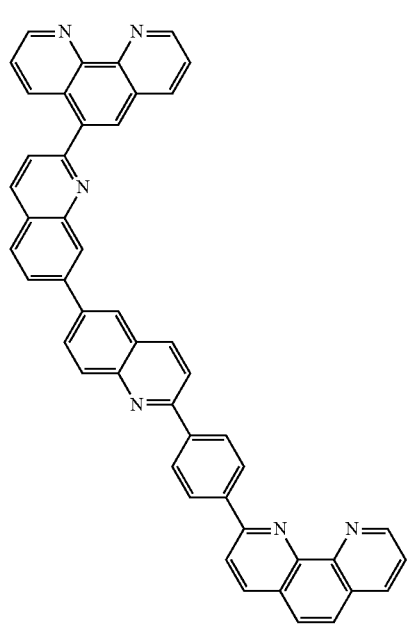
112
-continued
196
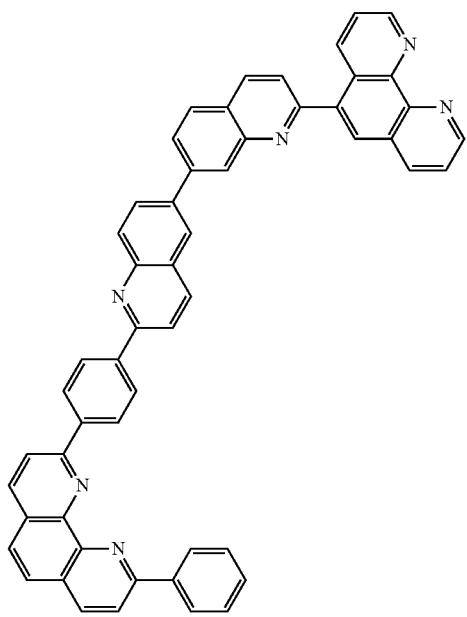
197
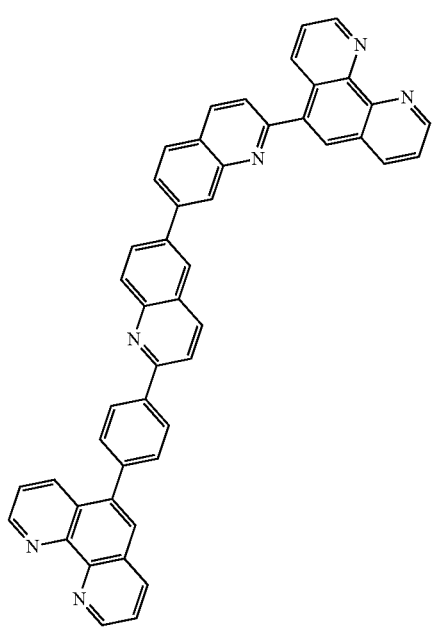

198
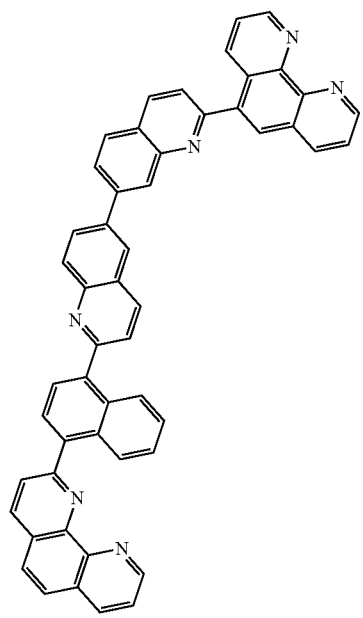
199
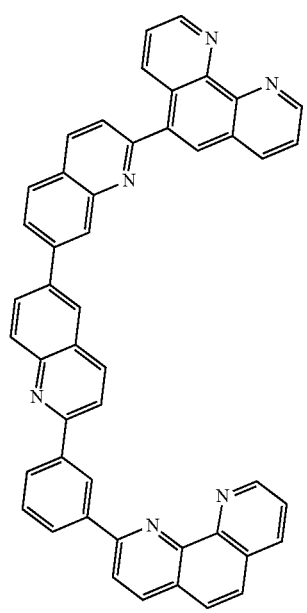
200
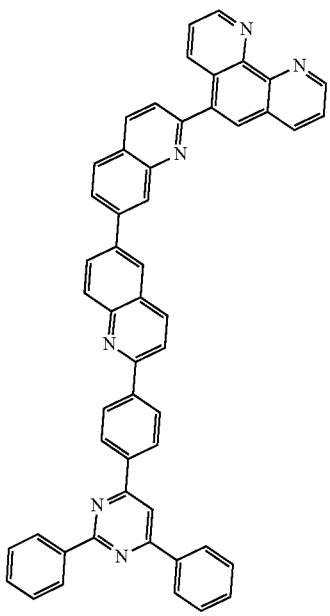
201
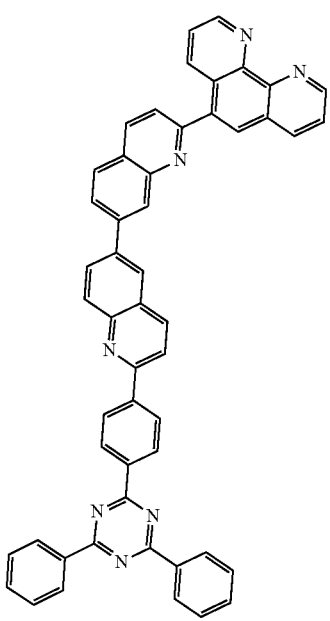

115
-continued
202
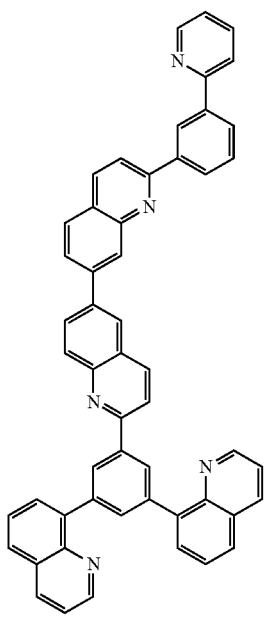
203
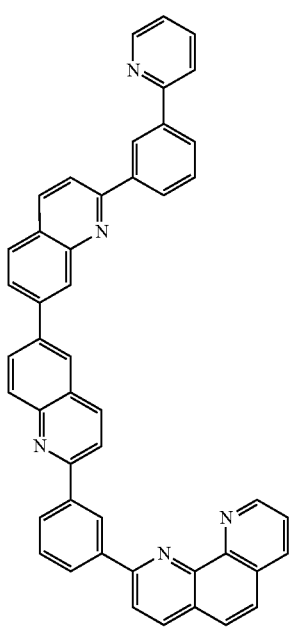
116
-continued
204
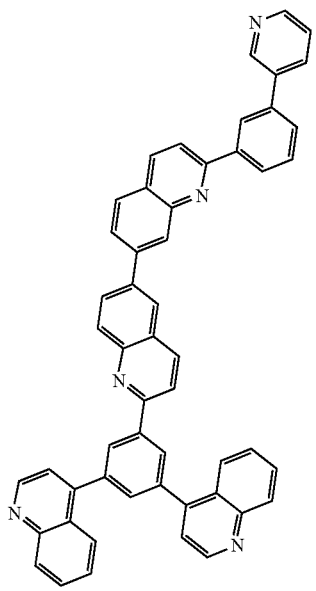
205
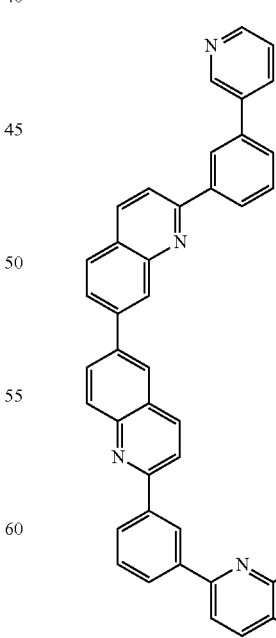

206
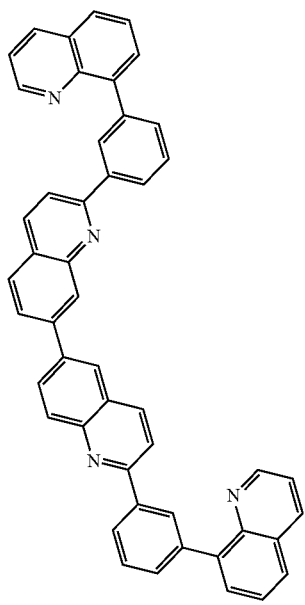
207
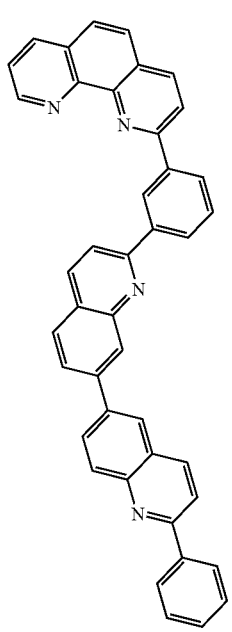
208
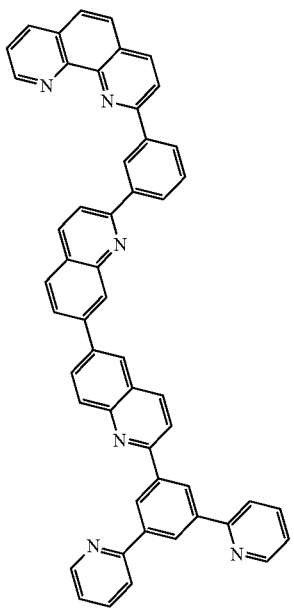
209
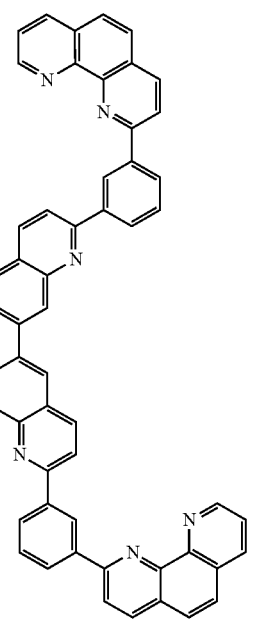

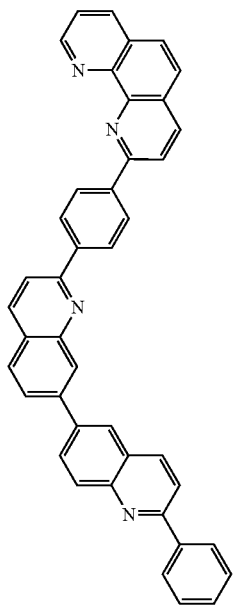
210
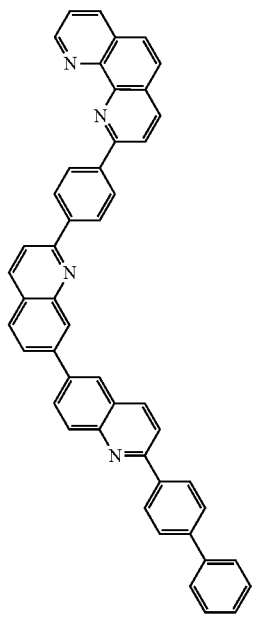
212
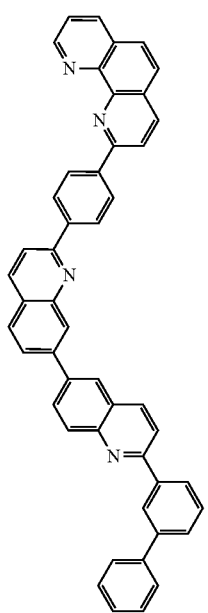
211
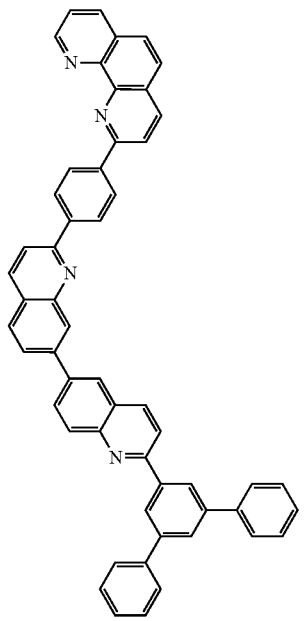
213

-continued
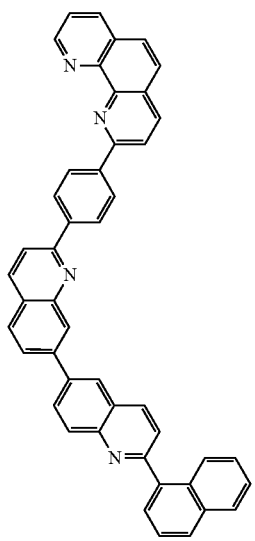
214
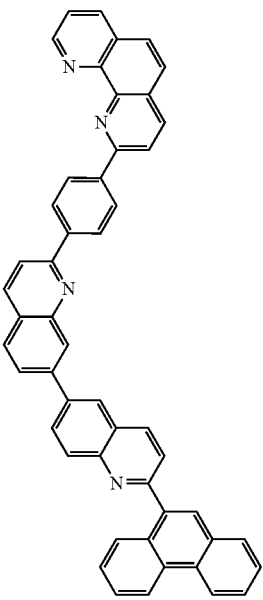
215
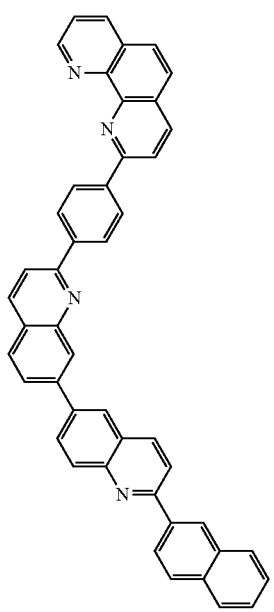
-continued
216
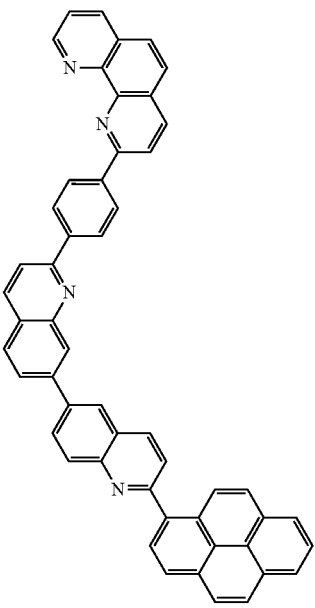
217

218
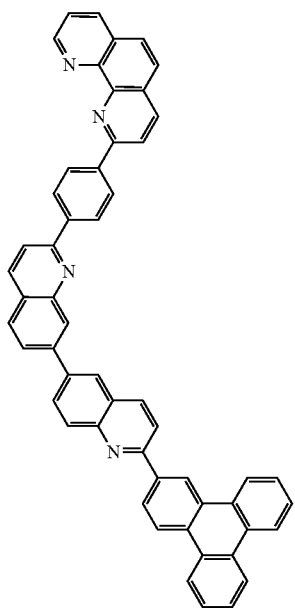
219
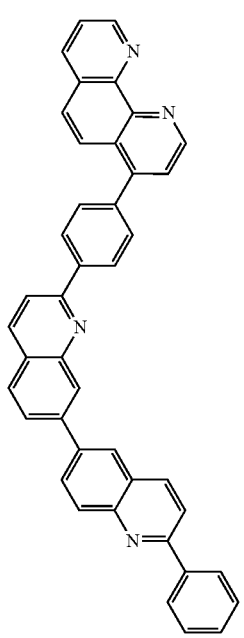
220
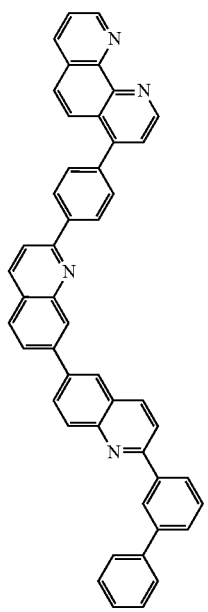
221
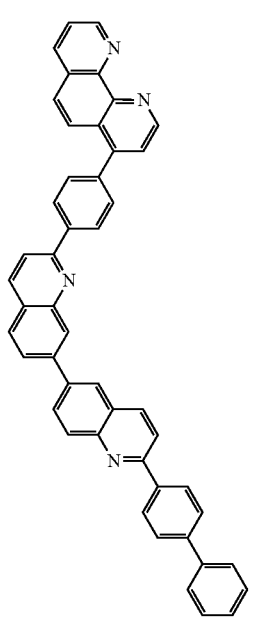

222
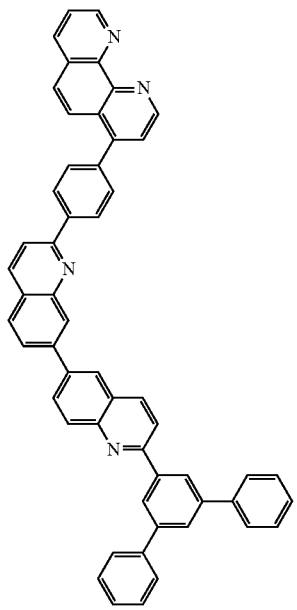
223
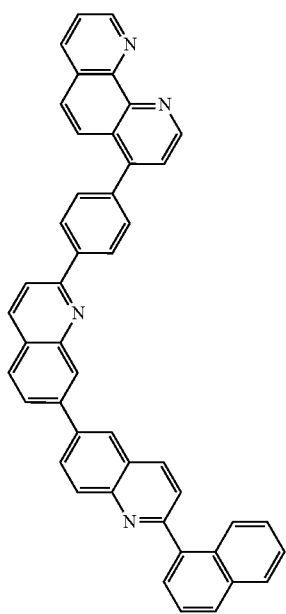
224
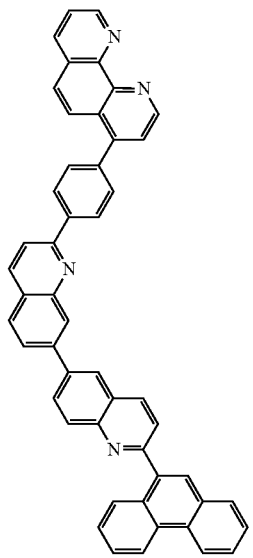
225
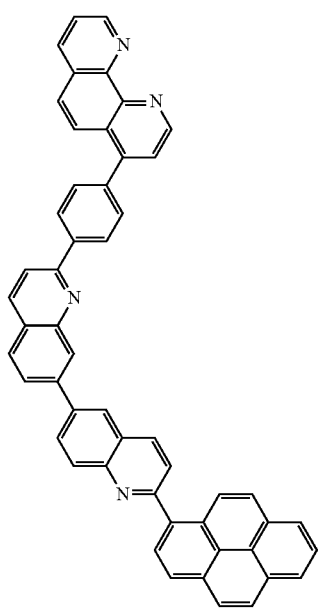

226
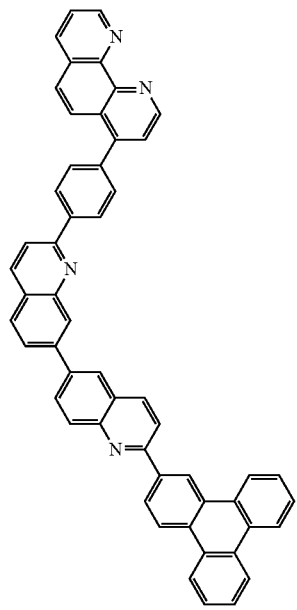
227
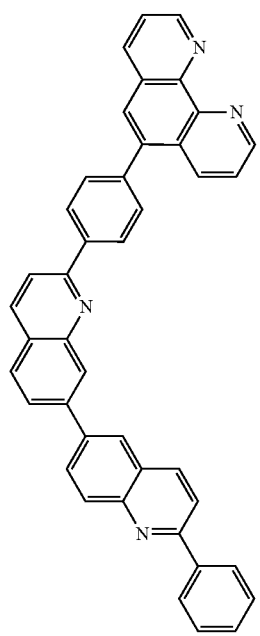
228
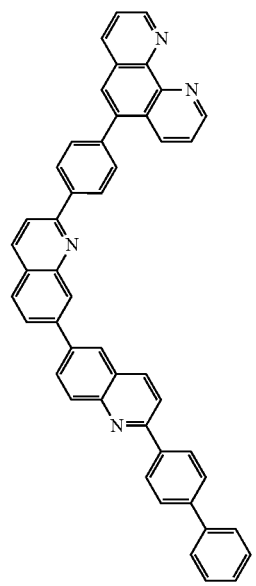
229
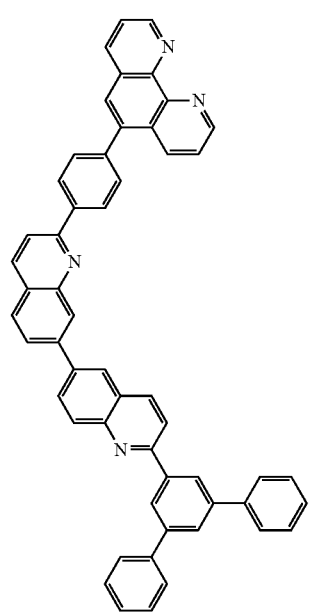

129
-continued
230
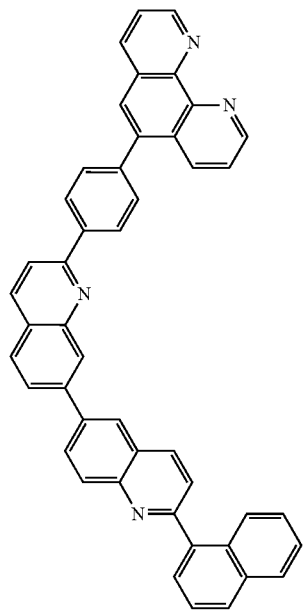
231
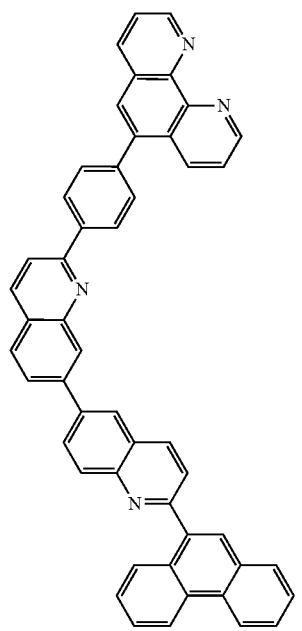
130
-continued
232
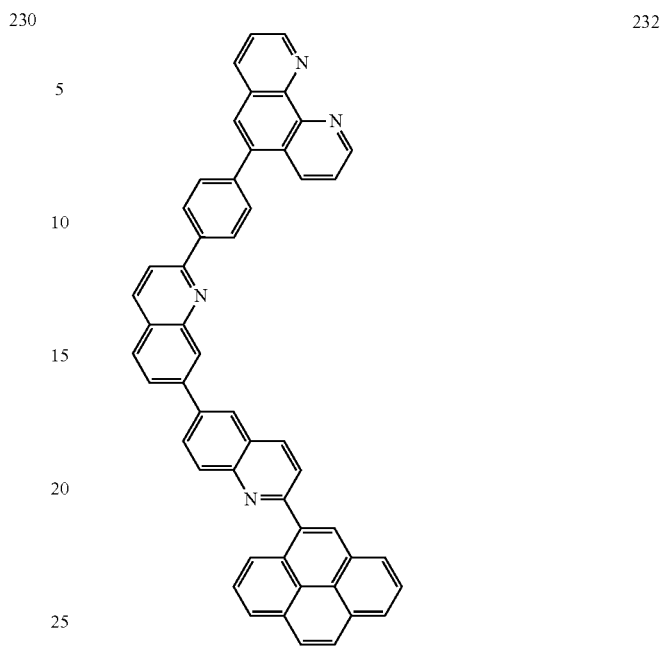
233
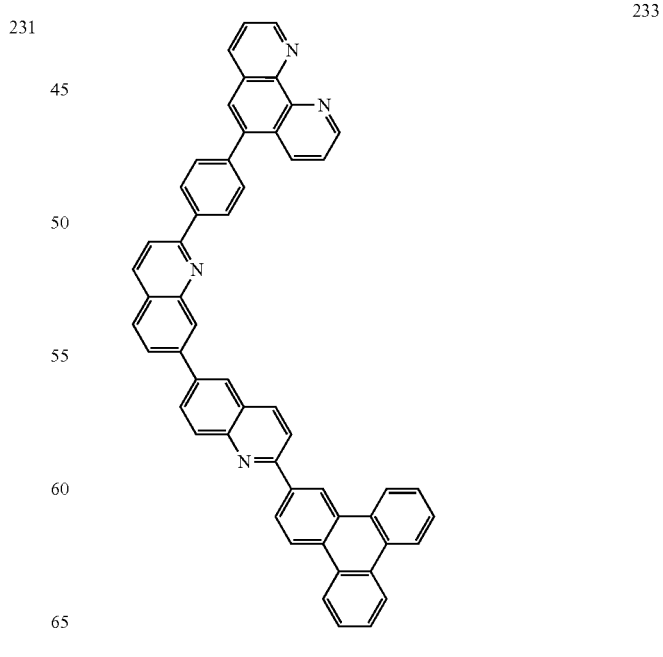

131
-continued
234
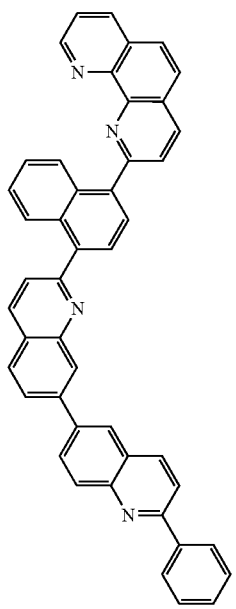
235
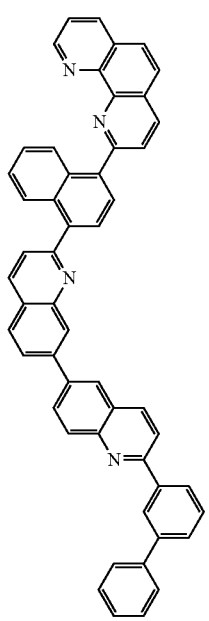
132
-continued
236
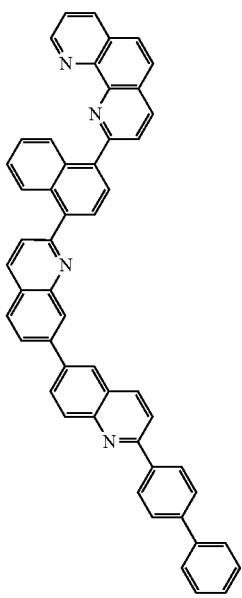
237

238
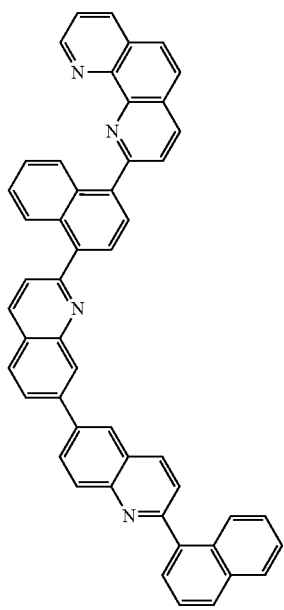
239
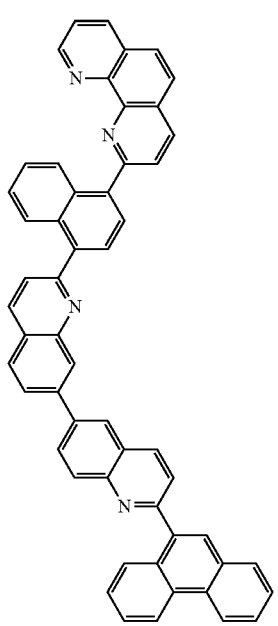
240
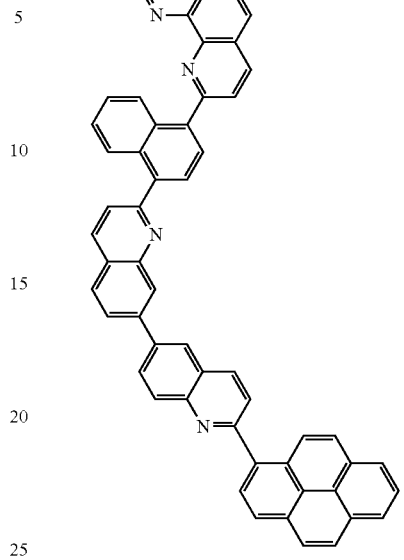
241
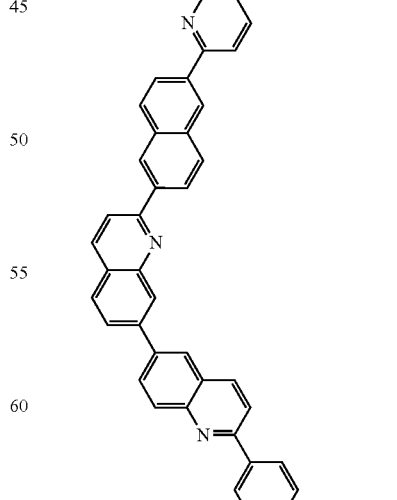

242
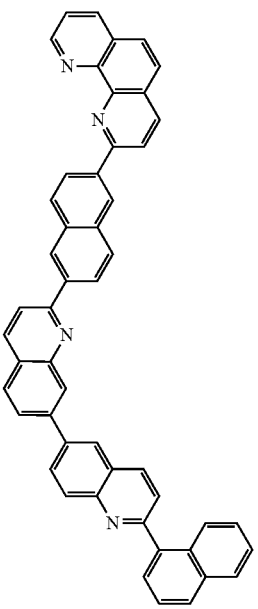
243
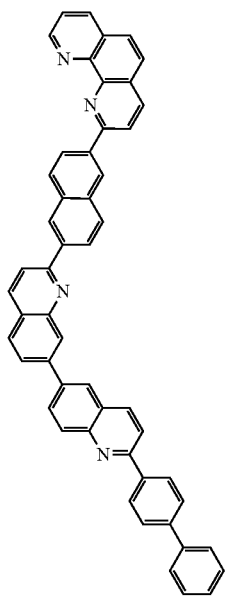
244
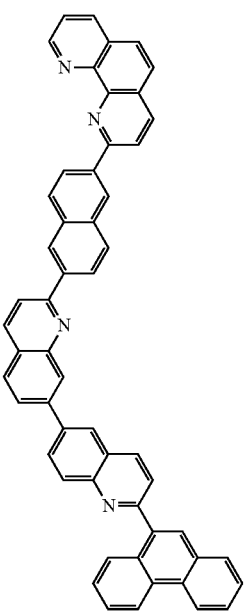
245
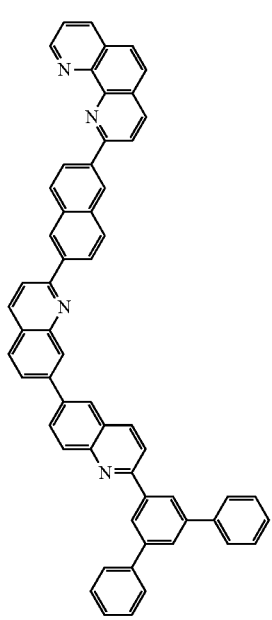

246
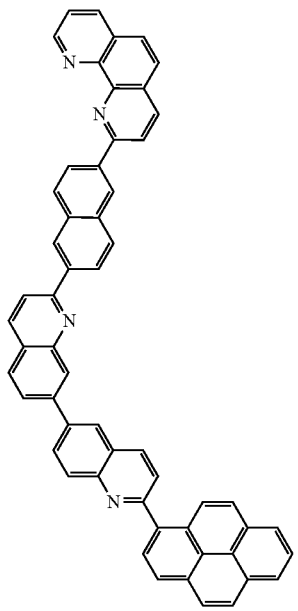
248
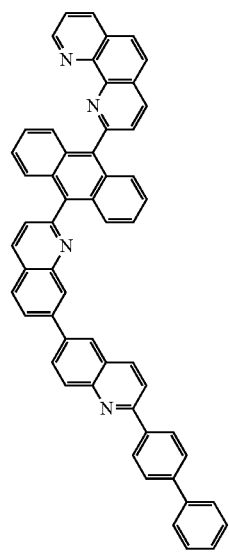
247
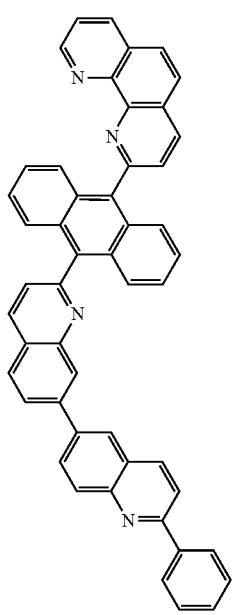
249
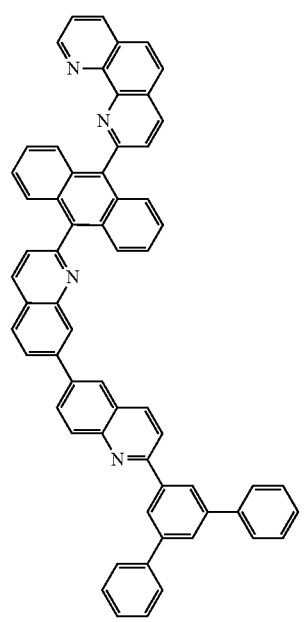

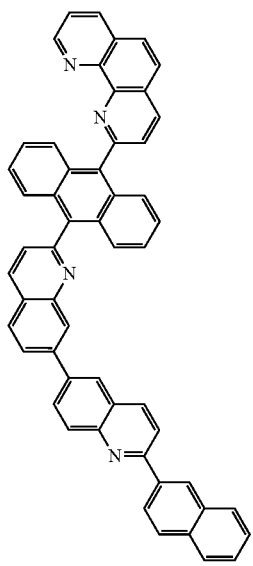
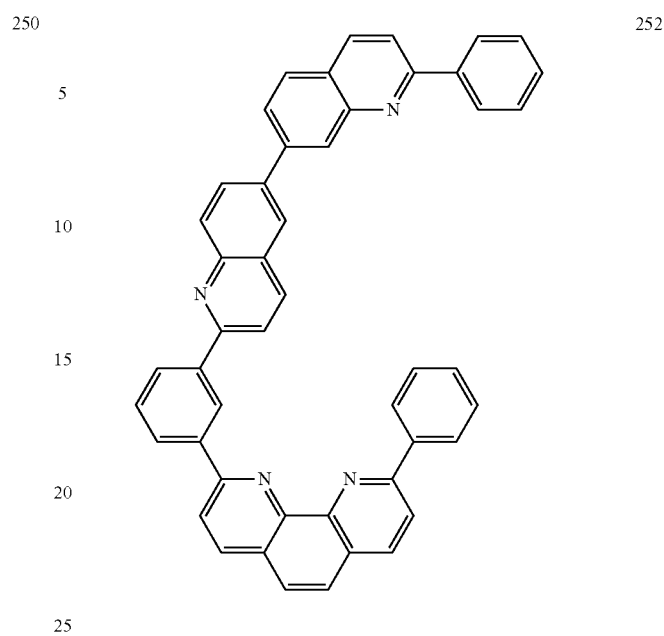
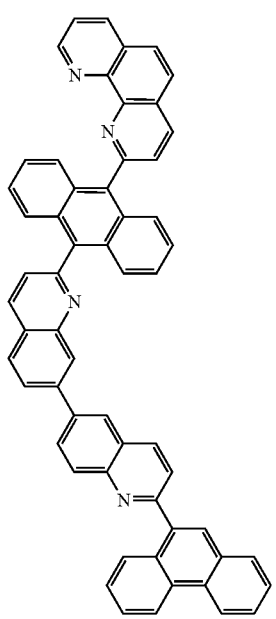
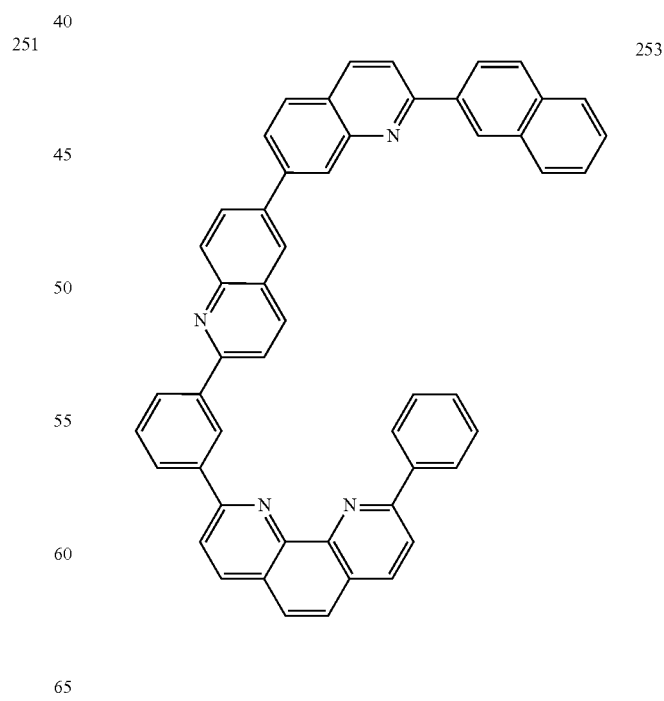

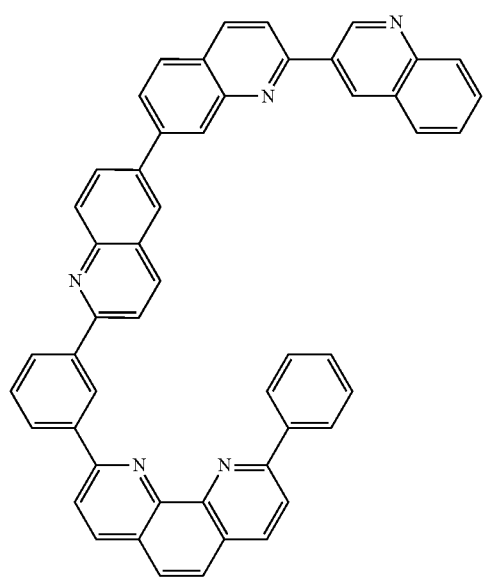
254
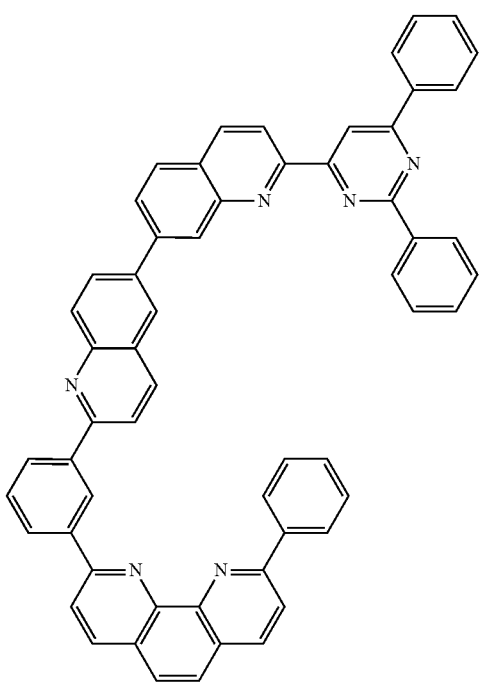
256
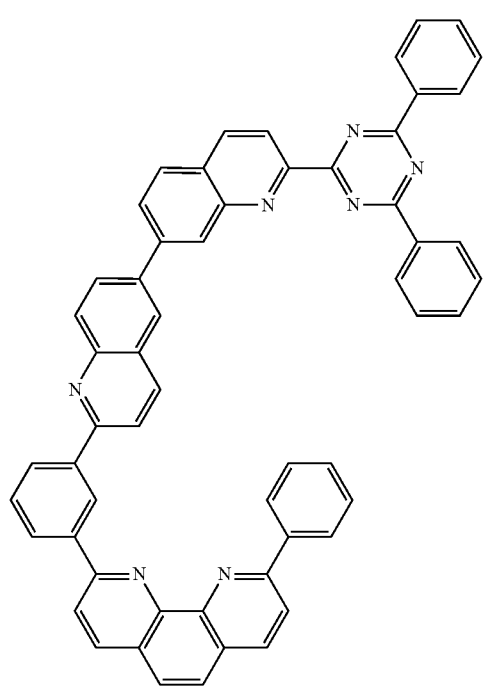
255
The compound of the one example described above may be represented by any one of compounds of the following Group III.
[Group III]
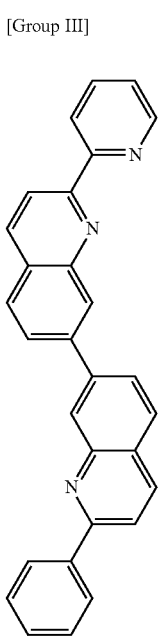
1

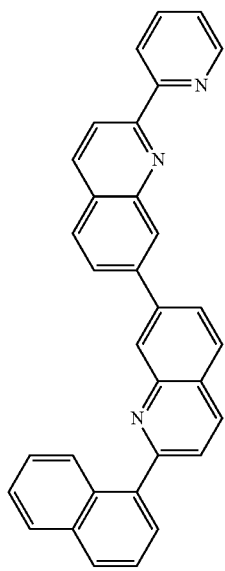
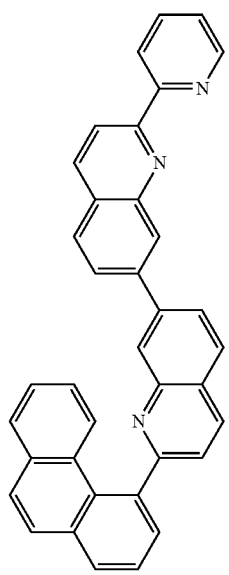
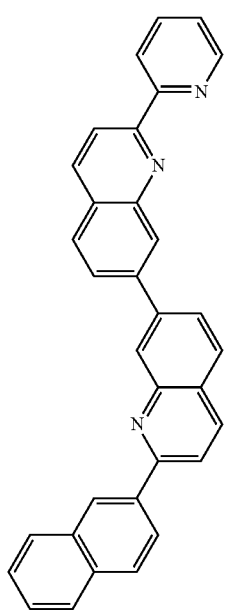
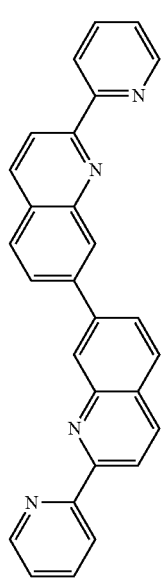

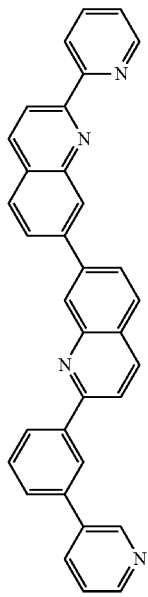
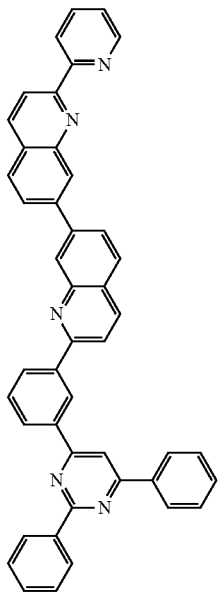
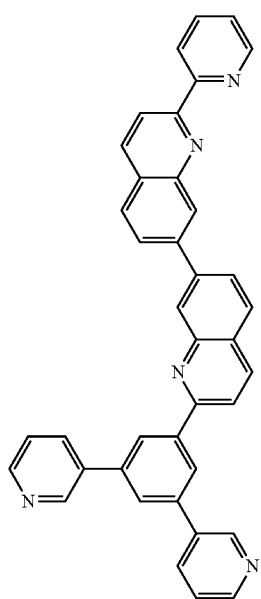
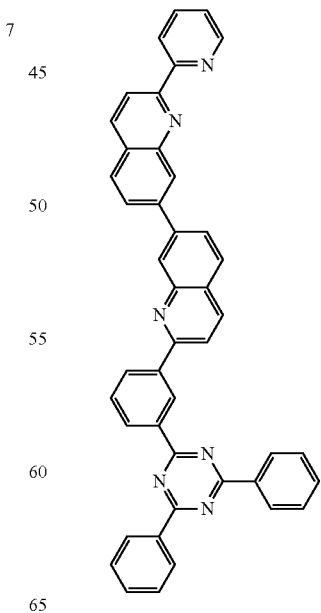

10
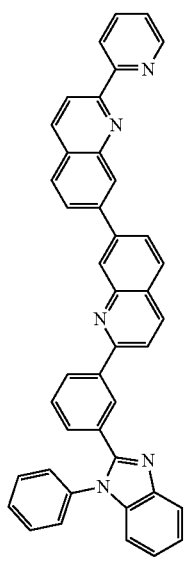
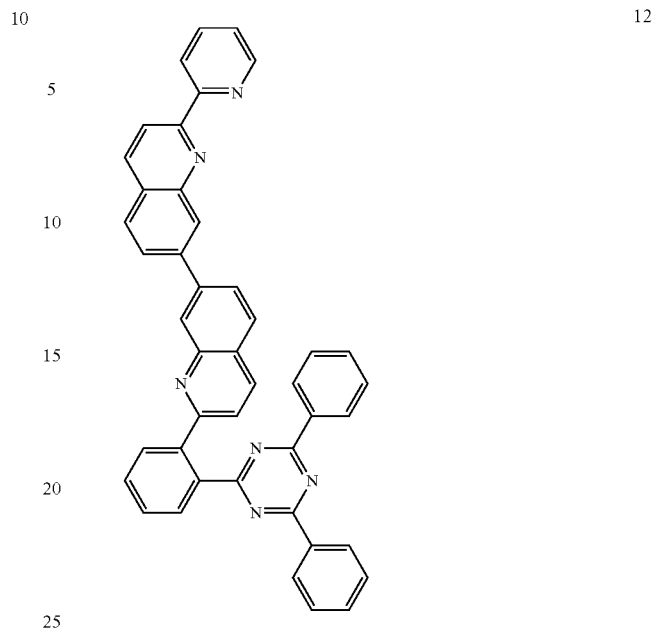
11
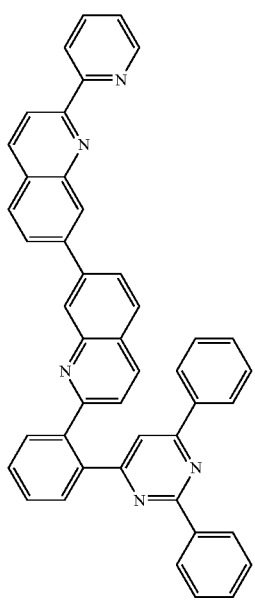
12
13
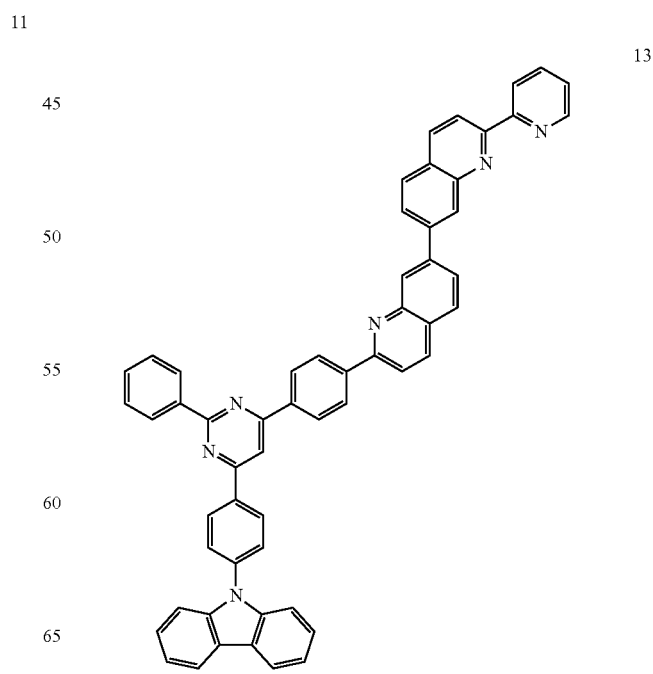

14
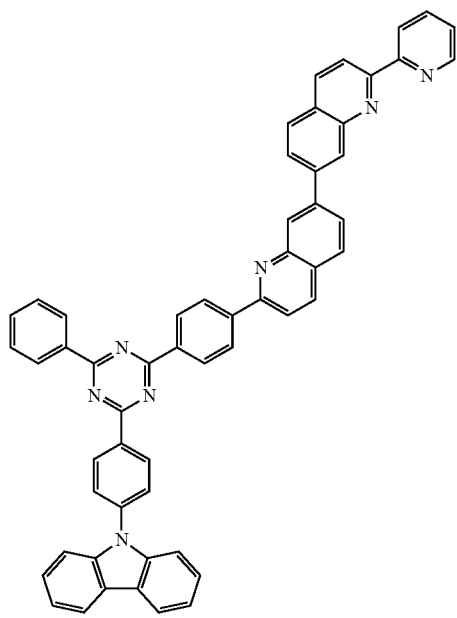
15
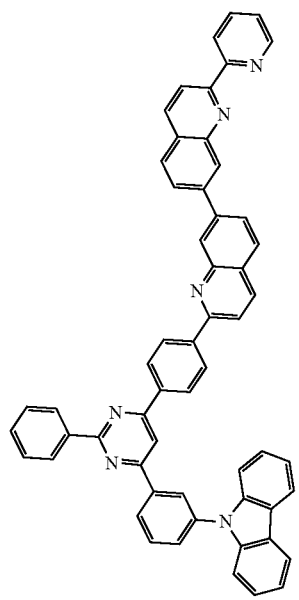
16
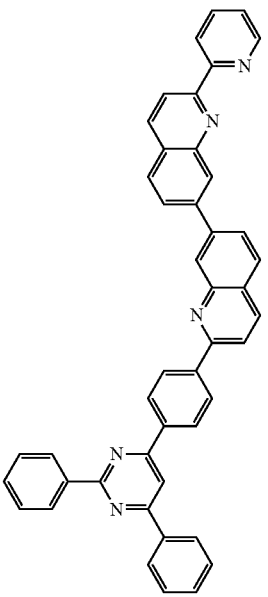
17
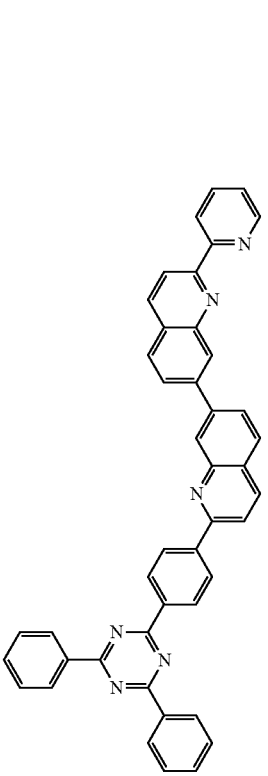

151
-continued
18
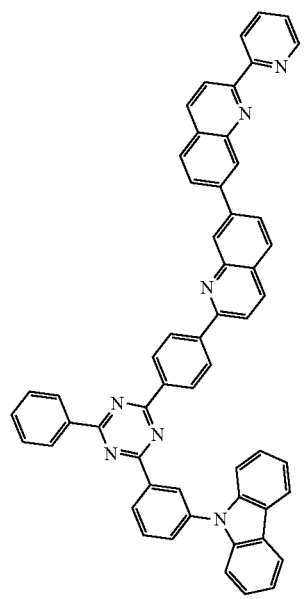
19
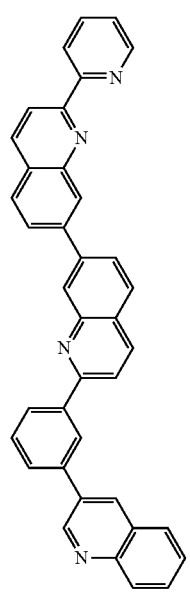
152
-continued
20
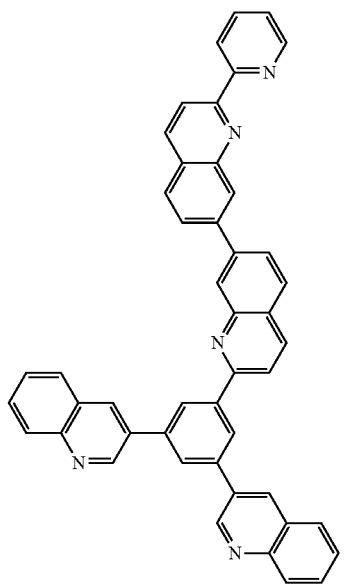
21

153
-continued
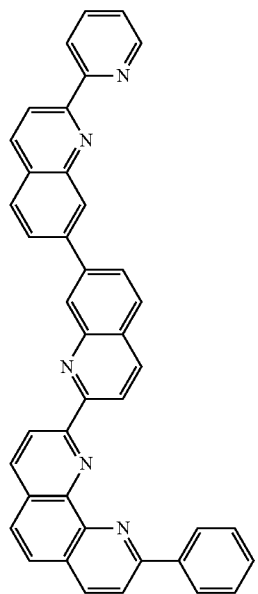
154
-continued
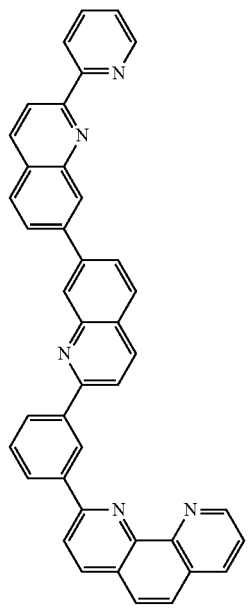
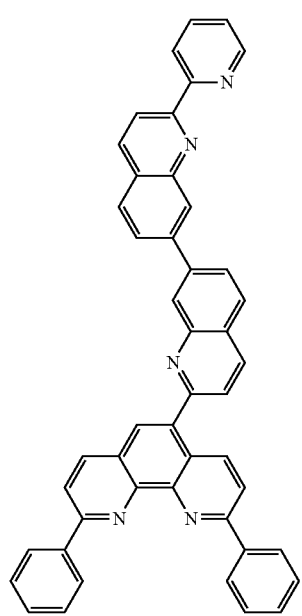
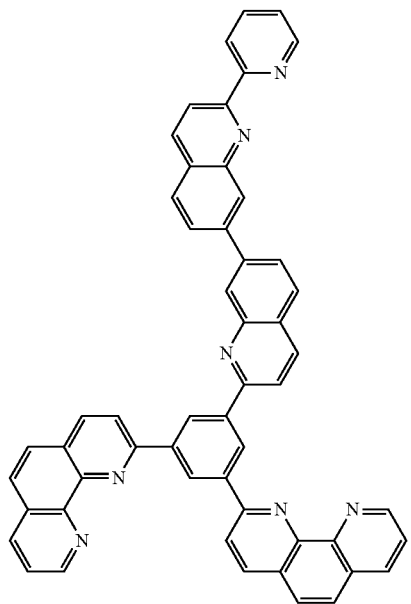

26
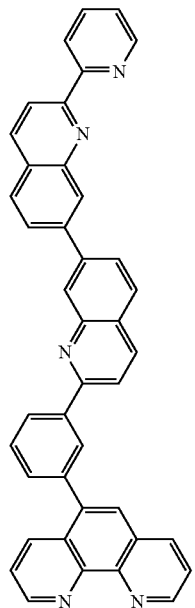
27
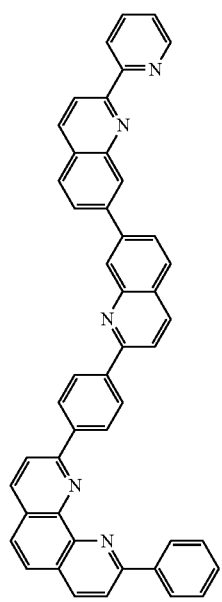
28
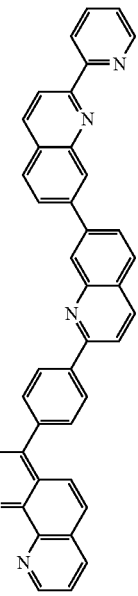
29
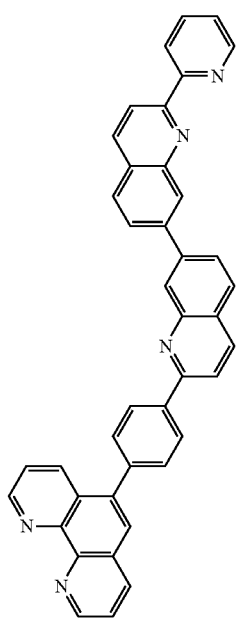

30
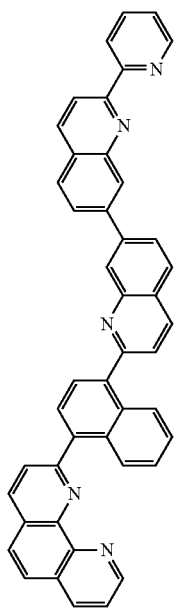
31
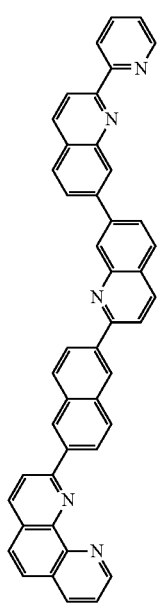
32
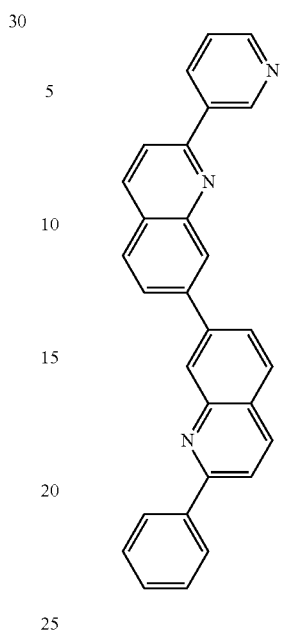
33
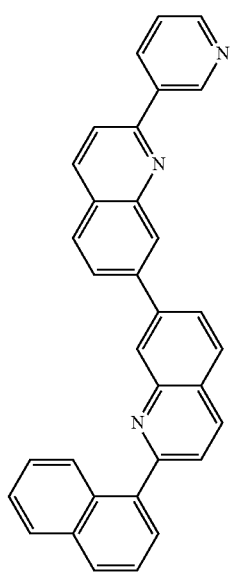

34
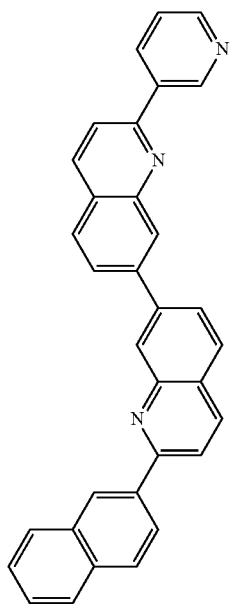
36
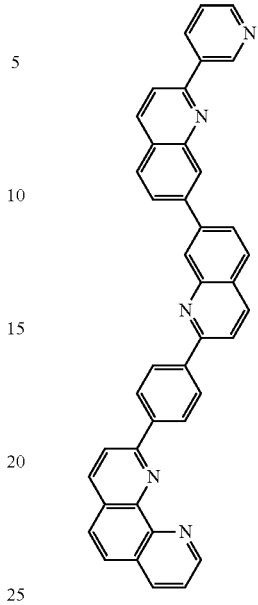
35
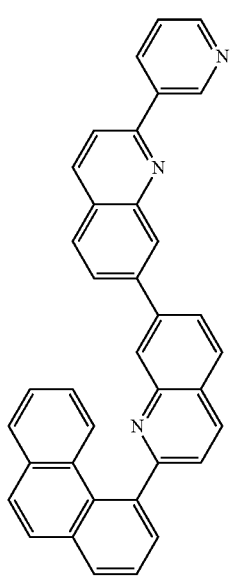
37
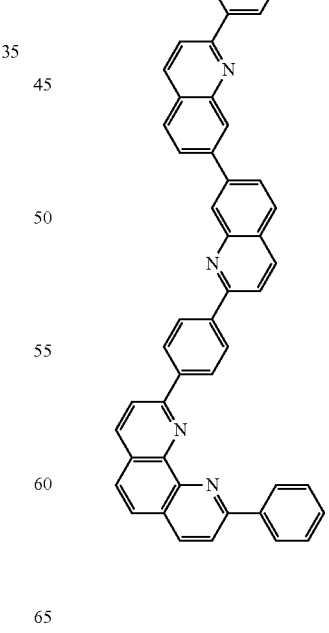

38
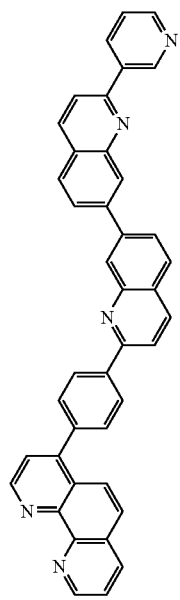
39
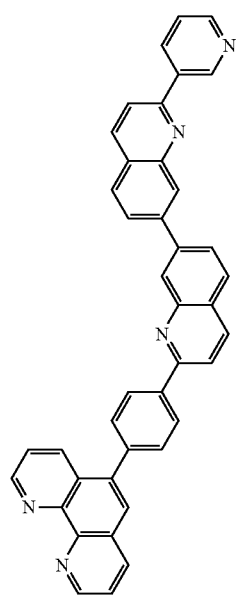
40
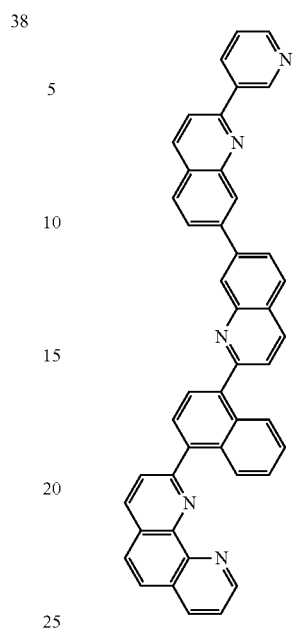
41
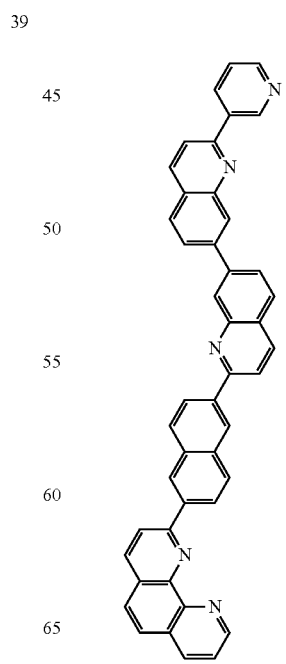

42
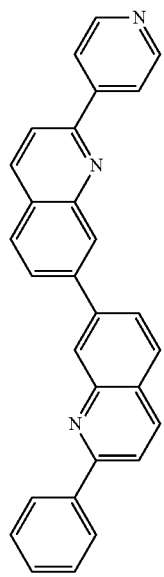
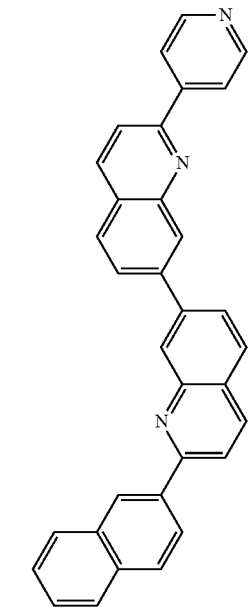
44
43
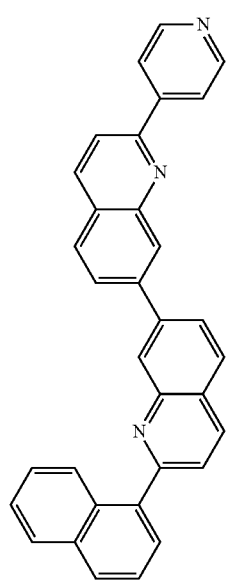
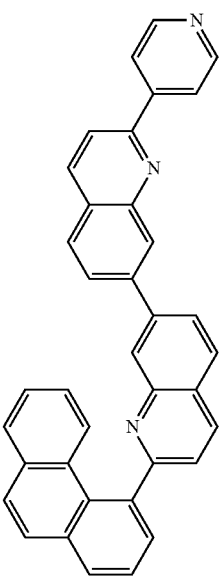
45

46
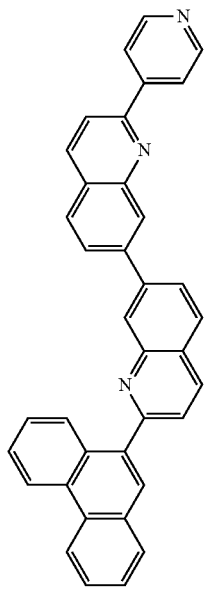
47
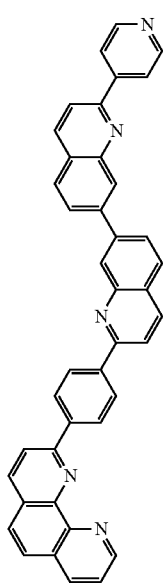
48
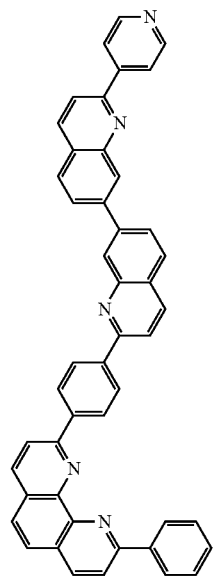
49
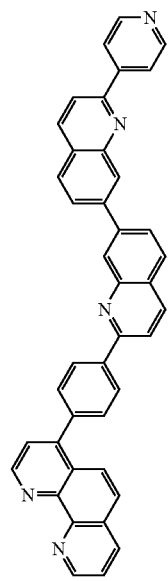

167
-continued
50
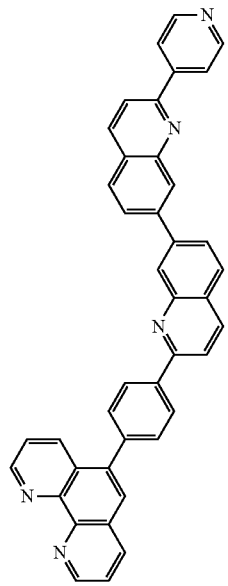
168
-continued
52
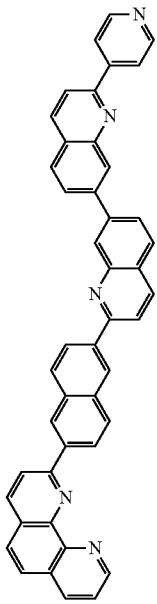
51
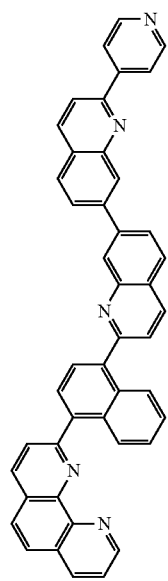
53
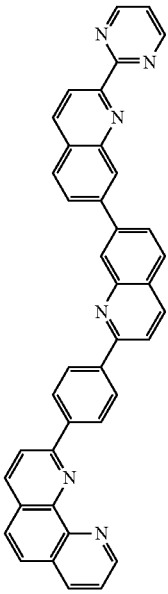

54
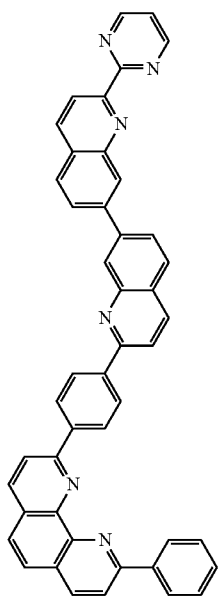
55
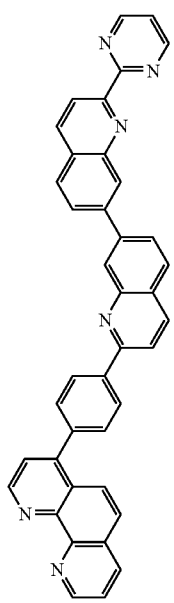
56
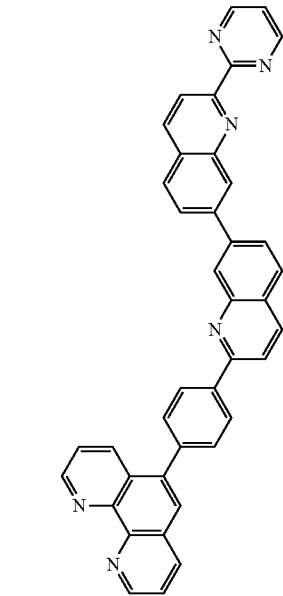
57
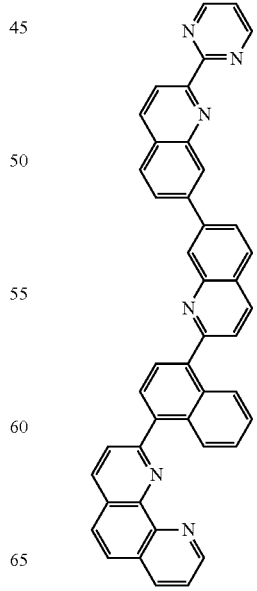

-continued
58
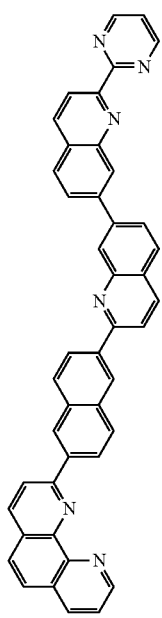
59
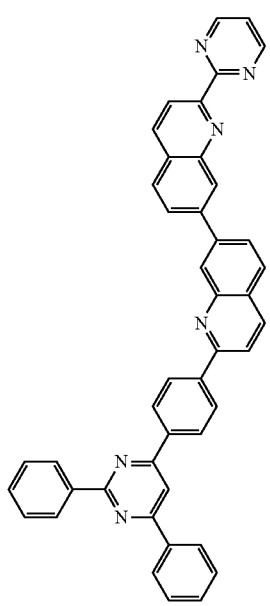
-continued
60
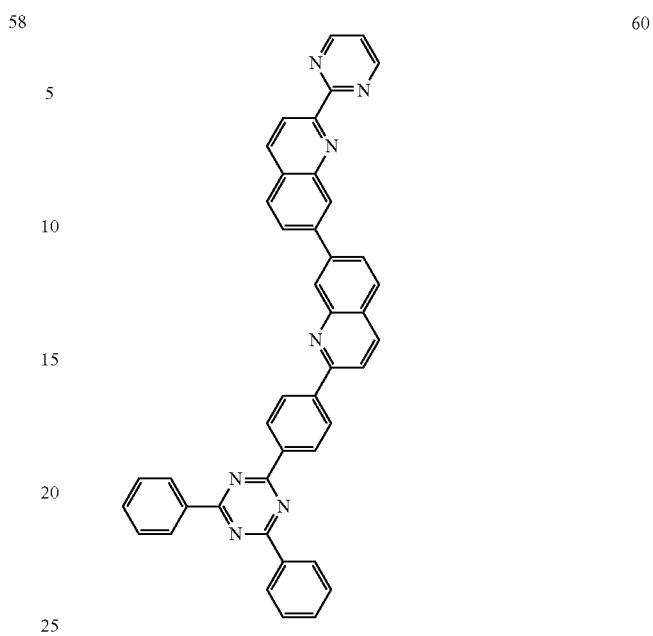
61
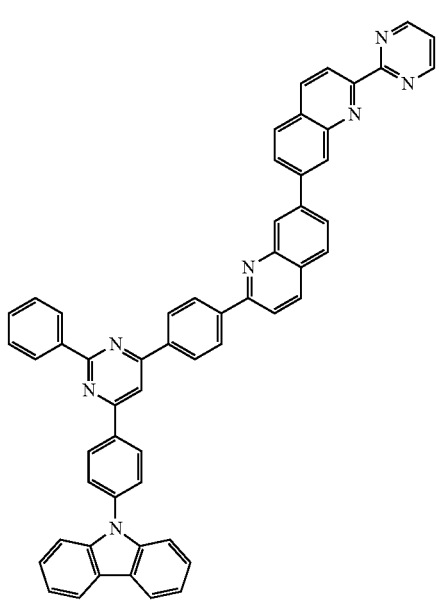

173
-continued
62
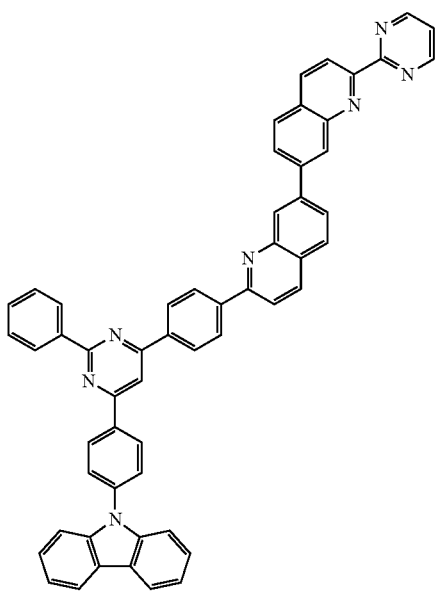
63
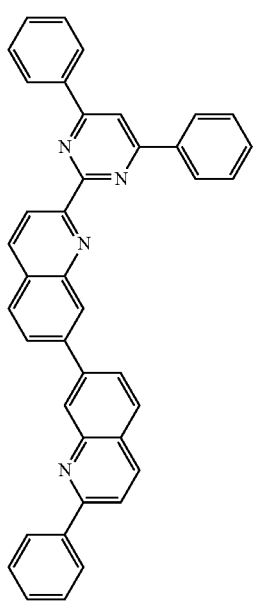
174
-continued
64
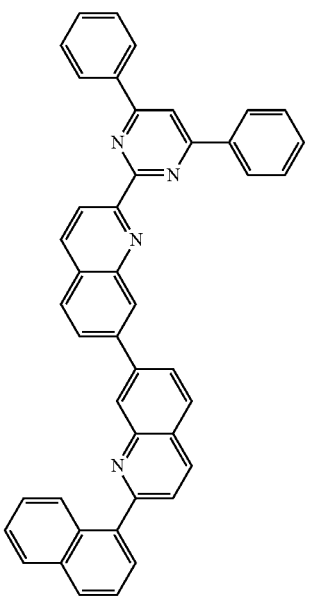
65
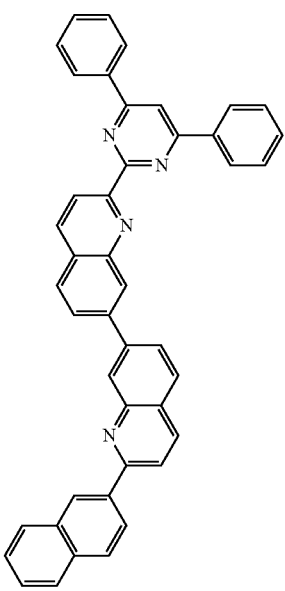

66
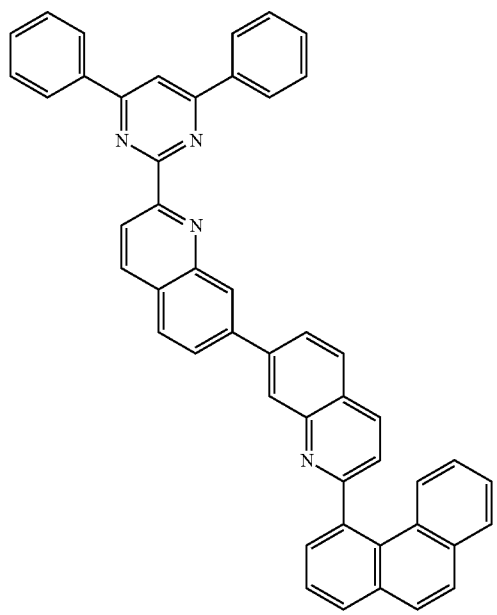
67
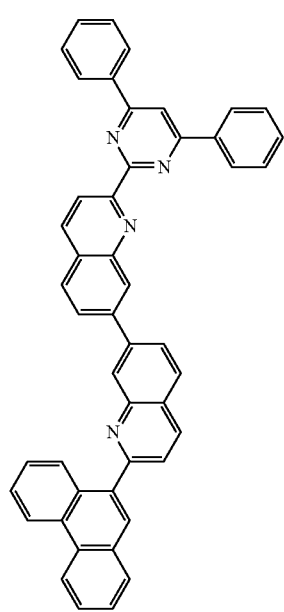
68
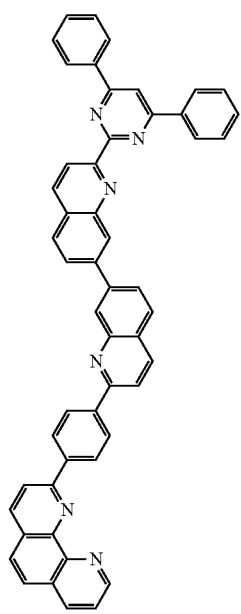
69
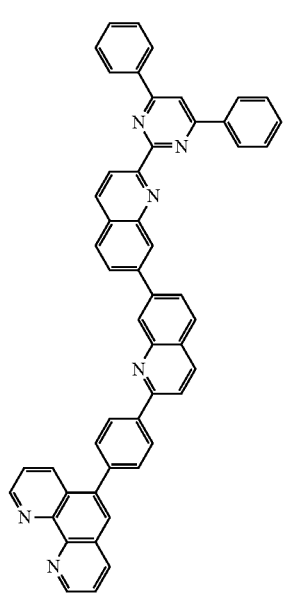

177
-continued
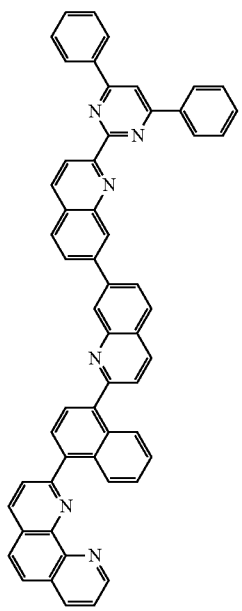
178
-continued
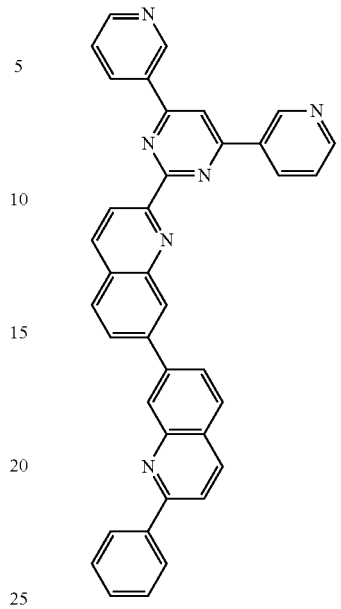
70
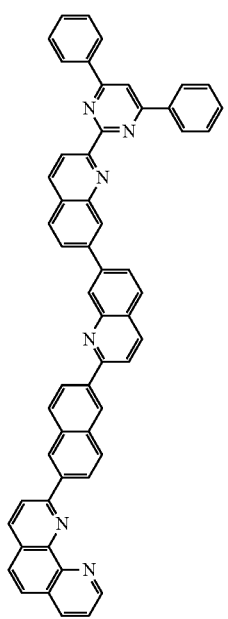
71
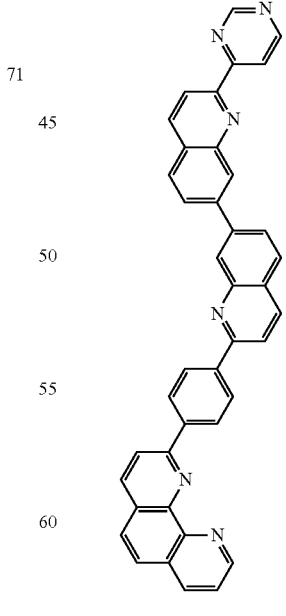
72
73

74
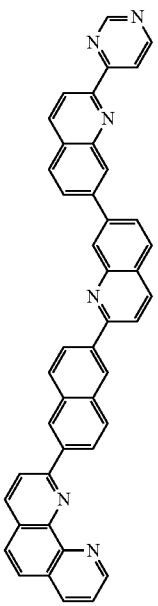
76
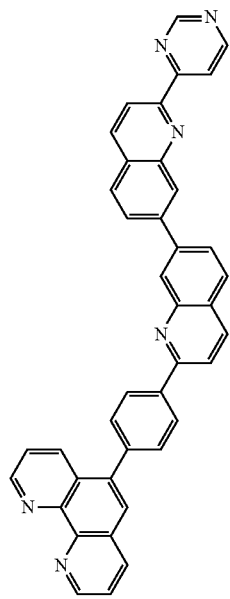
75
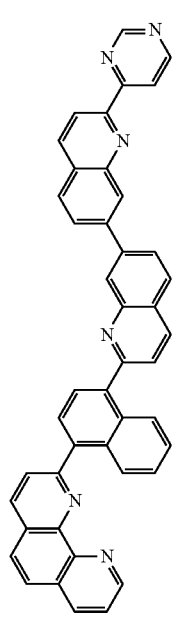
77
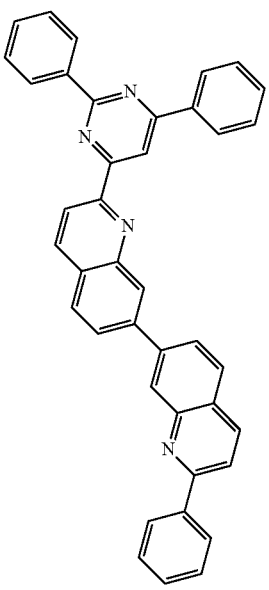

78
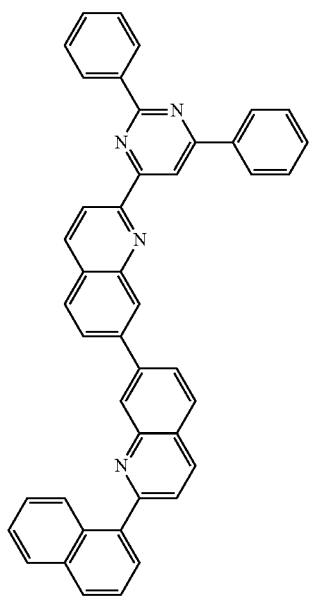
79
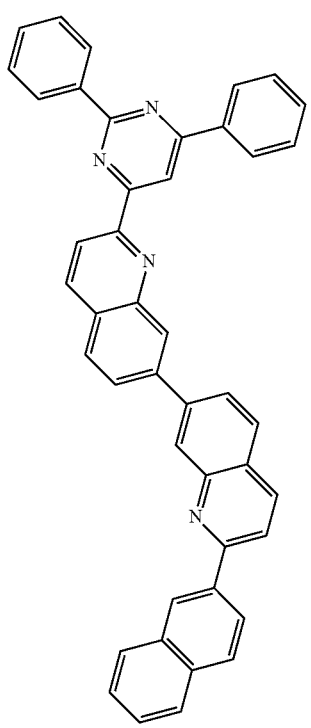
80
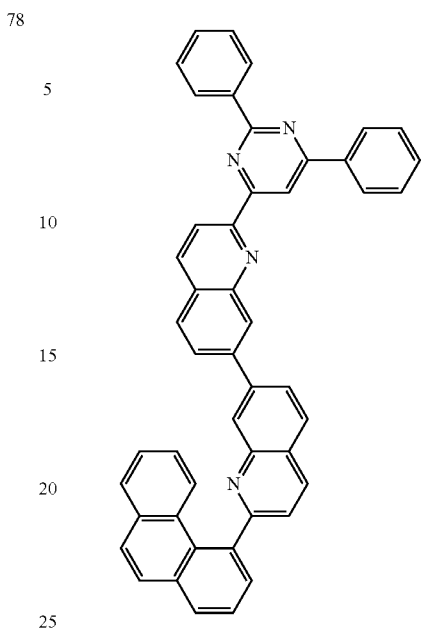
81
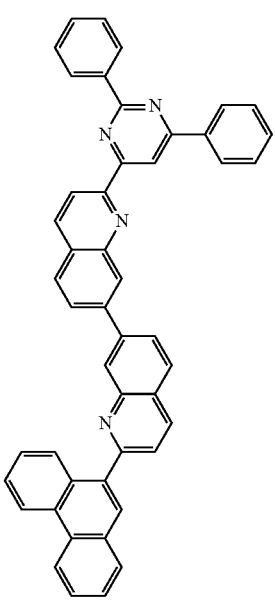

82
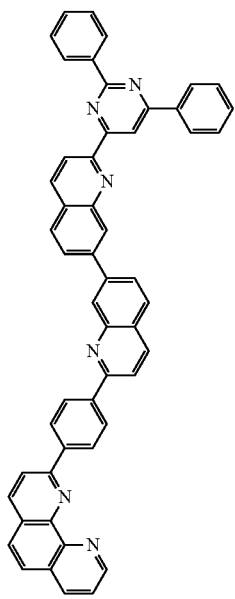
84
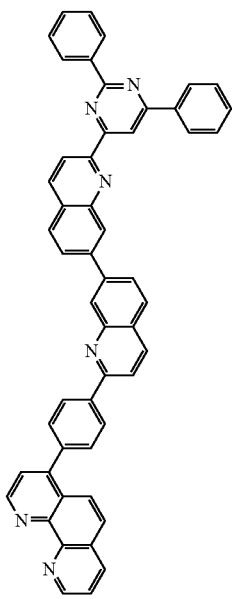
83
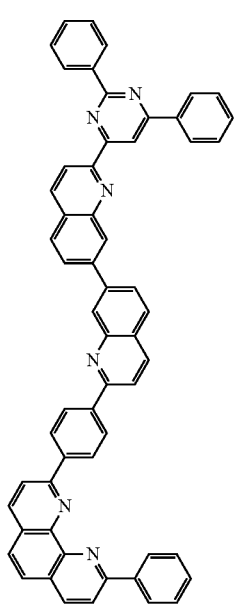
85
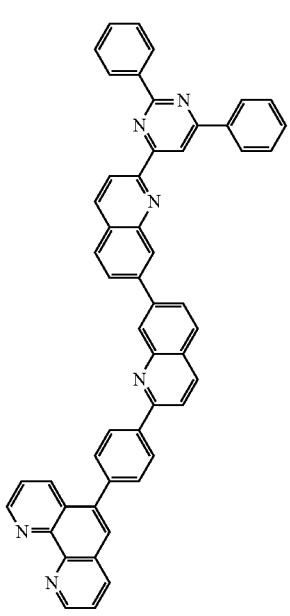

86
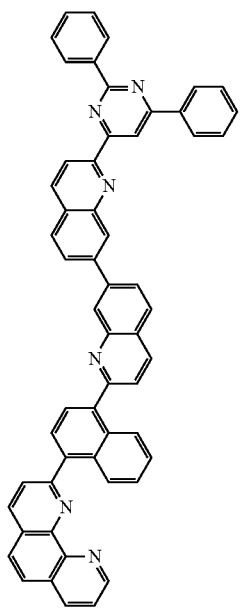
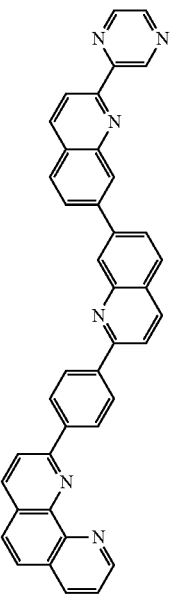
87
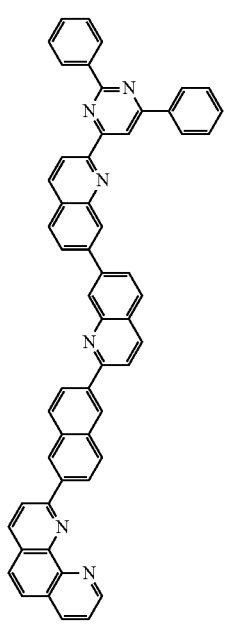
88
89
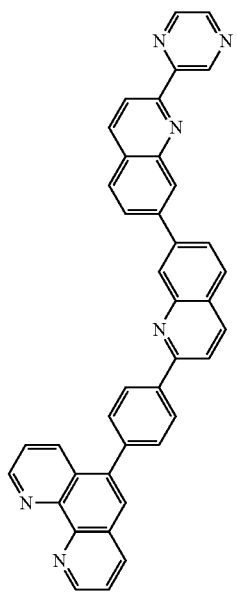

187
-continued
90
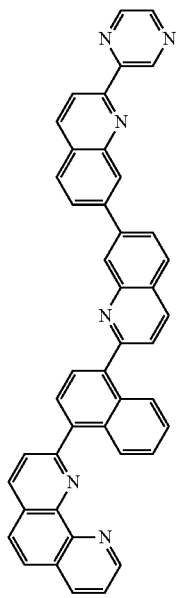
188
-continued
92
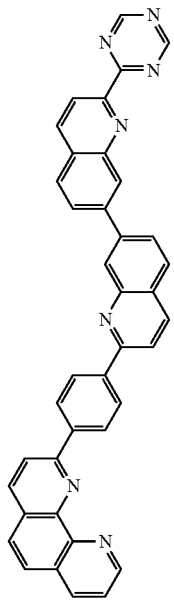
91
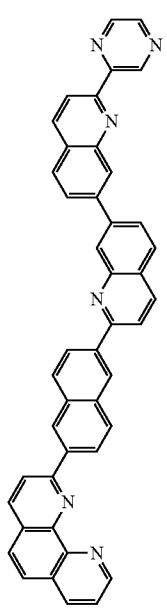
93
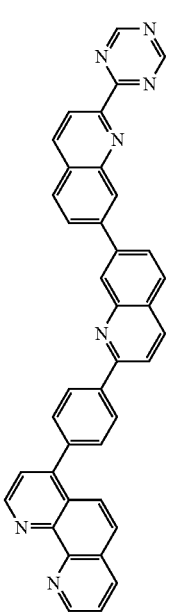

189 190
-continued -continued
94
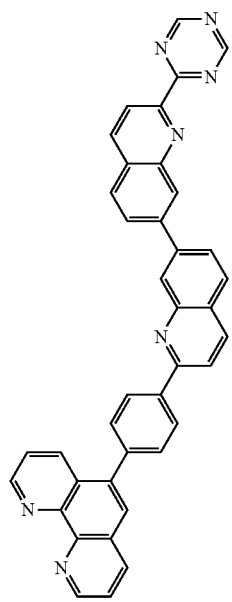
95
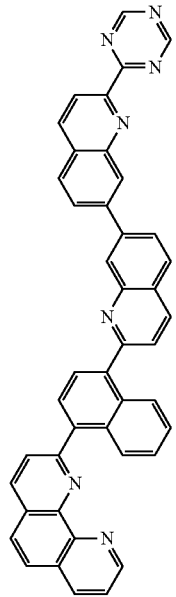
96
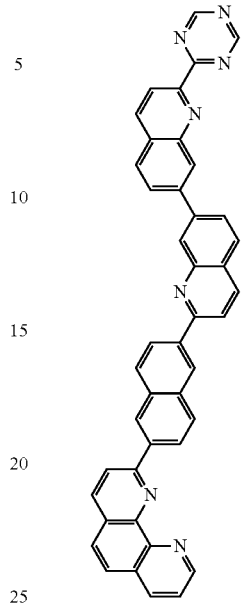
97
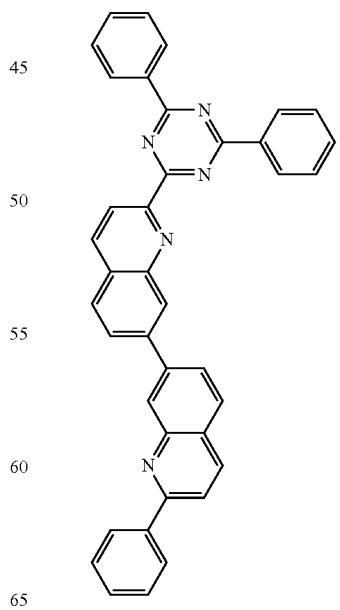

98
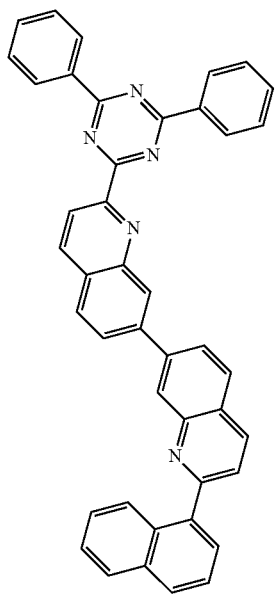
99
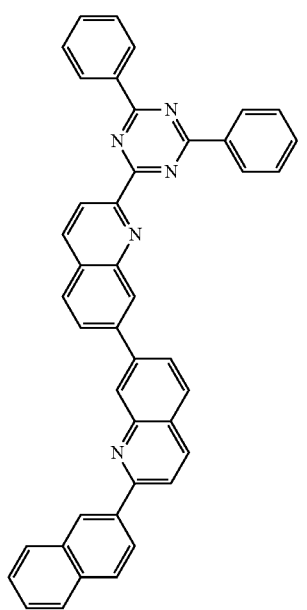
100
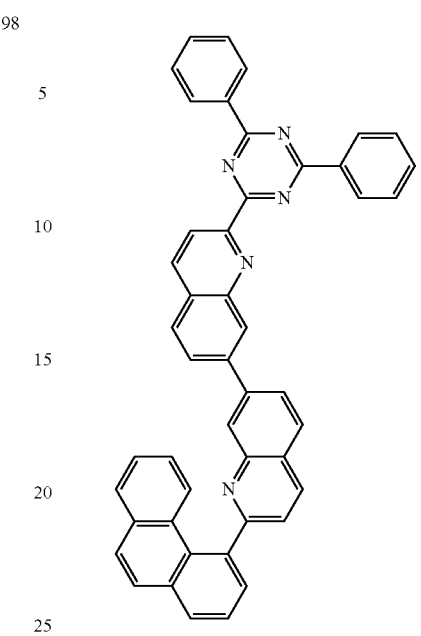
101
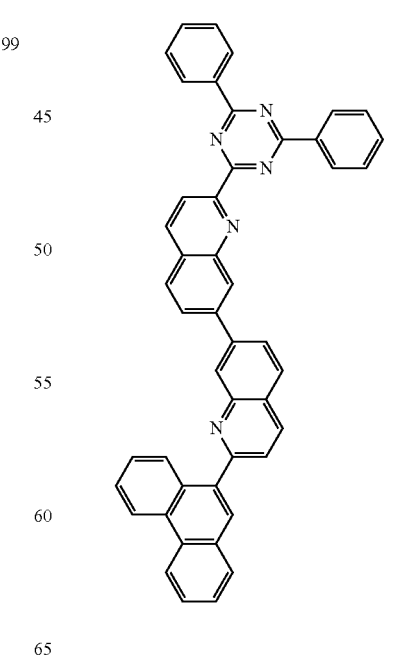

102
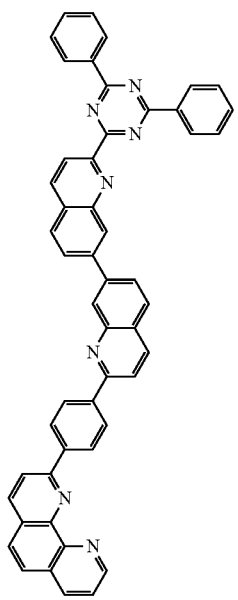
103
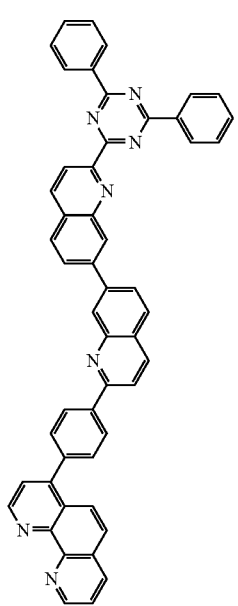
104
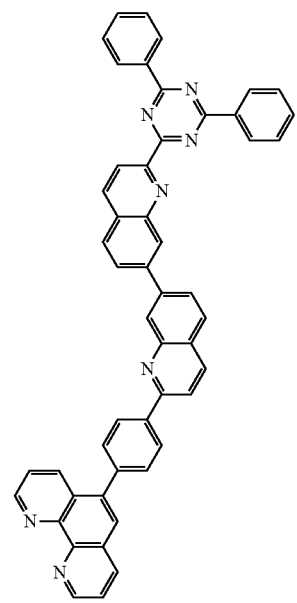
105
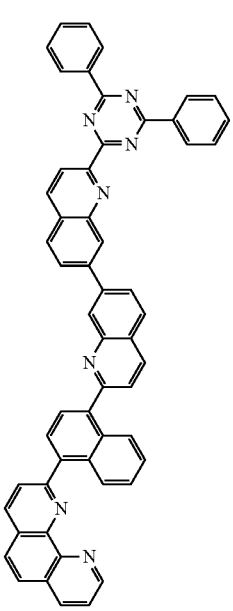

195
-continued
106
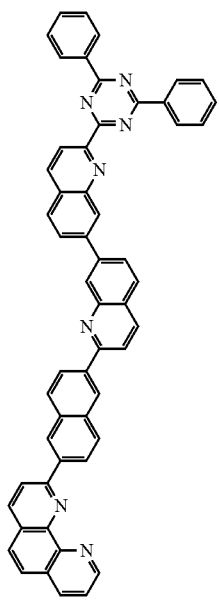
108
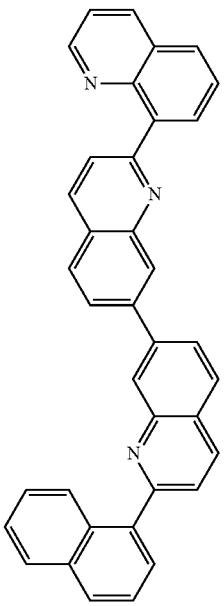
107
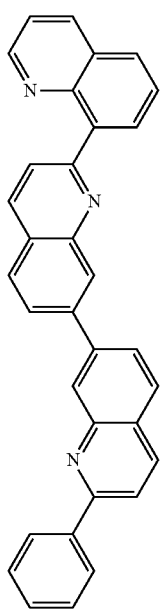
196
-continued
109
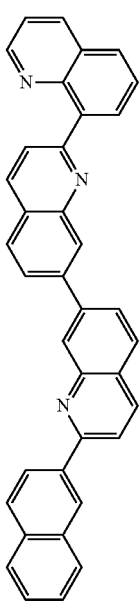

197
-continued
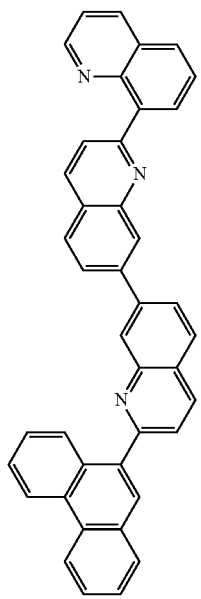
110
198
-continued
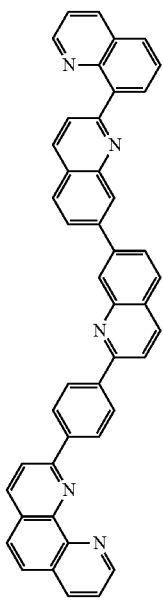
112
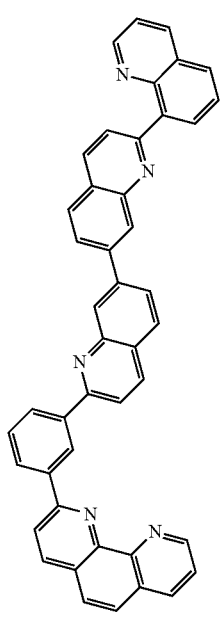
111
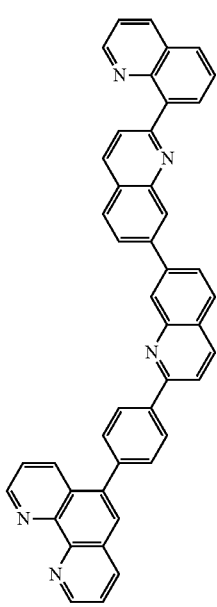
113

114
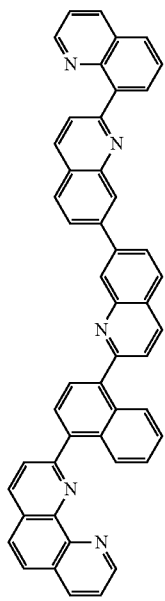
115
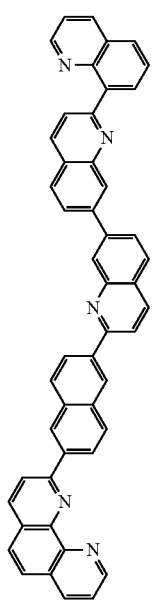
116
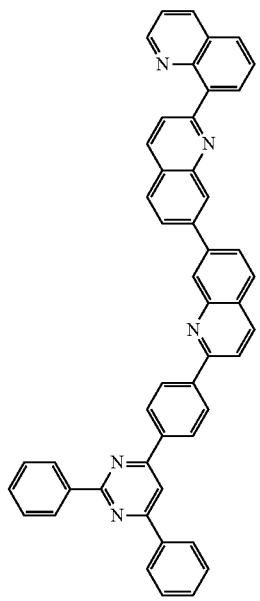
117
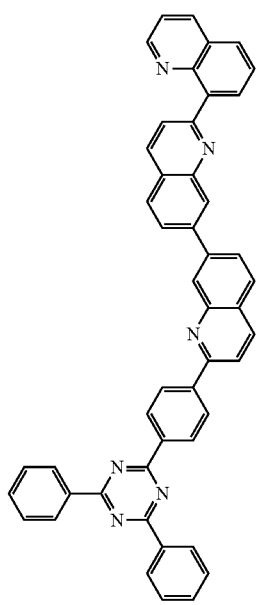

118
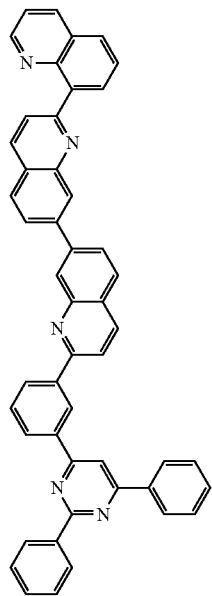
119
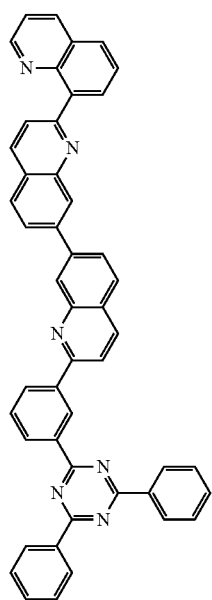
120
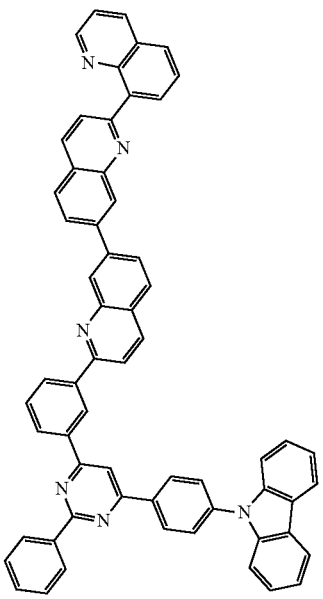
121
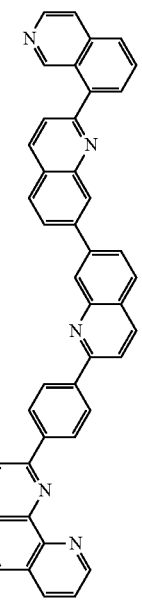

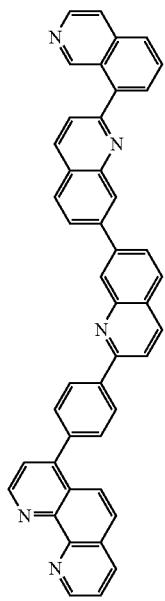
122
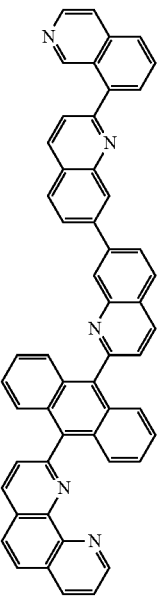
124
123
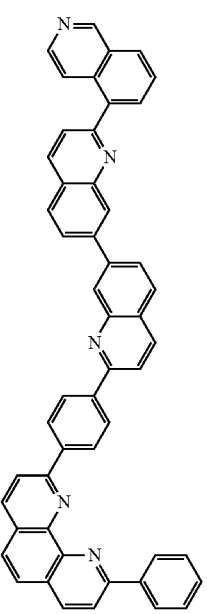
125

126
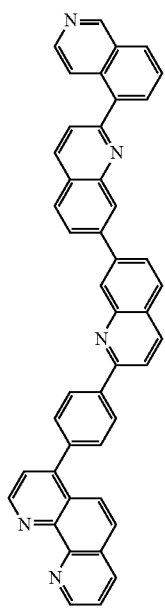
127
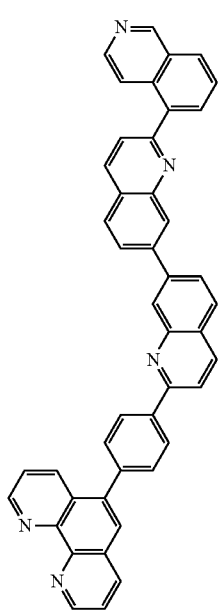
128
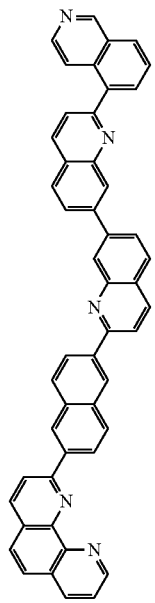
129
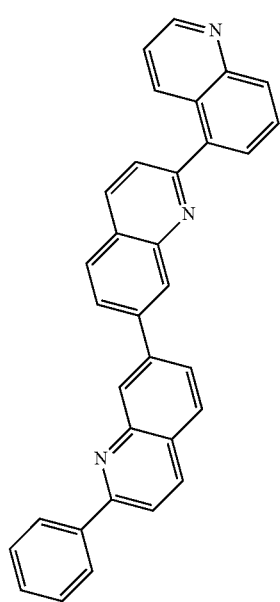

130
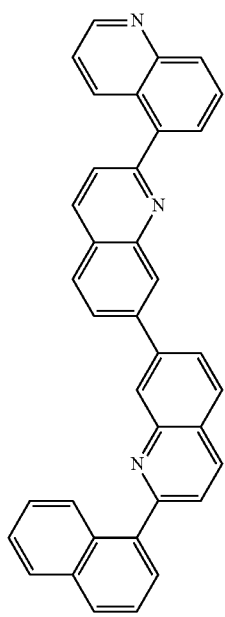
133
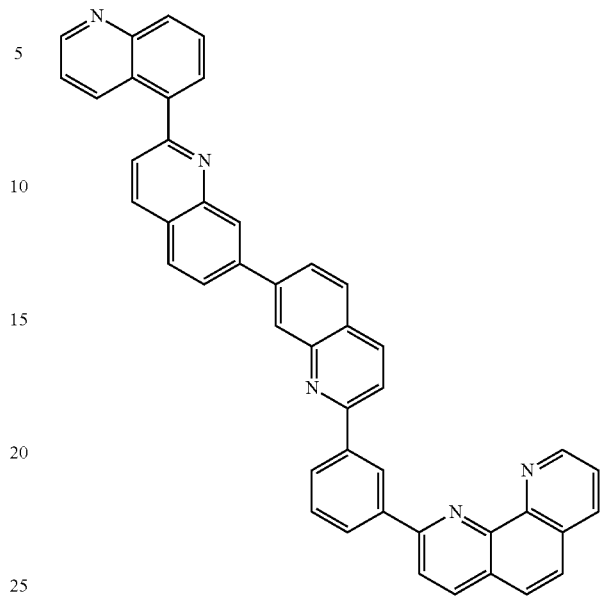
132
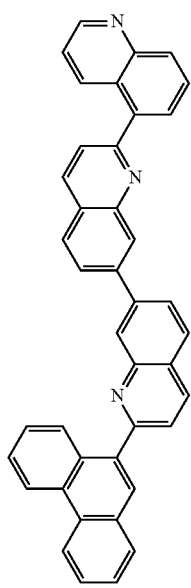
134
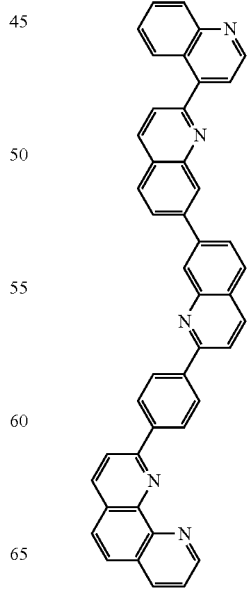

135
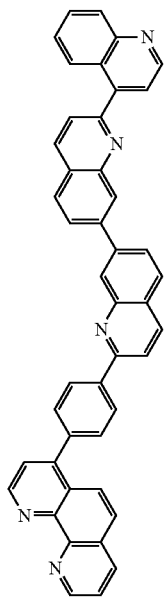
136
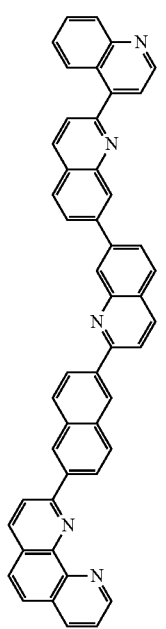
137
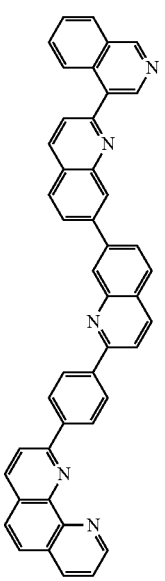

-continued
138
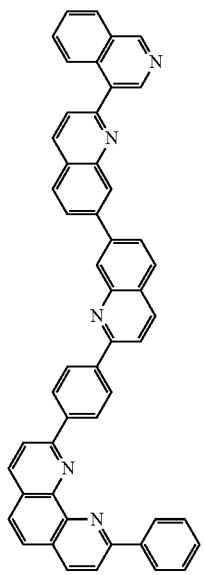
139
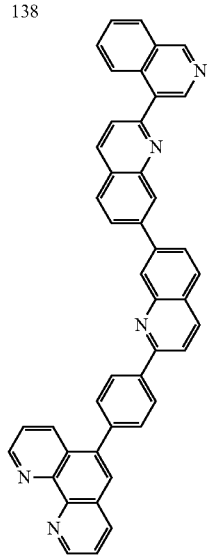
140
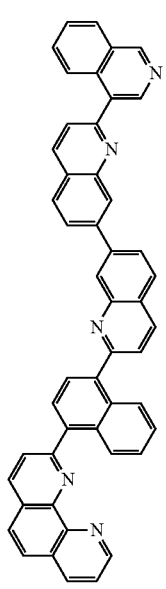
141
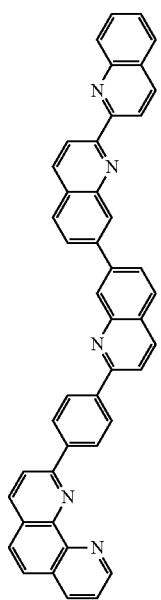

142
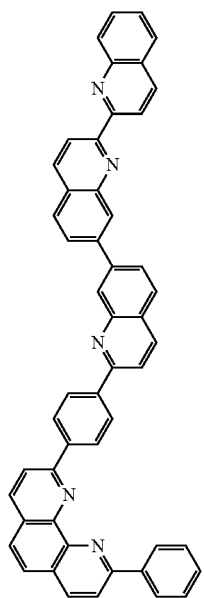
143
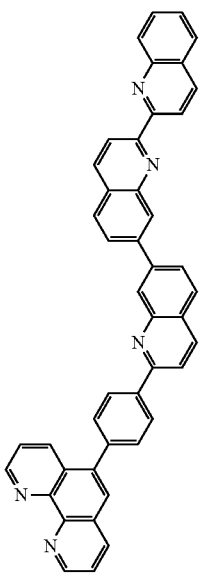
144
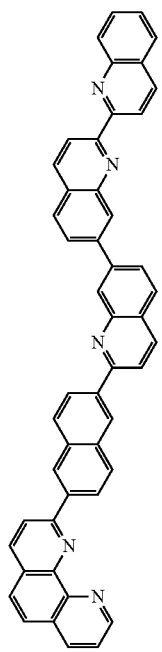
145
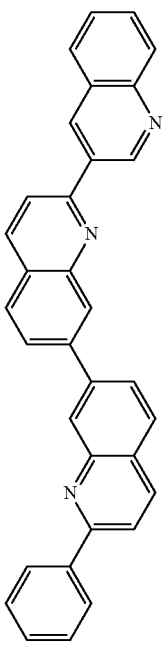

146
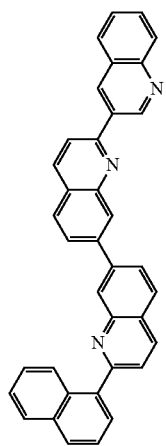
147
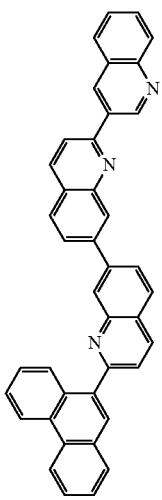
148
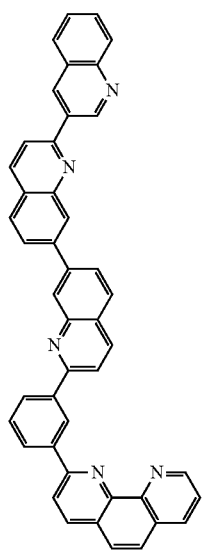
149
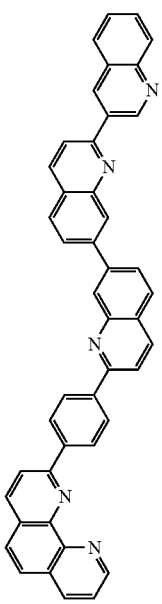

-continued
150 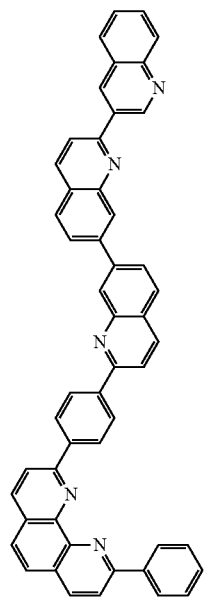 151 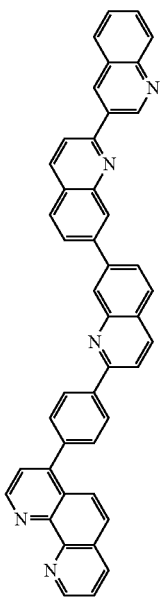
152 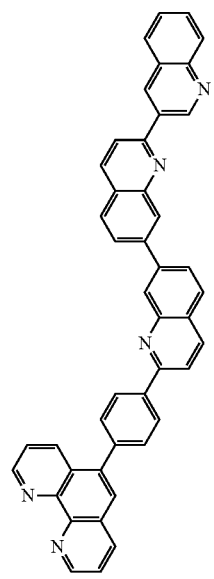 153 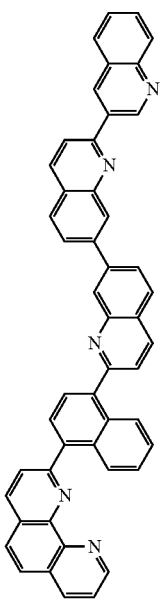

154
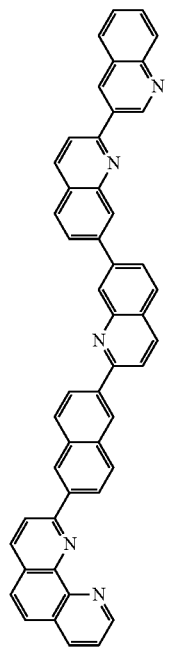
155
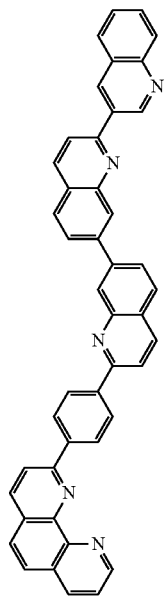
156
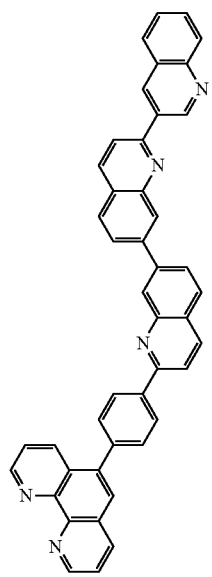
157
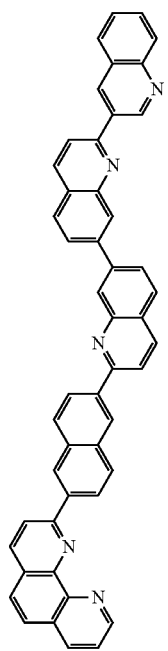

158
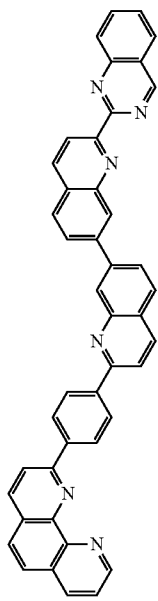
159
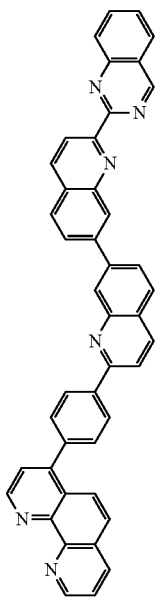
160
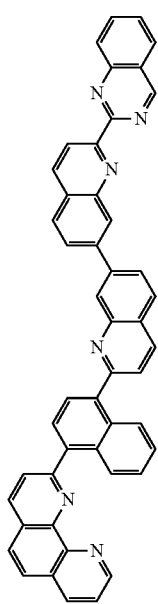
161
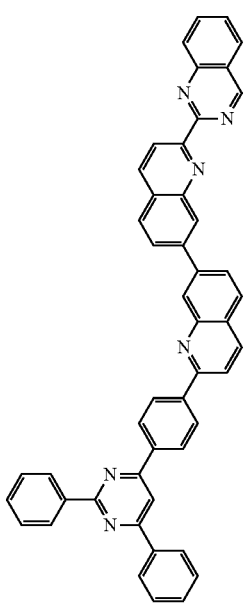

162
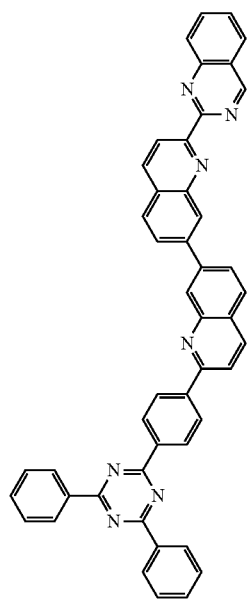
163
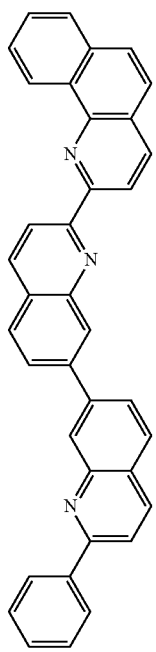
164
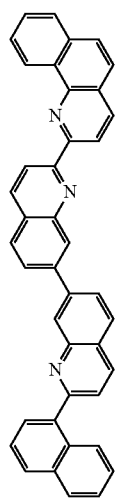
165
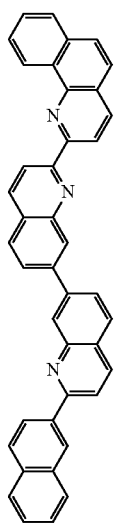

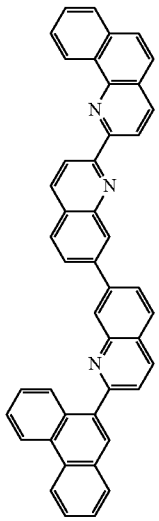
166
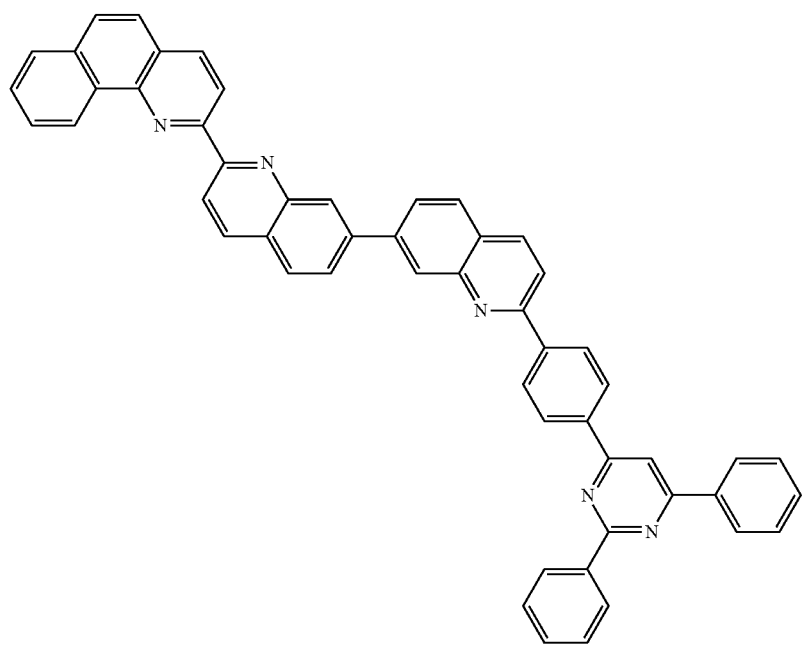
167

-continued
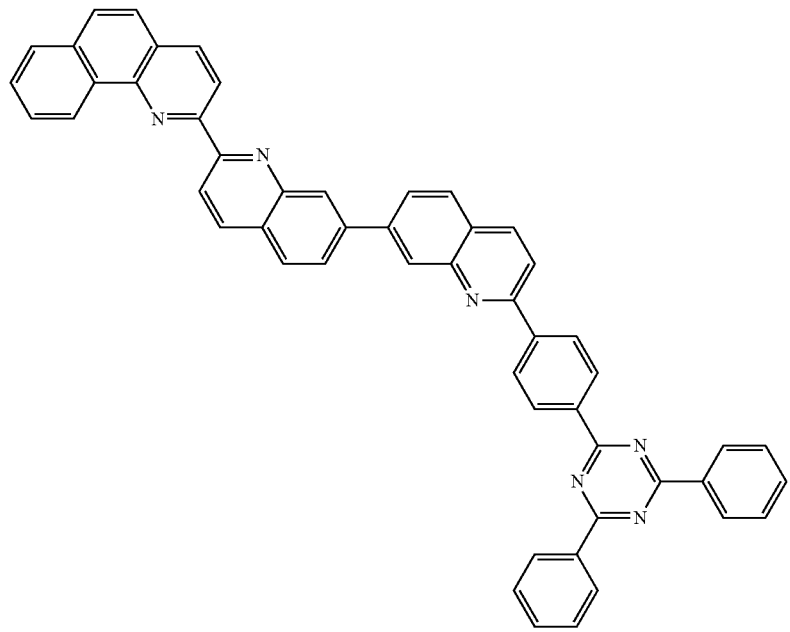
168
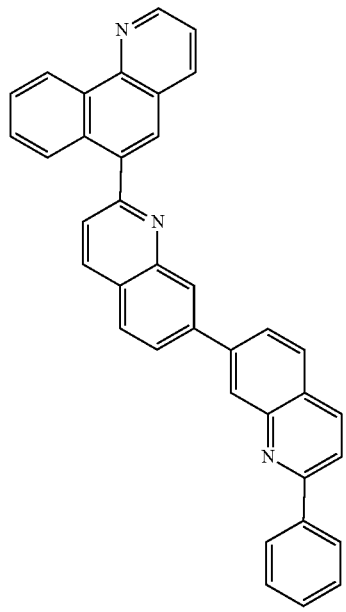
169
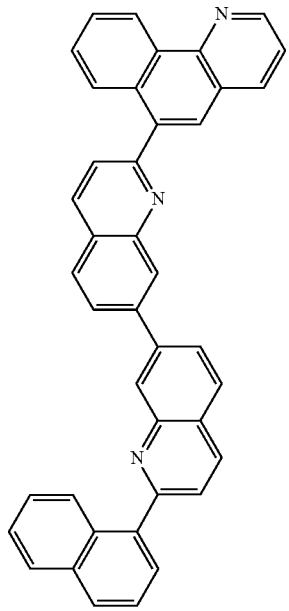
170

-continued
171 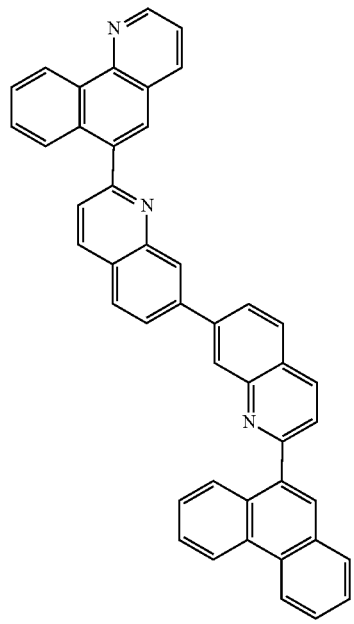
172 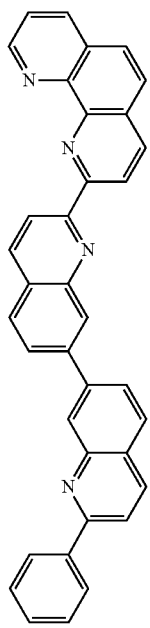
173 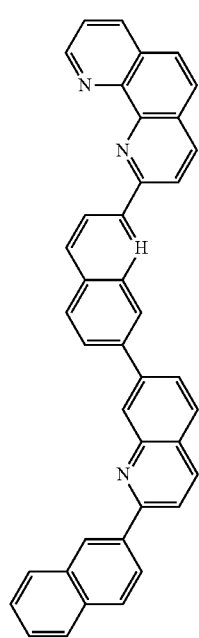
174 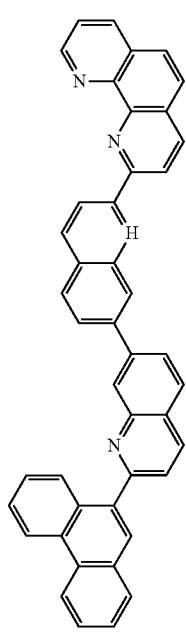

-continued
175 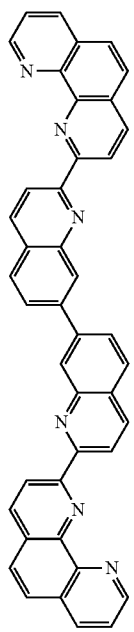 176 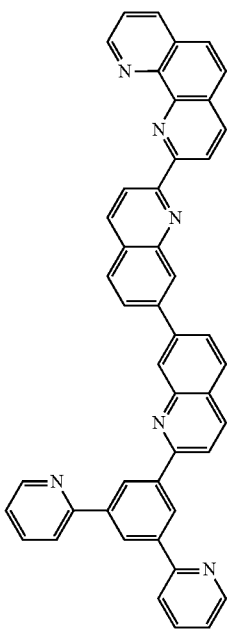
177 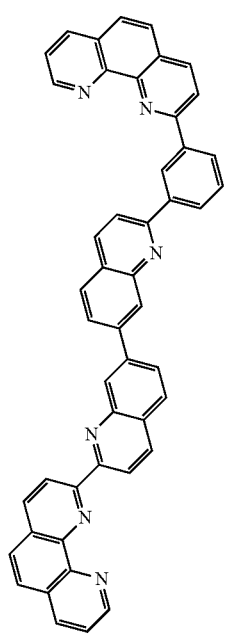 178 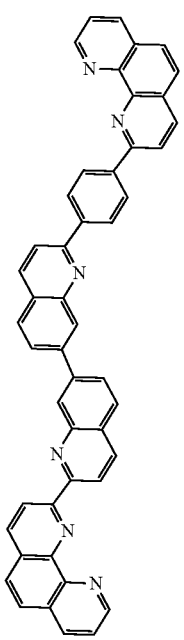

179
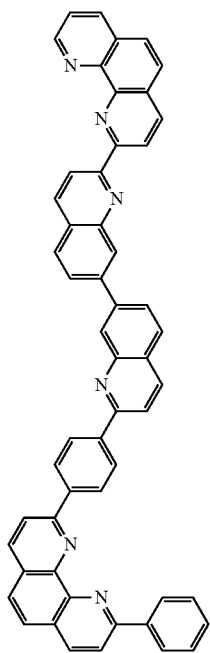
180
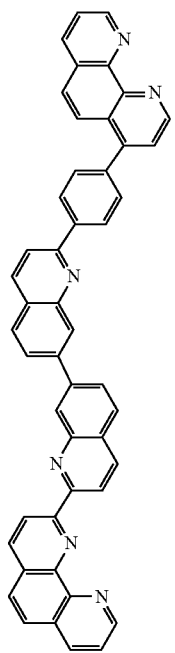
181
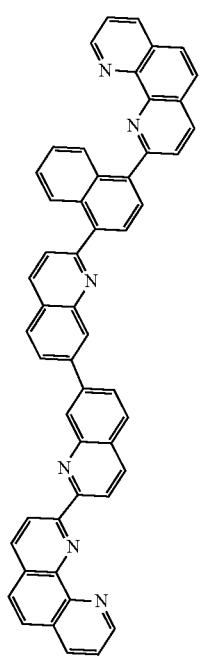
182
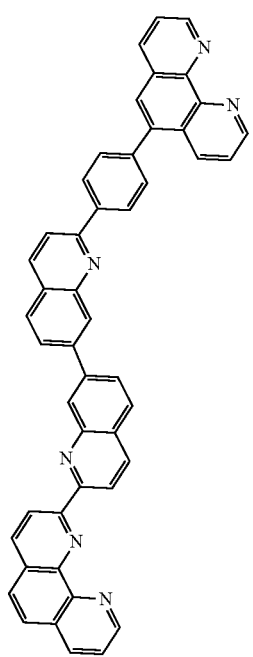

183
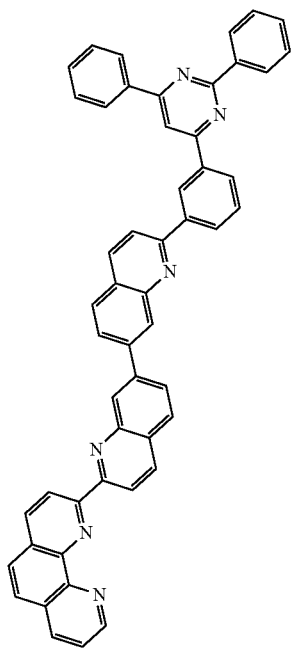
184
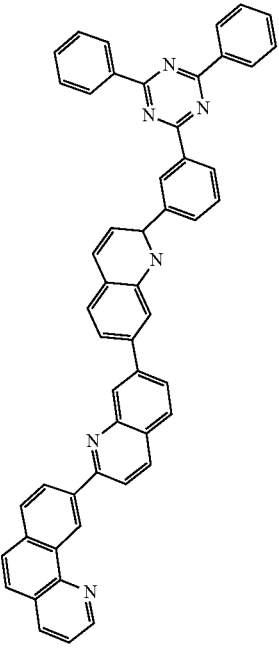
185
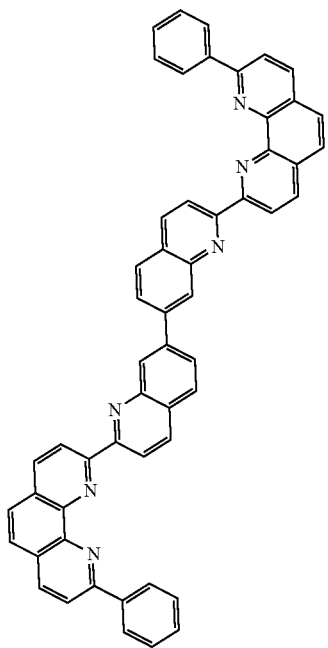
186
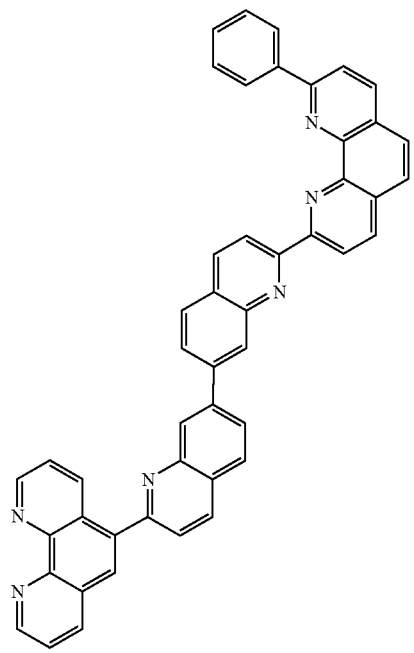

-continued
187
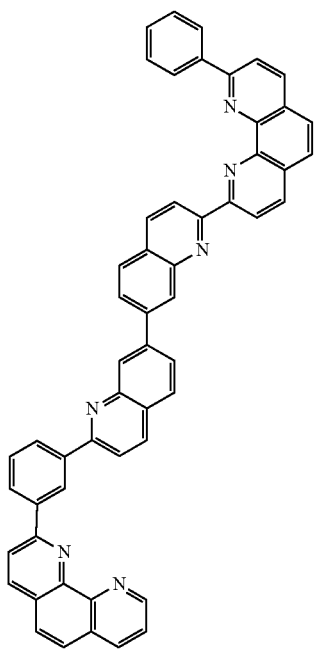
188
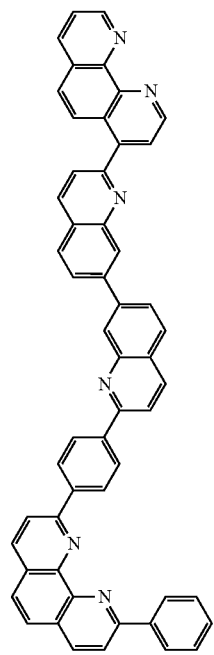
189
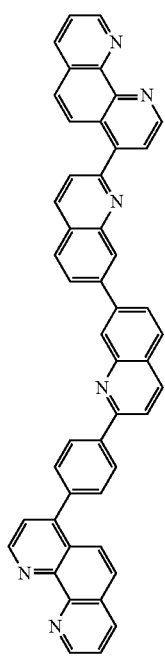
190
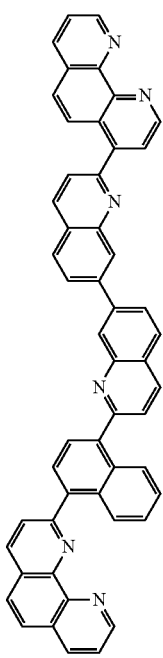

-continued
191 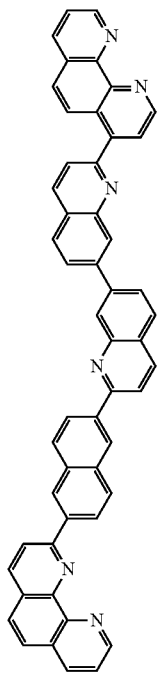 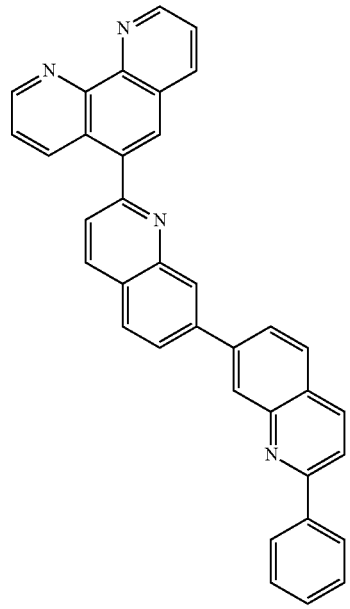 192
193 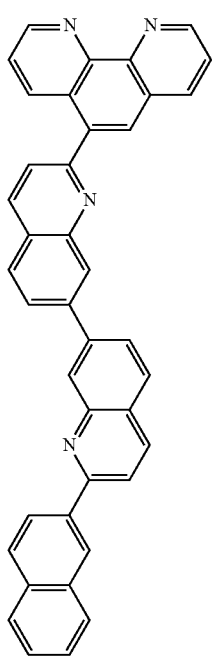 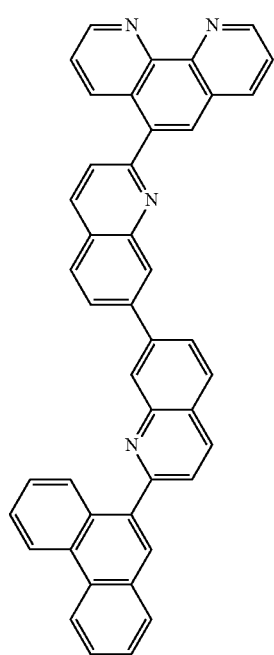 194

-continued
195
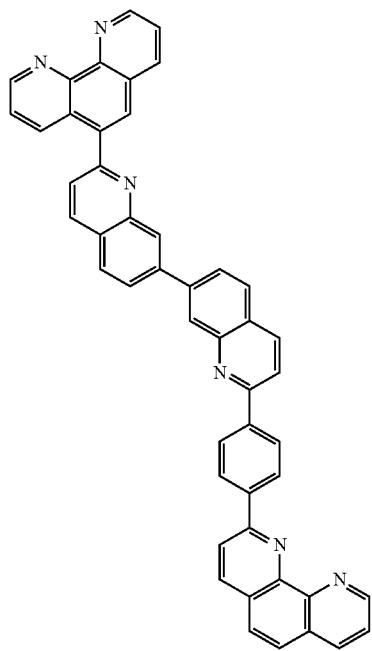
196
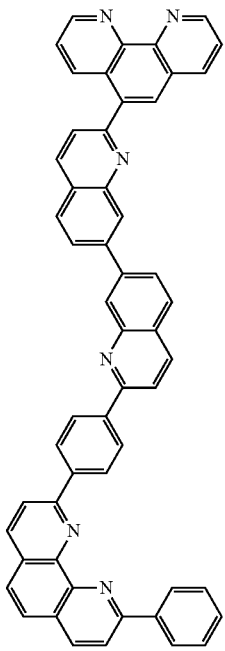
197
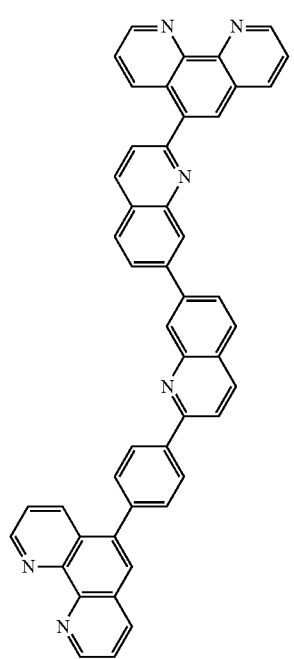
198
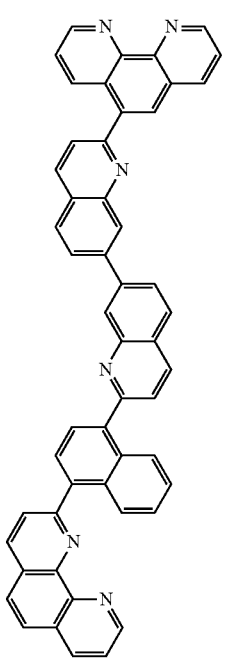

199
200
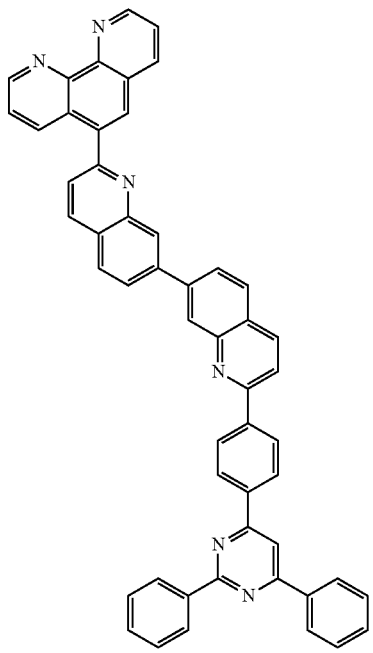
201
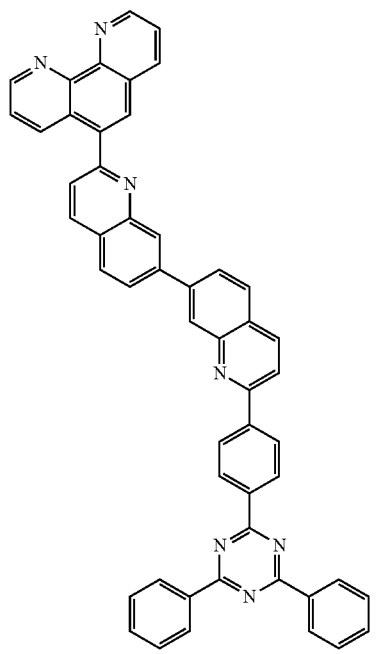
202
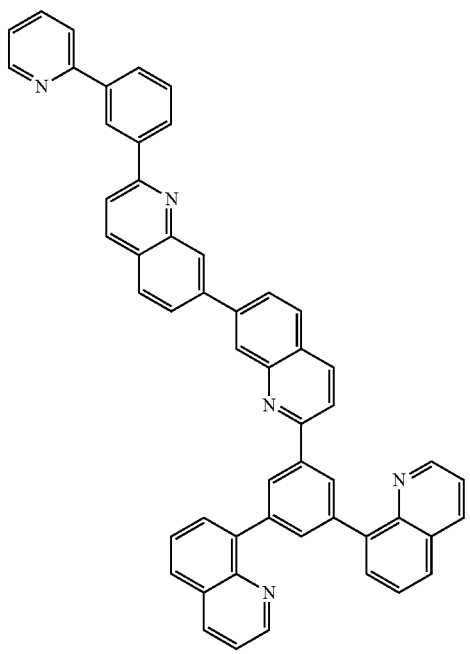

-continued
203
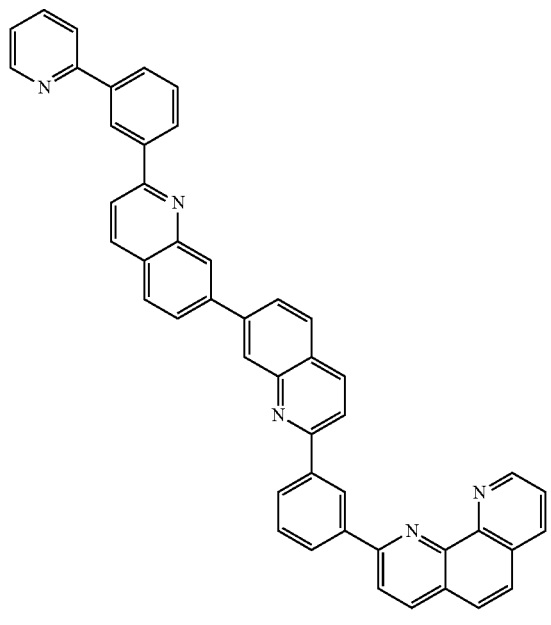
204
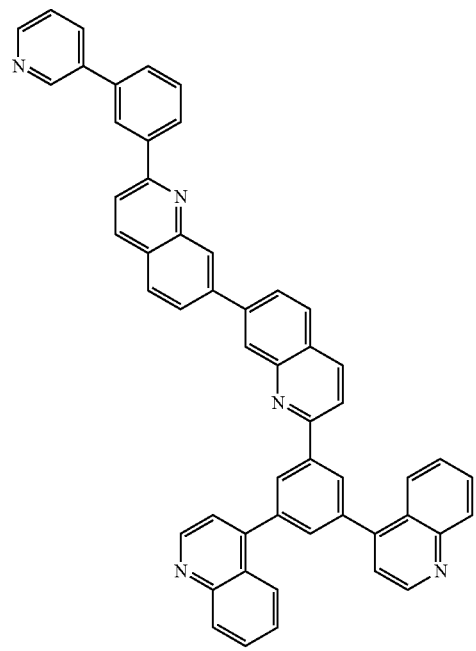
205
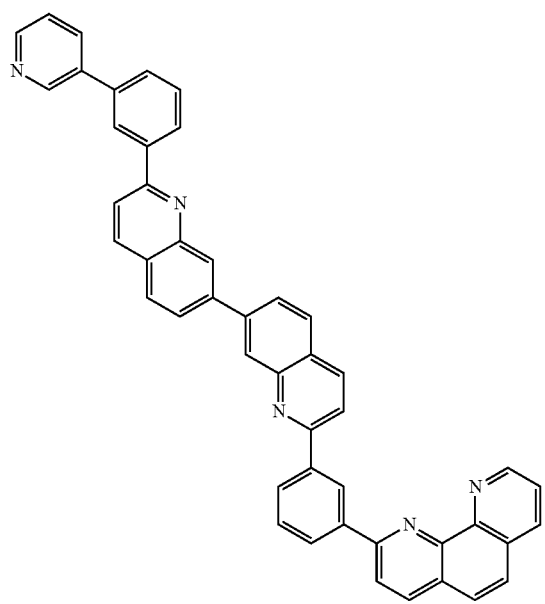
206
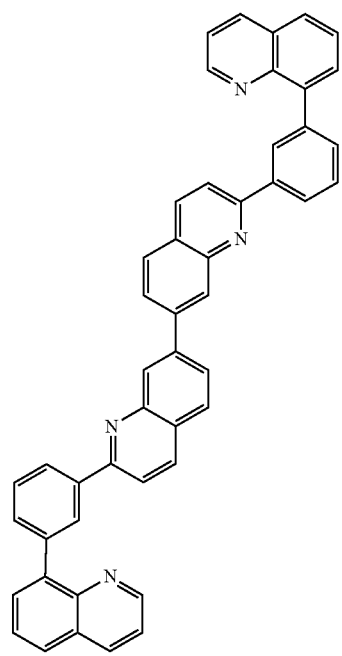

-continued
207
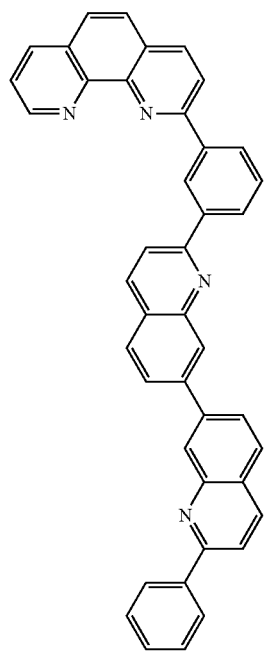
208
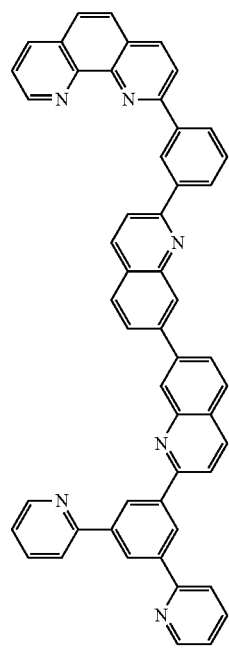
209
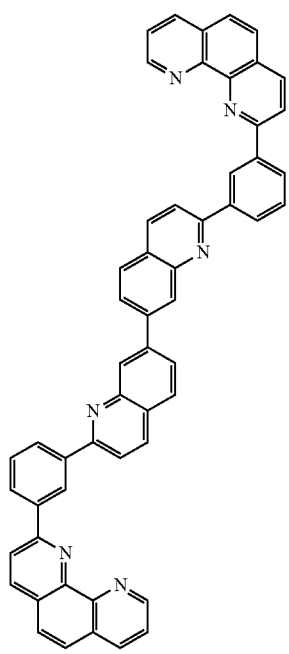
210
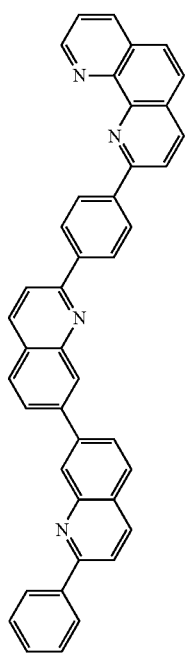

-continued
211
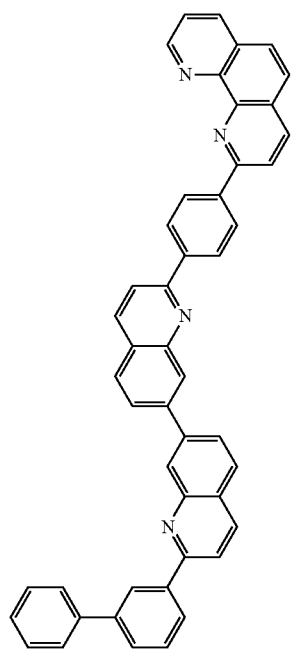
212
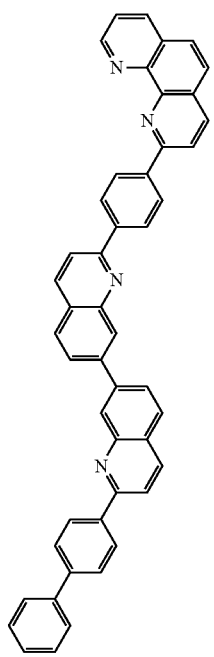
213
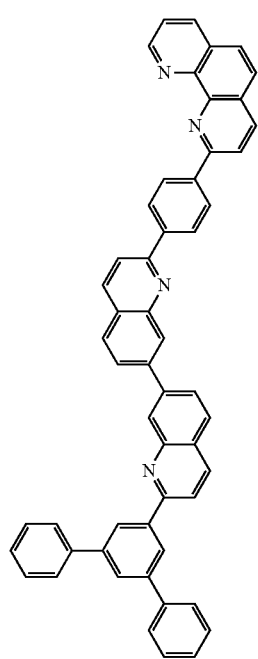
214
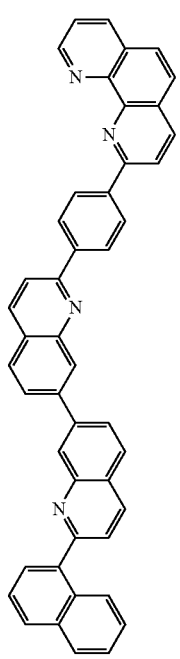

-continued
215 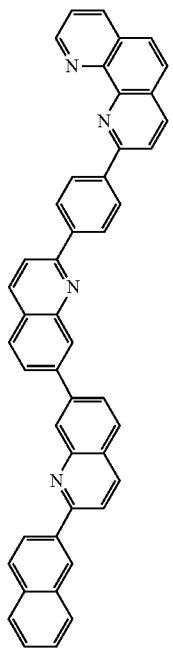 216 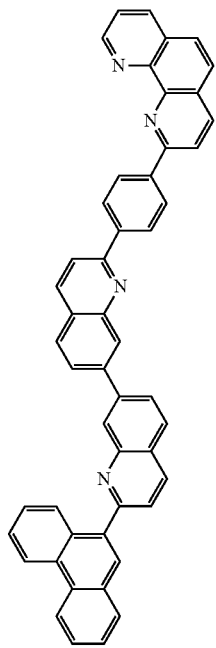
217 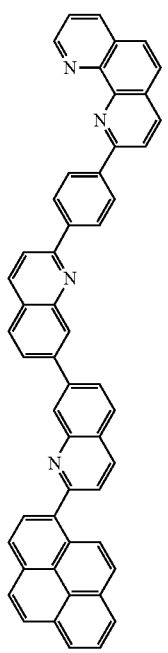 218 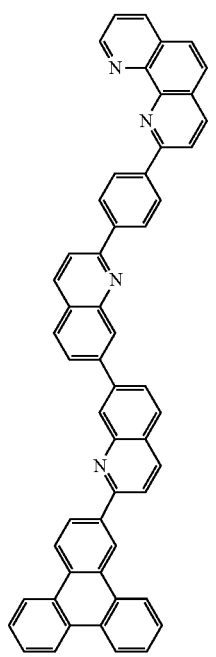

219
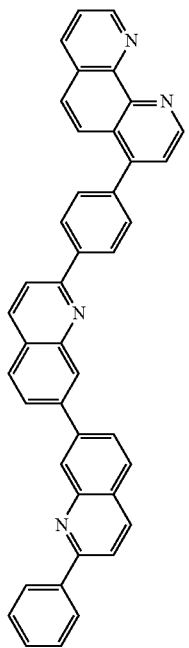
220
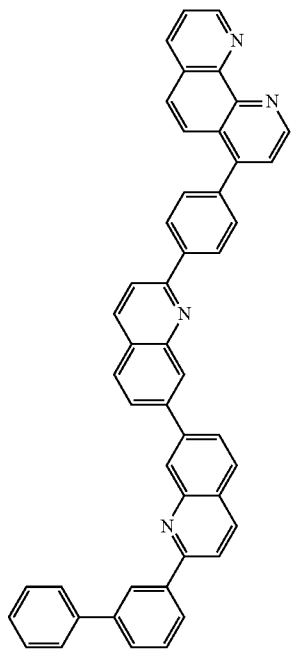
221
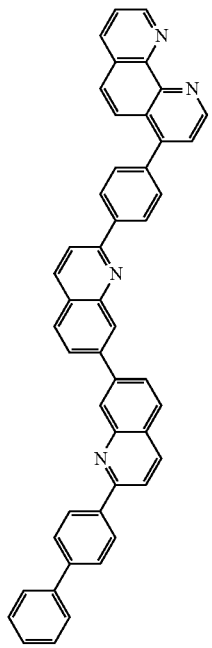
222
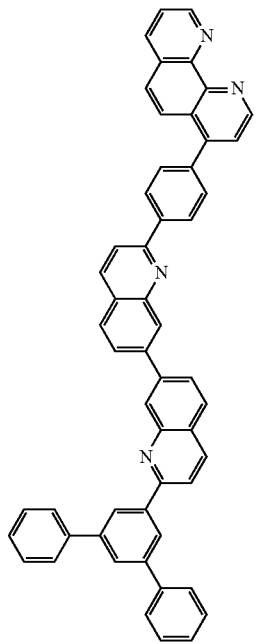

-continued
223
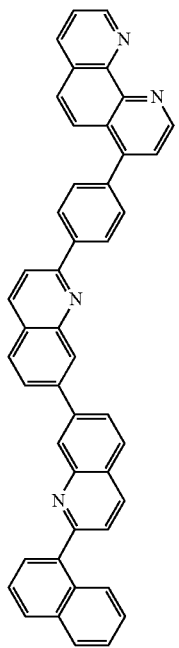
224
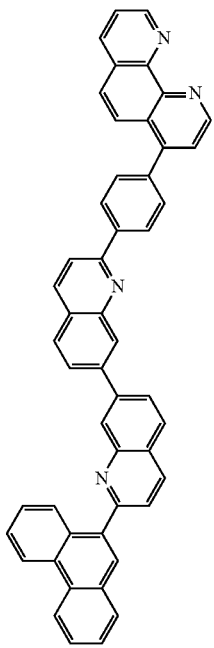
225
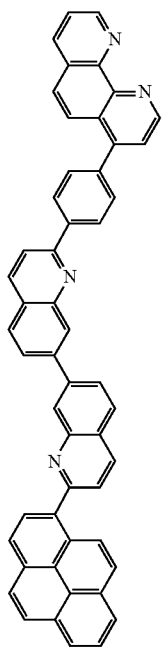
226
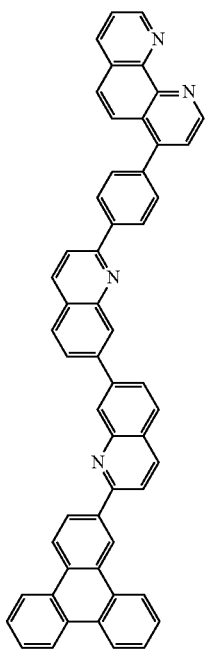

-continued
227
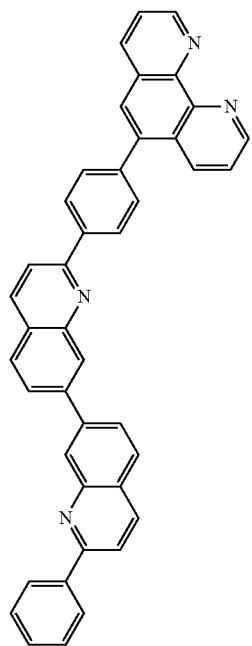
228
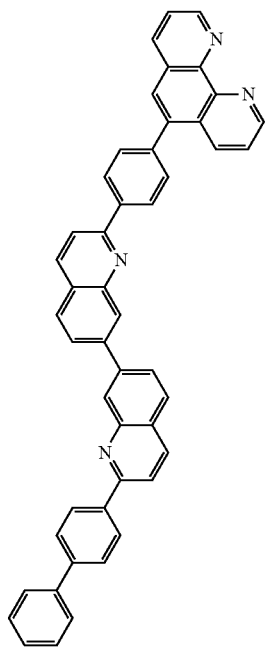
229
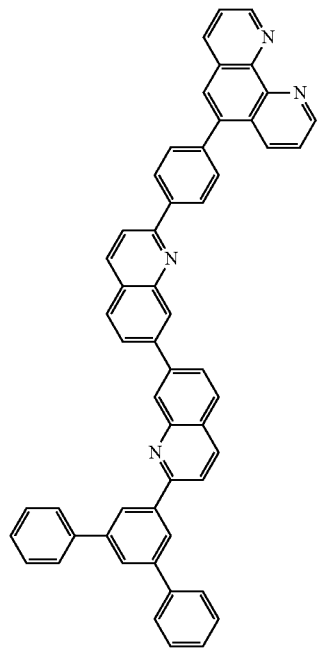
230
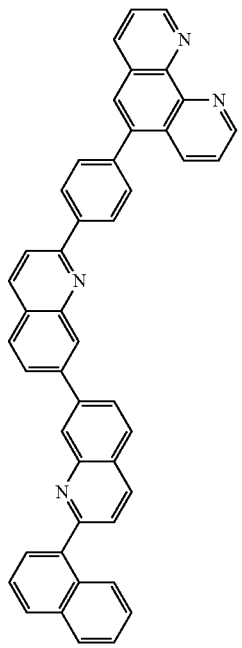

-continued
231
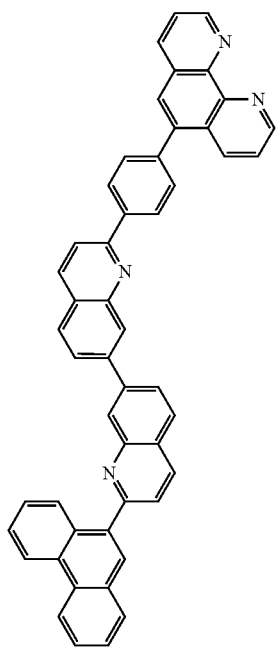
232
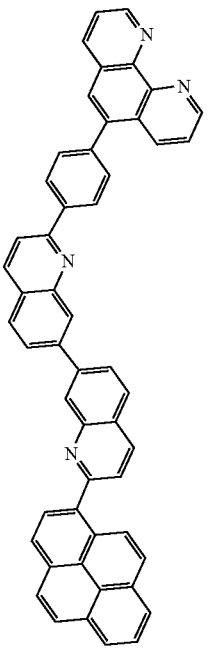
233
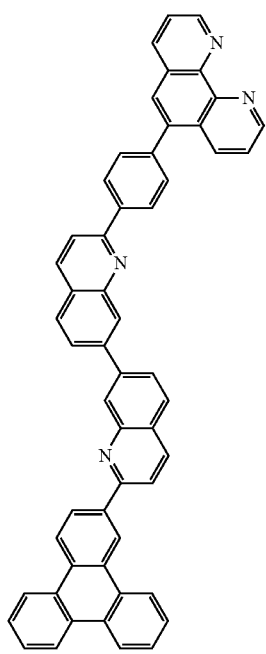
234
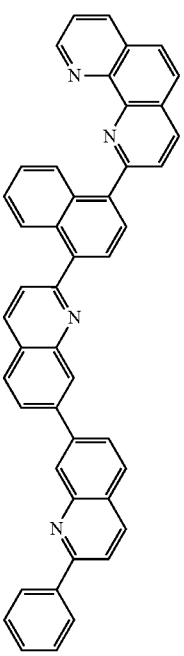

-continued
235 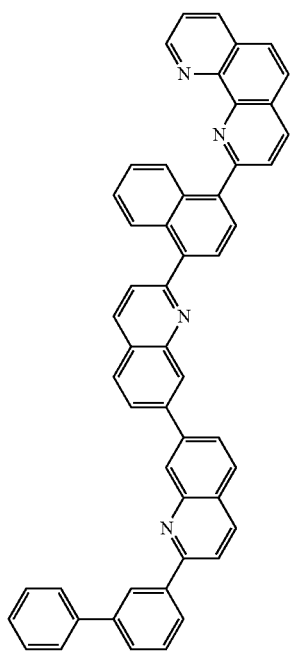 236 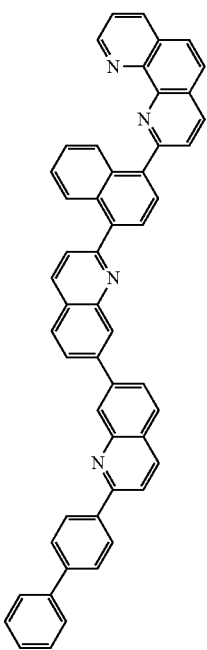
237 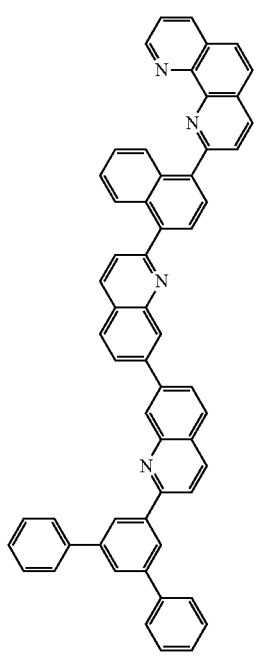 238 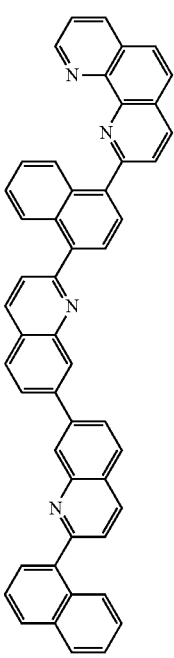

-continued
239
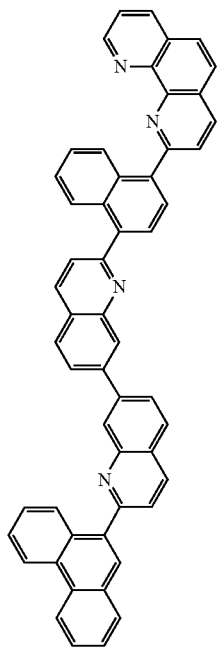
240
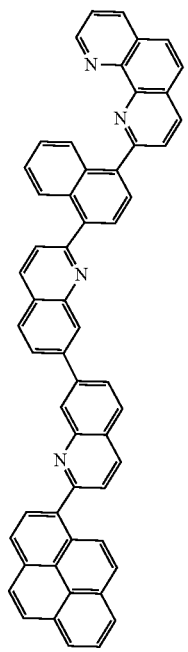
241
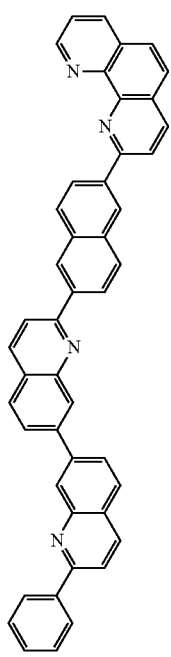
242
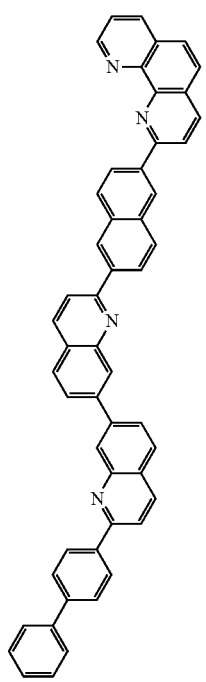

243
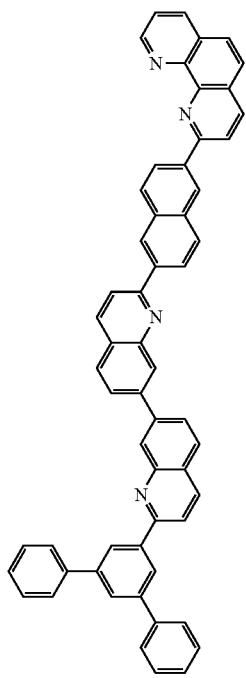
244
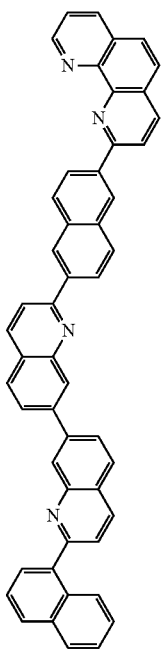
245
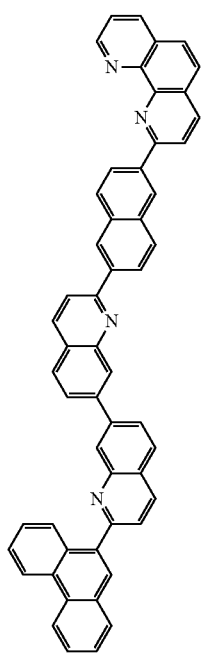
246
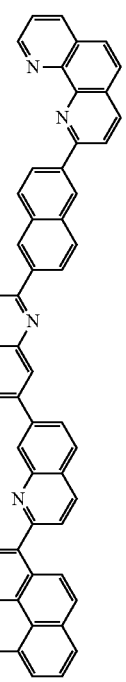

247
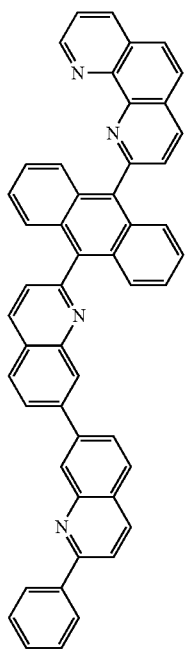
248
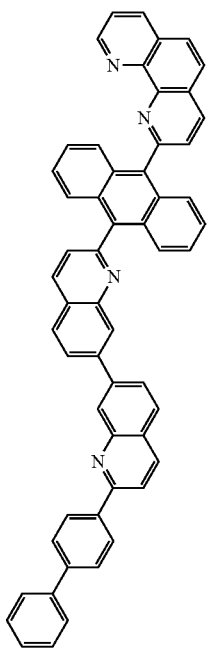
249
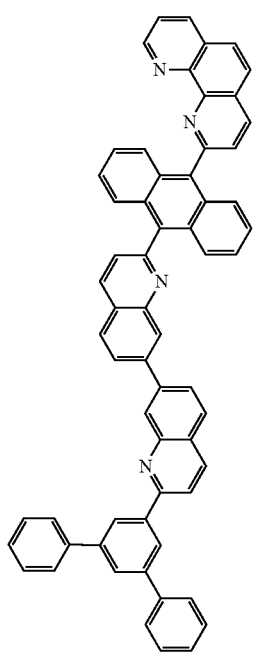
250
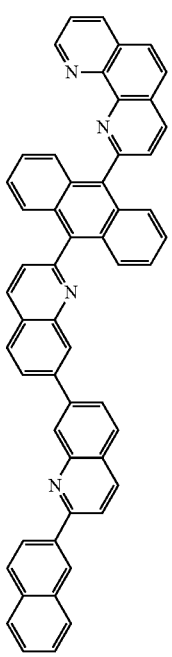

-continued
251
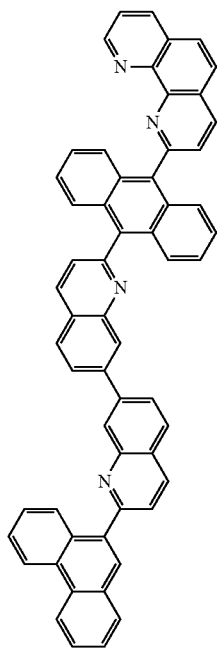
252
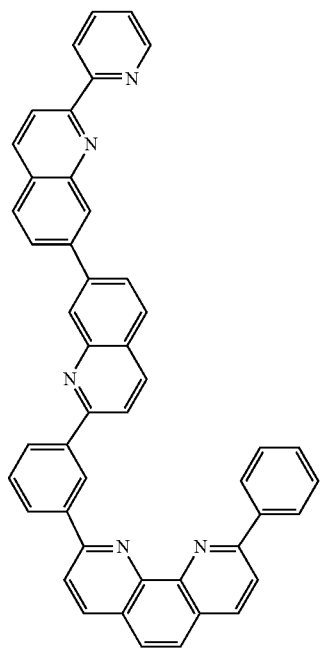
253
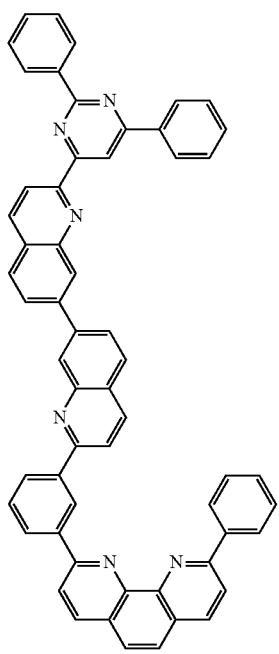
254
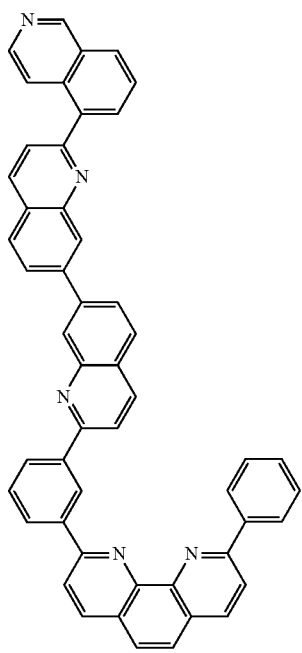

255
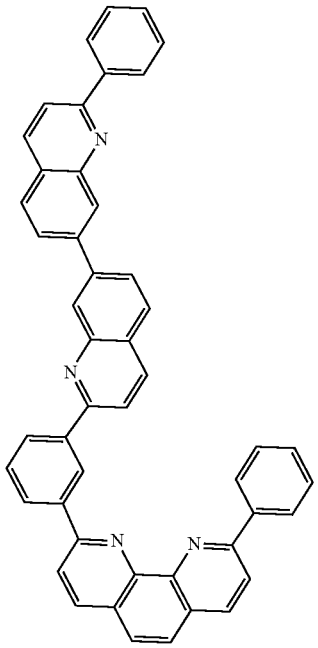

256
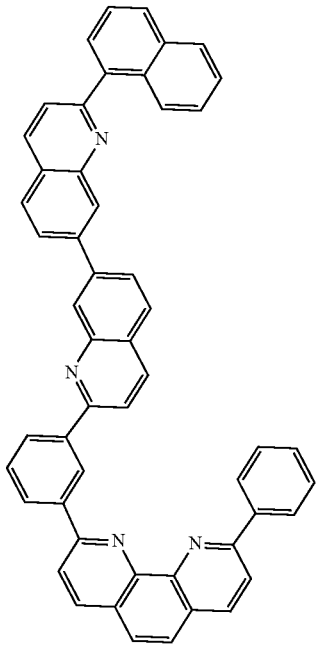

257
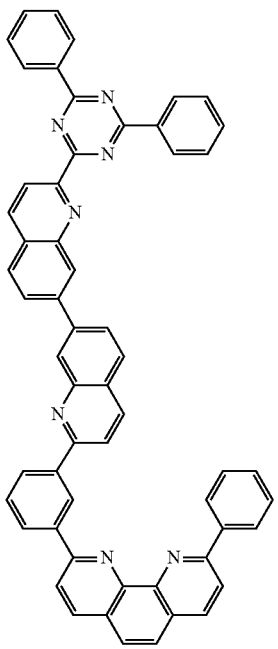

The compound described above may be for an organic optoelectronic diode, and the compound for an organic optoelectronic diode may be formed using a dry film-forming method such as chemical vapor deposition.

Hereinafter, an organic optoelectronic diode using the compound for an organic optoelectronic diode described above will be described.

The organic optoelectronic diode is not particularly limited as long as it is a device capable of interconverting electrical energy and light energy, and examples thereof may include an organic photoelectric diode, an organic light emitting diode, an organic solar cell, an organic photo conductor drum and the like.

Another embodiment of the present application provides an organic light emitting diode including a first electrode; a second electrode provided opposite to the first electrode; and one or more organic material layers provided between the first electrode and the second electrode, wherein one or more layers of the organic material layers include the compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the compound represented by Chemical Formula 1 are the same as the descriptions provided above.

In one embodiment of the present application, the organic light emitting diode may be a blue organic light emitting diode, and the compound according to Chemical Formula 1 may be used as a material of the blue organic light emitting diode.

In one embodiment of the present application, the organic light emitting diode may be a green organic light emitting diode, and the compound according to Chemical Formula 1 may be used as a material of the green organic light emitting diode.

In one embodiment of the present application, the organic light emitting diode may be a red organic light emitting diode, and the compound according to Chemical Formula 1 may be used as a material of the red organic light emitting diode.

In one embodiment of the present application, the organic light emitting diode may be a white organic light emitting diode, and the compound according to Chemical Formula 1 may be used as a material of the white organic light emitting diode, In one embodiment of the present application, the organic layer includes a charge generation layer and the charge generation layer includes the compound.

In one embodiment of the present application, the organic layer includes a hole blocking layer and the hole blocking layer includes the compound.

The organic light emitting diode of the present disclosure may be manufactured using common organic light emitting diode manufacturing methods and materials except that one or more organic material layers are formed using the compound described above.

The compound may be formed into an organic material layer using a solution coating method as well as a vacuum deposition method when manufacturing the organic light emitting diode. Herein, the solution coating method means spin coating, dip coating, inkjet printing, screen printing, a spray method, roll coating and the like, but is not limited thereto.

Herein, another example of the organic light emitting diode, one example of the organic optoelectronic diode, will be described with reference to accompanying drawings.

FIGS. 1 to 3 illustrate a lamination order of electrodes and organic material layers of an organic light emitting diode according to one embodiment of the present application. However, the scope of the present application is not limited to these diagrams, and structures of organic optoelectronic diodes known in the art may also be used in the present application.

FIG. 1 illustrates an organic light emitting diode in which an anode (200), an organic material layer (300) and a cathode (400) are consecutively laminated on a substrate (100). However, the structure is not limited to such a structure, and as illustrated in FIG. 2, an organic light emitting diode in which a cathode, an organic material layer and an anode are consecutively laminated on a substrate may also be obtained.

FIG. 3 illustrates a case of the organic material layer being a multilayer. The organic light emitting diode according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further included.

A charge generation layer may be present between the electron transfer layer (305) and the electron injection layer (306).

The compound represented by Chemical Formula 1 may be used as a material of an electron transfer layer, an electron delivery layer, a charge generation layer, a hole blocking layer, a light emitting layer or the like in the organic light emitting diode. As one example, the compound represented by Chemical Formula 1 may be used as a material of a charge generation layer or a hole blocking layer in the organic light emitting diode.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene](PEDT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature[Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among N-type host materials or P-type host materials may be selected, and used as a host material of a light emitting layer.

The charge generation material may be a compound of the claims of the present application.

The hole blocking layer may be a compound of the claims of the present application.

The organic light emitting diode according to one embodiment of the present application may be a top-emission type, a bottom-emission type or a dual-emission type depending on the materials used.

Hereinafter, the embodiments described above will be described in more detail through examples. However, the following examples are for illustrative purposes only and do not limit the scope of a right.

Starting materials and reaction materials used in examples and synthesis examples are, unless particularly mentioned otherwise, purchased from Sigma-Aldrich, TCI, Tokyo chemical industry or P&H tech, or synthesized using known methods.

(Preparation of Compound for Organic Optoelectronic Diode)

[Preparation Example 1] Preparation of Compound 1 of [Group II]

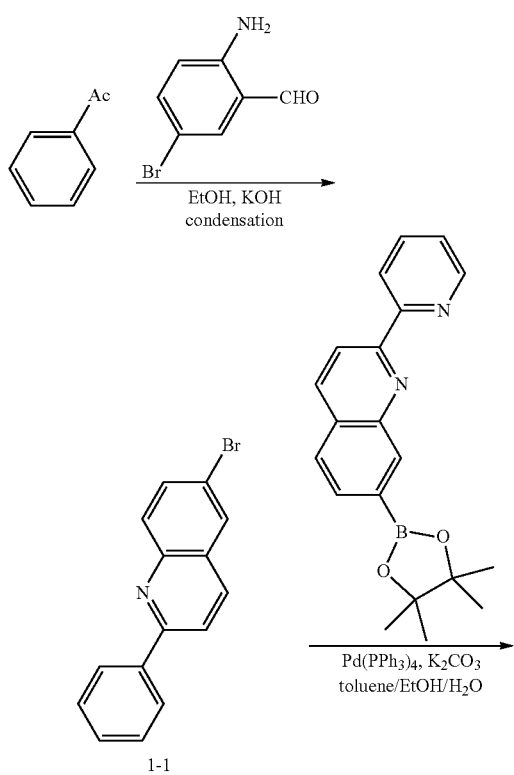

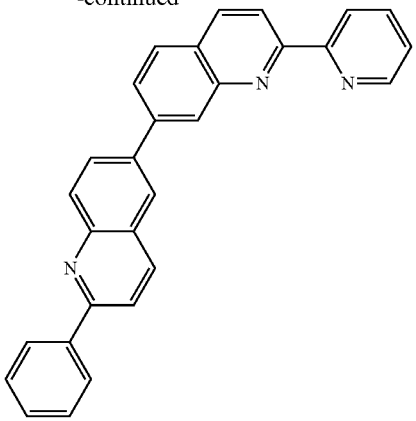

Preparation of Compound 1-1 of [Group II]

After dissolving acetophenone (11 g, 91.2 mmol) and 2-amino-5-bromobenzaldehyde (28 g, 91.2 mmol) in ethanol (EtOH) (300 mL), KOH (91.2 mmol) was introduced to the reaction vessel, and the result was heated to 80° C. After the reaction was completed, the result was cooled to room temperature, and then extracted with distilled water and ethyl acetate. The extracted organic layer was dried with anhydrous $Na_2SO_4$ and then filtered. The solvent of the filtered organic layer was removed using a rotary evaporator, and the result was purified by column chromatography using dichloromethane and hexane as a developing solvent to obtain target Compound 1-1 of [Group II](19 g, 80%).

Preparation of Compound 1 of [Group II]

After dissolving Compound 1-1 of [Group II](5 g, 22.2 mmol) and 2-(pyridin-2-yl)-7-(4,4,5,5-tetramethyl-1,3,2-dioxaborolan-2-yl)quinoline (7.4 g, 22.2 mmol) in toluene (50 ML), $Pd(PPh_3)_4$ (2.3 g, 2 mmol) and $K_2CO_3$ (8.3 g, 60 mmol) were introduced thereto, and the result was stirred for 10 minutes. To the reaction vessel, $H_2O$ (10 mL) and EtOH (6 mL) were further added dropwise, and the result was refluxed for 12 hours. After the reaction was completed, the result was cooled to room temperature, and then extracted with distilled water and dichloromethane. The extracted organic layer was dried with anhydrous $Na_2SO_4$ and then filtered. The solvent of the filtered organic layer was removed using a rotary evaporator, and the result was purified by column chromatography using ethyl acetate and hexane as a developing solvent to obtain target Compound 1 of [Group II](4.8 g, 64%).

Target compounds were synthesized in the same manner as in Preparation Example 1 except that Intermediate A(1) of the following Table 1-1 were used instead of acetophenone.

TABLE 1-1
| [Group II] Compound No. | Intermediate A(1) | Target Compound | Yield |
|---|---|---|---|
| 2 | 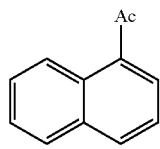 [SMILES: CC(=O)c1cccc2ccccc12] | 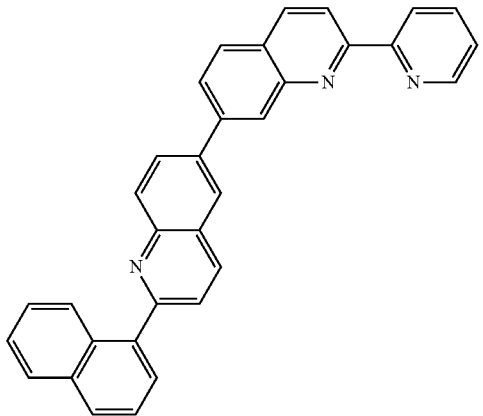 [SMILES: c1ccc(-c2ccc3ccc(-c4ccc5nc(-c6cccc7ccccc67)ccc5c4)cc3n2)nc1] | 72% |
| 8 | 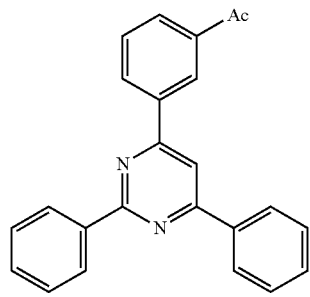 [SMILES: CC(=O)c1cccc(-c2cc(-c3ccccc3)nc(-c3ccccc3)n2)c1] | 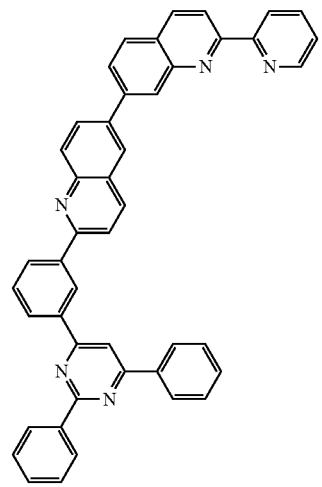 [SMILES: c1ccc(-c2cc(-c3cccc(-c4ccc5cc(-c6ccc7ccc(-c8ccccn8)nc7c6)ccc5n4)c3)nc(-c3ccccc3)n2)cc1] | 67% |
| 12 | 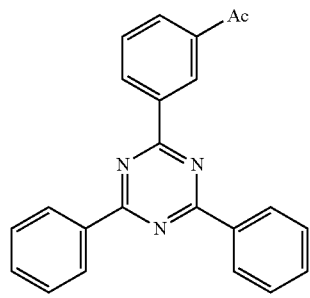 [SMILES: CC(=O)c1cccc(-c2nc(-c3ccccc3)nc(-c3ccccc3)n2)c1] | 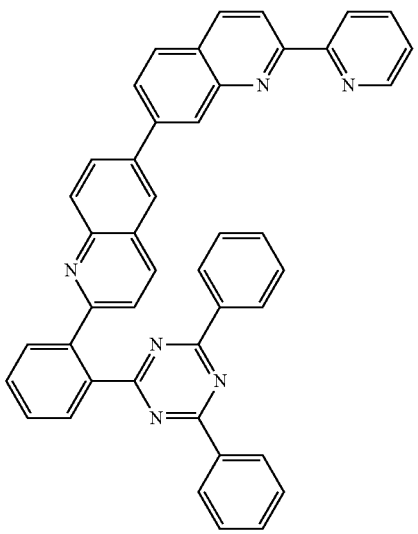 [SMILES: c1ccc(-c2nc(-c3ccccc3)nc(-c3ccccc3-c3ccc4cc(-c5ccc6ccc(-c7ccccn7)nc6c5)ccc4n3)n2)cc1] | 66% |

TABLE 1-1-continued
| [Group II] Compound No. | Intermediate A(1) | Target Compound | Yield |
|---|---|---|---|
| 13 | | | 70% |
| 17 | | | 71% |
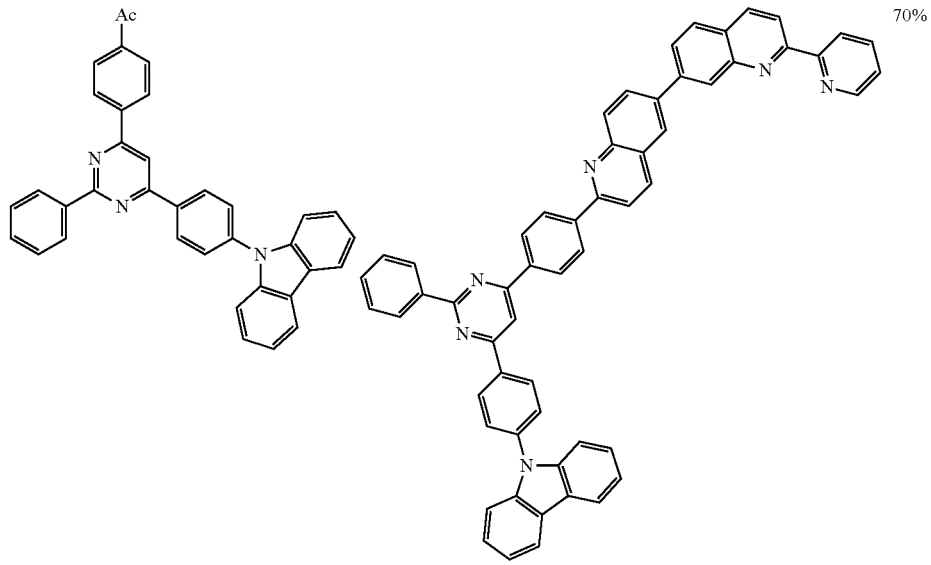
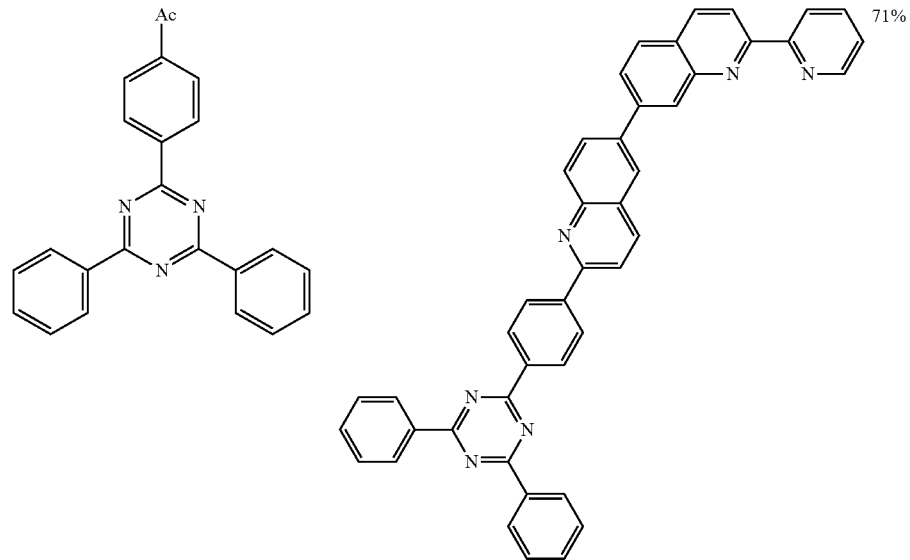

TABLE 1-1-continued
| [Group II] Compound No. | Intermediate A(1) | Target Compound | Yield |
|---|---|---|---|
| 19 | 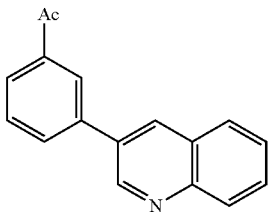 [SMILES: CC(=O)c1cccc(-c2cnc3ccccc3c2)c1] | 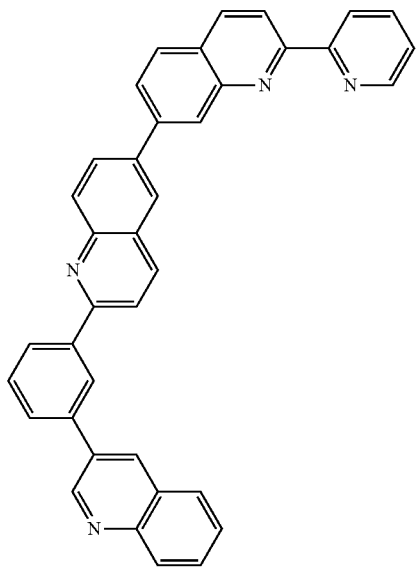 [SMILES: c1ccc(-c2ccc3ccc(-c4ccc5nc(-c6cccc(-c7cnc8ccccc8c7)c6)ccc5c4)cc3n2)nc1] | 65% |
| 21 | 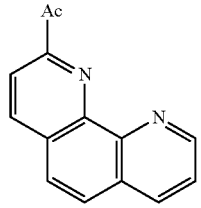 [SMILES: CC(=O)c1ccc2ccc3cccnc3c2n1] | 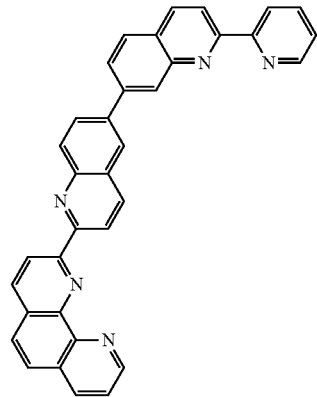 [SMILES: c1ccc(-c2ccc3ccc(-c4ccc5nc(-c6ccc7ccc8cccnc8c7n6)ccc5c4)cc3n2)nc1] | 66% |
| 24 | 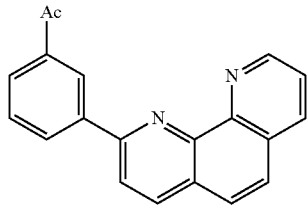 [SMILES: CC(=O)c1cccc(-c2ccc3ccc4cccnc4c3n2)c1] | 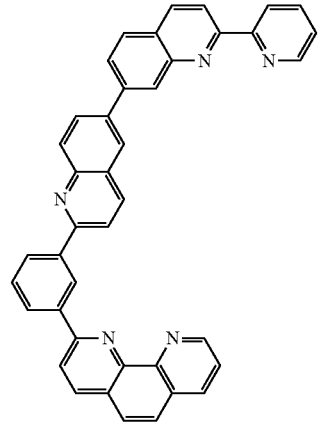 [SMILES: c1ccc(-c2ccc3ccc(-c4ccc5nc(-c6cccc(-c7ccc8ccc9cccnc9c8n7)c6)ccc5c4)cc3n2)nc1] | 66% |

TABLE 1-1-continued

| [Group II] Compound No. | Intermediate A(1) | Target Compound | Yield |
|---|---|---|---|
| 27 | (structure) | (structure) | 68% |

Target compounds were synthesized in the same manner as in Preparation Example 1 except that 2-(pyridin-3-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate B(1) of the following Table 1-2 was used instead of acetophenone.

TABLE 1-2

| [Group II] Compound No. | Intermediate B(1) | Target Compound | Yield |
|---|---|---|---|
| 32 | (structure) | (structure) | 69% |
| 34 | (structure) | (structure) | 67% |

TABLE 1-2-continued

| [Group II] Compound No. | Intermediate B(1) | Target Compound | Yield |
|---|---|---|---|
| 36 | Ac- (structure) | (structure) | 65% |
| 39 | Ac- (structure) | (structure) | 73% |

Target compounds were synthesized in the same manner as in Preparation Example 1 except that 2-(pyridin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate C(1) of the following Table 1-3 was used instead of acetophenone.

TABLE 1-3
| [Group II] Compound No. | Intermediate C(1) | Target Compound | Yield |
|---|---|---|---|
| 43 | 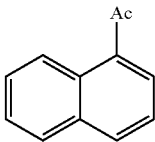 | 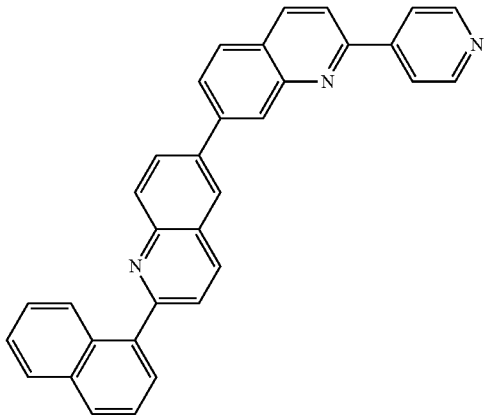 [SMILES: c1ccc2c(-c3ccc4cc(-c5ccc6ccc(-c7ccncc7)nc6c5)ccc4n3)cccc2c1] | 66% |
| 46 | 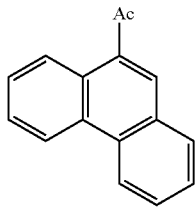 [SMILES: CC(=O)c1cc2ccccc2c2ccccc12] | 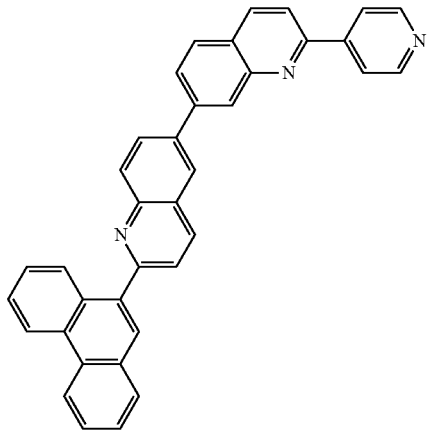 [SMILES: c1ccc2c(c1)cc(-c1ccc3cc(-c4ccc5ccc(-c6ccncc6)nc5c4)ccc3n1)c1ccccc12] | 71% |
| 47 | 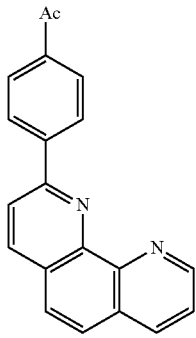 | 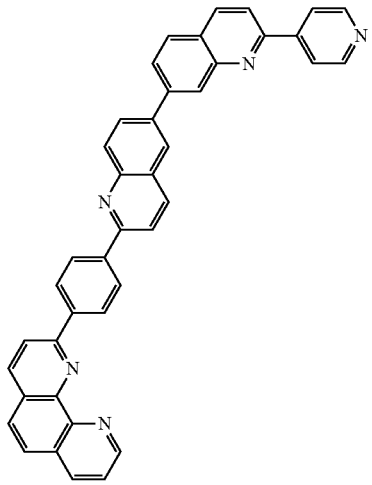 [SMILES: c1cnc2c(c1)ccc1ccc(-c3ccc(-c4ccc5cc(-c6ccc7ccc(-c8ccncc8)nc7c6)ccc5n4)cc3)nc12] | 73% |

TABLE 1-3-continued

| [Group II] Compound No. | Intermediate C(1) | Target Compound | Yield |
|---|---|---|---|
| 52 | 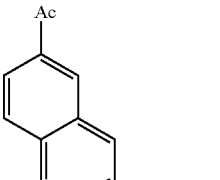 | 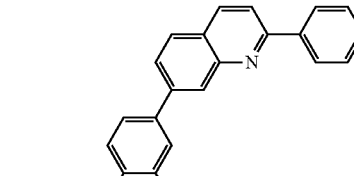 | 71% |

Target compounds were synthesized in the same manner as in Preparation Example 1 except that 2-(pyrimidin-2-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate D(1) of the following Table 1-4 was used instead of acetophenone.

TABLE 1-4

| [Group II] Compound No. | Intermediate D(1) | Target Compound | Yield |
|---|---|---|---|
| 59 | 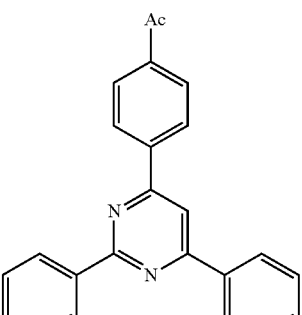 | 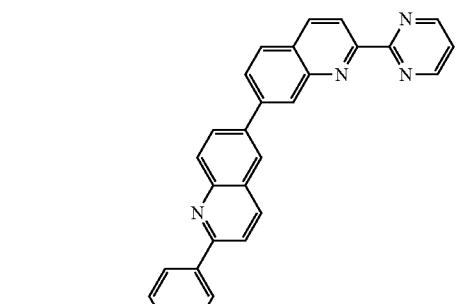 | 71% |

TABLE 1-4-continued

| [Group II] Compound No. | Intermediate D(1) | Target Compound | Yield |
|---|---|---|---|
| 60 | 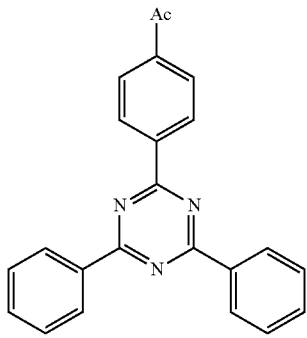 [SMILES: CC(=O)c1ccc(-c2nc(-c3ccccc3)nc(-c3ccccc3)n2)cc1] | 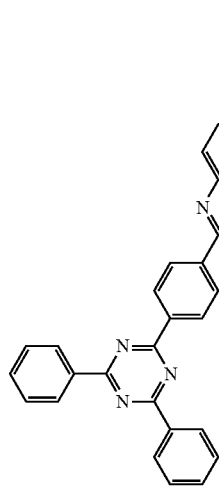 | 70% |
| 62 | 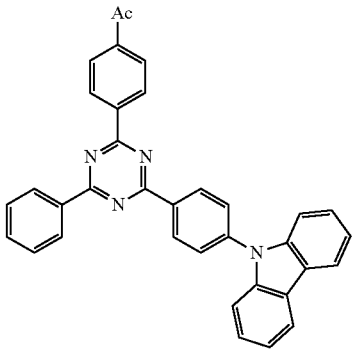 [SMILES: CC(=O)c1ccc(-c2nc(-c3ccccc3)nc(-c3ccc(-n4c5ccccc5c5ccccc54)cc3)n2)cc1] | 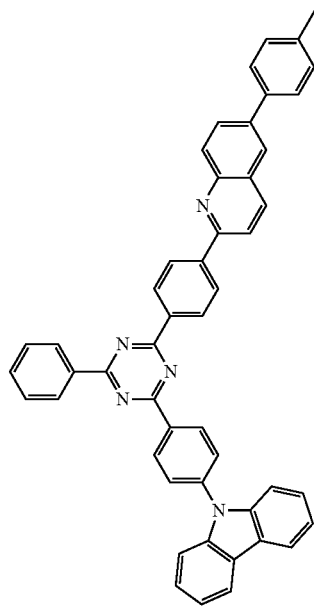 | 65% |

Target compounds were synthesized in the same manner as in Preparation Example 1 except that 2-(4,6-diphenylpyrimidin-2-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate E(1) of the following Table 1-5 was used instead of acetophenone.

TABLE 1-5

| [Group II] Compound No. | Intermediate E(1) | Target Compound | Yield |
|---|---|---|---|
| 63 | Ac-phenyl | (structure) | 67% |
| 68 | Ac-phenyl-phenanthroline | (structure) | 72% |

Target compounds were synthesized in the same manner as in Preparation Example 1 except that 2-(pyrimidin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate F(1) of the following Table 1-6 was used instead of acetophenone.

TABLE 1-6

| [Group II] Compound No. | Intermediate F(1) | Target Compound | Yield |
|---|---|---|---|
| 73 | Ac (structure) | (structure) | 69% |

Target compounds were synthesized in the same manner as in Preparation Example 1 except that 2-(2,6-diphenylpyrimidin-4-yl)-7-(4,4,5,5-tetramethyl-1,3,2-dioxaborolan-2-yl)quinoline was used instead of 2-(pyridin-2-yl)-7-4,4,5,5-tetramethyl-1,3,2-dioxaborolan-2-yl)quinoline, and Intermediate G(1) of the following Table 1-7 was used instead of acetophenone.

TABLE 1-7

| [Group II] Compound No. | Intermediate G(1) | Target Compound | Yield |
|---|---|---|---|
| 77 | Ac (structure) | (structure) | 76% |

TABLE 1-7-continued
| [Group II] Compound No. | Intermediate G(1) | Target Compound | Yield |
|---|---|---|---|
| 78 | 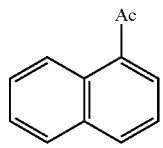 | 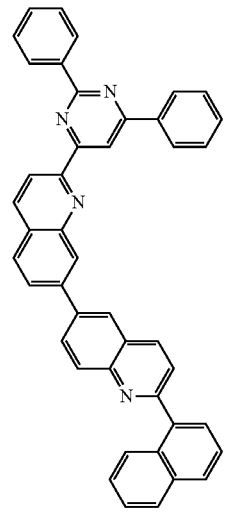 [SMILES: c1ccc(-c2cc(-c3ccc4ccc(-c5ccc6nc(-c7cccc8ccccc78)ccc6c5)cc4n3)nc(-c3ccccc3)n2)cc1] | 73% |
| 80 | 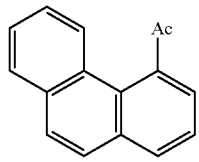 [SMILES: CC(=O)c1cccc2ccc3ccccc3c12] | 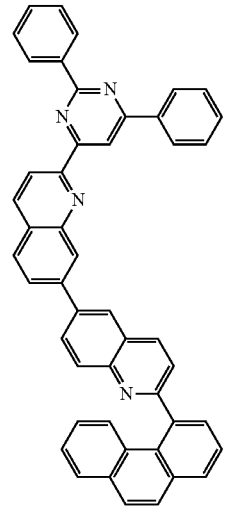 [SMILES: c1ccc(-c2cc(-c3ccc4ccc(-c5ccc6nc(-c7cccc8ccc9ccccc9c78)ccc6c5)cc4n3)nc(-c3ccccc3)n2)cc1] | 74% |

TABLE 1-7-continued

| [Group II] Compound No. | Intermediate G(1) | Target Compound | Yield |
|---|---|---|---|
| 83 | 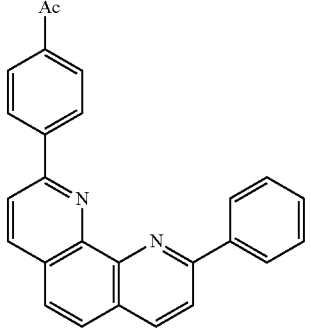 [SMILES: CC(=O)c1ccc(-c2ccc3ccc4ccc(-c5ccccc5)nc4c3n2)cc1] | 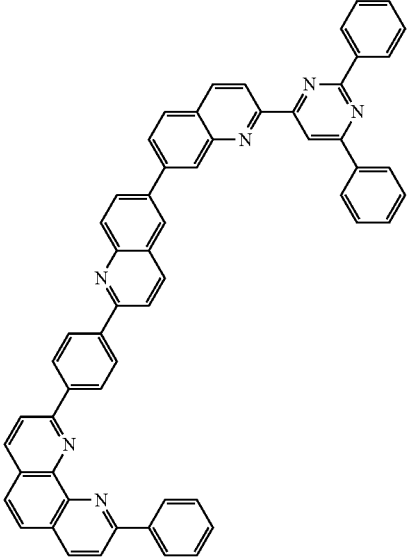 [SMILES: c1ccc(-c2cc(-c3ccc4ccc(-c5ccc6nc(-c7ccc(-c8ccc9ccc%10ccc(-c%11ccccc%11)nc%10c9n8)cc7)ccc6c5)cc4n3)nc(-c3ccccc3)n2)cc1] | 68% |
| 85 | 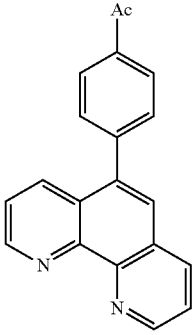 [SMILES: CC(=O)c1ccc(-c2cc3cccnc3c3ncccc23)cc1] | 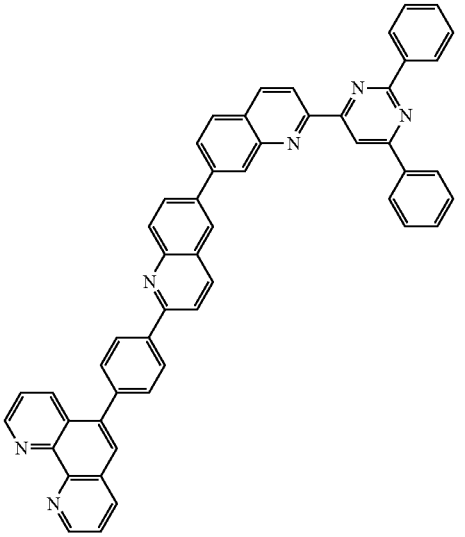 [SMILES: c1ccc(-c2cc(-c3ccc4ccc(-c5ccc6nc(-c7ccc(-c8cc9cccnc9c9ncccc89)cc7)ccc6c5)cc4n3)nc(-c3ccccc3)n2)cc1] | 67% |

Target compounds were synthesized in the same manner as in Preparation Example 1 except that 7-(4,4,5,5-tetramethyl-1,3,2-dioxaborolan-2-yl)-2-(1,3,5-triazin-2-yl) quinoline was used instead of 2-(pyridin-2-yl)-7-(4,4,5,5-tetramethyl-1,3,2-dioxaborolan-2-yl)quinoline, and Intermediate H(1) of the following Table 1-8 was used instead of acetophenone.

TABLE 1-8

| [Group II] Compound No. | Intermediate H(1) | Target Compound | Yield |
|---|---|---|---|
| 92 | Ac-[phenyl-phenanthroline structure] | [quinoline-triazine / quinoline / phenyl / phenanthroline structure] | 71% |

Target compounds were synthesized in the same manner as in Preparation Example 1 except that 2-(4,6-diphenyl-1,3,5-triazin-2-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl) quinoline, and Intermediate I(1) of the following Table 1-9 was used instead of acetophenone.

TABLE 1-9

| [Group II] Compound No. | Intermediate I(1) | Target Compound | Yield |
|---|---|---|---|
| 97 | Ac-[phenyl] | [diphenyltriazine-quinoline-quinoline-phenyl structure] | 65% |

TABLE 1-9-continued
| [Group II] Compound No. | Intermediate I(1) | Target Compound | Yield |
|---|---|---|---|
| 98 | 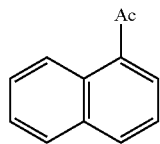 [SMILES: CC(=O)c1cccc2ccccc12] | 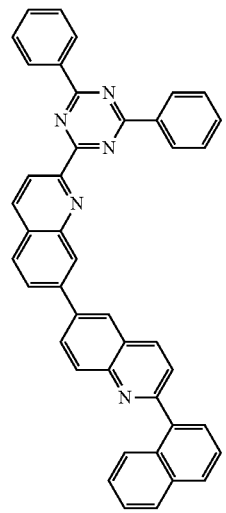 [SMILES: c1ccc(-c2nc(-c3ccccc3)nc(-c3ccc4ccc(-c5ccc6nc(-c7cccc8ccccc78)ccc6c5)cc4n3)n2)cc1] | 65% |
| 102 | 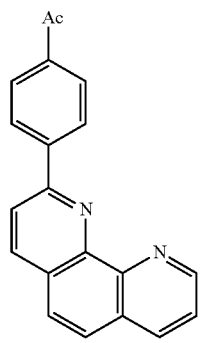 [SMILES: CC(=O)c1ccc(-c2ccc3ccc4cccnc4c3n2)cc1] | 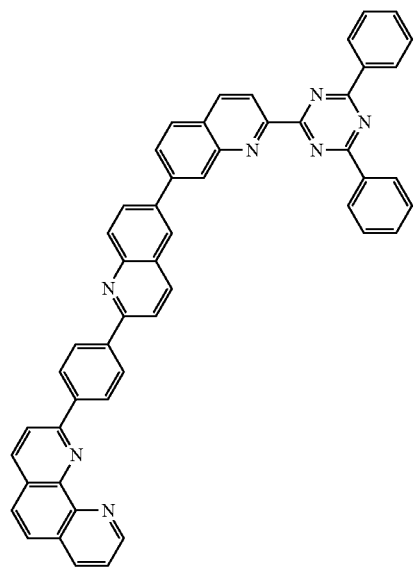 [SMILES: c1ccc(-c2nc(-c3ccccc3)nc(-c3ccc4ccc(-c5ccc6nc(-c7ccc(-c8ccc9ccc%10cccnc%10c9n8)cc7)ccc6c5)cc4n3)n2)cc1] | 72% |

TABLE 1-9-continued

| [Group II] Compound No. | Intermediate I(1) | Target Compound | Yield |
|---|---|---|---|
| 105 | Ac-naphthyl-phenanthroline | (structure) | 70% |
| 255 | Ac-phenyl-phenyl-phenanthroline | (structure) | 66% |

Target compounds were synthesized in the same manner as in Preparation Example 1 except that 7-(4,4,5,5-tetramethyl-1,3,2-dioxaborolan-2-yl)-2,8'-biquinoline was used instead of 2-(pyridin-2-yl)-7-(4,4,5,5-tetramethyl-1,3,2-dioxaborolan-2-yl)quinoline, and Intermediate J(1) of the following Table 1-10 was used instead of acetophenone.

TABLE 1-10
| [Group II] Compound No. | Intermediate J(1) | Target Compound | Yield |
|---|---|---|---|
| 107 | 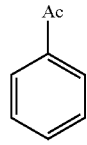 | 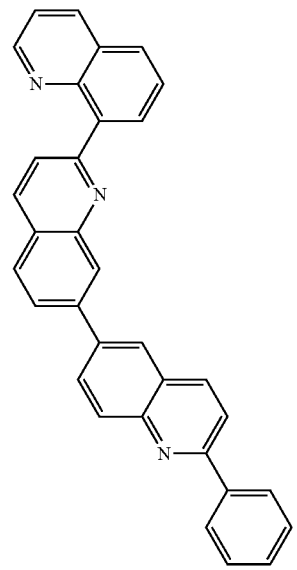 [SMILES: c1ccc(-c2ccc3cc(-c4ccc5ccc(-c6cccc7cccnc67)nc5c4)ccc3n2)cc1] | 72% |
| 111 | 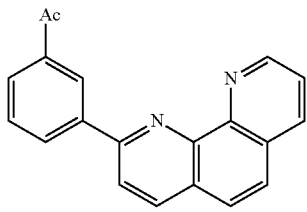 | 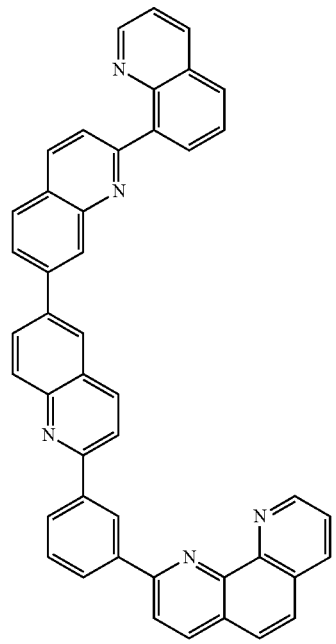 | 73% |

TABLE 1-10-continued
| [Group II] Compound No. | Intermediate J(1) | Target Compound | Yield |
|---|---|---|---|
| 116 | 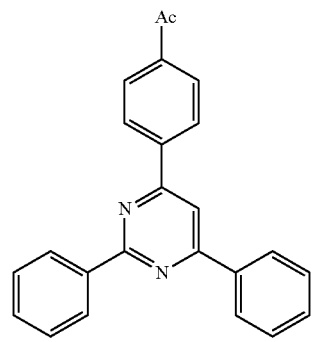 [SMILES: CC(=O)c1ccc(-c2cc(-c3ccccc3)nc(-c3ccccc3)n2)cc1] | 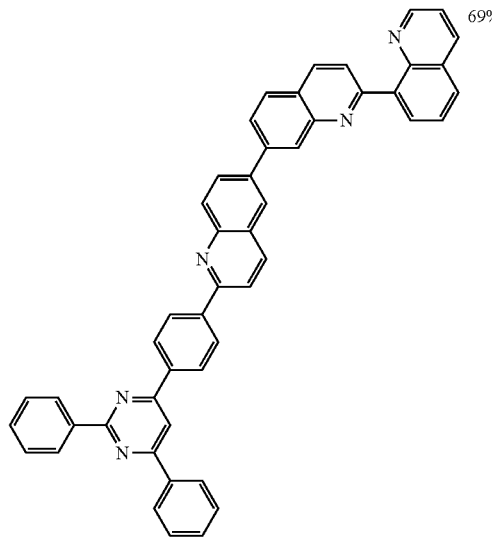 | 69% |
| 119 | 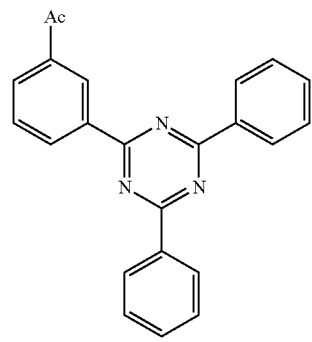 [SMILES: CC(=O)c1cccc(-c2nc(-c3ccccc3)nc(-c3ccccc3)n2)c1] | 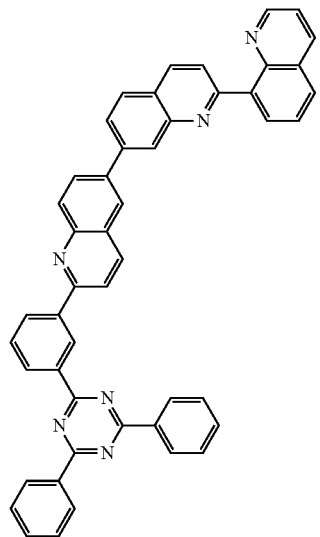 [SMILES: c1ccc(-c2nc(-c3ccccc3)nc(-c3cccc(-c4ccc5cc(-c6ccc7ccc(-c8cccc9cccnc89)nc7c6)ccc5n4)c3)n2)cc1] | 65% |

TABLE 1-10-continued

| [Group II] Compound No. | Intermediate J(1) | Target Compound | Yield |
|---|---|---|---|
| 120 | | | 65% |

Target compounds were synthesized in the same manner as in Preparation Example 1 except that 2-(isoquinolin-8-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate K(1) of the following Table 1-11 was used instead of acetophenone.

Target compounds were synthesized in the same manner as in Preparation Example 1 except that 2-(isoquinolin-5-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate L(1) of the following Table 1-12 was used instead of acetophenone.

TABLE 1-11

| [Group II] Compound No. | Intermediate K(1) | Target Compound | Yield |
|---|---|---|---|
| 121 | | | 70% |

TABLE 1-12

| [Group II] Compound No. | Intermediate L(1) | Target Compound | Yield |
|---|---|---|---|
| 125 | Ac-C6H4- (structure) | (structure) | 75% |

Target compounds were synthesized in the same manner as in Preparation Example 1 except that 7-(4,4,5,5-tetramethyl-1,3,2-dioxaborolan-2-yl)-2,5'-biquinoline was used instead of 2-(pyridin-2-yl)-7-(4,4,5,5-tetramethyl-1,3,2-dioxaborolan-2-yl)quinoline, and Intermediate M(1) of the following Table 1-13 was used instead of acetophenone.

TABLE 1-13

| [Group II] Compound No. | Intermediate M(1) | Target Compound | Yield |
|---|---|---|---|
| 129 | Ac-C6H5 (structure) | (structure) | 70% |

TABLE 1-13-continued

| [Group II] Compound No. | Intermediate M(1) | Target Compound | Yield |
|---|---|---|---|
| 131 | 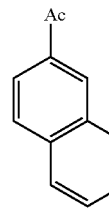 | 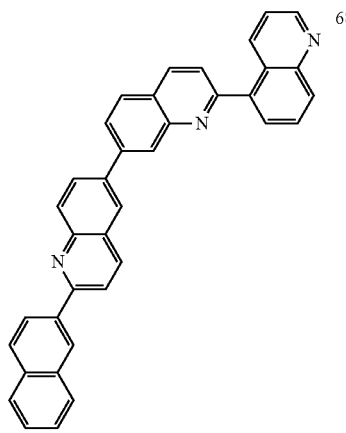 | 68% |
| 133 | 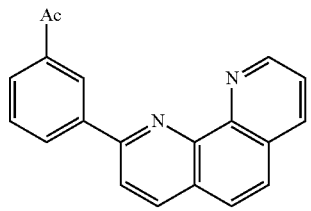 [SMILES: CC(=O)c1cccc(-c2ccc3ccc4cccnc4c3n2)c1] | 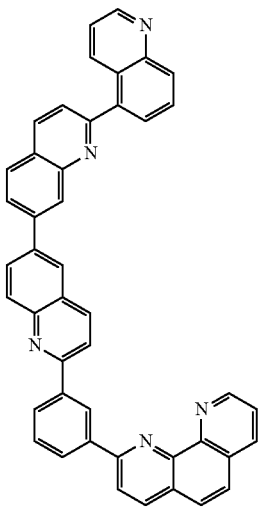 [SMILES: c1cc(-c2ccc3cc(-c4ccc5ccc(-c6cccc7ncccc67)nc5c4)ccc3n2)cc(-c2ccc3ccc4cccnc4c3n2)c1] | 76% |

Target compounds were synthesized in the same manner as in Preparation Example 1 except that 2-(isoquinolin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate N(1) of the following Table 1-14 was used instead of acetophenone.

TABLE 1-14

| [Group II] Compound No. | Intermediate N(1) | Target Compound | Yield |
|---|---|---|---|
| 137 | Ac | | 75% |
| 140 | Ac | | 74% |

Target compounds were synthesized in the same manner as in Preparation Example 1 except that 7-(4,4,5,5-tetramethyl-1,3,2-dioxaborolan-2-yl)-2,5'-biquinoline was used instead of 2-(pyridin-2-yl)-7-(4,4,5,5-tetramethyl-1,3,2-dioxaborolan-2-yl)quinoline, and Intermediate O(1) of the following Table 1-15 was used instead of acetophenone.

TABLE 1-15

| [Group II] Compound No. | Intermediate O(1) | Target Compound | Yield |
|---|---|---|---|
| 145 | Ac-phenyl | (structure) | 69% |
| 146 | Ac-naphthyl | (structure) | 68% |
| 148 | Ac-phenyl-phenanthroline | (structure) | 68% |

Target compounds were synthesized in the same manner as in Preparation Example 1 except that 2-(7-(4,4,5,5-tetramethyl-1,3,2-dioxaborolan-2-yl) quinolin-2-yl)benzo[h]quinoline was used instead of 2-(pyridin-2-yl)-7-(4,4,5,5-tetramethyl-1,3,2-dioxaborolan-2-yl)quinoline, and Intermediate P(1) of the following Table 1-16 was used instead of acetophenone.

TABLE 1-16

| [Group II] Compound No. | Intermediate P(1) | Target Compound | Yield |
|---|---|---|---|
| 167 | 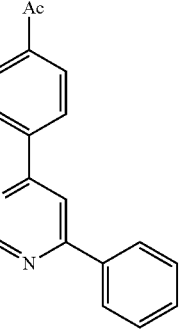 | 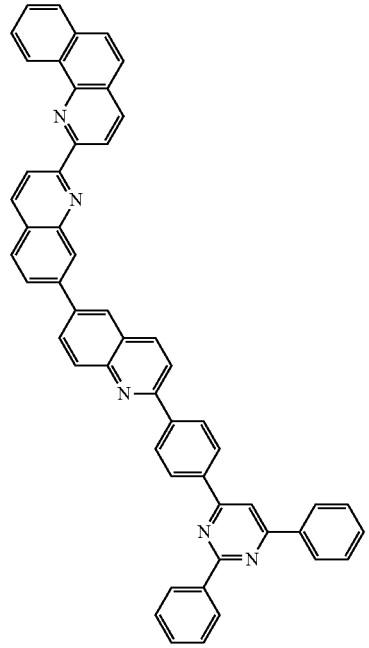 [SMILES: c1ccc(-c2cc(-c3ccc(-c4ccc5cc(-c6ccc7ccc(-c8ccc9ccc%10ccccc%10c9n8)nc7c6)ccc5n4)cc3)nc(-c3ccccc3)n2)cc1] | 75% |
| 168 | 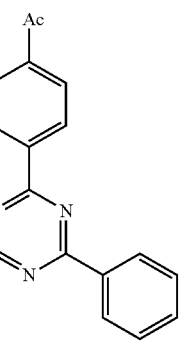 | 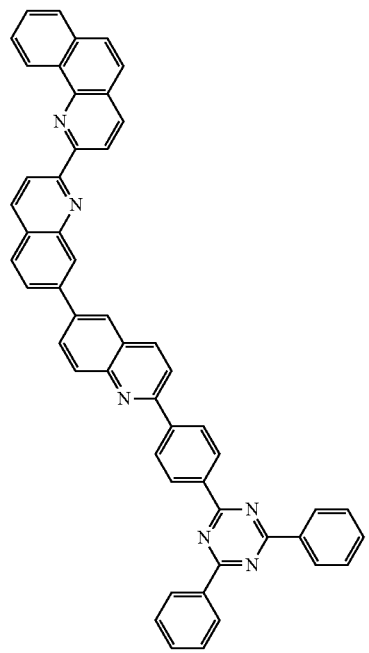 [SMILES: c1ccc(-c2nc(-c3ccccc3)nc(-c3ccc(-c4ccc5cc(-c6ccc7ccc(-c8ccc9ccc%10ccccc%10c9n8)nc7c6)ccc5n4)cc3)n2)cc1] | 77% |

Target compounds were synthesized in the same manner as in Preparation Example 1 except that 2-(7-(4,4,5,5-tetramethyl-1,3,2-dioxaborolan-2-yl) quinolin-2-yl)-1,10-phenanthroline was used instead of 2-(pyridin-2-yl)-7-(4,4,5,5-tetramethyl-1,3,2-dioxaborolan-2-yl)quinoline, and Intermediate Q(1) of the following Table 1-17 was used instead of acetophenone.

TABLE 1-17
| [Group II] Compound No. | Intermediate Q(1) | Target Compound | Yield |
|---|---|---|---|
| 172 | 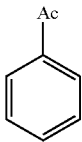 | 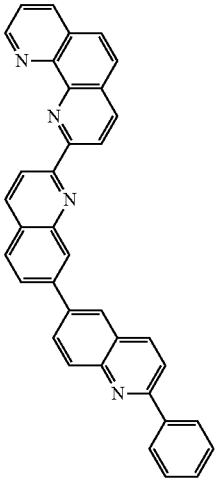 [SMILES: c1ccc(-c2ccc3cc(-c4ccc5ccc(-c6ccc7ccc8cccnc8c7n6)nc5c4)ccc3n2)cc1] | 70% |
| 177 | 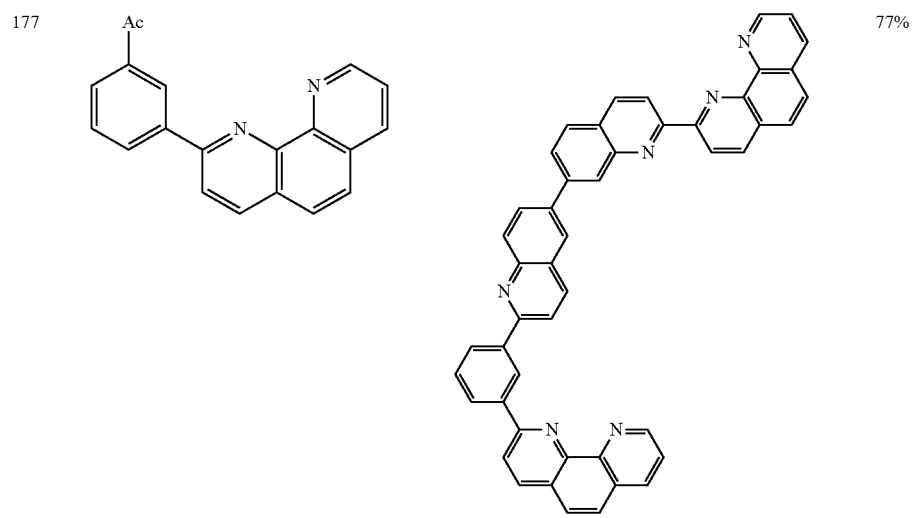 | | 77% |

TABLE 1-17-continued

| [Group II] Compound No. | Intermediate Q(1) | Target Compound | Yield |
|---|---|---|---|
| 180 | Ac 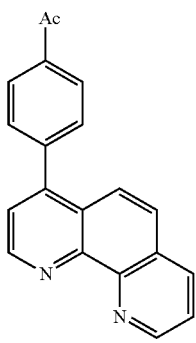 | 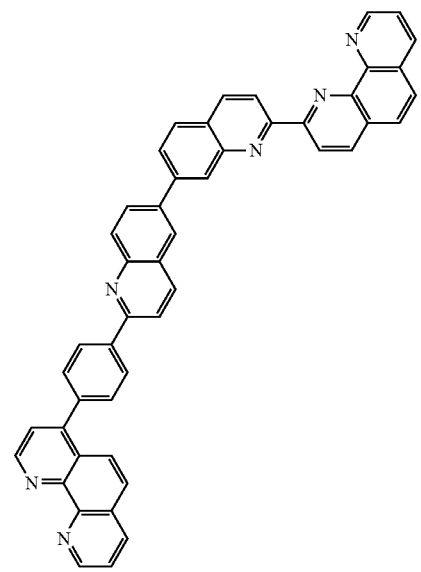 [SMILES: c1cnc2c(c1)ccc1ccc(-c3ccc4ccc(-c5ccc6nc(-c7ccc(-c8ccnc9c8ccc8cccnc89)cc7)ccc6c5)cc4n3)nc12] | 61% |
| 183 | Ac 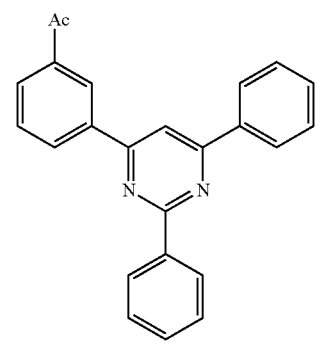 [SMILES: CC(=O)c1cccc(-c2cc(-c3ccccc3)nc(-c3ccccc3)n2)c1] | 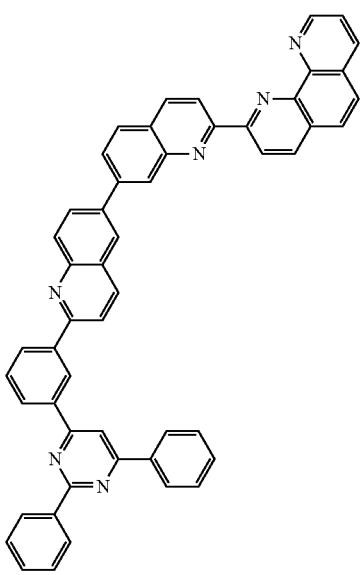 [SMILES: c1ccc(-c2cc(-c3cccc(-c4ccc5cc(-c6ccc7ccc(-c8ccc9ccc%10cccnc%10c9n8)nc7c6)ccc5n4)c3)nc(-c3ccccc3)n2)cc1] | 71% |

Target compounds were synthesized in the same manner as in Preparation Example 1 except that 2-phenyl-9-(7-(4,4,5,5-tetramethyl-1,3,2-dioxaborolan-2-yl) quinolin-2-yl)-1,10-phenanthroline was used instead of 2-(pyridin-2-yl)-7-(4,4,5,5-tetramethyl-1,3,2-dioxaborolan-2-yl) quinoline, and Intermediate R(1) of the following Table 1-18 was used instead of acetophenone.

TABLE 1-18

| [Group II] Compound No. | Intermediate R(1) | Target Compound | Yield |
|---|---|---|---|
| 185 | Ac | | 66% |
| 187 | Ac | | 67% |

Target compounds were synthesized in the same manner as in Preparation Example 1 except that 5-(7-(4,4,5,5-tetramethyl-1,3,2-dioxaborolan-2-yl) quinolin-2-yl)-1,10-phenanthroline was used instead of 2-(pyridin-2-yl)-7-(4,4,5,5-tetramethyl-1,3,2-dioxaborolan-2-yl)quinoline, and Intermediate S(1) of the following Table 1-19 was used instead of acetophenone.

TABLE 1-19
| [Group II] Compound No. | Intermediate S(1) | Target Compound | Yield |
|---|---|---|---|
| 192 | 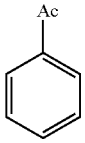 | 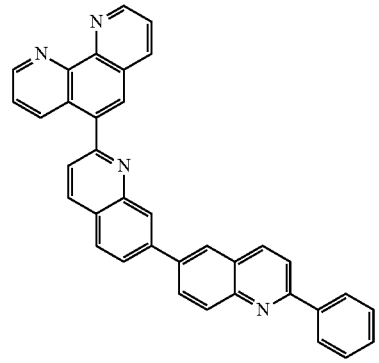 [SMILES: c1ccc(-c2ccc3cc(-c4ccc5ccc(-c6cc7cccnc7c7ncccc67)nc5c4)ccc3n2)cc1] | 72% |
| 196 | 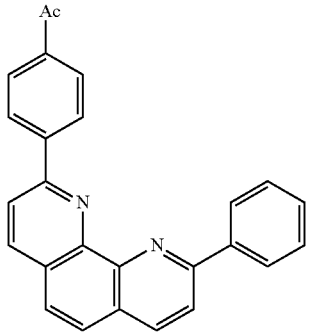 [SMILES: CC(=O)c1ccc(-c2ccc3ccc4ccc(-c5ccccc5)nc4c3n2)cc1] | 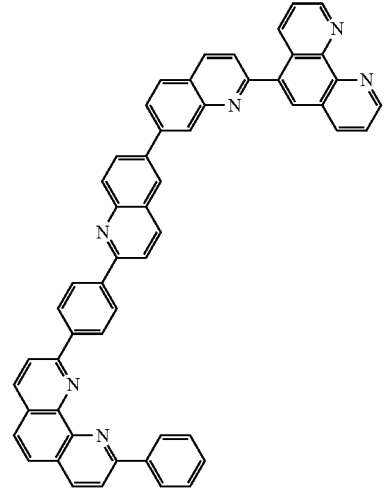 [SMILES: c1ccc(-c2ccc3ccc4ccc(-c5ccc(-c6ccc7cc(-c8ccc9ccc(-c%10cc%11cccnc%11c%11ncccc%10%11)nc9c8)ccc7n6)cc5)nc4c3n2)cc1] | 77% |
| 200 | 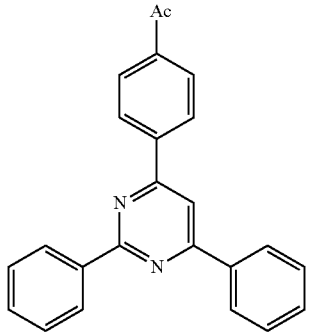 [SMILES: CC(=O)c1ccc(-c2cc(-c3ccccc3)nc(-c3ccccc3)n2)cc1] | 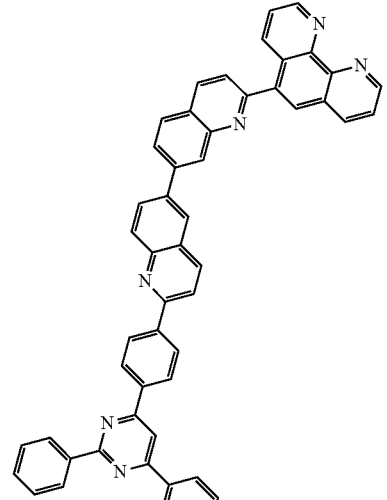 | 69% |

Target compounds were synthesized in the same manner as in Preparation Example 1 except that 2-(3-(pyridin-2-yl)phenyl)-7-(4,4,5,5-tetramethyl-1,3,2-dioxaborolan-2-yl) quinoline was used instead of 2-(pyridin-2-yl)-7-(4,4,5,5-ttetramethyl-1,3,2-dioxaborolan-2-yl) quinoline, and Intermediate T(1) of the following Table 1-20 was used instead of acetophenone.

TABLE 1-20

| [Group II] Compound No. | Intermediate T(1) | Target Compound | Yield |
|---|---|---|---|
| 202 | Ac 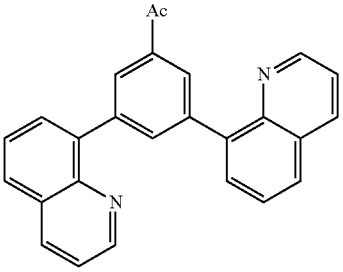 [SMILES: CC(=O)c1cc(-c2cccc3cccnc23)cc(-c2cccc3cccnc23)c1] | 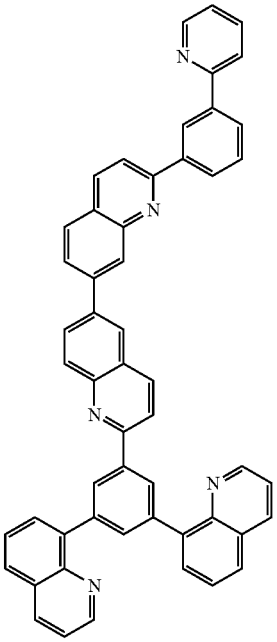 [SMILES: c1ccc(-c2cccc(-c3ccc4ccc(-c5ccc6nc(-c7cc(-c8cccc9cccnc89)cc(-c8cccc9cccnc89)c7)ccc6c5)cc4n3)c2)nc1] | 72% |

Target compounds were synthesized in the same manner as in Preparation Example 1 except that 2-(3-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate U(1) of the following Table 1-21 was used instead of acetophenone.

TABLE 1-21
| [Group II] Compound No. | Intermediate U(1) | Target Compound | Yield |
|---|---|---|---|
| 208 | | | 75% |
| 209 | | | 72% |
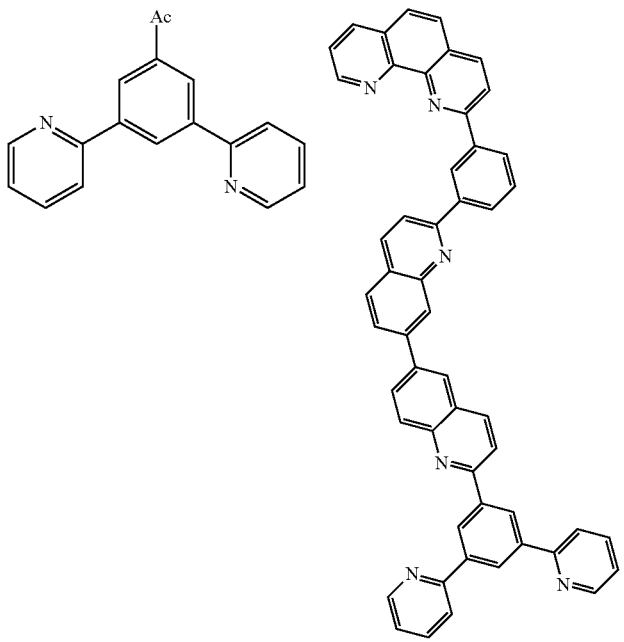
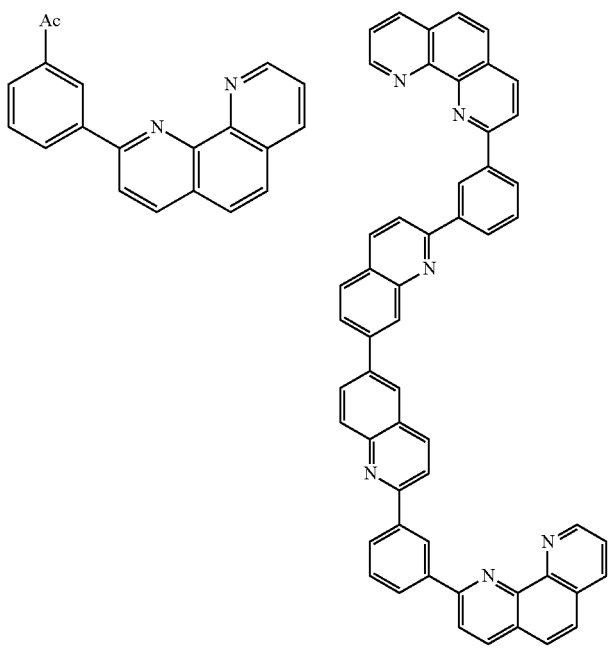

Target compounds were synthesized in the same manner as in Preparation Example 1 except that 2-(4-(7-(4,4,5,5-tetramethyl-1,3,2-dioxaborolan-2-yl)quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate V(1) of the following Table 1-22 was used instead of acetophenone.

TABLE 1-22

| [Group II] Compound No. | Intermediate V(1) | Target Compound | Yield |
|---|---|---|---|
| 212 | 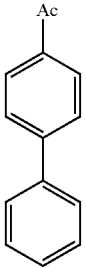 [SMILES: CC(=O)c1ccc(-c2ccccc2)cc1] | 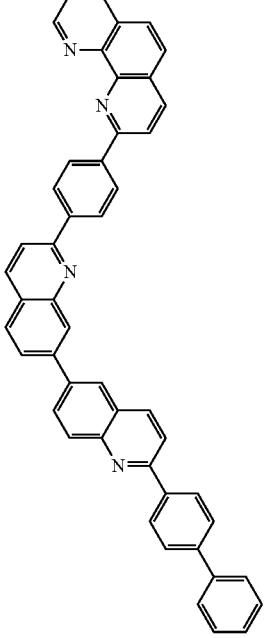 | 69% |
| 214 | 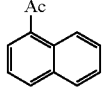 | 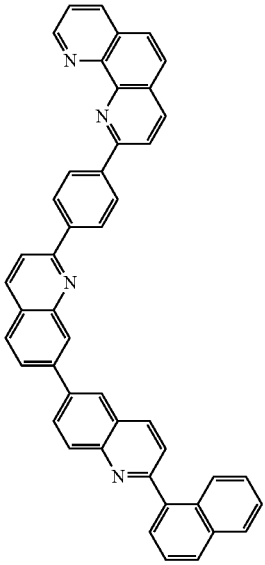 [SMILES: c1ccc2c(-c3ccc4cc(-c5ccc6ccc(-c7ccc(-c8ccc9ccc%10cccnc%10c9n8)cc7)nc6c5)ccc4n3)cccc2c1] | 70% |
| 216 | 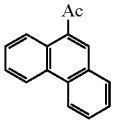 [SMILES: CC(=O)c1cc2ccccc2c2ccccc12] | 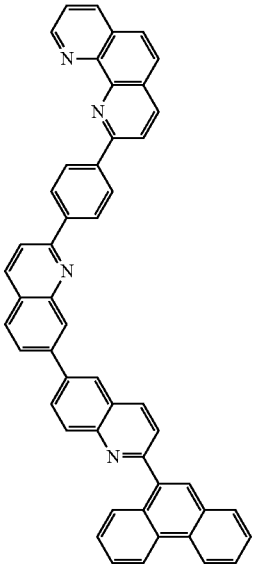 [SMILES: c1ccc2c(c1)cc(-c1ccc3cc(-c4ccc5ccc(-c6ccc(-c7ccc8ccc9cccnc9c8n7)cc6)nc5c4)ccc3n1)c1ccccc12] | 75% |

Target compounds were synthesized in the same manner as in Preparation Example 1 except that 4-(4-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate W(1) of the following Table 1-23 was used instead of acetophenone.

Target compounds were synthesized in the same manner as in Preparation Example 1 except that 5-(4-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate X(1) of the following Table 1-24 was used instead of acetophenone.
TABLE 1-24
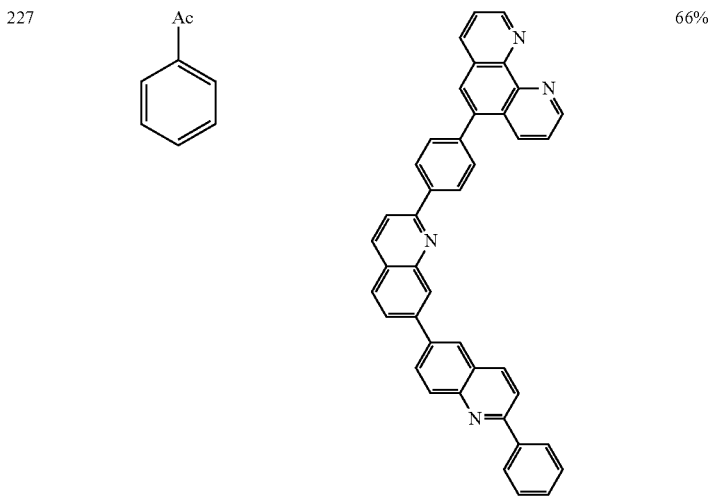

TABLE 1-24-continued

| [Group II] Compound No. | Intermediate X(1) | Target Compound | Yield |
|---|---|---|---|
| 232 | Ac-(pyrene) | (structure) | 68% |

Target compounds were synthesized in the same manner as in Preparation Example 1 except that 2-(4-(7-(4,4,5,5-tetramethyl-1,3,2-dioxaborolan-2-yl) quinolin-2-yl) naphthalen-1-yl)-1,10-phenanthroline was used instead of 2-(pyridin-2-yl)-7-(4,4,5,5-tetramethyl-1,3,2-dioxaborolan-2-yl) quinoline, and Intermediate Y(1) of the following Table 1-25 was used instead of acetophenone.

TABLE 1-25

| [Group II] Compound No. | Intermediate Y(1) | Target Compound | Yield |
|---|---|---|---|
| 234 | Ac-phenyl | (structure) | 71% |
| 236 | Ac-biphenyl | (structure) | 69% |

Target compounds were synthesized in the same manner as in Preparation Example 1 except that 2-(6-(7-(4,4,5,5-tetramethyl-1,3,2-dioxaborolan-2-yl) quinolin-2-yl) naphthalen-2-yl)-1,10-phenanthroline was used instead of 2-(pyridin-2-yl)-7-(4,4,5,5-tetramethyl-1,3,2-dioxaborolan- 2-yl) quinoline, and Intermediate Z(1) of the following Table 1-26 was used instead of acetophenone.

TABLE 1-26

| [Group II] Compound No. | Intermediate Z(1) | Target Compound | Yield |
|---|---|---|---|
| 241 | Ac-phenyl | (structure) | 78% |

TABLE 1-26-continued

| [Group II] Compound No. | Intermediate Z(1) | Target Compound | Yield |
|---|---|---|---|
| 244 | Ac-naphthyl | (structure) | 71% |

Target compounds were synthesized in the same manner as in Preparation Example 1 except that 2-phenyl-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate AA(1) of the following Table 1-27 was used instead of acetophenone.

TABLE 1-27

| [Group II] Compound No. | Intermediate AA(1) | Target Compound | Yield |
|---|---|---|---|
| 252 | (structure) | (structure) | 76% |

Syntheses of the prepared compounds were identified from Mass and NMR results, and the synthesis results are shown in the following Tables 1-28 and 1-29.

TABLE 1-28

| [Group II] Compound No. | $^1$H NMR (CDCl$_3$, 300 Mz) |
|---|---|
| 1 | δ = 9.30(1H, d), 8.53(1H, d), 8.21~8.31(6H, m), 8.03~8.12(4H, m), 7.90(1H, s), 7.70(1H, t), 7.47~7.54(3H, m), 7.35(1H, d), 7.14(1H, t) |
| 2 | δ = 9.30(1H, d), 8.46~8.55(3H, m), 8.21~8.31(4H, m), 8.03~8.12(6H, m), 7.90(1H, s), 7.55~7.70(4H, m), 7.35(1H, d), 7.14(1H, t) |
| 8 | δ = 9.30(1H, d), 8.53(1H, d), 8.21~8.31(9H, m), 8.03~8.12(4H, m), 7.90(1H, s), 7.70~7.81(4H, m), 7.35~7.60(8H, m), 7.14(1H, t) |
| 12 | δ = 9.30(1H, d), 8.53(1H, d), 8.21~8.31(9H, m), 8.03~8.12(4H, m), 7.88~7.90(2H, m), 7.70(1H, m), 7.35~7.53(9H, m), 7.14(1H, t) |
| 13 | δ = 9.30(1H, d), 8.81(2H, d), 8.53~8.55(2H, m), 8.21~8.33(8H, m), 8.03~8.12(5H, m), 7.90~7.94(2H, m), 7.63~7.79(6H, m), 7.25~7.51(8H, m), 7.14(1H, t) |
| 17 | δ = 9.30(1H, d), 8.81(2H, d), 8.53(1H, d), 8.21~8.31(8H, m), 8.03~8.12(4H, m), 7.88~7.90 (3H, d), 7.70(1H, t), 7.35~7.51(7H, m), 7.14(1H, t) |
| 19 | δ = 9.30(1H, d), 8.53~8.57(2H, m), 7.98~8.31(13H, m), 7.90(1H, d), 7.54~7.78(5H, m), 7.35(1H, d), 7.14(1H, t) |
| 21 | δ = 9.30(1H, d), 8.83(1H, d), 8.53(1H, d), 8.29~8.38(9H, m), 8.03~8.12(4H, m), 7.90(1H, s), 7.81(1H, d), 7.70 (1H, t), 7.58(1H, m), 7.14(1H, t) |
| 24 | δ = 9.30(1H, d), 8.83(1H, d), 8.72(1H, s), 8.53(1H, d), 8.21~8.38(7H, m), 8.03~8.12(6H, m), 7.90(1H, s), 7.81(1H, d), 7.58~7.70(3H, m), 7.35(2H, d), 7.14(1H, t) |
| 27 | δ = 9.30(1H, d), 8.84(4H, s), 8.53(1H, m), 8.21~8.31(6H, m), 8.03~8.12(7H, m), 7.90(1H, s), 7.81(1H, d), 7.70(1H, m), 7.47~7.54(3H, m), 7.35(3H, d), 7.14(1H, t) |
| 32 | δ = 9.75(1H, s), 8.93(1H, d), 8.76(1H, d), 8.44(1H, d), 8.03~8.30(8H, m), 7.90(1H, s), 7.41~7.60(6H, m) |
| 34 | δ = 9.75(1H, s), 8.93(1H, d), 8.85(1H, m), 8.76(1H, d), 8.38~8.44(2H, m), 7.90~8.21(10H, m), 7.59~7.60(3H, m), 7.35~7.41(2H, m) |
| 36 | δ = 9.75(1H, s), 8.93(1H, d), 8.76~8.84(6H, m), 8.38~8.44(2H, m), 8.27(1H, s), 8.21(1H, d), 8.03~8.10(6H, m), 7.90(1H, s), 7.81(1H, d), 7.58~7.60(2H, m), 7.35~7.41(3H, m) |
| 39 | δ = 9.75(1H, s), 8.93(1H, m), 8.76~8.83(5H, m), 8.38~8.44(3H, m), 8.27(1H, s), 8.21(1H, d), 8.03~8.12(4H, m), 7.90(1H, s), 7.58~7.65(4H, m), 7.28~7.41(4H, m) |
| 43 | δ = 8.78(2H, d), 8.44~8.55(5H, m), 8.27(1H, s), 8.21(1H, d), 8.03~8.12(6H, m), 7.90(1H, s), 7.55~7.64(3H, m), 7.41(1H, d), 7.35(1H, d) |
| 46 | δ = 8.93(2H, d), 8.78(2H, d), 8.44~8.50(4H, m), 8.03~8.27(8H, m), 7.82~7.90(5H, m), 7.41(1H, d), 7.35(1H, d) |
| 47 | δ = 8.78~8.84(7H, m), 8.38~8.50(4H, m), 8.21~8.27(2H, m), 8.03~8.12(6H, m), 7.90(1H, s), 7.81(1H, d), 7.58(1H, t), 7.35~7.41(3H, m) |
| 52 | δ = 8.78~8.85(5H, m), 8.38~8.50(6H, m), 8.21~8.27(2H, d), 7.90~8.12(9H, m), 7.81(1H, d), 7.58(1H, m), 7.35~7.41(3H, m) |
| 59 | δ = 8.97(2H, d), 8.81(2H, d), 8.44(1H, m), 8.21~8.33(7H, m), 8.03~8.12(4H, m), 7.90(1H, s), 7.79(2H, m), 7.35~7.51(9H, m) |
| 60 | δ = 8.97(2H, d), 8.81(2H, d), 8.44(1H, m), 8.21~8.28(6H, m), 8.03~8.12(4H, m), 7.88~7.90(3H, m), 7.35~7.51(9H, m) |
| 62 | δ = 8.97(2H, d), 8.81(2H, d), 8.55(1H, d), 8.44(1H, d), 8.03~8.27(9H, m), 7.88~7.94(6H, m), 7.63~7.68(3H, m), 7.25~7.51(10H, m) |
| 63 | δ = 8.44(1H, d), 8.37(1H, s), 8.21~8.30(4H, m), 8.03~8.12(4H, m), 7.90(1H, s), 7.79(4H, d), 7.35~7.54(11H, m) |
| 68 | δ = 8.84(4H, d), 8.37~8.44(3H, m), 8.21~8.27(2H, m), 8.03~8.12(6H, m), 7.90(1H, s), 7.79~7.81(5H, m), 7.35~7.51(10H, m) |
| 73 | δ = 9.30(1H, s), 9.05~9.07(2H, m), 8.84(4H, m), 8.38~8.44(2H, m), 8.27(1H, s), 8.21(1H, d), 8.03~8.12(6H, m), 7.90(1H, s), 7.81(1H, d), 7.58(1H, t), 7.41(1H, d), 7.35(1H, d) |
| 77 | δ = 9.19(1H, s), 8.44(1H, d), 8.21~8.30(6H, m), 8.03~8.12(4H, m), 7.90(1H, s), 7.79(2H, d), 7.35~7.54(11H, m) |
| 78 | δ = 9.19(1H, s), 8.55(1H, m), 8.44~8.46(2H, m), 8.21~8.28(4H, m), 8.03~8.12(6H, m), 7.90(1H, s), 7.79(2H, m), 7.35~7.64(11H, m) |
| 80 | δ = 9.19(1H, s), 8.93(1H, d), 8.61(1H, d), 8.44(1H, d), 8.04~8.28(10H, m), 7.71~7.90(8H, m), 7.35~7.51(8H, m) |
| 83 | δ = 9.19(1H, s), 8.84(4H, s), 8.44(1H, d), 8.21~8.30(6H, m), 8.03~8.12(7H, m), 7.90(1H, s), 7.79~7.81(3H, m), 7.35~7.51(13H, m) |
| 85 | δ = 9.19(1H, s), 8.81~8.83(4H, m), 8.38~8.44(3H, m), 8.21~8.28(4H, m), 8.03~8.12(4H, m), 7.90(1H, s), 7.79(2H, m), 7.28~7.58(13H, m) |
| 92 | δ = 8.82~8.84(7H, d), 8.38~8.44(2H, m), 8.27(1H, s), 8.21(1H, m), 8.03~8.12(6H, m), 7.90(1H, s), 7.81(1H, d), 7.58(1H, t), 7.41(1H, d), 7.35(2H, d) |
| 97 | δ = 8.44(1H, d), 8.21~8.30(8H, m), 8.03~8.12(4H, m), 7.90(1H, s), 7.35~7.54(11H, m) |

TABLE 1-28-continued

[Group II]

| Compound No. | $^1$H NMR (CDCl$_3$, 300 Mz) |
|---|---|
| 98 | δ = 8.55(1H, d), 8.44(1H, m), 8.21~8.28(6H, m), 8.03~8.12(6H, m), 7.90(1H, s), 7.35~7.55(11H, m) |
| 102 | δ = 8.83~8.84(5H, s), 8.38~8.44(2H, m), 8.21~8.28(6H, m), 8.03~8.12(6H, m), 7.90(1H, s), 7.81(1H, d), 7.35~7.58(10H, m) |
| 105 | δ = 8.83(1H, d), 8.55(4H, d), 8.38~8.44(2H, m), 8.21~8.28(6H, m), 8.03~8.12(6H, m), 7.90(1H, s), 7.81(1H, d), 7.35~7.58(12H, m) |
| 107 | δ = 8.83~8.88(2H, m), 8.21~8.30(4H, m), 8.03~8.12(6H, m), 7.90(1H, s), 7.69(1H, m), 7.47~7.58(4H, m), 7.35(2H, d) |
| 111 | δ = 8.83~8.88(3H, m), 8.72(1H, s), 8.21~8.38(6H, m), 8.03~8.12(8H, m), 7.90(1H, s), 7.81(1H, d), 7.58~7.63(4H, m), 7.35(3H, d) |
| 116 | δ = 8.81~8.88(4H, m), 8.21~8.38(8H, m), 8.03~8.12(5H, m), 7.90(1H, s), 7.79(2H, d), 7.69(1H, m), 7.35~7.58(9H, m) |
| 119 | δ = 8.83~8.88(2H, m), 8.38(1H, d), 8.21~8.30(9H, m), 8.03~8.12(6H, m), 7.90(1H, s), 7.35~7.69(11H, m) |
| 120 | δ = 8.83~8.88(2H, m), 8.55(1H, d), 8.38(1H, d), 8.03~8.28(14H, m), 7.90~7.94(2H, m), 7.79~7.81(3H, m), 7.25~7.68(15H, m) |
| 121 | δ = 8.91(1H, s), 8.84(4H, d), 8.45(1H, d), 8.38(1H, d), 8.21~8.28(3H, m), 8.03~8.12(7H, m), 7.90(1H, s), 7.81(1H, d), 7.50~7.65(4H, m), 7.35~7.39(3H, d) |
| 125 | δ = 8.91(1H, s), 8.84(4H, s), 8.45(1H, d), 8.21~8.35(4H, m), 8.04~8.12(8H, m), 7.90~7.94(2H, m), 7.81(1H, d), 7.47~7.54(5H, m), 7.35(4H, d) |
| 129 | δ = 8.83(1H, d), 8.54(1H, d), 8.21~8.38(5H, m), 7.90~8.12(8H, m), 7.47~7.58(4H, m), 7.35(2H, d) |
| 131 | δ = 8.83~8.85(2H, m), 8.54(1H, d), 8.38(2H, d), 8.27(1H, s), 8.21(1H, d), 7.90~8.12(11H, m), 7.58~7.59(3H, m), 7.35(2H, d) |
| 133 | δ = 8.83(2H, d), 8.72(1H, s), 8.54(1H, d), 8.21~8.38(6H, m), 7.90~8.12(10H, m), 7.81(1H, d), 7.58~7.63(3H, m), 7.35(2H, d) |
| 137 | δ = 8.93~8.94(2H, s), 8.83~8.84(5H, d), 8.38~8.44(2H, m), 8.27(1H, s), 8.21(1H, d), 8.03~8.12(6H, m), 7.90~7.92(2H, m), 7.76~7.81(2H, m), 7.35~7.58(6H, m) |
| 140 | δ = 8.93~8.94(2H, s), 8.83(1H, d), 8.55(4H, s), 8.38~8.44(2H, m), 8.27(1H, s), 8.21(1H, m), 8.03~8.12(6H, m), 7.90~7.92(2H, d), 7.76~7.81(2H, m), 7.35~7.58(8H, m) |
| 145 | δ = 9.08(1H, s), 8.73(1H, s), 8.44(1H, d), 7.90~8.30(11H, m), 7.78(1H, m), 7.35~7.60(6H, m) |
| 146 | δ = 9.08(1H, s), 8.73(1H, s), 8.55(1H, d), 8.44~8.46(2H, m), 8.27(1H, s), 8.21(1H, d), 7.98~8.12(8H, m), 7.90(1H, s), 7.78(1H, m), 7.55~7.64(4H, m), 7.35~7.41(2H, m) |
| 148 | δ = 9.08(1H, s), 8.83(1H, d), 8.72~8.73(2H, d), 8.21~8.44(6H, m), 7.89~8.12(8H, m), 7.90(1H, s), 7.78~7.81(2H, m), 7.58~7.63(3H, m), 7.35~7.41(3H, m) |
| 167 | δ = 8.81(2H, d), 8.51(1H, d), 8.03~8.33(17H, m), 7.90(1H, s), 7.79~7.81(3H, m), 7.67(2H, d), 7.35~7.51(7H, m) |
| 168 | δ = 8.81(2H, d), 8.51(1H, d), 8.03~8.31(16H, m), 7.81~7.90(4H, m), 7.67(2H, d), 7.51(4H, m), 7.35~7.41(3H, m) |
| 172 | δ = 8.83(1H, d), 8.21~8.38(9H, m), 8.03~8.12(5H, m), 7.90(1H, s), 7.81(1h, d), 7.47~7.58(4H, m), 7.35(1H, d) |
| 177 | δ = 8.83(2H, d), 8.72(1H, s), 8.21~8.38(10H, m), 8.03~8.12(7H, m), 7.90(1H, s), 7.81(2H, d), 7.58~7.63(3H, m), 7.35(2H, d) |
| 180 | δ = 8.81~8.83(5H, m), 8.21~8.38(8H, m), 8.03~8.12(6H, m), 7.90(1H, s), 7.81(2H, d), 7.58(2H, m), 7.48(1H, d), 7.28~7.35(3H, m) |
| 183 | δ = 8.83(1H, d), 8.21~8.38(12H, m), 8.03~8.12(5H, m), 7.90(1H, s), 7.79~7.81(4H, m), 7.35~7.60(9H, m) |
| 185 | δ = 8.29~8.31(13H, m), 8.03~8.12(7H, m), 7.90(1H, s), 7.81(2H, d), 7.47~7.54(6H, m), 7.35(2H, d) |
| 187 | δ = 8.83(1H, d), 8.72(1H, s), 8.21~8.38(11H, m), 8.03~8.12(8H, m), 7.90(1H, s), 7.81(2H, d), 7.47~7.63(5H, m), 7.35(3H, d) |
| 192 | δ = 8.83(2H, d), 8.03~8.38(12H, m), 7.90(1H, s), 7.47~7.58(5H, m), 7.35(2H, d) |
| 196 | δ = 8.83~8.84(5H, d), 8.03~8.38(15H, m), 7.90(1H, s), 7.81(1H, d), 7.47~7.58(5H, m), 7.35(3H, d) |
| 200 | δ = 8.81~8.83(4H, m), 8.03~8.38(15H, m), 7.90(1H, s), 7.79(2H, m), 7.35~7.58(10H, m) |
| 202 | δ = 8.83(2H, d), 8.72(1H, s), 8.50(1H, d), 8.02~8.38(17H, m), 7.90(1H, s), 7.51~7.72(7H, m), 7.35(2H, d), 7.26(1H, d), 7.00(1H, m) |
| 208 | δ = 8.83(1H, d), 8.72~8.74(4H, d), 8.50(2H, d), 8.21~8.38(5H, m), 8.03~8.12(7H, m), 7.90(1H, s), 7.81(1H, d), 7.51~7.63(4H, m), 7.35~7.26(5H, m), 7.00(2H, m) |
| 209 | δ = 8.83(2H, d), 8.72(2H, s), 8.21~8.38(8H, m), 8.03~8.12(9H, m), 7.90(1H, s), 7.81(2H, d), 7.58~7.63(4H, m), 7.35(3H, d) |
| 212 | δ = 8.81~8.84(7H, d), 8.38(1H, d), 8.27(1H, s), 8.21(1H, d), 8.03~8.12(7H, m), 7.81~7.90(4H, m), 7.35~7.58(9H, m) |
| 214 | δ = 8.83~8.84(5H, d), 8.55(1H, d), 8.46(1H, d), 8.38(1H, d), 8.27(1H, s), 8.21(1H, d), 8.03~8.12(9H, m), 7.90(1H, s), 7.81(1H, d), 7.55~7.64(4H, m), 7.35(3H, d) |

TABLE 1-28-continued

| [Group II] Compound No. | $^1$H NMR (CDCl$_3$, 300 Mz) |
|---|---|
| 216 | δ = 8.93(2H, d), 8.83~8.84(5H, s), 8.38~8.44(2H, m), 8.27(1H, s), 8.21(1H, d), 8.03~8.12(9H, m), 7.81~7.88(6H, m), 7.58(1H, t), 7.35(3H, d) |
| 219 | δ = 8.81~8.89(4H, m), 8.21~8.38(5H, m), 8.03~8.12(6H, m), 7.90(1H, s), 7.81(1H, m), 7.47~7.58(5H, m), 7.35(2H, d), 7.28(2H, d) |
| 223 | δ = 8.81~8.89(4H, m), 8.55(1H, d), 8.46(1H, d), 8.38(1H, d), 8.27(1H, s), 8.21(1H, m), 8.03~8.12(8H, m), 7.90(1H, s), 7.81(1H, m), 7.48~7.64(5H, m), 7.35(2H, d), 7.28(2H, d) |
| 227 | δ = 8.81~8.83(4H, m), 8.21~8.38(6H, m), 8.03~8.12(5H, m), 7.90(1H, s), 7.47~7.65(6H, m), 7.35(2H, d), 7.28(2H, d) |
| 232 | δ = 8.81~8.83(4H, m), 8.55(1H, d), 8.38(2H, d), 8.21~8.27(3H, m), 8.03~8.12(6H, m), 7.82~7.90(3H, m), 7.71(4H, s), 7.65(1H, s), 7.58(2H, d), 7.35(2H, d), 7.28(2H, d) |
| 234 | δ = 8.83(1H, d), 8.55(4H, d), 8.21~8.38(5H, m), 8.03~8.12(7H, m), 7.90(1H, s), 7.81(1H, d), 7.47~7.58(6H, m), 7.35(3H, d) |
| 236 | δ = 8.81~8.83(3H, m), 8.55(4H, s), 8.38(1H, d), 8.27(1H, s), 8.21(1H, d), 8.03~8.12(7H, m), 7.81~7.90(4H, m), 7.35~7.58(11H, m) |
| 241 | δ = 8.83~8.85(3H, m), 8.21~8.38(7H, m), 7.90~8.12(10H, m), 7.81(1H, d), 7.47~7.58(4H, m), 7.35(3H, d) |
| 244 | δ = 8.83~8.85(3H, m), 8.55(1H, m), 8.38~8.46(4H, m), 8.27(1H, s), 8.21(1H, d), 7.90~8.12(12H, m), 7.81(1H, d), 7.55~7.64(4H, m), 7.35(3H, d) |
| 252 | δ = 8.72(1H, s), 8.21~8.32(8H, m), 8.03~8.12(8H, m), 7.90(1H, s), 7.81(1H, d), 7.47~7.63(7H, m), 7.35(4H, d) |
| 255 | δ = 8.72(1H, s), 8.44(1H, d), 8.21~8.32(10H, m), 8.03~8.12(7H, m), 7.90(1H, s), 7.81(1H, d), 7.35~7.63(14H, m) |

TABLE 1-29

| [Group II] Compound No. | FD-MS | [Group II] Compound No. | FD-MS |
|---|---|---|---|
| 1 | m/z = 409.48 (C29H19N3 = 409.16) | 2 | m/z = 459.54 (C33H21N3 = 459.17) |
| 8 | m/z = 639.75 (C45H29N5 = 639.24) | 12 | m/z = 640.73 (C44H28N6 = 640.24) |
| 13 | m/z = 804.94 (C57H36N6 = 804.30) | 17 | m/z = 640.73 (C44H28N6 = 640.24) |
| 19 | m/z = 536.62 (C38H24N4 = 536.20) | 21 | m/z = 511.57 (C35H21N5 = 511.18) |
| 24 | m/z = 587.67 (C41H25N5 = 587.21) | 27 | m/z = 663.77 (C47H29N5 = 663.24) |
| 32 | m/z = 409.48 (C29H19N3 = 409.16) | 34 | m/z = 459.54 (C33H21N3 = 459.17) |
| 36 | m/z = 587.67 (C41H25N5 = 587.21) | 39 | m/z = 587.67 (C41H25N5 = 587.21) |
| 43 | m/z = 459.54 (C33H21N3 = 459.17) | 46 | m/z = 509.60 (C37H23N3 = 509.19) |
| 47 | m/z = 587.67 (C41H25N5 = 587.21) | 52 | m/z = 637.73 (C45H27N5 = 637.23) |
| 59 | m/z = 640.73 (C44H28N6 = 640.24) | 60 | m/z = 641.72 (C43H27N7 = 641.23) |
| 62 | m/z = 806.91 (C55H34N8 = 806.29) | 63 | m/z = 562.66 (C40H26N4 = 562.22) |
| 68 | m/z = 740.85 (C52H32N6 = 740.27) | 73 | m/z = 588.66 (C40H24N6 = 588.21) |
| 77 | m/z = 562.66 (C40H28N4 = 562.22) | 78 | m/z = 612.72 (C44H28N4 = 612.23) |
| 80 | m/z = 662.78 (C48H30N4 = 662.25) | 83 | m/z = 816.95 (C58H36N6 = 816.30) |
| 85 | m/z = 740.85 (C52H32N6 = 740.27) | 92 | m/z = 589.65 (C39H23N7 = 589.20) |
| 97 | m/z = 563.65 (C39H25N5 = 563.21) | 98 | m/z = 612.71 (C43H27N5 = 613.23) |
| 102 | m/z = 741.84 (C51H31N7 = 741.26) | 105 | m/z = 791.90 (C55H33N7 = 791.28) |
| 107 | m/z = 459.54 (C33H21N3 = 459.17) | 111 | m/z = 637.73 (C45H27N5 = 637.23) |
| 116 | m/z = 589.80 (C49H31N5 = 689.26) | 119 | m/z = 690.79 (C48H30N6 = 490.25) |
| 120 | m/z = 854.99 (C61H36N6 = 854.32) | 121 | m/z = 637.73 (C45H27N5 = 637.23) |
| 125 | m/z = 713.83 (C51H31N5 = 713.26) | 129 | m/z = 459.54 (C33H21N3 = 459.17) |

TABLE 1-29-continued

| [Group II] Compound No. | FD-MS | [Group II] Compound No. | FD-MS |
|---|---|---|---|
| 131 | m/z = 509.60 (C37H23N3 = 509.19) | 133 | m/z = 637.54 (C45H27N3 = 637.23) |
| 137 | m/z = 637.73 (C45H27N5 = 637.23) | 140 | m/z = 687.79 (C49H29N5 = 687.24) |
| 145 | m/z = 459.54 (C33H21N3 = 459.17) | 146 | m/z = 509.60 (C37H23N3 = 509.19) |
| 148 | m/z = 637.73 (C45H27N5 = 637.23) | 167 | m/z = 739.86 (C53H33N5 = 739.27) |
| 168 | m/z = 740.85 (C52H32N6 = 740.27) | 172 | m/z = 510.59 (C36H22N4 = 510.18) |
| 177 | m/z = 688.78 (C48H28N6 = 688.24) | 180 | m/z = 688.78 (C48H26N6 = 688.24) |
| 183 | m/z = 740.85 (C52H32N6 = 740.27) | 185 | m/z = 764.87 (C54H32N6 = 764.27) |
| 187 | m/z = 764.87 (C54H32N6 = 764.27) | 192 | m/z = 510.59 (C36H22N4 = 510.18) |
| 196 | m/z = 764.87 (C54H32N6 = 764.27) | 200 | m/z = 739.65 (C53H33N5 = 739.27) |
| 202 | m/z = 740.85 (C52H32N6 = 740.27) | 208 | m/z = 740.27 (C52H32N6 = 740.27) |
| 209 | m/z = 764.87 (C54H32N6 = 764.27) | 212 | m/z = 662.78 (C48H30N4 = 662.25) |
| 214 | m/z = 636.74 (C46H28N4 = 636.23) | 216 | m/z = 686.80 (C50H30N4 = 686.25) |
| 219 | m/z = 586.22 (C42H28N4 = 586.22) | 223 | m/z = 636.74 (C46H28N4 = 606.23) |
| 227 | m/z = 586.68 (C42H26N4 = 586.22) | 232 | m/z = 710.82 (C52H30N4 = 710.25) |
| 234 | m/z = 636.74 (C46H26N4 = 636.23) | 236 | m/z = 712.84 (C52H32N4 = 712.26) |
| 241 | m/z = 636.74 (C46H28N4 = 636.23) | 244 | m/z = 686.80 (C50H30N4 = 686.25) |
| 252 | m/z = 662.78 (C48H30N4 = 662.25) | 255 | m/z = 817.93 (C57H35N7 = 817.30) |

[Preparation Example 2] Preparation of Compound 1 of [Group III]

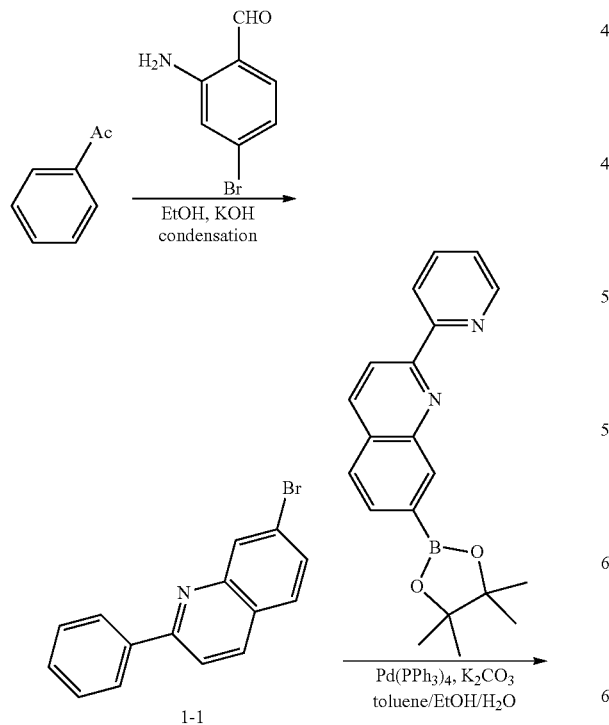

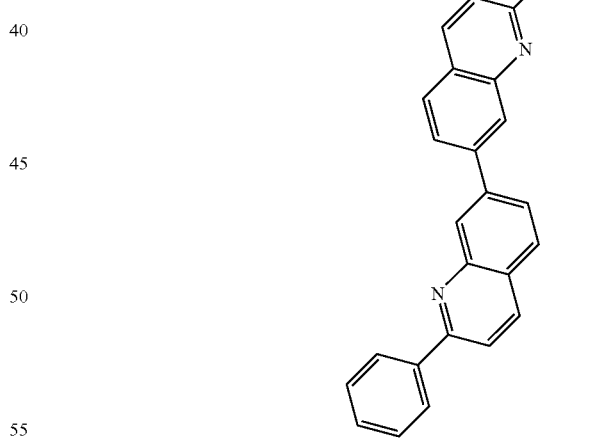

Preparation of Compound 1-1 of [Group III]

After dissolving acetophenone (11 g, 91.2 mmol) and 2-amino-4-bromobenzaldehyde (28 g, 91.2 mmol) in EtOH (300 mL), KOH (91.2 mmol) was introduced to the reaction vessel, and the result was heated to 80° C. After the reaction was completed, the result was cooled to room temperature, and then extracted with distilled water and ethyl acetate. The extracted organic layer was dried with anhydrous $Na_2SO_4$ and then filtered. The solvent of the filtered organic layer was removed using a rotary evaporator, and the result was purified by column chromatography using dichloromethane and hexane as a developing solvent to obtain target Compound 1-1 of [Group III] (19.2 g, 80%).

Preparation of Compound 1 of [Group III]

After dissolving Compound 1-1 of [Group III] (5 g, 22.2 mmol) and 2-(pyridin-2-yl)-7-(4,4,5,5-tetramethyl-1,3,2-dioxaborolan-2-yl)quinoline (7.4 g, 22.2 mmol) in toluene (50 ML), Pd(PPh$_3$)$_4$ (2.3 g, 2 mmol) and K$_2$CO$_3$ (8.3 g, 60 mmol) were introduced thereto, and the result was stirred for 10 minutes. To the reaction vessel, H$_2$O (10 mL) and EtOH (6 mL) were further added dropwise, and the result was refluxed for 12 hours. After the reaction was completed, the result was cooled to room temperature, and then extracted with distilled water and dichloromethane. The extracted organic layer was dried with anhydrous Na$_2$SO$_4$ and then filtered. The solvent of the filtered organic layer was removed using a rotary evaporator, and the result was purified by column chromatography using ethyl acetate and hexane as a developing solvent to obtain target Compound 1 of [Group III] (4.7 g, 64%).

Preparation of Other Compounds of [Group III]

Target compounds were synthesized in the same manner as in Preparation Example 2 except that Intermediate A(2) of the following Table 2-1 were used instead of acetophenone.

TABLE 2-1

| [Group III] Compound No. | Intermediate A(2) | Target Compound | Yield |
|---|---|---|---|
| 2 | | | 70% |
| 8 | | | 71% |

TABLE 2-1-continued

| [Group III] Compound No. | Intermediate A(2) | Target Compound | Yield |
|---|---|---|---|
| 12 | | | 65% |
| 13 | | | 72% |
| 17 | | | 69% |

TABLE 2-1-continued

| [Group III] Compound No. | Intermediate A(2) | Target Compound | Yield |
|---|---|---|---|
| 19 | | | 65% |
| 21 | | | 67% |
| 24 | | | 69% |

TABLE 2-1-continued

| [Group III] Compound No. | Intermediate A(2) | Target Compound | Yield |
|---|---|---|---|
| 27 | 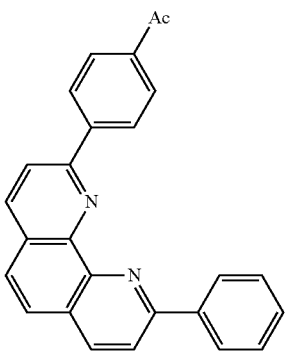 | 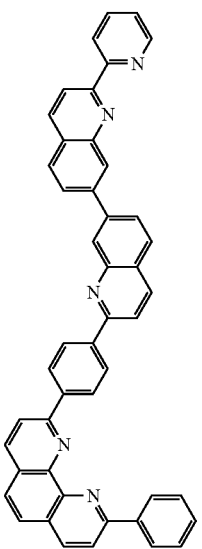 | 69% |

Target compounds were synthesized in the same manner as in Preparation Example 2 except that 2-(pyridin-3-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate B(2) of the following Table 2-2 was used instead of acetophenone.

TABLE 2-2

| [Group III] Compound No. | Intermediate B(2) | Target Compound | Yield |
|---|---|---|---|
| 32 | 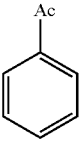 | 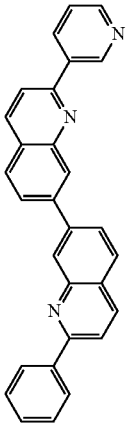 | 69% |

TABLE 2-2-continued

| [Group III] Compound No. | Intermediate B(2) | Target Compound | Yield |
|---|---|---|---|
| 34 | Ac-naphthalenyl | (structure) | 65% |
| 36 | Ac-phenyl-phenanthroline | (structure) | 76% |
| 39 | Ac-phenyl-phenanthroline | (structure) | 74% |

Target compounds were synthesized in the same manner as in Preparation Example 2 except that 2-(pyridin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate C(2) of the following Table 2-3 was used instead of acetophenone.

TABLE 2-3
| [Group III] Compound No. | Intermediate C(2) | Target Compound | Yield |
|---|---|---|---|
| 43 | 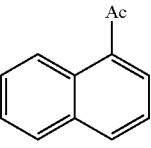 | 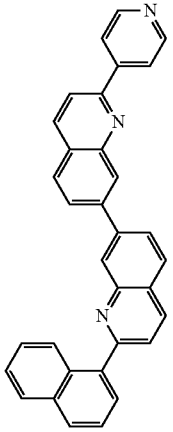 | 65% |
| 46 | 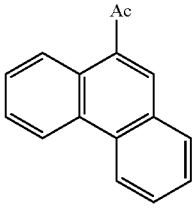 | 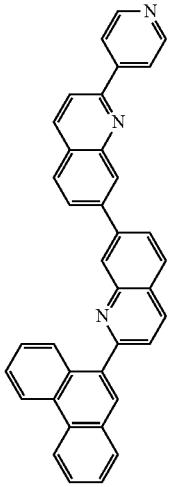 | 70% |
| 47 | 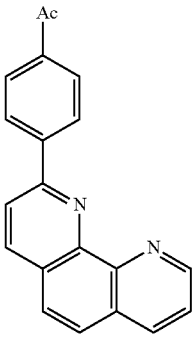 | 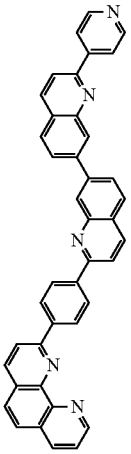 | 75% |

TABLE 2-3-continued

| [Group III] Compound No. | Intermediate C(2) | Target Compound | Yield |
|---|---|---|---|
| 52 | (structure) | (structure) | 76% |

Target compounds were synthesized in the same manner as in Preparation Example 2 except that 2-(pyrimidin-2-yl)-7-(4,4,5,5-tetramethyl-1,3,2-dioxaborolan-2-yl)quinoline was used instead of 2-(pyridin-2-yl)-7-(4,4,5,5-tetramethyl-1,3,2-dioxaborolan-2-yl)quinoline, and Intermediate D(2) of the following Table 2-4 was used instead of acetophenone.

TABLE 2-4

| [Group III] Compound No. | Intermediate D(2) | Target Compound | Yield |
|---|---|---|---|
| 59 | (structure) | (structure) | 66% |

TABLE 2-4-continued

| [Group III] Compound No. | Intermediate D(2) | Target Compound | Yield |
|---|---|---|---|
| 60 | Ac-C6H4-triazine(Ph)(Ph) | (pyrimidinyl-quinoline)-quinoline-C6H4-triazine(Ph)(Ph) | 70% |
| 62 | Ac-C6H4-triazine(Ph)(C6H4-carbazole) | (pyrimidinyl-quinoline)-quinoline-C6H4-triazine(Ph)(C6H4-carbazole) | 67% |

Target compounds were synthesized in the same manner as in Preparation Example 2 except that 2-(4,6-diphenylpyrimidin-2-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate E(2) of the following Table 2-5 was used instead of acetophenone.

TABLE 2-5

| [Group III] Compound No. | Intermediate E(2) | Target Compound | Yield |
|---|---|---|---|
| 63 | Ac-C6H5 | (structure) | 69% |
| 68 | Ac-C6H4-(2-phenyl-1,10-phenanthroline) | (structure) | 71% |

Target compounds were synthesized in the same manner as in Preparation Example 2 except that 2-(pyrimidin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate F(2) of the following Table 2-6 was used instead of acetophenone.

TABLE 2-6

| [Group III] Compound No. | Intermediate F(2) | Target Compound | Yield |
|---|---|---|---|
| 73 | Ac-(phenyl-phenanthroline) | (pyrimidine-quinoline-phenyl-phenanthroline) | 68% |

Target compounds were synthesized in the same manner as in Preparation Example 2 except that 2-(2,6-diphenylpyrimidin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate G(2) of the following Table 2-7 was used instead of acetophenone.

TABLE 2-7

| [Group III] Compound No. | Intermediate G(2) | Target Compound | Yield |
|---|---|---|---|
| 77 | Ac-phenyl | (2,6-diphenylpyrimidine-quinoline-quinoline-phenyl) | 77% |
| 78 | Ac-naphthyl | (2,6-diphenylpyrimidine-quinoline-quinoline-naphthyl) | 74% |

TABLE 2-7-continued

| [Group III] Compound No. | Intermediate G(2) | Target Compound | Yield |
|---|---|---|---|
| 80 | | | 73% |
| 83 | | | 69% |
| 85 | | | 66% |

Target compounds were synthesized in the same manner as in Preparation Example 2 except that 7-(4,4,5,5-tetramethyl-1,3,2-dioxaborolan-2-yl)-2-(1,3,5-triazin-2-yl) quinoline was used instead of 2-(pyridin-2-yl)-7-(4,4,5,5-tetramethyl-1,3,2-dioxaborolan-2-yl)quinoline, and Intermediate H(2) of the following Table 2-8 was used instead of acetophenone.

TABLE 2-8

| [Group III] Compound No. | Intermediate H(2) | Target Compound | Yield |
|---|---|---|---|
| 92 | Ac | | 75% |

Target compounds were synthesized in the same manner as in Preparation Example 2 except that 2-(4,6-diphenyl-1,3,5-triazin-2-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl) quinoline, and Intermediate I(2) of the following Table 2-9 was used instead of acetophenone.

TABLE 2-9

| [Group III] Compound No. | Intermediate I(2) | Target Compound | Yield |
|---|---|---|---|
| 97 | Ac | | 67% |

TABLE 2-9-continued

| [Group III] Compound No. | Intermediate I(2) | Target Compound | Yield |
|---|---|---|---|
| 98 | (structure) | (structure) | 63% |
| 102 | (structure) | (structure) | 71% |
| 105 | (structure) | (structure) | 73% |

Target compounds were synthesized in the same manner as in Preparation Example 2 except that 7-(4,4,5,5-tetramethyl-1,3,2-dioxaborolan-2-yl)-2,8'-biquinoline was used instead of 2-(pyridin-2-yl)-7-(4,4,5,5-tetramethyl-1,3,2-dioxaborolan-2-yl)quinoline, and Intermediate J(2) of the following Table 2-10 was used instead of acetophenone.

TABLE 2-10
| [Group III] Compound No. | Intermediate J(2) | Target Compound | Yield |
|---|---|---|---|
| 107 | 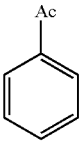 | 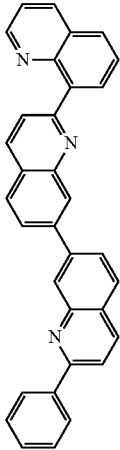 | 73% |
| 111 | 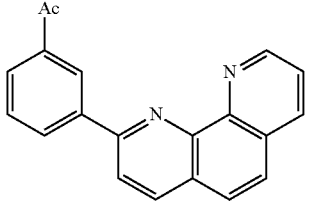 | 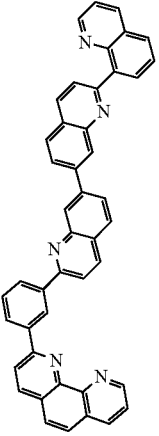 | 75% |
| 116 | 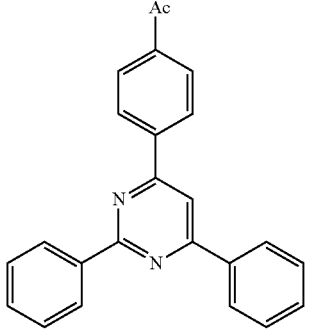 | 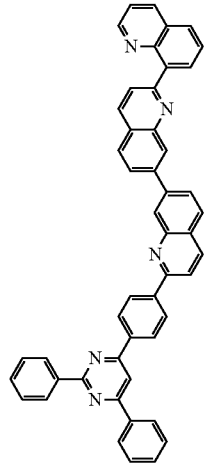 | 68% |

TABLE 2-10-continued

| [Group III] Compound No. | Intermediate J(2) | Target Compound | Yield |
|---|---|---|---|
| 119 | | | 67% |
| 120 | | | 65% |

Target compounds were synthesized in the same manner as in Preparation Example 2 except that 2-(isoquinolin-8-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate K(2) of the following Table 2-11 was used instead of acetophenone.

TABLE 2-11

| [Group III] Compound No. | Intermediate K(2) | Target Compound | Yield |
|---|---|---|---|
| 121 | Ac | | 71% |

Target compounds were synthesized in the same manner as in Preparation Example 2 except that 2-(isoquinolin-5-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate L(2) of the following Table 2-12 was used instead of acetophenone.

TABLE 2-12

| [Group III] Compound No. | Intermediate L(2) | Target Compound | Yield |
|---|---|---|---|
| 125 | Ac | | 74% |

Target compounds were synthesized in the same manner as in Preparation Example 2 except that 7-(4,4,5,5-tetramethyl-1,3,2-dioxaborolan-2-yl)-2,5'-biquinoline was used instead of 2-(pyridin-2-yl)-7-(4,4,5,5-tetramethyl-1,3,2-dioxaborolan-2-yl)quinoline, and Intermediate M(2) of the following Table 2-13 was used instead of acetophenone.

TABLE 2-13

| [Group III] Compound No. | Intermediate M(2) | Target Compound | Yield |
|---|---|---|---|
| 129 | Ac-phenyl | | 78% |
| 131 | Ac-naphthyl | | 68% |
| 133 | Ac-(3-(1,10-phenanthrolin-2-yl)phenyl) | | 76% |

Target compounds were synthesized in the same manner as in Preparation Example 2 except that 2-(isoquinolin-4-yl)-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate N(2) of the following Table 2-14 was used instead of acetophenone.

TABLE 2-14
| [Group III] Compound No. | Intermediate N(2) | Target Compound | Yield |
|---|---|---|---|
| 137 | 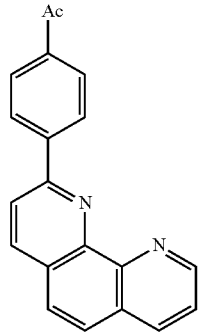 Ac | 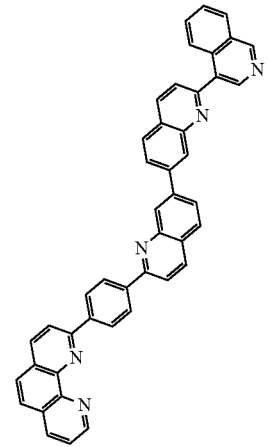 | 76% |
| 140 | 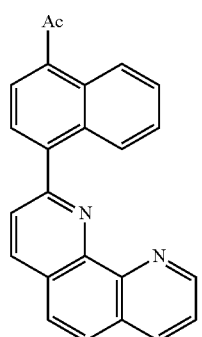 Ac | 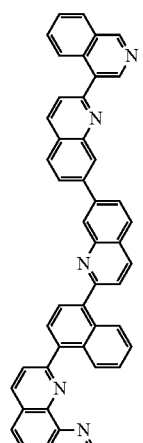 | 73% |
Target compounds were synthesized in the same manner as in Preparation Example 2 except that 7-(4,4,5,5-tetramethyl-1,3,2-dioxaborolan-2-yl)-2,5'-biquinoline was used instead of 2-(pyridin-2-yl)-7-(4,4,5,5-tetramethyl-1,3,2-dioxaborolan-2-yl)quinoline, and Intermediate O(2) of the following Table 2-15 was used instead of acetophenone.

TABLE 2-15

| [Group III] Compound No. | Intermediate O(2) | Target Compound | Yield |
|---|---|---|---|
| 145 | Ac-phenyl | (structure) | 68% |
| 146 | Ac-naphthyl | (structure) | 68% |
| 148 | Ac-(3-phenyl)-phenanthroline | (structure) | 67% |

Target compounds were synthesized in the same manner as in Preparation Example 2 except that 2-(7-(4,4,5,5-tetramethyl-1,3,2-dioxaborolan-2-yl) quinolin-2-yl)benzo [h] quinoline was used instead of 2-(pyridin-2-yl)-7-(4,4,5,5-tetramethyl-1,3,2-dioxaborolan-2-yl)quinoline, and Intermediate P(2) of the following Table 2-16 was used instead of acetophenone.

Table 2-16

| [Group III] Compound No. | Intermediate P(2) | Target Compound | Yield |
|---|---|---|---|
| 167 | Ac | | 75% |
| 168 | Ac | | 74% |

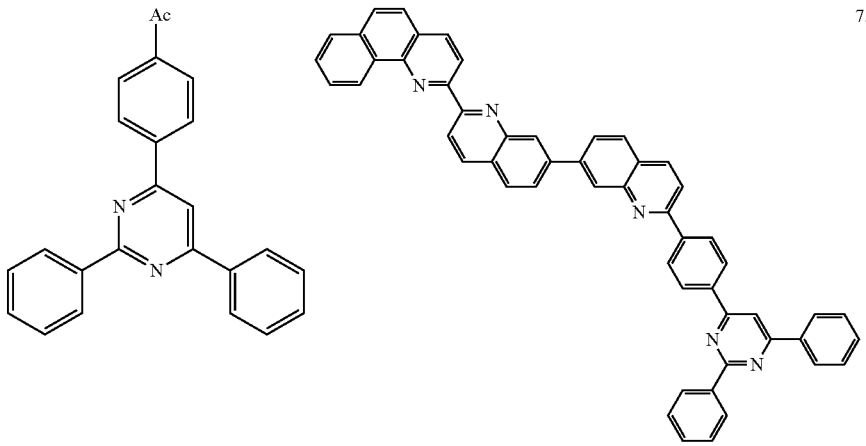
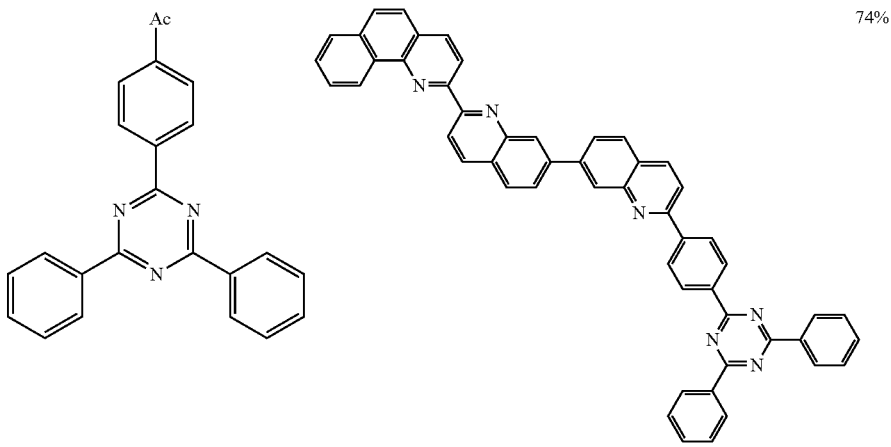

Target compounds were synthesized in the same manner as in Preparation Example 2 except that 2-(7-(4,4,5,5-tetramethyl-1,3,2-dioxaborolan-2-yl) quinolin-2-yl)-1,10-phenanthroline was used instead of 2-(pyridin-2-yl)-7-(4,4,5,5-tetramethyl-1,3,2-dioxaborolan-2-yl)quinoline, and Intermediate Q(2) of the following Table 2-17 was used instead of acetophenone.

391 392
TABLE 2-17
| [Group III] Compound No. | Intermediate Q(2) | Target Compound | Yield |
|---|---|---|---|
| 172 | 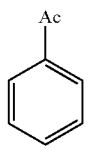 Ac | 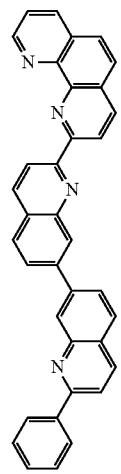 | 72% |
| 177 | 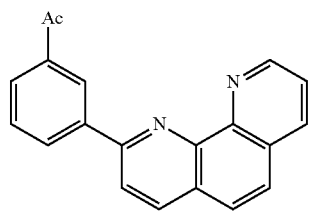 Ac | 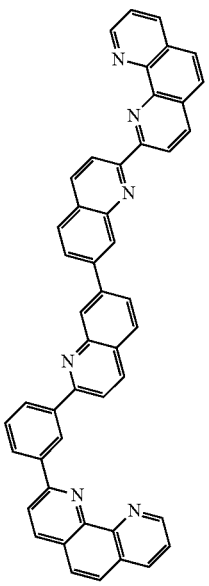 | 77% |

TABLE 2-17-continued

| [Group III] Compound No. | Intermediate Q(2) | Target Compound | Yield |
|---|---|---|---|
| 180 | Ac 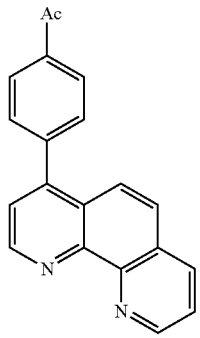 | 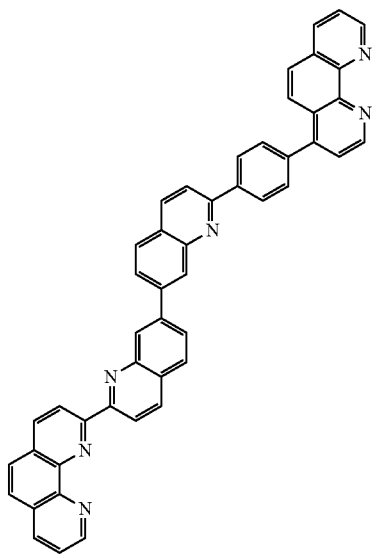 | 61% |
| 183 | Ac 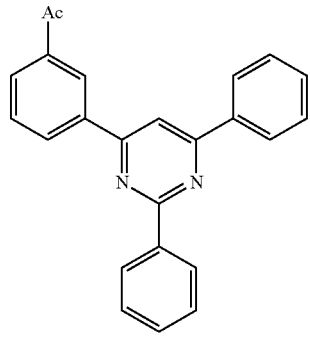 | 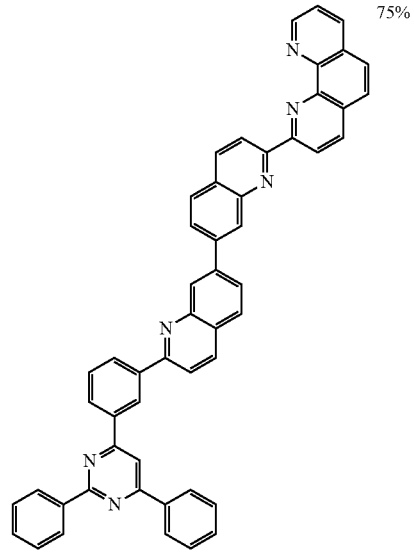 | 75% |

Target compounds were synthesized in the same manner as in Preparation Example 2 except that 2-phenyl-9-(7-(4,4,5,5-tetramethyl-1,3,2-dioxaborolan-2-yl) quinolin-2-yl)-1,10-phenanthroline was used instead of 2-(pyridin-2-yl)-7-(4,4,5,5-tetramethyl-1,3,2-dioxaborolan-2-yl) quinoline, and Intermediate R(2) of the following Table 2-18 was used instead of acetophenone.

TABLE 2-18

| [Group III] Compound No. | Intermediate R(2) | Target Compound | Yield |
|---|---|---|---|
| 185 | Ac 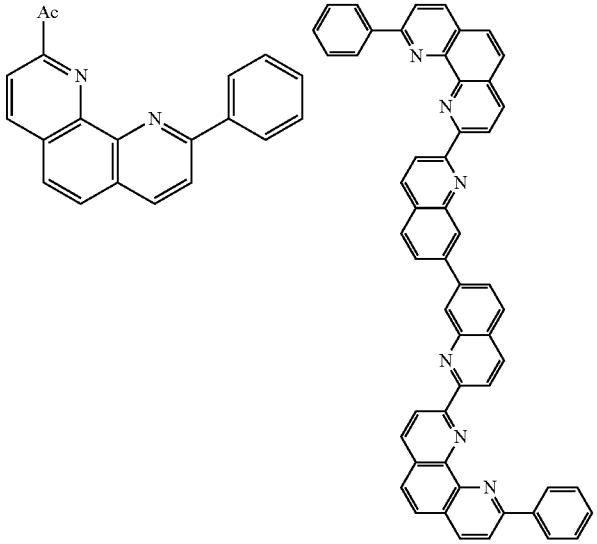 | 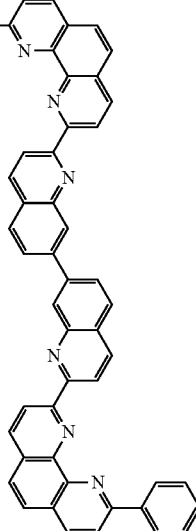 | 68% |
| 187 | Ac 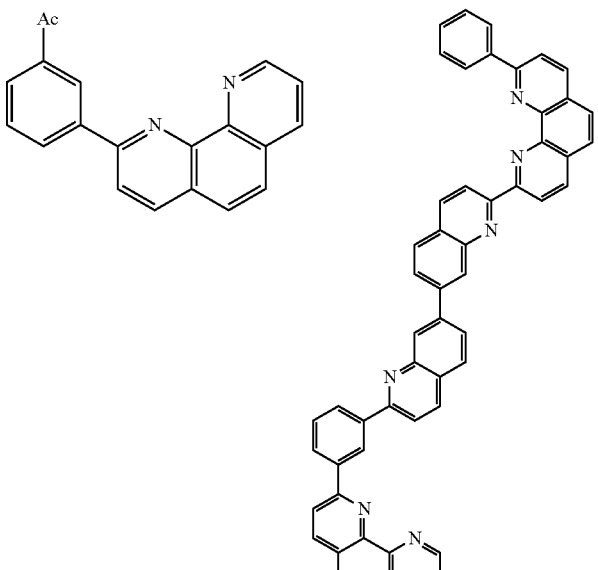 | 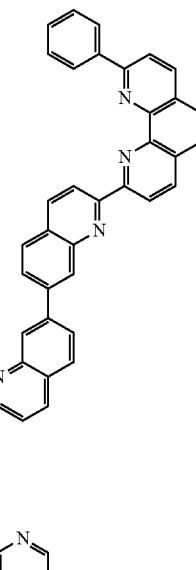 | 72% |

Target compounds were synthesized in the same manner as in Preparation Example 2 except that 5-(7-(4,4,5,5-tetramethyl-1,3,2-dioxaborolan-2-yl) quinolin-2-yl)-1,10-phenanthroline was used instead of 2-(pyridin-2-yl)-7-(4,4,5,5-tetramethyl-1,3,2-dioxaborolan-2-yl)quinoline, and Intermediate S(2) of the following Table 2-19 was used instead of acetophenone.

TABLE 2-19

| [Group III] Compound No. | Intermediate S(2) | Target Compound | Yield |
|---|---|---|---|
| 192 | (structure) | (structure) | 75% |
| 196 | (structure) | (structure) | 76% |
| 200 | (structure) | (structure) | 69% |

Target compounds were synthesized in the same manner as in Preparation Example 2 except that 2-(3-(pyridin-2-yl)phenyl)-7-(4,4,5,5-tetramethyl-1,3,2-dioxaborolan-2-yl)quinoline was used instead of 2-(pyridin-2-yl)-7-(4,4,5,5-tetramethyl-1,3,2-dioxaborolan-2-yl)quinoline, and Intermediate T(2) of the following Table 2-20 was used instead of acetophenone.

TABLE 2-20

| [Group III] Compound No. | Intermediate T(2) | Target Compound | Yield |
|---|---|---|---|
| 202 | Ac | | 72% |

Target compounds were synthesized in the same manner as in Preparation Example 2 except that 2-(3-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate U(2) of the following Table 2-21 was used instead of acetophenone.

TABLE 2-21

| [Group III] Compound No. | Intermediate U(2) | Target Compound | Yield |
|---|---|---|---|
| 208 | Ac | | 74% |

TABLE 2-21-continued

| [Group III] Compound No. | Intermediate U(2) | Target Compound | Yield |
|---|---|---|---|
| 209 | (structure) | (structure) | 72% |

Target compounds were synthesized in the same manner as in Preparation Example 2 except that 2-(4-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate V(2) of the following Table 2-22 was used instead of acetophenone.

TABLE 2-22

| [Group III] Compound No. | Intermediate V(2) | Target Compound | Yield |
|---|---|---|---|
| 212 | (structure) | (structure) | 68% |

TABLE 2-22-continued

| [Group III] Compound No. | Intermediate V(2) | Target Compound | Yield |
|---|---|---|---|
| 214 | (structure) | (structure) | 70% |

TABLE 2-22-continued

| [Group III] Compound No. | Intermediate V(2) | Target Compound | Yield |
|---|---|---|---|
| 216 | 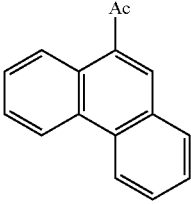 | 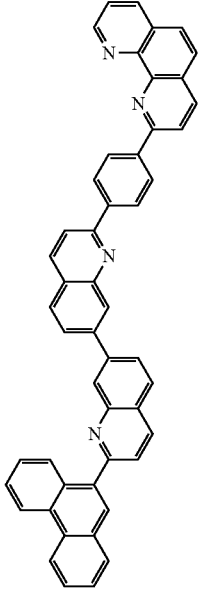 | 74% |

Target compounds were synthesized in the same manner as in Preparation Example 2 except that 4-(4-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate W(2) of the following Table 2-23 was used instead of acetophenone.

TABLE 2-23

| [Group III] Compound No. | Intermediate W(2) | Target Compound | Yield |
|---|---|---|---|
| 219 | 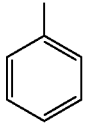 | 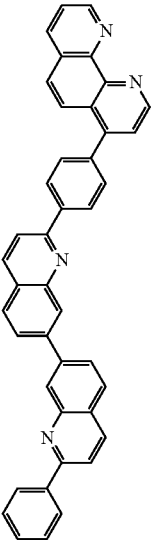 | 68% |

TABLE 2-23-continued

| [Group III] Compound No. | Intermediate W(2) | Target Compound | Yield |
|---|---|---|---|
| 223 | 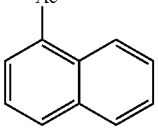 | 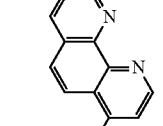 | 71% |

Target compounds were synthesized in the same manner as in Preparation Example 2 except that 5-(4-(7-(4,4,5,5-tetramethyl-1,3,2-dioxaborolan-2-yl) quinolin-2-yl)phenyl)-1,10-phenanthroline was used instead of 2-(pyridin-2-yl)-7-(4,4,5,5-tetramethyl-1,3,2-dioxaborolan-2-yl) quinoline, and Intermediate X(2) of the following Table 2-24 was used instead of acetophenone.

TABLE 2-24

| [Group III] Compound No. | Intermediate X(2) | Target Compound | Yield |
|---|---|---|---|
| 227 | 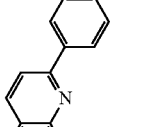 | 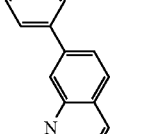 | 65% |

TABLE 2-24-continued

| [Group III] Compound No. | Intermediate X(2) | Target Compound | Yield |
|---|---|---|---|
| 232 | Ac 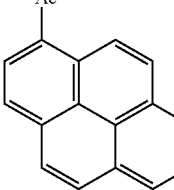 | 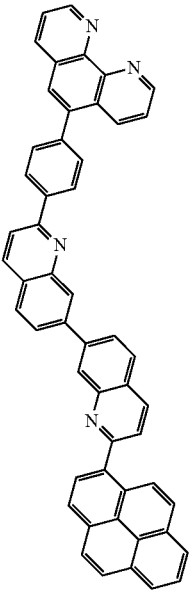 | 68% |

Target compounds were synthesized in the same manner as in Preparation Example 2 except that 2-(4-(7-(4,4,5,5-tetramethyl-1,3,2-dioxaborolan-2-yl) quinolin-2-yl) naphthalen-1-yl)-1,10-phenanthroline was used instead of 2-(pyridin-2-yl)-7-(4,4,5,5-tetramethyl-1,3,2-dioxaborolan-2-yl) quinoline, and Intermediate Y(2) of the following Table 2-25 was used instead of acetophenone.

TABLE 2-25

| [Group III] Compound No. | Intermediate Y(2) | Target Compound | Yield |
|---|---|---|---|
| 234 | Ac 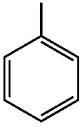 | 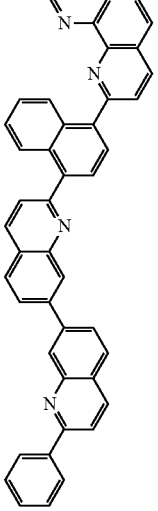 | 70% |

TABLE 2-25-continued

| [Group III] Compound No. | Intermediate Y(2) | Target Compound | Yield |
|---|---|---|---|
| 236 | Ac 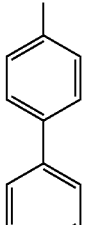 | 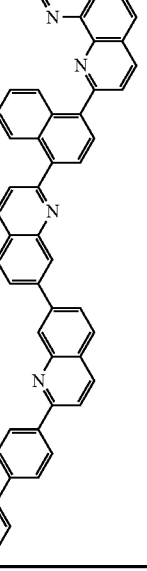 | 72% |

Target compounds were synthesized in the same manner as in Preparation Example 2 except that 2-(6-(7-(4,4,5,5-tetramethyl-1,3,2-dioxaborolan-2-yl) quinolin-2-yl) naphthalen-2-yl)-1,10-phenanthroline was used instead of 2-(pyridin-2-yl)-7-(4,4,5,5-tetramethyl-1,3,2-dioxaborolan-2-yl) quinoline, and Intermediate Z(2) of the following Table 2-26 was used instead of acetophenone.

TABLE 2-26

| [Group III] Compound No. | Intermediate Z(2) | Target Compound | Yield |
|---|---|---|---|
| 241 | Ac 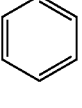 | 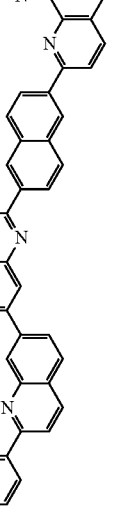 | 71% |

TABLE 2-26-continued

| [Group III] Compound No. | Intermediate Z(2) | Target Compound | Yield |
|---|---|---|---|
| 244 | 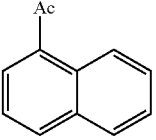 | 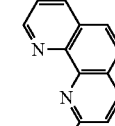 | 75% |

Target compounds were synthesized in the same manner as in Preparation Example 2 except that 2-phenyl-7-(4,4,5,5-tetramethyl-1,3,2-dioxaborolan-2-yl) quinoline was used instead of 2-(pyridin-2-yl)-7-(4,4,5,5-tetramethyl-1,3,2-dioxaborolan-2-yl)quinoline, and Intermediate AA(2) of the following Table 2-27 was used instead of acetophenone.

TABLE 2-27

| [Group III] Compound No. | Intermediate AA(2) | Target Compound | Yield |
|---|---|---|---|
| 255 | 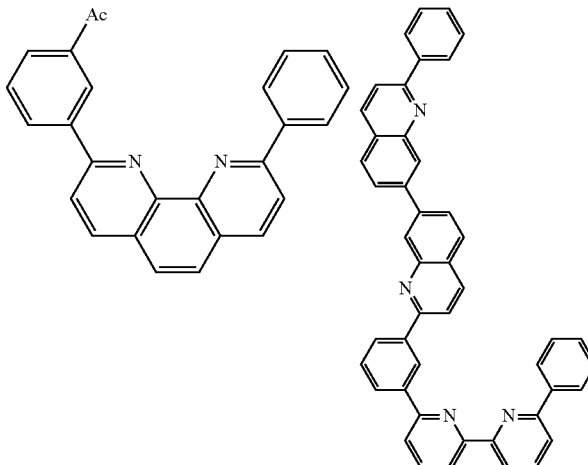 | 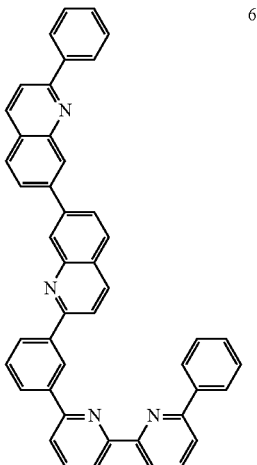 | 68% |

Syntheses of the prepared compounds were identified from Mass and NMR results, and the synthesis results are shown in the following Tables 2-28 and 2-29.

TABLE 2-28

| [Group III] Compound No. | ¹H NMR (CDCl₃, 300 Mz) |
|---|---|
| 1 | δ = 9.30(1H, d), 8.53(1H, d), 8.27~8.31(6H, m), 8.03~8.12(4H, m), 7.70(1H, m), 7.47~7.54(3H, m), 7.35(1H, d), 7.14(1H, t) |
| 2 | δ = 9.30(1H, d), 8.46~8.55(3H, m), 8.27~8.31(4H, m), 8.03~8.12(7H, m), 7.55~7.70(4H, m), 7.35(1H, d), 7.14(1H, t) |
| 8 | δ = 9.30(1H, d), 8.53(1H, d), 8.21~8.31(9H, m), 8.03~8.12(5H, m), 7.70~7.81(4H, m), 7.35~7.60(8H, m), 7.14(1H, m) |
| 12 | δ = 9.30(1H, d), 8.27~8.36(9H, m), 8.03~8.28(5H, m), 7.88(1H, d), 7.70(1H, m), 7.35~7.53(9H, m), 7.14(1H, t) |
| 13 | δ = 9.30(1H, d), 8.81(2H, d), 8.53~8.55(2H, m), 8.23~8.31(9H, m), 8.03~8.12(6H, m), 7.94(1H, m), 7.63~7.79(6H, m), 7.25~7.51(8H, m), 7.14(1H, t) |
| 17 | δ = 9.30(1H, d), 8.81(2H, d), 8.53(1H, d), 8.27~8.31(8H, m), 8.03~8.12(5H, m), 7.88 (2H, d), 7.70(1H, t), 7.35~7.51(7H, m), 7.14(1H, t) |
| 19 | δ = 9.30(1H, d), 8.53~8.57(2H, m), 8.21~8.31(7H, m), 7.98~8.12(7H, m), 7.54~7.78(5H, m), 7.35(1H, d), 7.14(1H, t) |
| 21 | δ = 9.30(1H, d), 8.83(1H, d), 8.53(1H, d), 8.27~8.38(9H, m), 8.03~8.12(5H, m), 7.81(1H, m), 7.70 (1H, t), 7.58(1H, m), 7.14(1H, t) |
| 24 | δ = 9.30(1H, d), 8.83(1H, d), 8.72(1H, s), 8.53(1H, d), 8.27~8.38(7H, m), 8.03~8.12(7H, m), 7.81(1H, d), 7.58~7.70(3H, m), 7.35(2H, d), 7.14(1H, t) |
| 27 | δ = 9.30(1H, d), 8.84(4H, s), 8.53(1H, m), 8.27~8.31(6H, m), 8.03~8.12(8H, m), 7.81(1H, d), 7.70(1H, m), 7.47~7.54(3H, m), 7.35(3H, d), 7.14(1H, t) |
| 32 | δ = 9.75(1H, s), 8.93(1H, d), 8.76(1H, d), 8.44(1H, d), 8.27~8.30(4H, m), 8.03~8.12(5H, m), 7.35~7.60(6H, m) |
| 34 | δ = 9.75(1H, s), 8.93(1H, d), 8.85(1H, s), 8.76(1H, d), 8.38~8.44(2H, m), 8.27(2H, s), 7.95~8.12(8H, m), 7.59~7.60(3H, m), 7.35~7.41(2H, m) |
| 36 | δ = 9.75(1H, s), 8.93(1H, d), 8.76~8.84(6H, m), 8.38~8.44(2H, m), 8.27(2H, s), 8.03~8.12(7H, m), 7.81(1H, d), 7.58~7.60(2H, m), 7.35~7.41(3H, m) |
| 39 | δ = 9.75(1H, s), 8.93(1H, m), 8.76~8.83(5H, m), 8.38~8.44(3H, m), 8.27(1H, s), 8.03~8.12(5H, m), 7.90(1H, s), 7.58~7.65(4H, m), 7.28~7.41(4H, m) |
| 43 | δ = 8.78(2H, d), 8.44~8.55(5H, m), 8.27(2H, s), 8.03~8.12(7H, m), 7.55~7.64(3H, m), 7.41(1H, d), 7.35(1H, d) |
| 46 | δ = 8.93(2H, d), 8.78(2H, d), 8.44~8.50(4H, m), 8.27(2H, s), 8.03~8.12(7H, m), 7.82~7.88(4H, m), 7.35~7.41(2H, m) |
| 47 | δ = 8.78~8.84(7H, m), 8.38~8.50(4H, m), 8.27(2H, s), 8.03~8.12(7H, m), 7.81(1H, d), 7.58(1H, t), 7.35~7.41(3H, m) |
| 52 | δ = 8.78~8.85(5H, m), 8.38~8.50(6H, m), 8.27(2H, s), 7.95~8.12(9H, m), 7.81(1H, d), 7.58(1H, m), 7.35~7.41(3H, m) |
| 59 | δ = 8.97(2H, d), 8.81(2H, d), 8.44(1H, m), 8.23~8.33(7H, m), 8.03~8.12(5H, m), 7.79(2H, d), 7.35~7.51(9H, m) |
| 60 | δ = 8.97(2H, d), 8.81(2H, d), 8.44(1H, m), 8.27~8.28(6H, m), 8.03~8.12(5H, m), 7.88(2H, d), 7.35~7.51(9H, m) |
| 62 | δ = 8.97(2H, d), 8.81(2H, d), 8.55(1H, d), 8.44(2H, d), 8.27~8.28(4H, m), 8.03~8.12(6H, m), 7.88~7.94(3H, m), 7.79(2H, d), 7.63~7.68(3H, m), 7.25~7.51(10H, m) |
| 63 | δ = 8.44(1H, d), 8.37(1H, s), 8.27~8.30(4H, m), 8.03~8.12(5H, m), 7.79(4H, d), 7.35~7.54(11H, m) |
| 68 | δ = 8.84(4H, s), 8.37~8.44(3H, m), 8.27(2H, s), 8.03~8.12(7H, m), 7.79~7.81(5H, m), 7.35~7.58(10H, m) |
| 73 | δ = 9.30(1H, s), 9.05~9.07(2H, m), 8.84(4H, m), 8.38~8.44(2H, m), 8.27(2H, s), 8.03~8.12(7H, m), 7.81(1H, d), 7.58(1H, t), 7.41(1H, d), 7.35(2H, d) |
| 77 | δ = 9.19(1H, s), 8.44(1H, m), 8.27~8.30(6H, m), 8.03~8.12(5H, m), 7.79(2H, d), 7.35~7.54(11H, m) |
| 78 | δ = 9.19(1H, s), 8.55(1H, m), 8.44~8.46(2H, m), 8.27~8.28(4H, m), 8.03~8.12(7H, m), 7.79(2H, d), 7.35~7.64(11H, m) |
| 80 | δ = 9.19(1H, s), 8.93(1H, d), 8.61(1H, m), 8.44(1H, m), 8.27~8.28(4H, m), 8.03~8.12(7H, m), 7.71~7.91(7H, m), 7.35~7.51(8H, m) |
| 83 | δ = 9.19(1H, s), 8.84(4H, s), 8.44(1H, m), 8.27~8.30(6H, m), 8.03~8.12(8H, m), 7.79~7.81(3H, m), 7.35~7.51(13H, m) |
| 85 | δ = 9.19(1H, s), 8.81~8.83(4H, m), 8.38~8.44(3H, m), 8.27~8.28(4H, m), 8.03~8.12(5H, m), 7.79(2H, m), 7.28~7.65(13H, m) |
| 92 | δ = 8.82~8.84(7H, d), 8.38~8.44(2H, m), 8.27(2H, s), 8.03~8.12(7H, m), 7.81(1H, d), 7.58(1H, t), 7.41(1H, d), 7.35(2H, d) |
| 97 | δ = 8.44(1H, d), 8.27~8.30(8H, m), 8.03~8.12(5H, m), 7.35~7.54(11H, m) |
| 98 | δ = 8.55(1H, d), 8.44~8.46(2H, m), 8.27~8.28(6H, m), 8.03~8.12(7H, m), 7.35~7.64(11H, m) |
| 102 | δ = 8.83~8.84(5H, s), 8.38~8.44(2H, m), 8.27~8.28(6H, m), 8.03~8.12(7H, m), 7.81(1H, d), 7.35~7.58(10H, m) |
| 105 | δ = 8.83(1H, d), 8.55(4H, d), 8.38~8.44(2H, m), 8.27~8.28(6H, m), 8.03~8.12(7H, m), 7.81(1H, d), 7.35~7.58(12H, m) |
| 107 | δ = 8.83~8.88(2H, m), 8.27~8.38(5H, m), 8.03~8.12(7H, m), 7.69(1H, m), 7.47~7.58(4H, m), 7.35(2H, d) |

TABLE 2-28-continued

| [Group III] Compound No. | ¹H NMR (CDCl₃, 300 Mz) |
|---|---|
| 111 | δ = 8.83~8.88(3H, m), 8.72(1H, s), 8.27~8.38(5H, m), 8.03~8.12(9H, m), 7.81(1H, d), 7.58~7.6(4H, m), 7.35(3H, d) |
| 116 | δ = 8.81~8.88(4H, m), 8.27~8.38(8H, m), 8.03~8.12(7H, m), 7.79(2H, d), 7.69(1H, t), 7.35~7.58(9H, m) |
| 119 | δ = 8.83~8.88(2H, m), 8.38(1H, d), 8.21~8.30(9H, m), 8.03~8.12(7H, m), 7.35~7.69(11H, m) |
| 120 | δ = 8.83~8.88(2H, m), 8.55(1H, d), 8.38(1H, d), 8.21~8.28(7H, m), 8.03~8.12(8H, m), 7.94(1H, d), 7.79~7.81(3H, m), 7.25~7.69(15H, m) |
| 121 | δ = 8.91(1H, s), 8.84(4H, d), 8.38~8.45(2H, m), 8.27~8.28(3H, d), 8.03~8.12(8H, m), 7.81(1H, d), 7.50~7.65(4H, m), 7.35(3H, d) |
| 125 | δ = 8.91(1H, s), 8.84(4H, s), 8.45(1H, d), 8.27~8.35(5H, m), 8.03~8.12(8H, m), 7.94(1H, m), 7.81(1H, d), 7.47~7.54(5H, m), 7.35(4H, d) |
| 129 | δ = 8.83(1H, d), 8.54(1H, d), 8.27~8.38(5H, m), 7.98~8.12(8H, m), 7.47~7.58(4H, m), 7.35(2H, d) |
| 131 | δ = 8.83~8.85(2H, m), 8.54(1H, d), 8.38(2H, d), 8.27(1H, s), 7.95~8.12(11H, m), 7.58~7.59(3H, m), 7.35(2H, d) |
| 133 | δ = 8.83(2H, d), 8.72(1H, s), 8.54(1H, d), 8.27~8.38(6H, m), 7.98~8.12(10H, m), 7.81(1H, d), 7.58~7.63(3H, m), 7.35(3H, d) |
| 137 | δ = 8.93~8.94(2H, s), 8.83~8.84(5H, d), 8.38~8.44(2H, m), 8.27(2H, s), 8.03~8.12(7H, m), 7.92(1H, d), 7.76~7.81(2H, m), 7.35~7.58(6H, m) |
| 140 | δ = 8.93~8.94(2H, s), 8.83(1H, d), 8.55(4H, s), 8.38~8.44(2H, m), 8.27(2H, s), 8.03~8.12(7H, m), 7.92(1H, d), 7.76~7.81(2H, m), 7.35~7.58(8H, m) |
| 145 | δ = 9.08(1H, s), 8.73(1H, s), 8.44(1H, d), 8.27~8.30(4H, m), 7.98~8.12(7H, m), 7.78(1H, m), 7.35~7.60(6H, m) |
| 146 | δ = 9.08(1H, s), 8.73(1H, s), 8.55(1H, d), 8.44~8.46(2H, m), 8.27(2H, s), 7.98~8.12(9H, m), 7.78(1H, m), 7.55~7.64(4H, m), 7.35~7.41(2H, m) |
| 148 | δ = 9.08(1H, s), 8.83(1H, d), 8.72~8.73(2H, d), 8.27~8.44(6H, m), 7.98~8.12(9H, m), 7.78~7.81(2H, m), 7.58~7.63(3H, m), 7.35~7.41(3H, m) |
| 167 | δ = 8.81(2H, d), 8.51(1H, d), 8.23~8.33(11H, m), 8.03~8.16(7H, m), 7.79~7.81(3H, m), 7.35~7.51(7H, m) |
| 168 | δ = 8.81(2H, d), 8.51(1H, d), 8.27~8.31(10H, m), 8.03~8.16(7H, m), 7.81~7.88(3H, m), 7.67(2H, d), 7.51(4H, m), 7.35~7.41(3H, m) |
| 172 | δ = 8.83(1H, d), 8.27~8.38(9H, m), 8.03~8.12(6H, m), 7.81(1H, d), 7.47~7.58(4H, m), 7.35(1H, d) |
| 177 | δ = 8.83(2H, d), 8.72(1H, s), 8.27~8.38(10H, m), 8.03~8.12(8H, m), 7.81(2H, d), 7.58~7.63(3H, m), 7.35(2H, d) |
| 180 | δ = 8.81~8.89(5H, m), 8.27~8.38(8H, m), 8.03~8.12(7H, m), 7.81(2H, d), 7.58(2H, m), 7.48(1H, d), 7.28~7.35(3H, m) |
| 183 | δ = 8.83(1H, d), 8.21~8.38(12H, m), 8.03~8.12(6H, m), 7.79~7.81(4H, m), 7.35~7.60(9H, m) |
| 185 | δ = 8.27~8.31(14H, m), 8.03~8.12(8H, m), 7.81(2H, d), 7.47~7.54(6H, m), 7.35(2H, d) |
| 187 | δ = 8.83(1H, d), 8.72(1H, s), 8.27~8.38(11H, m), 8.03~8.12(9H, m), 7.81(2H, d), 7.47~7.63(5H, m), 7.35(3H, d) |
| 192 | δ = 8.83(2H, d), 8.27~8.38(6H, m), 8.03~8.16(7H, m), 7.47~7.58(5H, m), 7.35(2H, d) |
| 196 | δ = 8.83~8.84(6H, d), 8.27~8.38(6H, m), 8.03~8.16(10H, m), 7.81(1H, d), 7.47~7.58(5H, m), 7.35(4H, d) |
| 200 | δ = 8.81~8.83(4H, m), 8.23~8.38(9H, m), 8.03~8.16(7H, m), 7.79(2H, d), 7.35~7.58(10H, m) |
| 202 | δ = 8.83(2H, d), 8.72(1H, s), 8.50(1H, d), 8.02~8.38(18H, m), 7.51~7.72(7H, m), 7.35(2H, d), 7.26(1H, d), 7.00(1H, m) |
| 208 | δ = 8.83(1H, d), 8.72~8.74(4H, m), 8.50(2H, d), 8.27~8.38(5H, m), 8.03~8.12(8H, m), 7.81(1H, d), 7.51~7.63(4H, m), 7.35 (3H, d), 7.26(2H, d), 7.00(2H, m) |
| 209 | δ = 8.83(2H, d), 8.72(2H, s), 8.27~8.38(8H, m), 8.03~8.12(10H, m), 7.81(2H, d), 7.58~7.63(4H, m), 7.35(4H, d) |
| 212 | δ = 8.81~8.84(7H, d), 8.38(1H, d), 8.27(2H, s), 8.03~8.12(8H, m), 7.81~7.88(3H, m), 7.35~7.58(9H, m) |
| 214 | δ = 8.83~8.84(5H, m), 8.55(1H, d), 8.46(1H, d), 8.38(1H, d), 8.27(2H, s), 8.03~8.12(10H, m), 7.81(1H, d), 7.55~7.64(4H, m), 7.35(3H, d) |
| 216 | δ = 8.93(2H, d), 8.83~8.84(5H, s), 8.38~8.44(2H, m), 8.27(2H, s), 8.03~8.12(10H, m), 7.81~7.88(5H, m), 7.58(1H, t), 7.35(3H, d) |
| 219 | δ = 8.81~8.89(4H, m), 8.27~8.38(5H, m), 8.03~8.12(7H, m), 7.81(1H, d), 7.48~7.58(5H, m), 7.35(2H, d), 7.28(2H, d) |
| 223 | δ = 8.81~8.89(4H, m), 8.55(1H, d), 8.46(1H, d), 8.38(1H, d), 8.27(2H, s), 8.03~8.12(9H, m), 7.81(1H, m), 7.48~7.64(5H, m), 7.35(2H, d), 7.28(2H, d) |
| 227 | δ = 8.81~8.83(4H, m), 8.27~8.38(6H, m), 8.03~8.12(6H, m), 7.47~7.65(6H, m), 7.35(2H, d), 7.28(2H, d) |
| 232 | δ = 8.81~8.83(4H, m), 8.55(1H, d), 8.38(2H, d), 8.21~8.27(3H, m), 8.03~8.12(7H, m), 7.82~7.88(2H, m), 7.71(4H, s), 7.58~7.65(3H, d), 7.35(2H, d), 7.28(2H, d) |

TABLE 2-28-continued

| [Group III] Compound No. | $^1$H NMR (CDCl$_3$, 300 Mz) |
|---|---|
| 234 | δ = 8.83(1H, d), 8.55(4H, d), 8.27~8.38(5H, m), 8.03~8.12(8H, m), 7.81(1H, d), 7.47~7.58(6H, m), 7.35(3H, d) |
| 236 | δ = 8.81~8.83(3H, m), 8.55(4H, s), 8.38(1H, d), 8.27(2H, s), 8.03~8.12(8H, m), 7.81~7.88(3H, m), 7.35~7.58(11H, m) |
| 241 | δ = 8.83~8.85(3H, m), 8.27~8.38(7H, m), 7.95~8.12(10H, m), 7.81(1H, d), 7.47~7.58(4H, m), 7.35(3H, d) |
| 244 | δ = 8.83~8.85(3H, m), 8.55(1H, m), 8.38~8.46(4H, m), 8.27(2H, s), 7.95~8.12(12H, m), 7.81(1H, d), 7.55~7.64(4H, m), 7.35(3H, d) |
| 255 | δ = 8.72(1H, s), 8.27~8.32(8H, m), 8.03~8.12(9H, m), 7.81(1H, d), 7.47~7.63(7H, m), 7.35(4H, d) |

TABLE 2-29

| [Group III] Compound No. | FD-MS | [Group III] Compound No. | FD-MS |
|---|---|---|---|
| 1 | m/z = 409.48 (C29H19N3 = 409.16) | 2 | m/z = 459.54 (C33H21N3 = 459.17) |
| 8 | m/z = 639.75 (C45H29N5 = 639.24) | 12 | m/z = 640.73 (C44H28N6 = 640.24) |
| 13 | m/z = 804.94 (C57H36N6 = 804.30) | 17 | m/z = 640.73 (C44H28N6 = 640.24) |
| 19 | m/z = 536.62 (C38H24N4 = 536.20) | 21 | m/z = 511.57 (C35H21N5 = 511.18) |
| 24 | m/z = 587.67 (C41H25N5 = 587.21) | 27 | m/z = 663.77 (C47H29N5 = 663.24) |
| 32 | m/z = 409.48 (C29H19N3 = 409.16) | 34 | m/z = 459.54 (C33H21N3 = 459.17) |
| 36 | m/z = 587.67 (C41H25N5 = 587.21) | 39 | m/z = 587.67 (C41H25N5 = 587.21) |
| 43 | m/z = 459.54 (C33H21N3 = 459.17) | 46 | m/z = 509.60 (C37H23N3 = 509.19) |
| 47 | m/z = 587.67 (C41H25N5 = 587.21) | 52 | m/z = 637.73 (C45H27N5 = 637.23) |
| 59 | m/z = 640.73 (C44H28N6 = 640.24) | 60 | m/z = 641.72 (C43H27N7 = 641.23) |
| 62 | m/z = 806.91 (C55H34N8 = 806.29) | 63 | m/z = 562.66 (C40H26N4 = 562.22) |
| 68 | m/z = 740.85 (C52H32N6 = 740.27) | 73 | m/z = 588.66 (C40H24N6 = 588.21) |
| 77 | m/z = 562.66 (C40H28N4 = 562.22) | 78 | m/z = 612.72 (C44H28N4 = 612.23) |
| 80 | m/z = 662.78 (C48H30N4 = 662.25) | 83 | m/z = 816.95 (C58H36N6 = 816.30) |
| 85 | m/z = 740.85 (C52H32N6 = 740.27) | 92 | m/z = 589.65 (C39H23N7 = 589.20) |
| 97 | m/z = 563.65 (C39H25N5 = 563.21) | 98 | m/z = 612.71 (C43H27N5 = 613.23) |
| 102 | m/z = 741.84 (C51H31N7 = 741.26) | 105 | m/z = 791.90 (C55H33N7 = 791.28) |
| 107 | m/z = 459.54 (C33H21N3 = 459.17) | 111 | m/z = 637.73 (C45H27N5 = 637.23) |
| 116 | m/z = 589.80 (C49H31N5 = 689.26) | 119 | m/z = 690.79 (C48H30N6 = 490.25) |
| 120 | m/z = 854.99 (C61H36N6 = 854.32) | 121 | m/z = 637.73 (C45H27N5 = 637.23) |
| 125 | m/z = 713.83 (C51H31N5 = 713.26) | 129 | m/z = 459.54 (C33H21N3 = 459.17) |
| 131 | m/z = 509.60 (C37H23N3 = 509.19) | 133 | m/z = 637.54 (C45H27N3 = 637.23) |
| 137 | m/z = 637.73 (C45H27N5 = 637.23) | 140 | m/z = 687.79 (C49H29N5 = 687.24) |
| 145 | m/z = 459.54 (C33H21N3 = 459.17) | 146 | m/z = 509.60 (C37H23N3 = 509.19) |
| 148 | m/z = 637.73 (C45H27N5 = 637.23) | 167 | m/z = 739.86 (C53H33N5 = 739.27) |
| 168 | m/z = 740.85 (C52H32N6 = 740.27) | 172 | m/z = 510.59 (C36H22N4 = 510.18) |
| 177 | m/z = 688.78 (C48H28N6 = 688.24) | 180 | m/z = 688.78 (C48H26N6 = 688.24) |
| 183 | m/z = 740.85 (C52H32N6 = 740.27) | 185 | m/z = 764.87 (C54H32N6 = 764.27) |
| 187 | m/z = 764.87 (C54H32N6 = 764.27) | 192 | m/z = 510.59 (C36H22N4 = 510.18) |

TABLE 2-29-continued

| [Group III] Compound No. | FD-MS | [Group III] Compound No. | FD-MS |
|---|---|---|---|
| 196 | m/z = 764.87 (C54H32N6 = 764.27) | 200 | m/z = 739.65 (C53H33N5 = 739.27) |
| 202 | m/z = 740.85 (C52H32N6 = 740.27) | 208 | m/z = 740.27 (C52H32N6 = 740.27) |
| 209 | m/z = 764.87 (C54H32N6 = 764.27) | 212 | m/z = 662.78 (C48H30N4 = 662.25) |
| 214 | m/z = 636.74 (C46H28N4 = 636.23) | 216 | m/z = 686.80 (C50H30N4 = 686.25) |
| 219 | m/z = 586.22 (C42H28N4 = 586.22) | 223 | m/z = 636.74 (C46H28N4 = 606.23) |
| 227 | m/z = 586.68 (C42H26N4 = 586.22) | 232 | m/z = 710.82 (C52H30N4 = 710.25) |
| 234 | m/z = 636.74 (C46H26N4 = 636.23) | 236 | m/z = 712.84 (C52H32N4 = 712.26) |
| 241 | m/z = 636.74 (C46H28N4 = 636.23) | 244 | m/z = 686.80 (C50H30N4 = 686.25) |
| 255 | m/z = 662.78 (C48H30N4 = 662.25) | | |

(Manufacture of Organic Light Emitting Diode)

Experimental Example 1-1

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), an organic material was formed in a 2-stack white organic light emitting diode (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping FIrpic to TCz1, a host, by 8% as a blue phosphorescent dopant. After forming an electron transfer layer to 400 Å using TmPyPB, a charge generation layer was formed to 100 Å by doping $Cs_2CO_3$ to a compound described in the following Table 3 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and then depositing TAPC to 300 Å. A light emitting layer was deposited thereon to 300 Å by doping Ir (ppy)$_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent diode was manufactured.

Meanwhile, all the organic compounds required to manufacture the OLED were vacuum sublimation purified under $10^{-6}$ torr to $10^{-8}$ torr by each material to be used in the OLED manufacture.

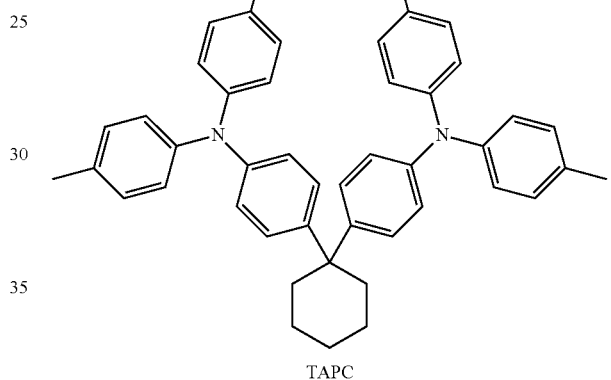

TAPC

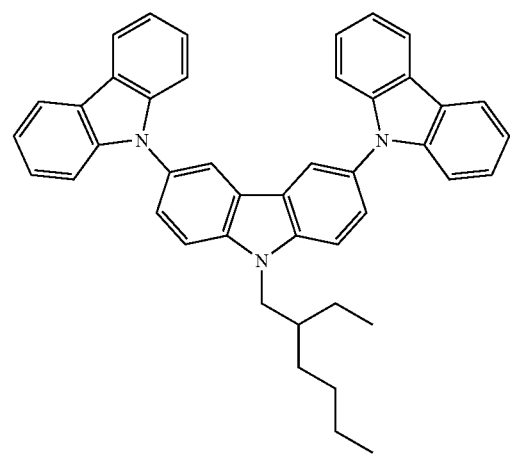

TCz1

-continued
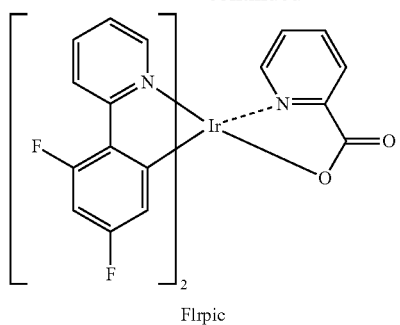
FIrpic
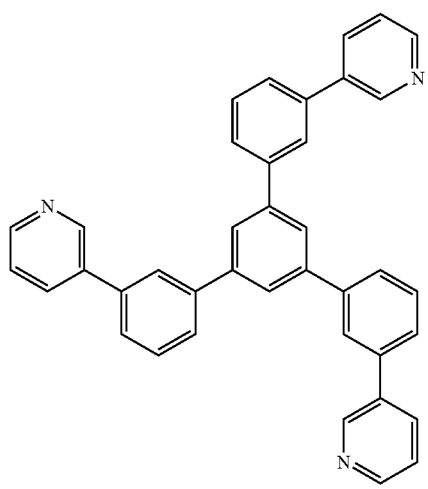
TmPyPB
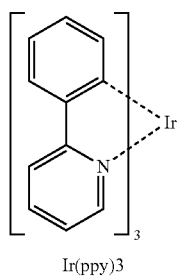
Ir(ppy)3
-continued
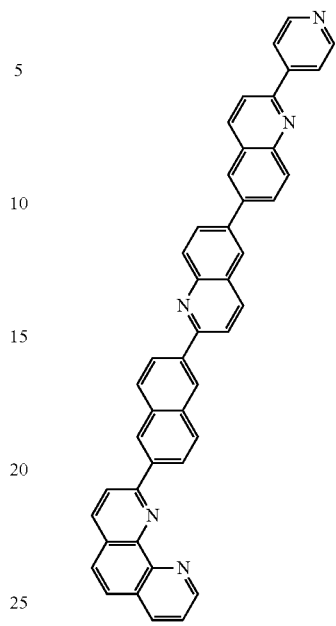
C1
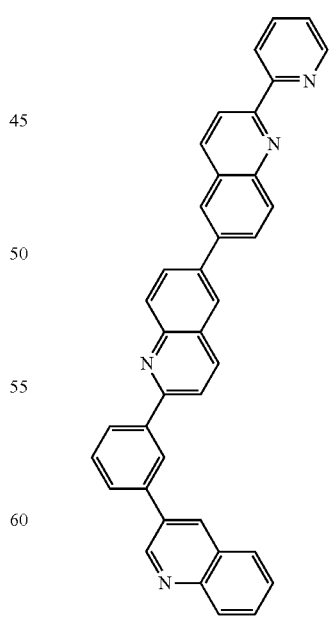
C2

-continued

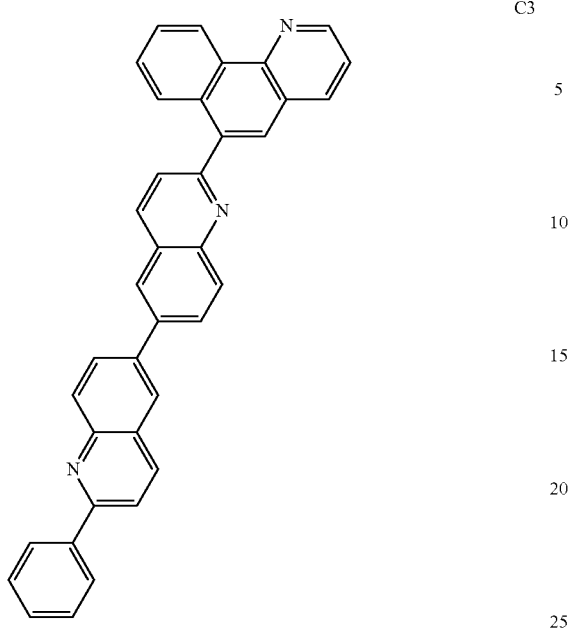

C3

Evaluation: Driving Voltage and Light Emission Efficiency of Organic Electroluminescent Diode For the organic electroluminescent diodes manufactured as above, electroluminescent (EL) properties were measured using M7000 manufactured by McScience Inc., and results of measuring driving voltage, light emission efficiency, external quantum efficiency and color coordinate (CIE) of the white organic electroluminescent diodes manufactured according to the present disclosure are as shown in Table 3.

TABLE 3

| | [Group II] Compound No. | Driving Voltage (V) | Light Emission Efficiency (cd/A) | External Quantum Efficiency (%) | CIE (x, y) |
| --- | --- | --- | --- | --- | --- |
| Example 1-1 | 1 | 7.55 | 65.21 | 31.45 | 0.228, 0.481 |
| Example 1-2 | 2 | 7.43 | 63.86 | 31.92 | 0.220, 0.481 |
| Example 1-3 | 13 | 7.17 | 65.26 | 35.13 | 0.232, 0.482 |
| Example 1-4 | 17 | 7.32 | 61.92 | 31.28 | 0.226, 0.434 |
| Example 1-5 | 19 | 8.23 | 62.27 | 25.04 | 0.211, 0.424 |
| Example 1-6 | 21 | 7.42 | 68.81 | 32.24 | 0.209, 0.423 |
| Example 1-7 | 24 | 7.65 | 68.13 | 34.14 | 0.233, 0.463 |
| Example 1-8 | 27 | 7.78 | 67.14 | 30.06 | 0.208, 0.420 |
| Example 1-9 | 32 | 7.49 | 71.18 | 30.01 | 0.211, 0.420 |
| Example 1-10 | 34 | 7.43 | 67.34 | 35.02 | 0.207, 0.422 |
| Example 1-11 | 36 | 8.25 | 58.85 | 29.75 | 0.210, 0.391 |
| Example 1-12 | 39 | 7.45 | 63.18 | 36.06 | 0.211, 0.425 |
| Example 1-13 | 43 | 7.37 | 65.83 | 34.82 | 0.208, 0.421 |
| Example 1-14 | 46 | 7.56 | 62.25 | 28.04 | 0.214, 0.422 |
| Example 1-15 | 47 | 7.62 | 66.06 | 34.45 | 0.234, 0.478 |
| Example 1-16 | 52 | 7.32 | 60.47 | 35.58 | 0.207, 0.419 |
| Example 1-17 | 59 | 7.58 | 68.68 | 29.65 | 0.217, 0.464 |
| Example 1-18 | 60 | 7.29 | 66.52 | 32.51 | 0.211, 0.423 |
| Example 1-19 | 62 | 8.13 | 60.43 | 28.63 | 0.216, 0.484 |
| Example 1-20 | 63 | 7.98 | 58.25 | 27.21 | 0.202, 0.483 |
| Example 1-21 | 68 | 7.43 | 68.57 | 36.46 | 0.208, 0.416 |
| Example 1-22 | 73 | 7.48 | 65.28 | 33.91 | 0.211, 0.422 |
| Example 1-23 | 77 | 7.55 | 67.60 | 31.64 | 0.208, 0.416 |
| Example 1-24 | 78 | 7.68 | 64.76 | 30.95 | 0.207, 0.422 |
| Example 1-25 | 80 | 7.88 | 65.34 | 35.02 | 0.209, 0.421 |
| Example 1-26 | 83 | 7.72 | 67.23 | 32.18 | 0.212, 0.427 |
| Example 1-27 | 85 | 7.57 | 66.73 | 34.22 | 0.209, 0.421 |
| Example 1-28 | 92 | 7.54 | 68.16 | 32.24 | 0.209, 0.419 |
| Example 1-29 | 97 | 7.43 | 66.35 | 29.26 | 0.212, 0.421 |

TABLE 3-continued

|  | [Group II] Compound No. | Driving Voltage (V) | Light Emission Efficiency (cd/A) | External Quantum Efficiency (%) | CIE (x, y) |
| --- | --- | --- | --- | --- | --- |
| Example 1-30 | 98 | 8.15 | 62.83 | 25.72 | 0.208, 0.416 |
| Example 1-31 | 102 | 8.18 | 64.84 | 31.90 | 0.207, 0.420 |
| Example 1-32 | 105 | 7.58 | 67.20 | 32.82 | 0.208, 0.418 |
| Example 1-33 | 107 | 7.56 | 66.31 | 31.83 | 0.206, 0.414 |
| Example 1-34 | 111 | 7.53 | 66.42 | 32.14 | 0.206, 0.416 |
| Example 1-35 | 116 | 7.72 | 62.77 | 25.17 | 0.211, 0.423 |
| Example 1-36 | 119 | 7.42 | 68.81 | 32.24 | 0.208, 0.422 |
| Example 1-37 | 120 | 7.65 | 68.13 | 34.14 | 0.234, 0.462 |
| Example 1-38 | 121 | 7.78 | 67.14 | 30.06 | 0.209, 0.421 |
| Example 1-39 | 125 | 7.49 | 71.18 | 30.01 | 0.211, 0.420 |
| Example 1-40 | 129 | 7.32 | 61.47 | 31.58 | 0.208, 0.418 |
| Example 1-41 | 131 | 7.58 | 68.68 | 25.65 | 0.216, 0.463 |
| Example 1-42 | 133 | 7.49 | 65.28 | 33.91 | 0.210, 0.421 |
| Example 1-43 | 137 | 7.55 | 67.62 | 29.64 | 0.207, 0.419 |
| Example 1-44 | 140 | 7.78 | 64.76 | 25.95 | 0.208, 0.421 |
| Example 1-45 | 145 | 7.38 | 65.34 | 32.07 | 0.207, 0.420 |
| Example 1-46 | 146 | 7.37 | 65.88 | 34.82 | 0.208, 0.422 |
| Example 1-47 | 148 | 7.46 | 62.25 | 26.14 | 0.214, 0.422 |
| Example 1-48 | 167 | 7.62 | 66.26 | 34.45 | 0.233, 0.478 |
| Example 1-49 | 168 | 7.57 | 66.75 | 31.22 | 0.209, 0.421 |
| Example 1-50 | 172 | 7.33 | 68.16 | 32.25 | 0.207, 0.419 |
| Example 1-51 | 177 | 7.36 | 66.35 | 30.27 | 0.212, 0.421 |
| Example 1-52 | 180 | 8.15 | 62.85 | 25.62 | 0.208, 0.416 |
| Example 1-53 | 183 | 7.43 | 68.81 | 32.24 | 0.209, 0.421 |
| Example 1-54 | 185 | 7.65 | 68.23 | 34.14 | 0.233, 0.463 |
| Example 1-55 | 187 | 7.79 | 67.14 | 30.26 | 0.208, 0.422 |
| Example 1-56 | 192 | 7.31 | 71.18 | 30.11 | 0.211, 0.420 |
| Example 1-57 | 196 | 7.43 | 66.45 | 29.26 | 0.212, 0.421 |
| Example 1-58 | 200 | 8.16 | 62.83 | 25.73 | 0.208, 0.416 |
| Example 1-59 | 202 | 8.18 | 64.88 | 31.90 | 0.208, 0.421 |
| Example 1-60 | 208 | 7.68 | 67.20 | 32.83 | 0.208, 0.418 |
| Example 1-61 | 209 | 7.78 | 67.15 | 30.06 | 0.207, 0.421 |
| Example 1-62 | 212 | 7.49 | 71.18 | 30.21 | 0.212, 0.420 |
| Example 1-63 | 214 | 7.43 | 67.34 | 33.02 | 0.206, 0.421 |
| Example 1-64 | 216 | 7.31 | 66.21 | 33.45 | 0.229, 0.482 |
| Example 1-65 | 219 | 7.53 | 63.86 | 30.92 | 0.221, 0.480 |
| Example 1-66 | 223 | 7.39 | 65.26 | 35.23 | 0.234, 0.484 |
| Example 1-67 | 227 | 7.47 | 66.73 | 31.32 | 0.208, 0.420 |
| Example 1-68 | 232 | 7.54 | 68.26 | 32.24 | 0.208, 0.418 |
| Example 1-69 | 234 | 7.44 | 66.35 | 29.26 | 0.213, 0.420 |
| Example 1-70 | 236 | 7.68 | 64.76 | 26.85 | 0.208, 0.421 |
| Example 1-71 | 241 | 7.89 | 65.34 | 32.02 | 0.210, 0.420 |
| Example 1-72 | 244 | 7.37 | 65.83 | 34.82 | 0.208, 0.422 |
| Example 1-73 | 252 | 7.36 | 64.97 | 33.99 | 0.207, 0.420 |
| Example 1-74 | 255 | 7.33 | 65.04 | 34.19 | 0.206, 0.421 |
| Comparative Example 1-1 | TmPyPB | 8.68 | 53.95 | 20.73 | 0.213, 0.443 |
| Comparative Example 1-2 | C1 | 7.56 | 62.05 | 26.04 | 0.215, 0.422 |
| Comparative Example 1-3 | C2 | 8.12 | 59.44 | 26.67 | 0.214, 0.423 |
| Comparative Example 1-4 | C3 | 8.08 | 61.07 | 25.49 | 0.215, 0.423 |

As seen from the results of Table 3, the organic electroluminescent diode using the charge generation layer material of the white organic electroluminescent diode of the present disclosure had lower driving voltage and significantly improved light emission efficiency compared to Comparative Examples 1-1 to 1-4.

Experimental Example 1-2

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4′,4″-tris(N,N— (2-naphthyl)-phenylamino)triphenylamine (2-TNATA) was introduced to a cell in the vacuum deposition apparatus.

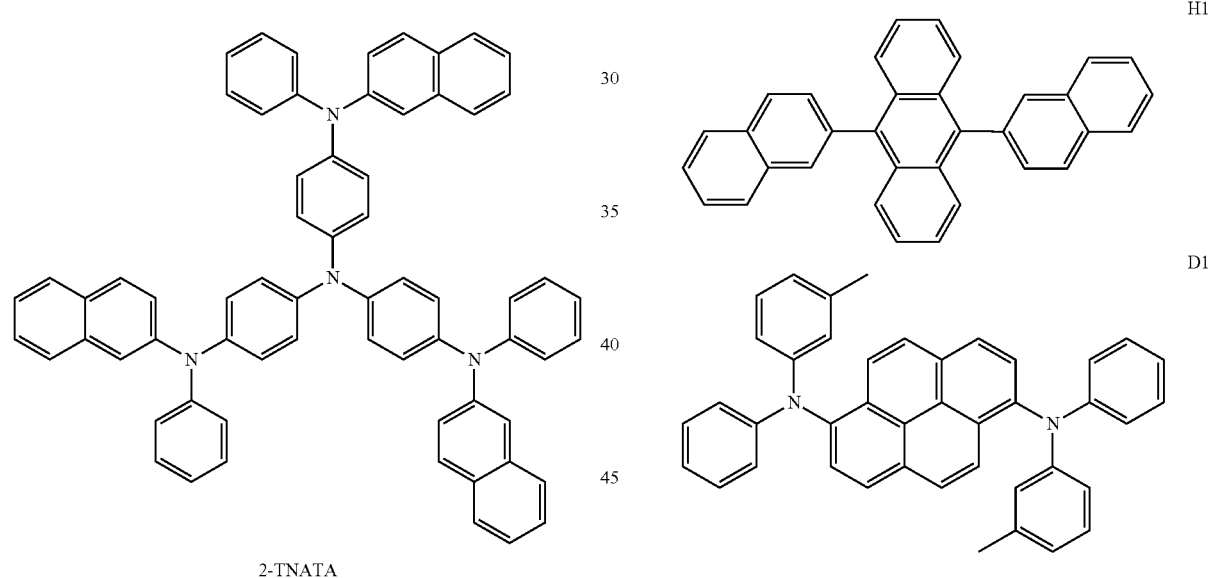

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N′-bis(α-naphthyl)-N,N′-diphenyl-4,4′-diamine (NPB) was introduced, and evaporated by applying a current to the cell to deposit a hole transfer layer having a thickness of 300 Å on the hole injection layer.

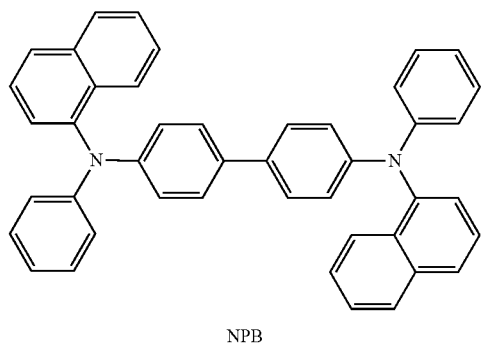

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

An electron transfer layer was formed to 300 Å using TmPyPB, and a charge generation layer was formed to 100 Å by doping $Cs_2CO_3$ to a compound described in the following Table 4 by 20%.

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Results of measuring driving voltage, light emission efficiency and color coordinate (CIE) of the blue organic light emitting diodes manufactured according to the present disclosure are as shown in Table 4.

TABLE 4

| | [Group II] Compound No. | Driving Voltage (V) | Light Emission Efficiency (cd/A) | External Quantum Efficiency (%) | CIE (x, y) |
|---|---|---|---|---|---|
| Example 2-1 | 1 | 7.55 | 65.21 | 31.45 | 0.228, 0.481 |
| Example 2-2 | 2 | 7.43 | 63.88 | 31.93 | 0.220, 0.481 |
| Example 2-3 | 13 | 7.17 | 65.26 | 35.13 | 0.232, 0.482 |
| Example 2-4 | 17 | 7.32 | 62.92 | 30.28 | 0.226, 0.434 |
| Example 2-5 | 19 | 7.56 | 62.27 | 28.04 | 0.211, 0.424 |
| Example 2-6 | 21 | 7.42 | 68.88 | 32.25 | 0.209, 0.423 |
| Example 2-7 | 24 | 7.65 | 68.23 | 34.14 | 0.233, 0.463 |
| Example 2-8 | 27 | 7.54 | 67.14 | 31.06 | 0.208, 0.420 |
| Example 2-9 | 32 | 7.49 | 71.18 | 30.02 | 0.211, 0.420 |
| Example 2-10 | 34 | 7.43 | 68.35 | 33.02 | 0.207, 0.422 |
| Example 2-11 | 36 | 7.65 | 59.85 | 28.75 | 0.210, 0.391 |
| Example 2-12 | 39 | 7.45 | 63.19 | 29.06 | 0.211, 0.425 |
| Example 2-13 | 43 | 7.37 | 66.83 | 34.82 | 0.208, 0.421 |
| Example 2-14 | 46 | 7.56 | 62.25 | 27.04 | 0.214, 0.422 |
| Example 2-15 | 47 | 7.54 | 65.06 | 34.55 | 0.234, 0.478 |
| Example 2-16 | 52 | 7.32 | 63.47 | 31.58 | 0.207, 0.419 |
| Example 2-17 | 59 | 7.58 | 68.69 | 28.65 | 0.217, 0.464 |
| Example 2-18 | 60 | 7.29 | 67.52 | 32.41 | 0.211, 0.423 |
| Example 2-19 | 62 | 7.45 | 60.43 | 28.63 | 0.216, 0.484 |
| Example 2-20 | 63 | 7.54 | 58.35 | 27.21 | 0.202, 0.483 |
| Example 2-21 | 68 | 7.43 | 67.57 | 32.36 | 0.208, 0.416 |
| Example 2-22 | 73 | 7.48 | 65.18 | 33.91 | 0.211, 0.422 |
| Example 2-23 | 77 | 7.55 | 67.63 | 29.74 | 0.208, 0.416 |
| Example 2-24 | 78 | 7.68 | 64.77 | 26.95 | 0.207, 0.422 |
| Example 2-25 | 80 | 7.48 | 66.34 | 32.52 | 0.209, 0.421 |
| Example 2-26 | 83 | 7.52 | 67.13 | 32.18 | 0.212, 0.427 |
| Example 2-27 | 85 | 7.57 | 66.72 | 31.25 | 0.209, 0.421 |
| Example 2-28 | 92 | 7.54 | 68.36 | 33.24 | 0.209, 0.419 |
| Example 2-29 | 97 | 7.43 | 66.25 | 29.86 | 0.212, 0.421 |
| Example 2-30 | 98 | 7.35 | 62.73 | 25.72 | 0.208, 0.416 |
| Example 2-31 | 102 | 7.54 | 64.94 | 30.90 | 0.207, 0.420 |
| Example 2-32 | 105 | 7.58 | 67.25 | 32.82 | 0.208, 0.418 |
| Example 2-33 | 107 | 7.56 | 66.33 | 31.87 | 0.206, 0.414 |
| Example 2-34 | 111 | 7.53 | 67.42 | 31.14 | 0.206, 0.416 |
| Example 2-35 | 116 | 7.72 | 62.67 | 25.17 | 0.211, 0.423 |
| Example 2-36 | 119 | 7.42 | 68.83 | 32.24 | 0.208, 0.422 |
| Example 2-37 | 120 | 7.55 | 69.13 | 35.14 | 0.234, 0.462 |
| Example 2-38 | 121 | 7.78 | 67.34 | 32.06 | 0.209, 0.421 |
| Example 2-39 | 125 | 7.49 | 71.28 | 31.01 | 0.211, 0.420 |
| Example 2-40 | 129 | 7.32 | 61.48 | 31.68 | 0.208, 0.418 |
| Example 2-41 | 131 | 7.58 | 67.68 | 28.65 | 0.216, 0.463 |
| Example 2-42 | 133 | 7.49 | 66.28 | 33.91 | 0.210, 0.421 |
| Example 2-43 | 137 | 7.55 | 67.42 | 29.64 | 0.207, 0.419 |
| Example 2-44 | 140 | 7.78 | 64.36 | 27.95 | 0.208, 0.421 |
| Example 2-45 | 145 | 7.38 | 65.37 | 32.27 | 0.207, 0.420 |
| Example 2-46 | 146 | 7.37 | 65.89 | 34.72 | 0.208, 0.422 |
| Example 2-47 | 148 | 7.46 | 62.25 | 26.14 | 0.214, 0.422 |
| Example 2-48 | 167 | 7.62 | 66.56 | 34.45 | 0.233, 0.478 |
| Example 2-49 | 168 | 7.57 | 67.75 | 31.52 | 0.209, 0.421 |
| Example 2-50 | 172 | 7.33 | 68.36 | 32.25 | 0.207, 0.419 |
| Example 2-51 | 177 | 7.36 | 66.38 | 30.67 | 0.212, 0.421 |
| Example 2-52 | 180 | 8.15 | 64.85 | 25.62 | 0.208, 0.416 |
| Example 2-53 | 183 | 7.43 | 68.88 | 31.24 | 0.209, 0.421 |
| Example 2-54 | 185 | 7.55 | 68.23 | 34.14 | 0.233, 0.463 |
| Example 2-55 | 187 | 7.79 | 67.25 | 31.26 | 0.208, 0.422 |
| Example 2-56 | 192 | 7.31 | 70.18 | 30.11 | 0.211, 0.420 |
| Example 2-57 | 196 | 7.43 | 68.45 | 28.26 | 0.212, 0.421 |
| Example 2-58 | 200 | 8.16 | 64.83 | 27.73 | 0.208, 0.416 |
| Example 2-59 | 202 | 8.18 | 64.78 | 31.80 | 0.208, 0.421 |
| Example 2-60 | 208 | 7.68 | 66.20 | 32.15 | 0.208, 0.418 |
| Example 2-61 | 209 | 7.78 | 67.15 | 30.86 | 0.207, 0.421 |
| Example 2-62 | 212 | 7.49 | 72.18 | 30.71 | 0.212, 0.420 |
| Example 2-63 | 214 | 7.43 | 67.44 | 33.03 | 0.206, 0.421 |
| Example 2-64 | 216 | 7.31 | 66.81 | 33.45 | 0.229, 0.482 |
| Example 2-65 | 219 | 7.53 | 64.86 | 30.99 | 0.221, 0.480 |
| Example 2-66 | 223 | 7.39 | 65.16 | 33.23 | 0.234, 0.484 |
| Example 2-67 | 227 | 7.47 | 66.73 | 31.32 | 0.208, 0.420 |
| Example 2-68 | 232 | 7.54 | 68.27 | 32.25 | 0.208, 0.418 |
| Example 2-69 | 234 | 7.44 | 67.35 | 28.26 | 0.213, 0.420 |
| Example 2-70 | 236 | 7.68 | 65.76 | 29.85 | 0.208, 0.421 |
| Example 2-71 | 241 | 7.89 | 65.44 | 32.52 | 0.210, 0.420 |
| Example 2-72 | 244 | 7.37 | 65.93 | 34.82 | 0.208, 0.422 |

TABLE 4-continued

| | [Group II] Compound No. | Driving Voltage (V) | Light Emission Efficiency (cd/A) | External Quantum Efficiency (%) | CIE (x, y) |
|---|---|---|---|---|---|
| Example 2-73 | 252 | 7.42 | 64.96 | 33.87 | 0.206, 0.421 |
| Example 2-74 | 255 | 7.41 | 65.11 | 34.64 | 0.207, 0.420 |
| Comparative Example 2-1 | TmPyPB | 8.68 | 53.95 | 20.73 | 0.213, 0.443 |
| Comparative Example 2-2 | C1 | 7.56 | 62.05 | 26.04 | 0.215, 0.422 |
| Comparative Example 2-3 | C2 | 8.12 | 59.44 | 26.67 | 0.214, 0.423 |
| Comparative Example 2-4 | C3 | 8.08 | 61.07 | 25.49 | 0.215, 0.423 |

As seen from the results of Table 4, the organic electroluminescent diode using the charge generation layer material of the blue organic electroluminescent diode of the present disclosure had lower driving voltage and significantly improved light emission efficiency compared to Comparative Examples 2-1 to 2-4.

Experimental Example 1-3

Comparative Example 3-1

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N— (2-naphthyl)-phenylamino)triphenylamine (2-TNATA) was introduced to a cell in the vacuum deposition apparatus.

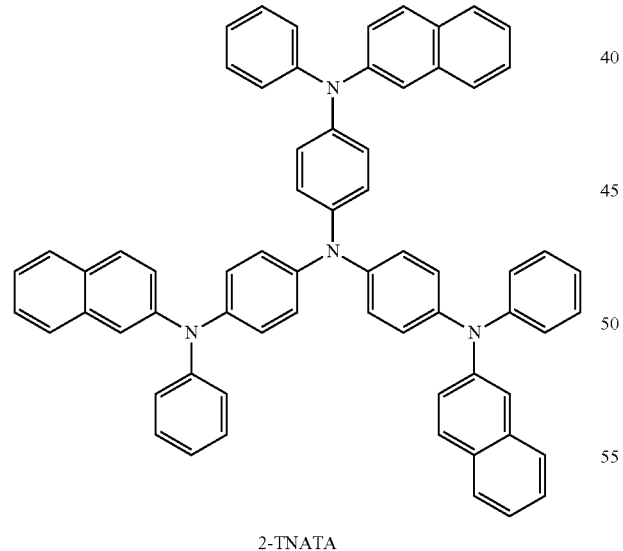

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

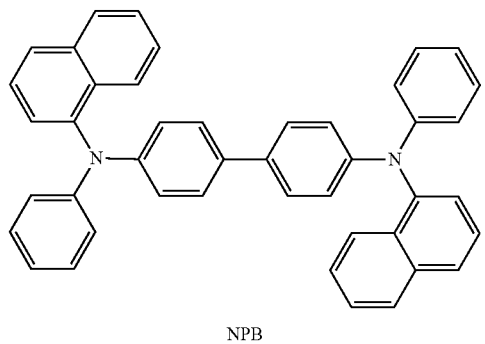

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

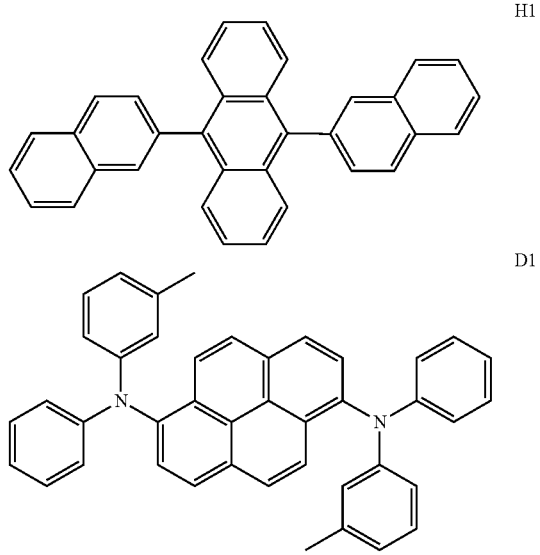

An electron transfer layer was formed to 300 Å using TmPyPB, and a charge generation layer was formed to 100 Å by doping $Cs_2CO_3$ to a compound of the following structural formula C1 by 20%.

C1

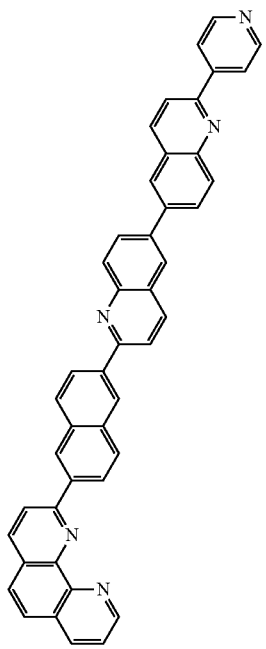

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Examples 3-1 to 3-74 and Comparative Examples 3-2 to 3-4

Organic light emitting diodes were manufactured in the same manner as in Experimental Example 1-3 except that TmPyPB was formed to a thickness of 250 Å as the electron transfer layer, and on the electron transfer layer, a hole blocking layer having a thickness of 50 Å was formed using a compound presented in Table 5.

Results of measuring driving voltage, light emission efficiency and color coordinate (CIE) of the blue organic light emitting diode manufactured according to the present disclosure are as shown in Table 5.

TABLE 5

|  | [Group II] Compound No. | Driving Voltage (V) | Light Emission Efficiency (cd/A) | External Quantum Efficiency (%) | CIE (x, y) |
| --- | --- | --- | --- | --- | --- |
| Example 3-1 | 1 | 7.45 | 64.22 | 32.46 | 0.228, 0.481 |
| Example 3-2 | 2 | 7.43 | 64.88 | 32.93 | 0.220, 0.481 |
| Example 3-3 | 13 | 7.16 | 65.26 | 35.15 | 0.232, 0.482 |
| Example 3-4 | 17 | 7.35 | 61.92 | 30.19 | 0.226, 0.434 |
| Example 3-5 | 19 | 7.47 | 62.27 | 28.94 | 0.211, 0.424 |
| Example 3-6 | 21 | 7.42 | 68.98 | 32.28 | 0.209, 0.423 |
| Example 3-7 | 24 | 7.55 | 68.13 | 34.21 | 0.233, 0.463 |
| Example 3-8 | 27 | 7.51 | 67.14 | 32.06 | 0.208, 0.420 |
| Example 3-9 | 32 | 7.49 | 71.29 | 30.12 | 0.211, 0.420 |
| Example 3-10 | 34 | 7.44 | 68.35 | 33.15 | 0.207, 0.422 |
| Example 3-11 | 36 | 7.66 | 59.75 | 28.69 | 0.210, 0.391 |
| Example 3-12 | 39 | 7.43 | 63.29 | 30.06 | 0.211, 0.425 |
| Example 3-13 | 43 | 7.29 | 66.79 | 34.72 | 0.208, 0.421 |
| Example 3-14 | 46 | 7.54 | 62.55 | 29.04 | 0.214, 0.422 |
| Example 3-15 | 47 | 7.55 | 65.17 | 34.66 | 0.234, 0.478 |
| Example 3-16 | 52 | 7.29 | 63.58 | 32.59 | 0.207, 0.419 |
| Example 3-17 | 59 | 7.49 | 68.68 | 28.61 | 0.217, 0.464 |
| Example 3-18 | 60 | 7.37 | 67.49 | 33.41 | 0.211, 0.423 |
| Example 3-19 | 62 | 7.39 | 61.43 | 29.65 | 0.216, 0.484 |
| Example 3-20 | 63 | 7.44 | 58.55 | 28.25 | 0.202, 0.483 |
| Example 3-21 | 68 | 7.43 | 67.67 | 33.36 | 0.208, 0.416 |
| Example 3-22 | 73 | 7.45 | 65.28 | 33.92 | 0.211, 0.422 |
| Example 3-23 | 77 | 7.54 | 67.65 | 29.78 | 0.208, 0.416 |
| Example 3-24 | 78 | 7.58 | 64.87 | 30.95 | 0.207, 0.422 |
| Example 3-25 | 80 | 7.47 | 66.35 | 32.69 | 0.209, 0.421 |
| Example 3-26 | 83 | 7.42 | 67.58 | 32.17 | 0.212, 0.427 |
| Example 3-27 | 85 | 7.57 | 65.72 | 30.26 | 0.209, 0.421 |
| Example 3-28 | 92 | 7.55 | 68.26 | 32.54 | 0.209, 0.419 |
| Example 3-29 | 97 | 7.43 | 66.19 | 29.88 | 0.212, 0.421 |
| Example 3-30 | 98 | 7.36 | 62.73 | 29.72 | 0.208, 0.416 |
| Example 3-31 | 102 | 7.49 | 64.83 | 31.95 | 0.207, 0.420 |
| Example 3-32 | 105 | 7.56 | 67.55 | 32.88 | 0.208, 0.418 |
| Example 3-33 | 107 | 7.56 | 66.38 | 31.85 | 0.206, 0.414 |

TABLE 5-continued

|  | [Group II] Compound No. | Driving Voltage (V) | Light Emission Efficiency (cd/A) | External Quantum Efficiency (%) | CIE (x, y) |
|---|---|---|---|---|---|
| Example 3-34 | 111 | 7.49 | 67.42 | 31.29 | 0.206, 0.416 |
| Example 3-35 | 116 | 7.72 | 62.66 | 30.17 | 0.211, 0.423 |
| Example 3-36 | 119 | 7.43 | 68.72 | 32.34 | 0.208, 0.422 |
| Example 3-37 | 120 | 7.55 | 69.25 | 35.24 | 0.234, 0.462 |
| Example 3-38 | 121 | 7.61 | 67.34 | 33.06 | 0.209, 0.421 |
| Example 3-39 | 125 | 7.49 | 71.29 | 30.91 | 0.211, 0.420 |
| Example 3-40 | 129 | 7.31 | 61.48 | 31.69 | 0.208, 0.418 |
| Example 3-41 | 131 | 7.58 | 67.66 | 29.65 | 0.216, 0.463 |
| Example 3-42 | 133 | 7.45 | 66.19 | 31.91 | 0.210, 0.421 |
| Example 3-43 | 137 | 7.55 | 67.37 | 29.58 | 0.207, 0.419 |
| Example 3-44 | 140 | 7.69 | 64.45 | 28.95 | 0.208, 0.421 |
| Example 3-45 | 145 | 7.39 | 65.37 | 31.28 | 0.207, 0.420 |
| Example 3-46 | 146 | 7.41 | 65.79 | 34.72 | 0.208, 0.422 |
| Example 3-47 | 148 | 7.46 | 62.31 | 27.94 | 0.214, 0.422 |
| Example 3-48 | 167 | 7.61 | 66.56 | 33.44 | 0.233, 0.478 |
| Example 3-49 | 168 | 7.49 | 67.64 | 30.59 | 0.209, 0.421 |
| Example 3-50 | 172 | 7.31 | 68.36 | 32.35 | 0.207, 0.419 |
| Example 3-51 | 177 | 7.36 | 66.27 | 31.07 | 0.212, 0.421 |
| Example 3-52 | 180 | 8.05 | 64.74 | 28.66 | 0.208, 0.416 |
| Example 3-53 | 183 | 7.39 | 68.98 | 30.94 | 0.209, 0.421 |
| Example 3-54 | 185 | 7.54 | 68.23 | 34.16 | 0.233, 0.463 |
| Example 3-55 | 187 | 7.79 | 67.37 | 32.26 | 0.208, 0.422 |
| Example 3-56 | 192 | 7.35 | 70.09 | 30.81 | 0.211, 0.420 |
| Example 3-57 | 196 | 7.44 | 68.45 | 29.29 | 0.212, 0.421 |
| Example 3-58 | 200 | 8.16 | 64.67 | 27.71 | 0.208, 0.416 |
| Example 3-59 | 202 | 8.09 | 64.78 | 30.80 | 0.208, 0.421 |
| Example 3-60 | 208 | 7.68 | 66.25 | 32.55 | 0.208, 0.418 |
| Example 3-61 | 209 | 7.68 | 67.15 | 31.96 | 0.207, 0.421 |
| Example 3-62 | 212 | 7.49 | 72.08 | 31.77 | 0.212, 0.420 |
| Example 3-63 | 214 | 7.39 | 67.37 | 33.53 | 0.206, 0.421 |
| Example 3-64 | 216 | 7.34 | 66.81 | 32.45 | 0.229, 0.482 |
| Example 3-65 | 219 | 7.53 | 64.79 | 31.97 | 0.221, 0.480 |
| Example 3-66 | 223 | 7.38 | 65.16 | 30.25 | 0.234, 0.484 |
| Example 3-67 | 227 | 7.47 | 66.65 | 31.33 | 0.208, 0.420 |
| Example 3-68 | 232 | 7.48 | 68.27 | 31.24 | 0.208, 0.418 |
| Example 3-69 | 234 | 7.44 | 67.54 | 29.56 | 0.213, 0.420 |
| Example 3-70 | 236 | 7.59 | 65.76 | 29.75 | 0.208, 0.421 |
| Example 3-71 | 241 | 7.89 | 65.49 | 31.53 | 0.210, 0.420 |
| Example 3-72 | 244 | 7.38 | 65.87 | 33.72 | 0.208, 0.422 |
| Example 3-73 | 252 | 7.39 | 65.01 | 33.88 | 0.207, 0.420 |
| Example 3-74 | 255 | 7.46 | 67.16 | 34.59 | 0.207, 0.421 |
| Comparative Example 3-1 | TmPyPB | 8.68 | 53.95 | 20.73 | 0.213, 0.443 |
| Comparative Example 3-2 | C1 | 7.56 | 62.05 | 26.04 | 0.215, 0.422 |
| Comparative Example 3-3 | C2 | 8.12 | 59.44 | 26.67 | 0.214, 0.423 |
| Comparative Example 3-4 | C3 | 8.08 | 61.07 | 25.49 | 0.215, 0.423 |

As seen from the results of Table 5, the organic light emitting diode using the hole blocking layer material of the blue organic light emitting diode of the present disclosure had lower driving voltage and improved light emission efficiency compared to Comparative Examples 3-1 to 3-4, and in the compound according to the present disclosure, the device lifetime was also enhanced due to excellent thermal stability.

Experimental Example 2-1

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treated for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), an organic material was formed in a 2-stack white organic light emitting diode (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping FIrpic to TCz1, a host, by 8% as a blue phosphorescent dopant. After forming an electron transfer layer to 400 Å using TmPyPB, a charge generation layer was formed to 100 Å by doping $Cs_2CO_3$ to a compound described in the following Table 6 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and then depositing TAPC to 300 Å. A light emitting layer was deposited thereon to 300 Å by doping Ir (ppy)$_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent diode was manufactured.

Meanwhile, all the organic compounds required to manufacture the OLED were vacuum sublimation purified under $10^{-6}$ torr to $10^{-8}$ torr by each material to be used in the OLED manufacture.

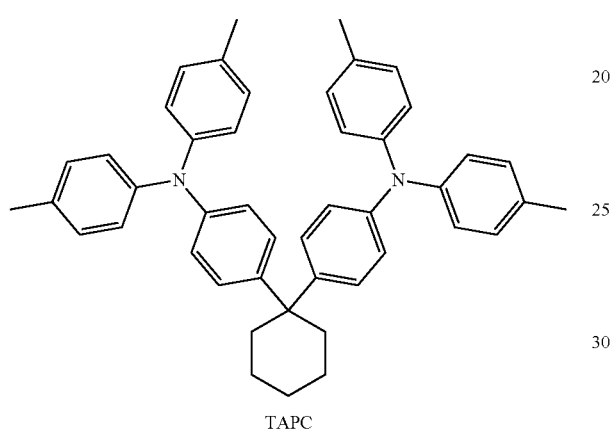

TAPC

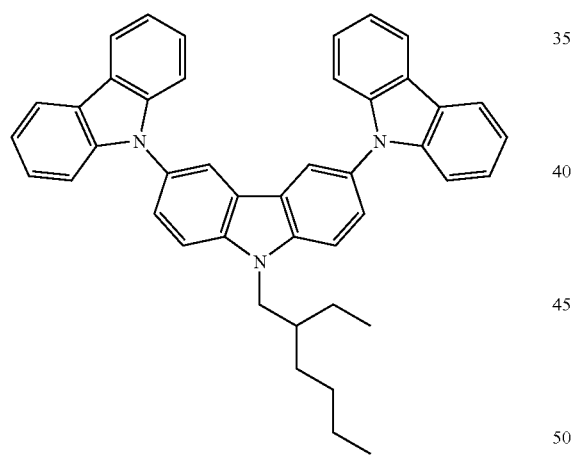

TCz1

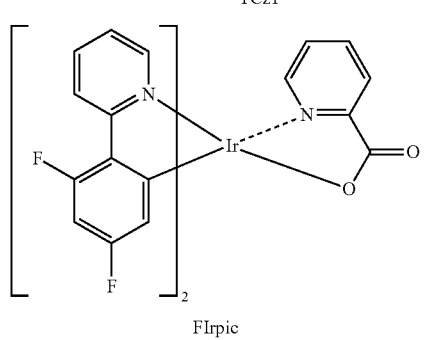

FIrpic

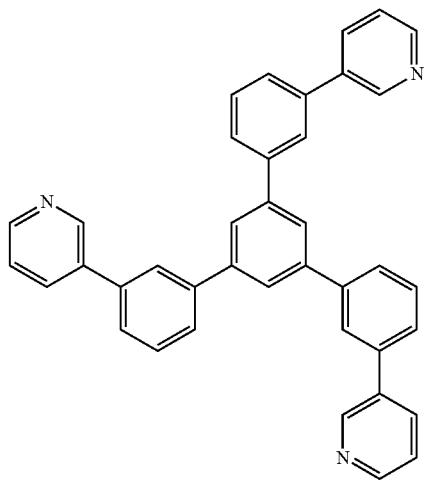

TmPyPB

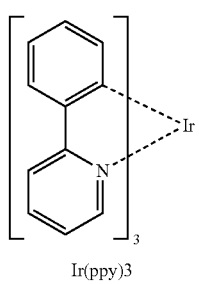

Ir(ppy)3

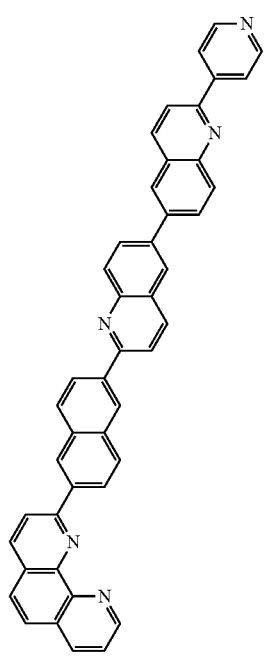

C1

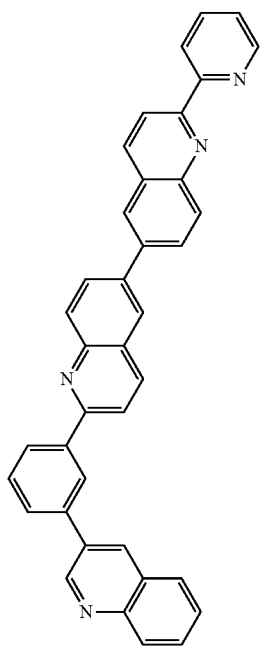

C2

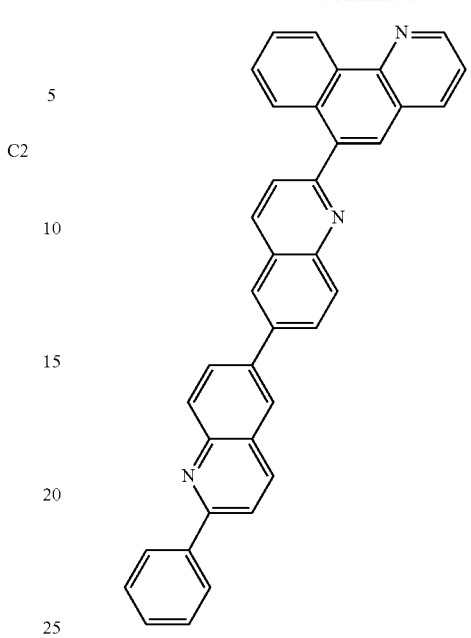

C3

Evaluation: Driving Voltage and Light Emission Efficiency of Organic Electroluminescent Diode For the organic electroluminescent diodes manufactured as above, electroluminescent (EL) properties were measured using M7000 manufactured by McScience Inc., and results of measuring driving voltage, light emission efficiency, external quantum efficiency and color coordinate (CIE) of the white organic electroluminescent diodes manufactured according to the present disclosure are as shown in Table 6.

TABLE 6

|  | [Group III] Compound No. | Driving Voltage (V) | Light Emission Efficiency (cd/A) | External Quantum Efficiency (%) | CIE (x, y) |
|---|---|---|---|---|---|
| Example 4-1 | 1 | 7.55 | 65.20 | 31.44 | 0.227, 0.481 |
| Example 4-2 | 2 | 7.44 | 63.86 | 31.92 | 0.220, 0.480 |
| Example 4-3 | 13 | 7.17 | 65.16 | 35.12 | 0.231, 0.482 |
| Example 4-4 | 17 | 7.33 | 61.92 | 31.28 | 0.226, 0.434 |
| Example 4-5 | 19 | 8.23 | 61.27 | 26.04 | 0.211, 0.425 |
| Example 4-6 | 21 | 7.43 | 68.80 | 32.24 | 0.209, 0.423 |
| Example 4-7 | 24 | 7.65 | 68.13 | 34.24 | 0.231, 0.463 |
| Example 4-8 | 27 | 7.78 | 67.15 | 30.06 | 0.208, 0.421 |
| Example 4-9 | 32 | 7.48 | 71.18 | 30.01 | 0.210, 0.421 |
| Example 4-10 | 34 | 7.43 | 67.33 | 33.03 | 0.207, 0.422 |
| Example 4-11 | 36 | 8.24 | 58.88 | 24.65 | 0.211, 0.391 |
| Example 4-12 | 39 | 7.44 | 63.18 | 27.06 | 0.211, 0.426 |
| Example 4-13 | 43 | 7.37 | 65.81 | 34.82 | 0.207, 0.421 |
| Example 4-14 | 46 | 7.56 | 62.24 | 26.04 | 0.211, 0.422 |
| Example 4-15 | 47 | 7.61 | 66.06 | 34.46 | 0.233, 0.478 |
| Example 4-16 | 52 | 7.30 | 60.47 | 31.52 | 0.207, 0.419 |
| Example 4-17 | 59 | 7.59 | 68.67 | 22.66 | 0.216, 0.464 |
| Example 4-18 | 60 | 7.28 | 66.51 | 32.51 | 0.211, 0.422 |
| Example 4-19 | 62 | 8.13 | 60.44 | 28.63 | 0.216, 0.484 |
| Example 4-20 | 63 | 7.97 | 58.25 | 22.20 | 0.201, 0.483 |
| Example 4-21 | 68 | 7.43 | 68.58 | 32.46 | 0.208, 0.417 |
| Example 4-22 | 73 | 7.47 | 65.28 | 33.90 | 0.211, 0.422 |
| Example 4-23 | 77 | 7.55 | 67.60 | 29.65 | 0.207, 0.416 |
| Example 4-24 | 78 | 7.66 | 64.76 | 26.95 | 0.207, 0.421 |
| Example 4-25 | 80 | 7.88 | 65.44 | 32.02 | 0.209, 0.421 |
| Example 4-26 | 83 | 7.71 | 67.23 | 32.19 | 0.212, 0.426 |
| Example 4-27 | 85 | 7.54 | 66.73 | 31.23 | 0.208, 0.421 |
| Example 4-28 | 92 | 7.54 | 68.26 | 32.24 | 0.210, 0.419 |
| Example 4-29 | 97 | 7.43 | 66.38 | 29.26 | 0.211, 0.421 |
| Example 4-30 | 98 | 8.11 | 62.83 | 25.82 | 0.209, 0.416 |

TABLE 6-continued

| | [Group III] Compound No. | Driving Voltage (V) | Light Emission Efficiency (cd/A) | External Quantum Efficiency (%) | CIE (x, y) |
|---|---|---|---|---|---|
| Example 4-31 | 102 | 8.18 | 64.85 | 31.90 | 0.207, 0.421 |
| Example 4-32 | 105 | 7.59 | 67.20 | 32.83 | 0.209, 0.418 |
| Example 4-33 | 107 | 7.56 | 66.35 | 31.83 | 0.206, 0.415 |
| Example 4-34 | 111 | 7.51 | 66.42 | 32.15 | 0.207, 0.416 |
| Example 4-35 | 116 | 7.72 | 62.87 | 25.17 | 0.211, 0.424 |
| Example 4-36 | 119 | 7.42 | 68.81 | 32.14 | 0.207, 0.422 |
| Example 4-37 | 120 | 7.66 | 68.13 | 34.24 | 0.234, 0.461 |
| Example 4-38 | 121 | 7.78 | 67.15 | 30.06 | 0.208, 0.421 |
| Example 4-39 | 125 | 7.48 | 71.18 | 30.11 | 0.211, 0.421 |
| Example 4-40 | 129 | 7.32 | 61.37 | 31.58 | 0.207, 0.418 |
| Example 4-41 | 131 | 7.58 | 68.66 | 25.65 | 0.215, 0.463 |
| Example 4-42 | 133 | 7.48 | 65.28 | 33.81 | 0.210, 0.421 |
| Example 4-43 | 137 | 7.55 | 67.64 | 29.64 | 0.208, 0.419 |
| Example 4-44 | 140 | 7.78 | 64.77 | 25.95 | 0.208, 0.420 |
| Example 4-45 | 145 | 7.48 | 65.54 | 32.07 | 0.206, 0.420 |
| Example 4-46 | 146 | 7.37 | 65.98 | 34.82 | 0.208, 0.421 |
| Example 4-47 | 148 | 7.45 | 62.25 | 26.14 | 0.213, 0.422 |
| Example 4-48 | 167 | 7.63 | 66.26 | 34.35 | 0.233, 0.477 |
| Example 4-49 | 168 | 7.57 | 66.77 | 31.22 | 0.208, 0.421 |
| Example 4-50 | 172 | 7.34 | 68.16 | 32.35 | 0.206, 0.419 |
| Example 4-51 | 177 | 7.35 | 66.35 | 30.28 | 0.212, 0.420 |
| Example 4-52 | 180 | 8.14 | 62.85 | 25.63 | 0.208, 0.416 |
| Example 4-53 | 183 | 7.44 | 68.81 | 33.24 | 0.208, 0.421 |
| Example 4-54 | 185 | 7.66 | 68.23 | 34.14 | 0.234, 0.462 |
| Example 4-55 | 187 | 7.78 | 67.24 | 30.36 | 0.207, 0.422 |
| Example 4-56 | 192 | 7.31 | 71.18 | 30.21 | 0.211, 0.421 |
| Example 4-57 | 196 | 7.44 | 66.45 | 29.36 | 0.211, 0.421 |
| Example 4-58 | 200 | 8.16 | 63.83 | 25.73 | 0.209, 0.416 |
| Example 4-59 | 202 | 8.19 | 64.88 | 31.90 | 0.207, 0.421 |
| Example 4-60 | 208 | 7.68 | 67.21 | 32.83 | 0.208, 0.419 |
| Example 4-61 | 209 | 7.77 | 67.15 | 31.06 | 0.208, 0.421 |
| Example 4-62 | 212 | 7.48 | 71.18 | 32.21 | 0.212, 0.421 |
| Example 4-63 | 214 | 7.42 | 67.34 | 31.02 | 0.205, 0.421 |
| Example 4-64 | 216 | 7.31 | 66.31 | 33.45 | 0.229, 0.481 |
| Example 4-65 | 219 | 7.52 | 63.86 | 32.92 | 0.220, 0.480 |
| Example 4-66 | 223 | 7.39 | 65.27 | 35.23 | 0.234, 0.483 |
| Example 4-67 | 227 | 7.48 | 66.73 | 33.32 | 0.207, 0.420 |
| Example 4-68 | 232 | 7.44 | 68.26 | 32.24 | 0.208, 0.419 |
| Example 4-69 | 234 | 7.44 | 66.85 | 29.46 | 0.212, 0.420 |
| Example 4-70 | 236 | 7.68 | 64.77 | 26.85 | 0.208, 0.422 |
| Example 4-71 | 241 | 7.79 | 65.34 | 32.52 | 0.210, 0.421 |
| Example 4-72 | 244 | 7.37 | 65.85 | 34.82 | 0.209, 0.422 |
| Example 4-73 | 255 | 7.39 | 65.88 | 33.78 | 0.207, 0.422 |
| Comparative Example 4-1 | TmPyPB | 8.68 | 53.95 | 20.73 | 0.213, 0.443 |
| Comparative Example 4-2 | C1 | 7.56 | 62.05 | 26.04 | 0.215, 0.422 |
| Comparative Example 4-3 | C2 | 8.12 | 59.44 | 26.67 | 0.214, 0.423 |
| Comparative Example 4-4 | C3 | 8.08 | 61.07 | 25.49 | 0.215, 0.423 |

As seen from the results of Table 6, the organic electroluminescent diode using the charge generation layer material of the white organic electroluminescent diode of the present disclosure had lower driving voltage and significantly improved light emission efficiency compared to Comparative Examples 4-1 to 4-4.

Experimental Example 2-2

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

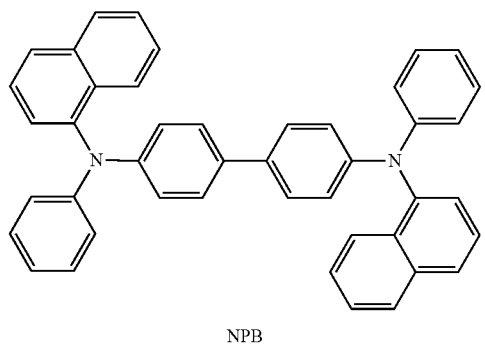

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

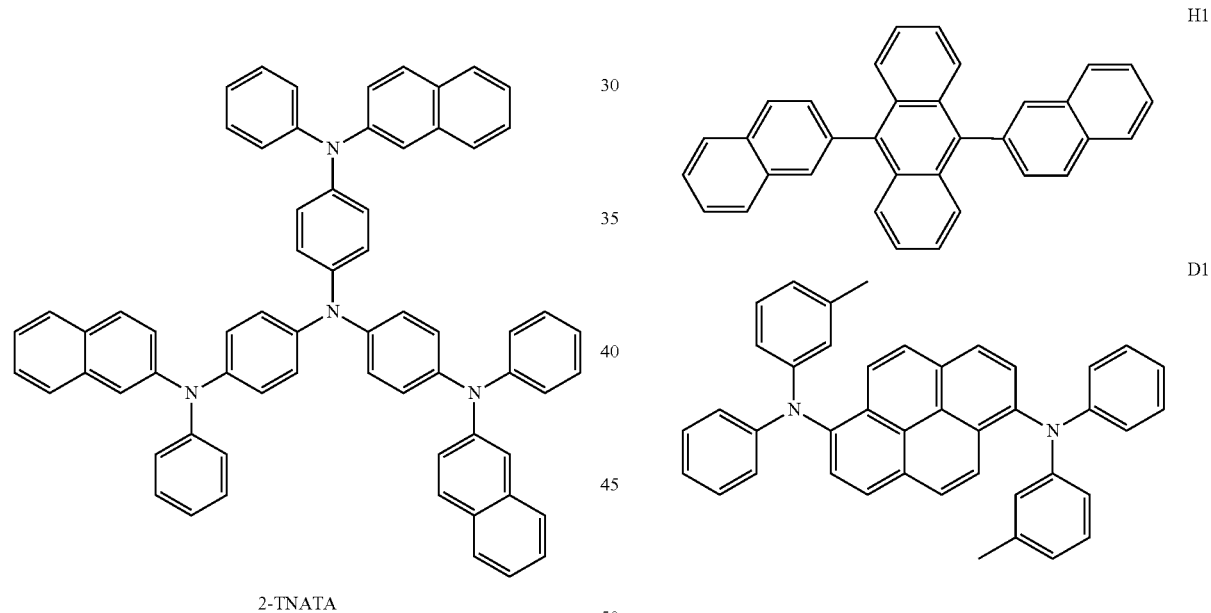

An electron transfer layer was formed to 300 Å using TmPyPB, and a charge generation layer was formed to 100 Å by doping $Cs_2CO_3$ to a compound described in the following Table 7 by 20%.

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Results of measuring driving voltage, light emission efficiency and color coordinate (CIE) of the blue organic light emitting diodes manufactured according to the present disclosure are as shown in Table 7.

TABLE 7

| | [Group III] Compound No. | Driving Voltage (V) | Light Emission Efficiency (cd/A) | External Quantum Efficiency (%) | CIE (x, y) |
|---|---|---|---|---|---|
| Example 5-1 | 1 | 7.53 | 65.83 | 31.45 | 0.228, 0.481 |
| Example 5-2 | 2 | 7.43 | 62.72 | 32.13 | 0.220, 0.481 |
| Example 5-3 | 13 | 7.16 | 65.16 | 34.13 | 0.232, 0.482 |
| Example 5-4 | 17 | 7.32 | 61.92 | 32.29 | 0.226, 0.434 |
| Example 5-5 | 19 | 7.46 | 62.38 | 29.16 | 0.211, 0.424 |
| Example 5-6 | 21 | 7.44 | 68.88 | 31.23 | 0.209, 0.423 |
| Example 5-7 | 24 | 7.54 | 69.25 | 33.16 | 0.233, 0.463 |
| Example 5-8 | 27 | 7.55 | 67.14 | 31.06 | 0.208, 0.420 |
| Example 5-9 | 32 | 7.49 | 71.21 | 30.16 | 0.211, 0.420 |
| Example 5-10 | 34 | 7.39 | 68.38 | 33.22 | 0.207, 0.422 |
| Example 5-11 | 36 | 7.64 | 59.75 | 29.75 | 0.210, 0.391 |
| Example 5-12 | 39 | 7.45 | 62.39 | 29.36 | 0.211, 0.425 |
| Example 5-13 | 43 | 7.40 | 66.73 | 33.92 | 0.208, 0.421 |
| Example 5-14 | 46 | 7.54 | 62.25 | 27.25 | 0.214, 0.422 |
| Example 5-15 | 47 | 7.54 | 65.16 | 33.55 | 0.234, 0.478 |
| Example 5-16 | 52 | 7.34 | 64.37 | 32.81 | 0.207, 0.419 |
| Example 5-17 | 59 | 7.48 | 67.69 | 29.43 | 0.217, 0.464 |
| Example 5-18 | 60 | 7.30 | 67.57 | 32.33 | 0.211, 0.423 |
| Example 5-19 | 62 | 7.41 | 60.33 | 29.52 | 0.216, 0.484 |
| Example 5-20 | 63 | 7.44 | 59.91 | 28.21 | 0.202, 0.483 |
| Example 5-21 | 68 | 7.43 | 64.57 | 32.87 | 0.208, 0.416 |
| Example 5-22 | 73 | 7.47 | 65.18 | 31.91 | 0.211, 0.422 |
| Example 5-23 | 77 | 7.49 | 67.53 | 29.77 | 0.208, 0.416 |
| Example 5-24 | 78 | 7.58 | 65.77 | 28.87 | 0.207, 0.422 |
| Example 5-25 | 80 | 7.48 | 66.26 | 31.83 | 0.209, 0.421 |
| Example 5-26 | 83 | 7.51 | 67.33 | 32.29 | 0.212, 0.427 |
| Example 5-27 | 85 | 7.47 | 68.72 | 30.31 | 0.209, 0.421 |
| Example 5-28 | 92 | 7.44 | 68.56 | 33.27 | 0.209, 0.419 |
| Example 5-29 | 97 | 7.40 | 66.25 | 29.56 | 0.212, 0.421 |
| Example 5-30 | 98 | 7.35 | 62.84 | 28.71 | 0.208, 0.416 |
| Example 5-31 | 102 | 7.34 | 64.99 | 31.90 | 0.207, 0.420 |
| Example 5-32 | 105 | 7.51 | 67.35 | 31.64 | 0.208, 0.418 |
| Example 5-33 | 107 | 7.46 | 66.13 | 31.88 | 0.206, 0.414 |
| Example 5-34 | 111 | 7.51 | 67.42 | 31.94 | 0.206, 0.416 |
| Example 5-35 | 116 | 7.72 | 63.67 | 25.12 | 0.211, 0.423 |
| Example 5-36 | 119 | 7.32 | 67.83 | 33.24 | 0.208, 0.422 |
| Example 5-37 | 120 | 7.45 | 69.13 | 35.84 | 0.234, 0.462 |
| Example 5-38 | 121 | 7.51 | 67.84 | 31.06 | 0.209, 0.421 |
| Example 5-39 | 125 | 7.39 | 70.19 | 31.57 | 0.211, 0.420 |
| Example 5-40 | 129 | 7.37 | 68.57 | 33.68 | 0.208, 0.418 |
| Example 5-41 | 131 | 7.48 | 67.68 | 29.79 | 0.216, 0.463 |
| Example 5-42 | 133 | 7.49 | 66.61 | 32.91 | 0.210, 0.421 |
| Example 5-43 | 137 | 7.59 | 67.42 | 29.68 | 0.207, 0.419 |
| Example 5-44 | 140 | 7.58 | 63.36 | 28.91 | 0.208, 0.421 |
| Example 5-45 | 145 | 7.38 | 66.37 | 32.88 | 0.207, 0.420 |
| Example 5-46 | 146 | 7.33 | 65.94 | 33.72 | 0.208, 0.422 |
| Example 5-47 | 148 | 7.45 | 62.25 | 28.67 | 0.214, 0.422 |
| Example 5-48 | 167 | 7.52 | 66.66 | 34.45 | 0.233, 0.478 |
| Example 5-49 | 168 | 7.57 | 67.75 | 32.61 | 0.209, 0.421 |
| Example 5-50 | 172 | 7.34 | 68.37 | 31.25 | 0.207, 0.419 |
| Example 5-51 | 177 | 7.36 | 67.91 | 32.88 | 0.212, 0.421 |
| Example 5-52 | 180 | 7.49 | 64.85 | 28.33 | 0.208, 0.416 |
| Example 5-53 | 183 | 7.43 | 68.76 | 30.24 | 0.209, 0.421 |
| Example 5-54 | 185 | 7.31 | 68.53 | 33.67 | 0.233, 0.463 |
| Example 5-55 | 187 | 7.63 | 67.35 | 30.27 | 0.208, 0.422 |
| Example 5-56 | 192 | 7.37 | 70.18 | 31.01 | 0.211, 0.420 |
| Example 5-57 | 196 | 7.43 | 67.55 | 29.80 | 0.212, 0.421 |
| Example 5-58 | 200 | 7.49 | 65.16 | 27.73 | 0.208, 0.416 |
| Example 5-59 | 202 | 8.00 | 64.78 | 31.81 | 0.208, 0.421 |
| Example 5-60 | 208 | 7.69 | 69.20 | 33.46 | 0.208, 0.418 |
| Example 5-61 | 209 | 7.78 | 68.35 | 30.88 | 0.207, 0.421 |
| Example 5-62 | 212 | 7.48 | 71.09 | 30.71 | 0.212, 0.420 |
| Example 5-63 | 214 | 7.33 | 67.44 | 31.08 | 0.206, 0.421 |
| Example 5-64 | 216 | 7.39 | 65.81 | 34.91 | 0.229, 0.482 |
| Example 5-65 | 219 | 7.51 | 64.86 | 31.89 | 0.221, 0.480 |
| Example 5-66 | 223 | 7.39 | 64.16 | 30.23 | 0.234, 0.484 |
| Example 5-67 | 227 | 7.37 | 66.73 | 31.82 | 0.208, 0.420 |
| Example 5-68 | 232 | 7.54 | 69.27 | 32.15 | 0.208, 0.418 |
| Example 5-69 | 234 | 7.40 | 67.35 | 29.94 | 0.213, 0.420 |
| Example 5-70 | 236 | 7.61 | 64.76 | 28.86 | 0.208, 0.421 |
| Example 5-71 | 241 | 7.39 | 65.44 | 33.42 | 0.210, 0.420 |
| Example 5-72 | 244 | 7.47 | 66.98 | 30.62 | 0.208, 0.422 |
| Example 5-73 | 255 | 7.39 | 65.88 | 33.78 | 0.207, 0.422 |
| Comparative Example 5-1 | TmPyPB | 8.68 | 53.95 | 20.73 | 0.213, 0.443 |

TABLE 7-continued

| | [Group III] Compound No. | Driving Voltage (V) | Light Emission Efficiency (cd/A) | External Quantum Efficiency (%) | CIE (x, y) |
|---|---|---|---|---|---|
| Comparative Example 5-2 | C1 | 7.56 | 62.05 | 26.04 | 0.215, 0.422 |
| Comparative Example 5-3 | C2 | 8.12 | 59.44 | 26.67 | 0.214, 0.423 |
| Comparative Example 5-4 | C3 | 8.08 | 61.07 | 25.49 | 0.215, 0.423 |

As seen from the results of Table 7, the organic electroluminescent diode using the charge generation layer material of the blue organic electroluminescent diode of the present disclosure had lower driving voltage and significantly improved light emission efficiency compared to Comparative Examples 5-1 to 5-4.

Experimental Example 2-3

Comparative Example 6-1

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

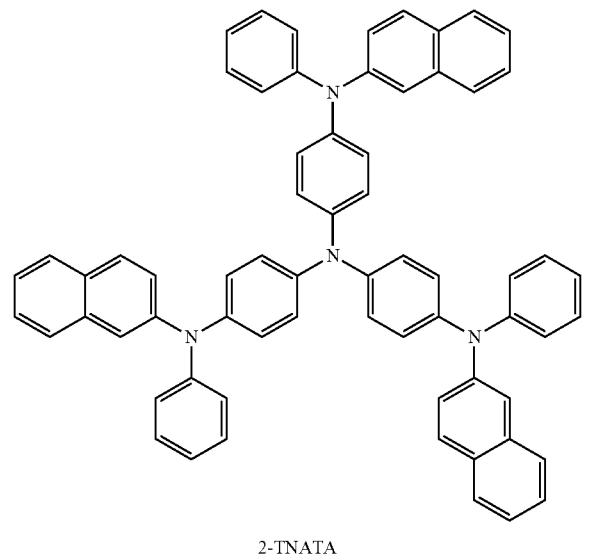

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

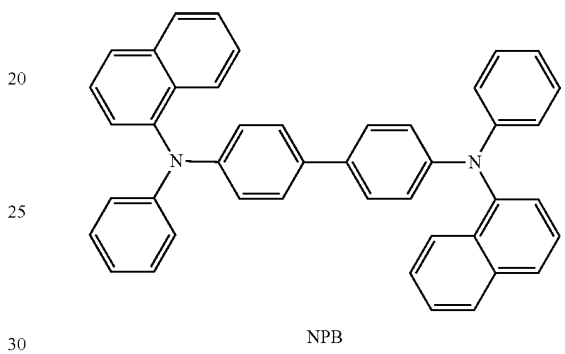

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

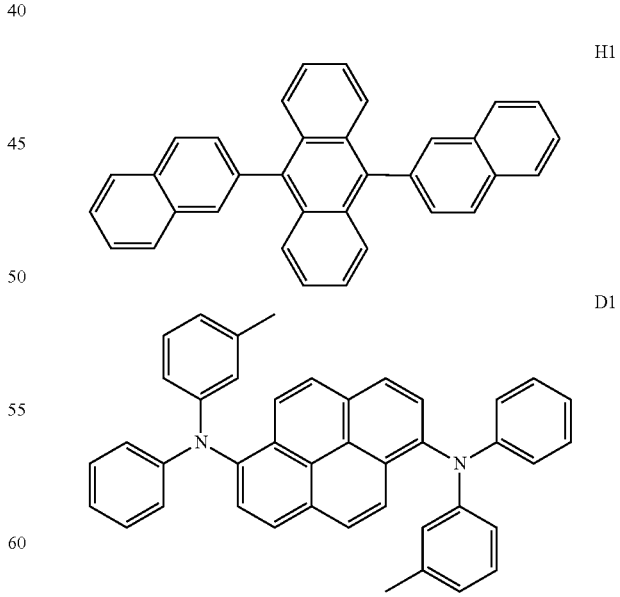

An electron transfer layer was formed to 300 Å using TmPyPB, and a charge generation layer was formed to 100 Å by doping $Cs_2CO_3$ to a compound of the following structural formula C1 b 20%.

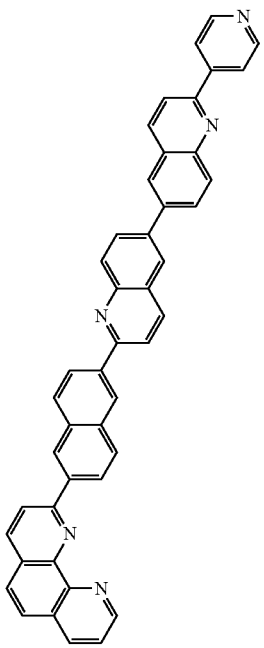

C1

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Examples 6-1 to 6-73 and Comparative Examples 6-2 to 6-4

Organic light emitting diodes were manufactured in the same manner as in Experimental Example 2-3 except that TmPyPB was formed to a thickness of 250 Å as the electron transfer layer, and on the electron transfer layer, a hole blocking layer having a thickness of 50 Å was formed using a compound presented in Table 8.

Results of measuring driving voltage, light emission efficiency and color coordinate (CIE) of the blue organic light emitting diode manufactured according to the present disclosure are as shown in Table 8.

TABLE 8

| | [Group III] Compound No. | Driving Voltage (V) | Light Emission Efficiency (cd/A) | External Quantum Efficiency (%) | CIE (x, y) |
|---|---|---|---|---|---|
| Example 6-1 | 1 | 7.44 | 64.22 | 31.56 | 0.228, 0.481 |
| Example 6-2 | 2 | 7.38 | 64.78 | 32.83 | 0.220, 0.481 |
| Example 6-3 | 13 | 7.36 | 63.86 | 34.49 | 0.232, 0.482 |
| Example 6-4 | 17 | 7.41 | 62.92 | 32.18 | 0.226, 0.434 |
| Example 6-5 | 19 | 7.39 | 62.57 | 29.99 | 0.211, 0.424 |
| Example 6-6 | 21 | 7.43 | 67.97 | 33.28 | 0.209, 0.423 |
| Example 6-7 | 24 | 7.45 | 68.03 | 34.59 | 0.233, 0.463 |
| Example 6-8 | 27 | 7.50 | 67.14 | 32.86 | 0.208, 0.420 |
| Example 6-9 | 32 | 7.39 | 70.87 | 30.92 | 0.211, 0.420 |
| Example 6-10 | 34 | 7.47 | 69.35 | 33.48 | 0.207, 0.422 |
| Example 6-11 | 36 | 7.46 | 61.85 | 29.49 | 0.210, 0.391 |
| Example 6-12 | 39 | 7.33 | 62.99 | 31.26 | 0.211, 0.425 |
| Example 6-13 | 43 | 7.28 | 66.80 | 34.62 | 0.208, 0.421 |
| Example 6-14 | 46 | 7.51 | 62.75 | 30.04 | 0.214, 0.422 |
| Example 6-15 | 47 | 7.55 | 64.17 | 34.56 | 0.234, 0.478 |
| Example 6-16 | 52 | 7.34 | 63.48 | 33.91 | 0.207, 0.419 |
| Example 6-17 | 59 | 7.39 | 68.49 | 29.65 | 0.217, 0.464 |
| Example 6-18 | 60 | 7.33 | 68.49 | 32.41 | 0.211, 0.423 |
| Example 6-19 | 62 | 7.38 | 63.64 | 31.95 | 0.216, 0.484 |
| Example 6-20 | 63 | 7.43 | 58.95 | 29.05 | 0.202, 0.483 |
| Example 6-21 | 68 | 7.39 | 67.72 | 32.36 | 0.208, 0.416 |
| Example 6-22 | 73 | 7.41 | 65.18 | 34.09 | 0.211, 0.422 |
| Example 6-23 | 77 | 7.44 | 67.19 | 31.78 | 0.208, 0.416 |
| Example 6-24 | 78 | 7.51 | 64.77 | 33.01 | 0.207, 0.422 |
| Example 6-25 | 80 | 7.46 | 66.39 | 32.69 | 0.209, 0.421 |
| Example 6-26 | 83 | 7.42 | 66.58 | 33.17 | 0.212, 0.427 |
| Example 6-27 | 85 | 7.47 | 65.82 | 30.56 | 0.209, 0.421 |
| Example 6-28 | 92 | 7.51 | 66.61 | 33.84 | 0.209, 0.419 |
| Example 6-29 | 97 | 7.38 | 66.59 | 29.16 | 0.212, 0.421 |
| Example 6-30 | 98 | 7.35 | 62.73 | 29.62 | 0.208, 0.416 |
| Example 6-31 | 102 | 7.41 | 63.94 | 31.25 | 0.207, 0.420 |
| Example 6-32 | 105 | 7.51 | 66.23 | 32.78 | 0.208, 0.418 |
| Example 6-33 | 107 | 7.50 | 66.67 | 31.15 | 0.206, 0.414 |
| Example 6-34 | 111 | 7.49 | 67.42 | 32.59 | 0.206, 0.416 |
| Example 6-35 | 116 | 7.71 | 63.46 | 30.67 | 0.211, 0.423 |
| Example 6-36 | 119 | 7.45 | 67.71 | 33.59 | 0.208, 0.422 |
| Example 6-37 | 120 | 7.45 | 69.85 | 35.12 | 0.234, 0.462 |
| Example 6-38 | 121 | 7.51 | 66.34 | 33.19 | 0.209, 0.421 |
| Example 6-39 | 125 | 7.48 | 70.04 | 31.91 | 0.211, 0.420 |

TABLE 8-continued

|  | [Group III] Compound No. | Driving Voltage (V) | Light Emission Efficiency (cd/A) | External Quantum Efficiency (%) | CIE (x, y) |
|---|---|---|---|---|---|
| Example 6-40 | 129 | 7.38 | 63.59 | 32.69 | 0.208, 0.418 |
| Example 6-41 | 131 | 7.37 | 66.87 | 29.94 | 0.216, 0.463 |
| Example 6-42 | 133 | 7.42 | 68.28 | 31.68 | 0.210, 0.421 |
| Example 6-43 | 137 | 7.50 | 67.18 | 29.51 | 0.207, 0.419 |
| Example 6-44 | 140 | 7.68 | 65.45 | 29.95 | 0.208, 0.421 |
| Example 6-45 | 145 | 7.41 | 65.57 | 31.48 | 0.207, 0.420 |
| Example 6-46 | 146 | 7.40 | 65.79 | 34.63 | 0.208, 0.422 |
| Example 6-47 | 148 | 7.46 | 61.58 | 28.32 | 0.214, 0.422 |
| Example 6-48 | 167 | 7.53 | 66.62 | 33.41 | 0.233, 0.478 |
| Example 6-49 | 168 | 7.40 | 66.64 | 31.38 | 0.209, 0.421 |
| Example 6-50 | 172 | 7.35 | 67.66 | 32.31 | 0.207, 0.419 |
| Example 6-51 | 177 | 7.36 | 63.27 | 32.07 | 0.212, 0.421 |
| Example 6-52 | 180 | 7.45 | 64.74 | 29.88 | 0.208, 0.416 |
| Example 6-53 | 183 | 7.38 | 67.15 | 30.67 | 0.209, 0.421 |
| Example 6-54 | 185 | 7.51 | 68.66 | 33.96 | 0.233, 0.463 |
| Example 6-55 | 187 | 7.61 | 67.17 | 32.22 | 0.208, 0.422 |
| Example 6-56 | 192 | 7.36 | 69.09 | 31.51 | 0.211, 0.420 |
| Example 6-57 | 196 | 7.43 | 68.45 | 29.19 | 0.212, 0.421 |
| Example 6-58 | 200 | 8.15 | 64.67 | 26.71 | 0.208, 0.416 |
| Example 6-59 | 202 | 8.07 | 64.78 | 30.83 | 0.208, 0.421 |
| Example 6-60 | 208 | 7.68 | 66.15 | 31.96 | 0.208, 0.418 |
| Example 6-61 | 209 | 7.60 | 66.35 | 34.96 | 0.207, 0.421 |
| Example 6-62 | 212 | 7.45 | 72.08 | 31.77 | 0.212, 0.420 |
| Example 6-63 | 214 | 7.36 | 66.37 | 33.50 | 0.206, 0.421 |
| Example 6-64 | 216 | 7.32 | 66.81 | 31.45 | 0.229, 0.482 |
| Example 6-65 | 219 | 7.50 | 64.79 | 32.87 | 0.221, 0.480 |
| Example 6-66 | 223 | 7.41 | 65.06 | 31.25 | 0.234, 0.484 |
| Example 6-67 | 227 | 7.46 | 66.85 | 31.73 | 0.208, 0.420 |
| Example 6-68 | 232 | 7.47 | 68.77 | 31.24 | 0.208, 0.418 |
| Example 6-69 | 234 | 7.44 | 67.51 | 30.56 | 0.213, 0.420 |
| Example 6-70 | 236 | 7.51 | 65.77 | 29.85 | 0.208, 0.421 |
| Example 6-71 | 241 | 7.62 | 65.39 | 30.53 | 0.210, 0.420 |
| Example 6-72 | 244 | 7.31 | 65.77 | 32.65 | 0.208, 0.422 |
| Example 6-73 | 255 | 7.37 | 66.16 | 32.71 | 0.208, 0.420 |
| Comparative Example 6-1 | TmPyPB | 8.68 | 53.95 | 20.73 | 0.213, 0.443 |
| Comparative Example 6-2 | C1 | 7.56 | 62.05 | 26.04 | 0.215, 0.422 |
| Comparative Example 6-3 | C2 | 8.12 | 59.44 | 26.67 | 0.214, 0.423 |
| Comparative Example 6-4 | C3 | 8.08 | 61.07 | 25.49 | 0.215, 0.423 |

As seen from the results of Table 8, the organic light emitting diode using the hole blocking layer material of the blue organic light emitting diode of the present disclosure had lower driving voltage and improved light emission efficiency compared to Comparative Examples 6-1 to 6-4, and in the compound according to the present disclosure, the device lifetime was also enhanced due to excellent thermal stability.

Hereinbefore, preferred examples of the present disclosure have been described in detail, however, the scope of a right of the present disclosure is not limited thereto, and various modifications and improvements made by those skilled in the art using the basic concept of the present disclosure defined in the attached claims also fall within the scope of a right of the present disclosure.

The invention claimed is:
1. A compound represented by the following Chemical Formula 1:

[Chemical Formula 1]

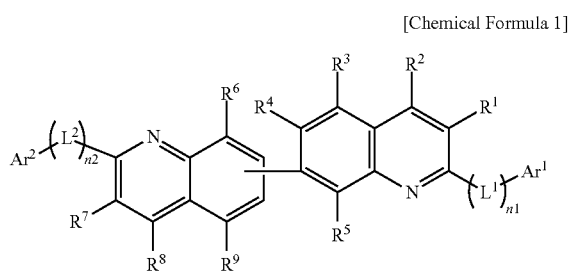

wherein, in Chemical Formula 1,
$Ar^1$ and $Ar^2$ are each independently a substituted or unsubstituted C6 to C60 aryl group or a substituted or unsubstituted C2 to C60 heteroaryl group, and at least one of $Ar^1$ and $Ar^2$ is a substituted or unsubstituted C2 to C60 heteroaryl group;
$L^1$ and $L^2$ are each independently a single bond, a substituted or unsubstituted C6 to C60 arylene group, or a substituted or unsubstituted C2 to C60 heteroarylene group;
n1 and n2 are each independently one of integers of 0 to 2; and $R^1$ to $R^9$ are each independently hydrogen, deuterium, a cyano group, a substituted or unsubstituted C1 to C60 alkyl group, or a substituted or unsubstituted C6 to C60 aryl group.

2. The compound of claim 1, which is represented by the following Chemical Formula 2:

[Chemical Formula 2]

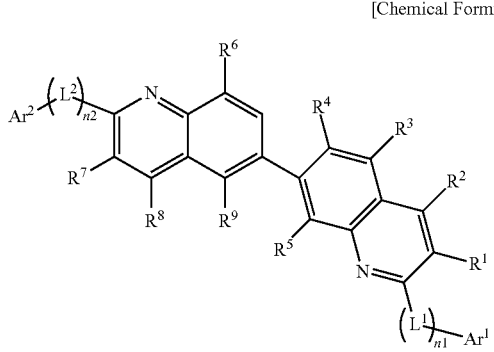

in Chemical Formula 2, $Ar^1$ and $Ar^2$ are each independently a substituted or unsubstituted C6 to C60 aryl group or a substituted or unsubstituted C2 to C60 heteroaryl group, and at least one of $Ar^1$ and $Ar^2$ is a substituted or unsubstituted C2 to C60 heteroaryl group;

$L^1$ and $L^2$ are each independently a single bond, a substituted or unsubstituted C6 to C60 arylene group, or a substituted or unsubstituted C2 to C60 heteroarylene group;

n1 and n2 are each independently one of integers of 0 to 2; and $R^1$ to $R^9$ are each independently hydrogen, deuterium, a cyano group, a substituted or unsubstituted C1 to C60 alkyl group, or a substituted or unsubstituted C6 to C60 aryl group.

3. The compound of claim 1, which is represented by the following Chemical Formula 3:

[Chemical Formula 3]

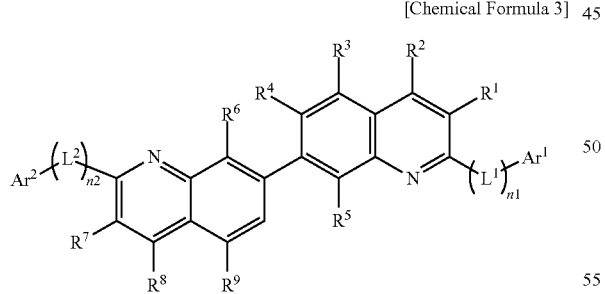

in Chemical Formula 3, $Ar^1$ and $Ar^2$ are each independently a substituted or unsubstituted C6 to C60 aryl group or a substituted or unsubstituted C2 to C60 heteroaryl group, and at least one of $Ar^1$ and $Ar^2$ is a substituted or unsubstituted C2 to C60 heteroaryl group;

$L^1$ and $L^2$ are each independently a single bond, a substituted or unsubstituted C6 to C60 arylene group, or a substituted or unsubstituted C2 to C60 heteroarylene group;

n1 and n2 are each independently one of integers of 0 to 2; and $R^1$ to $R^9$ are each independently hydrogen, deuterium, a cyano group, a substituted or unsubstituted C1 to C60 alkyl group, or a substituted or unsubstituted C6 to C60 aryl group.

4. The compound of claim 1, wherein $Ar^1$ is any one of the following Chemical Formula 4-1 to Chemical Formula 4-5:

[Chemical Formula 4-1]

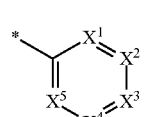

[Chemical Formula 4-2]

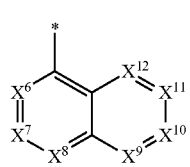

[Chemical Formula 4-3]

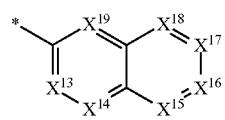

[Chemical Formula 4-4]

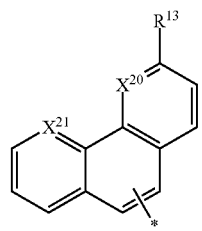

[Chemical Formula 4-5]

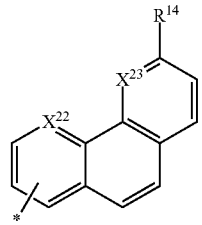

in Chemical Formula 4-1 to Chemical Formula 4-5, at least one of $X^1$ to $X^5$ is —N—, and the rest are —CH—, —CR—, or —CR$^{10}$—;

at least one of $X^6$ to $X^{12}$ is —N—, and the rest are —CH—, —CR— or —CR$^{11}$—;

at least one of $X^{13}$ to $X^{19}$ is —N—, and the rest are —CH—, —CR— or —CR$^{12}$—;

$X^{20}$ and $X^{21}$ are each independently —N—, —CH— or —CR—, and at least one of $X^{20}$ and $X^{21}$ is —N—;

$X^{22}$ and $X^{23}$ are each independently —N—, —CH— or —CR—, and at least one of $X^{22}$ and $X^{23}$ is —N—, Rs are each independently deuterium, a cyano group, a substituted or unsubstituted C1 to C60 alkyl group, or a substituted or unsubstituted C6 to C60 aryl group;

$R^{10}$ to $R^{12}$ are each independently any one of a phenyl group, a pyridinyl group and a substituent of the following Chemical Formula 5; and $R^{13}$ and $R^{14}$ are each independently any one of hydrogen, deuterium, a phenyl group, a pyridinyl group and a substituent of the following Chemical Formula 5,

[Chemical Formula 5]

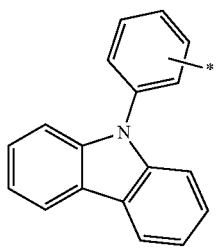

in Chemical Formula 4-1 to Chemical Formula 4-5 and Chemical Formula 5,
* means a bonding position.

5. The compound of claim 4, wherein $Ar^1$ is represented by Chemical Formula 4-1, and in Chemical Formula 4-1,
   (1) $X^1$ is —N—, and the rest are —CH—;
   (2) $X^2$ is —N—, and the rest are —CH—;
   (3) $X^3$ is —N—, and the rest are —CH—;
   (4) $X^1$ and $X^5$ are —N—, $X^3$ is —CH—, the rest are one of —CH— and —$CR^{10}$— and $R^{10}$ is a phenyl group or a pyridyl group;
   (5) $X^1$ and $X^3$ are —N—, $X^5$ is —CH—, the rest are one of —CH— and —$CR^{10}$— and $R^{10}$ is a phenyl group;
   (6) $X^1$ and $X^4$ are —N—, and the rest are —CH—;
   (7) $X^1$, $X^3$ and $X^5$ are —N—, the rest are —$CR^{10}$—, and $R^{10}$ is a phenyl group; or
   (8) $X^1$, $X^3$ and $X^5$ are —N—, and the rest are —CH—.

6. The compound of claim 4, wherein $Ar^1$ is represented by Chemical Formula 4-2, and in Chemical Formula 4-2,
   (1) $X^7$ is —N—, and the rest are —CH—;
   (2) $X^8$ is —N—, and the rest are —CH—;
   (3) $X^9$ is —N—, and the rest are —CH—;
   (4) $X^{10}$ is —N—, and the rest are —CH—;
   (5) $X^{11}$ is —N—, and the rest are —CH—; or
   (6) $X^{12}$ is —N—, and the rest are —CH—.

7. The compound of claim 4, wherein $Ar^1$ is represented by Chemical Formula 4-3, and in Chemical Formula 4-3,
   (1) $X^{13}$ is —N—, and the rest are —CH—;
   (2) $X^{14}$ is —N—, and the rest are —CH—;
   (3) $X^{15}$ is —N—, and the rest are —CH—;
   (4) $X^{17}$ is —N—, and the rest are —CH—;
   (5) $X^{18}$ is —N—, and the rest are —CH—;
   (6) $X^{19}$ is —N—, and the rest are —CH—; or
   (7) $X^{13}$ and $X^{19}$ are —N—, and the rest are —CH—.

8. The compound of claim 4, wherein $Ar^1$ is represented by Chemical Formula 4-4, and in Chemical Formula 4-4,
   (1) $X^{20}$ is —N—, $X^{21}$ is —CH—, and $R^{13}$ is hydrogen; or
   (2) $X^{20}$ and $X^{21}$ are —N—, and $R^{13}$ is hydrogen or deuterium.

9. The compound of claim 4, wherein $Ar^1$ is represented by Chemical Formula 4-5, and in Chemical Formula 4-5,
   (1) $X^{22}$ is —N—, $X^{23}$ is —CH—, and $R^{14}$ is hydrogen; or
   (2) $X^{22}$ and $X^{23}$ are and $R^{14}$ is one of hydrogen, deuterium and a phenyl group.

10. The compound of claim 1, wherein $Ar^2$ is any one of the following Chemical Formula 6-1 to Chemical Formula 6-8:

[Chemical Formula 6-1]

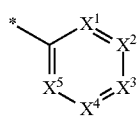

[Chemical Formula 6-2]

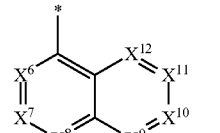

[Chemical Formula 6-3]

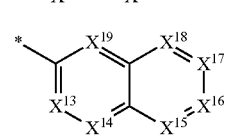

[Chemical Formula 6-4]

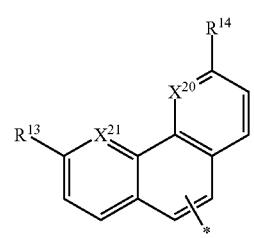

[Chemical Formula 6-5]

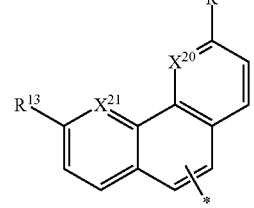

[Chemical Formula 6-6]

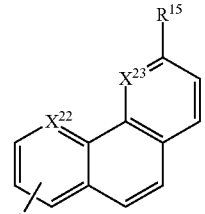

[Chemical Formula 6-7]

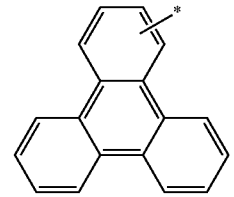

[Chemical Formula 6-8]

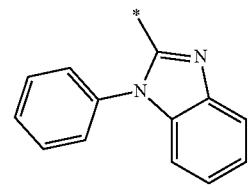

in Chemical Formula 6-1 to Chemical Formula 6-8,
$X^1$ to $X^5$ are each independently —N—, —CH—, —CR— or —$CR^{10}$—;
$X^6$ to $X^{12}$ are each independently —N—, —CH—, —CR— or —$CR^{11}$—,
$X^{13}$ to $X^{19}$ are each independently —N—, —CH—, —CR— or —$CR^{12}$—;
$X^{20}$ and $X^{21}$ are each independently —N—, —CH— or —CR—;
$X^{22}$ and $X^{23}$ are each independently —N—, —CH— or —CR—;

Rs are each independently deuterium, a cyano group, a substituted or unsubstituted C1 to C60 alkyl group, or a substituted or unsubstituted C6 to C60 aryl group;

$R^{10}$ to $R^{12}$ are each independently any one of a phenyl group, a pyridinyl group and a substituent of the following Chemical Formula 5; and $R^{13}$ to $R^{15}$ are each independently any one of hydrogen, deuterium, a phenyl group, a pyridinyl group and a substituent of the following Chemical Formula 5,

[Chemical Formula 5]

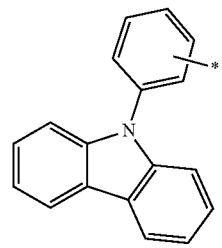

in Chemical Formula 6-1 to Chemical Formula 6-8 and Chemical Formula 5,

* means a bonding site.

11. The compound of claim 10, wherein $Ar^2$ is represented by Chemical Formula 6-1, and in Chemical Formula 6-1,
(1) $X^1$ to $X^5$ are —CH—;
(2) $X^1$, $X^3$ and $X^5$ are —CH—, the rest are —$CR^{10}$—, and $R^{10}$ is a phenyl group or a pyridinyl group;
(3) $X^1$ is —N—, and the rest are —CH—;
(4) $X^2$ is —N—, and the rest are —CH—;
(5) $X^1$ and $X^5$ are —N—, $X^3$ is —CH—, the rest are one of —CH— and —$CR^{10}$— and $R^{10}$ is a phenyl group or the substituent of Chemical Formula 5;
(6) $X^1$ and $X^3$ are —N—, $X^5$ is —CH—, the rest are one of —CH— and —$CR^{10}$— and $R^{10}$ is a phenyl group or the substituent of Chemical Formula 5;
(7) $X^1$, $X^3$ and $X^5$ are —N—, the rest are one of —CH— and —$CR^{10}$—, and $R^{10}$ is the substituent of Chemical Formula 5; or
(8) $X^1$, $X^3$ and $X^5$ are —N—, the rest are one of —CH— and —$CR^{10}$—, and $R^{10}$ is a phenyl group.

12. The compound of claim 10, wherein $Ar^2$ is represented by Chemical Formula 6-2, and in Chemical Formula 6-2,
(1) $X^6$ to $X^{12}$ are —CH—;
(2) $X^9$ is —N—, and the rest are —CH—;
(3) $X^{11}$ is —N—, and the rest are —CH—; or
(4) $X^{12}$ is —N—, and the rest are —CH—.

13. The compound of claim 10, wherein $Ar^2$ is represented by Chemical Formula 6-3, and in Chemical Formula 6-3,
(1) $X^{13}$ to $X^{19}$ are —CH—;
(2) $X^{15}$ is —N—, and the rest are —CH—;
(3) $X^{17}$ is —N—, and the rest are —CH—; or
(4) $X^{18}$ is —N—, and the rest are —CH—.

14. The compound of claim 10, wherein $Ar^2$ is represented by Chemical Formula 6-4, and in Chemical Formula 6-4,
(1) $X^{20}$ and $X^{21}$ are —CH—, and $R^{13}$ and $R^{14}$ are each independently hydrogen or deuterium;
(2) $X^{20}$ and $X^{21}$ are —N—, and $R^{13}$ and $R^{14}$ are each independently hydrogen or deuterium;
(3) $X^{20}$ and $X^{21}$ are —N—, and $R^{13}$ and $R^{14}$ are a phenyl group; or
(4) $X^{20}$ and $X^{21}$ are —N—, any one of $R^{13}$ and $R^{14}$ is a phenyl group, and the rest is hydrogen or deuterium.

15. The compound of claim 10, wherein $Ar^2$ is represented by Chemical Formula 6-5, and in Chemical Formula 6-5,
(1) $X^{22}$ and $X^{23}$ are —N—, and $R^{15}$ is hydrogen or deuterium; or
(2) $X^{22}$ and $X^{23}$ are —N—, and $R^{15}$ is a phenyl group.

16. The compound of claim 2, wherein the compound represented by Chemical Formula 2 is any one of compounds of the following Group II:

[Group II]

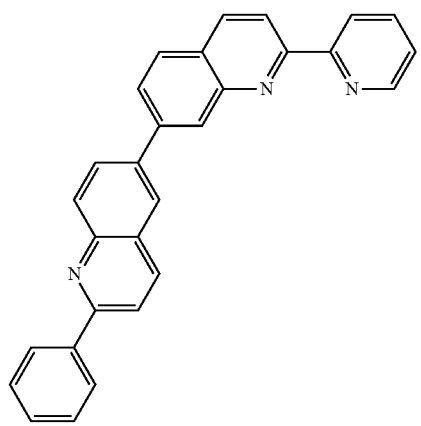

1

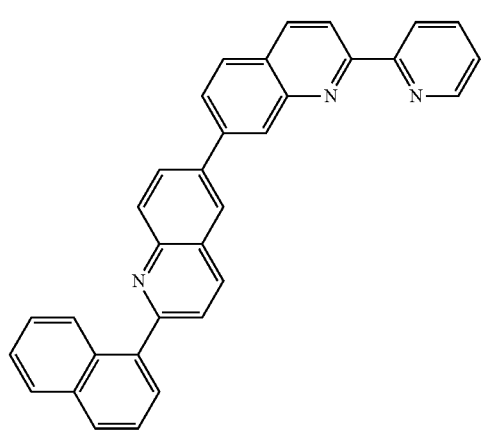

2

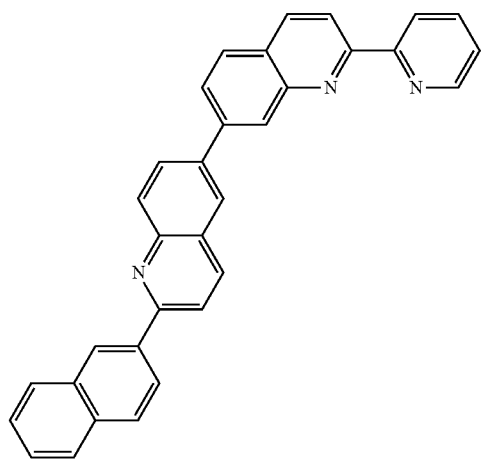

3

4
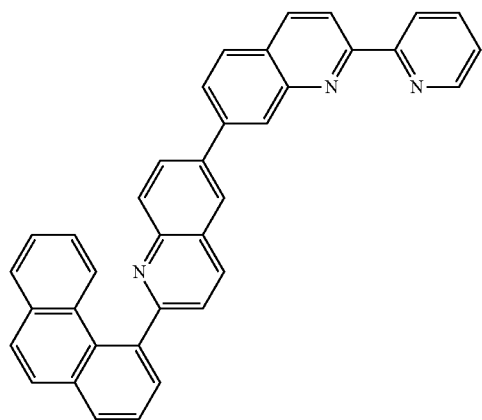
5
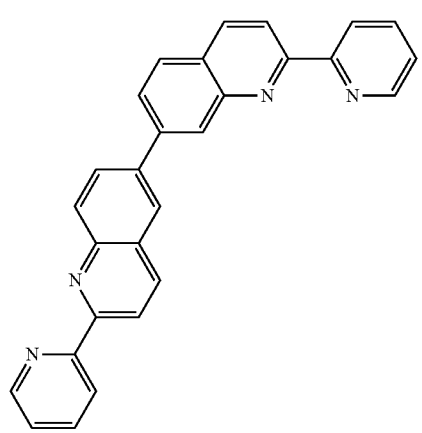
6
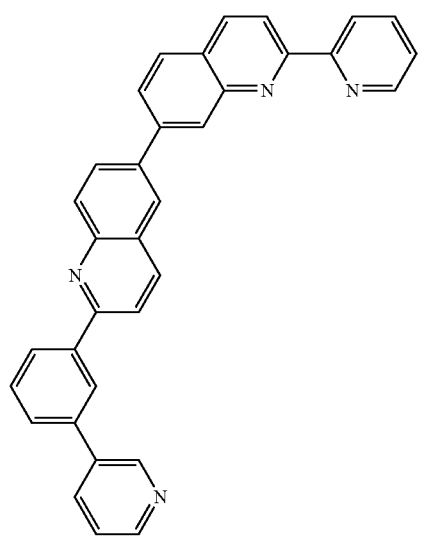
7
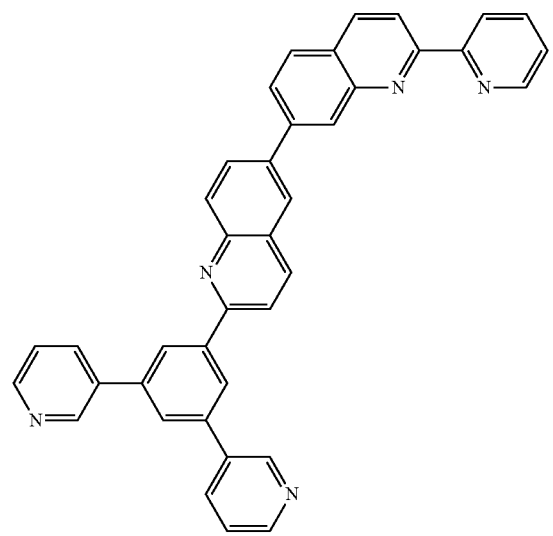
8
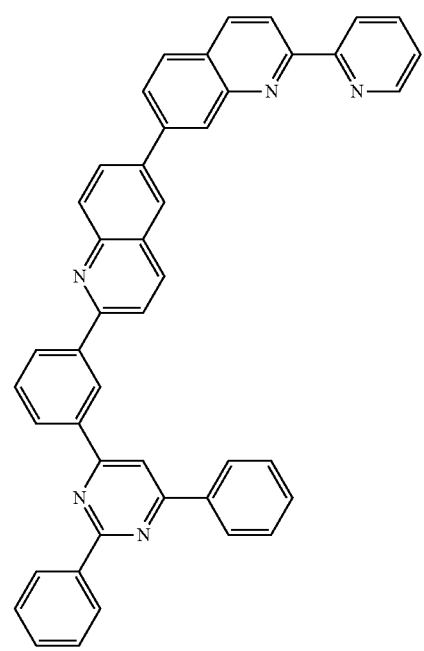

457
-continued
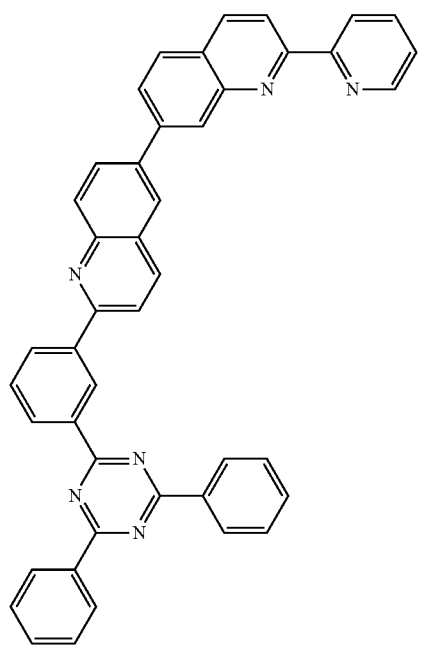
458
-continued
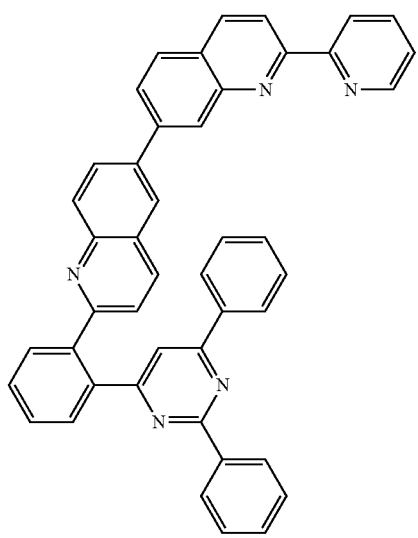
10
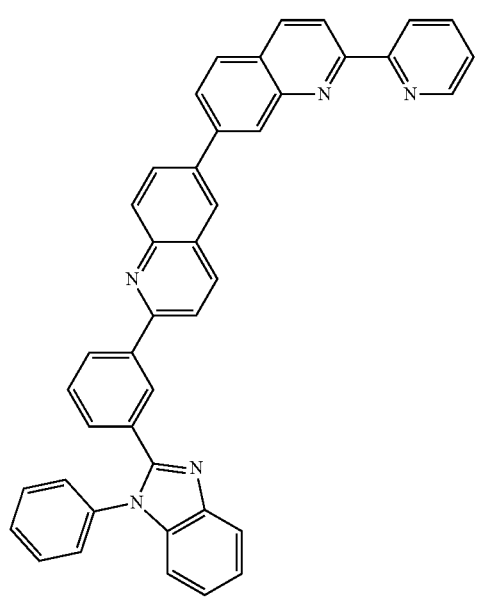
12
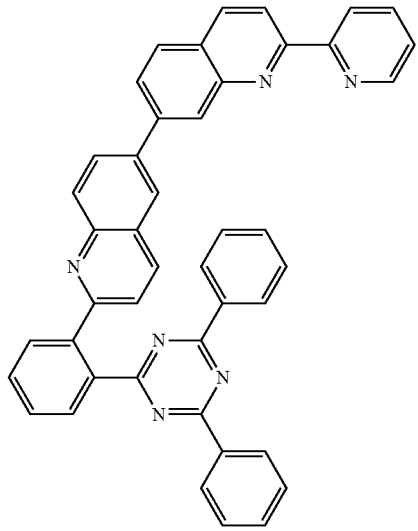

-continued
13
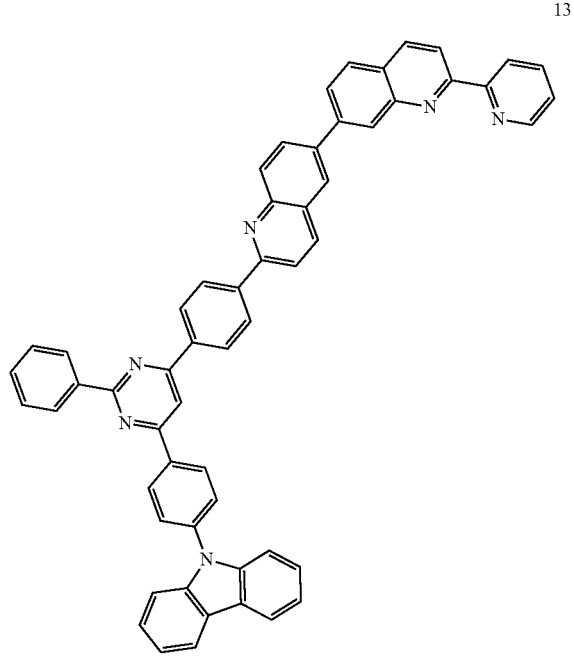
14
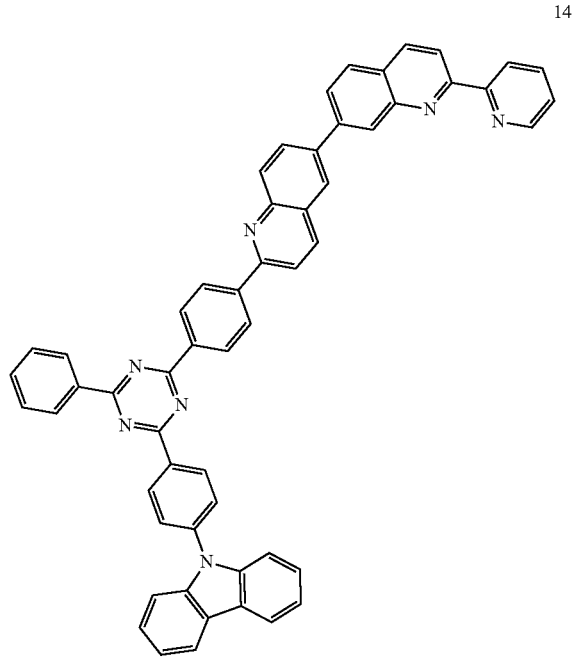
-continued
15
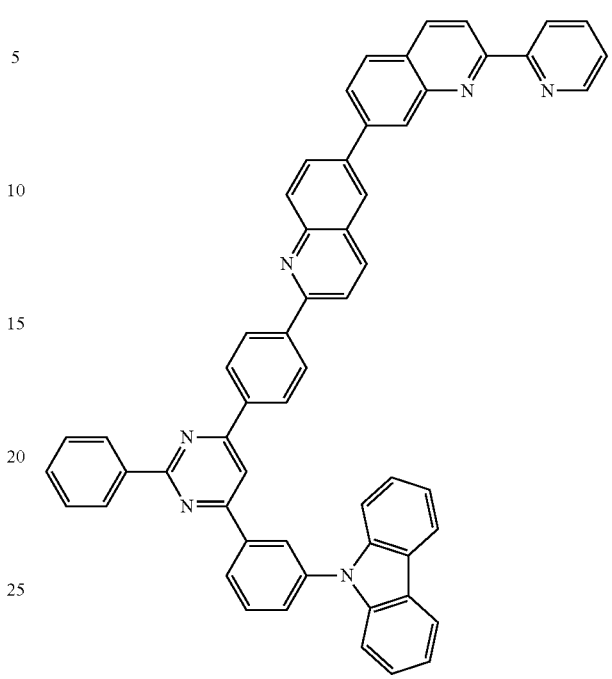
16
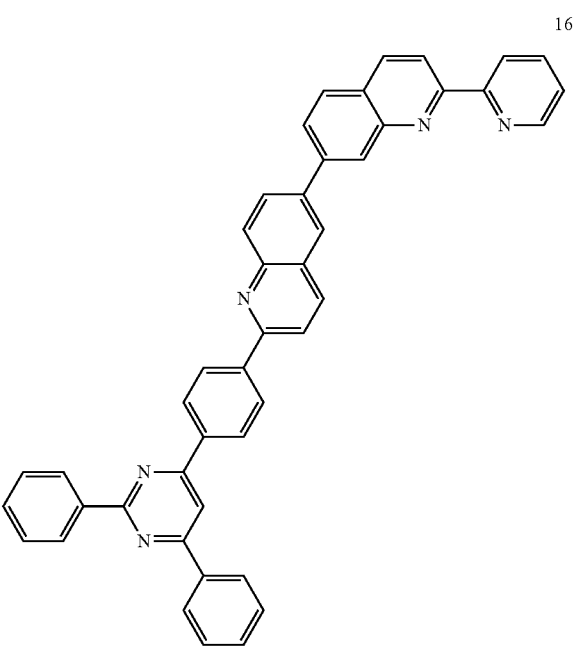

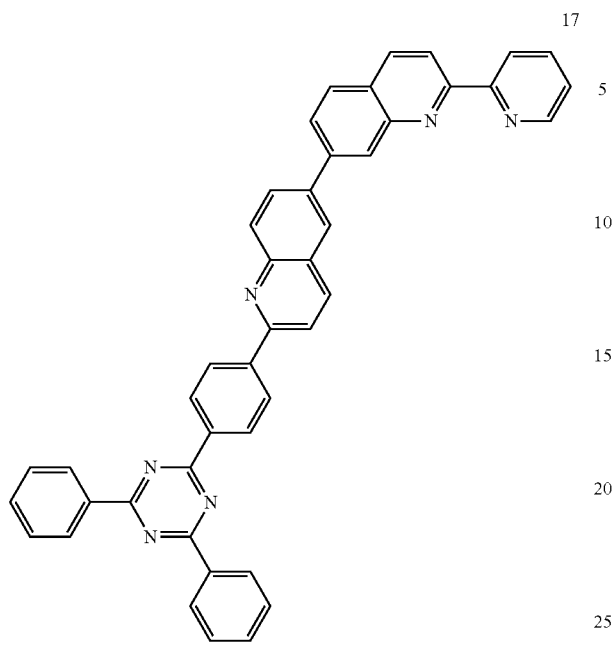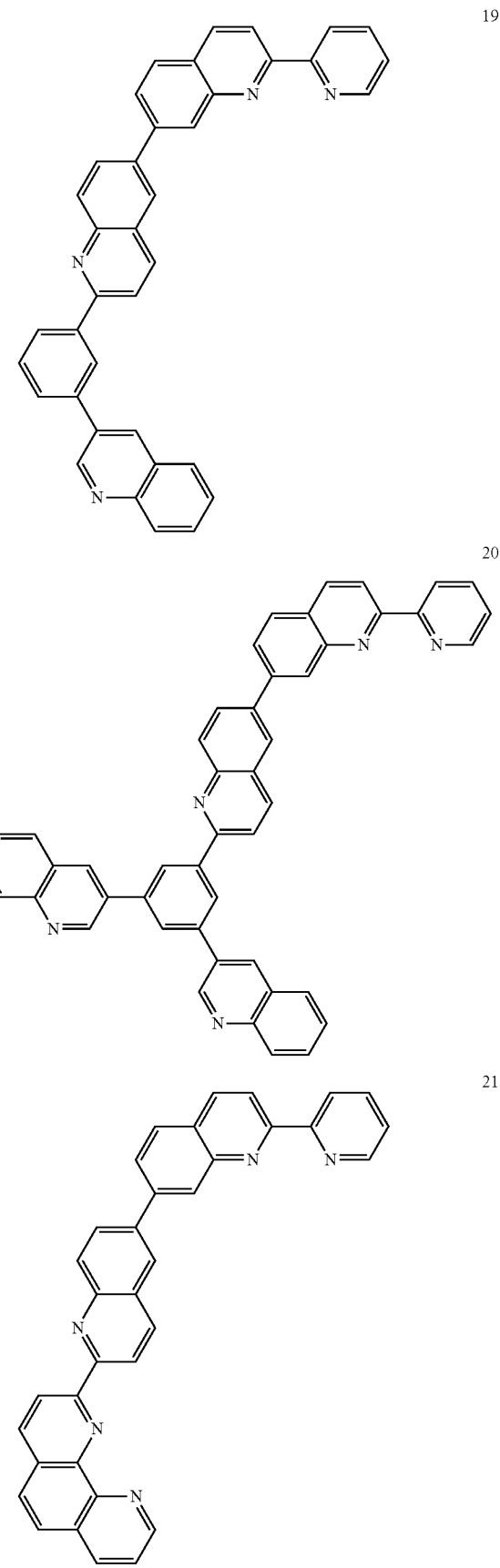

463
-continued
22
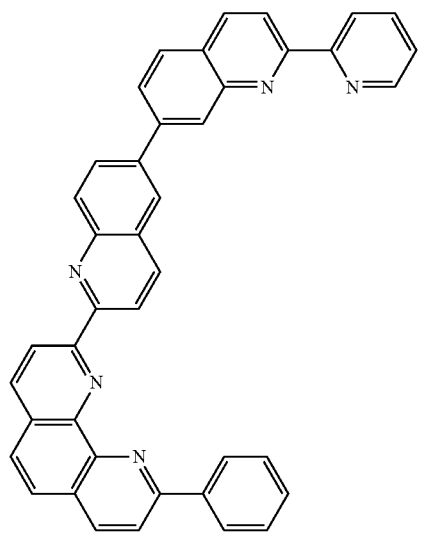
23
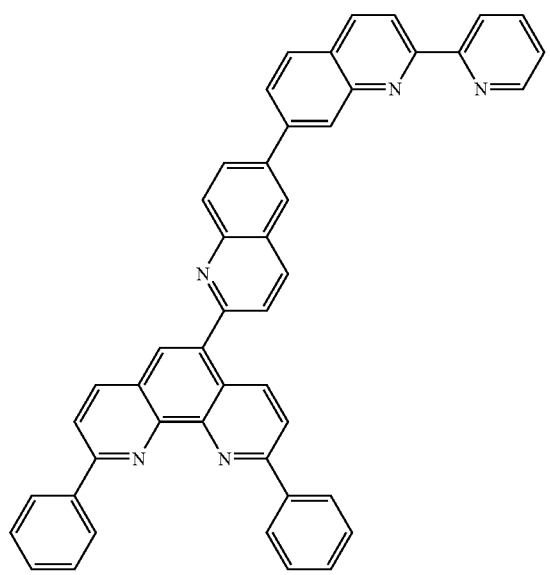
464
-continued
24
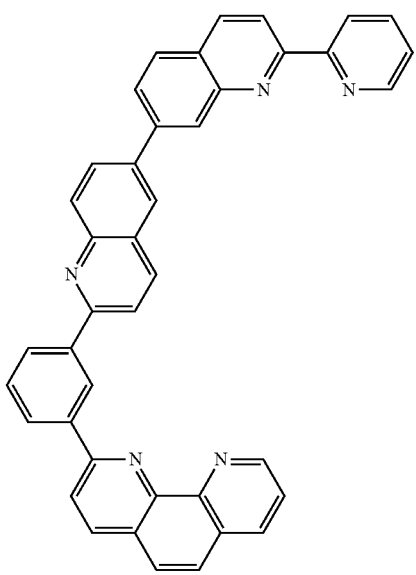
25
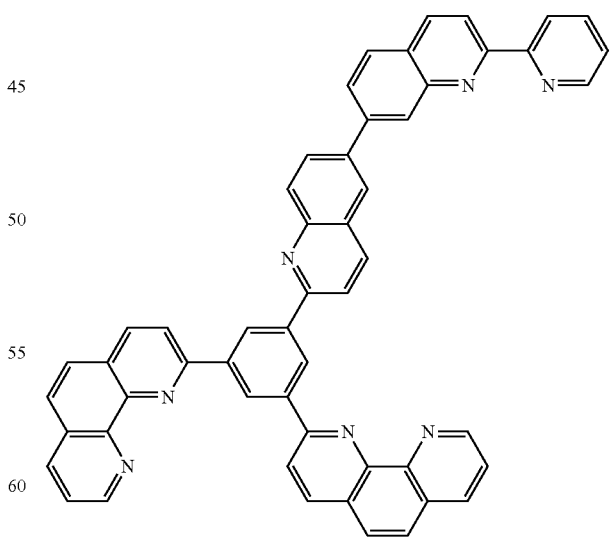

465
-continued
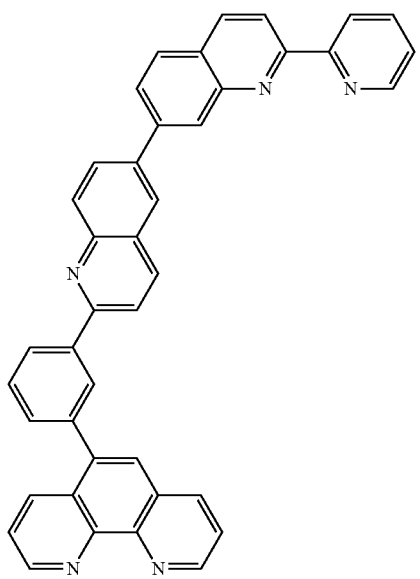
26
466
-continued
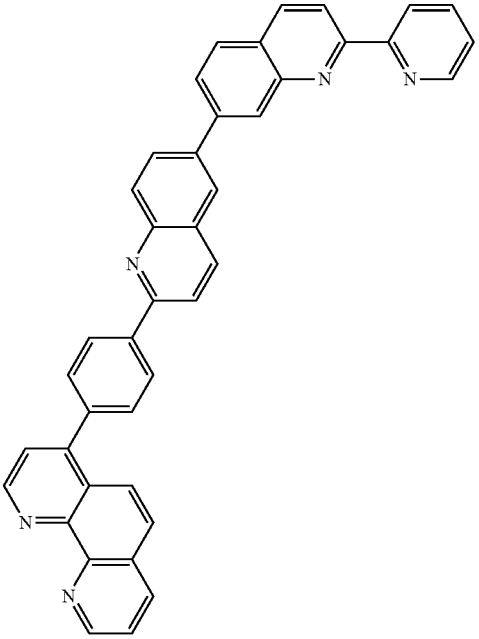
27
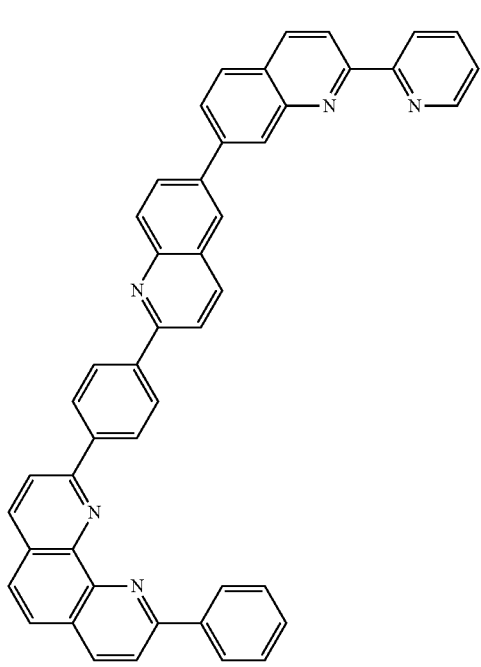
28
29

30
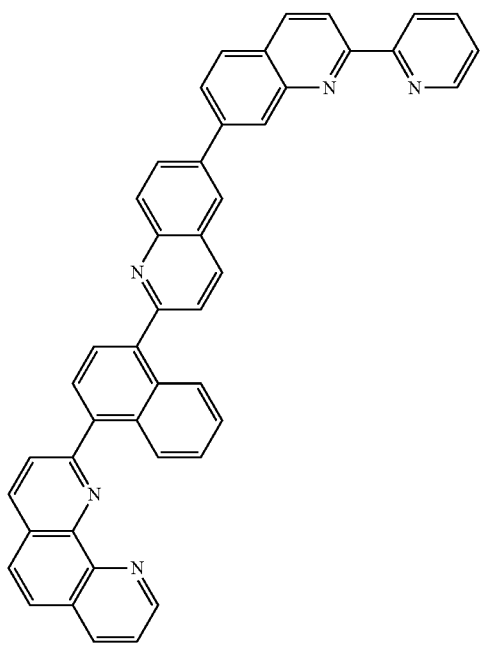
31
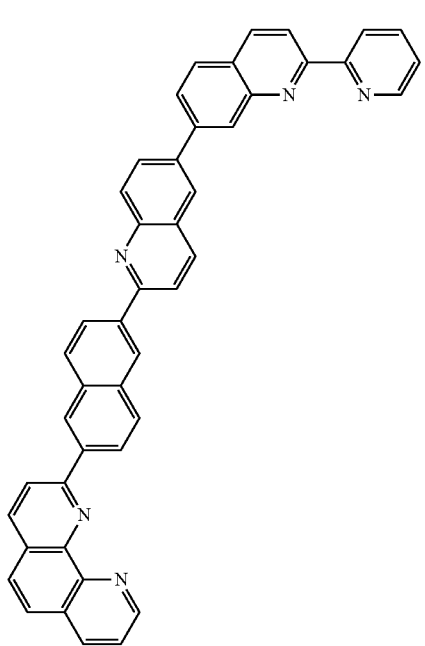
32
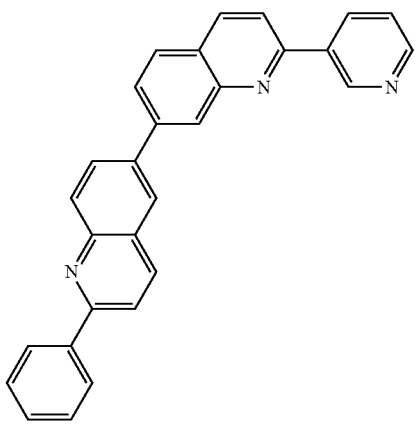
33
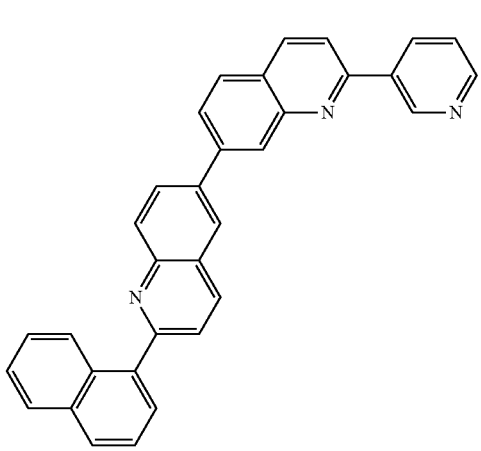
34

469
35
36
470
37
38
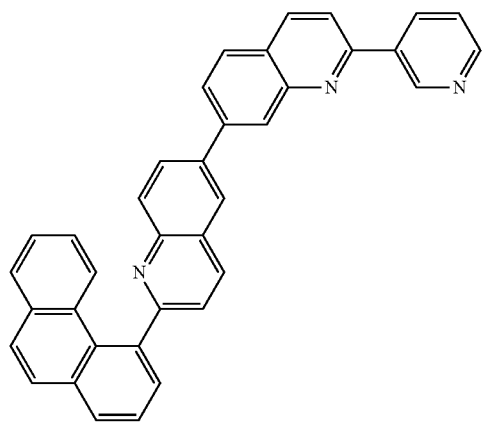
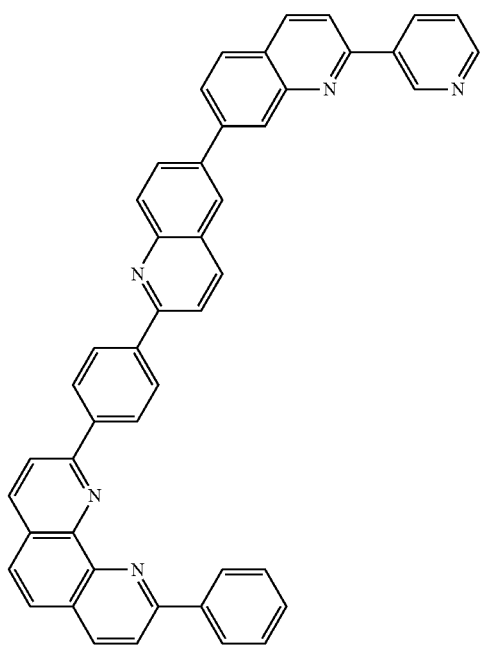

-continued
39
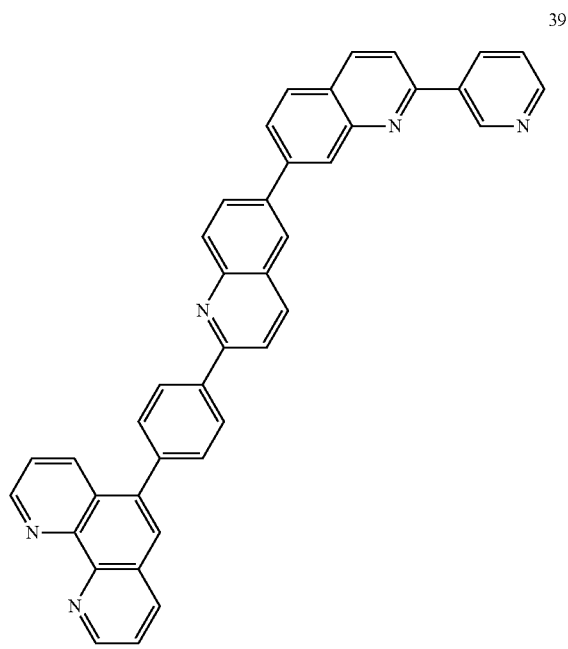
40
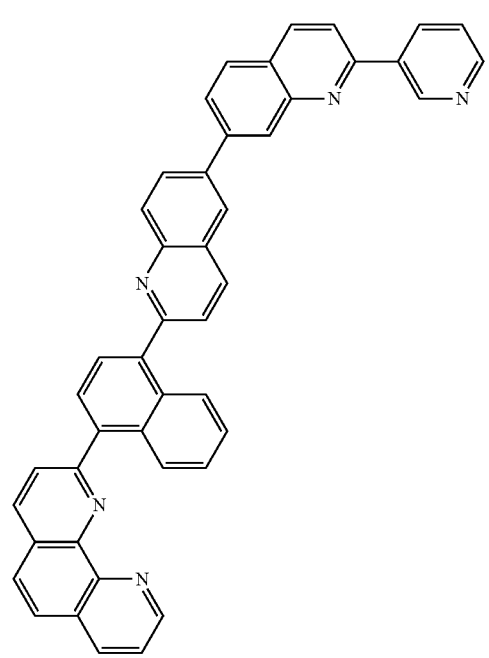
-continued
41
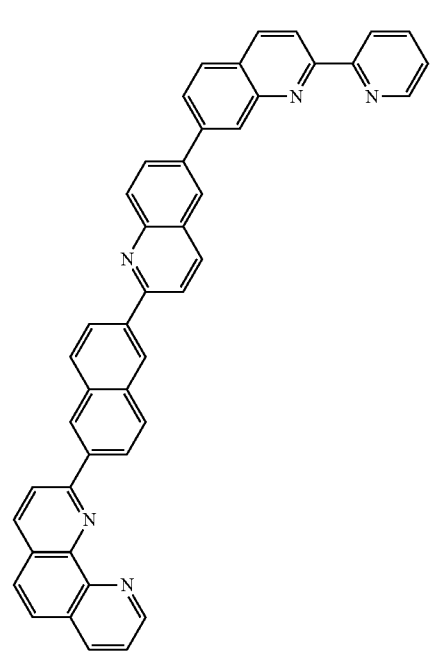
42
43
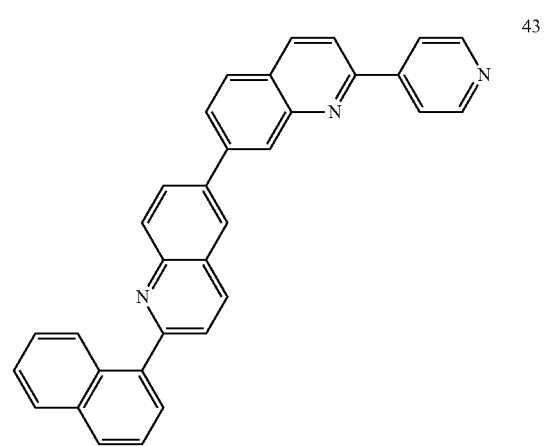

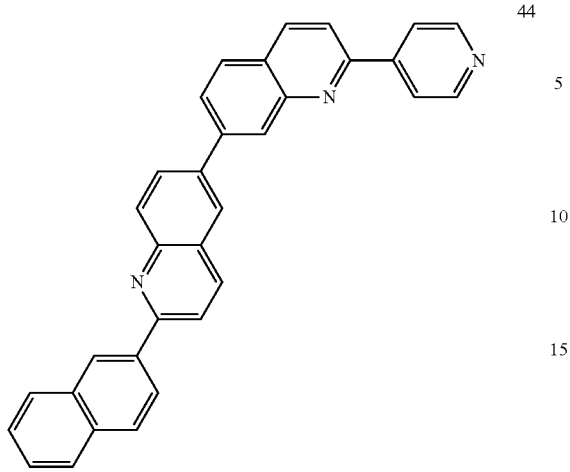
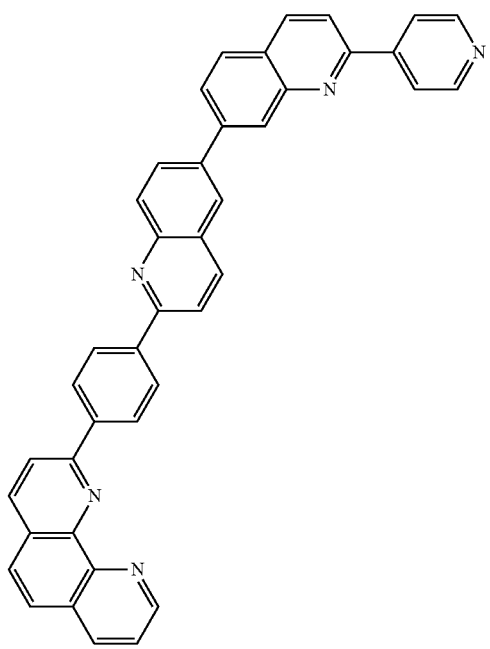

-continued
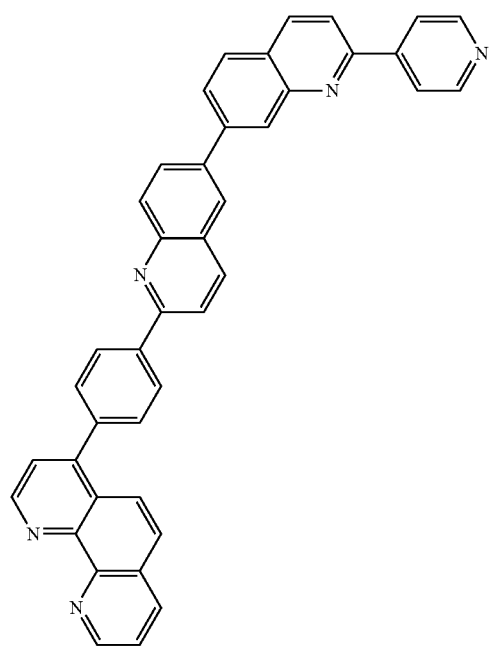
49
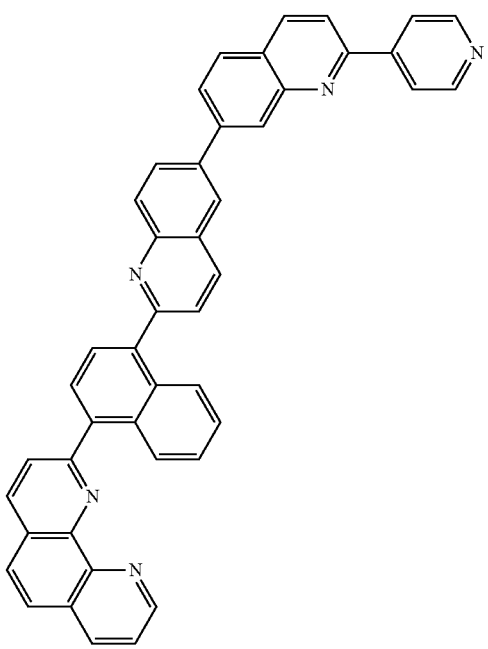
51
50
52

477
-continued
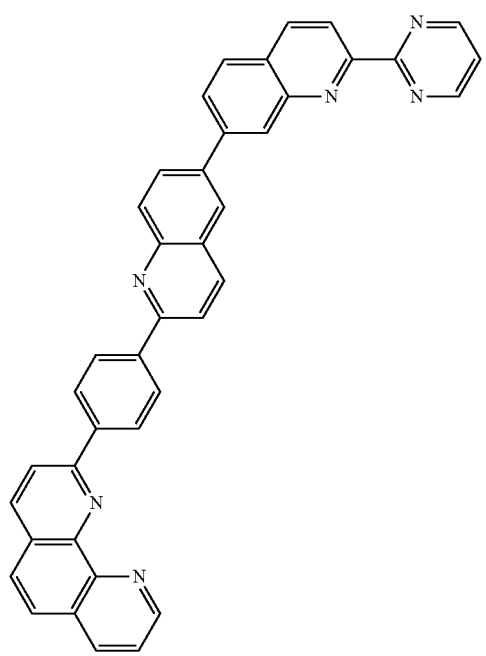
53
54
478
-continued
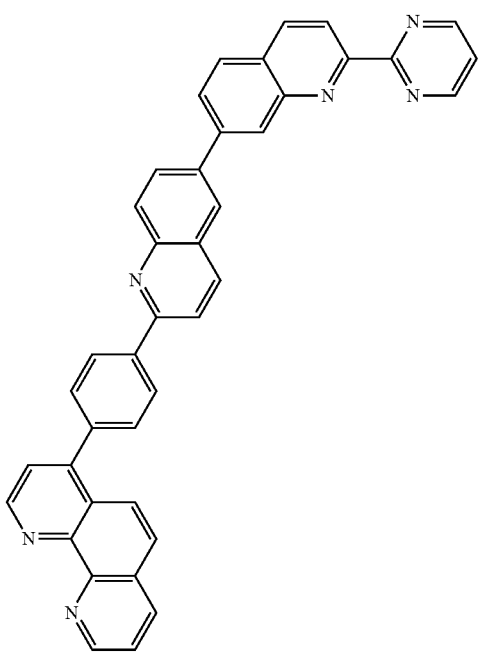
55
56

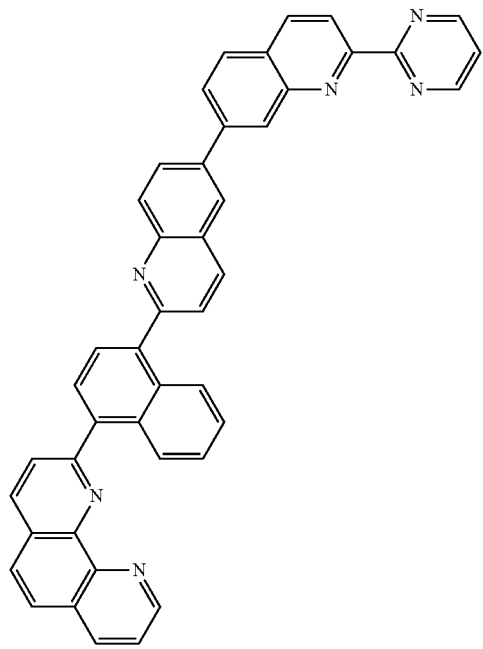
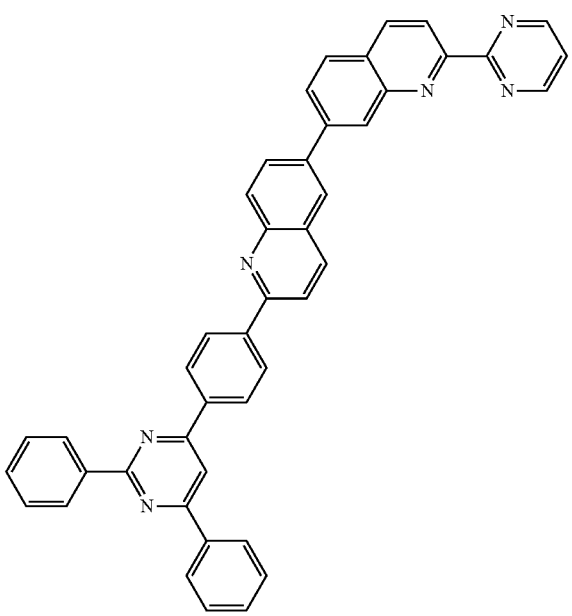

61
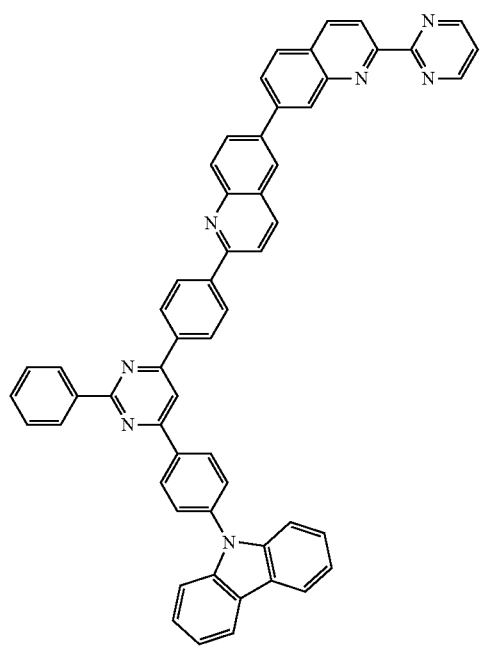
62
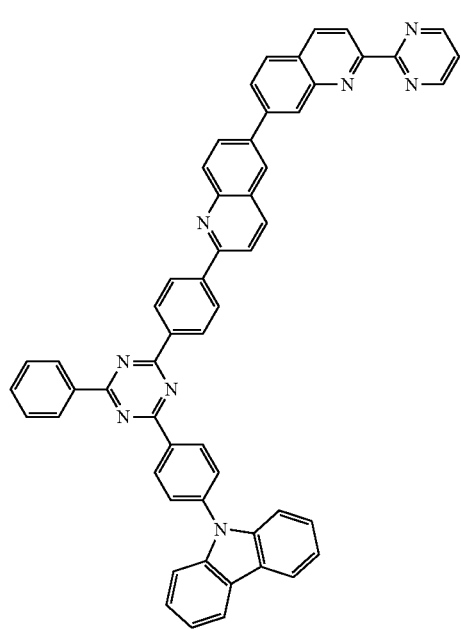
63
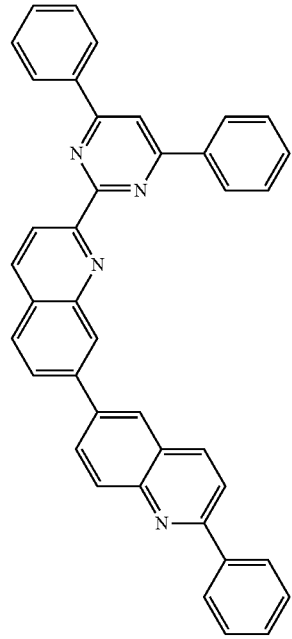
64
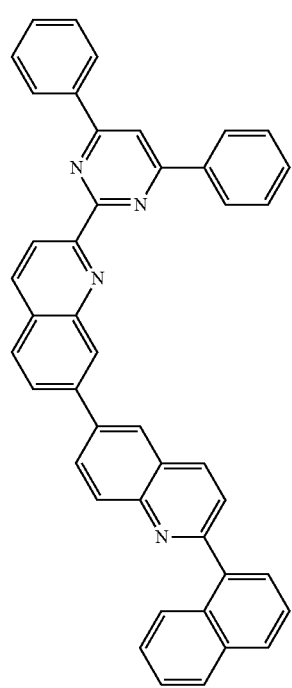

483
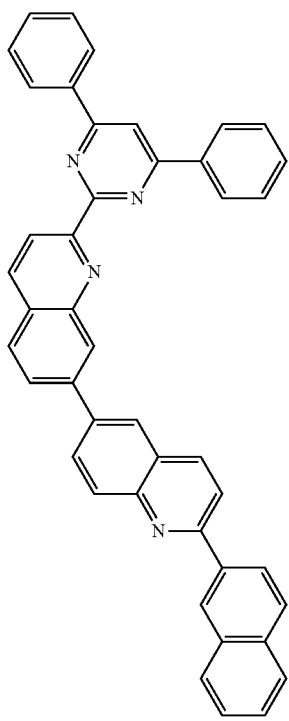
484
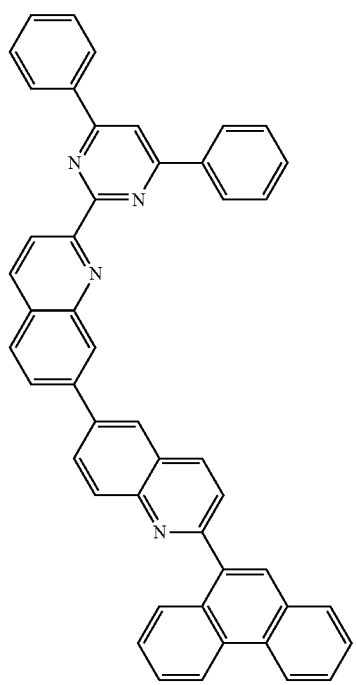
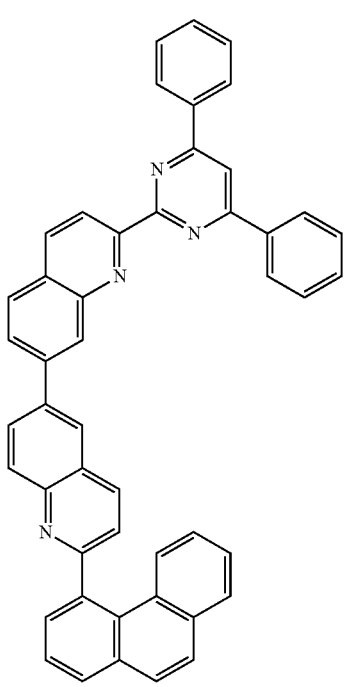
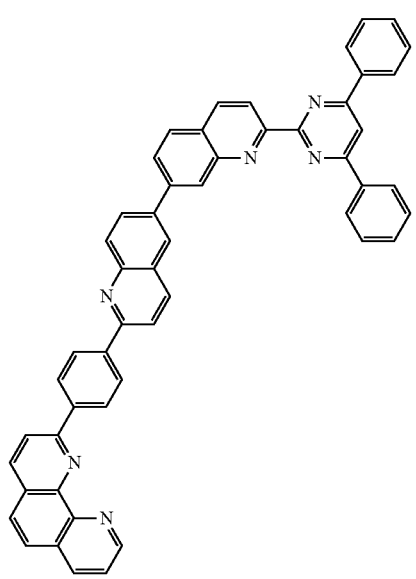

485
-continued
486
-continued
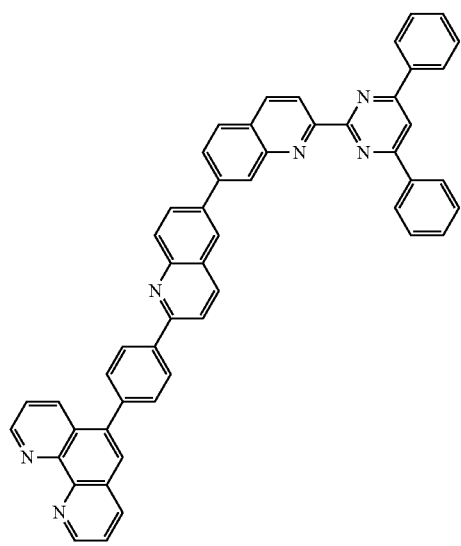
69
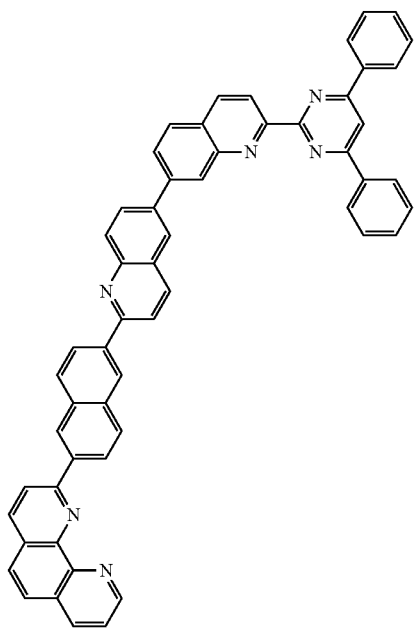
71
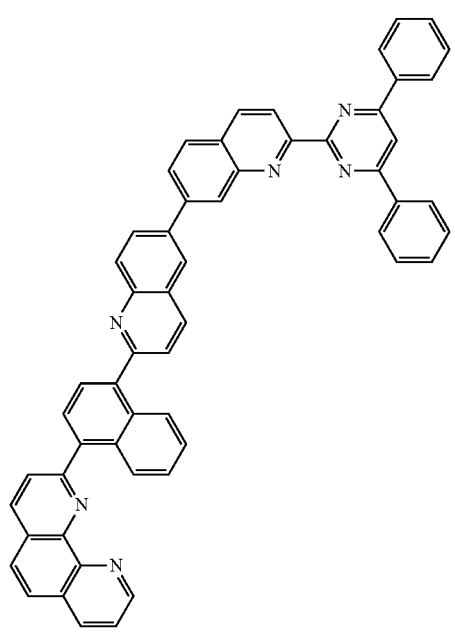
70
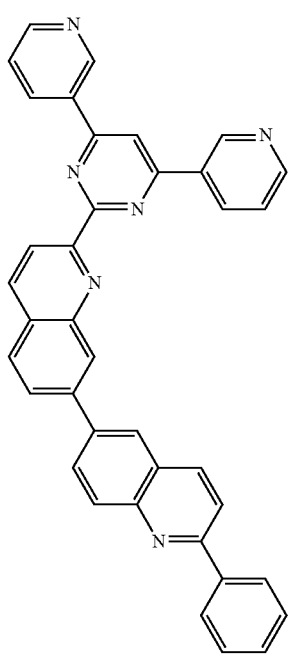
72

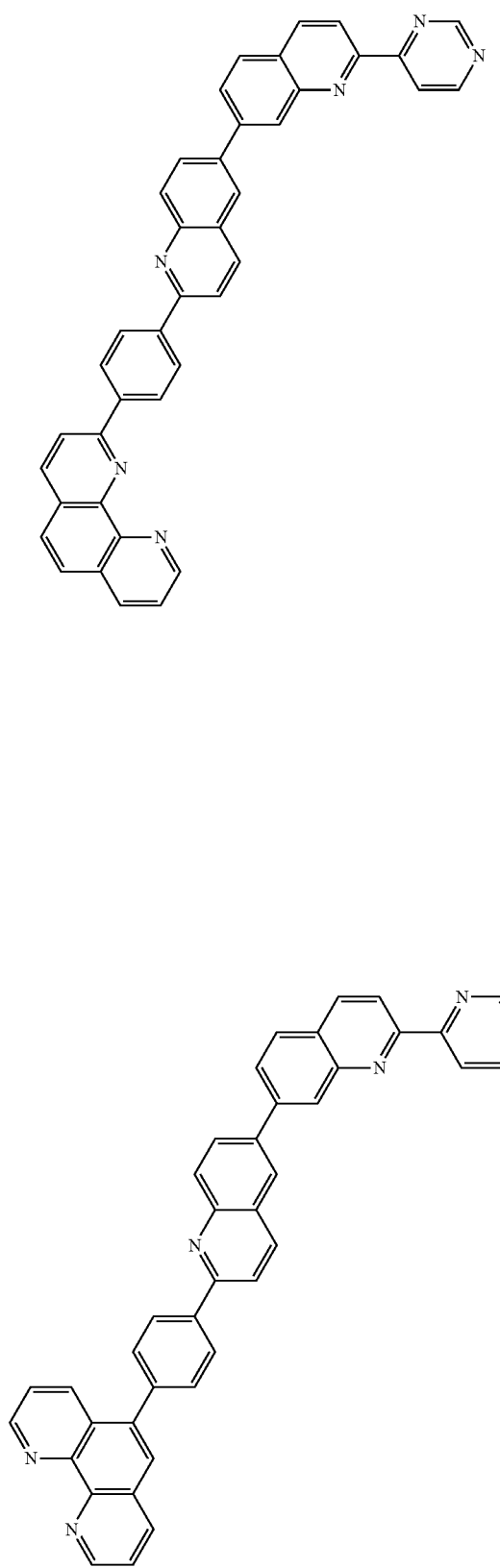
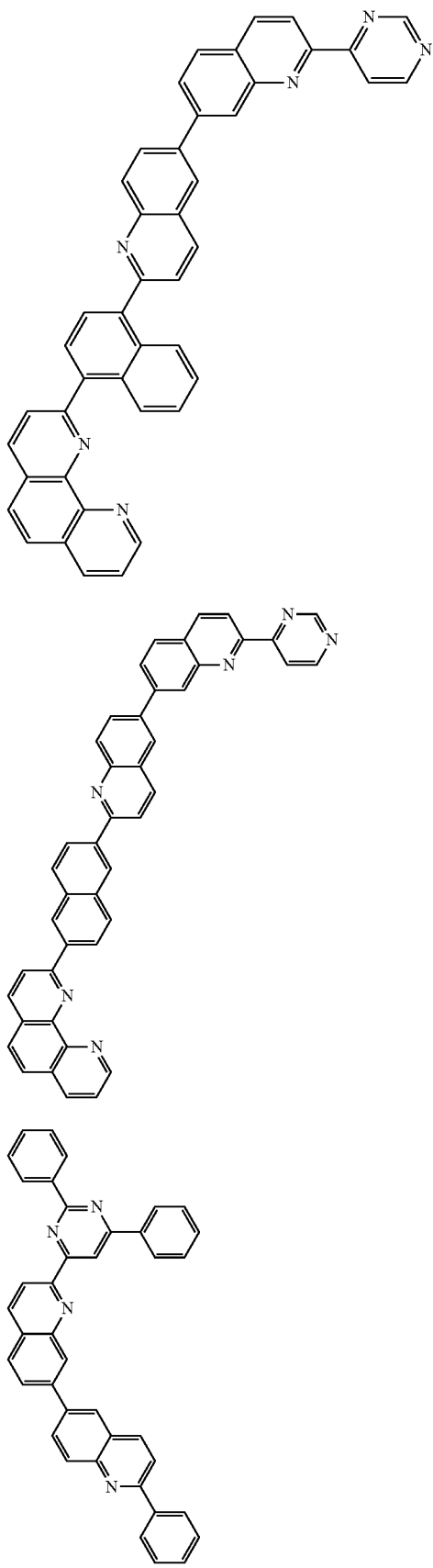

489
-continued
78
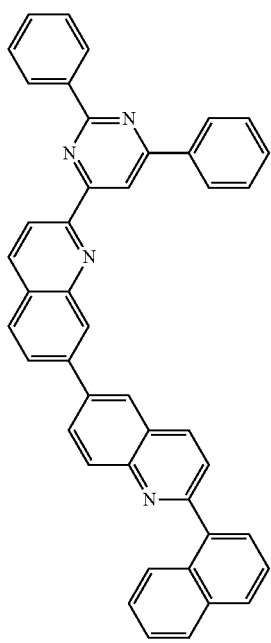
490
-continued
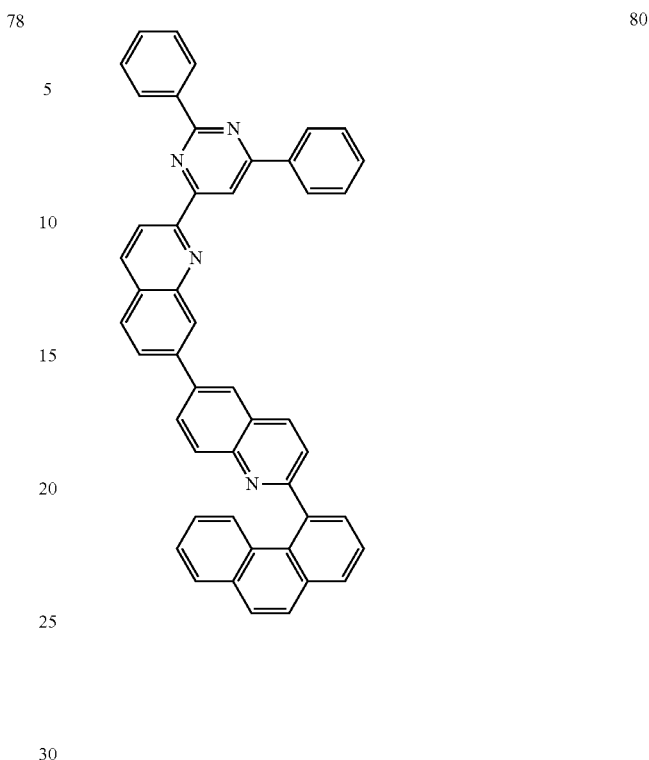
79
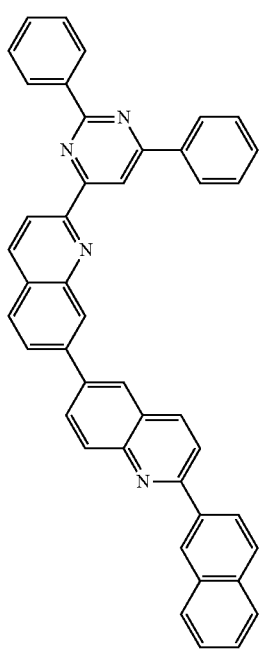
81
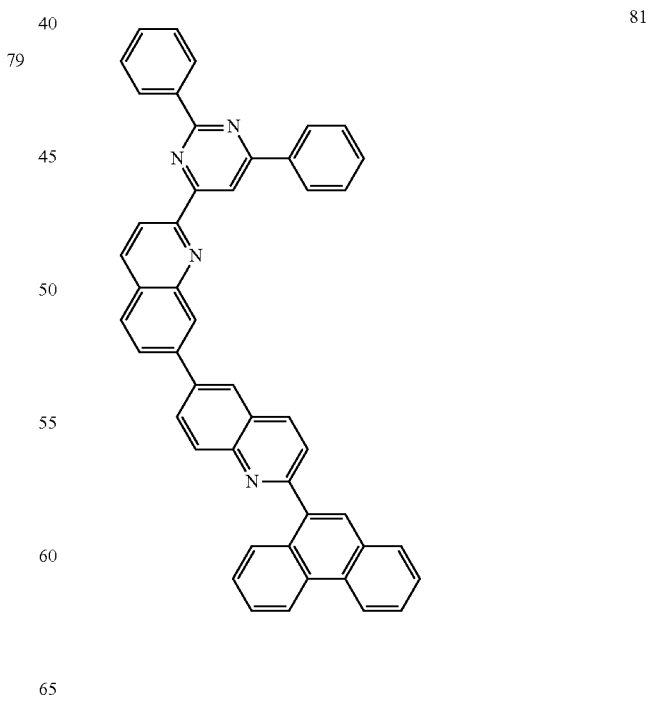

491 492
-continued -continued
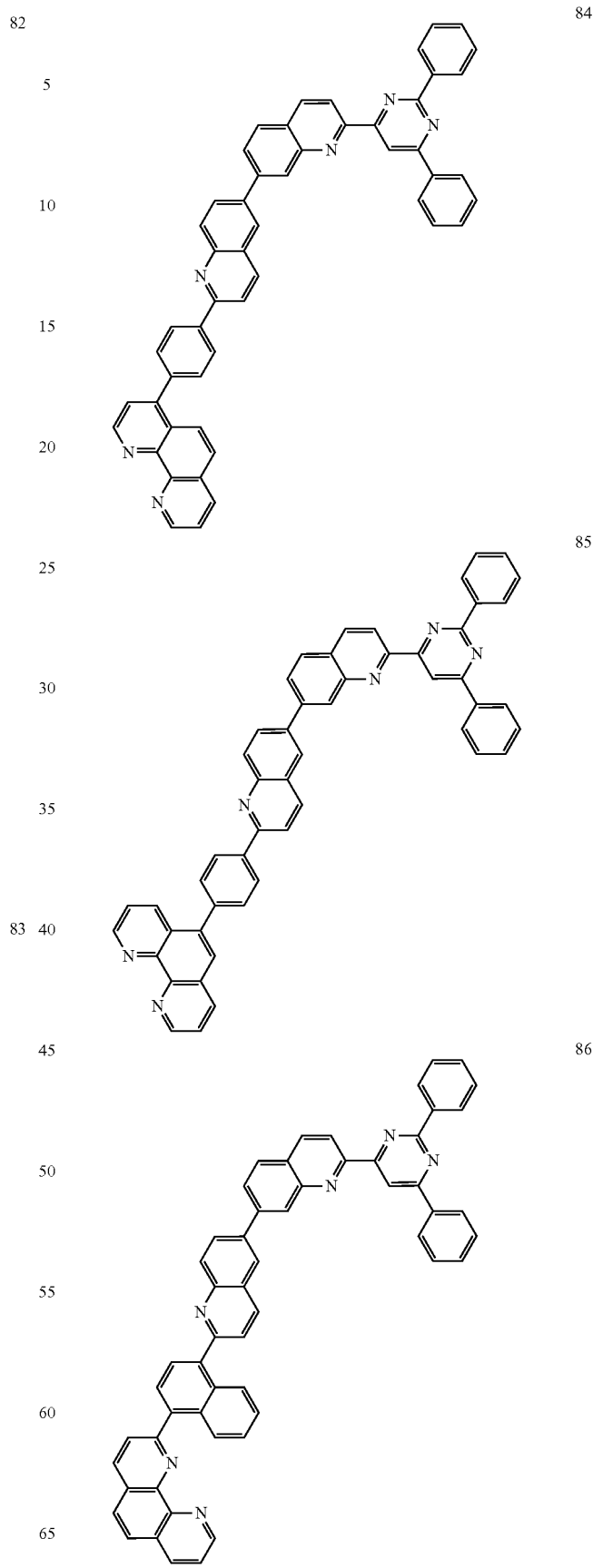

493
-continued
494
-continued
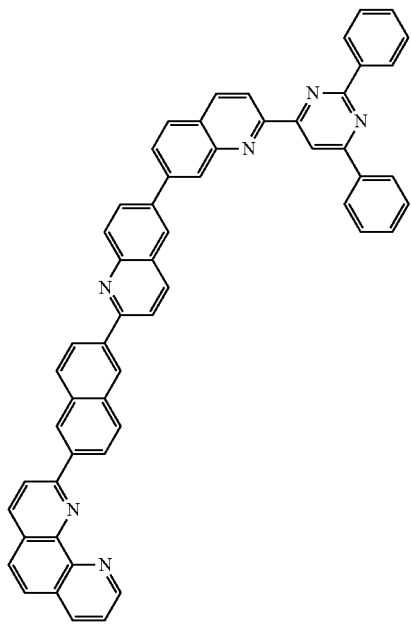
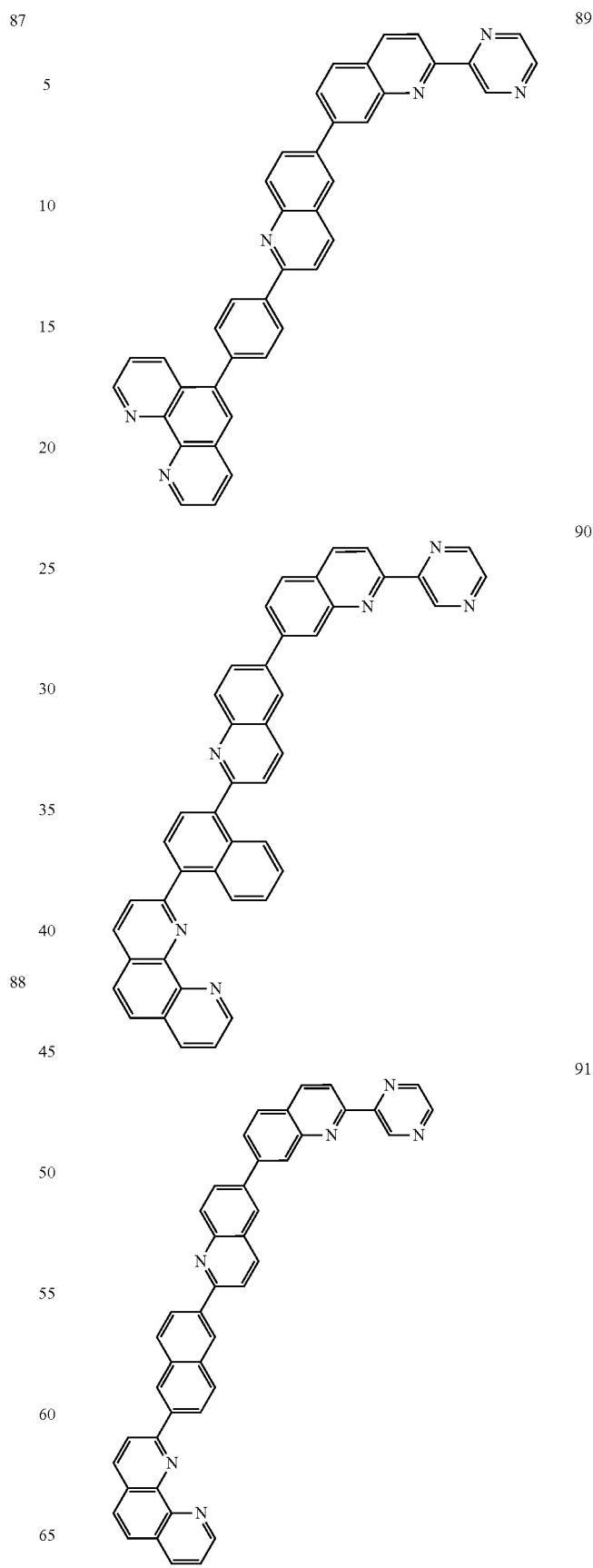

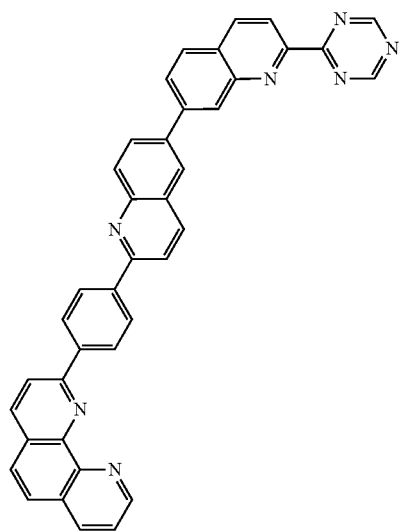
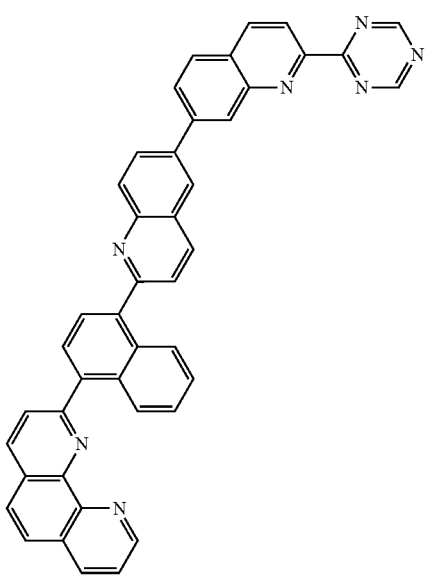

97
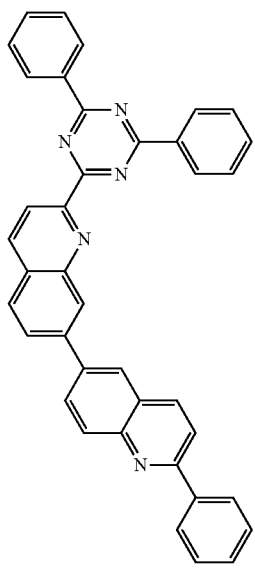
98
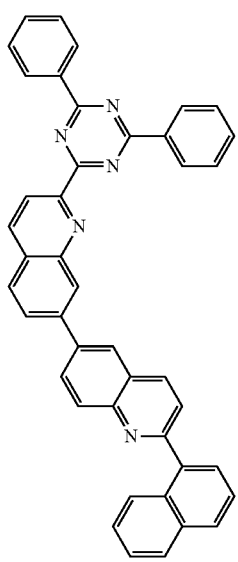
99
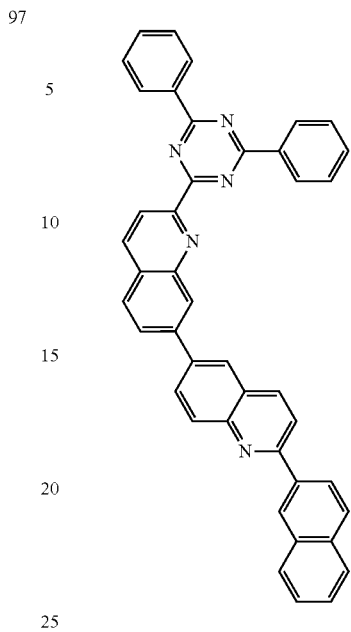
100
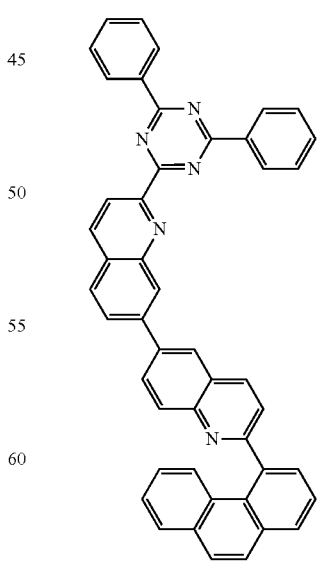

499
-continued
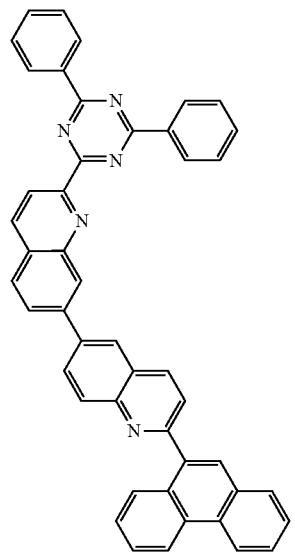
500
-continued
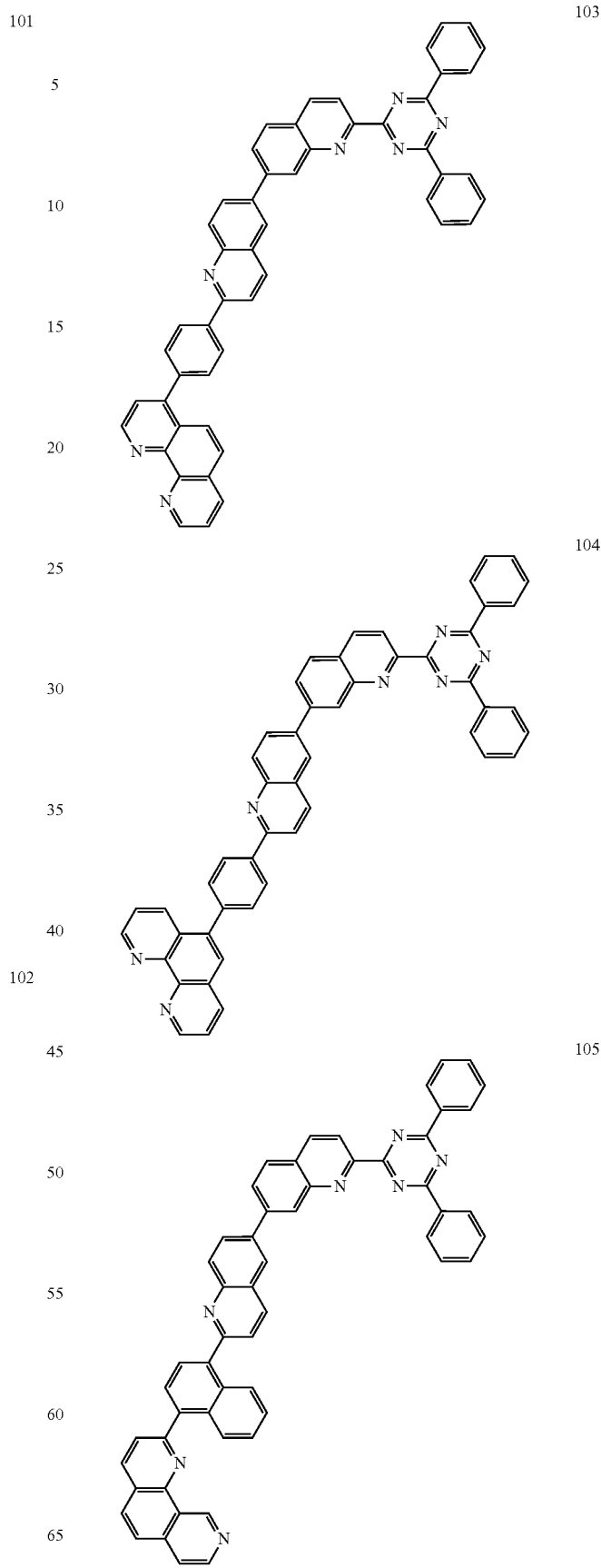

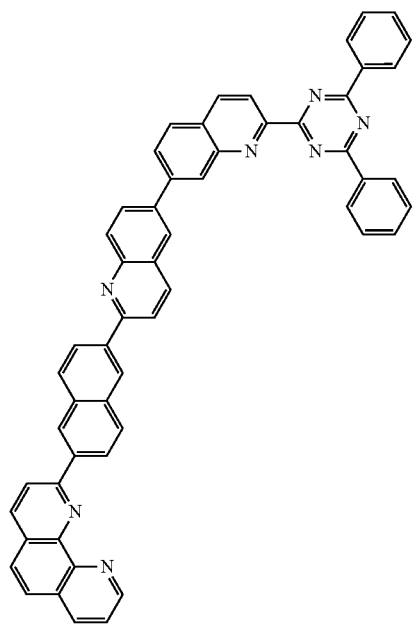
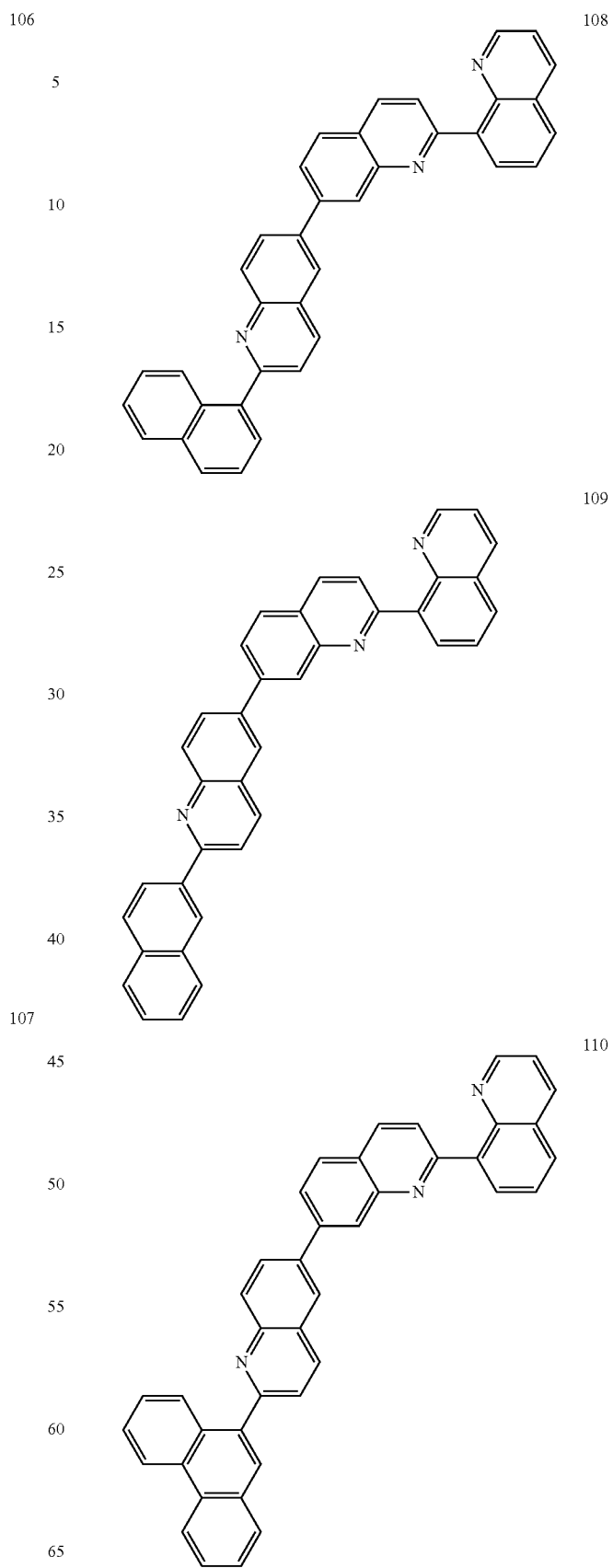

503
-continued
111
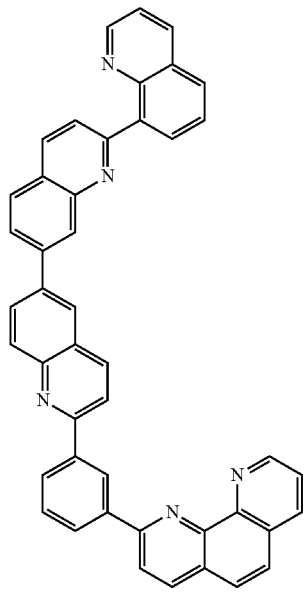
112
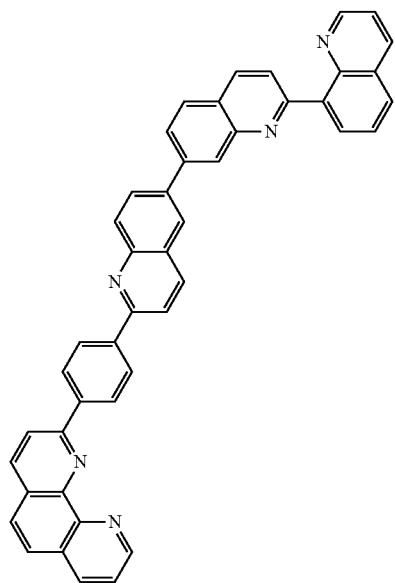
504
-continued
113
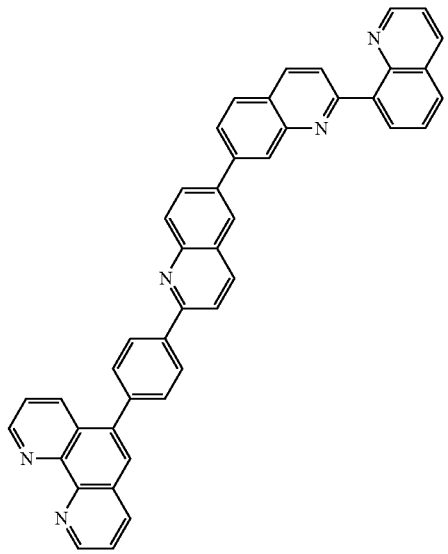
114
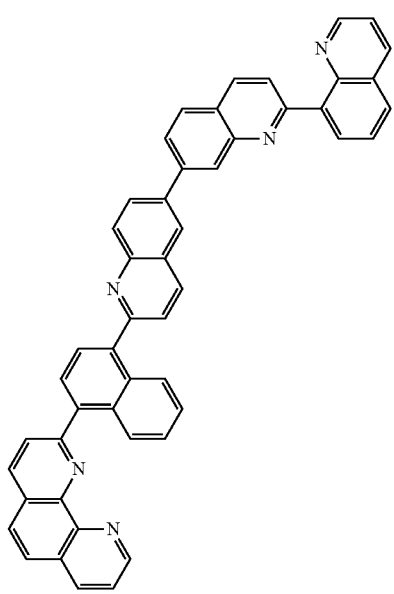

505
-continued
115
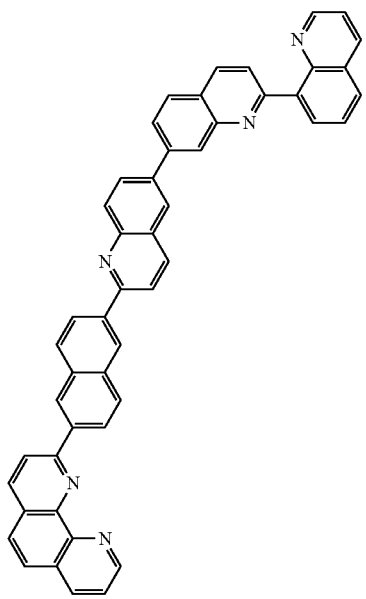
116
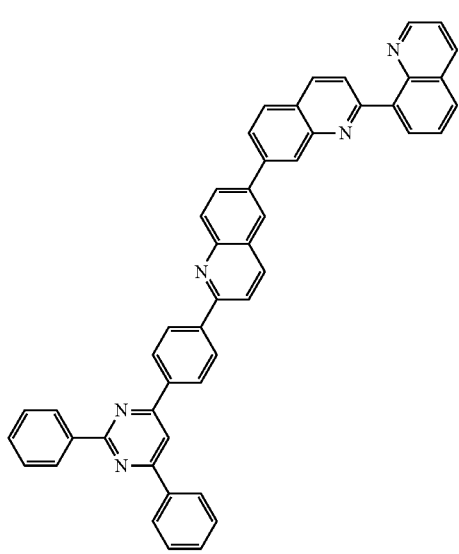
117
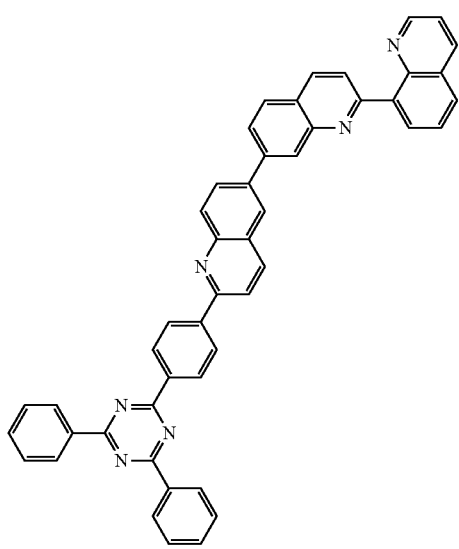
506
-continued
118
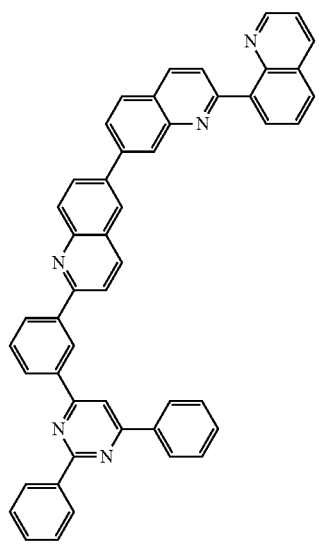
119
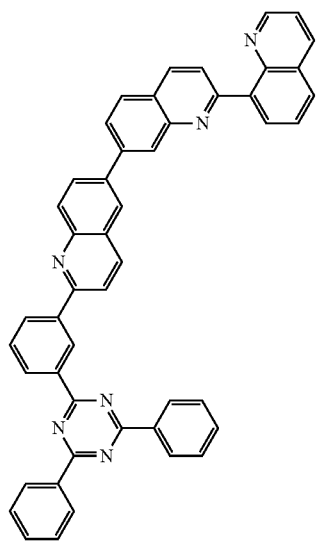
120
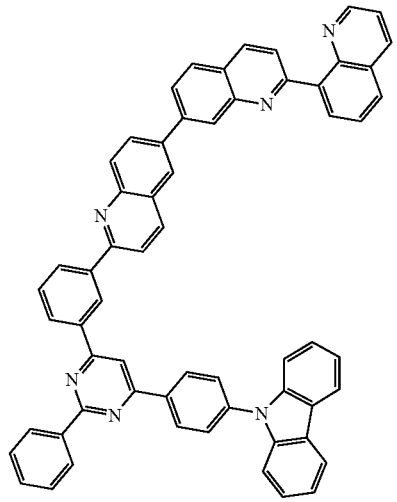

121
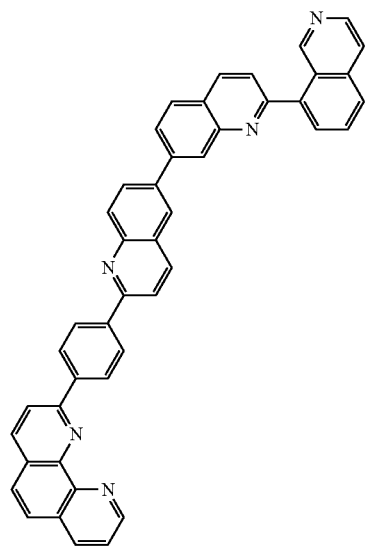
122
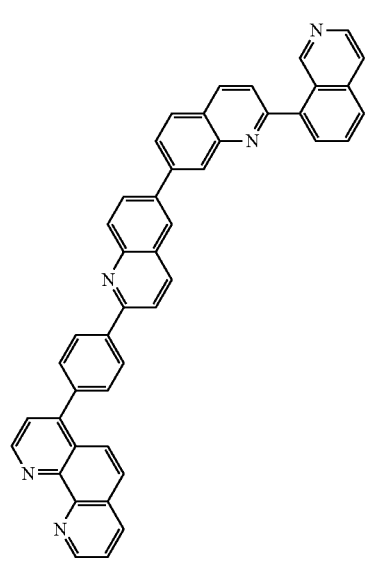
123
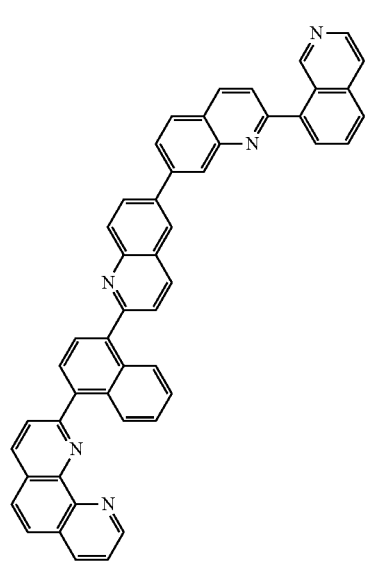
124
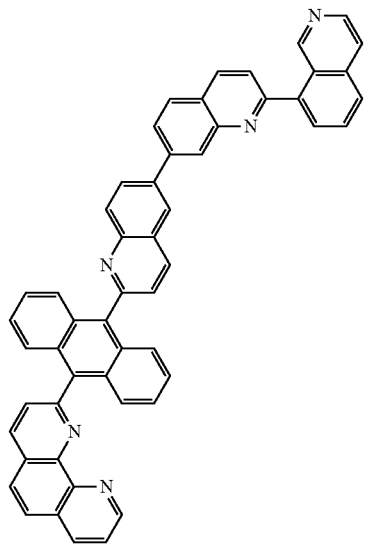
125
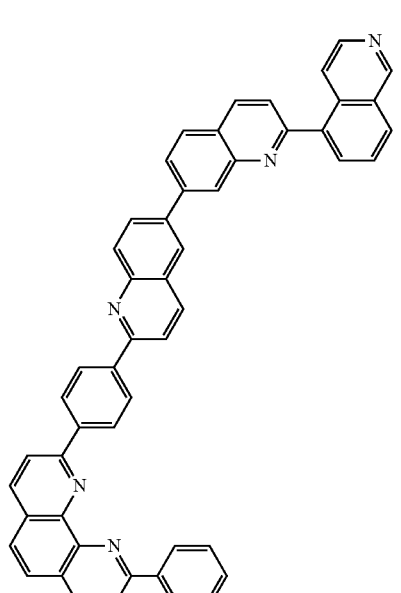

509
-continued
510
-continued
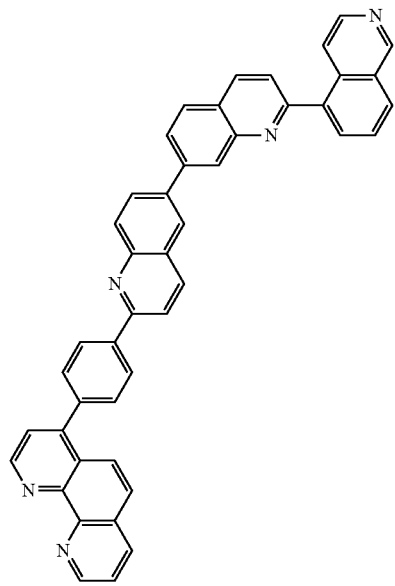
126
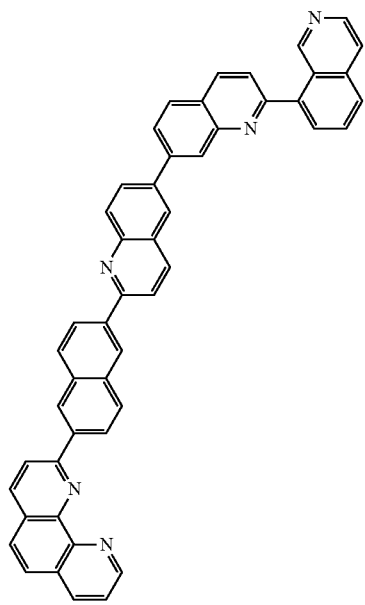
128
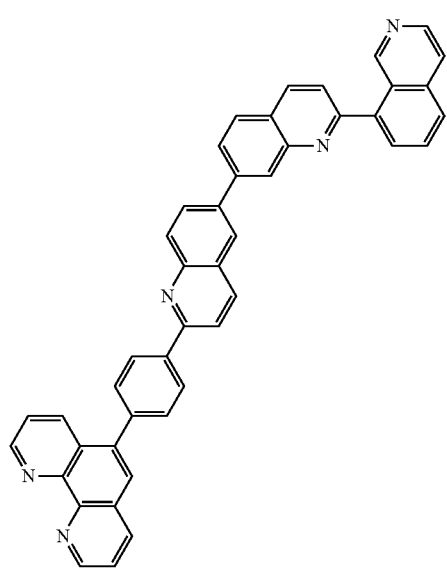
127
129
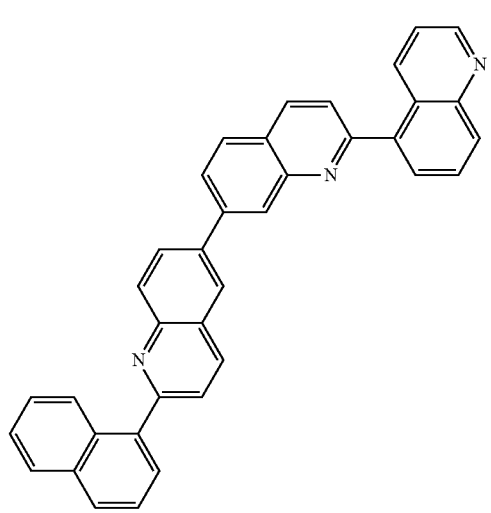
130

511
-continued
131
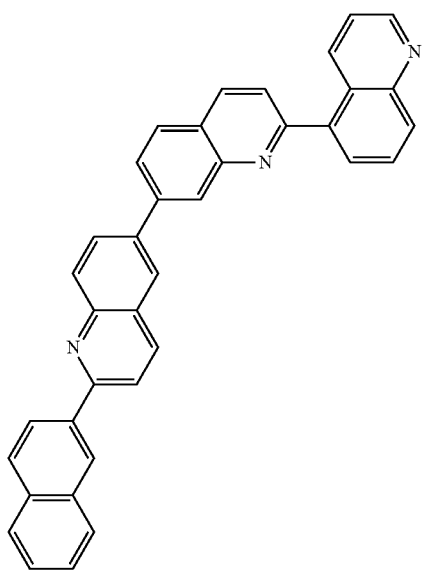
132
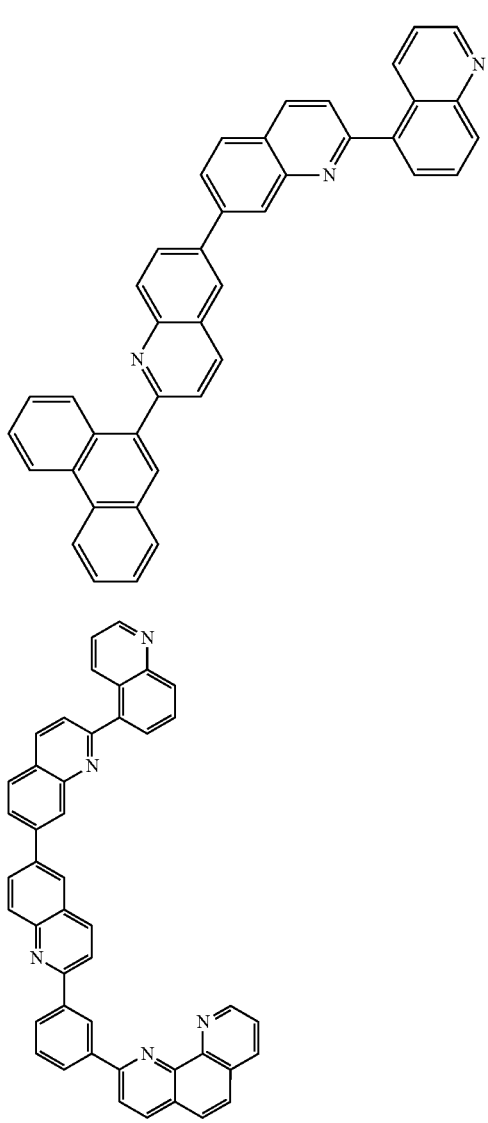
133
512
-continued
134
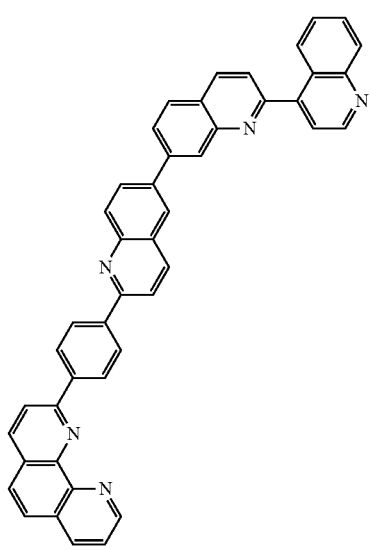
135
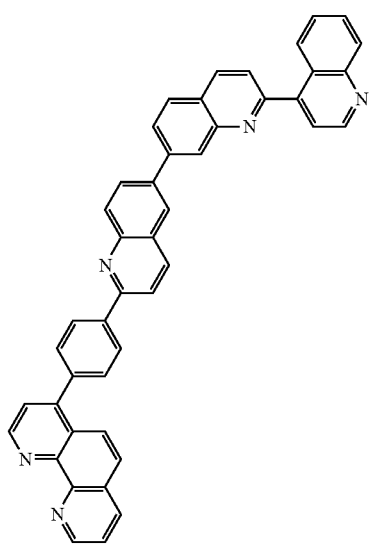

513 514
-continued
136 138
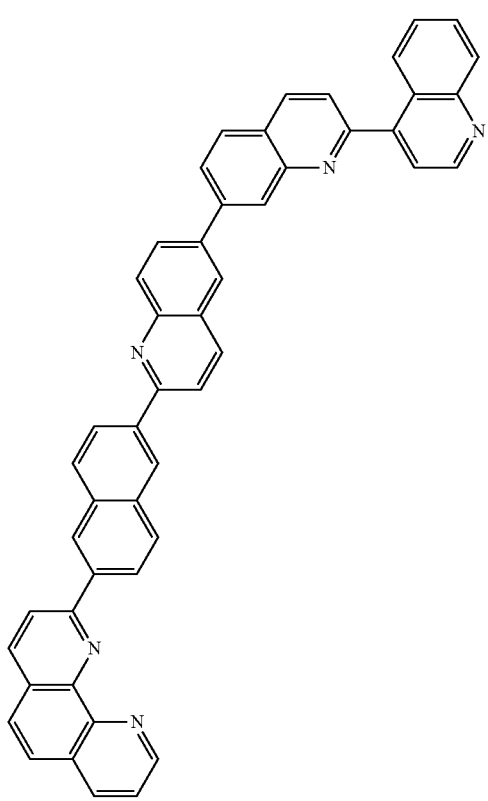
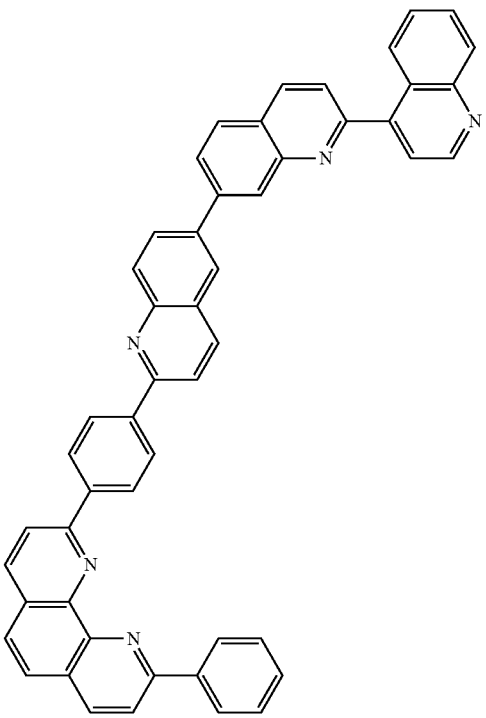
137 139
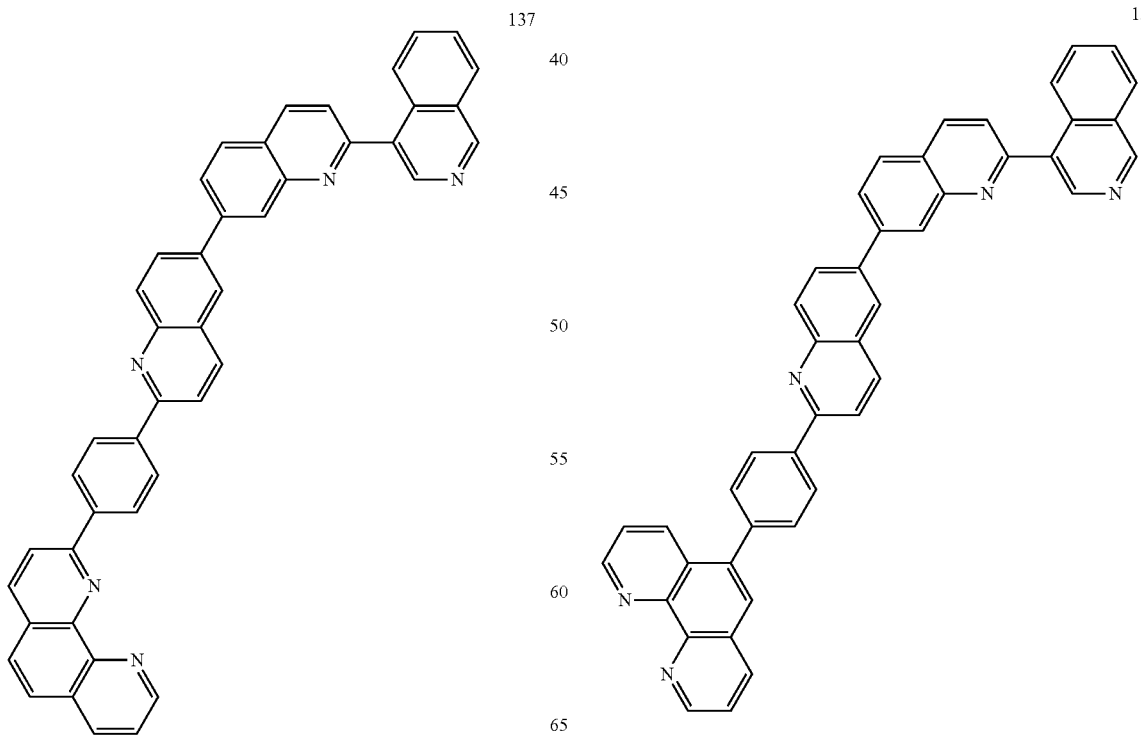

515
-continued
516
-continued
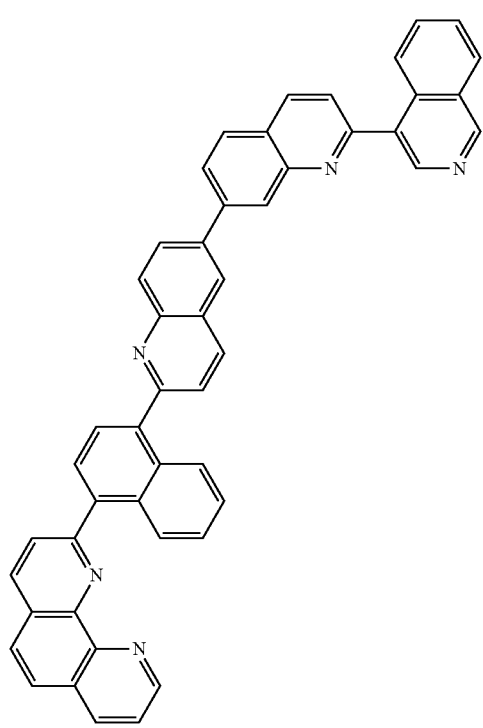
140
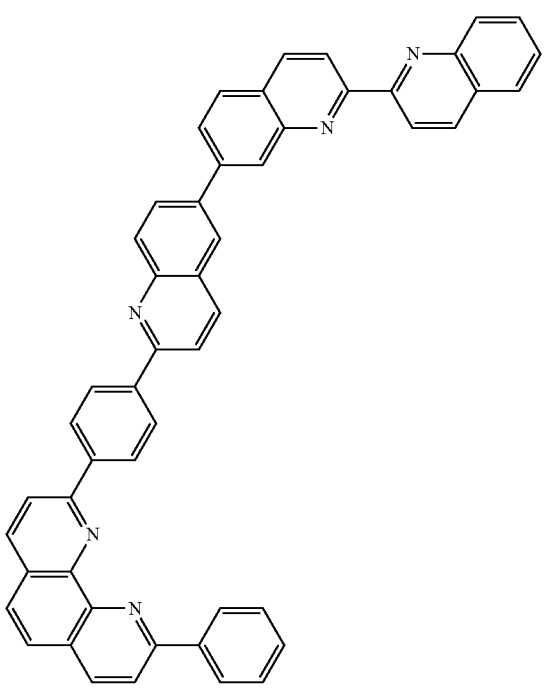
142
141
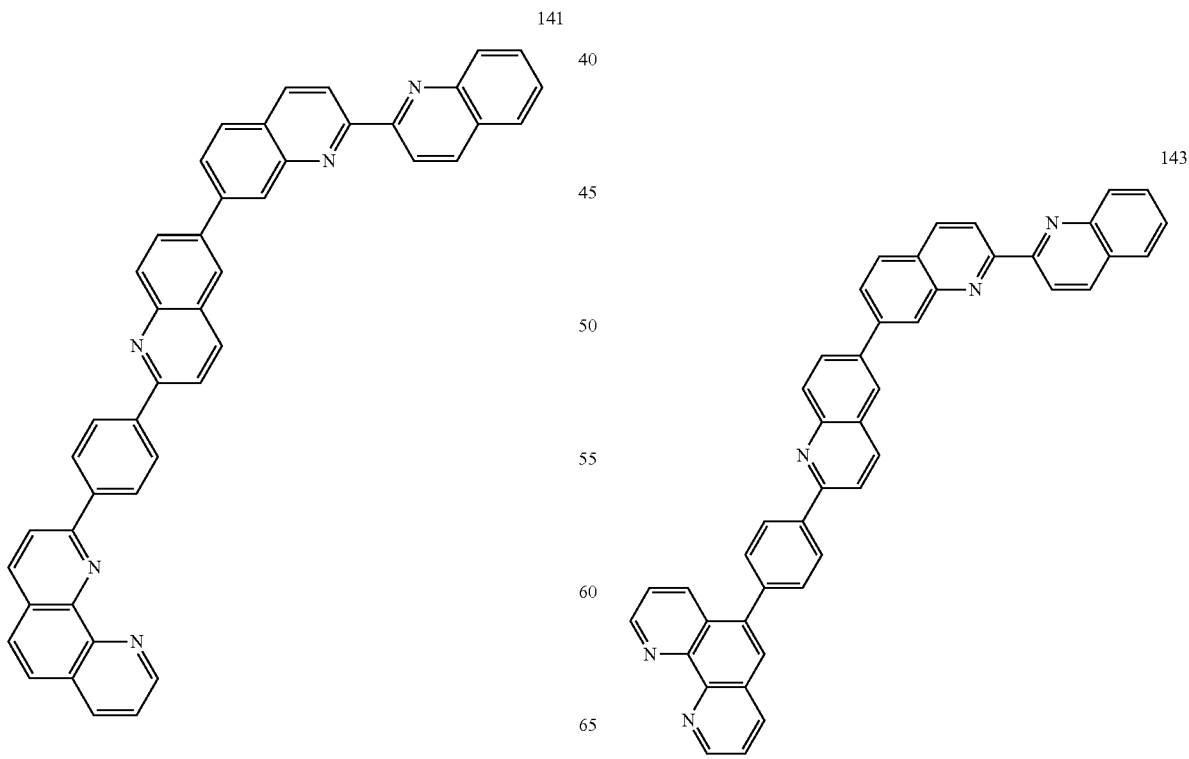
143

517
-continued
144
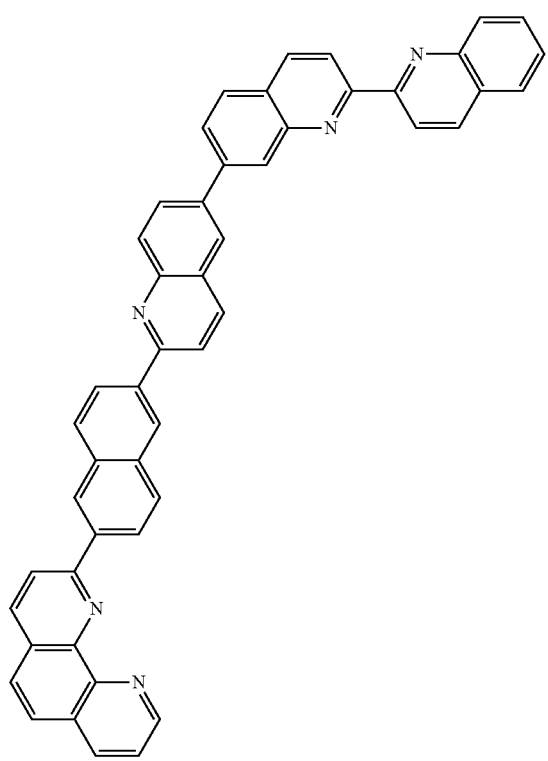
145
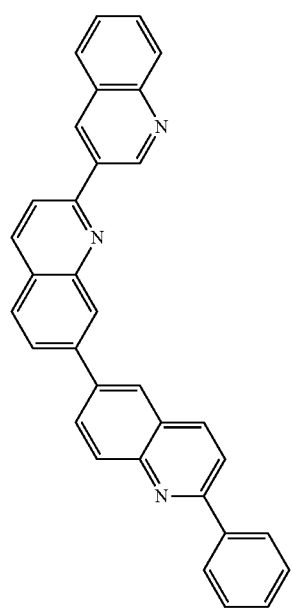
518
-continued
146
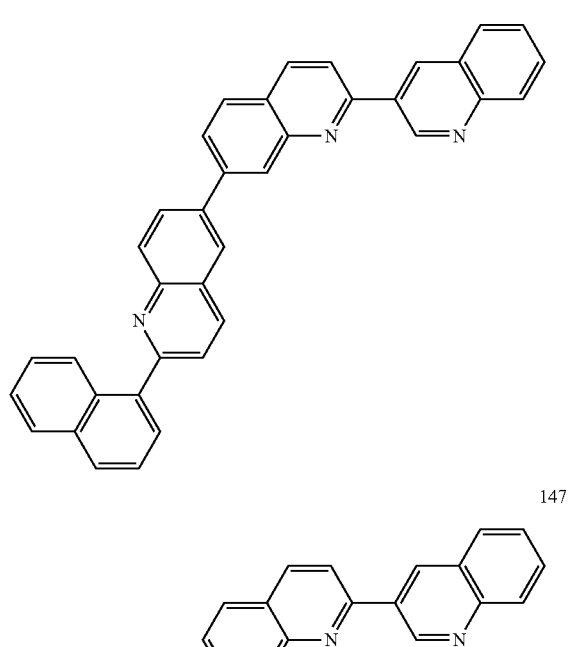
147
148
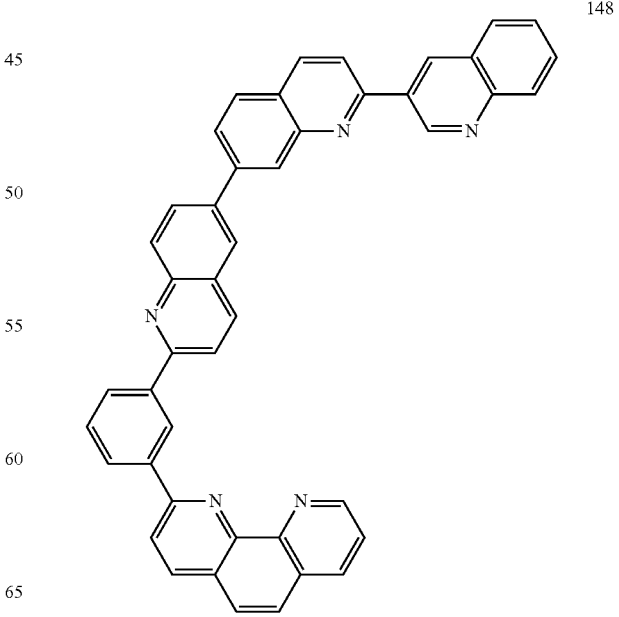

519
-continued
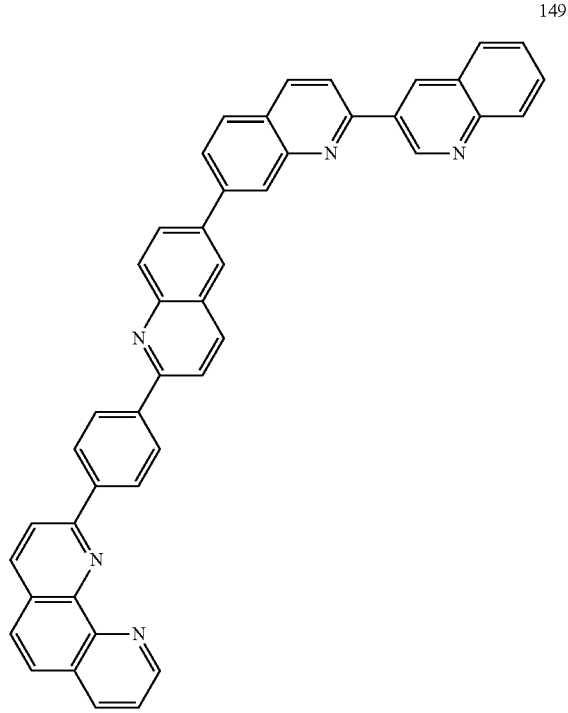
149
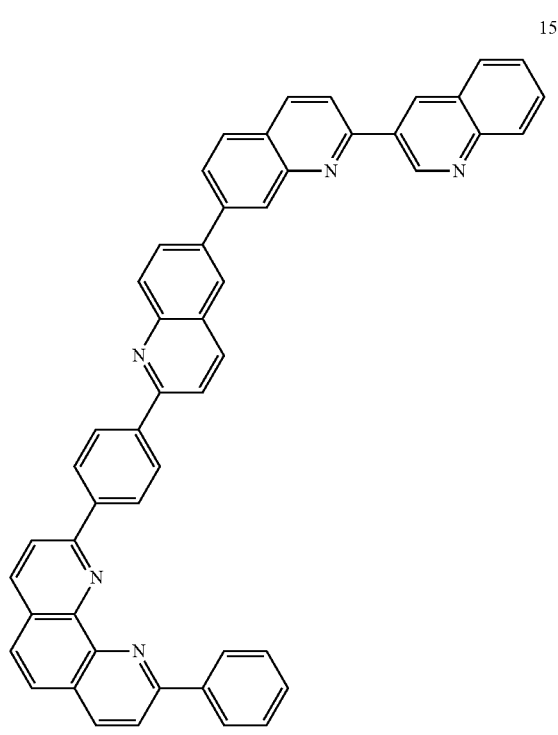
150
520
-continued
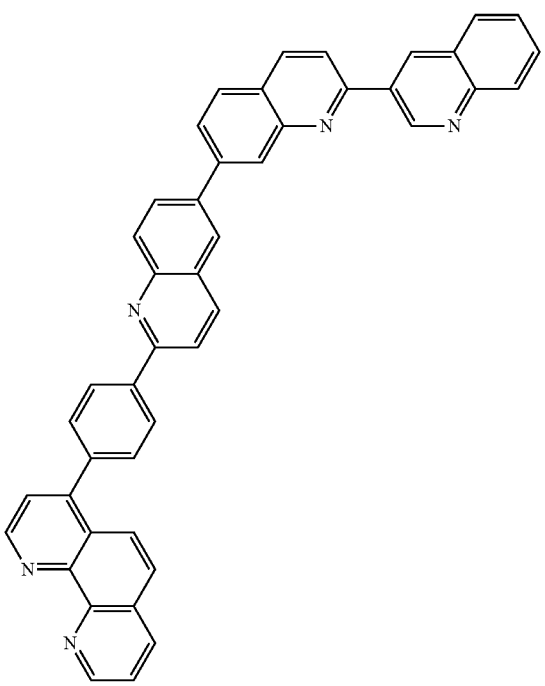
151
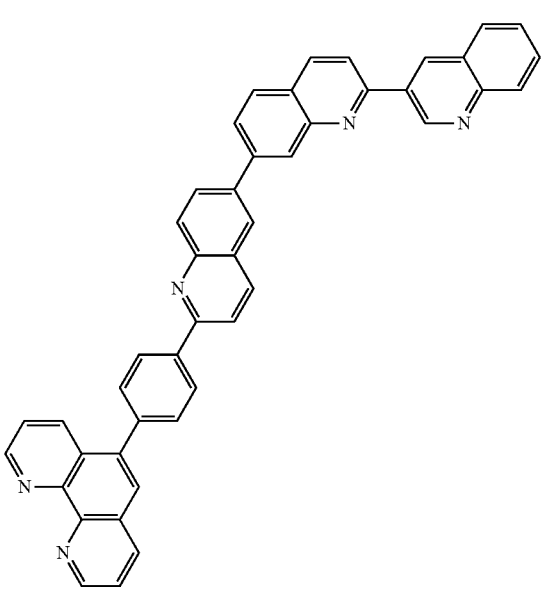
152

521
-continued
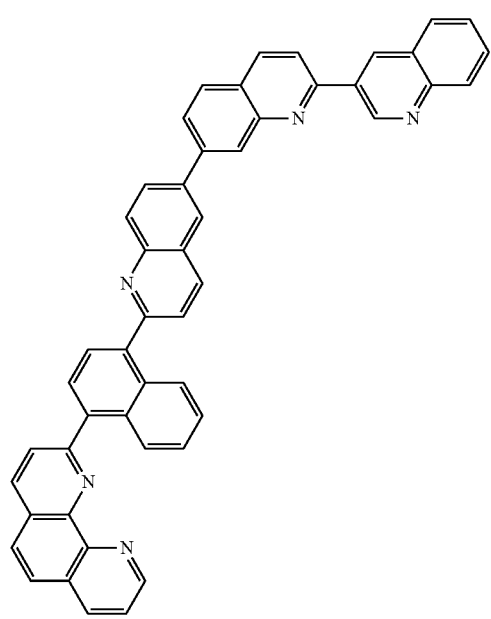
153
522
-continued
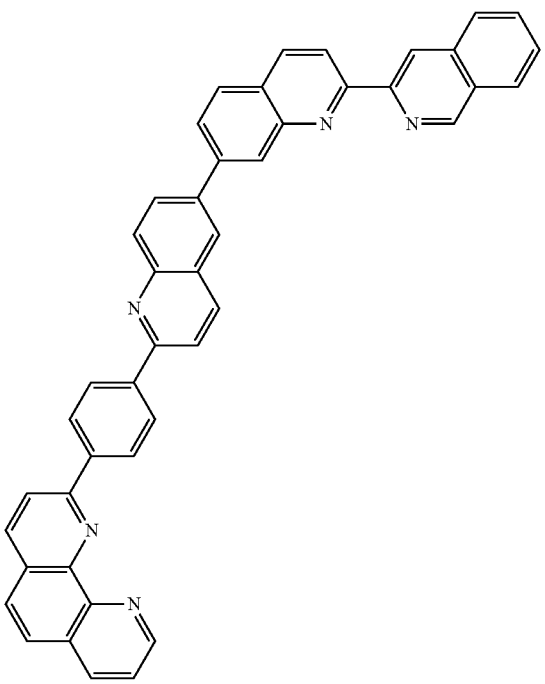
155
154
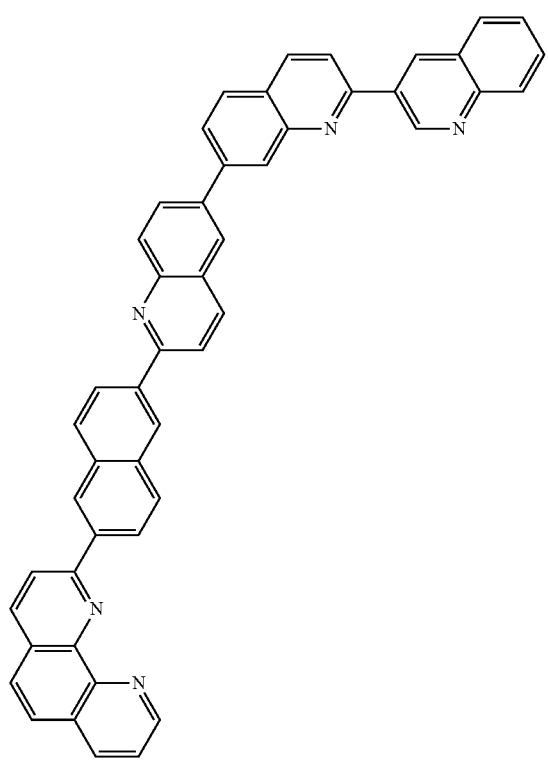
156
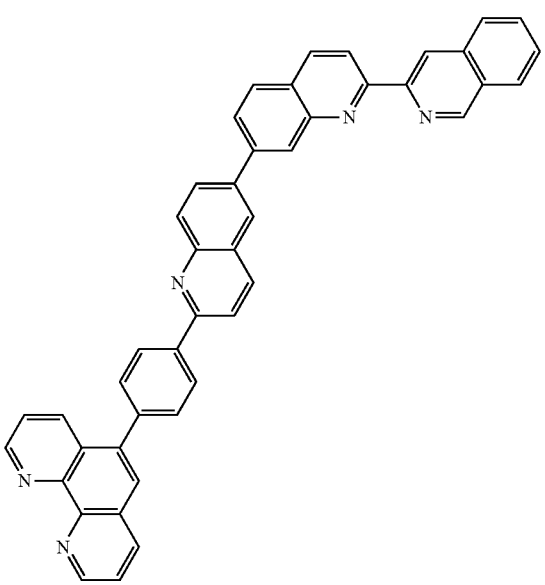

523
-continued
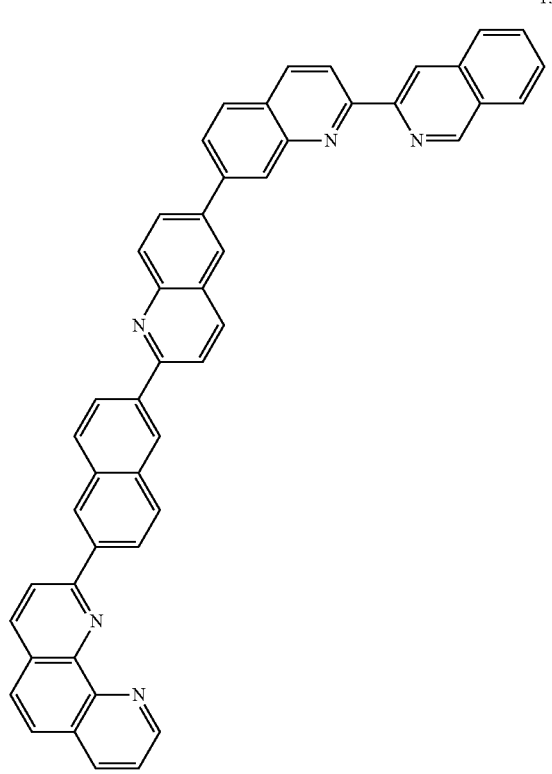
157
158
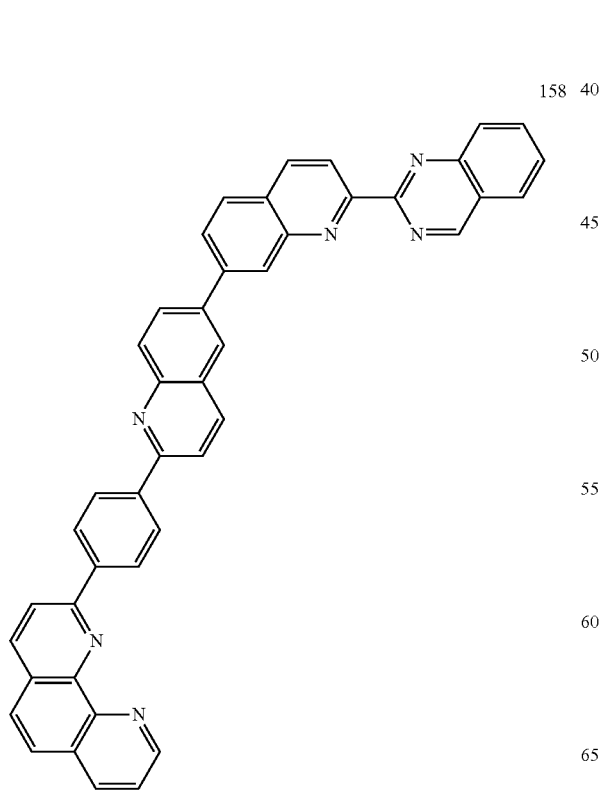
524
-continued
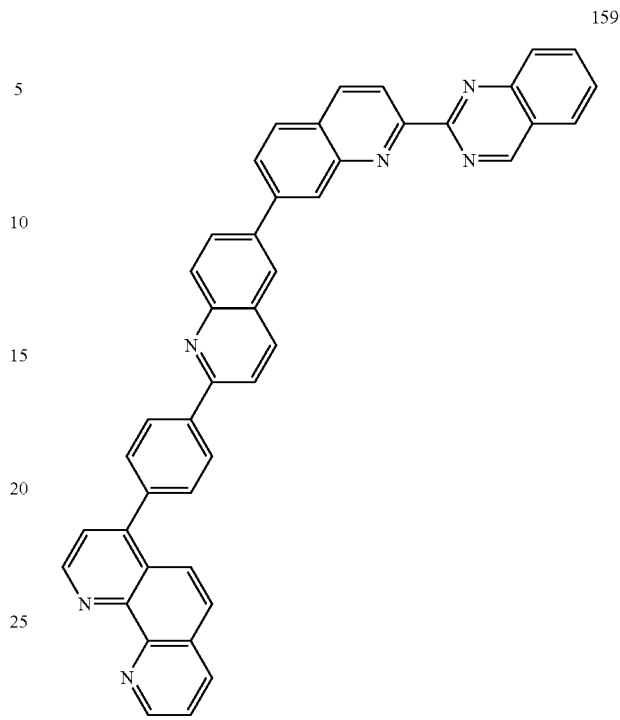
159
160
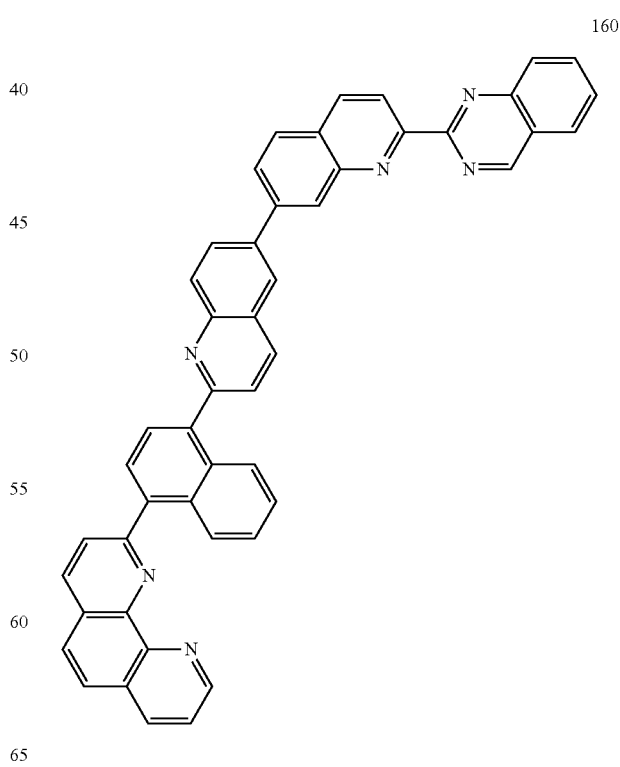

161
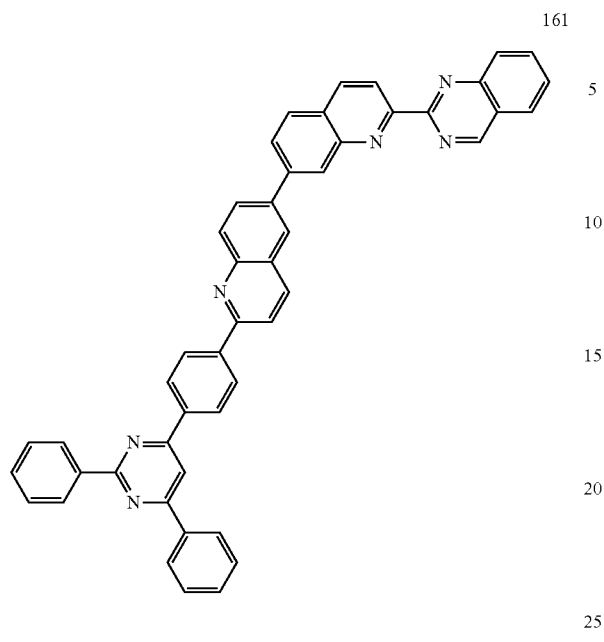
163
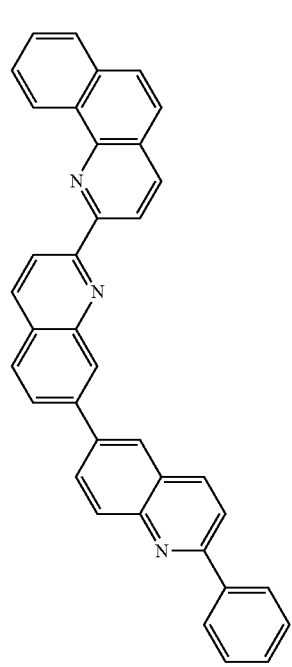
162
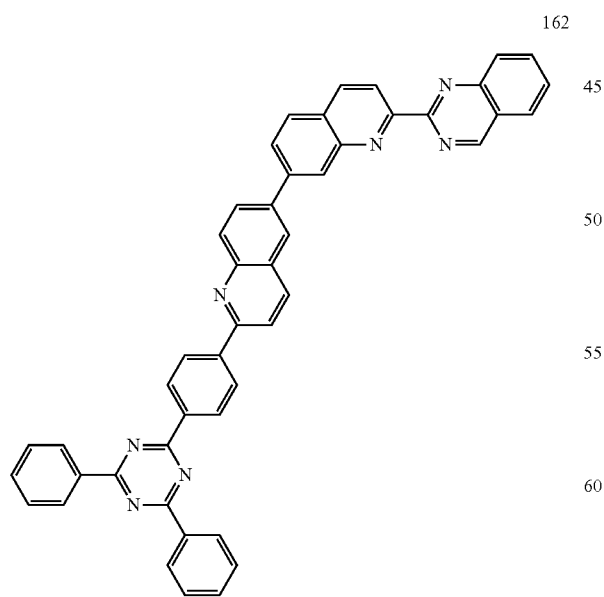
164
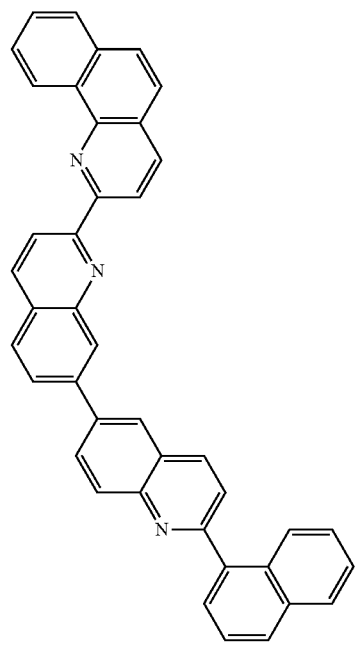

527
-continued
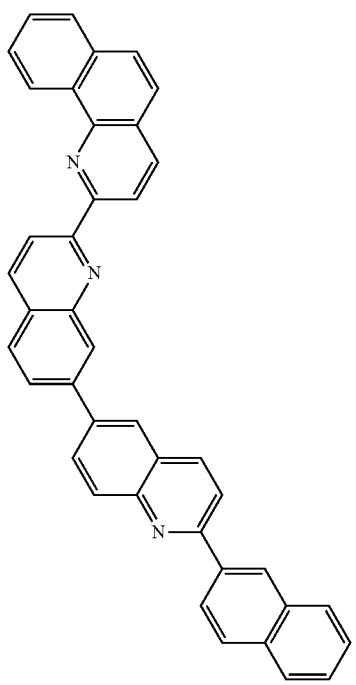
165
166
528
-continued
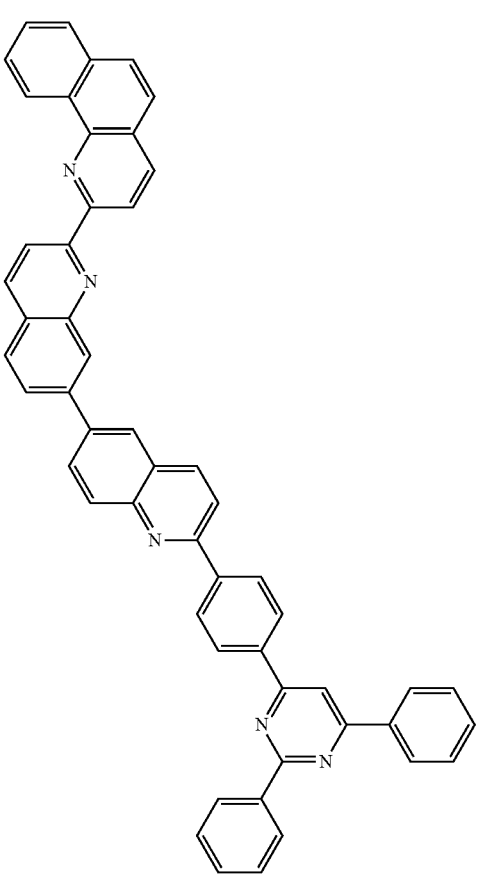
167

529
-continued
168
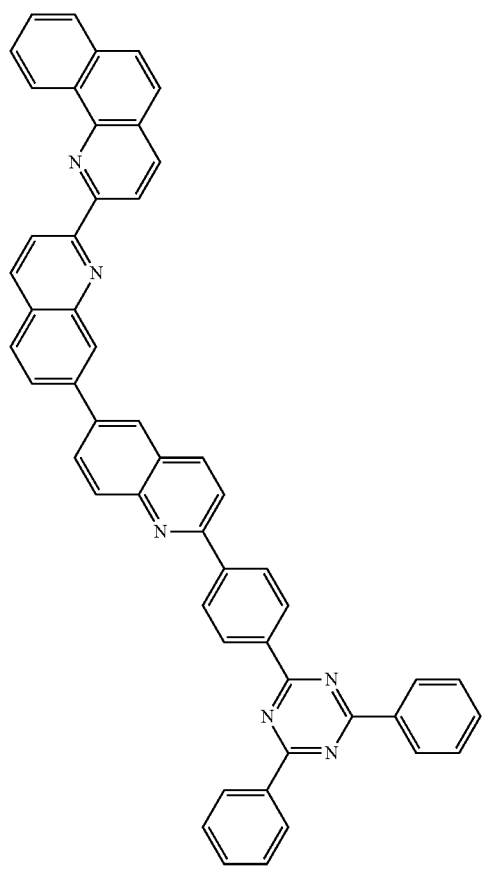
169
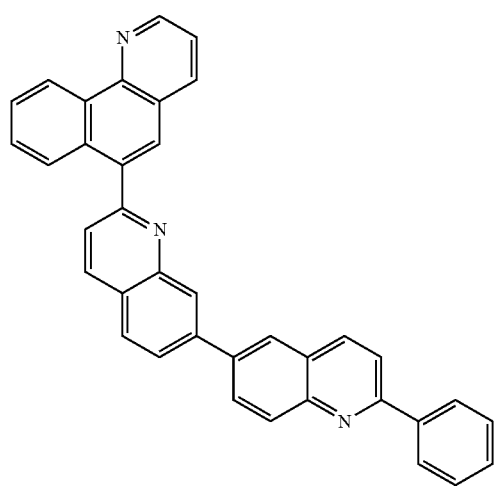
530
-continued
170
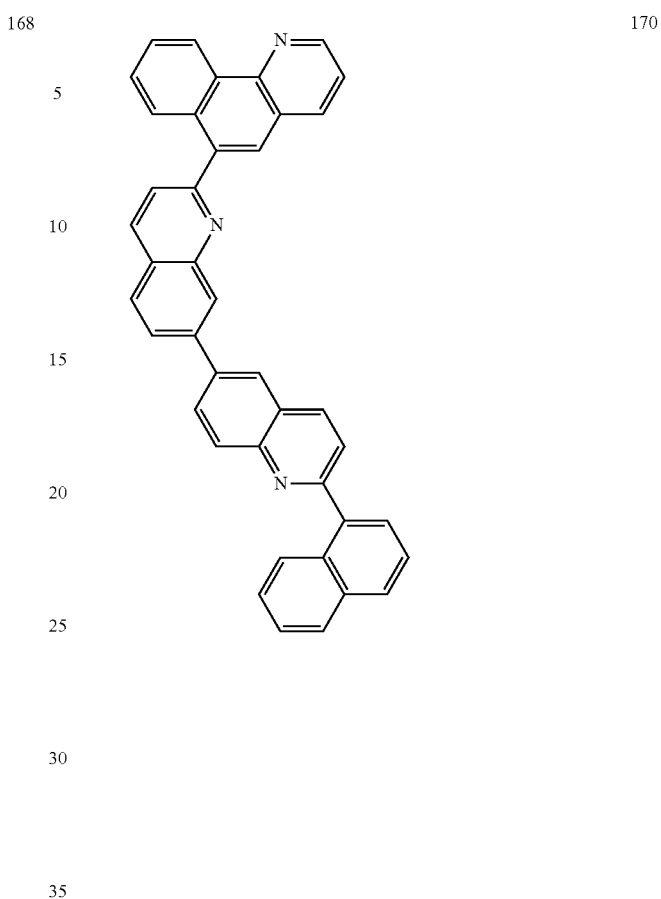
171

531
-continued
172
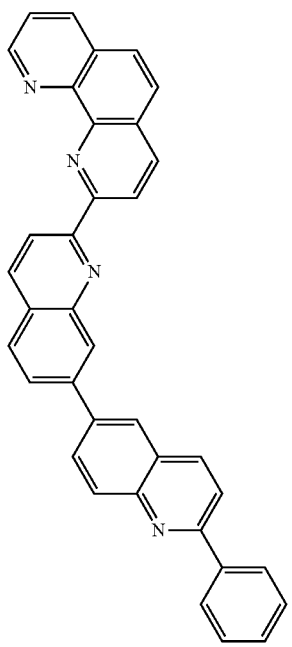
532
-continued
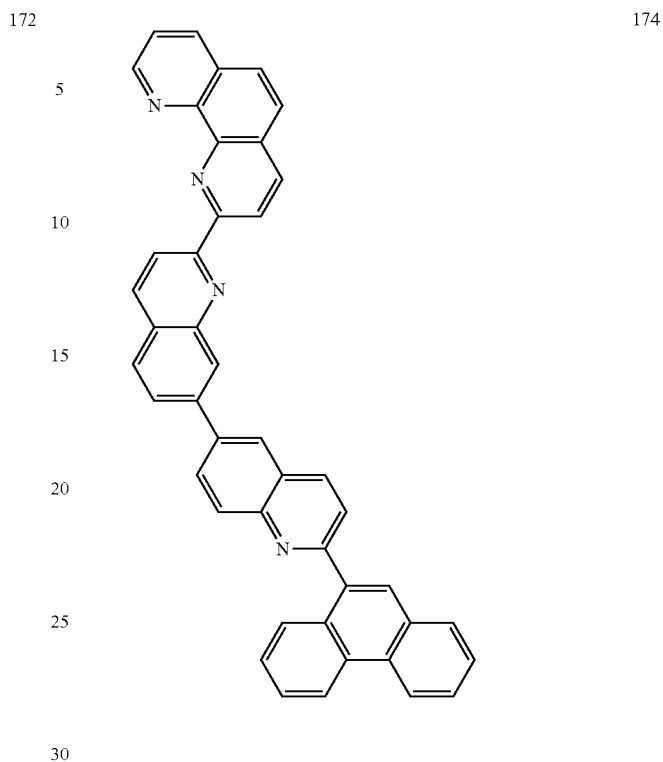
173
174
175
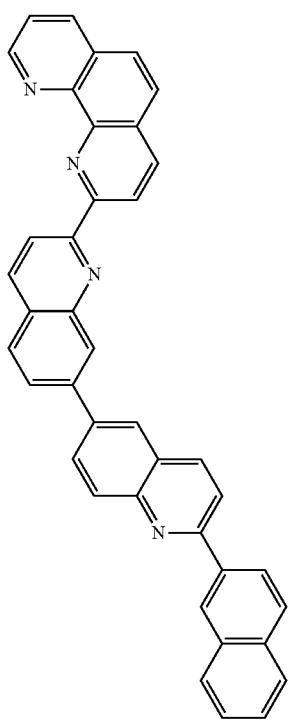
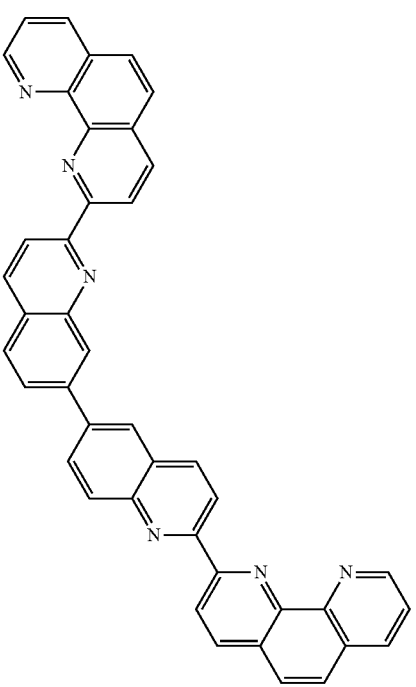

533
-continued
176
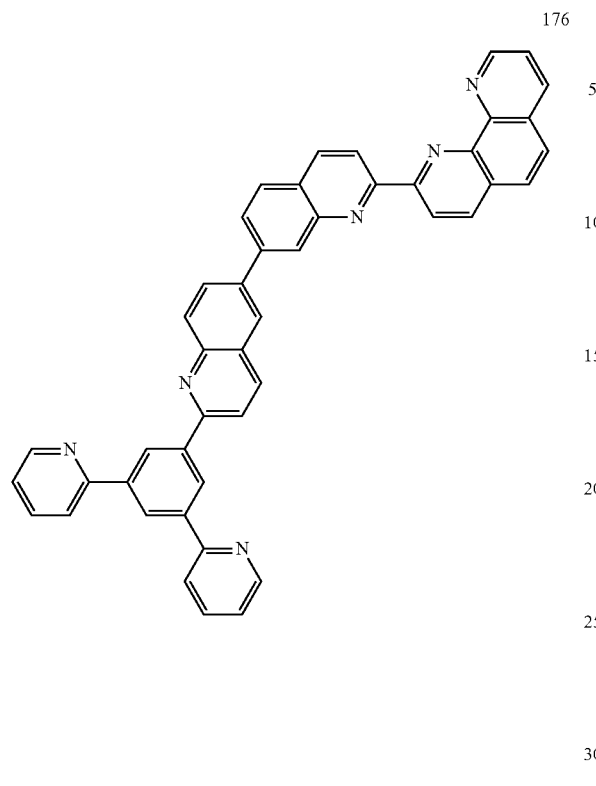
177
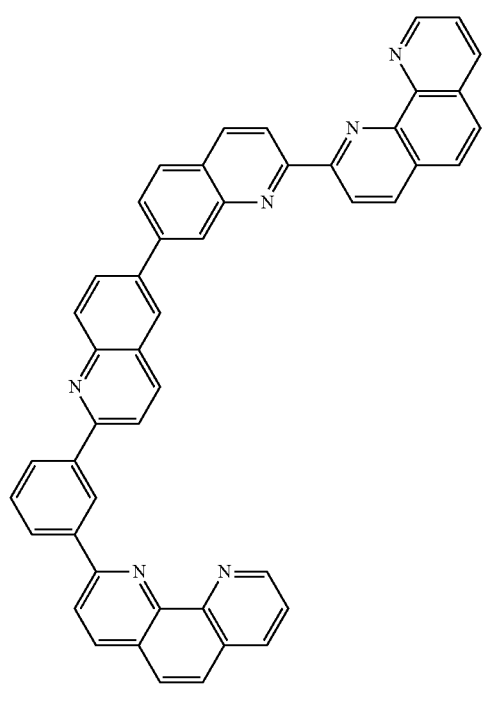
534
-continued
178
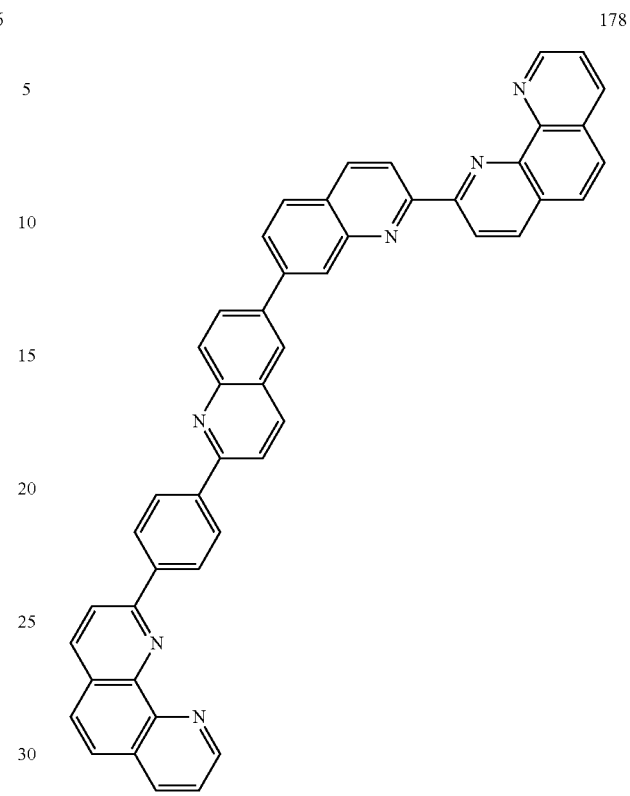
179
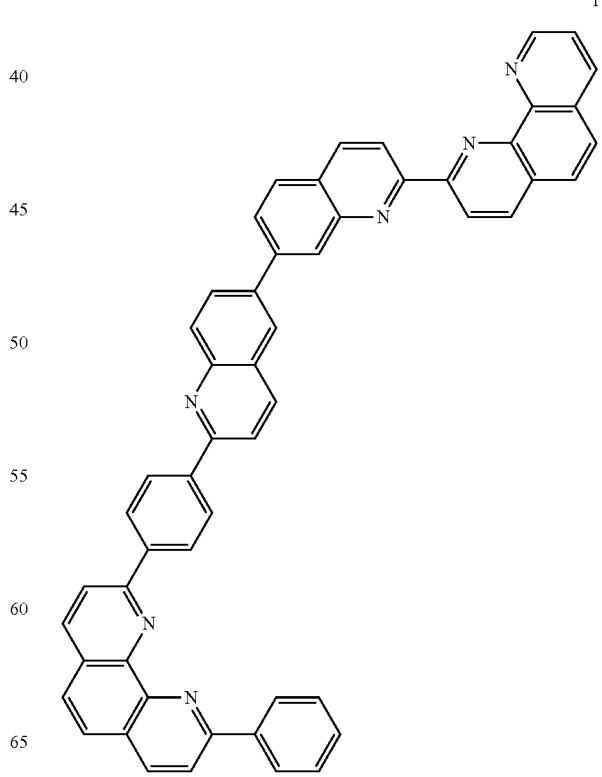

535
-continued
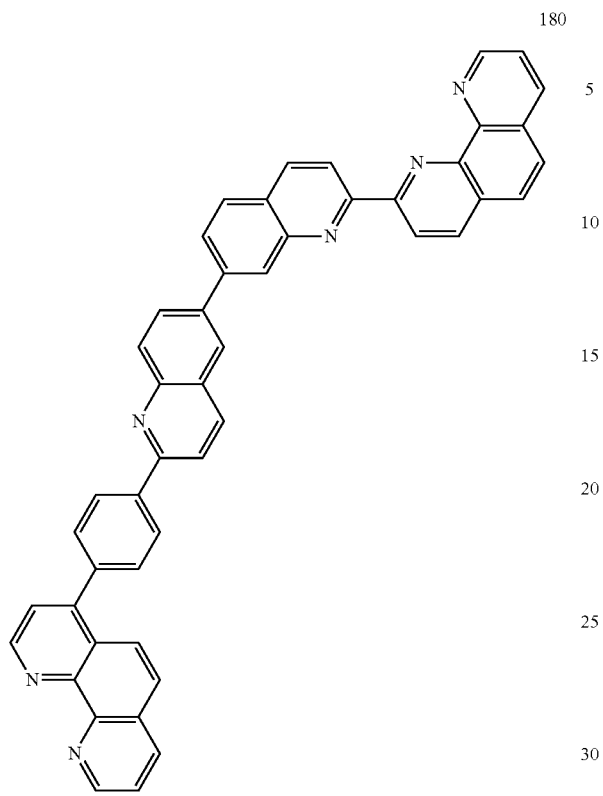
180
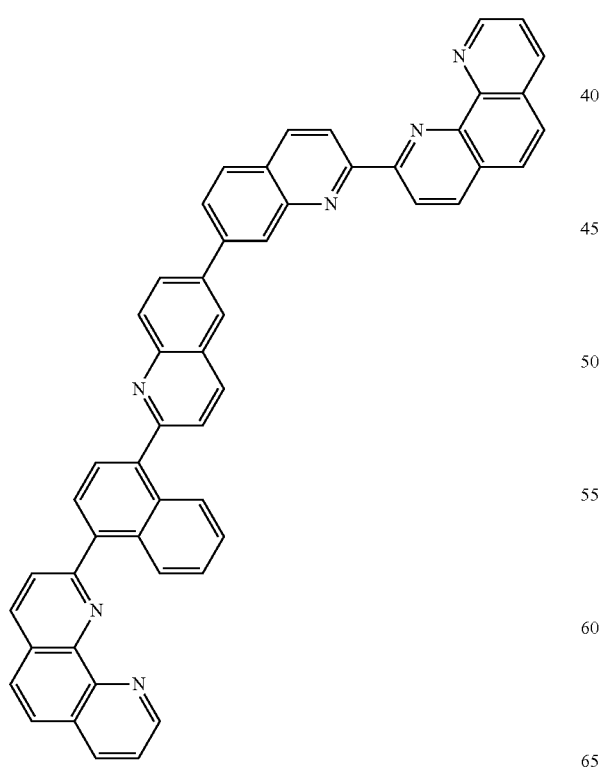
181
536
-continued
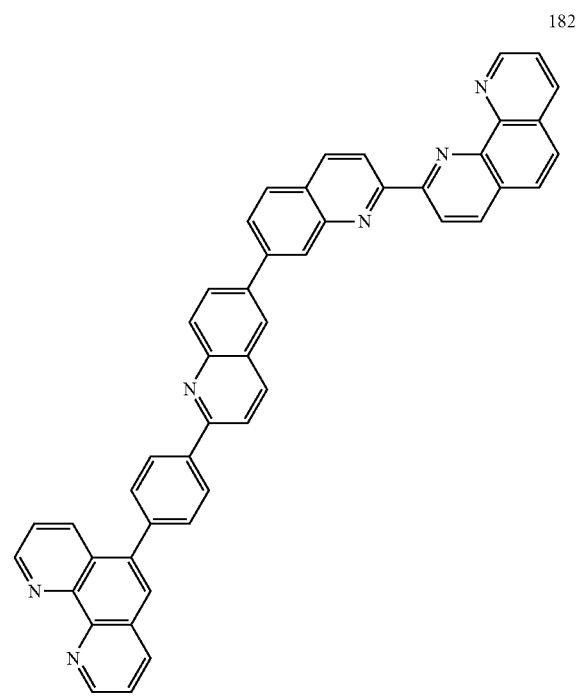
182
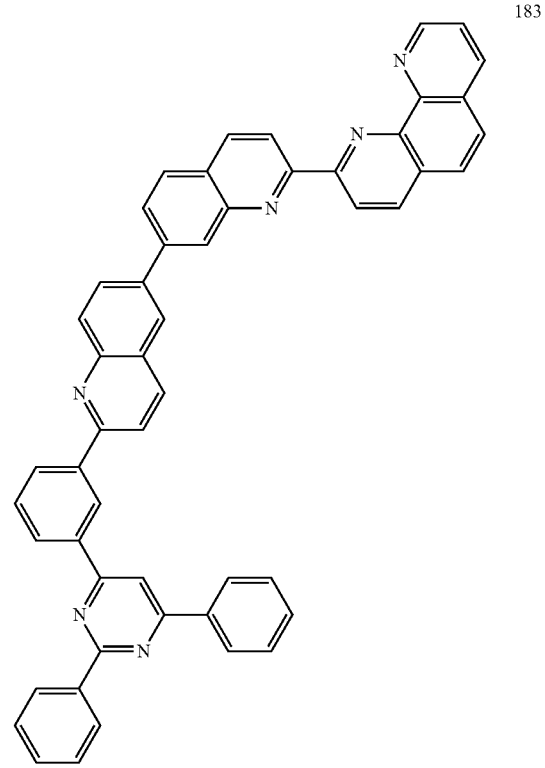
183

537
-continued
184
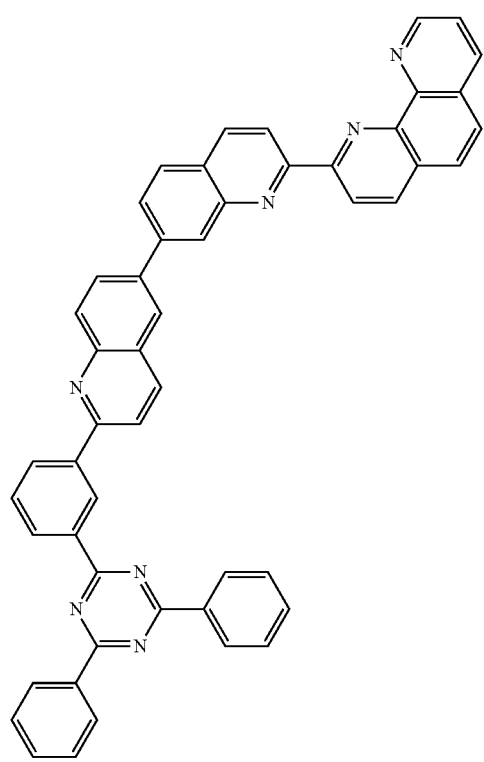
185
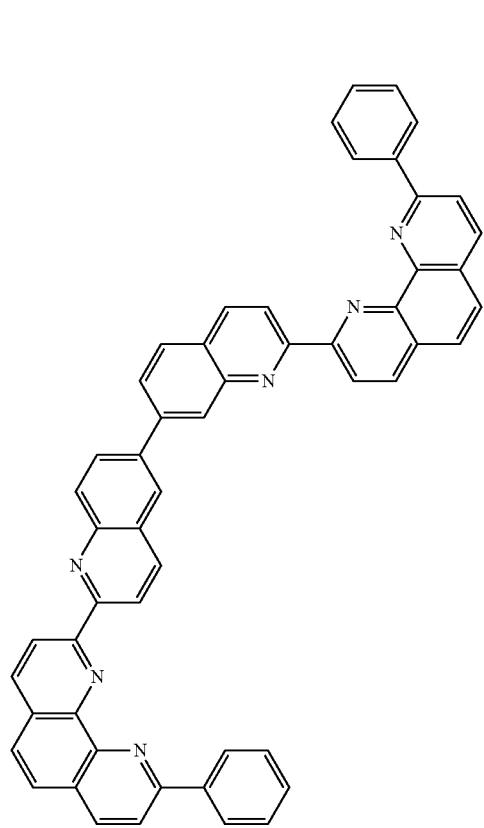
538
-continued
186
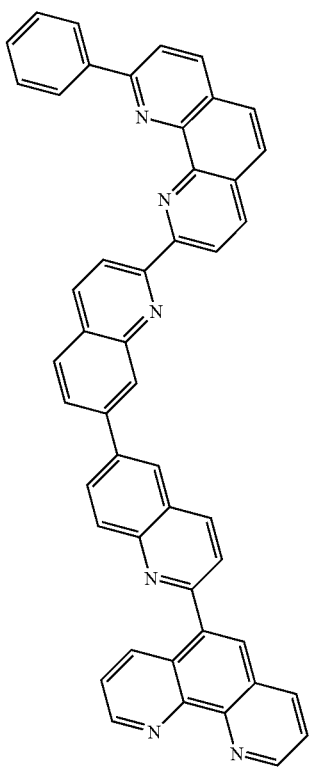
187
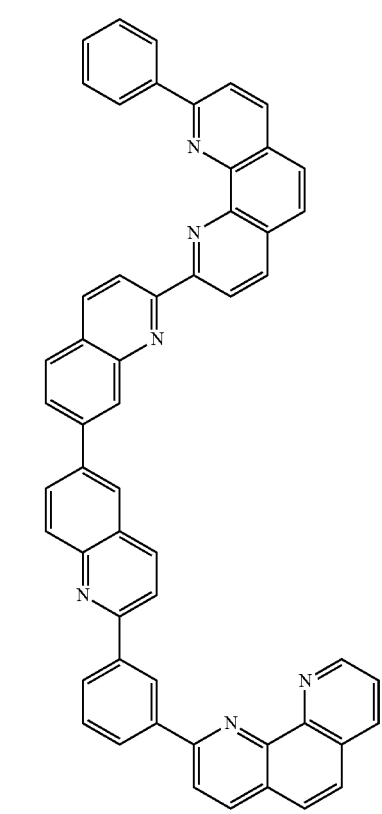

188
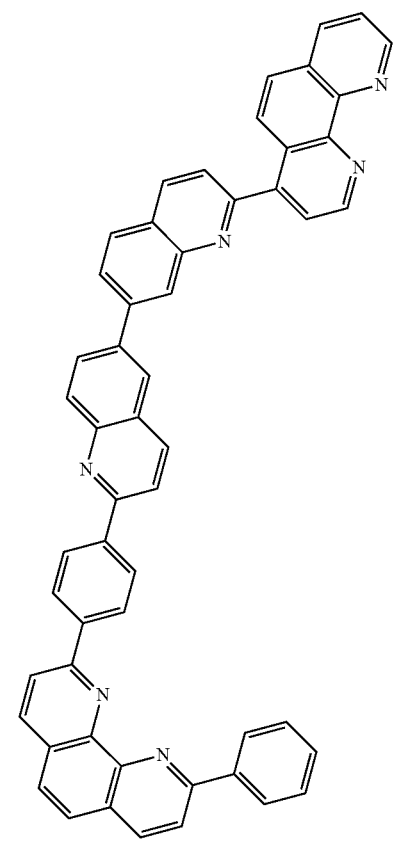
189
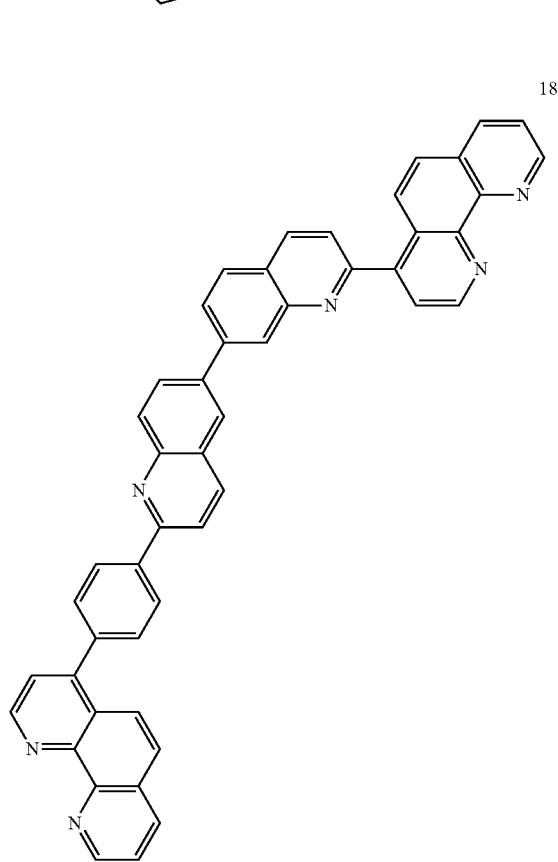
190
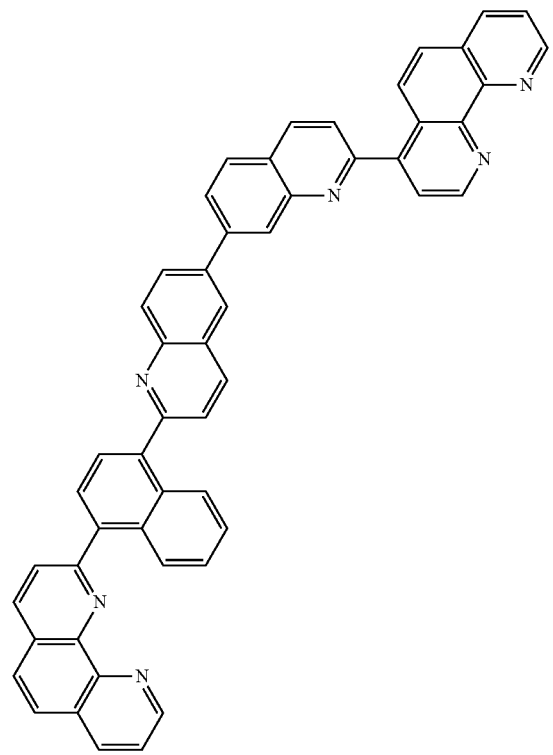
191
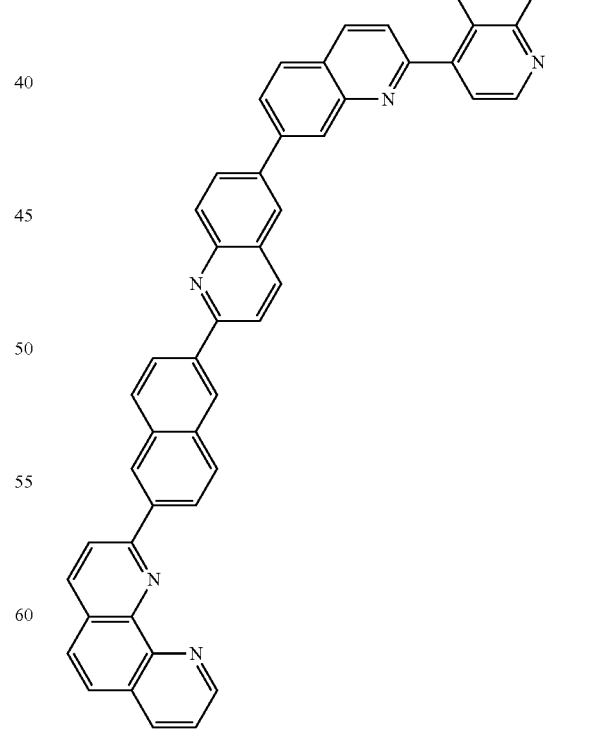

541
-continued
542
-continued
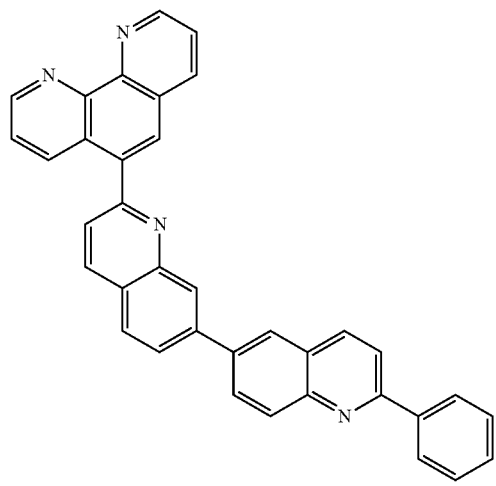
192
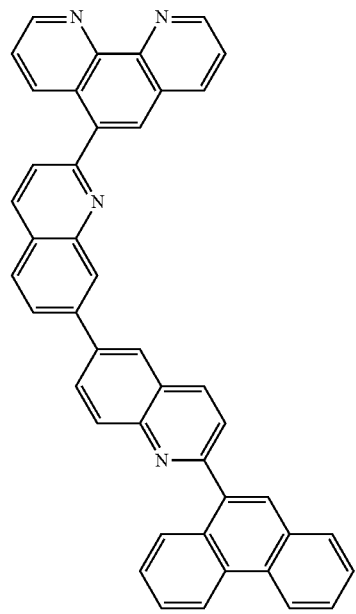
194
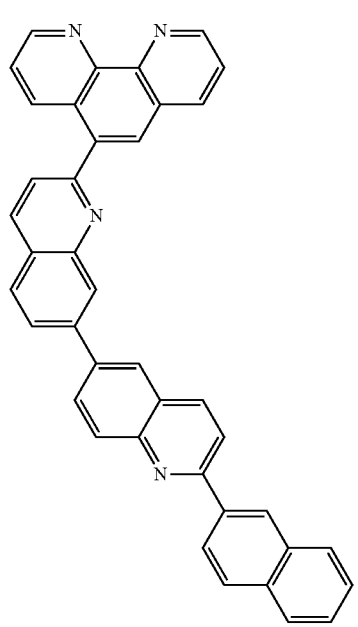
193
195

196
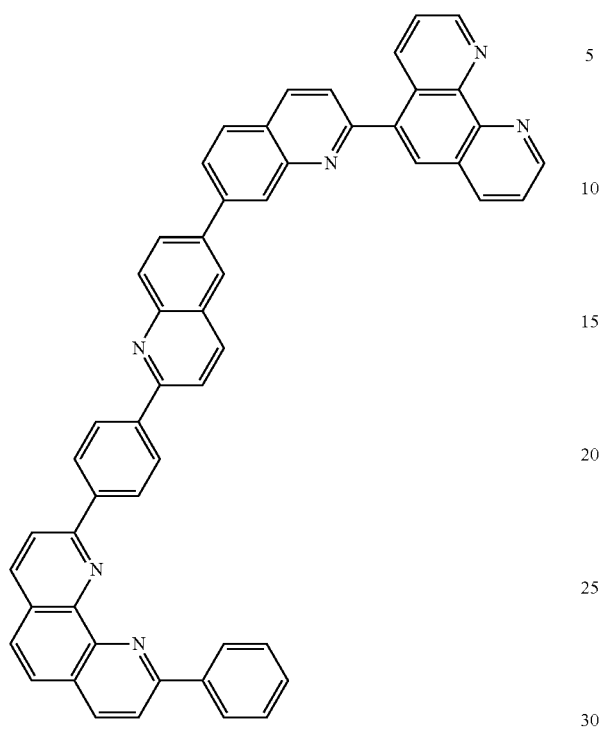
197
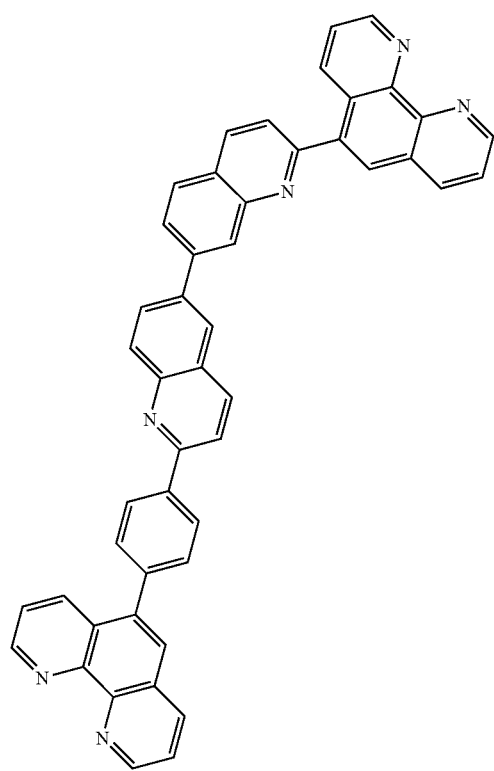
198
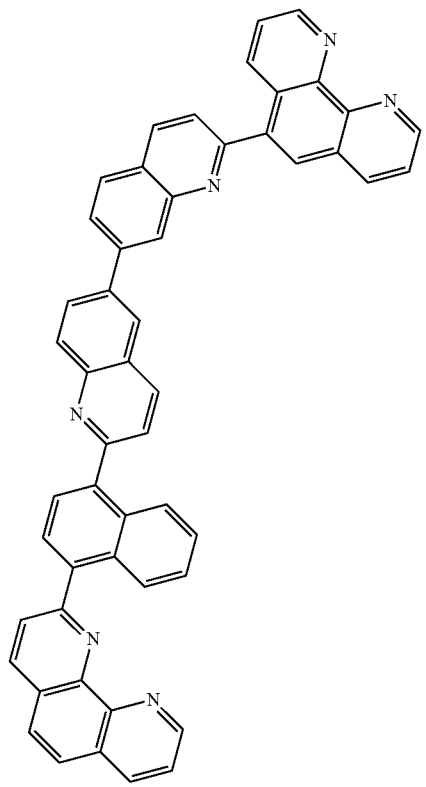
199
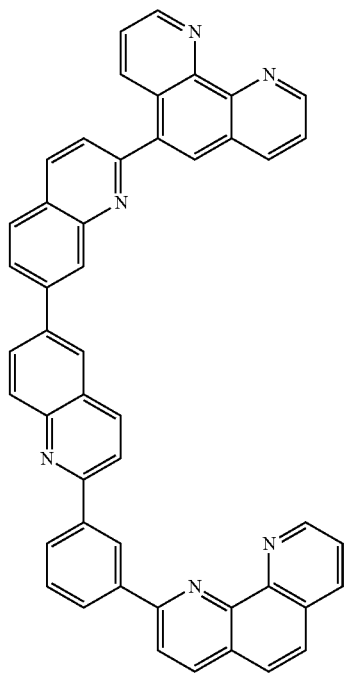

545
-continued
200
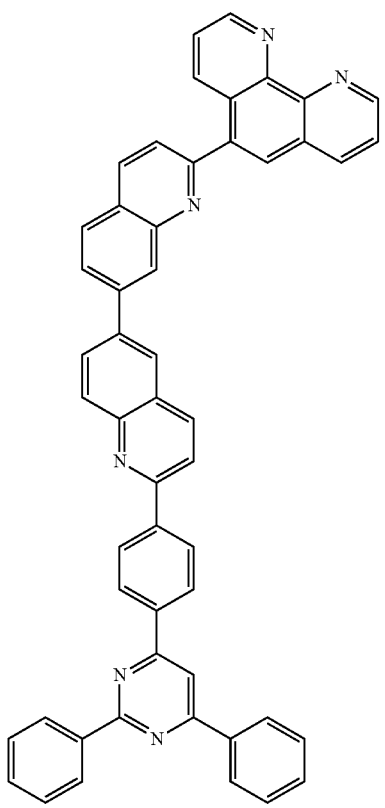
201
546
-continued
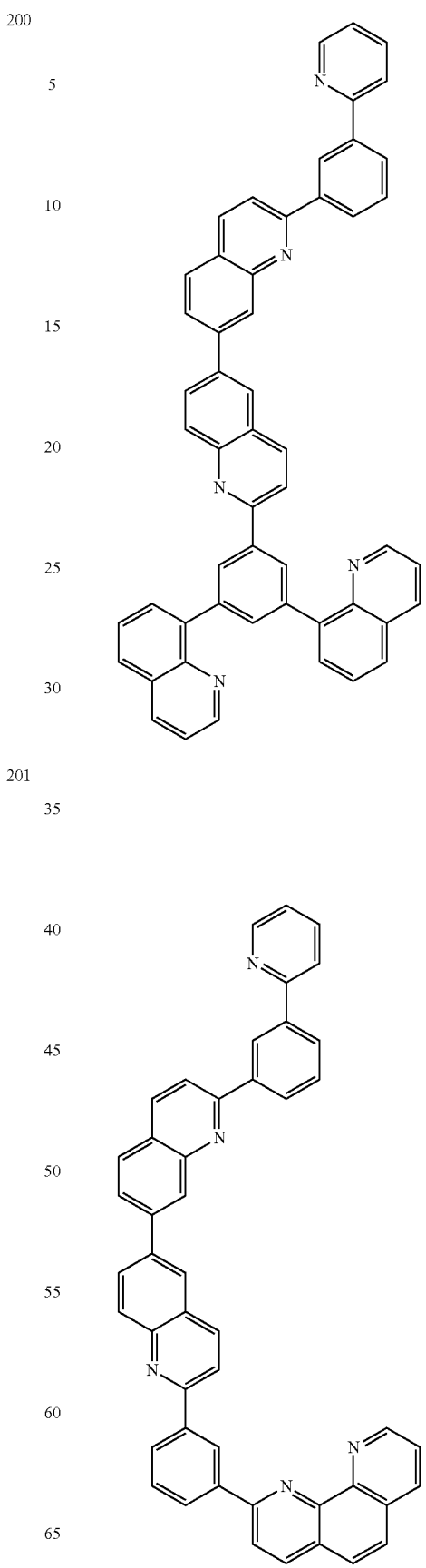

547
-continued
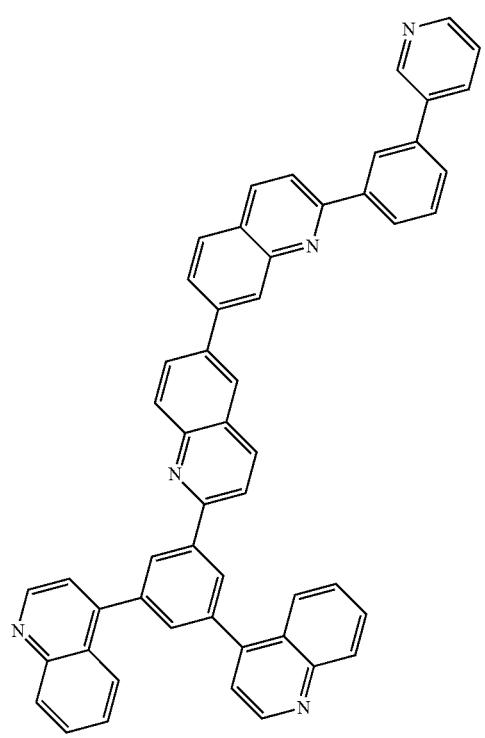
204
205
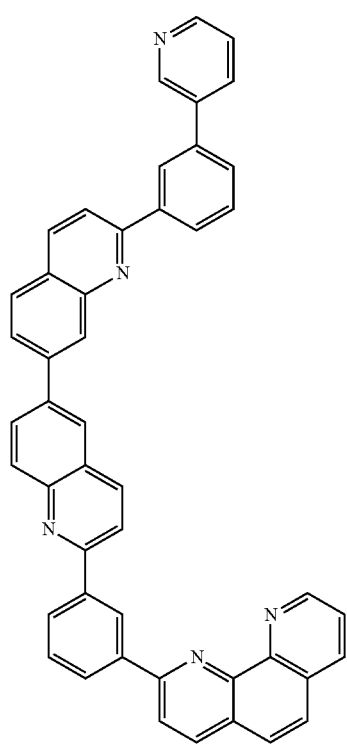
548
-continued
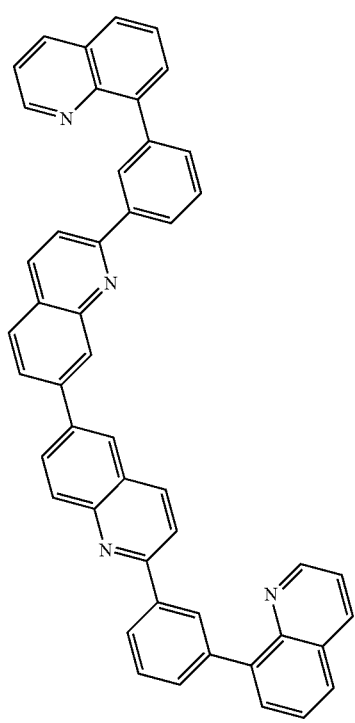
206
207
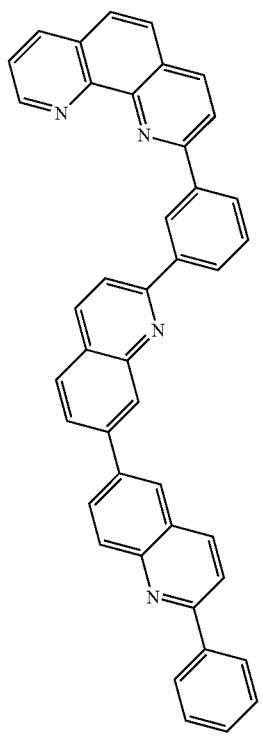

549
-continued
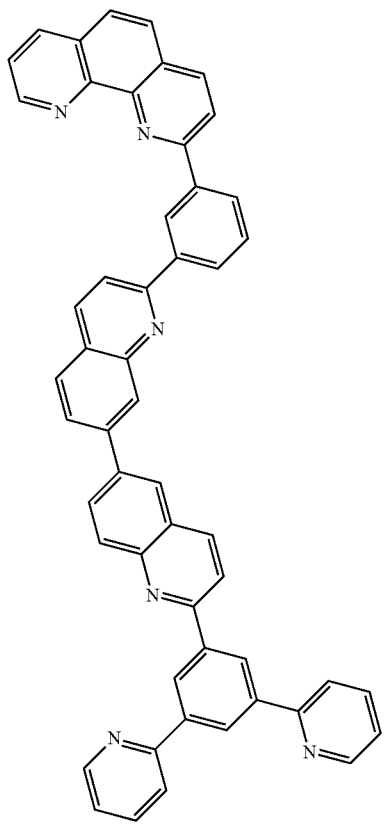
208
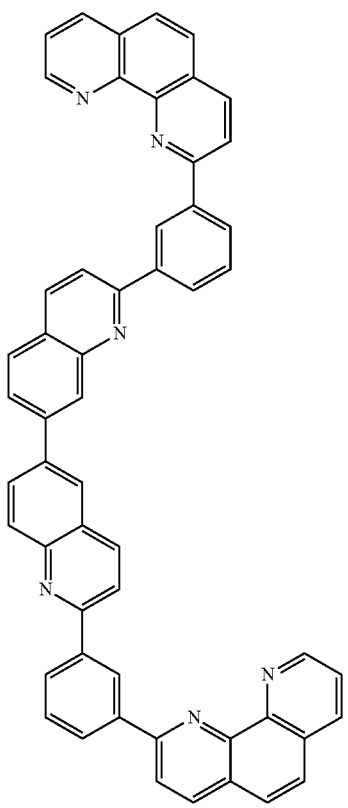
209
550
-continued
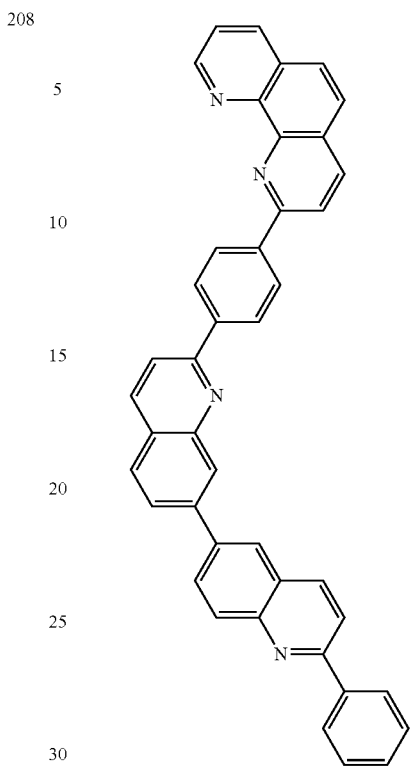
210
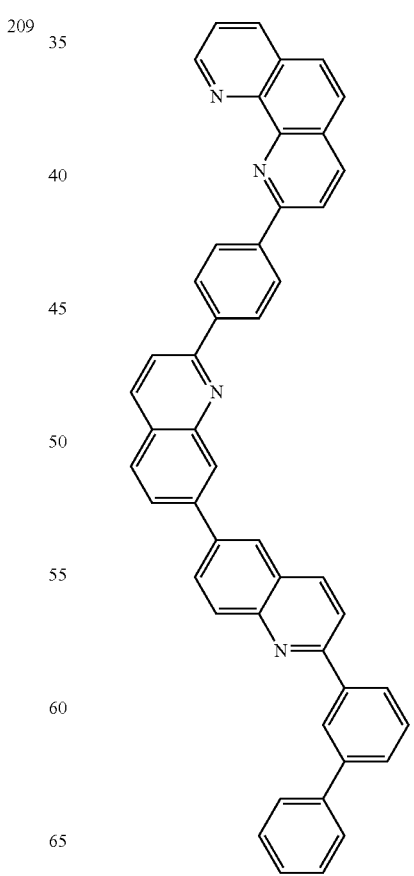
211

551
-continued
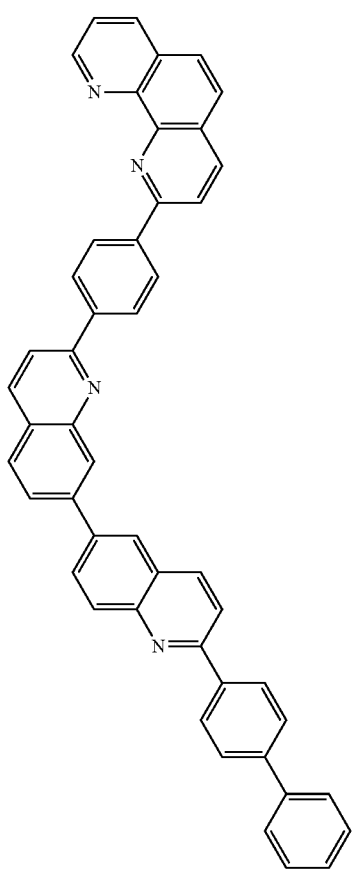
552
-continued
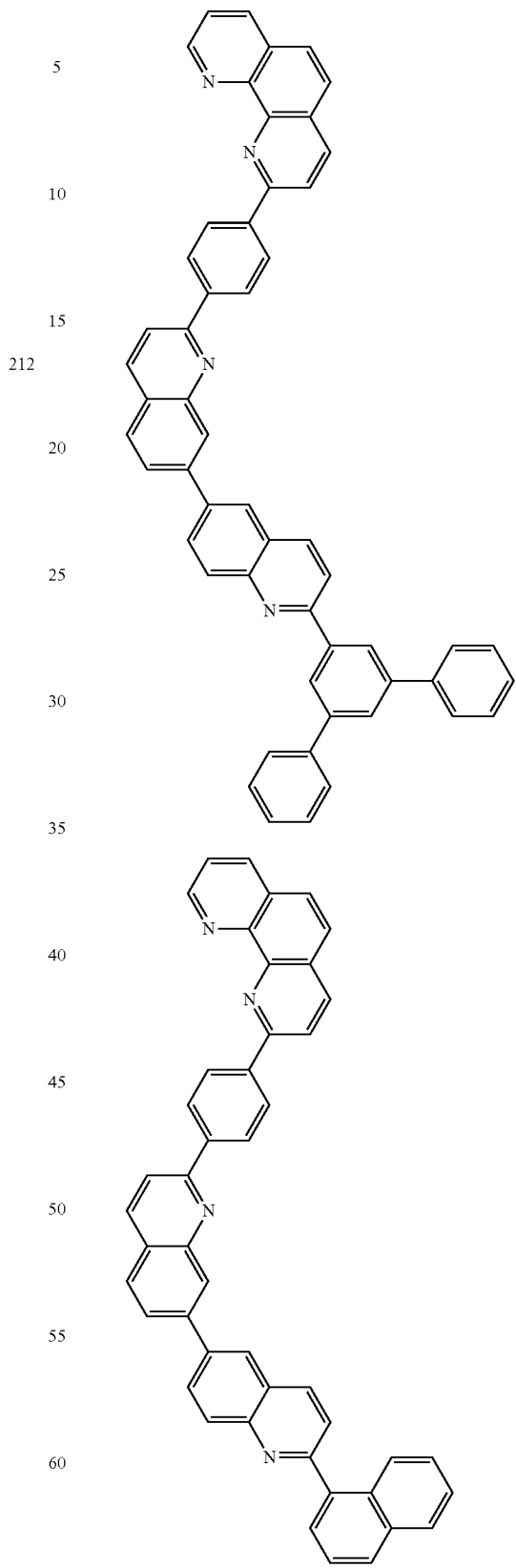

553
-continued
215
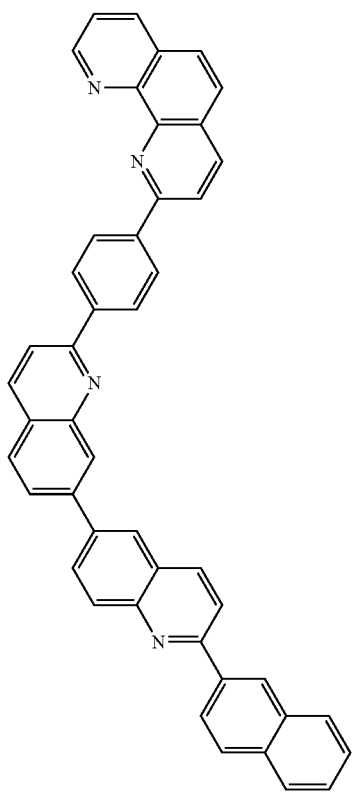
216
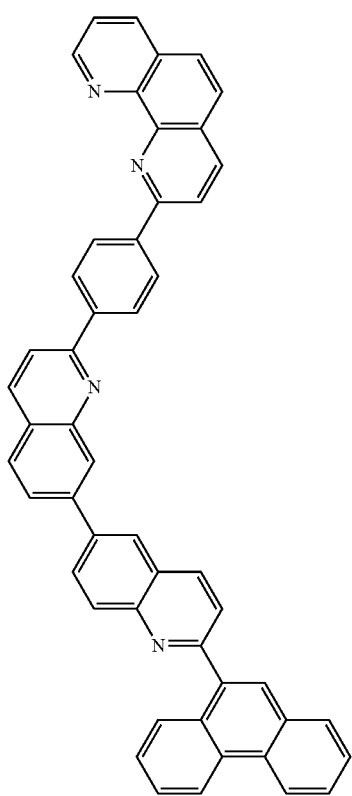
554
-continued
217
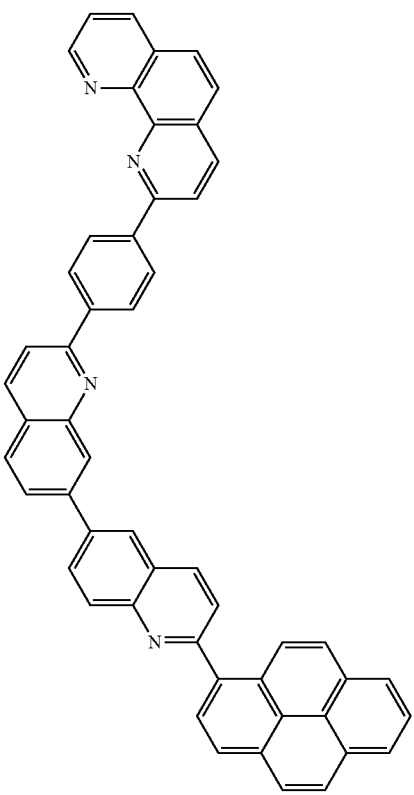
218
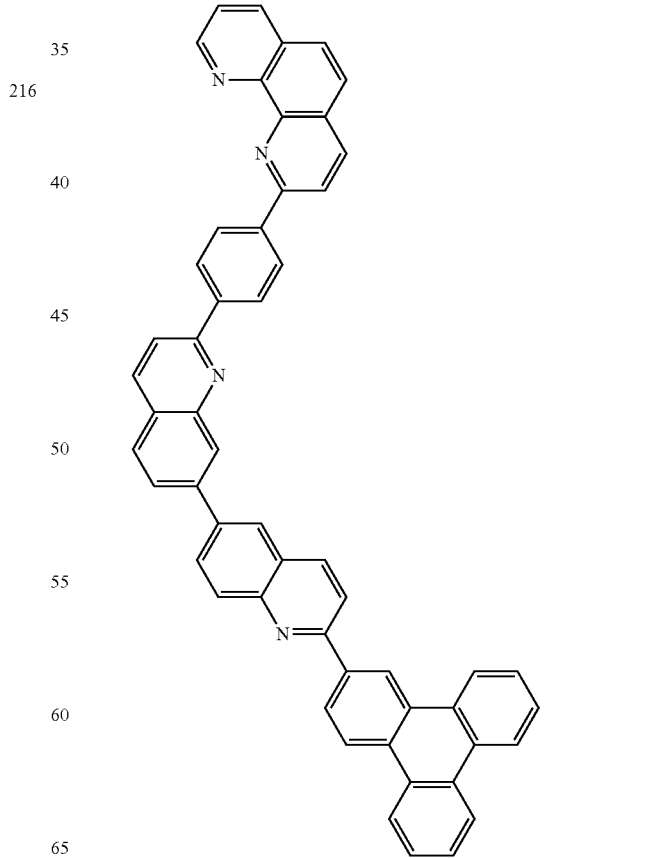

219
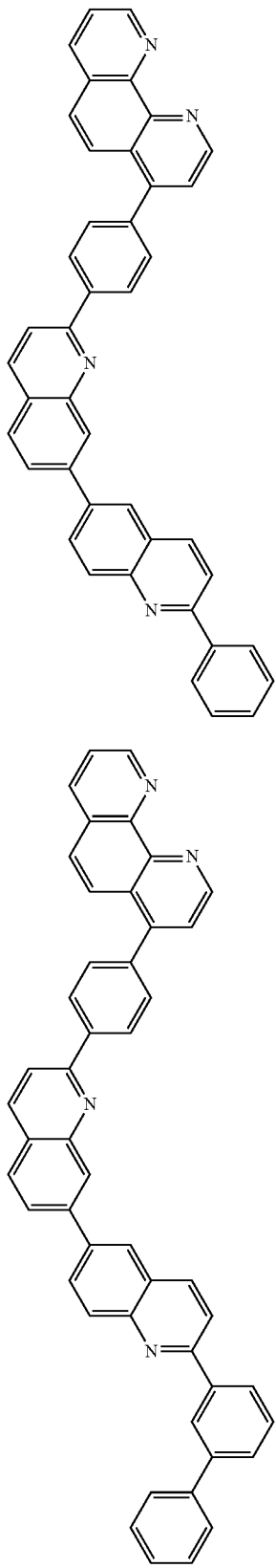
220
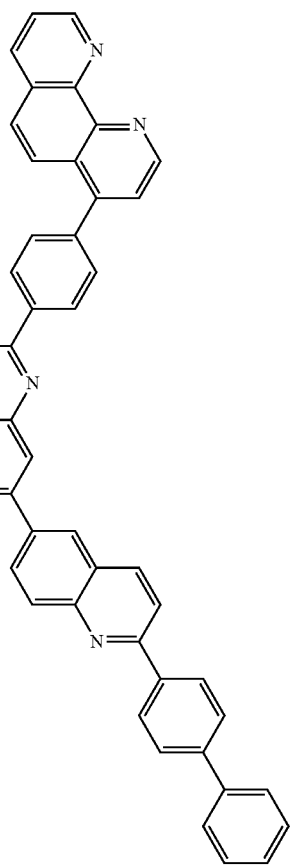
221

222
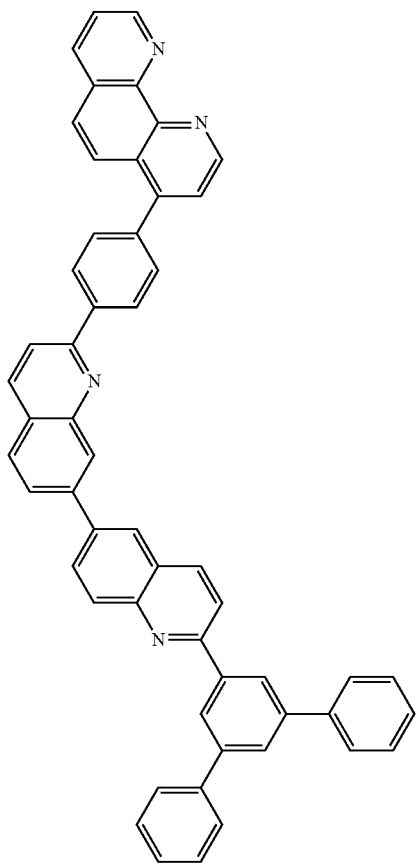
223
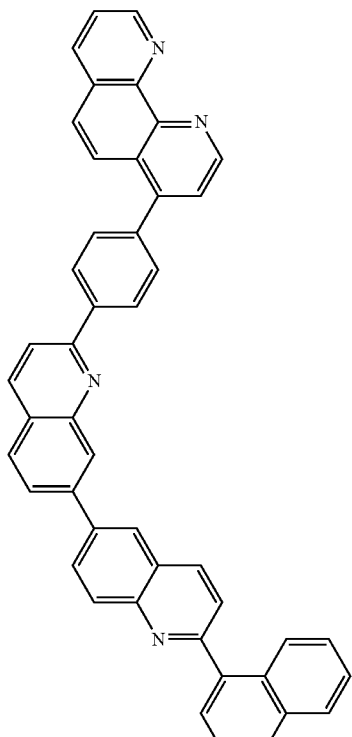
224
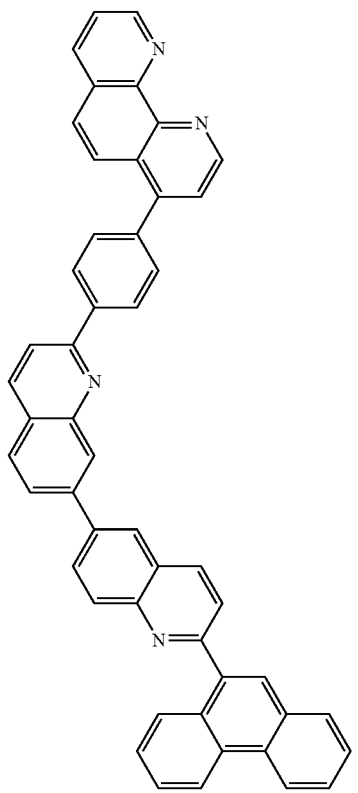
225
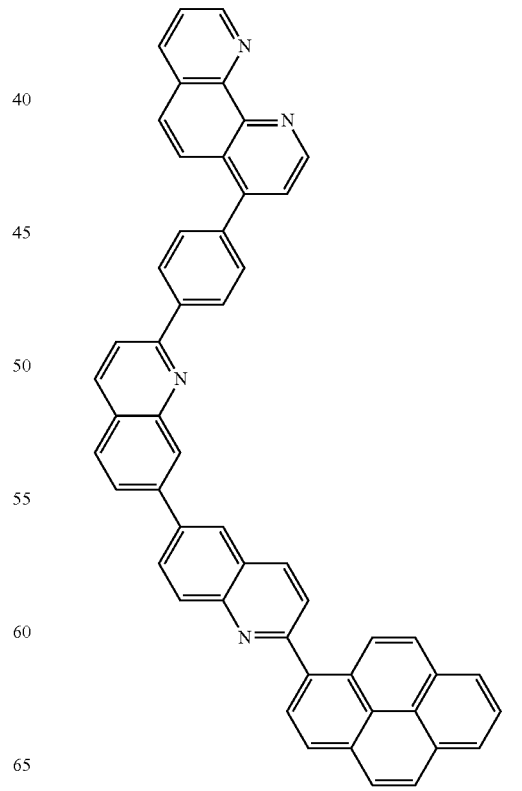

559
-continued
560
-continued
226
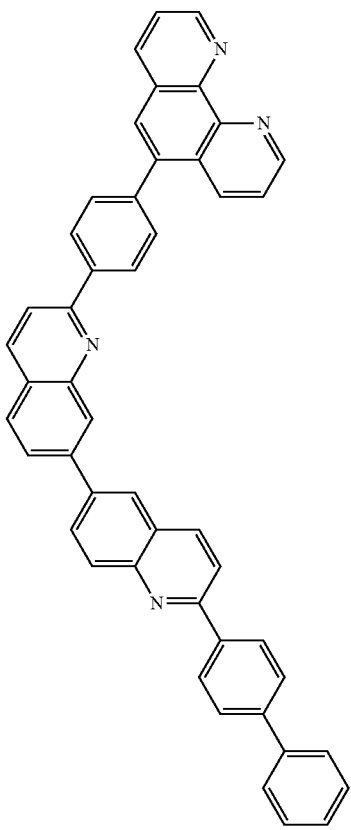
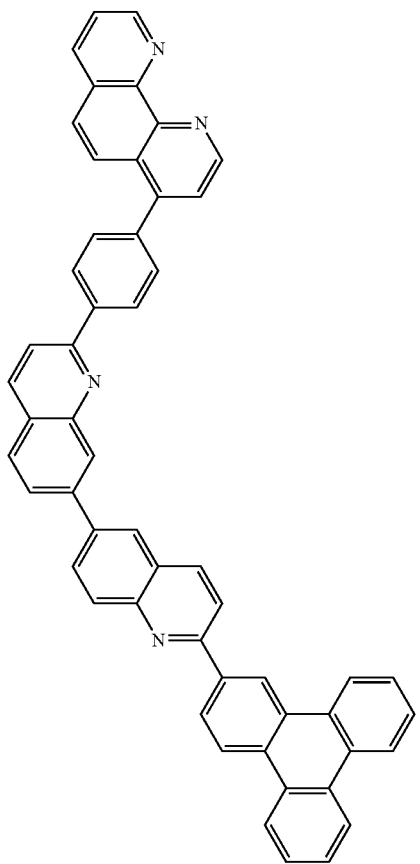
228
227
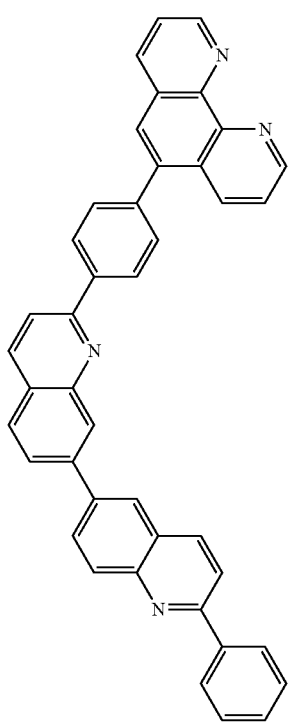 [SMILES: c1ccc(-c2ccc3cc(-c4ccc5ccc(-c6ccc(-c7cc8cccnc8c8ncccc78)cc6)nc5c4)ccc3n2)cc1]
229
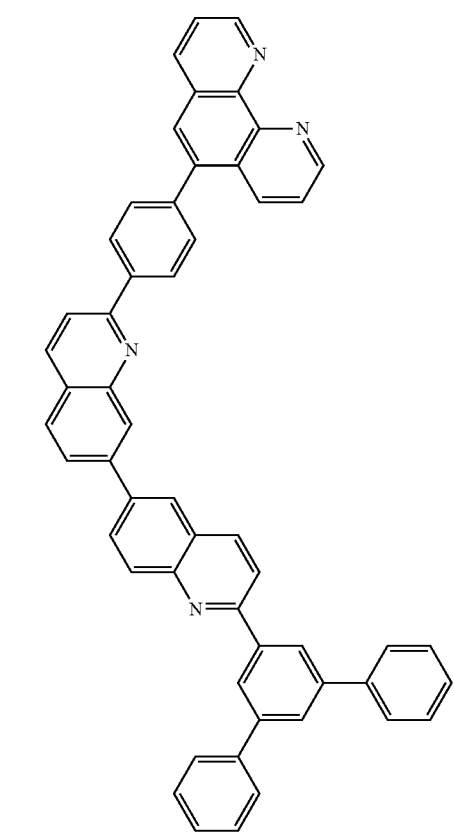

230
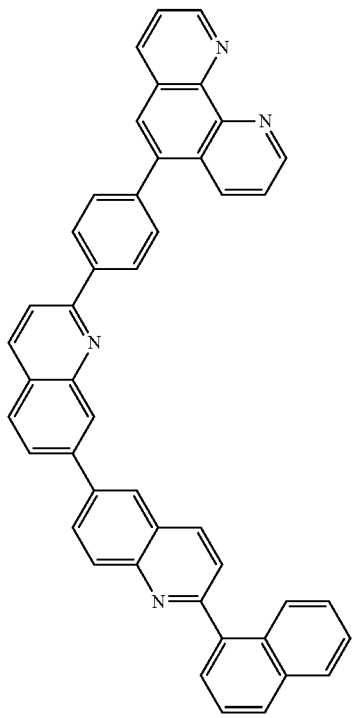
231
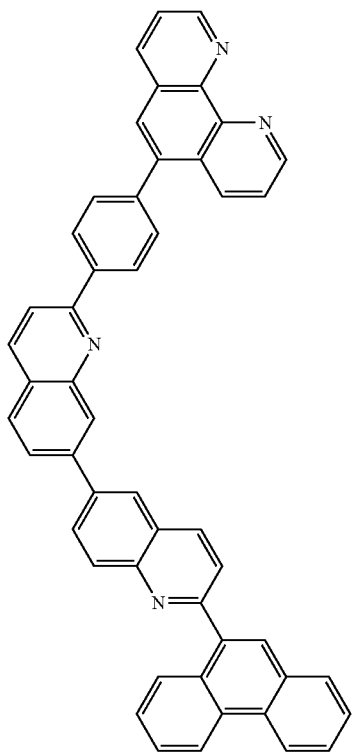
232
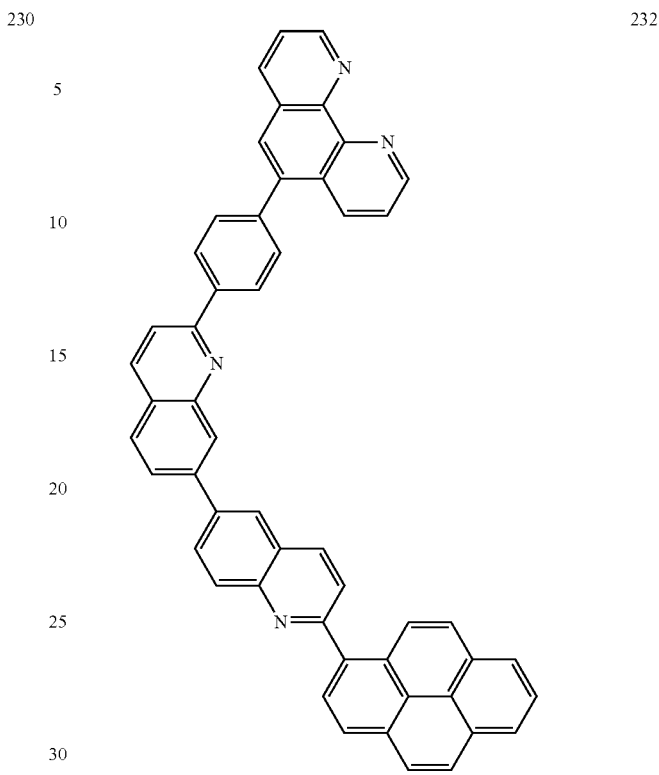
233
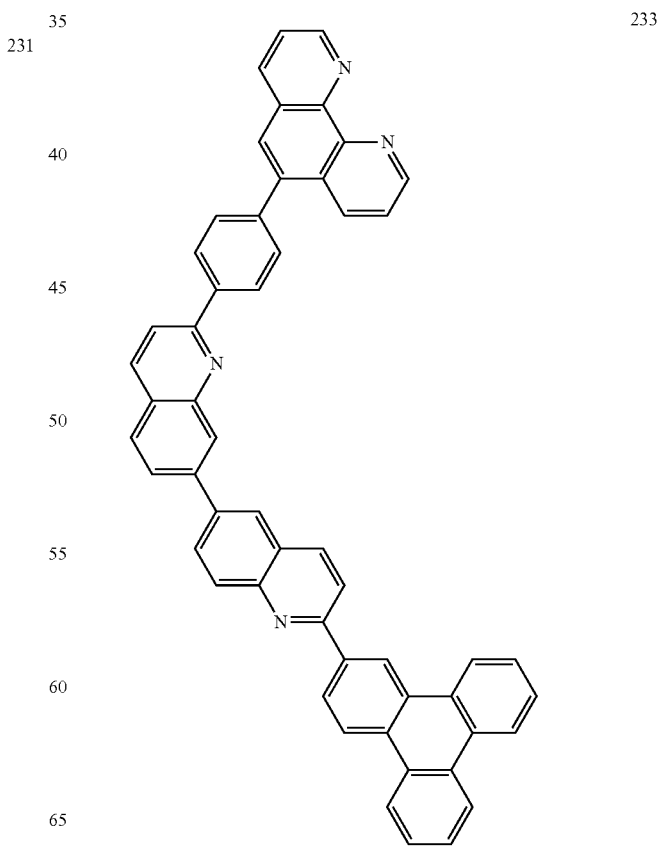

563
-continued
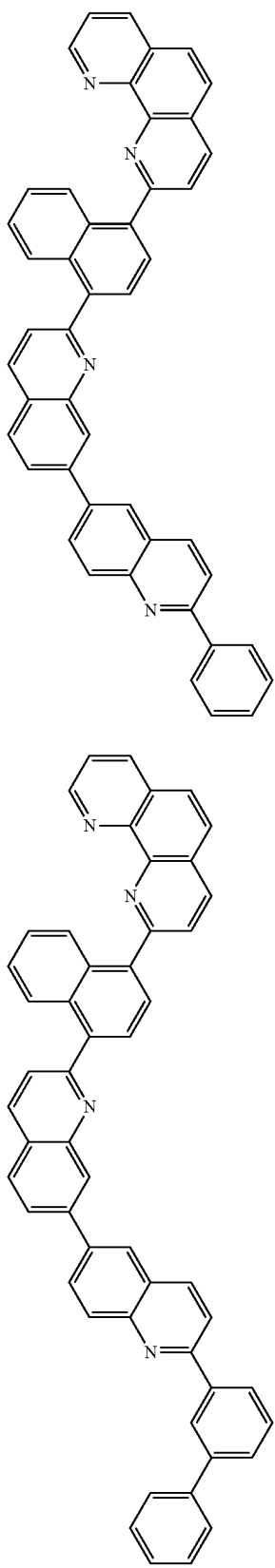
564
-continued
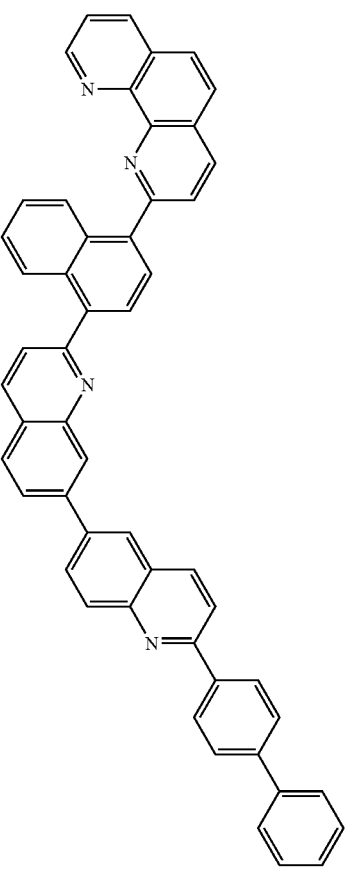 [SMILES: c1ccc(-c2ccc(-c3ccc4cc(-c5ccc6ccc(-c7ccc(-c8ccc9ccc%10cccnc%10c9n8)c8ccccc78)nc6c5)ccc4n3)cc2)cc1]

565
-continued
237
238
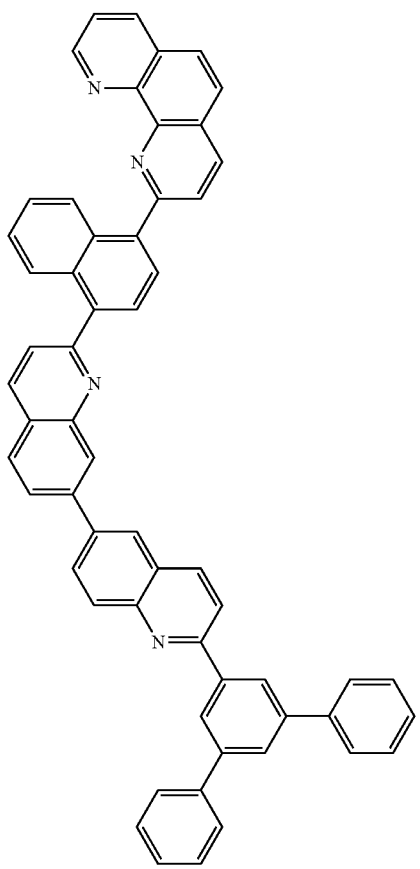
566
-continued
239
240
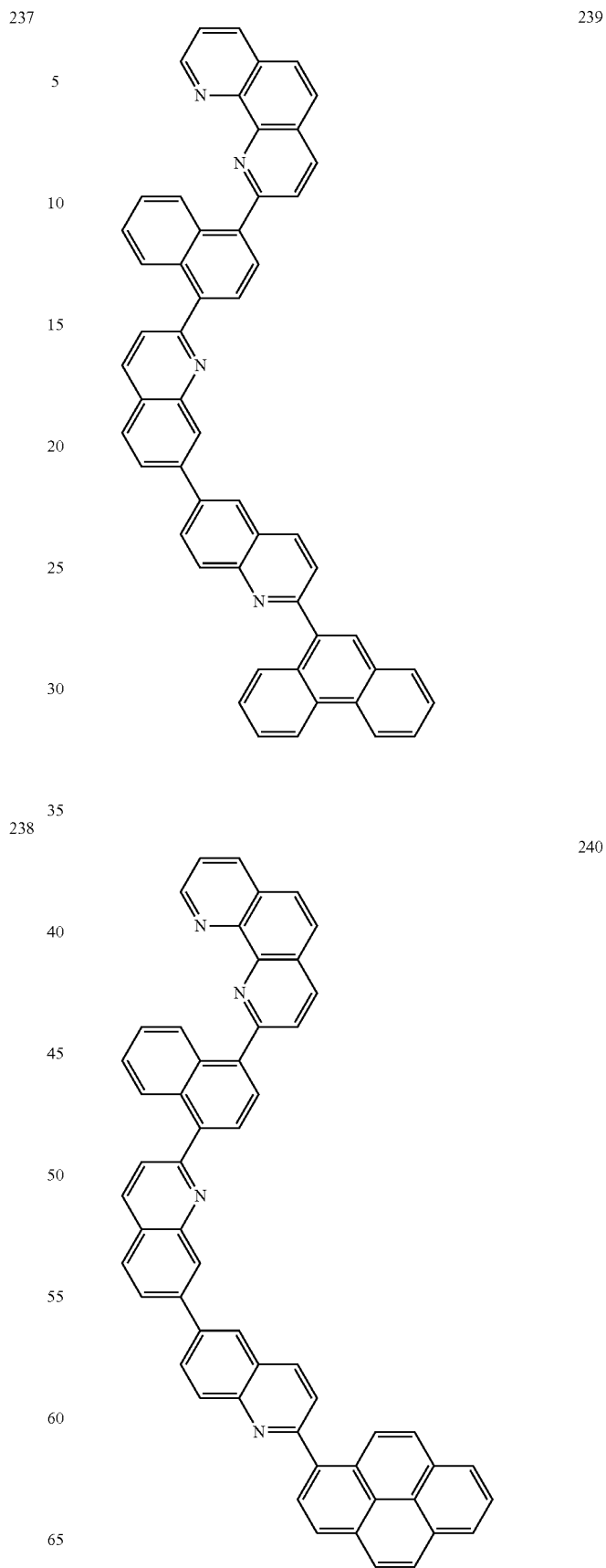

567
-continued
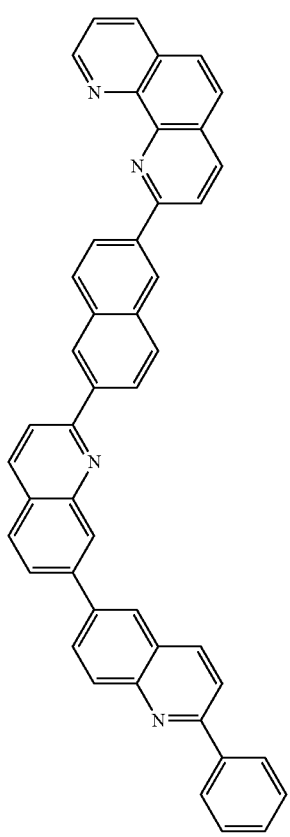 [SMILES: c1ccc(-c2ccc3cc(-c4ccc5ccc(-c6ccc7cc(-c8ccc9ccc%10cccnc%10c9n8)ccc7c6)nc5c4)ccc3n2)cc1]
241
568
-continued
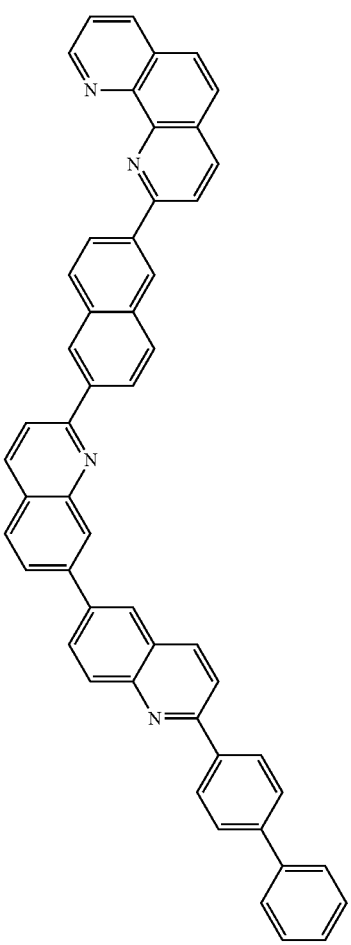
242

569
-continued
570
-continued
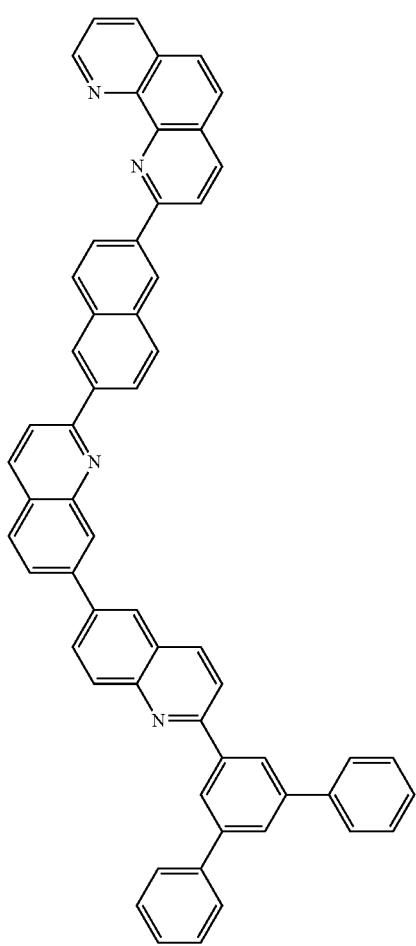
243
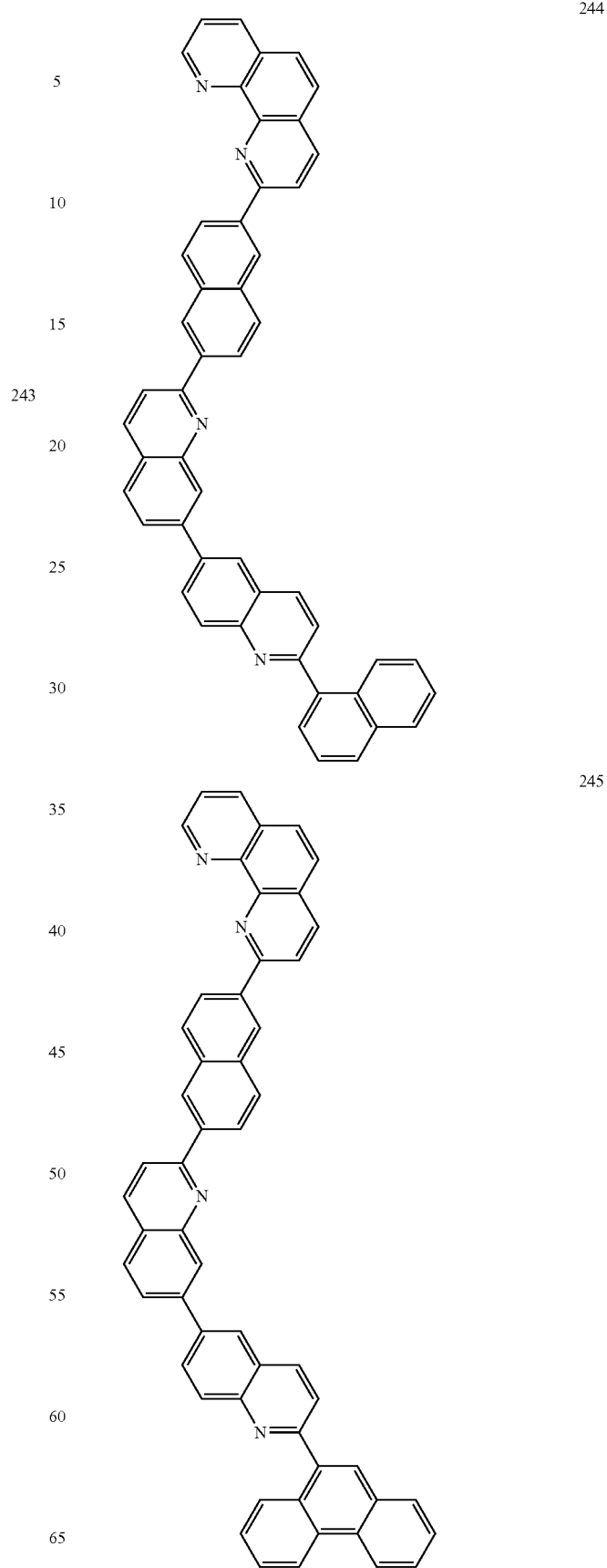
244
245

571
-continued
246
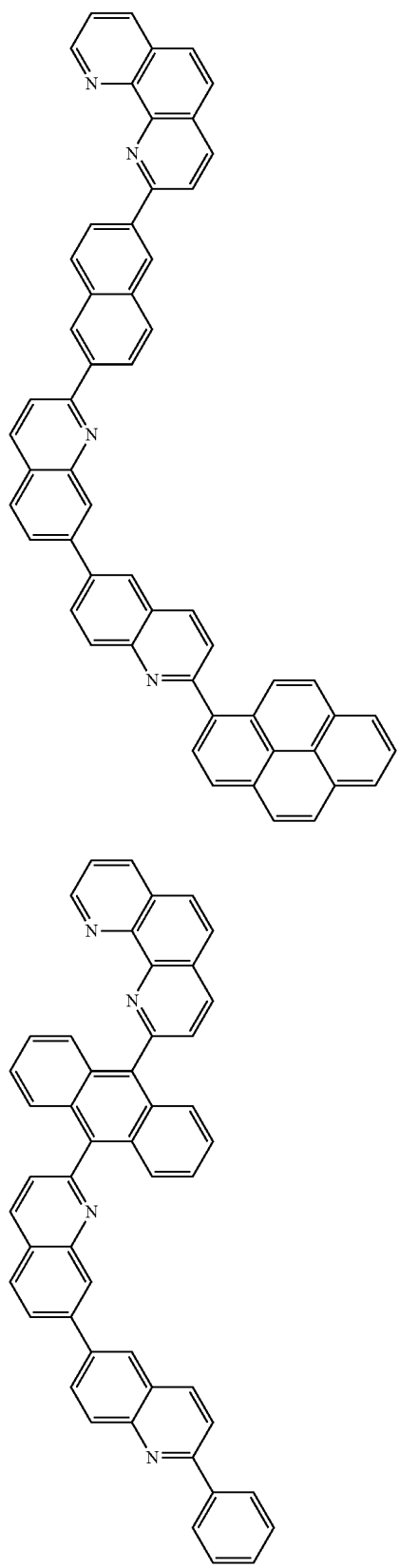
247
572
-continued
248
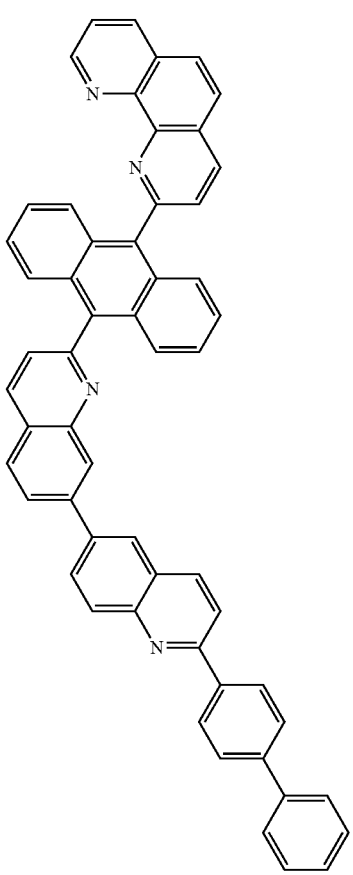

573
-continued
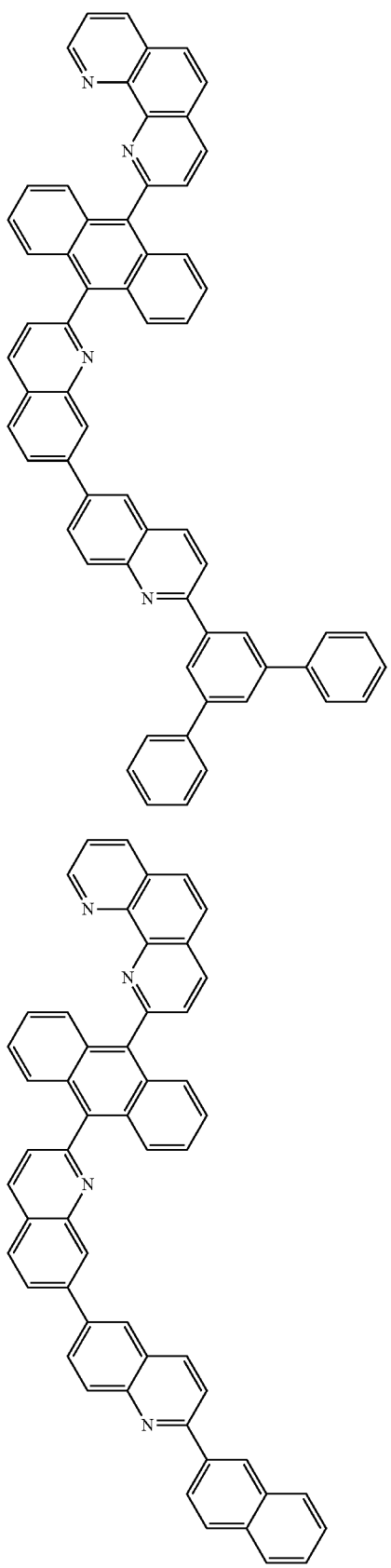
574
-continued
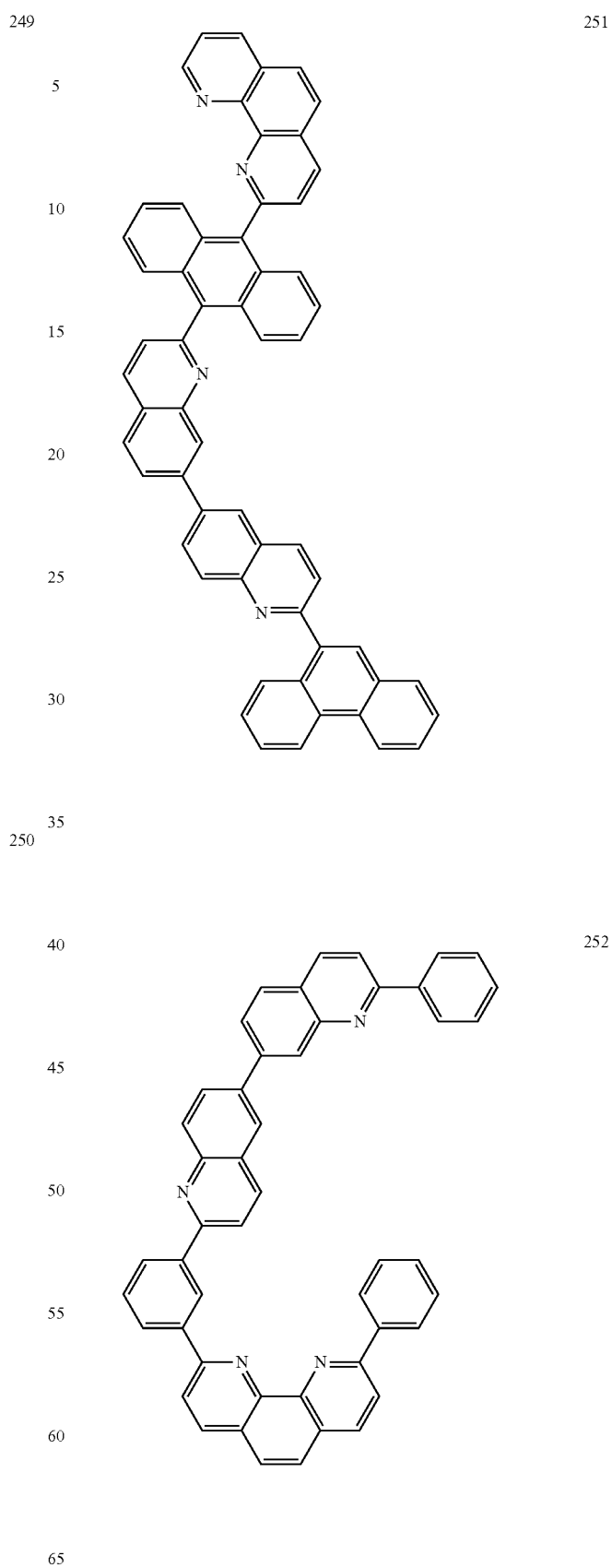

575
-continued
253
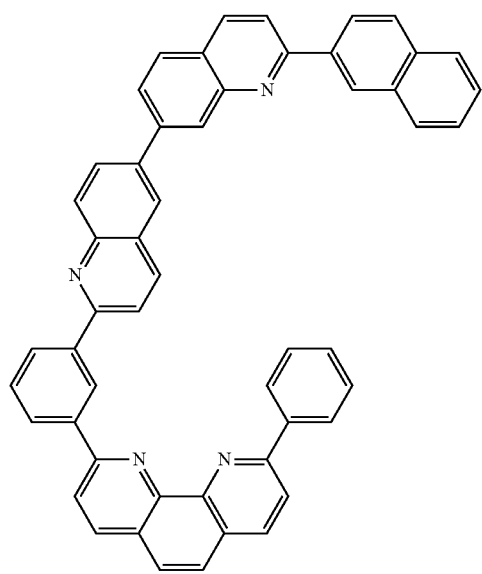
254
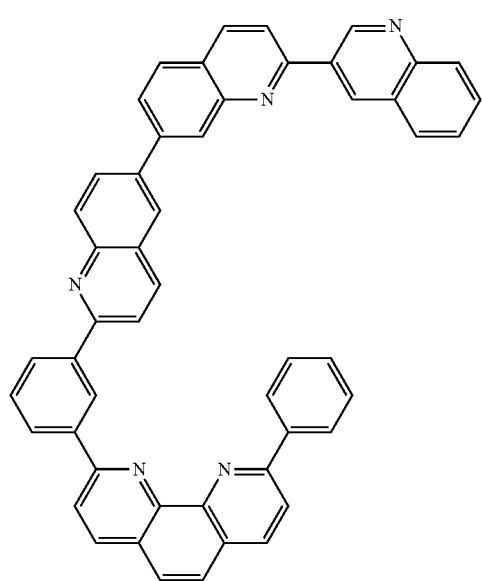
576
-continued
255
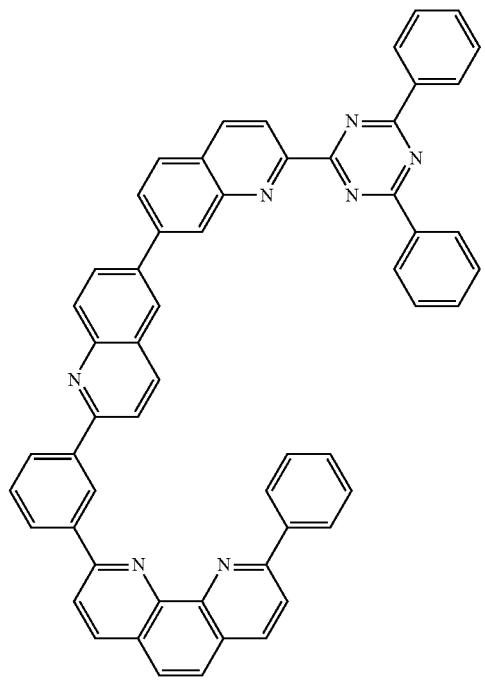
256
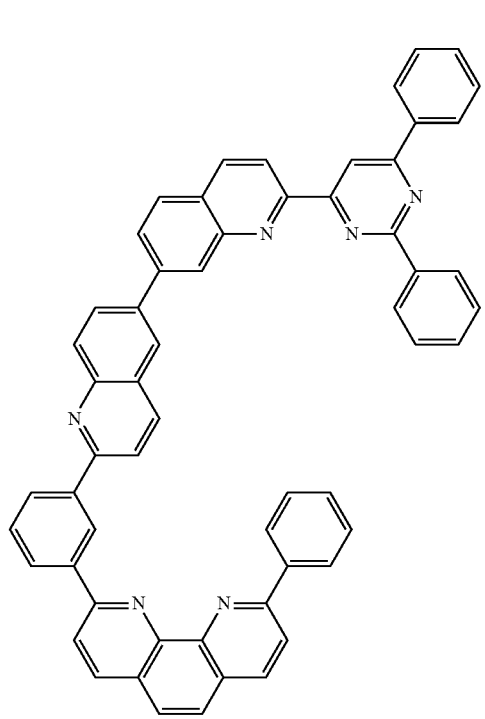
17. The compound of claim 3, wherein the compound represented by Chemical Formula 3 is any one of compounds of the following Group Ill:

[Group III]
1
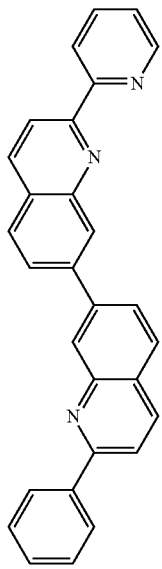
2
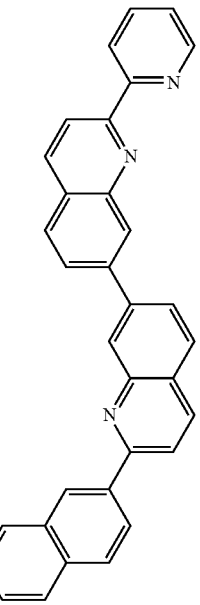
3
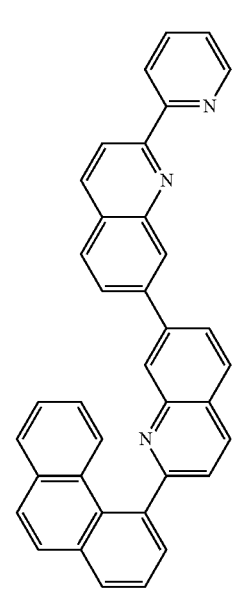
4

-continued
5
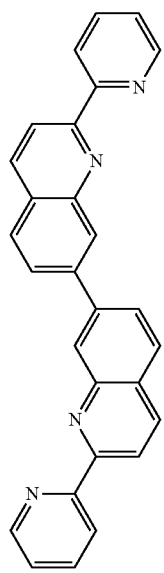
6
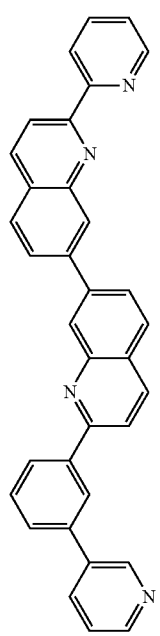
-continued
7
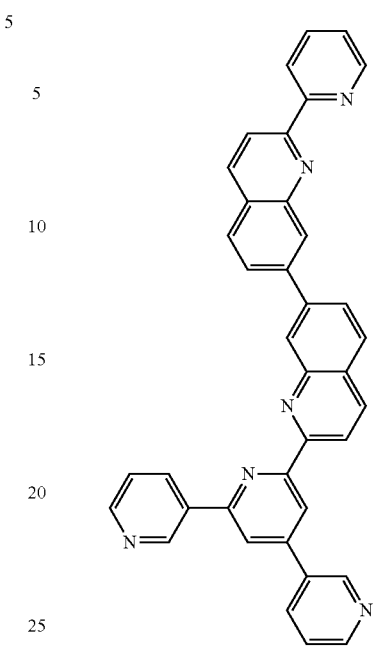
8
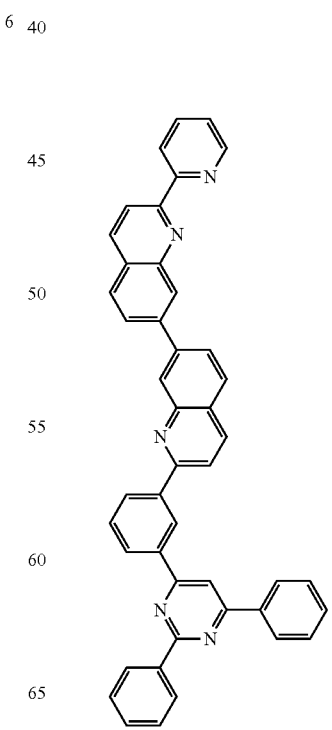

581
-continued
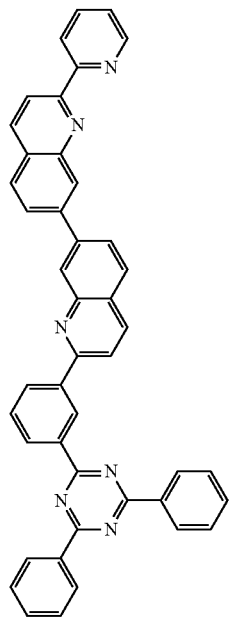 [SMILES: c1ccc(-c2cc(-c3cccc(-c4ccc5ccc(-c6ccc7ccc(-c8ccccn8)nc7c6)cc5n4)c3)nc(-c3ccccc3)n2)cc1]
9
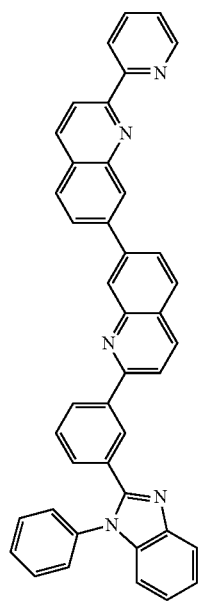
582
-continued
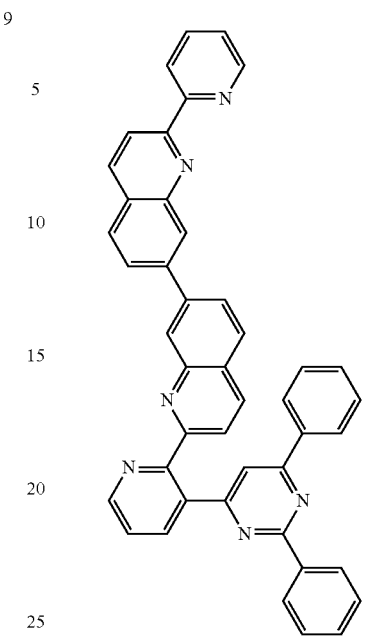
11
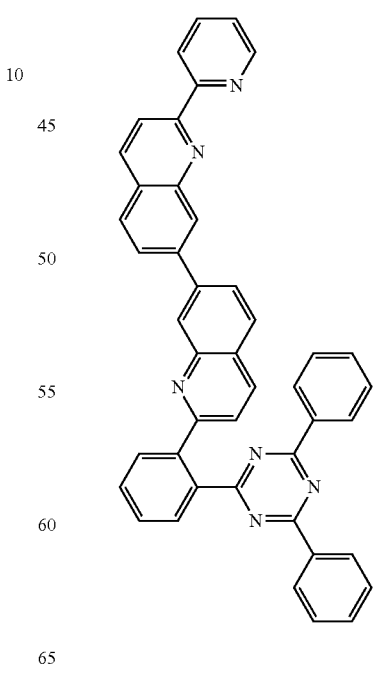
12

583
-continued
13
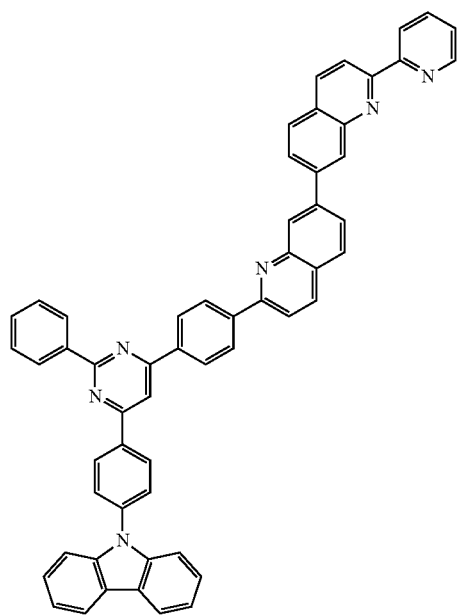 [SMILES: c1ccc(-c2nc(-c3ccc(-c4ccc5ccc(-c6ccc7ccc(-c8ccccn8)nc7c6)cc5n4)cc3)cc(-c3ccc(-n4c5ccccc5c5ccccc54)cc3)n2)cc1]
14
584
-continued
15
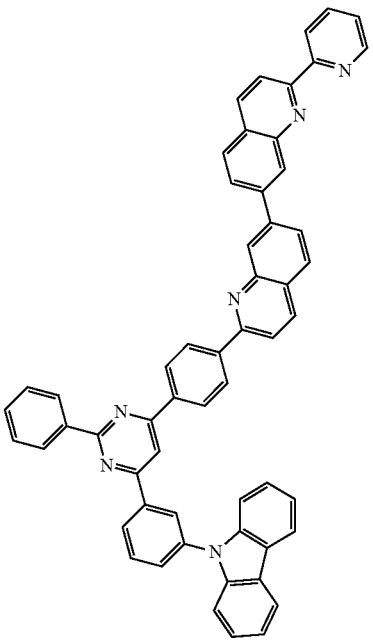
16
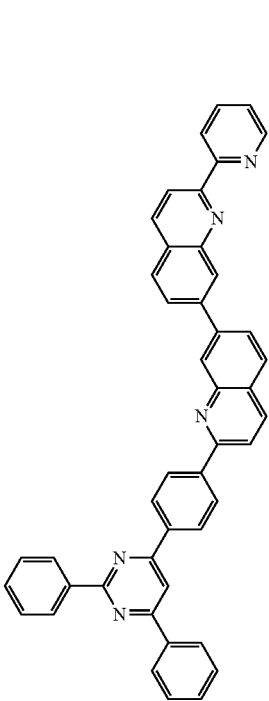

585
-continued
17
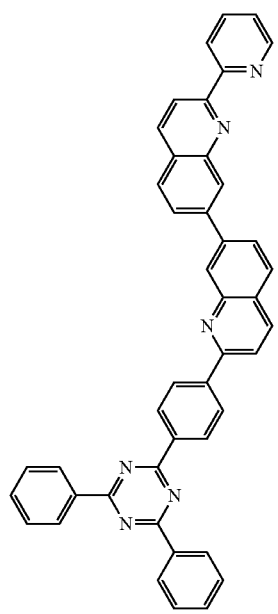 [SMILES: c1ccc(-c2nc(-c3ccccc3)nc(-c3ccc(-c4ccc5ccc(-c6ccc7ccc(-c8ccccn8)nc7c6)cc5n4)cc3)n2)cc1]
18
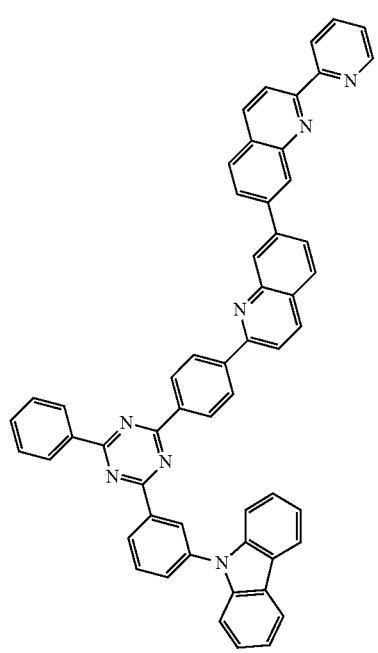
586
-continued
19
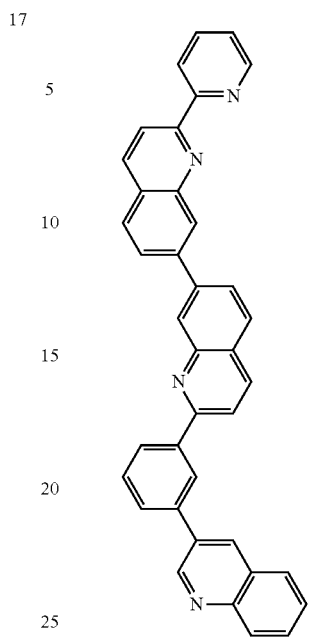
20
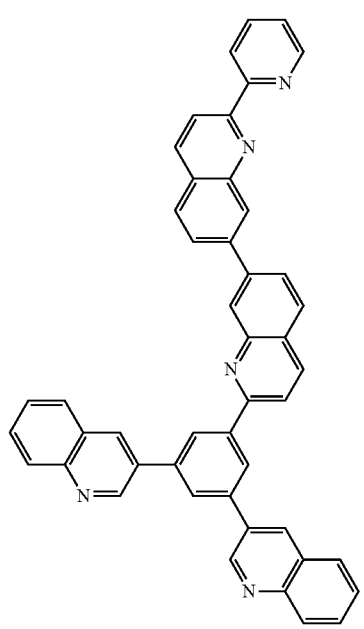

587
21
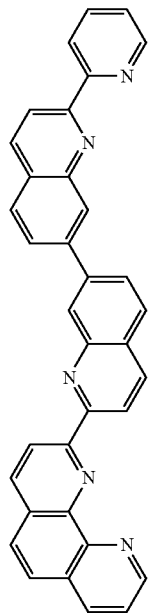 [SMILES: c1ccc(-c2ccc3ccc(-c4ccc5ccc(-c6ccc7ccc8cccnc8c7n6)nc5c4)cc3n2)nc1]
22
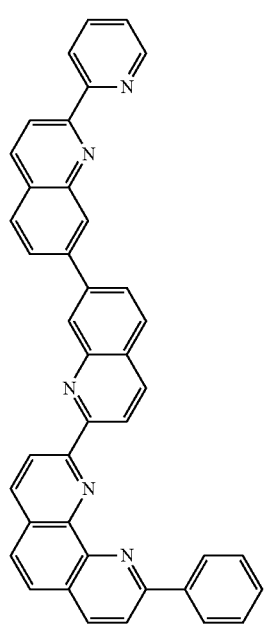
588
23
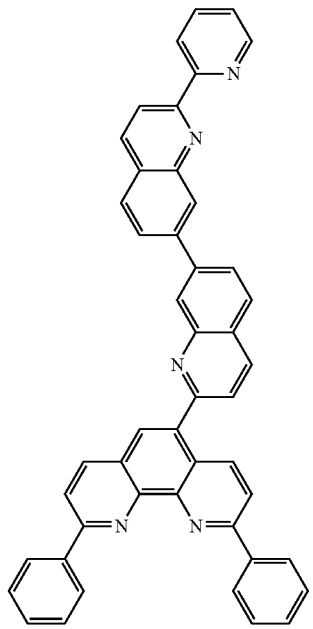
24
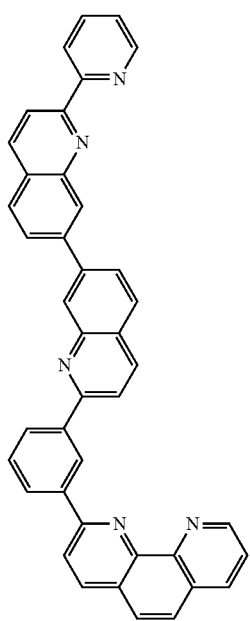 [SMILES: c1ccc(-c2ccc3ccc(-c4ccc5ccc(-c6cccc(-c7ccc8ccc9cccnc9c8n7)c6)nc5c4)cc3n2)nc1]

25
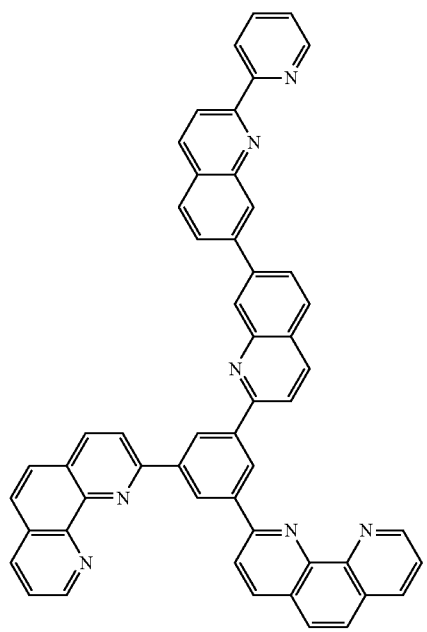
26
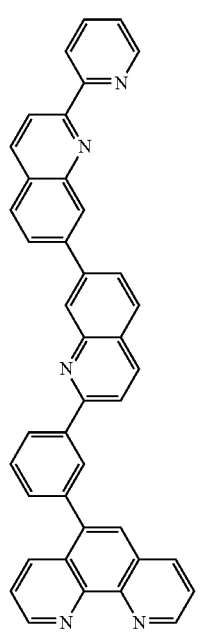
27
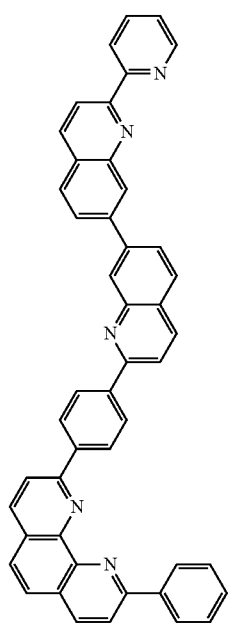
28
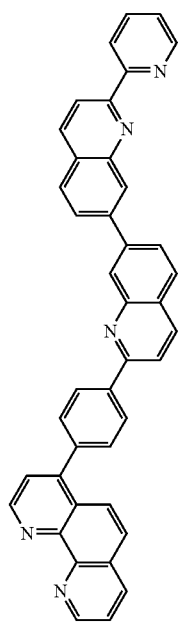

591 592
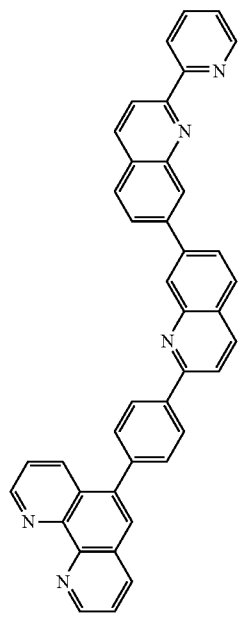
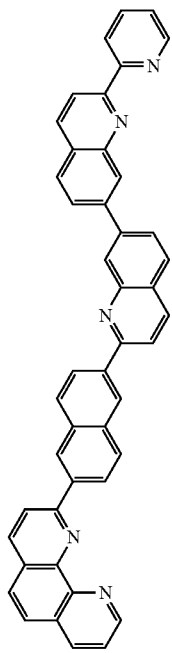
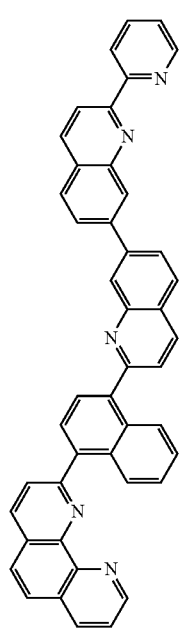
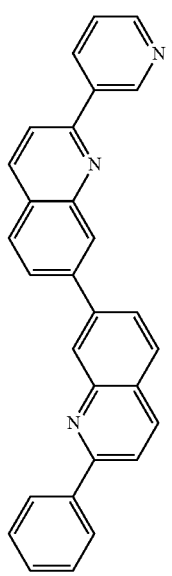 [SMILES: c1ccc(-c2ccc3ccc(-c4ccc5ccc(-c6cccnc6)nc5c4)cc3n2)cc1]

33
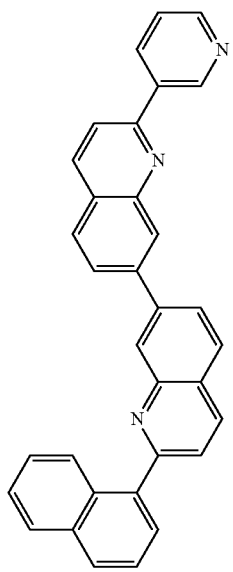
34
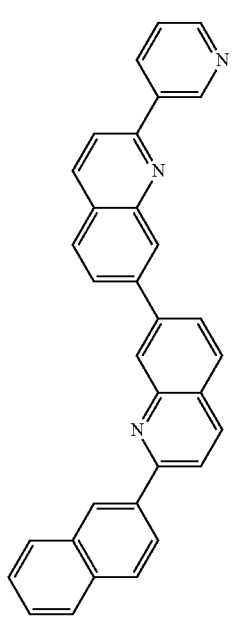 [SMILES: c1cncc(-c2ccc3ccc(-c4ccc5ccc(-c6ccc7ccccc7c6)nc5c4)cc3n2)c1]
35
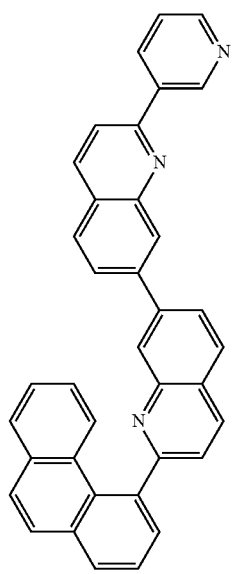
36
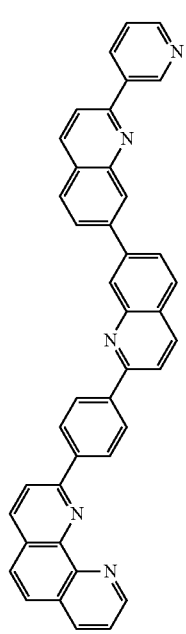 [SMILES: c1cncc(-c2ccc3ccc(-c4ccc5ccc(-c6ccc(-c7ccc8ccc9cccnc9c8n7)cc6)nc5c4)cc3n2)c1]

37
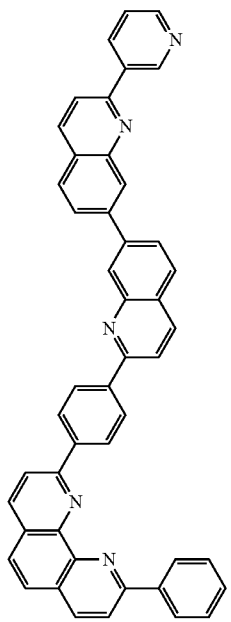
38
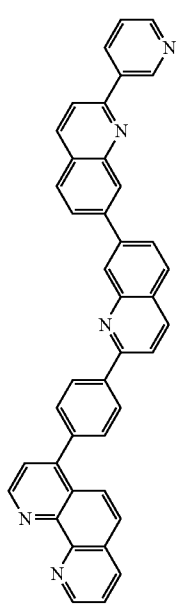
39
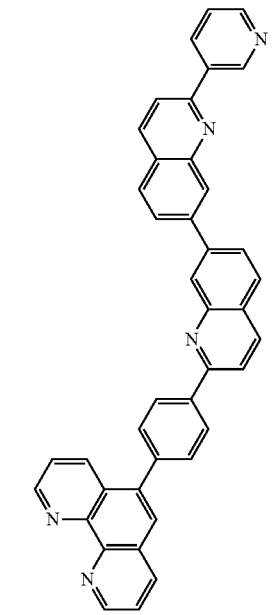
40
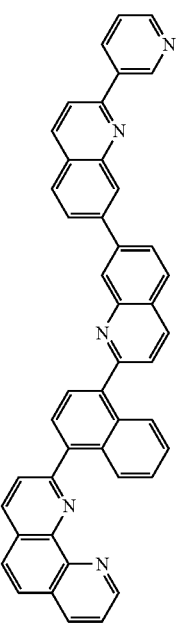

41
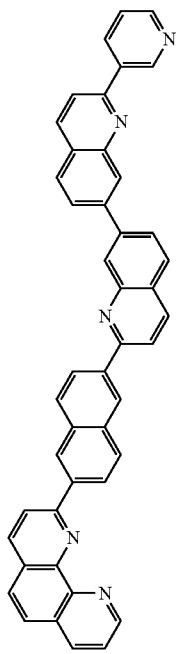
42
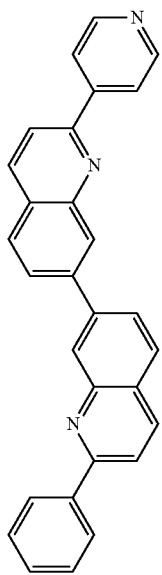
43
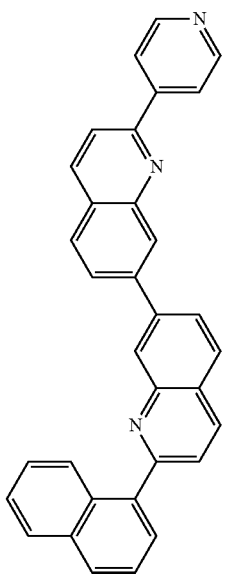 [SMILES: c1ccc2c(-c3ccc4ccc(-c5ccc6ccc(-c7ccncc7)nc6c5)cc4n3)cccc2c1]
44
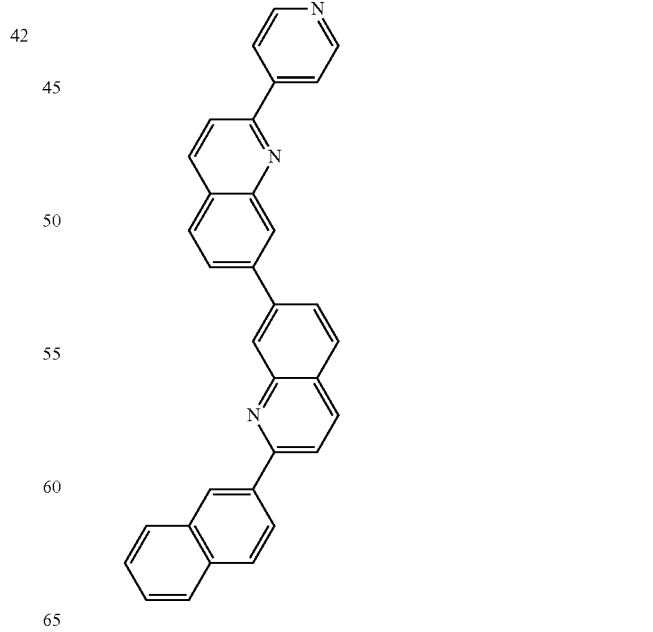

45
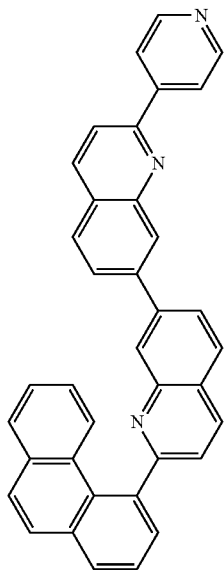
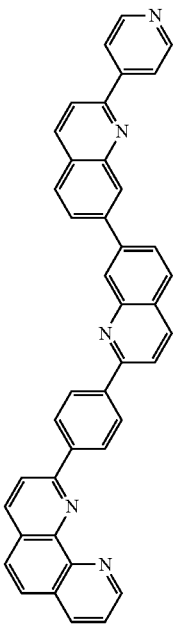 [SMILES: c1cnc2c(c1)ccc1ccc(-c3ccc(-c4ccc5ccc(-c6ccc7ccc(-c8ccncc8)nc7c6)cc5n4)cc3)nc12]
46
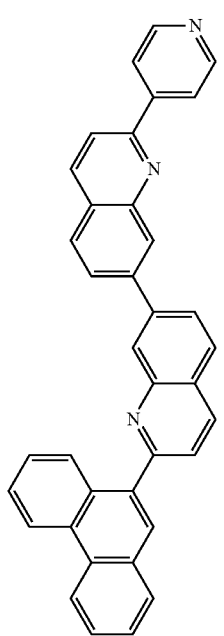
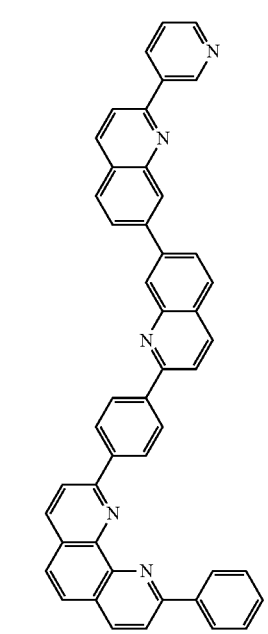

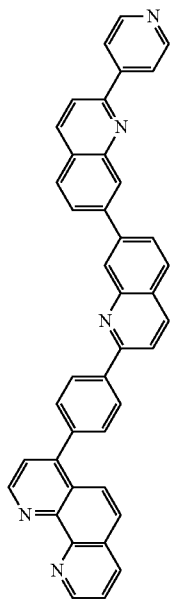
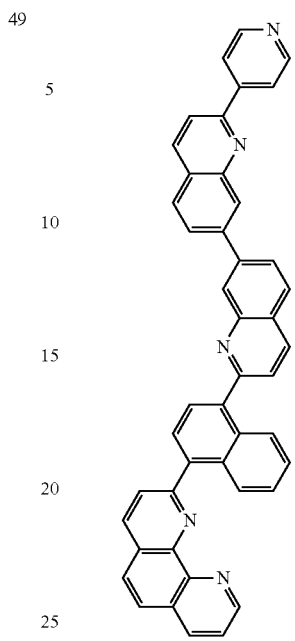
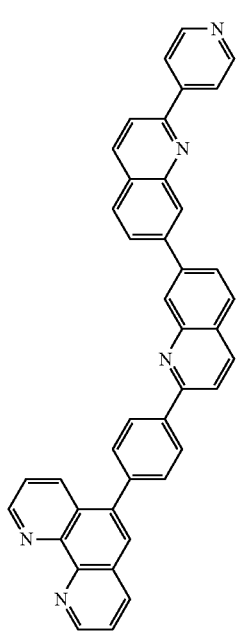
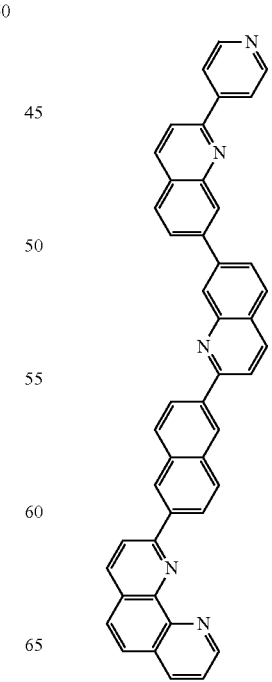

603
-continued
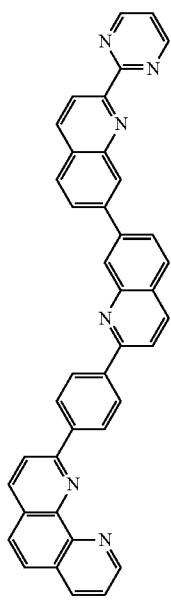
53
604
-continued
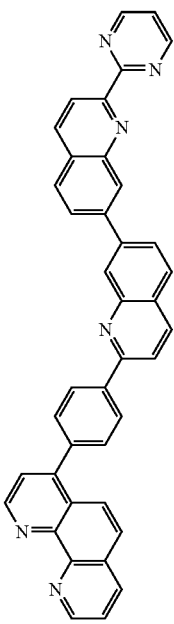
54
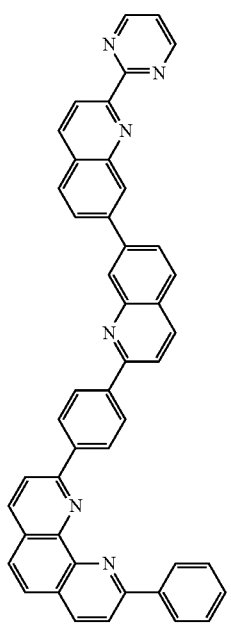
55
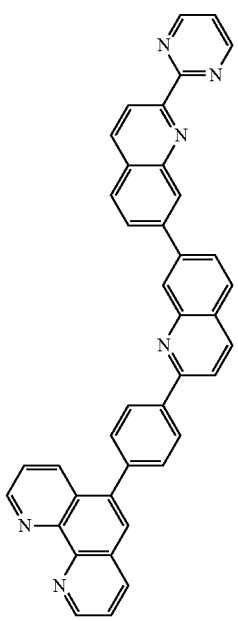
56

605
-continued
57
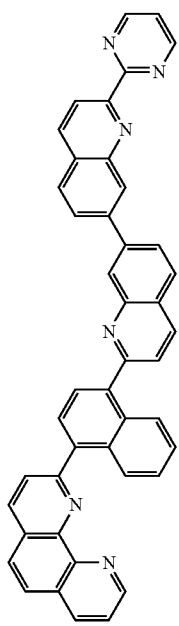
58
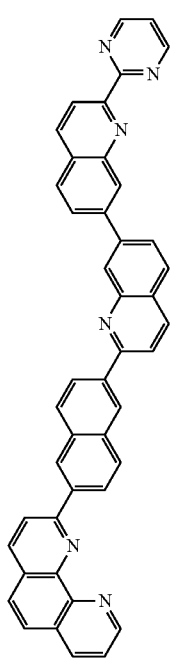
606
-continued
59
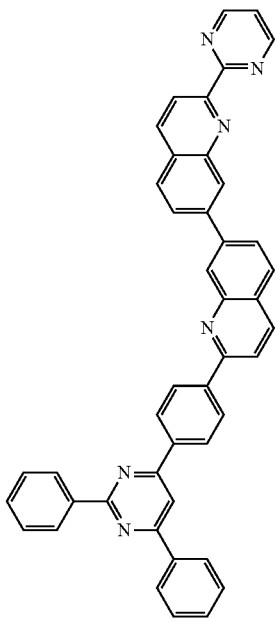 [SMILES: c1ccc(-c2cc(-c3ccc(-c4ccc5ccc(-c6ccc7ccc(-c8ncccn8)nc7c6)cc5n4)cc3)nc(-c3ccccc3)n2)cc1]
60
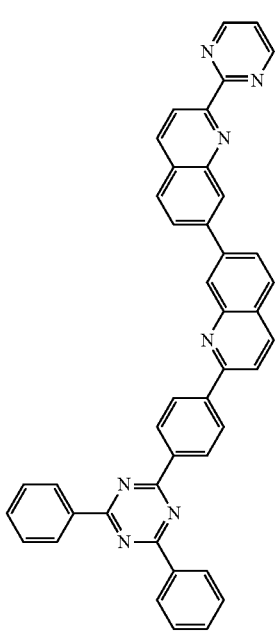 [SMILES: c1ccc(-c2nc(-c3ccccc3)nc(-c3ccc(-c4ccc5ccc(-c6ccc7ccc(-c8ncccn8)nc7c6)cc5n4)cc3)n2)cc1]

-continued
61
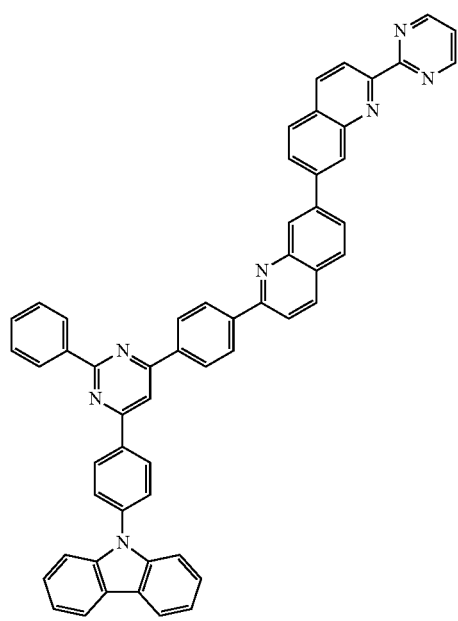
63
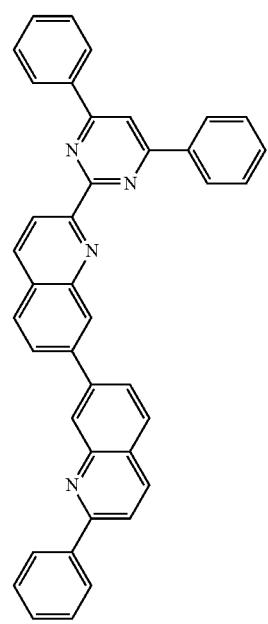
62
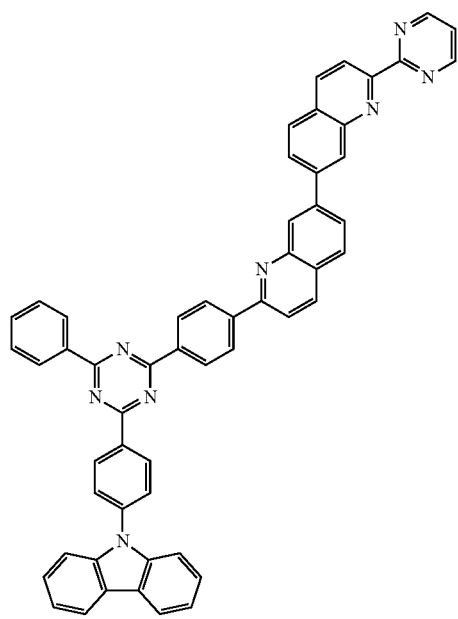 [SMILES: c1ccc(-c2nc(-c3ccc(-c4ccc5ccc(-c6ccc7ccc(-c8ncccn8)nc7c6)cc5n4)cc3)nc(-c3ccc(-n4c5ccccc5c5ccccc54)cc3)n2)cc1]
64
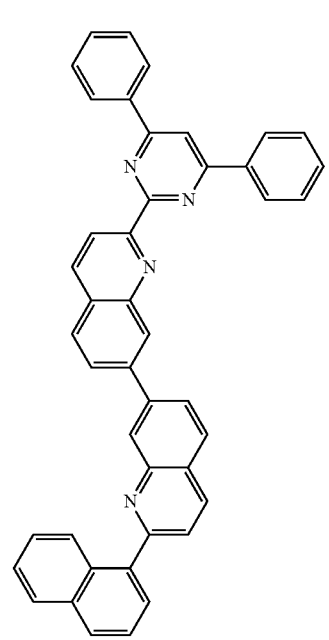

609
-continued
65
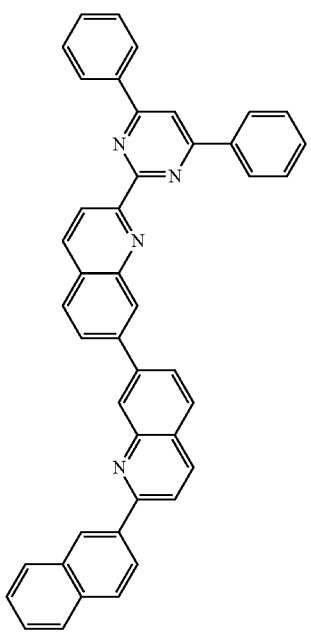
66
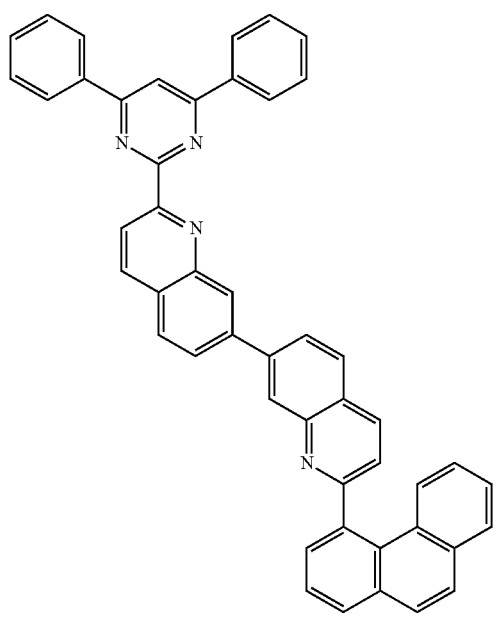
610
-continued
67
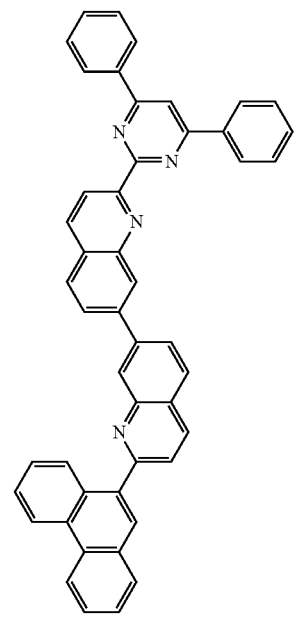
68
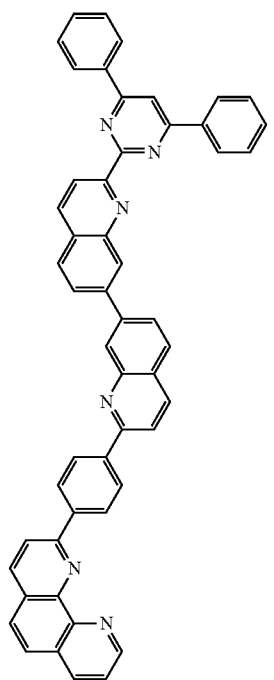 [SMILES: c1ccc(-c2cc(-c3ccccc3)nc(-c3ccc4ccc(-c5ccc6ccc(-c7ccc(-c8ccc9ccc%10cccnc%10c9n8)cc7)nc6c5)cc4n3)n2)cc1]

611
-continued
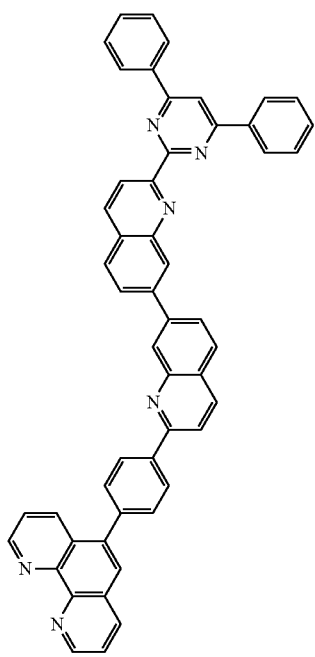
69
612
-continued
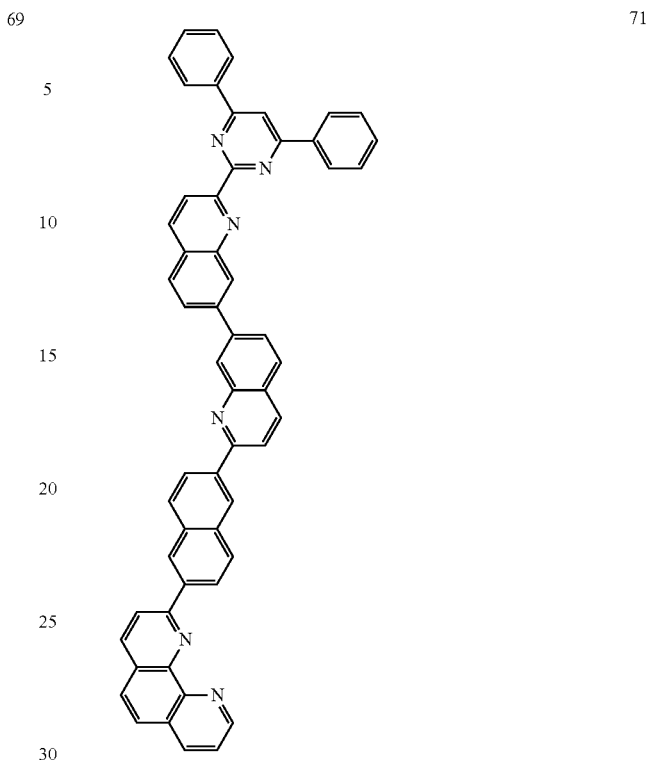
71
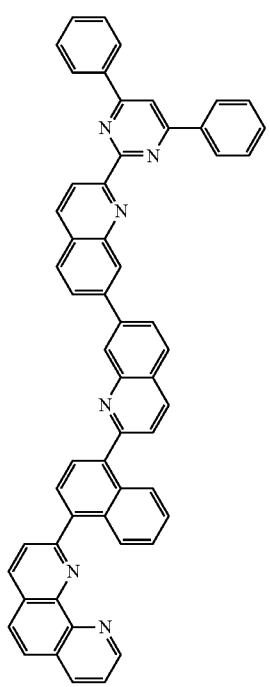
70
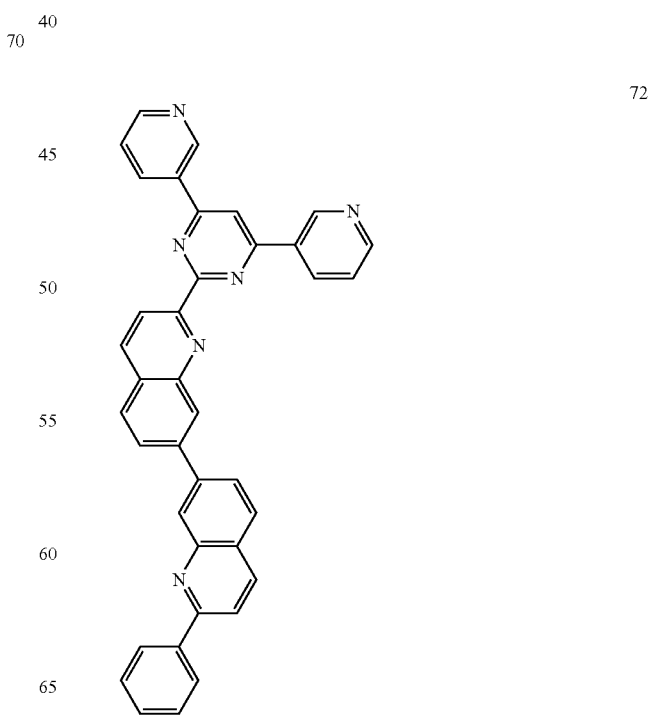
72

73
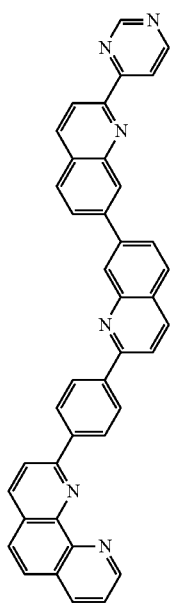 [SMILES: c1cnc2c(c1)ccc1ccc(-c3ccc(-c4ccc5ccc(-c6ccc7ccc(-c8ccncn8)nc7c6)cc5n4)cc3)nc12]
74
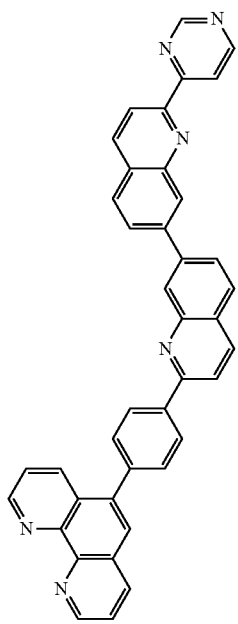
75
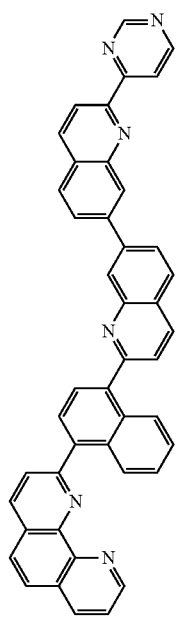
76
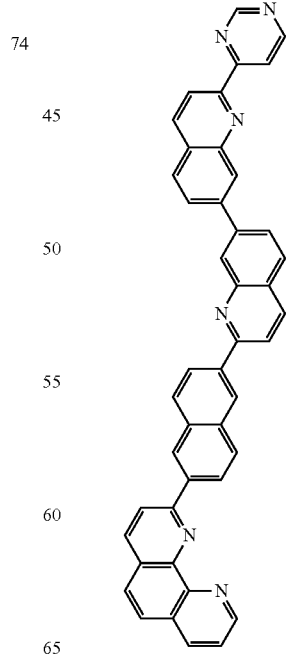

615
-continued
77
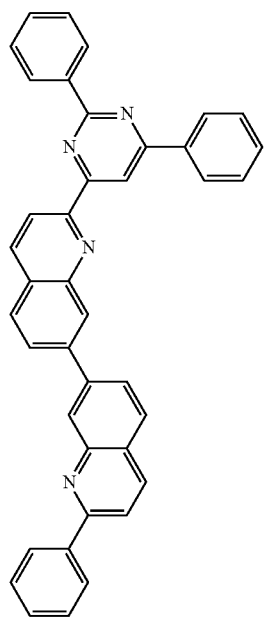
616
-continued
79
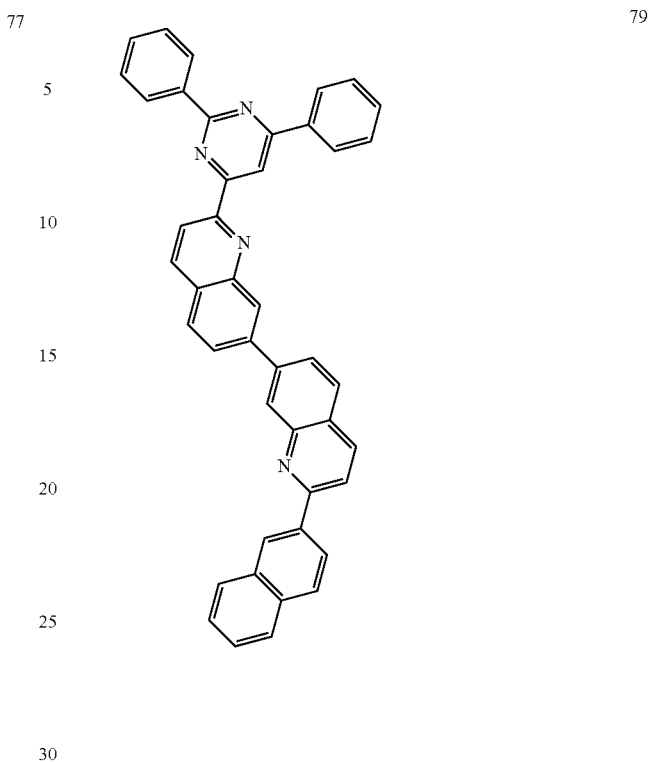
78
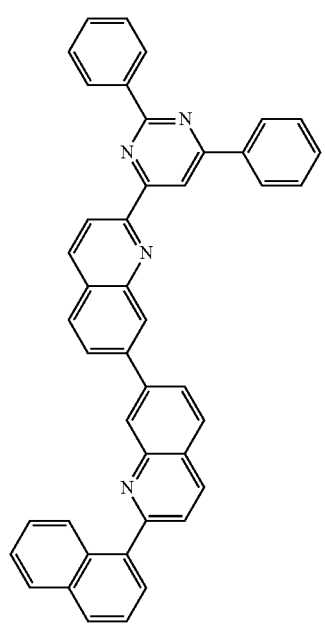 [SMILES: c1ccc(-c2cc(-c3ccc4ccc(-c5ccc6ccc(-c7cccc8ccccc78)nc6c5)cc4n3)nc(-c3ccccc3)n2)cc1]
80
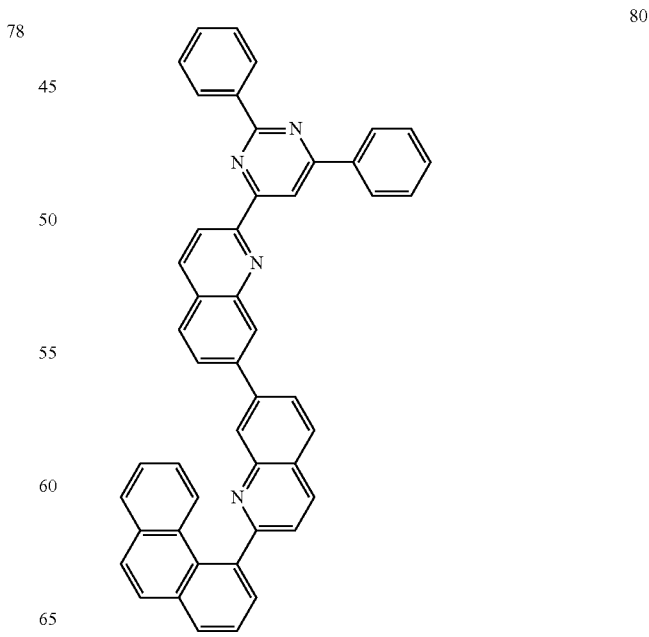

617
-continued
81
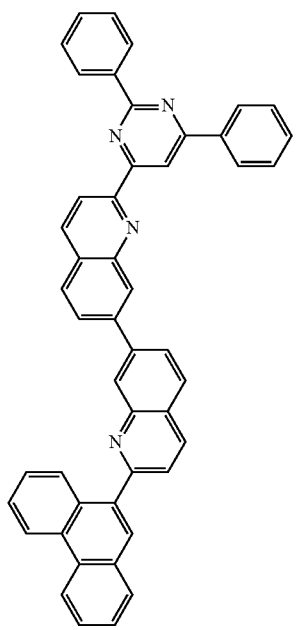
82
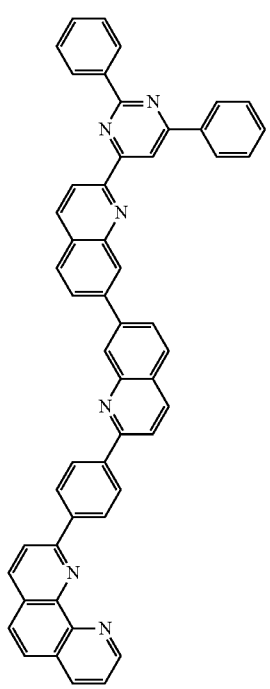
618
-continued
83
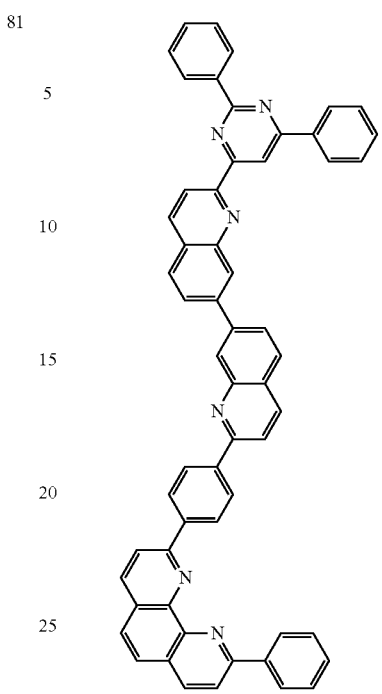
84
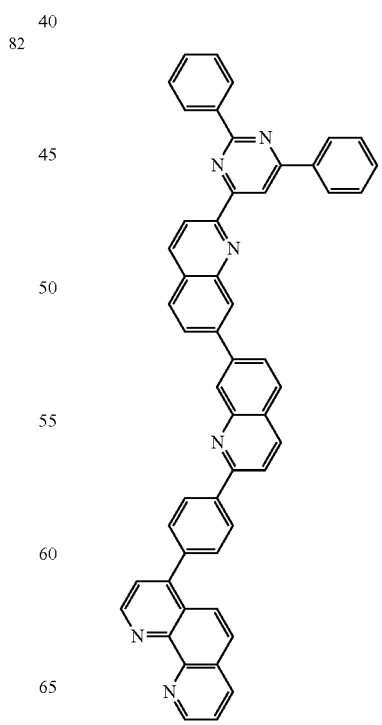

619
-continued
85
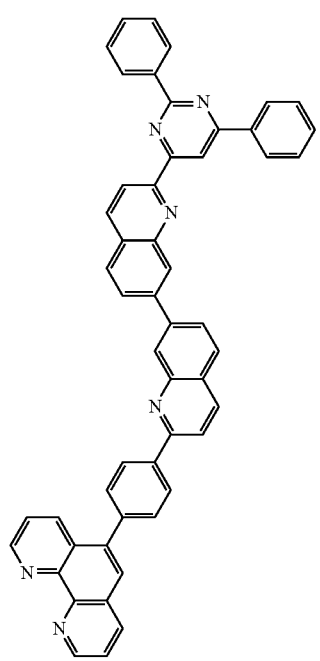 [SMILES: c1ccc(-c2cc(-c3ccc4ccc(-c5ccc6ccc(-c7ccc(-c8cc9cccnc9c9ncccc89)cc7)nc6c5)cc4n3)nc(-c3ccccc3)n2)cc1]
620
-continued
87
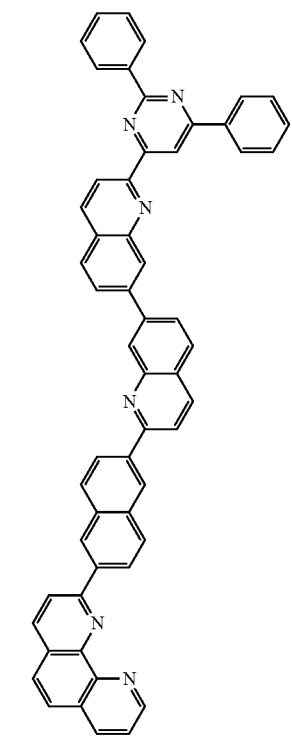
86
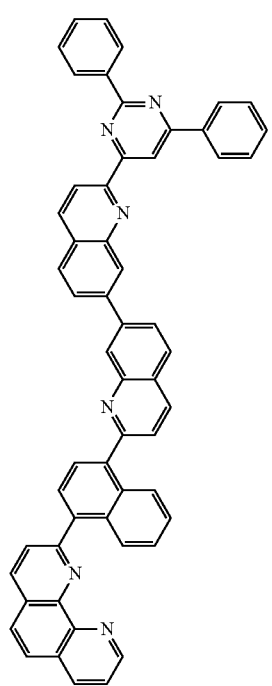
88
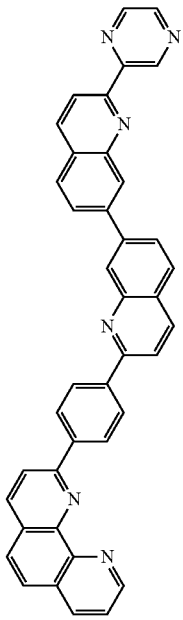

621
-continued
89
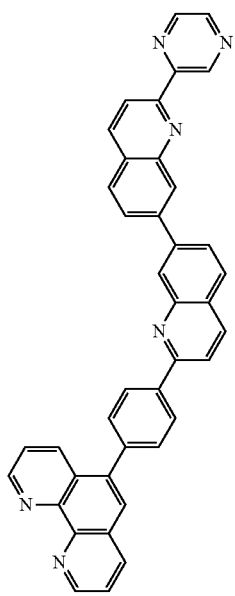
90
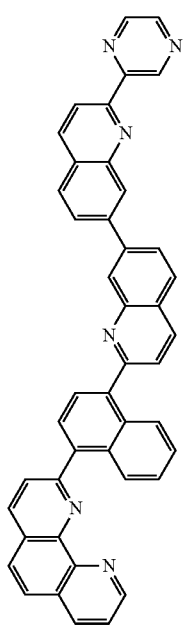
622
-continued
91
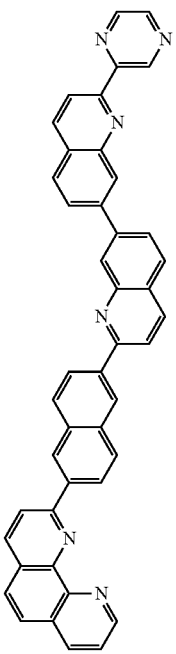
92
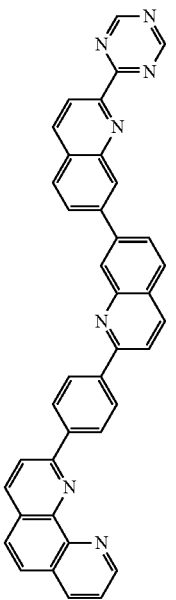 [SMILES: c1cnc2c(c1)ccc1ccc(-c3ccc(-c4ccc5ccc(-c6ccc7ccc(-c8ncncn8)nc7c6)cc5n4)cc3)nc12]

93
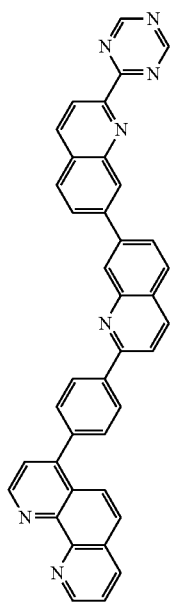
95
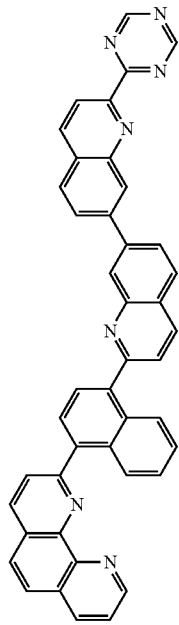
94
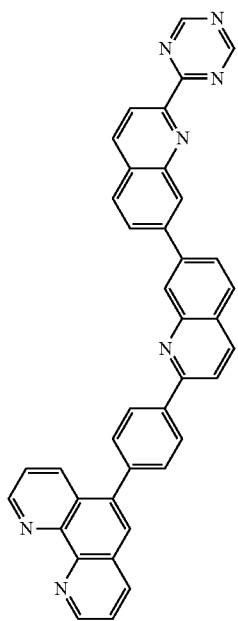
96
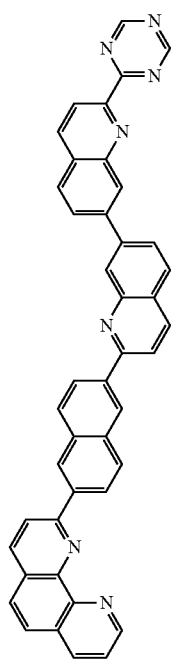

97
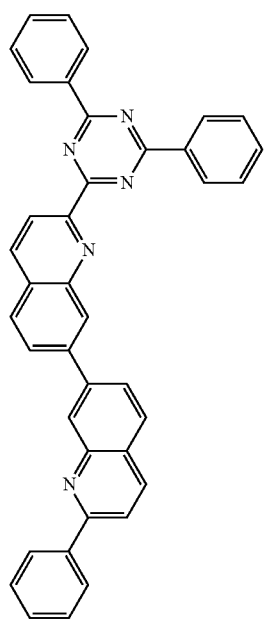 [SMILES: c1ccc(-c2ccc3ccc(-c4ccc5ccc(-c6nc(-c7ccccc7)nc(-c7ccccc7)n6)nc5c4)cc3n2)cc1]
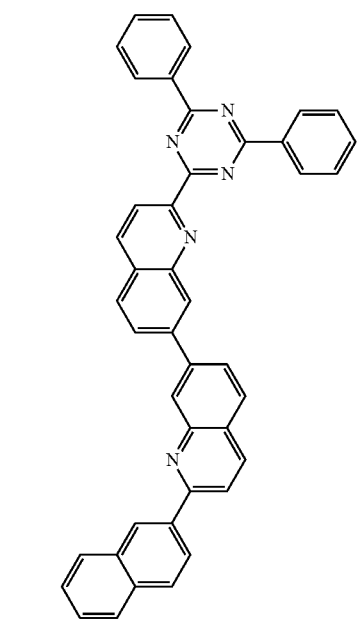
98
99
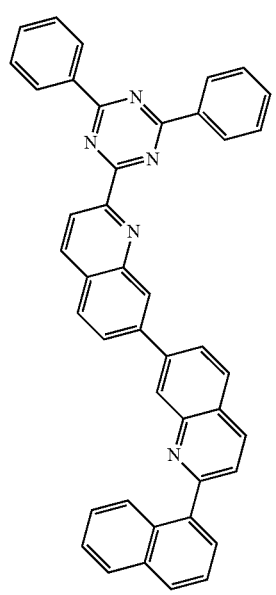
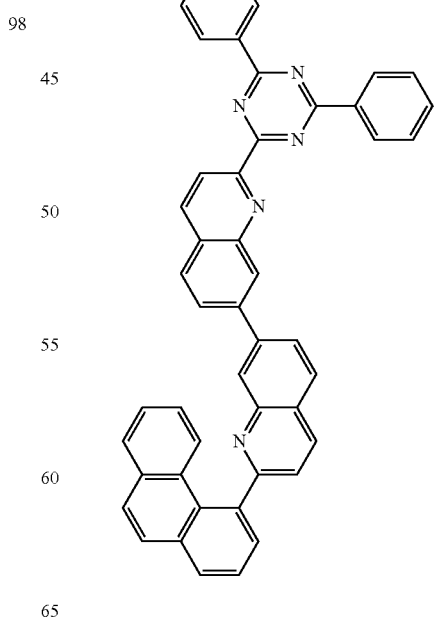
100

627
-continued
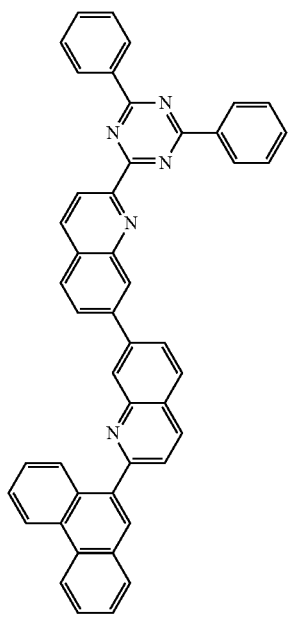
628
-continued
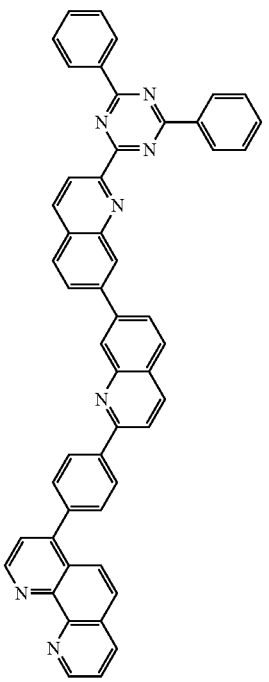
101
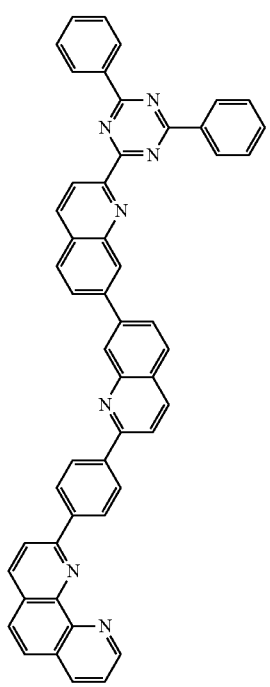 [SMILES: c1ccc(-c2nc(-c3ccccc3)nc(-c3ccc4ccc(-c5ccc6ccc(-c7ccc(-c8ccc9ccc%10cccnc%10c9n8)cc7)nc6c5)cc4n3)n2)cc1]
102
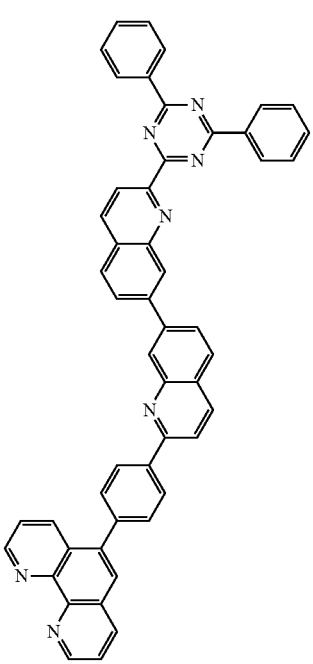
103
104

629
-continued
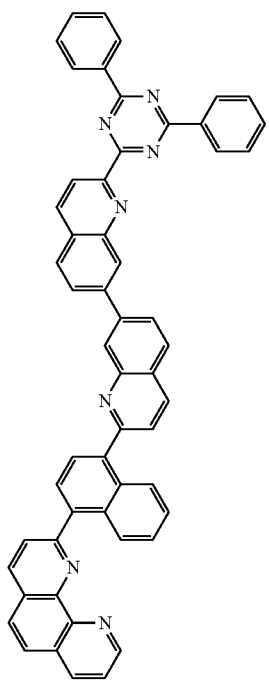 [SMILES: c1ccc(-c2nc(-c3ccccc3)nc(-c3ccc4ccc(-c5ccc6ccc(-c7ccc(-c8ccc9ccc%10cccnc%10c9n8)c8ccccc78)nc6c5)cc4n3)n2)cc1]
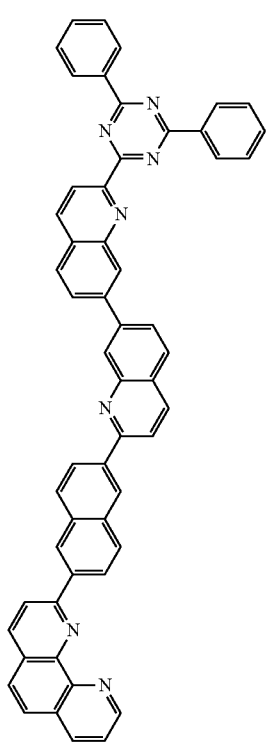
630
-continued
105
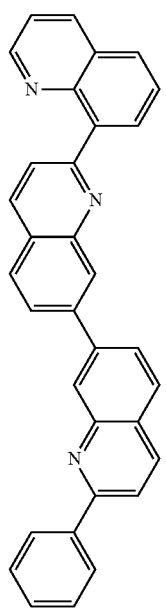 [SMILES: c1ccc(-c2ccc3ccc(-c4ccc5ccc(-c6cccc7cccnc67)nc5c4)cc3n2)cc1]
106
107
108
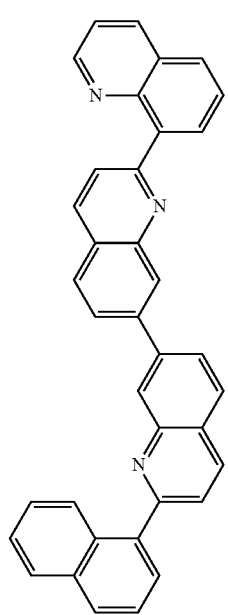

631
-continued
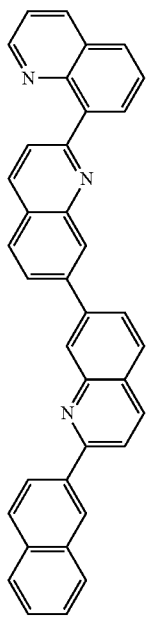
632
-continued
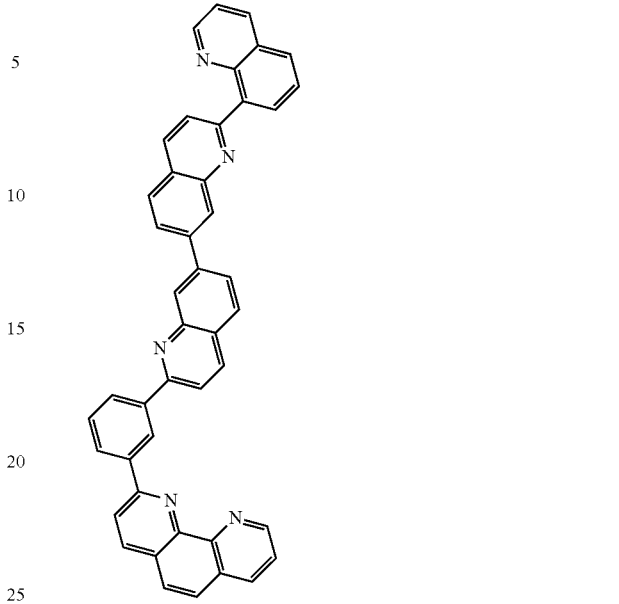
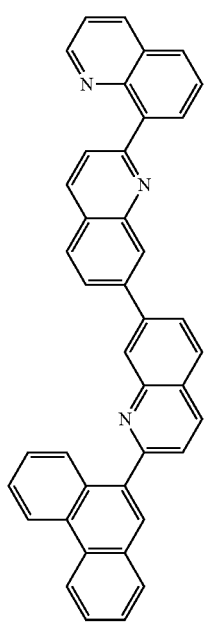
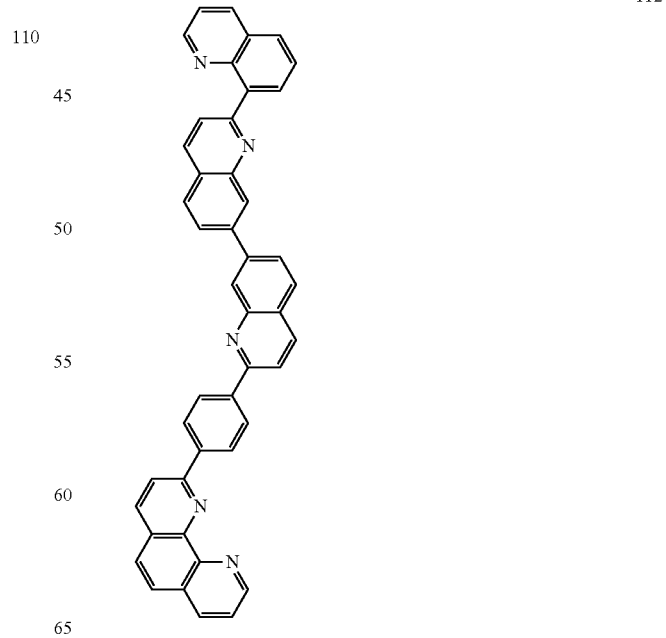

113
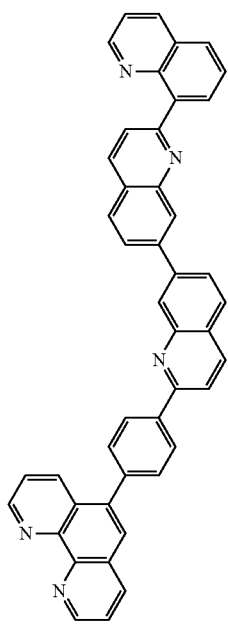
114
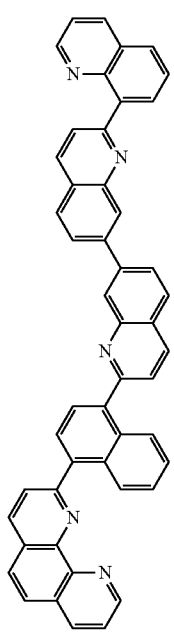
115
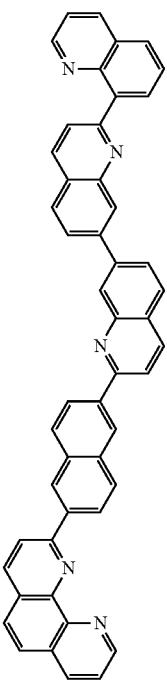
116
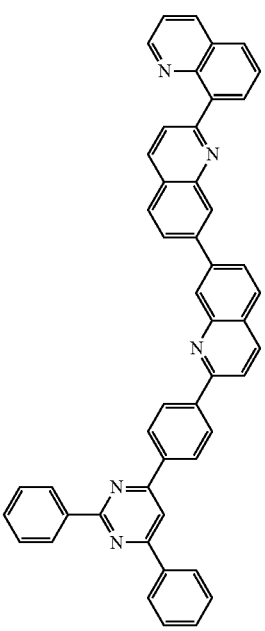 [SMILES: c1ccc(-c2cc(-c3ccc(-c4ccc5ccc(-c6ccc7ccc(-c8cccc9cccnc89)nc7c6)cc5n4)cc3)nc(-c3ccccc3)n2)cc1]

117
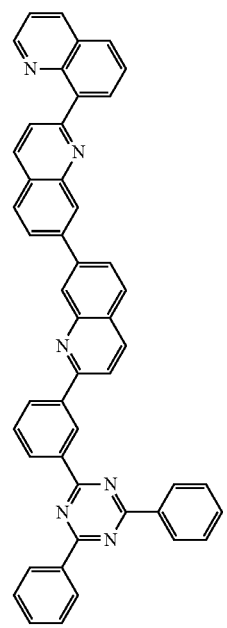 [SMILES: c1ccc(-c2nc(-c3ccccc3)nc(-c3cccc(-c4ccc5ccc(-c6ccc7ccc(-c8cccc9cccnc89)nc7c6)cc5n4)c3)n2)cc1]
118
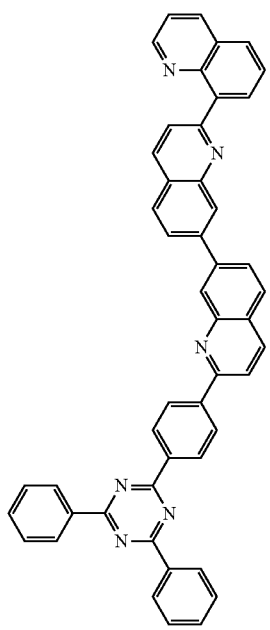
119
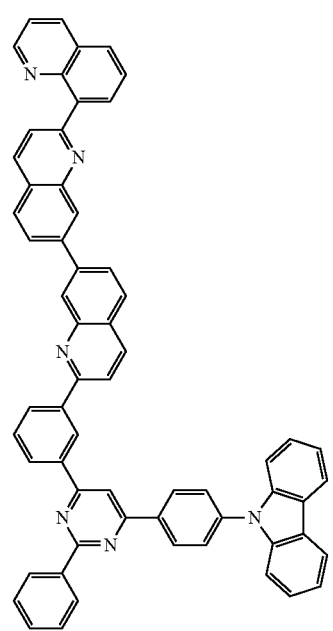
120
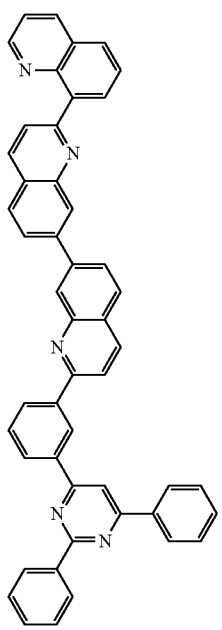

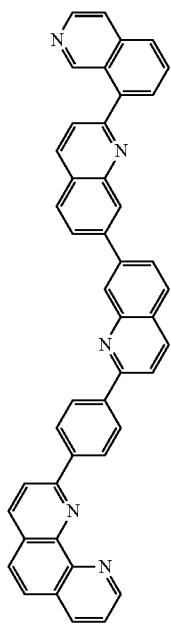 [SMILES: c1cc(-c2ccc3ccc(-c4ccc5ccc(-c6ccc(-c7ccc8ccc9cccnc9c8n7)cc6)nc5c4)cc3n2)c2cnccc2c1]
121
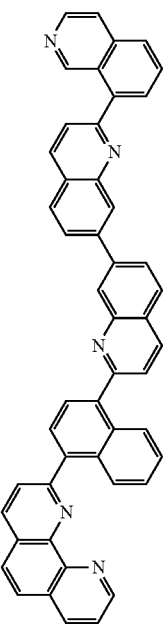
123
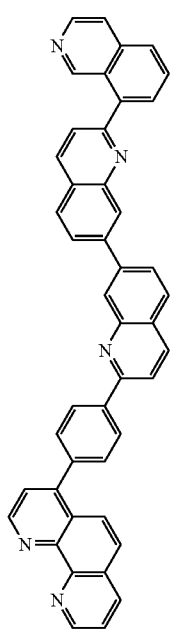
122
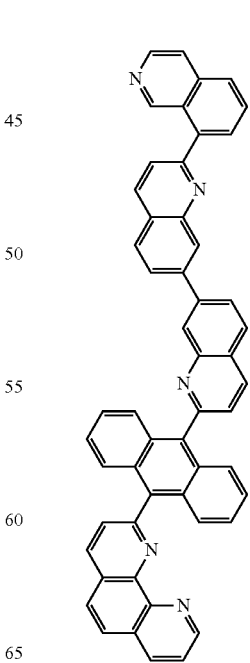
124

125
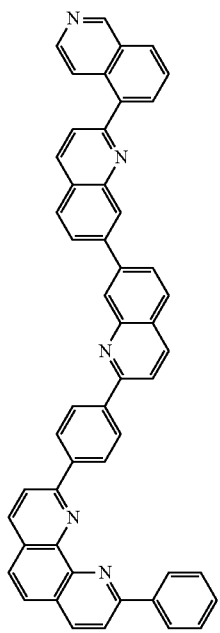 [SMILES: c1ccc(-c2ccc3ccc4ccc(-c5ccc(-c6ccc7ccc(-c8ccc9ccc(-c%10cccc%11cnccc%10%11)nc9c8)cc7n6)cc5)nc4c3n2)cc1]
126
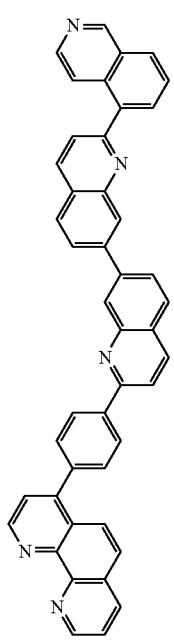
127
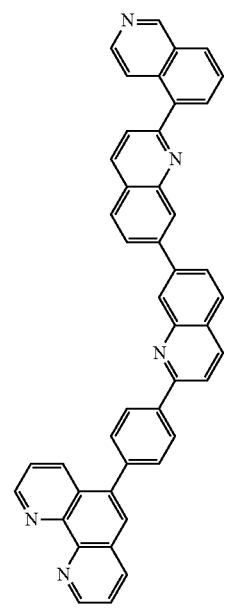
128
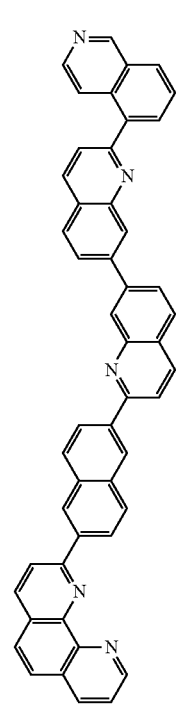

641
-continued
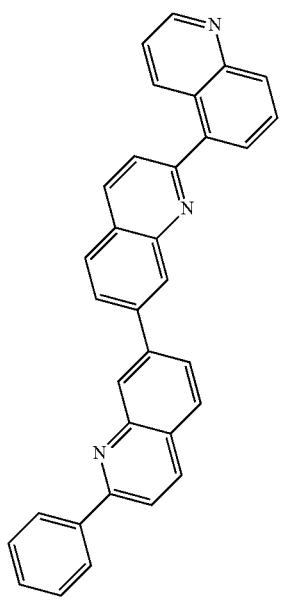
642
-continued
129
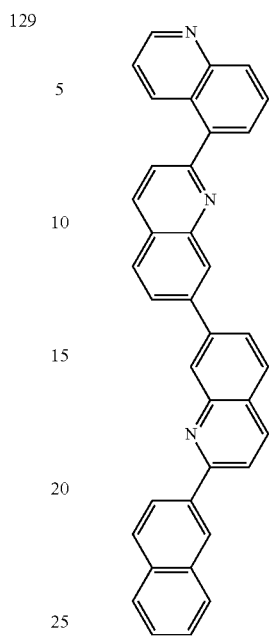
130
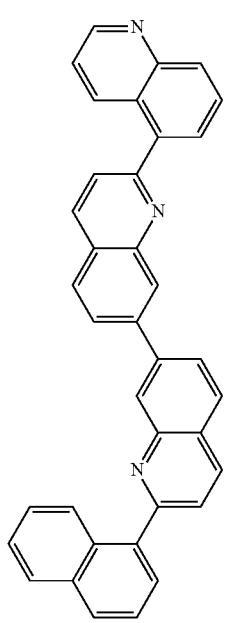
131
132
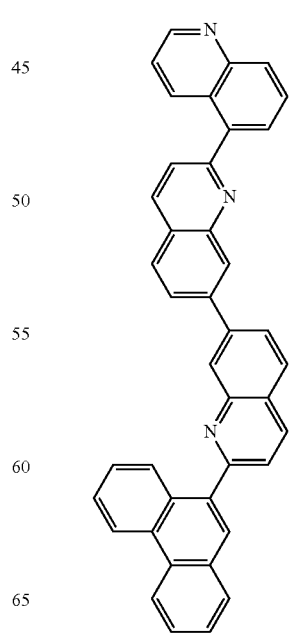

133
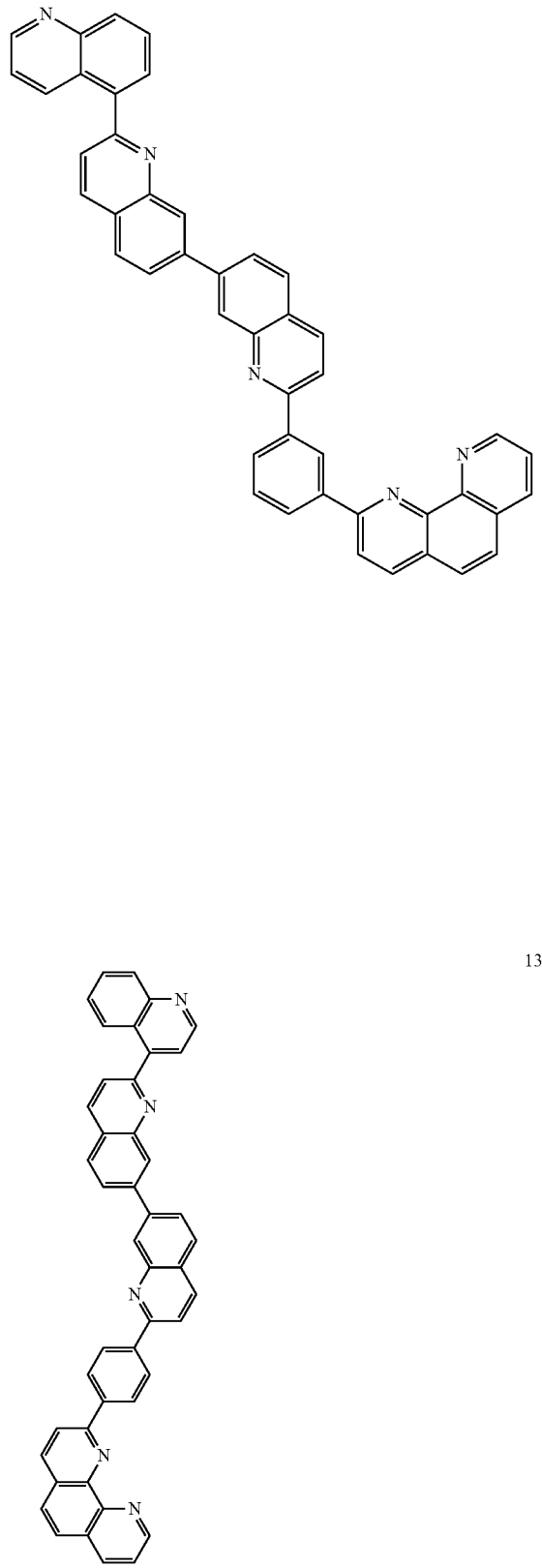
134
135

136 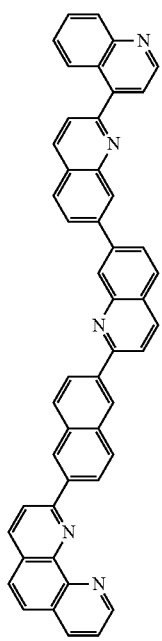
137 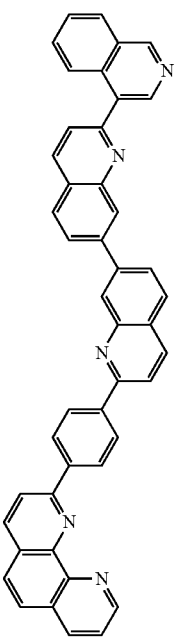
138 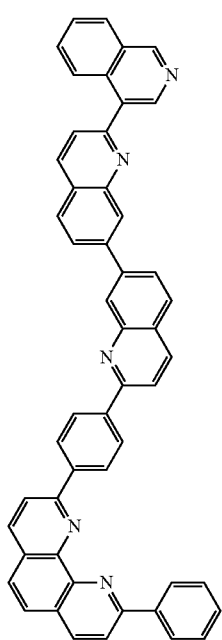
139 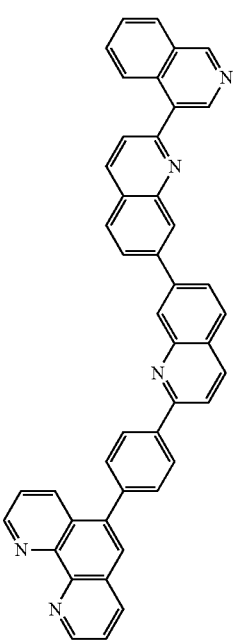

-continued
140
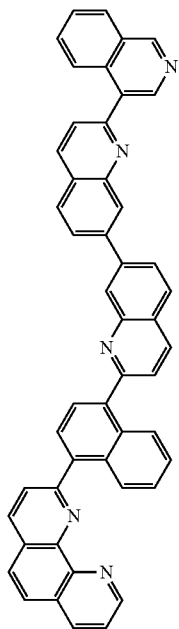 [SMILES: c1ccc2c(-c3ccc4ccc(-c5ccc6ccc(-c7ccc(-c8ccc9ccc%10cccnc%10c9n8)c8ccccc78)nc6c5)cc4n3)cncc2c1]
141
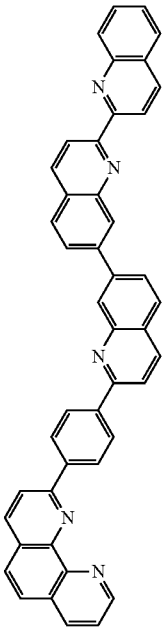
142
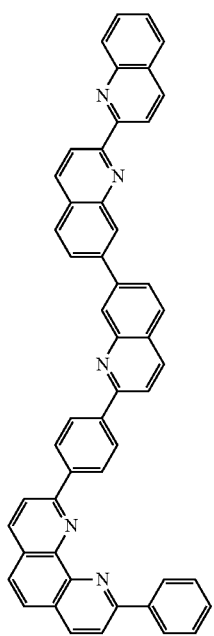
143
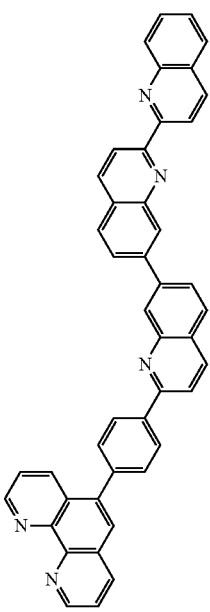

-continued

144

145

146

147

-continued
148
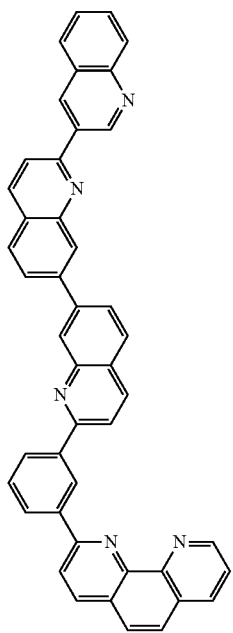 [SMILES: c1cc(-c2ccc3ccc(-c4ccc5ccc(-c6cnc7ccccc7c6)nc5c4)cc3n2)cc(-c2ccc3ccc4cccnc4c3n2)c1]
149
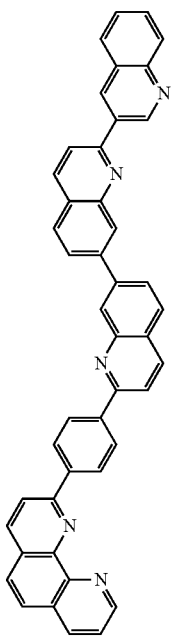
150
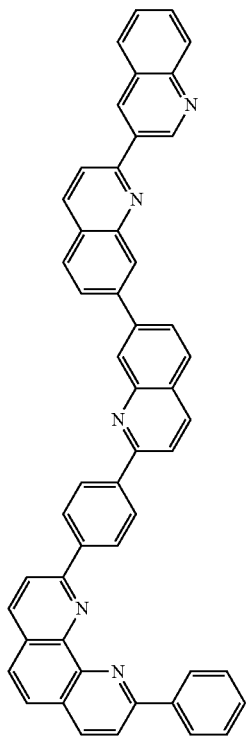
151
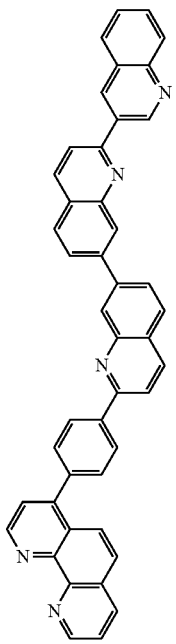

-continued
152
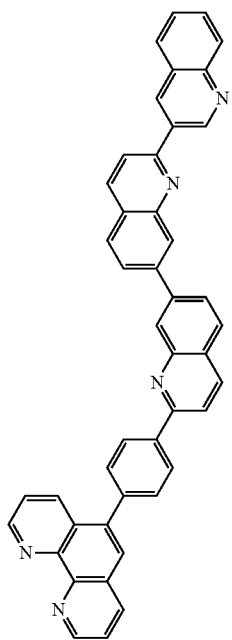
153
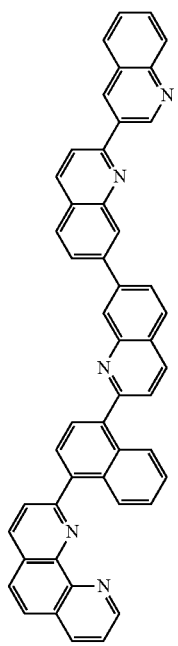
154
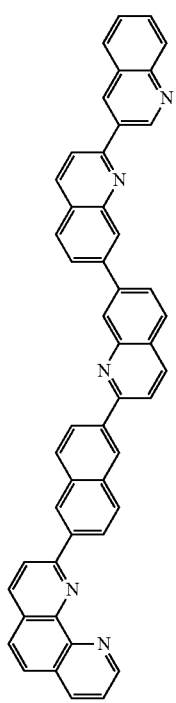
155
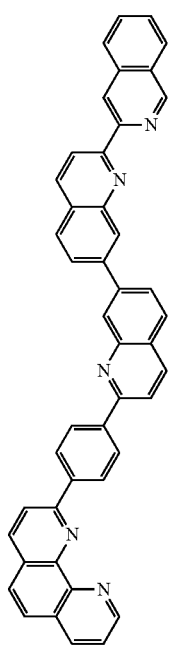

156
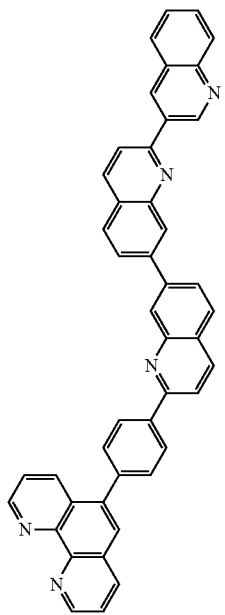
157
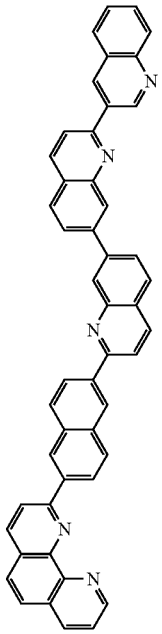
158
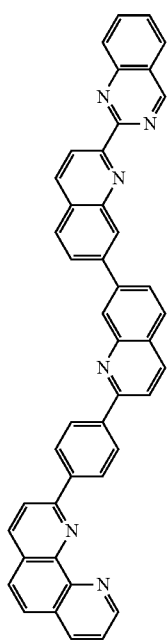
159
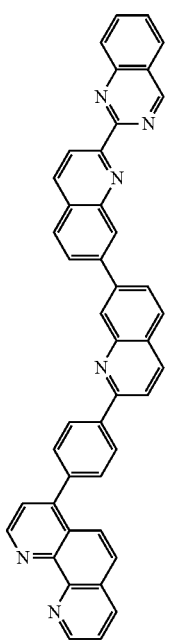

-continued
160
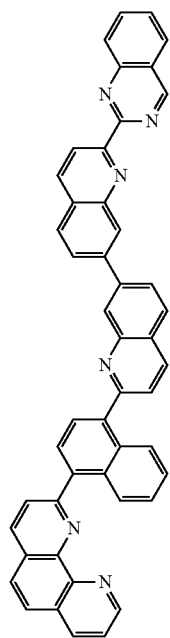
161
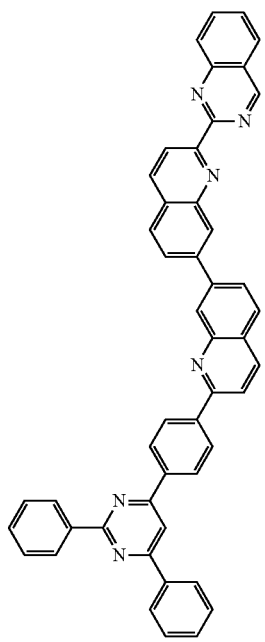
162
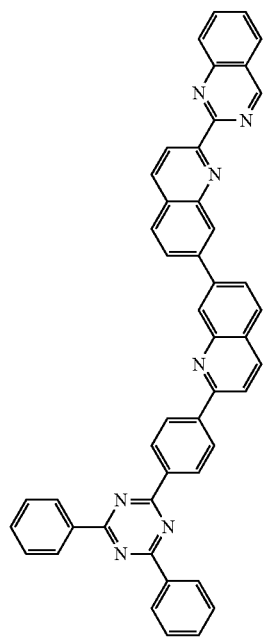
163
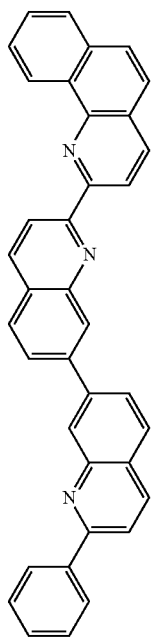

-continued
164
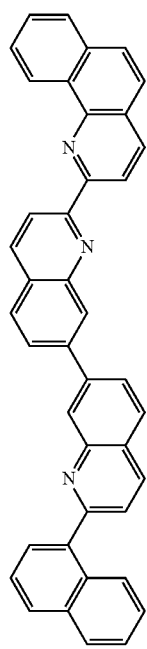
165
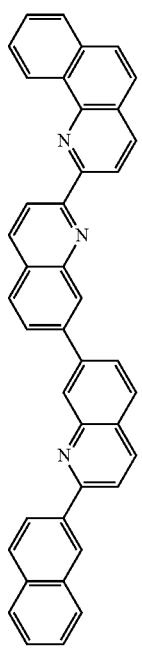
166
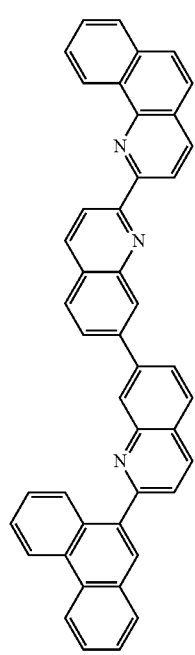

167
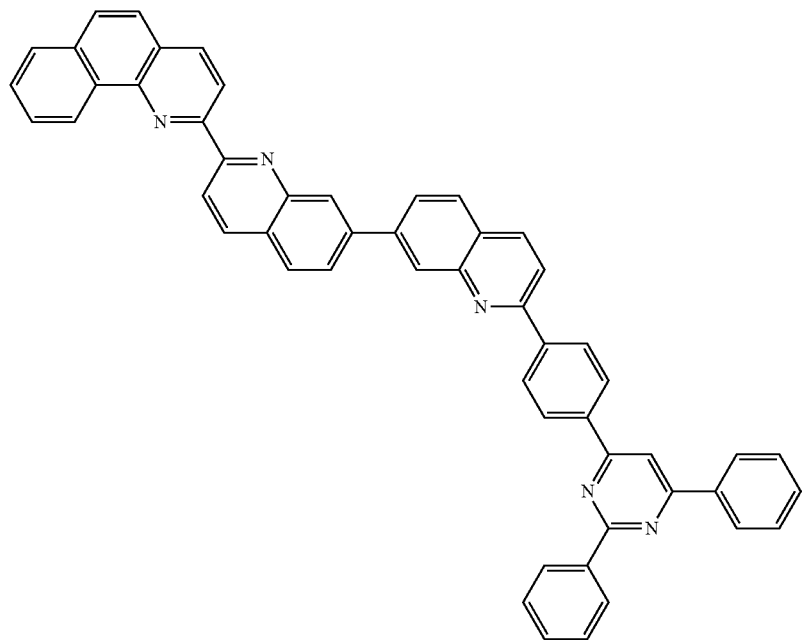
168
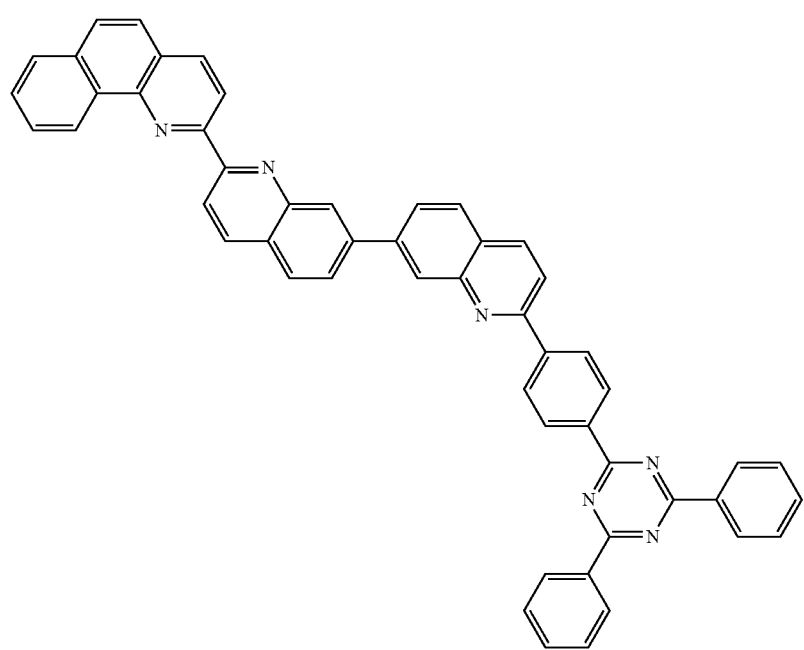 [SMILES: c1ccc(-c2nc(-c3ccccc3)nc(-c3ccc(-c4ccc5ccc(-c6ccc7ccc(-c8ccc9ccc%10ccccc%10c9n8)nc7c6)cc5n4)cc3)n2)cc1]

-continued
663
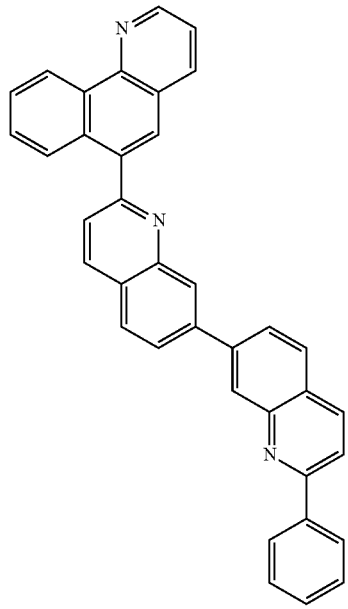
664
169
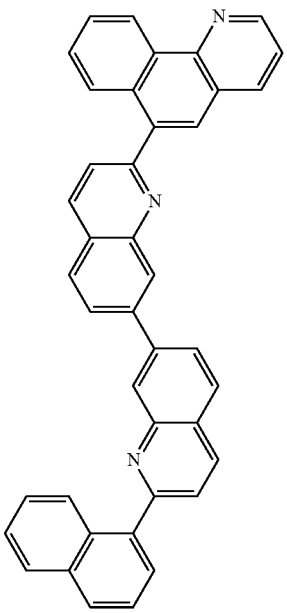
170
171
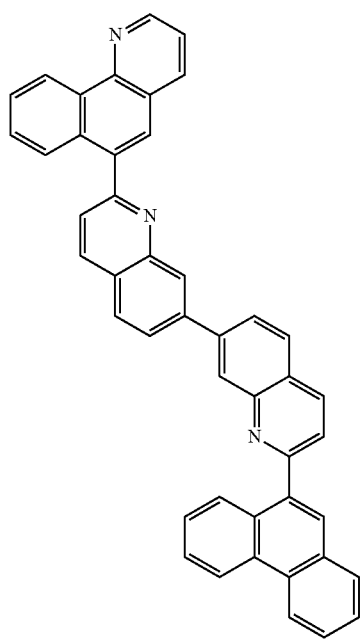
172

173
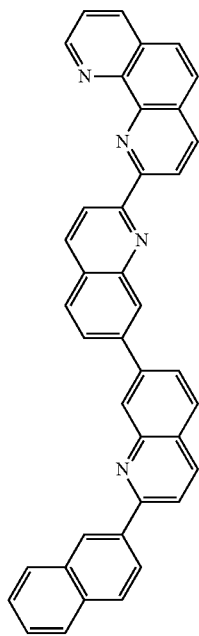
174
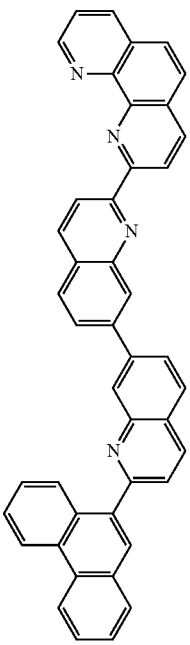
175
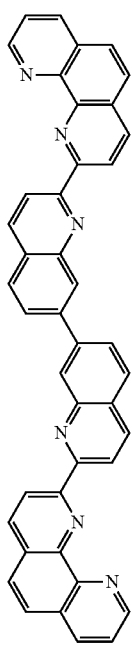
176
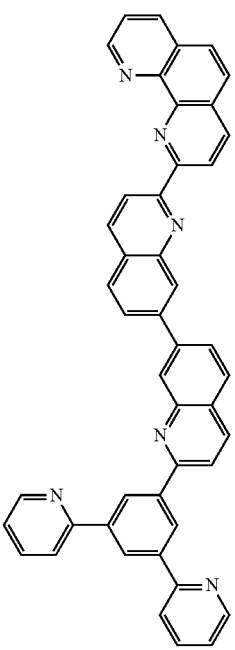

-continued
177 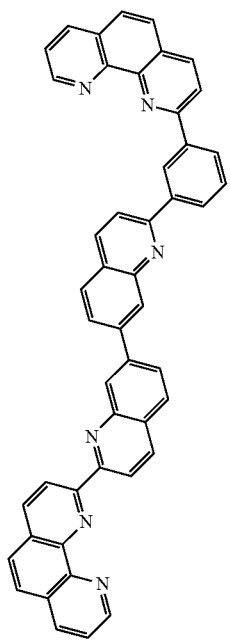 178 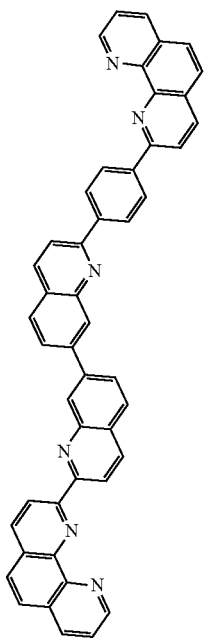
179 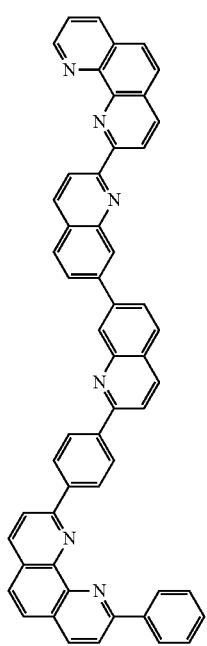 180 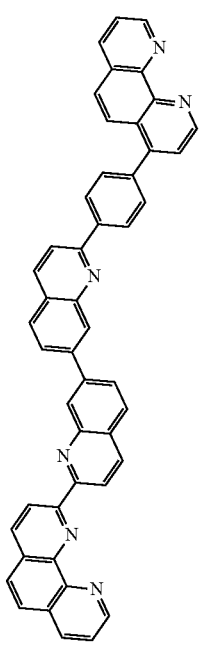

181
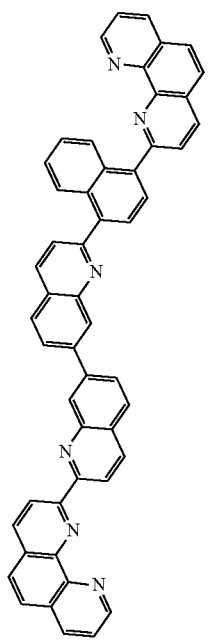
182
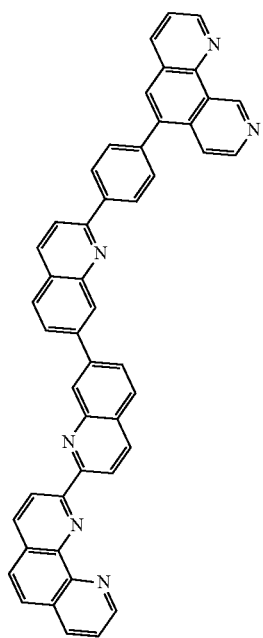
183
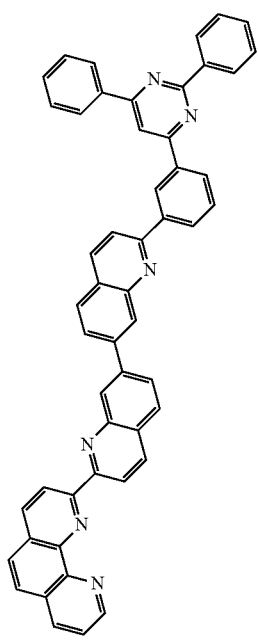
184
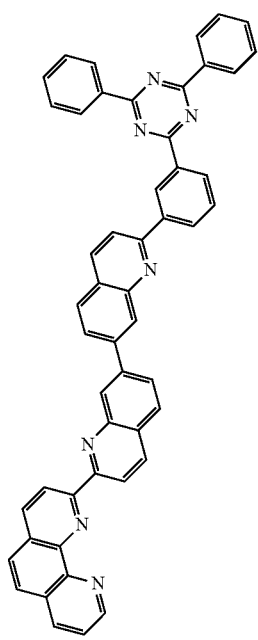

671
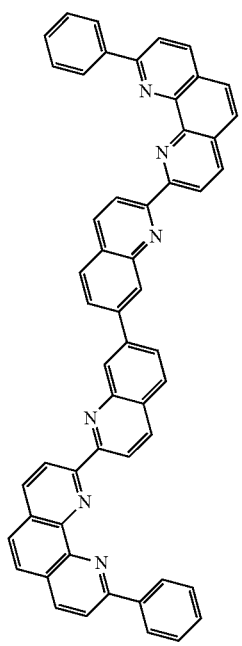
672
-continued
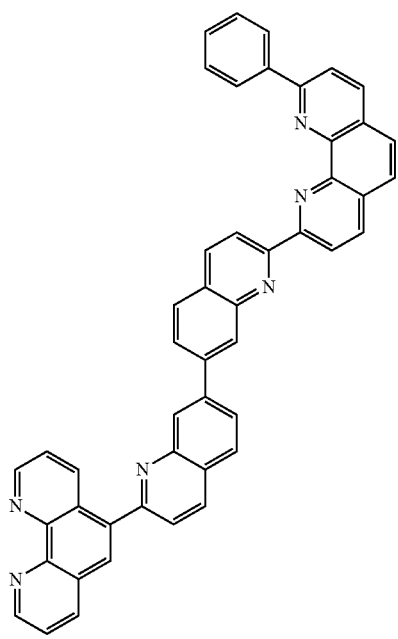
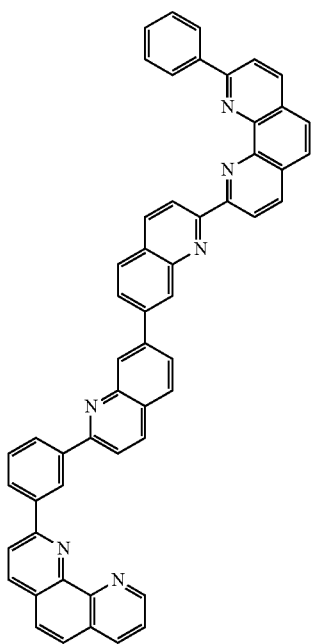 [SMILES: c1ccc(-c2ccc3ccc4ccc(-c5ccc6ccc(-c7ccc8ccc(-c9cccc(-c%10ccc%11ccc%12cccnc%12c%11n%10)c9)nc8c7)cc6n5)nc4c3n2)cc1]
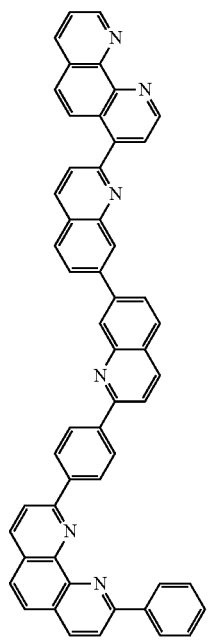

189
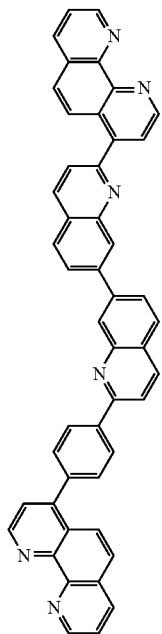
190
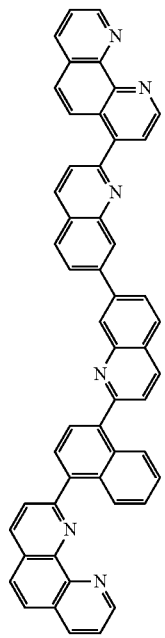
191
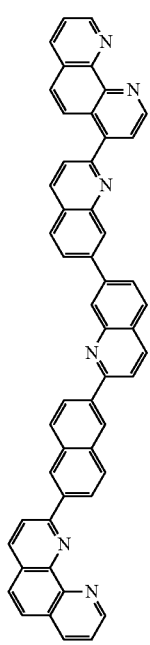
192
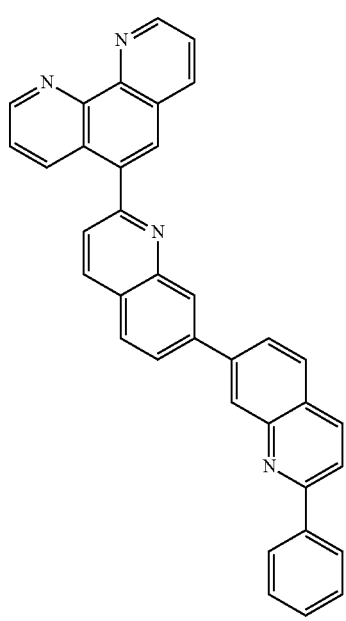 [SMILES: c1ccc(-c2ccc3ccc(-c4ccc5ccc(-c6cc7cccnc7c7ncccc67)nc5c4)cc3n2)cc1]

193
194

195
196

-continued
197
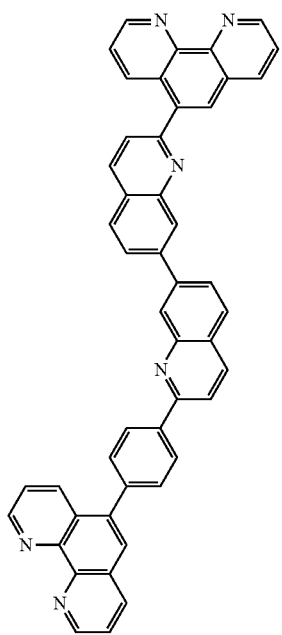
198
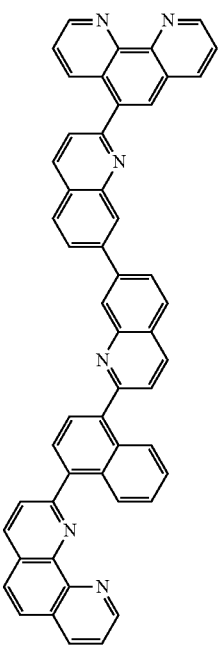
199
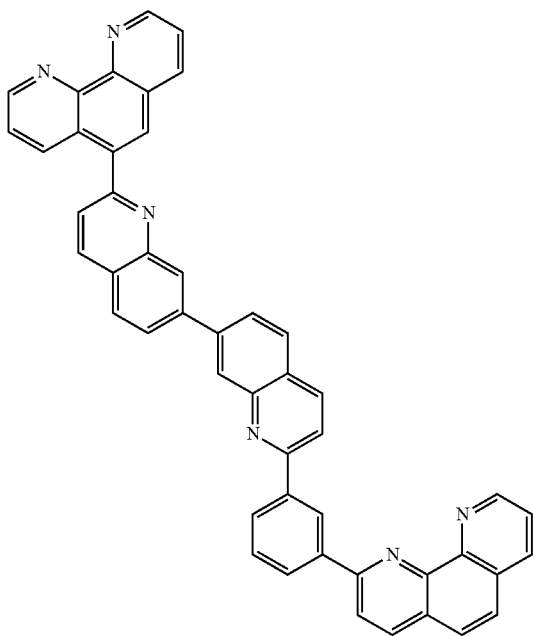
200
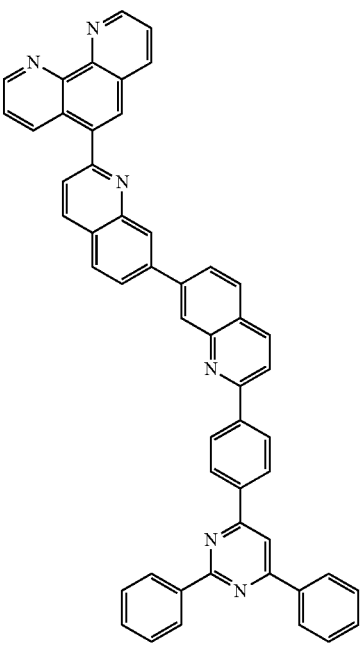 [SMILES: c1ccc(-c2cc(-c3ccc(-c4ccc5ccc(-c6ccc7ccc(-c8cc9cccnc9c9ncccc89)nc7c6)cc5n4)cc3)nc(-c3ccccc3)n2)cc1]

-continued
201
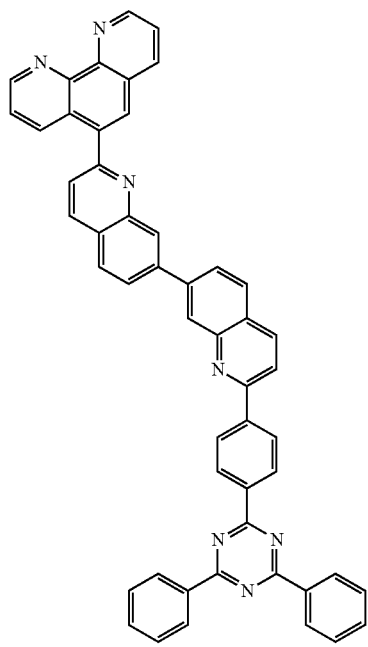
202
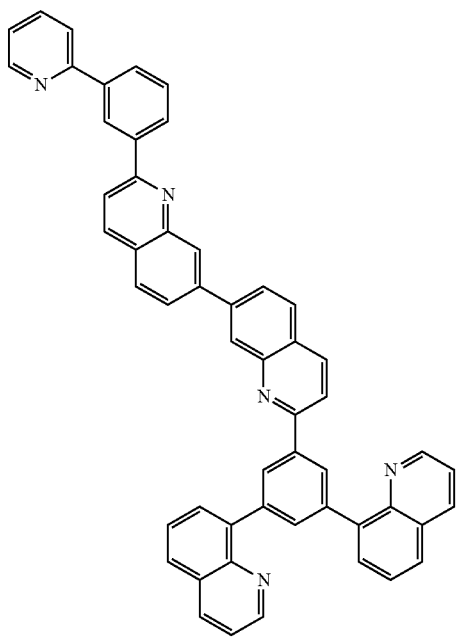 [SMILES: c1ccc(-c2cccc(-c3ccc4ccc(-c5ccc6ccc(-c7cc(-c8cccc9cccnc89)cc(-c8cccc9cccnc89)c7)nc6c5)cc4n3)c2)nc1]
203
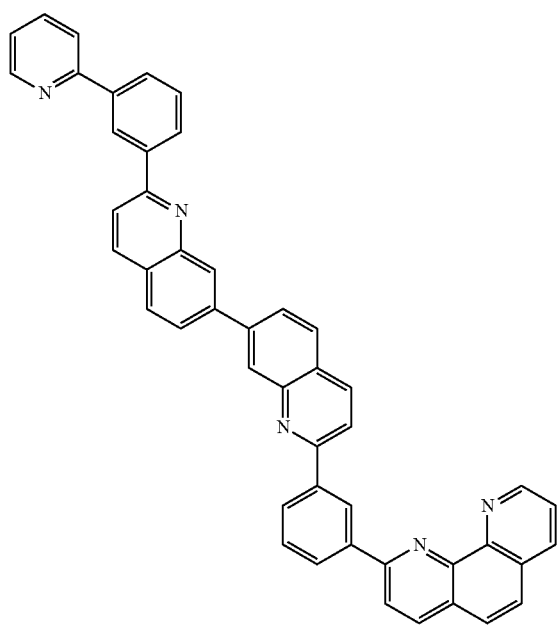
204
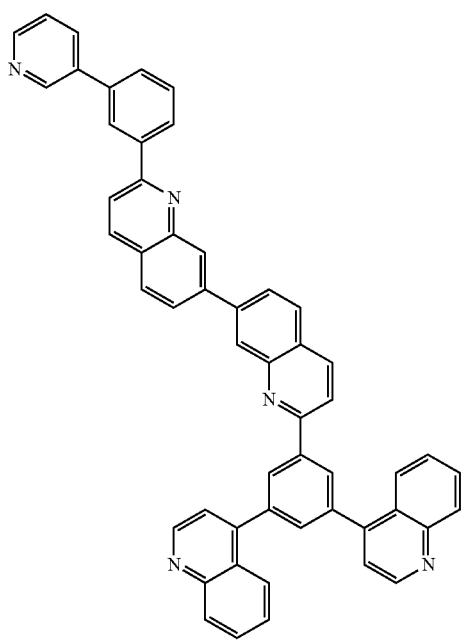

681 682
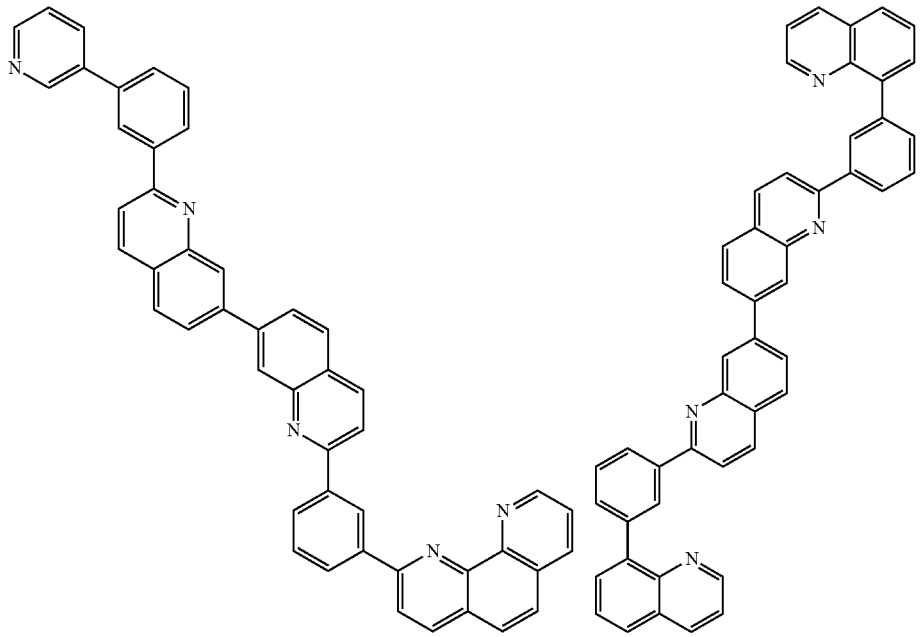
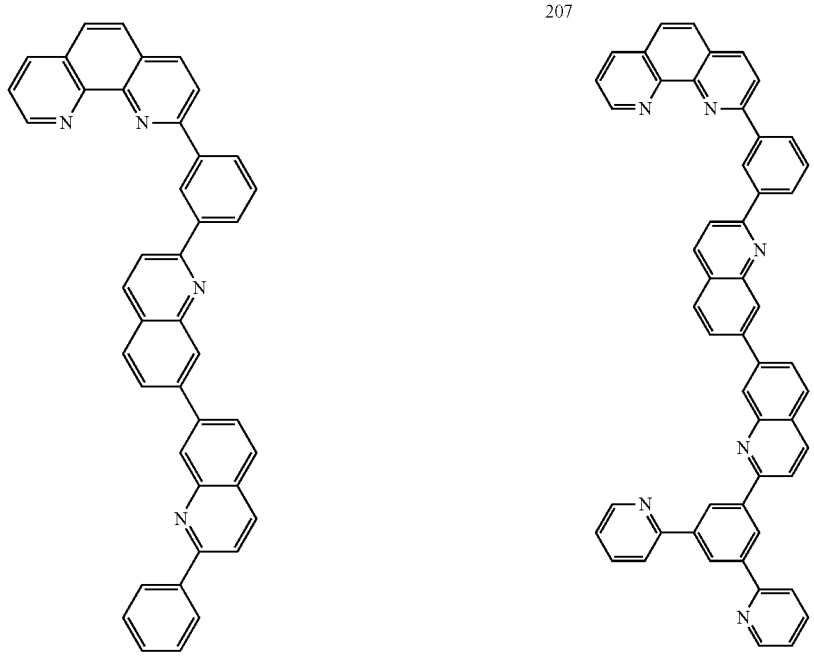

-continued
683     684
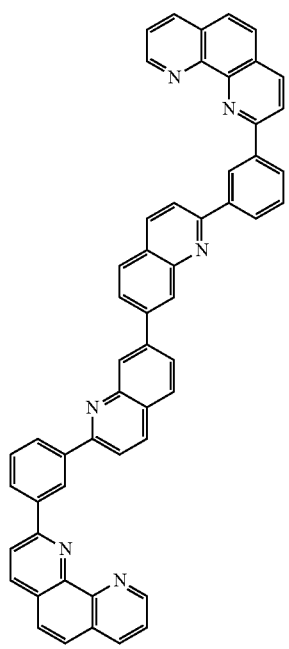 [SMILES: c1cc(-c2ccc3ccc(-c4ccc5ccc(-c6cccc(-c7ccc8ccc9cccnc9c8n7)c6)nc5c4)cc3n2)cc(-c2ccc3ccc4cccnc4c3n2)c1]
209
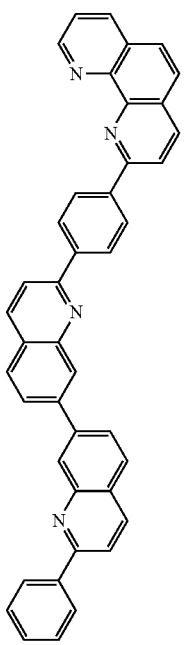
210
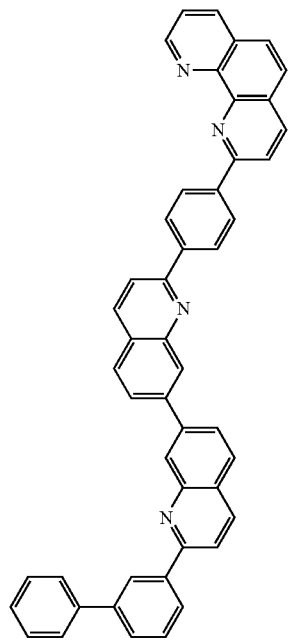
211
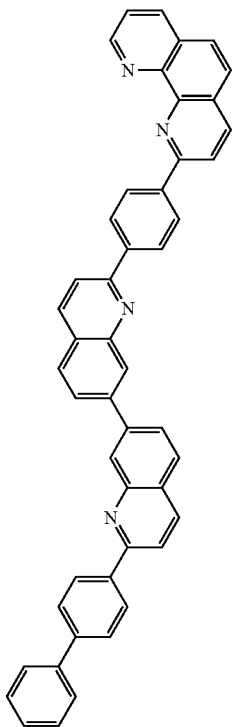 [SMILES: c1ccc(-c2ccc(-c3ccc4ccc(-c5ccc6ccc(-c7ccc(-c8ccc9ccc%10cccnc%10c9n8)cc7)nc6c5)cc4n3)cc2)cc1]
212

-continued
213 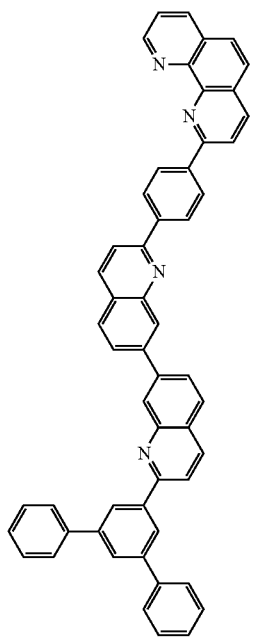
214 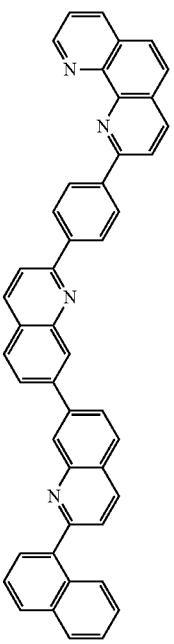 [SMILES: c1ccc2c(-c3ccc4ccc(-c5ccc6ccc(-c7ccc(-c8ccc9ccc%10cccnc%10c9n8)cc7)nc6c5)cc4n3)cccc2c1]
215 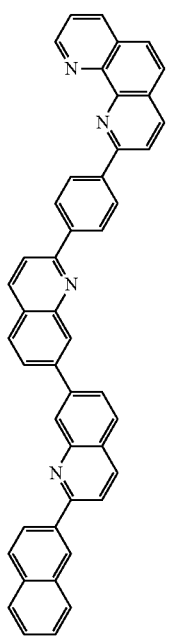
216 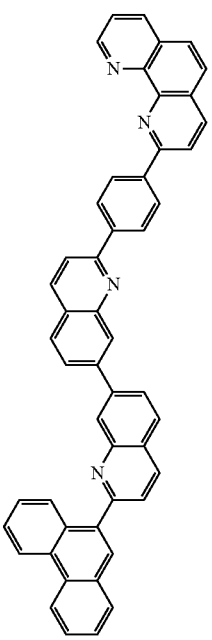 [SMILES: c1ccc2c(c1)cc(-c1ccc3ccc(-c4ccc5ccc(-c6ccc(-c7ccc8ccc9cccnc9c8n7)cc6)nc5c4)cc3n1)c1ccccc12]

217
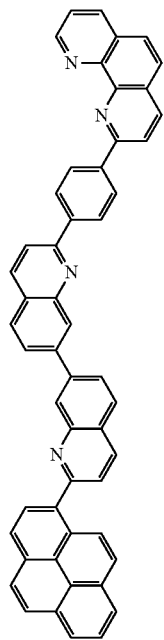
218
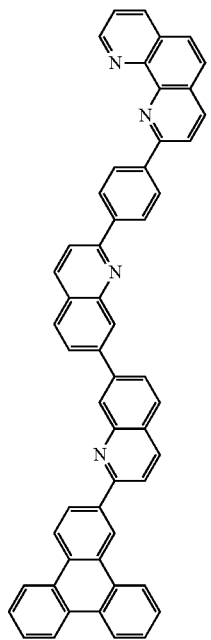
219
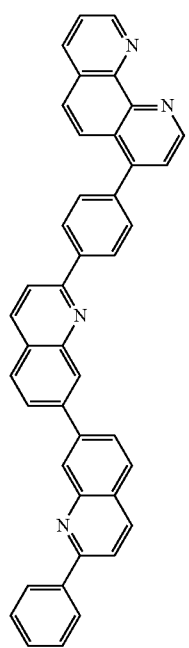 [SMILES: c1ccc(-c2ccc3ccc(-c4ccc5ccc(-c6ccc(-c7ccnc8c7ccc7cccnc78)cc6)nc5c4)cc3n2)cc1]
220
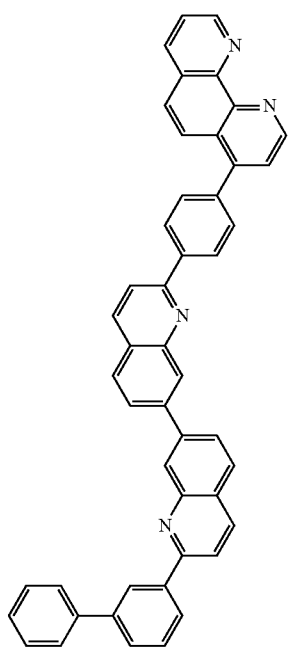

-continued
221
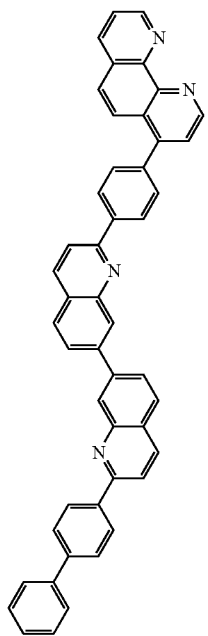
222
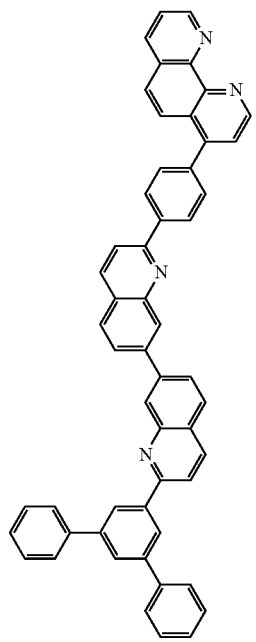
223
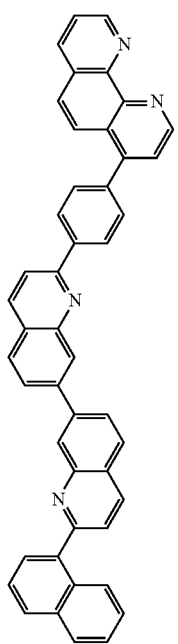 [SMILES: c1ccc2c(-c3ccc4ccc(-c5ccc6ccc(-c7ccc(-c8ccnc9c8ccc8cccnc89)cc7)nc6c5)cc4n3)cccc2c1]
224
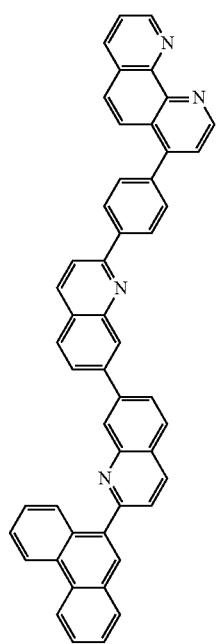

-continued
225 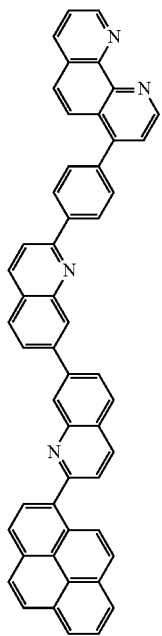 226 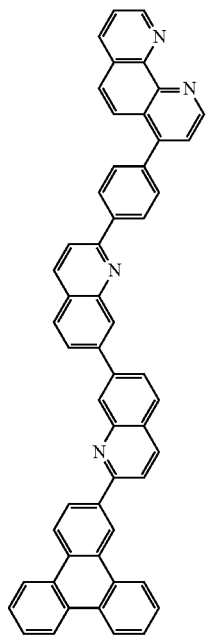
227 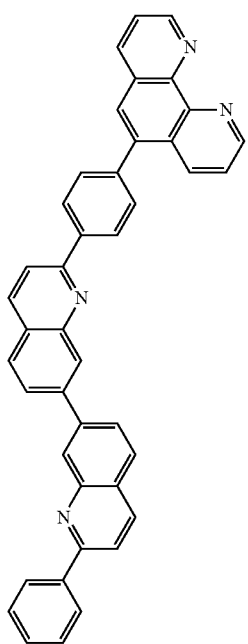 [SMILES: c1ccc(-c2ccc3ccc(-c4ccc5ccc(-c6ccc(-c7cc8cccnc8c8ncccc78)cc6)nc5c4)cc3n2)cc1] 228 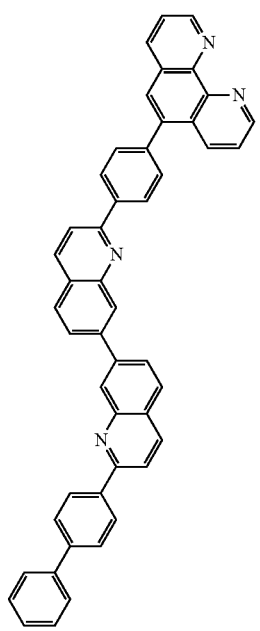

-continued
229 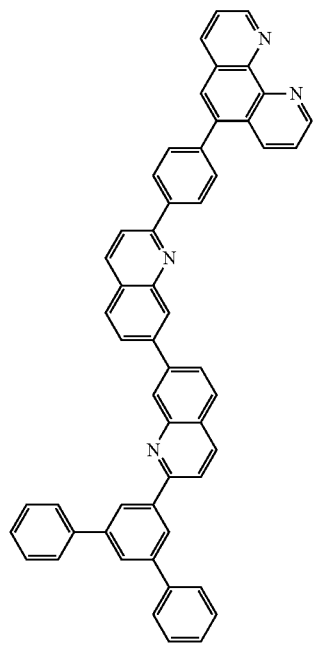
230 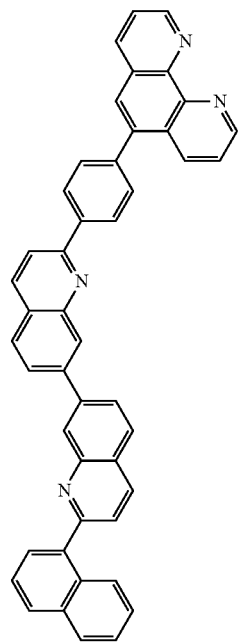
231 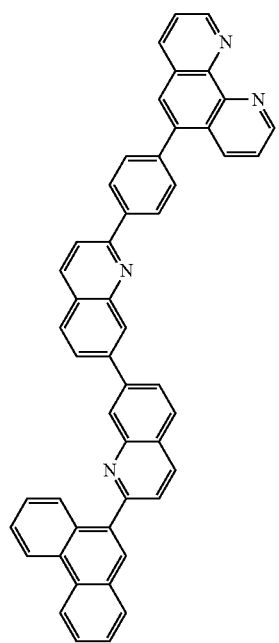
232 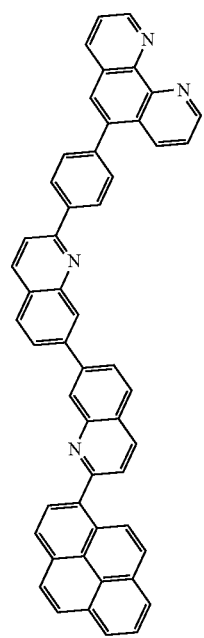

-continued
233 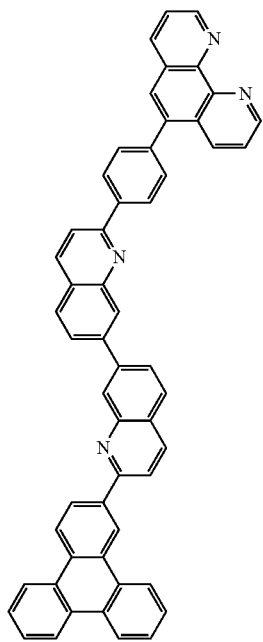
234 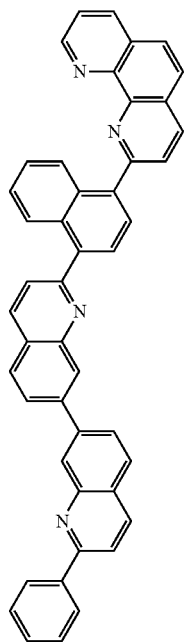 [SMILES: c1ccc(-c2ccc3ccc(-c4ccc5ccc(-c6ccc(-c7ccc8ccc9cccnc9c8n7)c7ccccc67)nc5c4)cc3n2)cc1]
235 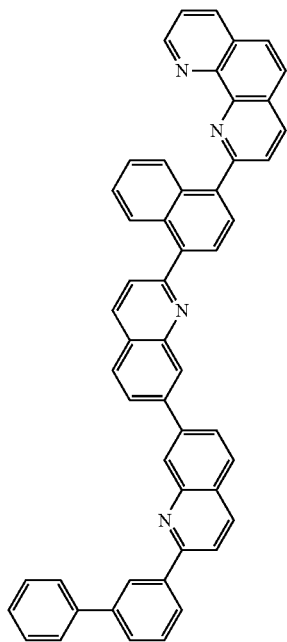
236 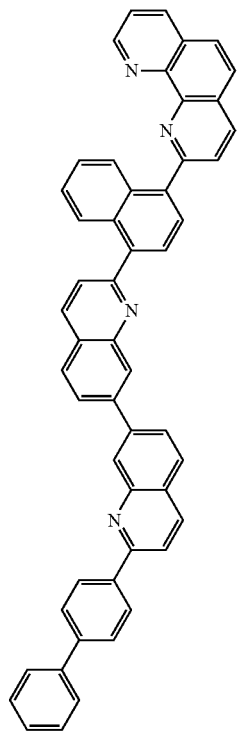 [SMILES: c1ccc(-c2ccc(-c3ccc4ccc(-c5ccc6ccc(-c7ccc(-c8ccc9ccc%10cccnc%10c9n8)c8ccccc78)nc6c5)cc4n3)cc2)cc1]

-continued
237
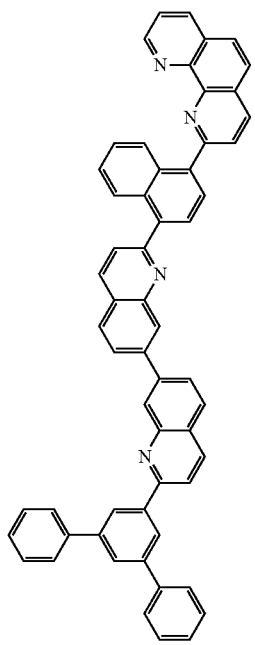
238
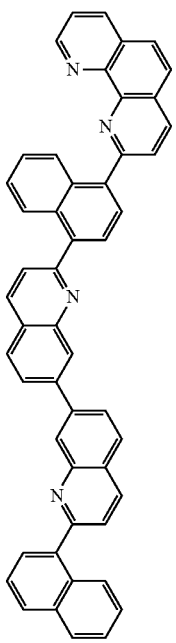
239
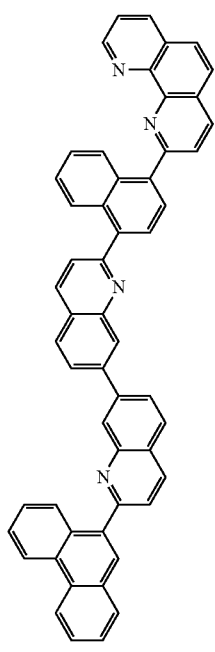
240
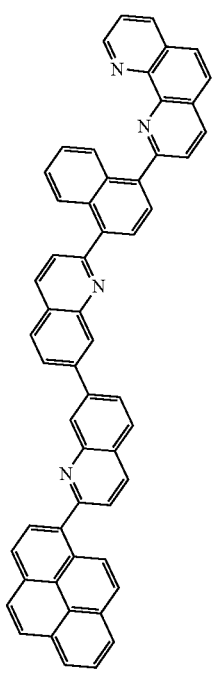

241 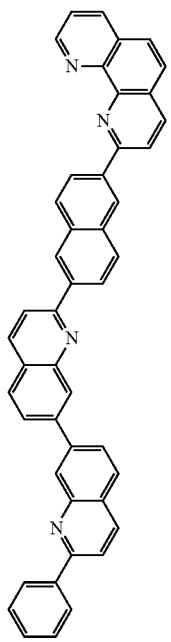 [SMILES: c1ccc(-c2ccc3ccc(-c4ccc5ccc(-c6ccc7cc(-c8ccc9ccc%10cccnc%10c9n8)ccc7c6)nc5c4)cc3n2)cc1]
242 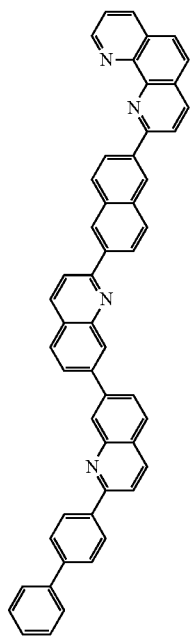
243 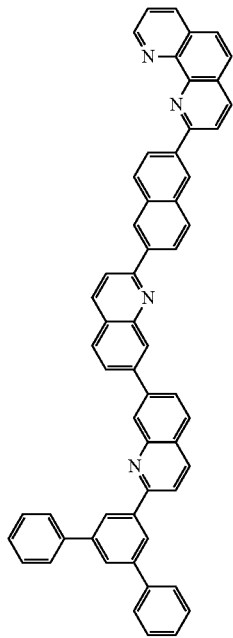
244 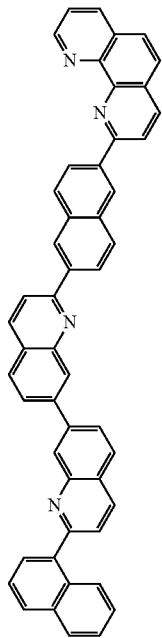 [SMILES: c1ccc2c(-c3ccc4ccc(-c5ccc6ccc(-c7ccc8cc(-c9ccc%10ccc%11cccnc%11c%10n9)ccc8c7)nc6c5)cc4n3)cccc2c1]

245
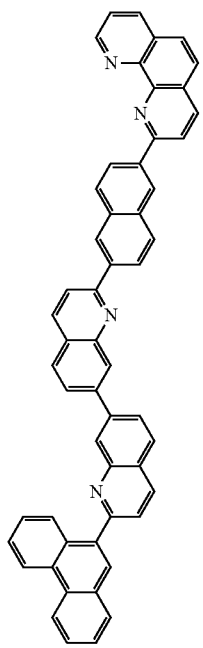
246
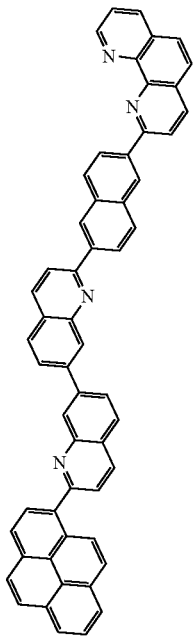
247
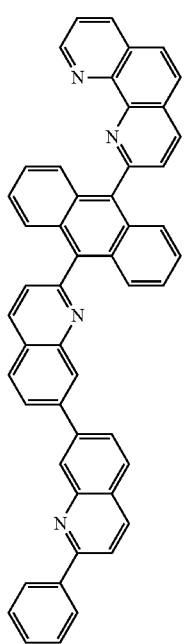
248
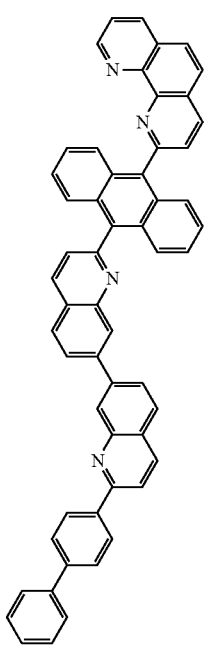

-continued
249 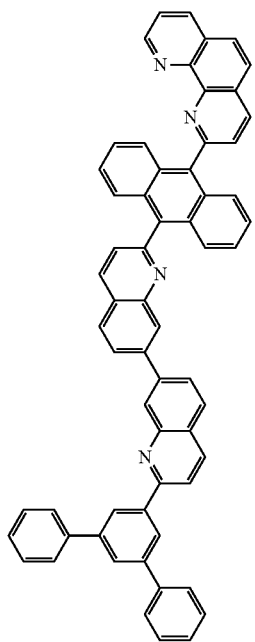
250 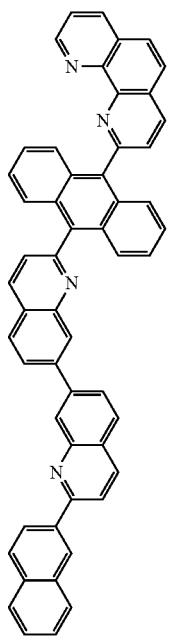
251 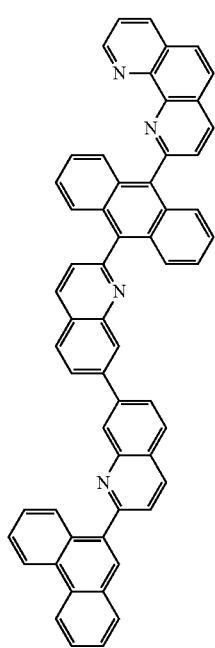
252 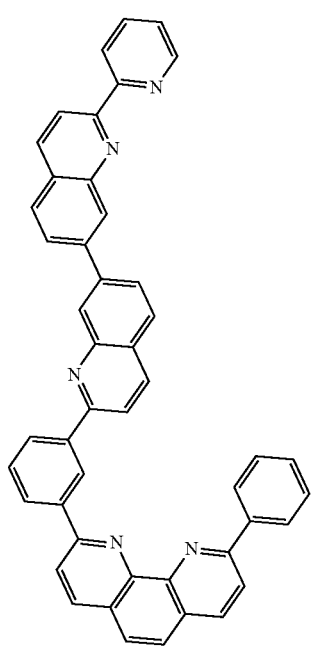

-continued
253
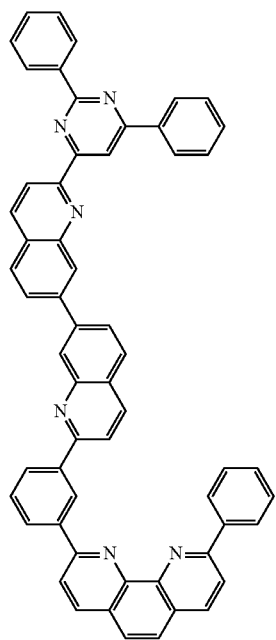
254
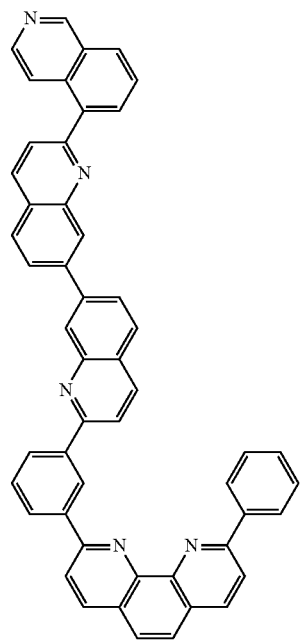
255
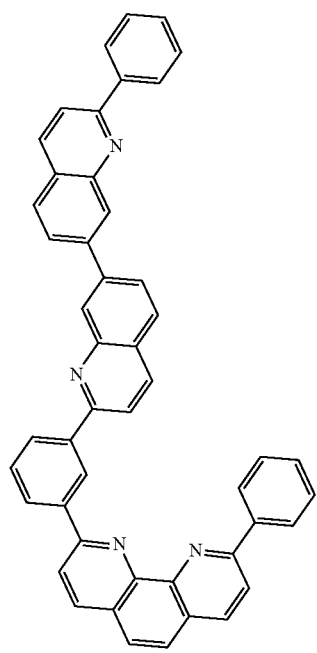
256
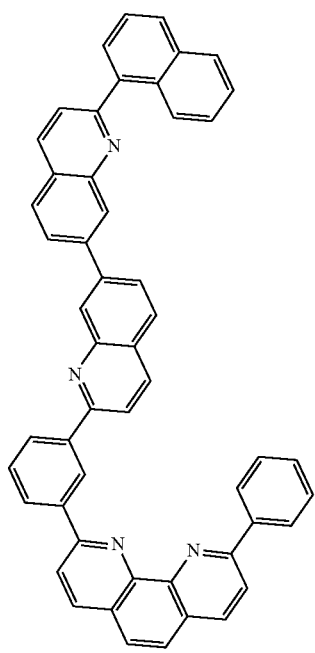

-continued

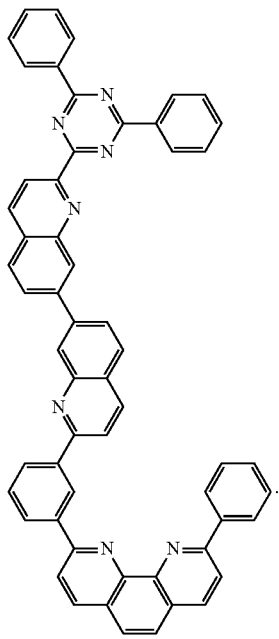

257

18. An organic optoelectronic diode comprising:
an anode and a cathode facing each other; and
at least one organic layer disposed between the anode and the cathode,
wherein the organic layer includes the compound of claim 1.

19. The organic optoelectronic diode of claim 18, wherein the organic layer includes a charge generation layer or a hole blocking layer, and the charge generation layer or the hole blocking layer includes the compound.

20. A display device comprising the organic optoelectronic diode of claim 18.

* * * * *